(12) United States Patent
Knecht et al.

(10) Patent No.: US 11,198,875 B2
(45) Date of Patent: Dec. 14, 2021

(54) METHODS FOR MODULATING INSECT HYGRO- AND/OR THERMOSENSATION

(71) Applicant: BRANDEIS UNIVERSITY, Waltham, MA (US)

(72) Inventors: Zachary Knecht, Waltham, MA (US); Paul Garrity, Waltham, MA (US); Lina Ni, Waltham, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 0 days.

(21) Appl. No.: 16/099,277

(22) PCT Filed: May 9, 2017

(86) PCT No.: PCT/US2017/031781
§ 371 (c)(1),
(2) Date: Nov. 6, 2018

(87) PCT Pub. No.: WO2017/196861
PCT Pub. Date: Nov. 16, 2017

(65) Prior Publication Data
US 2019/0153451 A1    May 23, 2019

Related U.S. Application Data

(60) Provisional application No. 62/333,655, filed on May 9, 2016.

(51) Int. Cl.
| | |
|---|---|
| *A61K 48/00* | (2006.01) |
| *C12N 15/11* | (2006.01) |
| *C07H 21/02* | (2006.01) |
| *C07H 21/04* | (2006.01) |
| *C12N 15/113* | (2010.01) |

(Continued)

(52) U.S. Cl.
CPC .... *C12N 15/1138* (2013.01); *C07K 14/43581* (2013.01); *C12N 9/22* (2013.01); *C12N 15/11* (2013.01); *G01N 33/5085* (2013.01); *G01N 33/68* (2013.01); *C12N 2310/20* (2017.05); *C12N 2800/80* (2013.01)

(58) Field of Classification Search
CPC ................ C12N 15/11; C12N 15/1138; C07K 14/43581; G01N 33/5085; G01N 2333/705
See application file for complete search history.

(56) References Cited

FOREIGN PATENT DOCUMENTS

WO    2014153190 A1    9/2014

OTHER PUBLICATIONS

Chen et al. (Nature, Nov. 26, 2015 vol. 527:516-532).*

(Continued)

*Primary Examiner* — Terra C Gibbs
(74) *Attorney, Agent, or Firm* — Cantor Colburn LLP

(57) ABSTRACT

A method of modulating hygrosensing and/or thermosensing in an animal, particularly, an insect or disease vector, is provided. Also provided is a method of reducing survival, host-seeking, and/or reproductive capability of an animal, particularly an insect or disease vector. The methods involve an effective amount of an agent that modulates the activity and/or expression of a polynucleotide or polypeptide of an ionotropic receptor (Ir) selected from one or more of Ir25a, Ir93a, Ir40a, Ir68a, or Ir21a. A method of identifying an agent that modulates survival, host-seeking, and/or reproductive capability of an animal, e.g., an insect, is further provided.

8 Claims, 69 Drawing Sheets
Specification includes a Sequence Listing.

(51) Int. Cl.
  *G01N 33/68* (2006.01)
  *C07K 14/435* (2006.01)
  *C12N 9/22* (2006.01)
  *G01N 33/50* (2006.01)

(56) References Cited

OTHER PUBLICATIONS

Ni et al. (eLife Apr. 29, 2016;5:e13254, pp. 1-12).*
Knecht et al. (eLife, 2017 vol. 6, pp. 1-11).*
Kain et al. (Nature, 2013 vol. 502:507-514).*
Rytz et al. (Insect Biochemistry and Molecular Biology, 2013 vol. 43:888-897).*
Zhu et al. (Annu. Rev. Entomol., 2020 vol. 65:293-311).*
Zotti and Smagghe (Neotropical Entomology, published online Apr. 17, 2015, DOI 10.1007/s13744-015-0291-8).*
Benton, B. et al., "Variant ionotropic glutamate receptors as chemosensory receptors in *Drosophia*," Cell, vol. 136(1), pp. 149-162 (2009).
Eijin, et al., "Humidity Sensing in *Drosophilia*," Curr. Biol. ePub, May 5, 2016, vol. 26, pp. 1352-1358.
Liu, L. et al., "*Drosophila* hygrosensation requires the TRP channels water witch and nanchung," Nature, vol. 450(8), pp. 294-297 (2007).
Sayeed, O. et al., "Behavioral genetics of thermosensation and hygrosenation in *Drosophila*," Proc. Natl. Acad. Sci., USA, vol. 93, pp. 6079-6084 (1996).
Tichy, H. et al., "The Evaporative Function of Cockroach Hygroreceptors," PLOS One, vol. 8, Issue 1 (2013).
International Search Report and Written Opinion for corresponding PCT/US217/31781, dated Oct. 12, 2017 (11 pages).
Anonymous, Horizon Discovery Ltd; "siRNA Solutions: Reliably silence gene function in any cell type"; 2020; Available online at https://horizondiscovery.com/en/products/gene-modulation/knockdown-reagents/sirna; printed Oct. 8, 2020.
Nandety et al.; "Emerging strategies for RNA interference (RNAi) applications in Insects"; Bioengineered, vol. 6, Issue No. 1; 2015; pp. 8-9.
Airs, P. et al.; "RNA Interference for Mosquito and Mosquito-Borne Disease Control"; Insects, vol. 8, Issue No. 4; 2017; 21 pages; doi: 10.3990/insects8010004.
Anonymous; "siRNA Wizard—The Online tool to choose and design short hairpin RNAs by InvivoGen"; InvivoGen; available online at www.invivogen.com/sirnawizard/ [retrieved on Jun. 28, 2021]; 2021; 3 pages.
Dietzl, G. et al.; "A genome-wide transgenic RNAi library for conditional gene inactivation in *Drosophila*"; Nature, vol. 448, Issue No. 7150; 2007; pp. 151-156.
Hamada, F. et al.; "An internal thermal sensor controlling temperature preference in *Drosophila*"; Nature, vol. 454, Issue No. 7201; 2008; pp. 217-220; doi: 10.1038/nature07001.
Heigwer, F. et al.; "RNA Interference (RNAi) Screening in *Drosophila*"; Genetics, vol. 208, Issue No. 3; 2018; pp. 853-874.

* cited by examiner

Load Flies

Sayeed and Benzer (1996)

Dry Air: 1-4% RH    Moist Air: 90-96% RH 5 minutes, raise elevator $$DPI = \frac{\text{\# flies on dry side} - \text{\# flies on moist side}}{\text{\# flies on dry side} + \text{\# flies on moist side}}$$

$$\text{Relative Ir93a intensity} = \frac{\left(\frac{\text{mean Ir93a intensity at sensory ending}}{\text{mean GFP intensity at sensory ending}}\right)}{\left(\frac{\text{mean Ir93a intensity at cell body}}{\text{mean GFP intensity at cell body}}\right)}$$

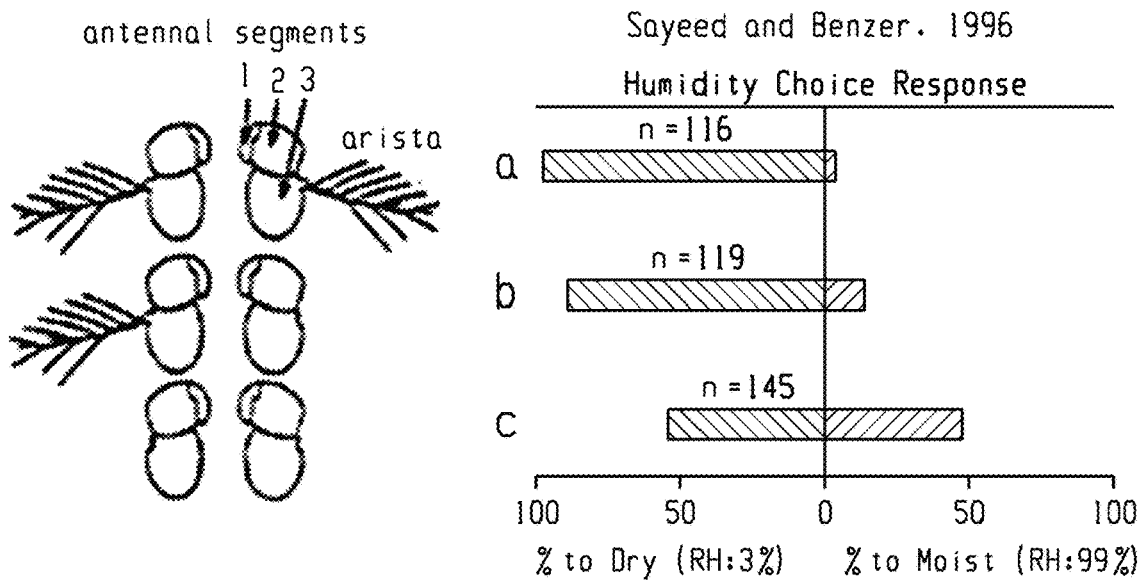
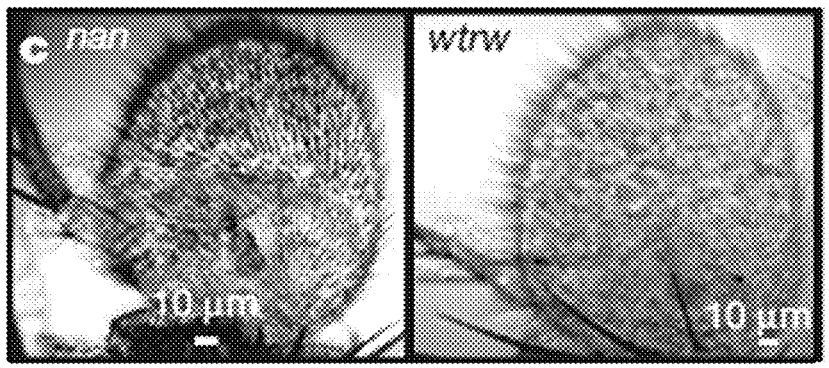
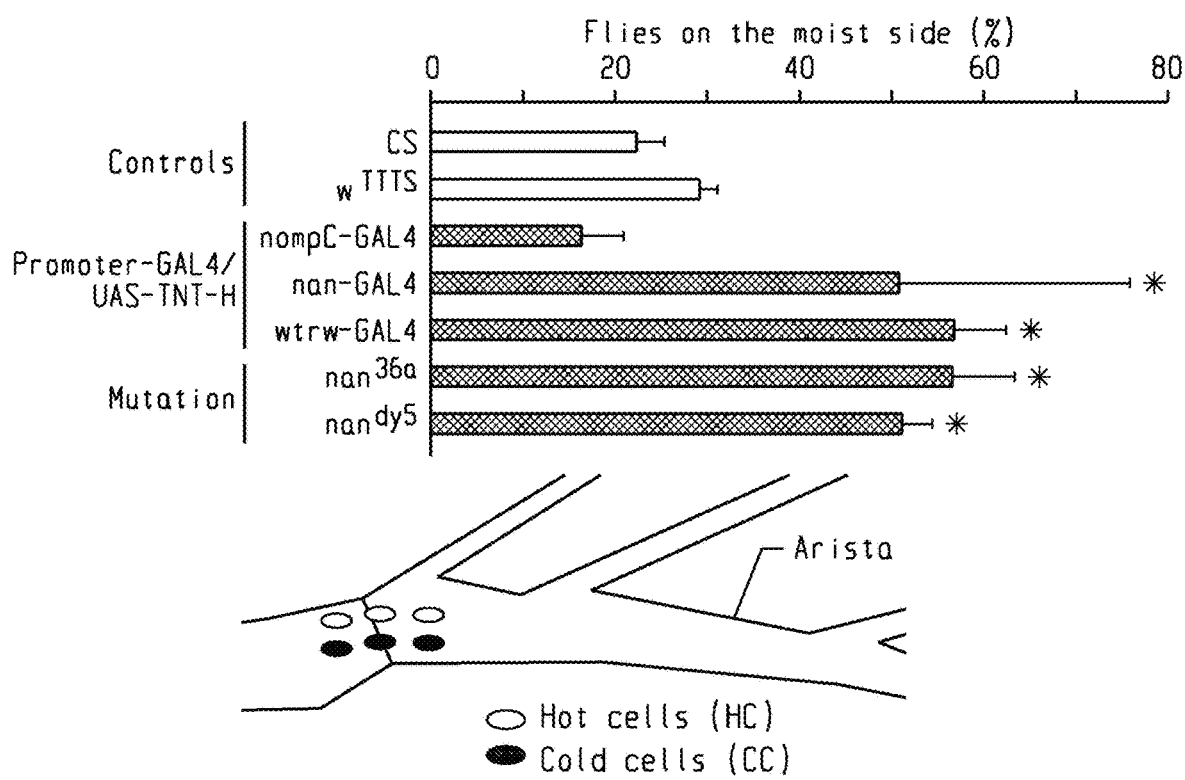
Fig. 13

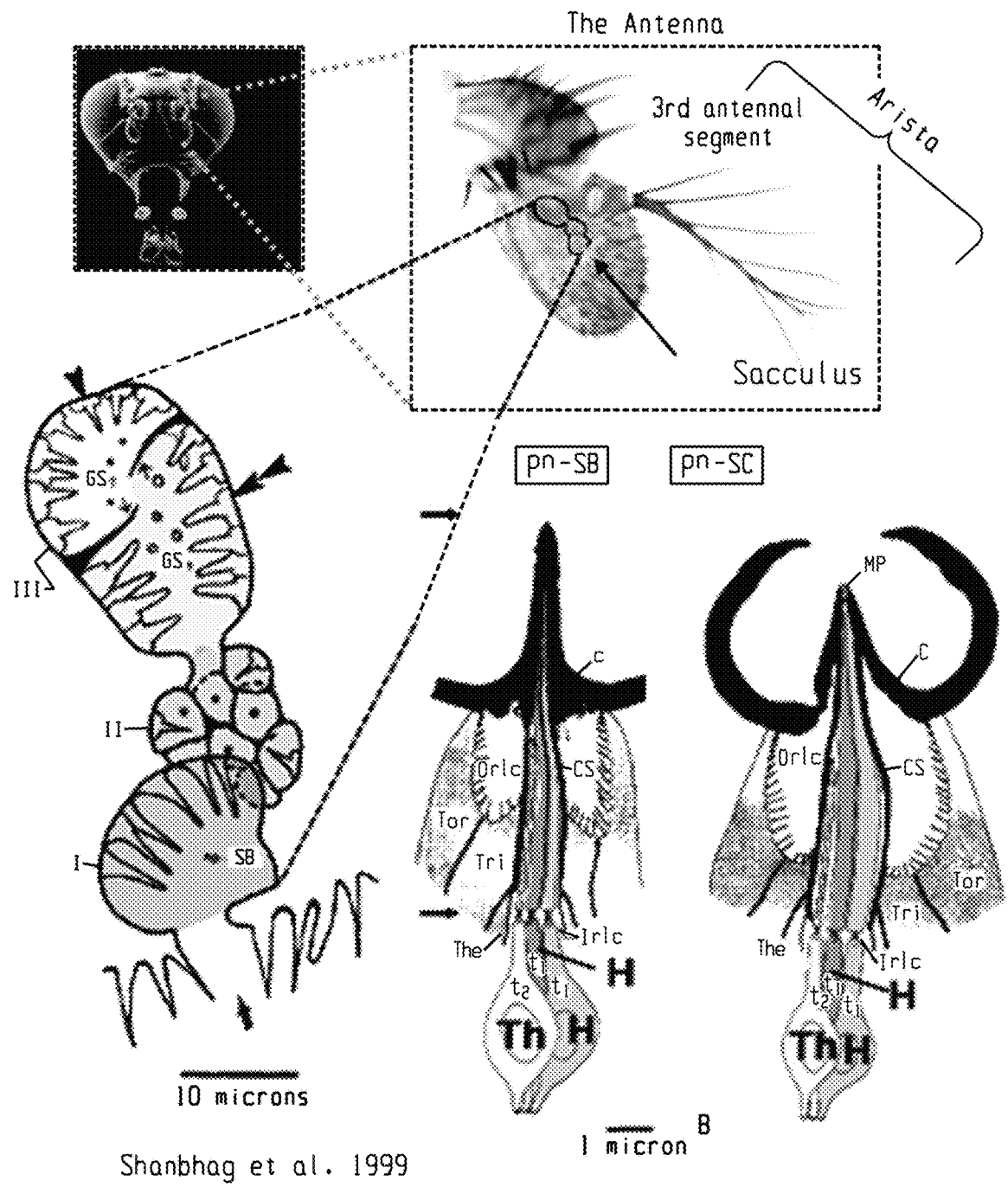
Shanbhag et al. 1999
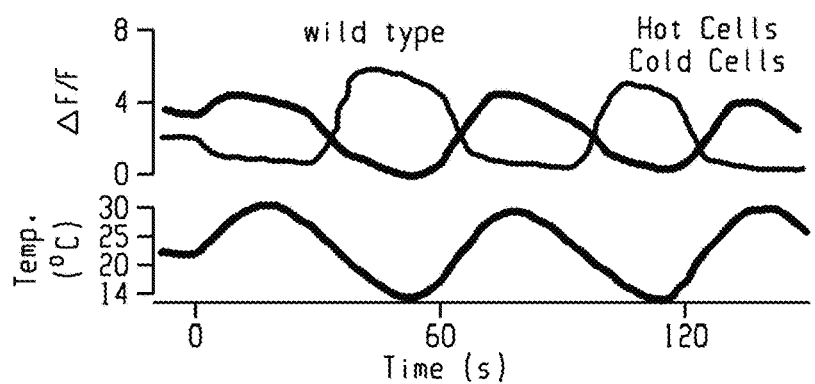
Fig. 13 (con't)

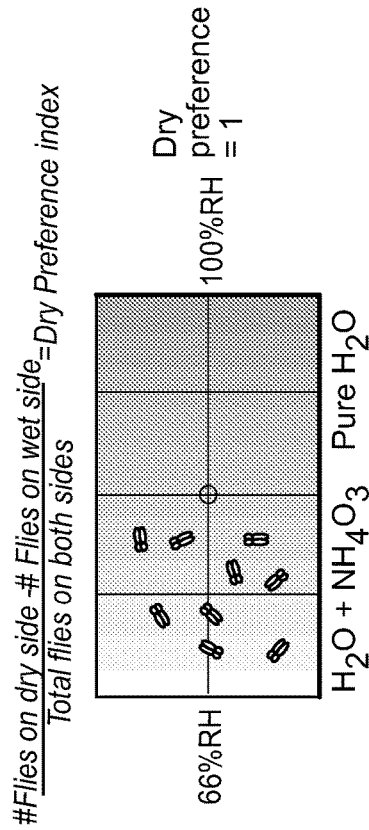
FIG. 17A
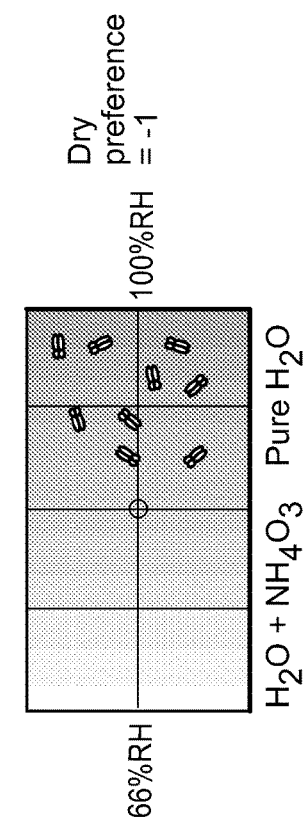
FIG. 17B
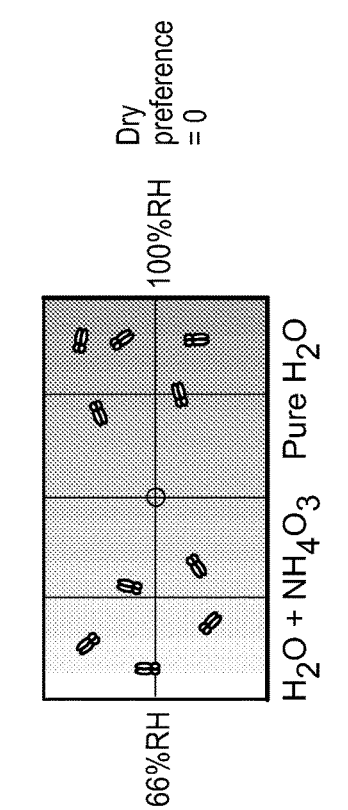
FIG. 17C
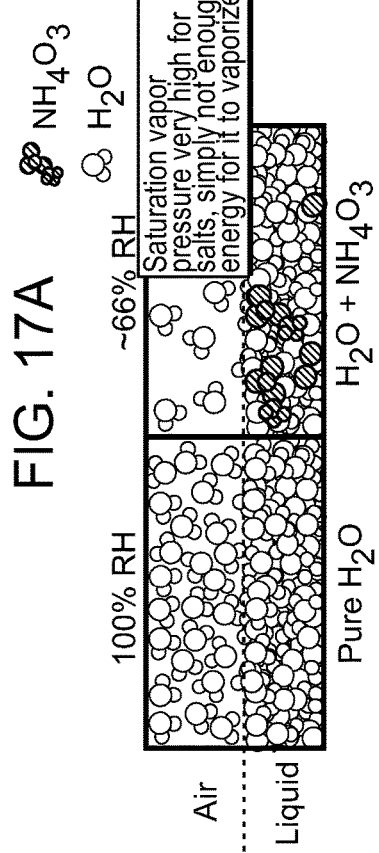
FIG. 17D
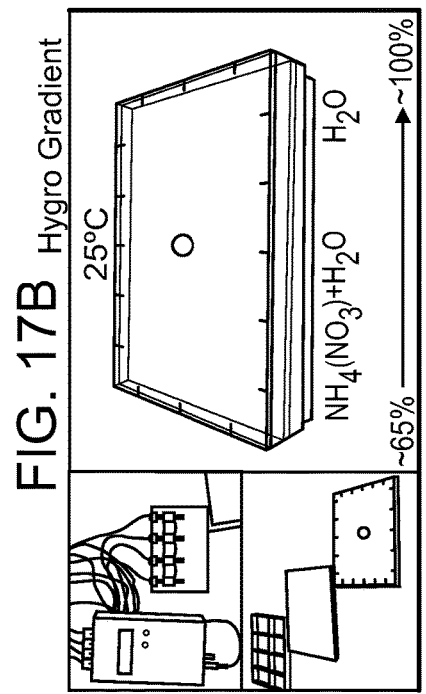
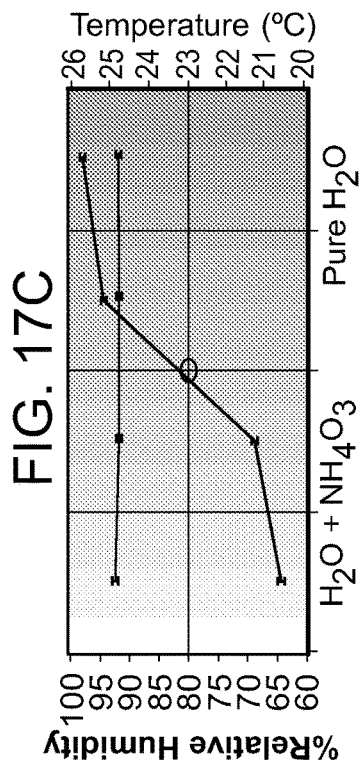

Fig. 19A

"Antennal IRs" — Croset et al. 2010

| Species | IR25a | IR93a | IR8a | IR68a | IR76b | IR21a | IR40a | other IR75 | IR75d | IR41a/IR76a | IR64a/IR84a | IR31a | IR60a | IR92a | Total IRs |
|---|---|---|---|---|---|---|---|---|---|---|---|---|---|---|---|
| Drosophila melanogaster | 1 | 1 | 1 | 1 | 1 | 1 | 1 | 3 | 1 | 2 | 2 | 1 | 1 | 1 | 66 |
| Aedes aegypti | 1 | 1 | 1 | 1 | 1 | 1 | 1 | 10 | 1 | 14,1p | 1 | 1 | 1 | 1 | 95 |
| Culex quinquefasciatus | 1 | 1 | 1 | 1 | 2 | 1 | 1 | 15 | 1 | 9,2p | 1 | 1 | 1 | 1 | 69 |
| Anopheles gambiae | 1 | 1 | 1 | 1 | 1 | 1 | 1 | 5 | 1 | 6 | 1 | 1 | 1 | | 46 |
| Bombyx mori | 1 | 1 | 1 | 1p | 1 | 1 | 1 | 2,1p | | 1 | 1 | | | | 18 |
| Tribolium castaneum | 1 | 1 | 1 | 1 | 1 | 1 | 1 | | | 1,1p | 1,2p | | | | 23 |
| Apis mellifera | 1 | 1 | 1 | 1 | 1 | 1 | | 4 | | 1 | | | | | 10 |
| Nasonia vitripennis | 2 | 1 | 1 | 1 | 1 | 1 | | 2 | 2 | | 1p | | | | 10 |
| Acyrthosiphon pisum | 1 | 1 | 1 | 1 | 1 | 1 | 1 | 1p | | 1 | | | | | 11 |
| Pediculus humanus humanus | 1 | 1 | 1 | 1 | 1 | 1 | 1 | 1 | | | | | | | 12 |
| Daphnia pulex | 1 | 1 | | | | | | | | | | | | | 85 |
| Caenorhabditis elegans | 1 | | | | | | | | | | | | | | 3 |
| Capitella capitata | 1 | | | | | | | | | | | | | | 41 |
| Aplysia californica | 1 | | | | | | | | | | | | | | 10 |
| Lottia gigantea | 2 | | | | | | | | | | | | | | 27 |

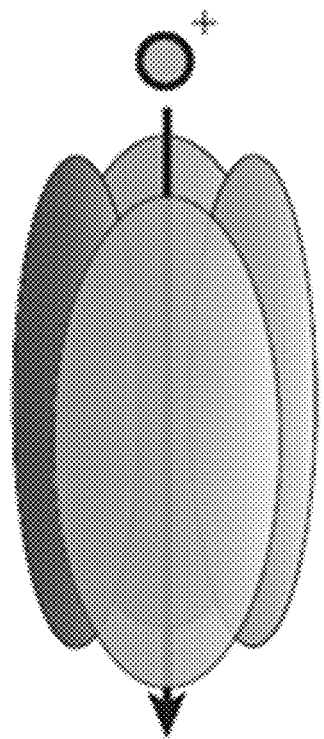 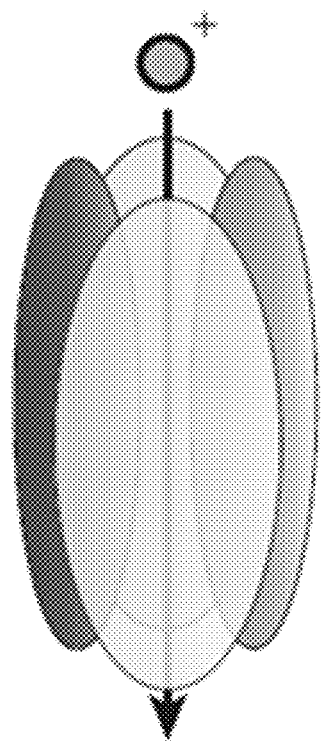
IR25a + IR76b + IR76a
phenylethylamine
IR25a + IR76b + IR41a
1,4-diaminobutane
Fig. 19B

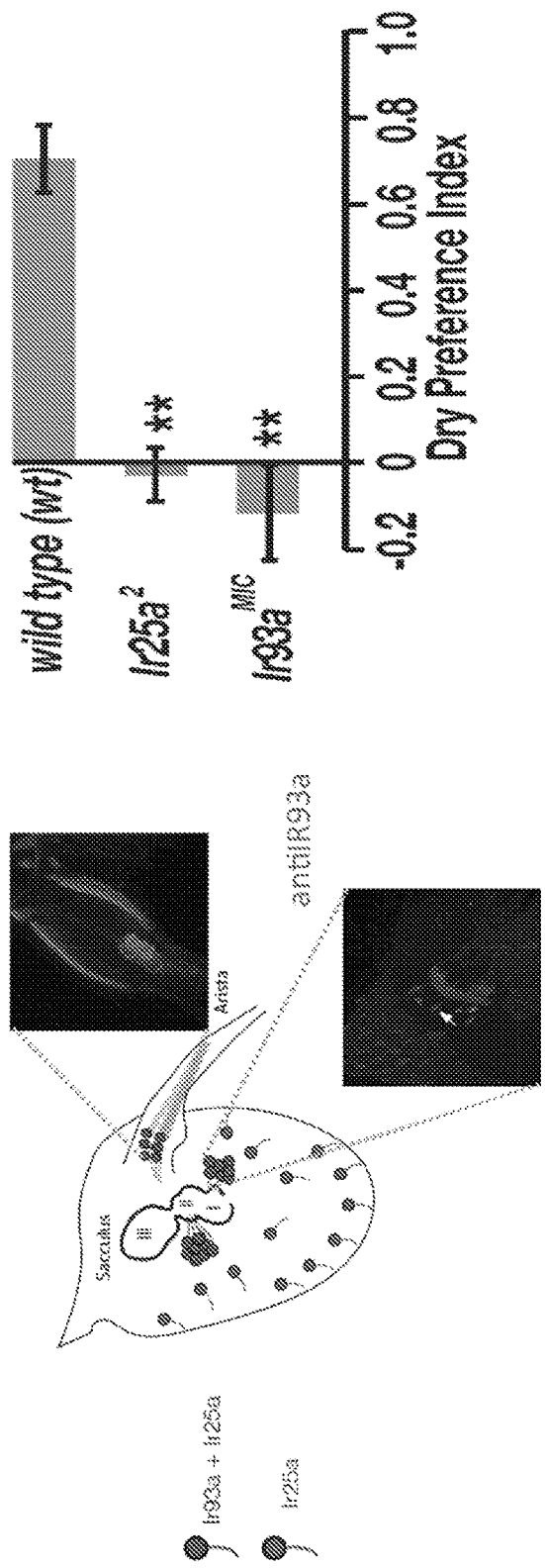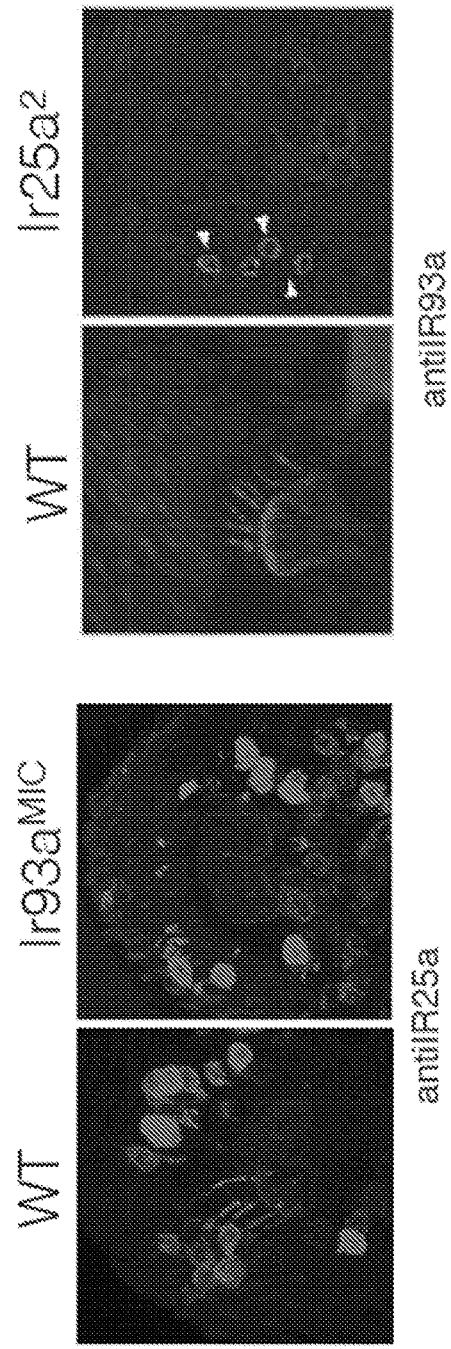
FIG. 20A
FIG. 20B
FIG. 20C

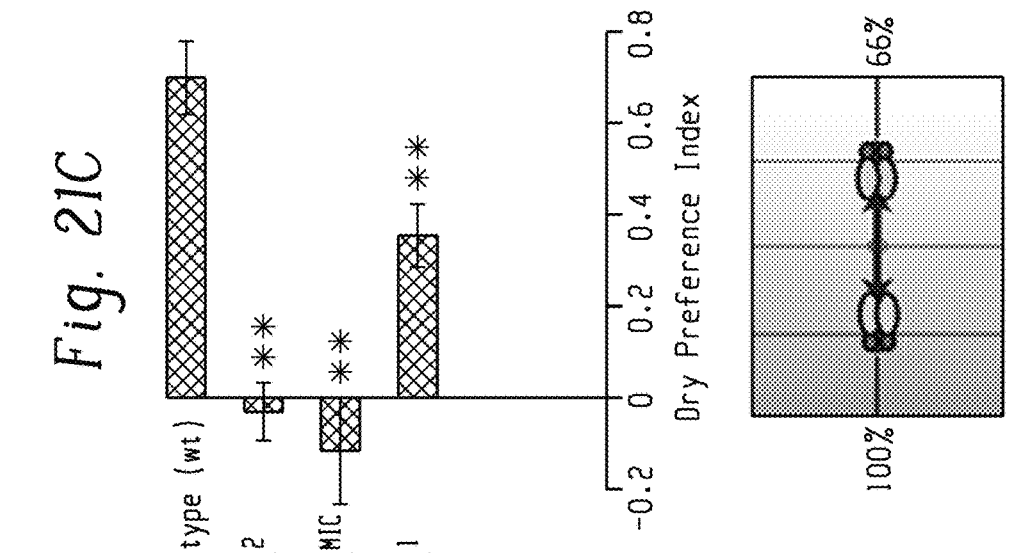
Fig. 21C
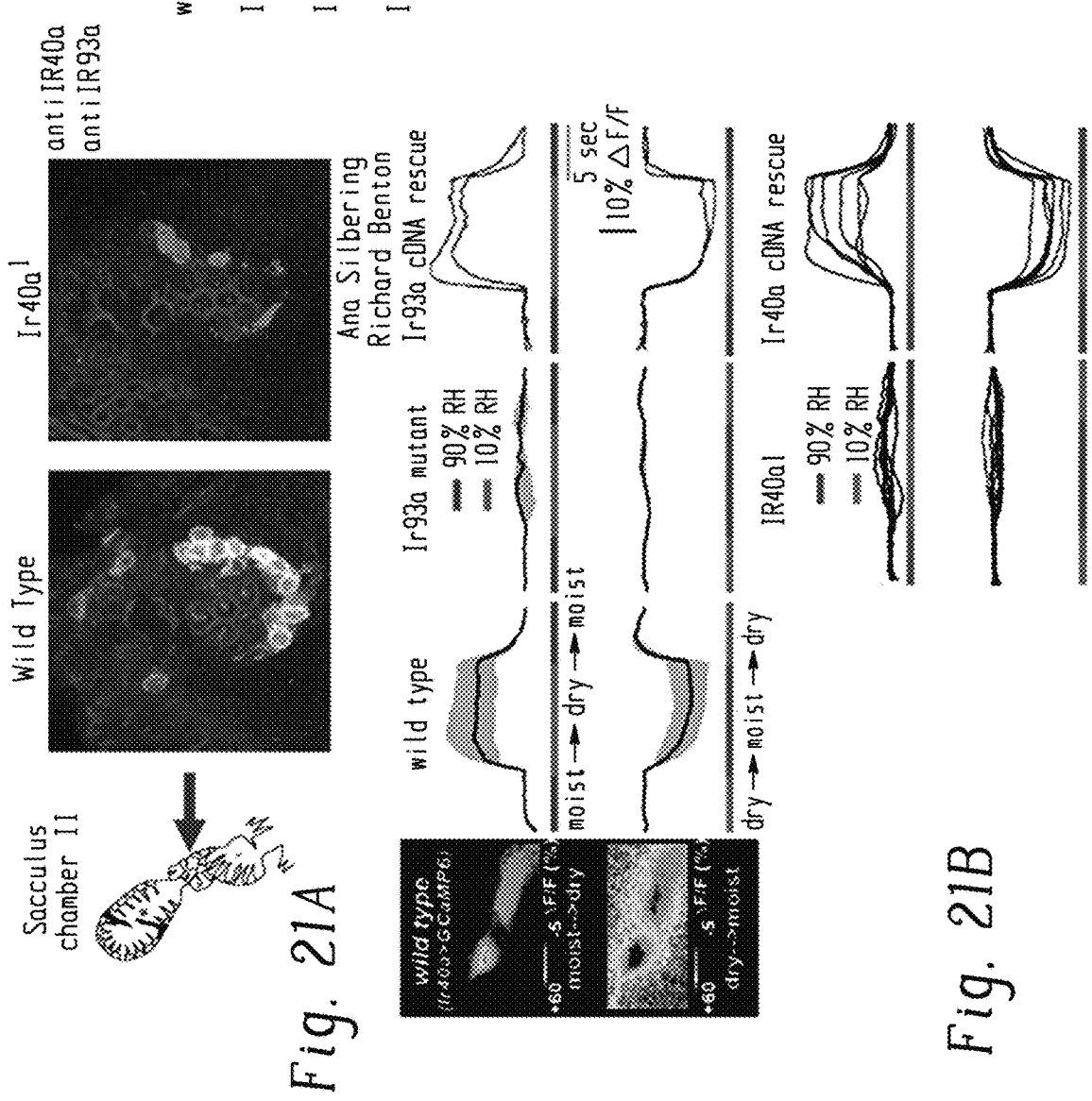
Fig. 21A
Fig. 21B

FIG. 30

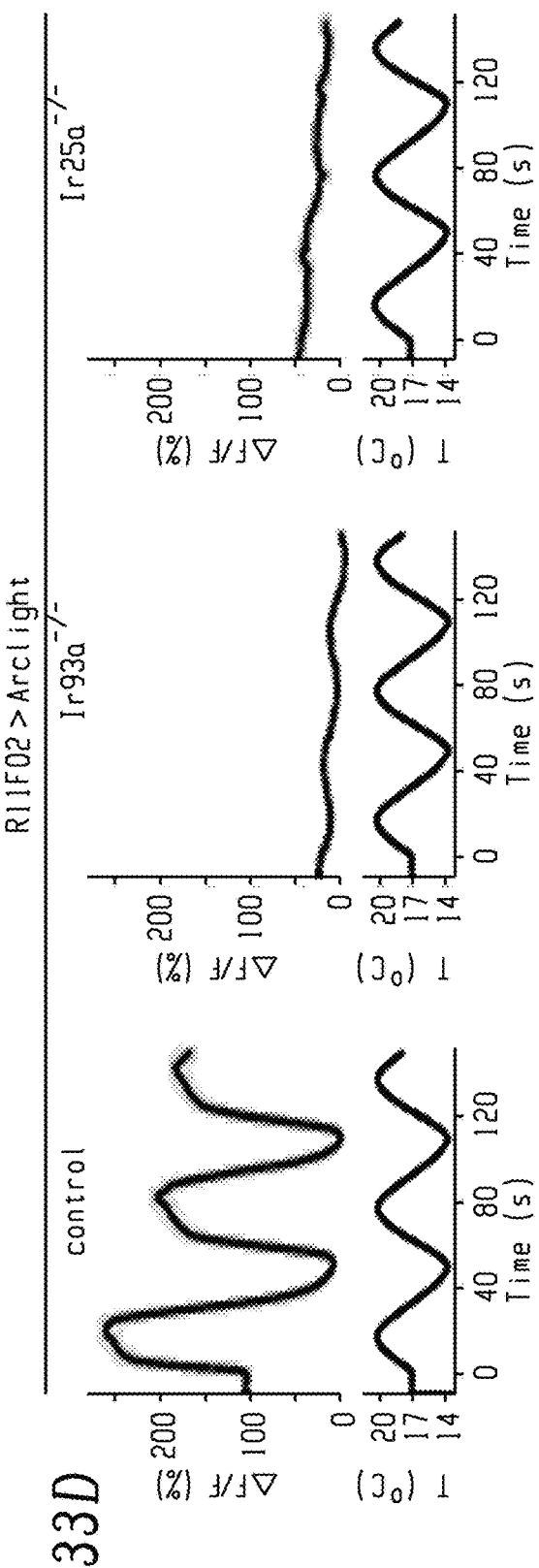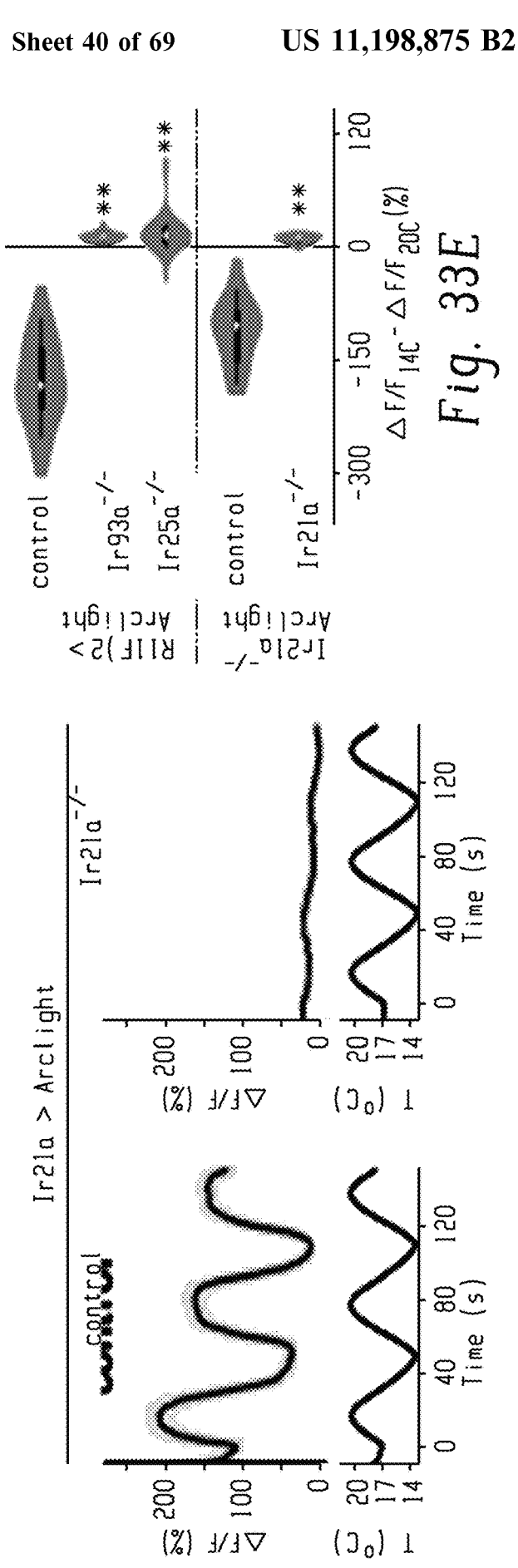
Fig. 33D
Fig. 33E

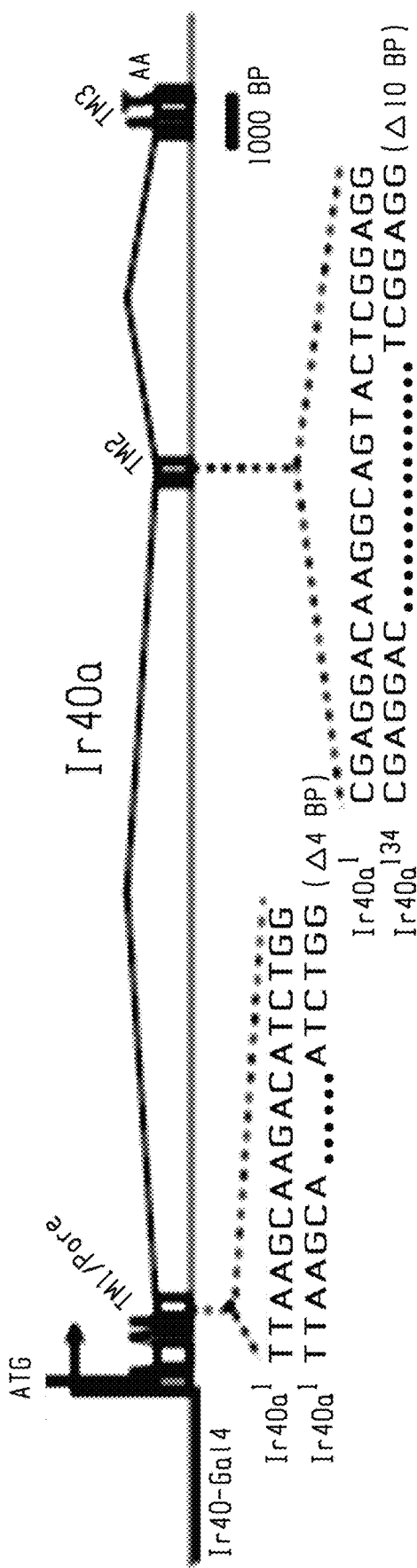
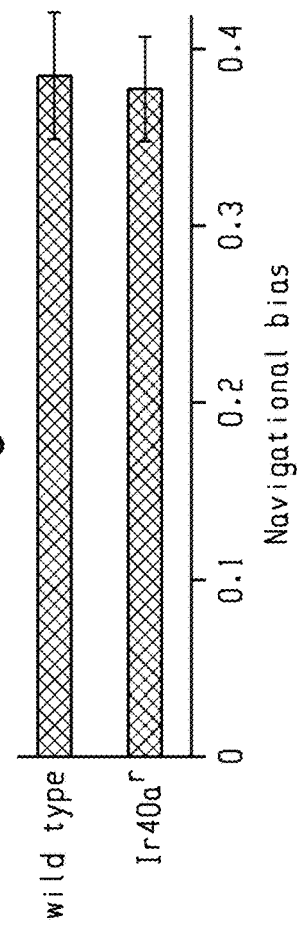
Fig. 36A
Fig. 36B

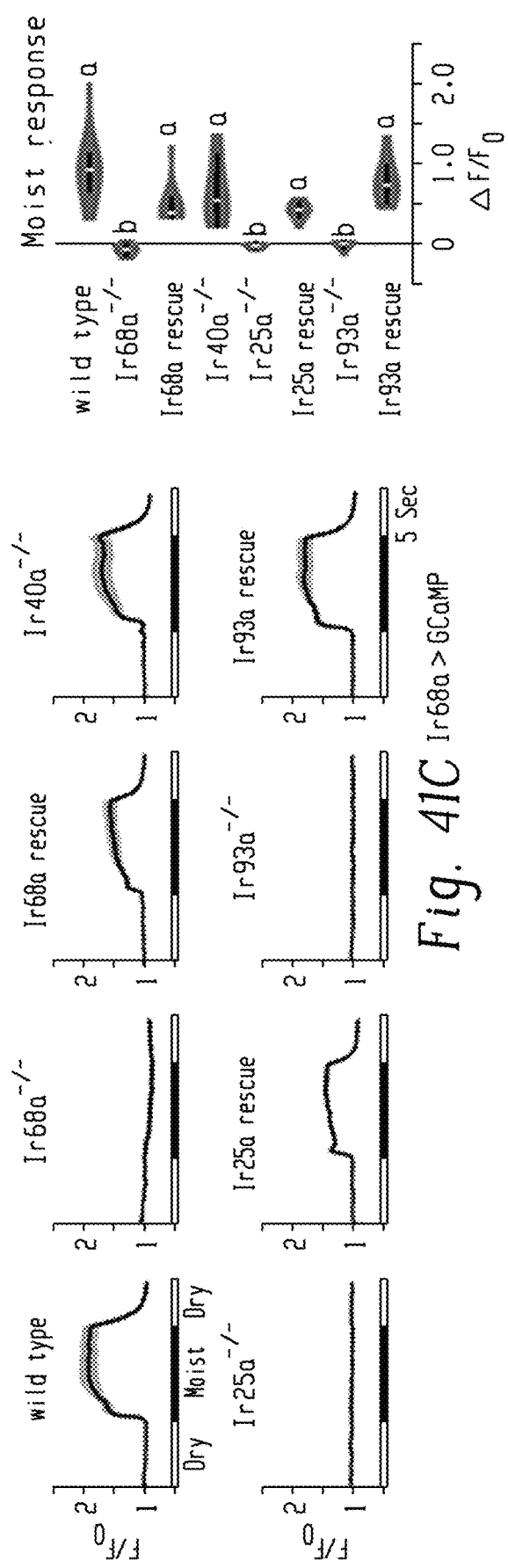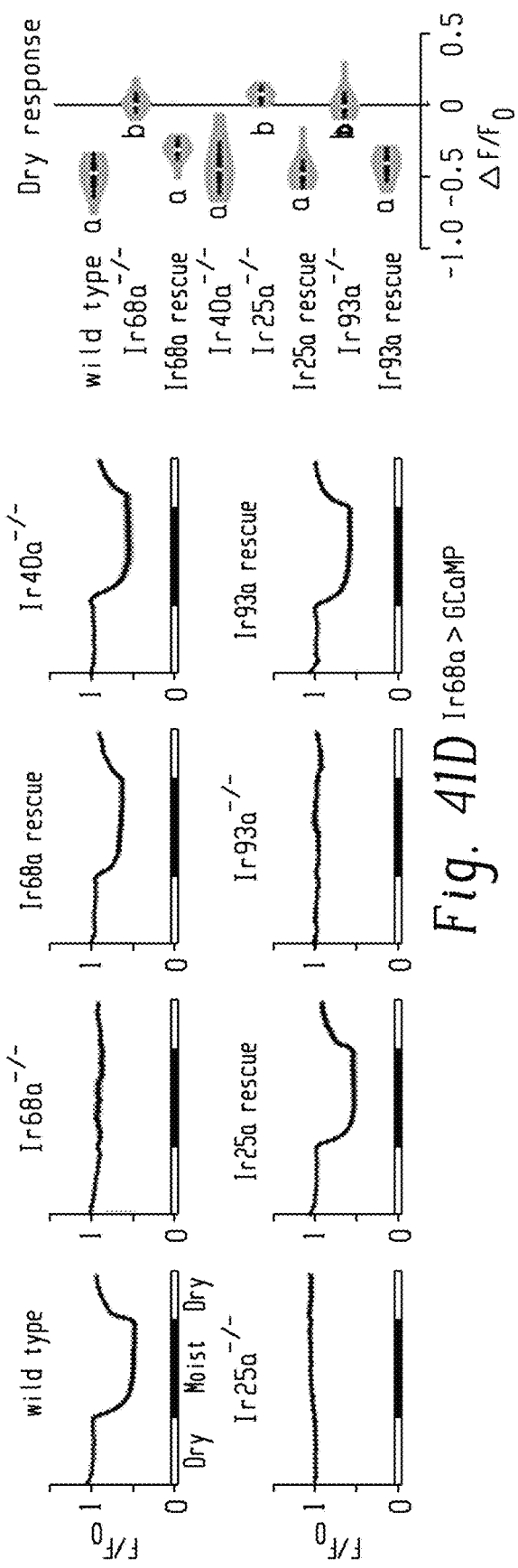
Fig. 41C Ir68a > GCaMP
Fig. 41D Ir68a > GCaMP

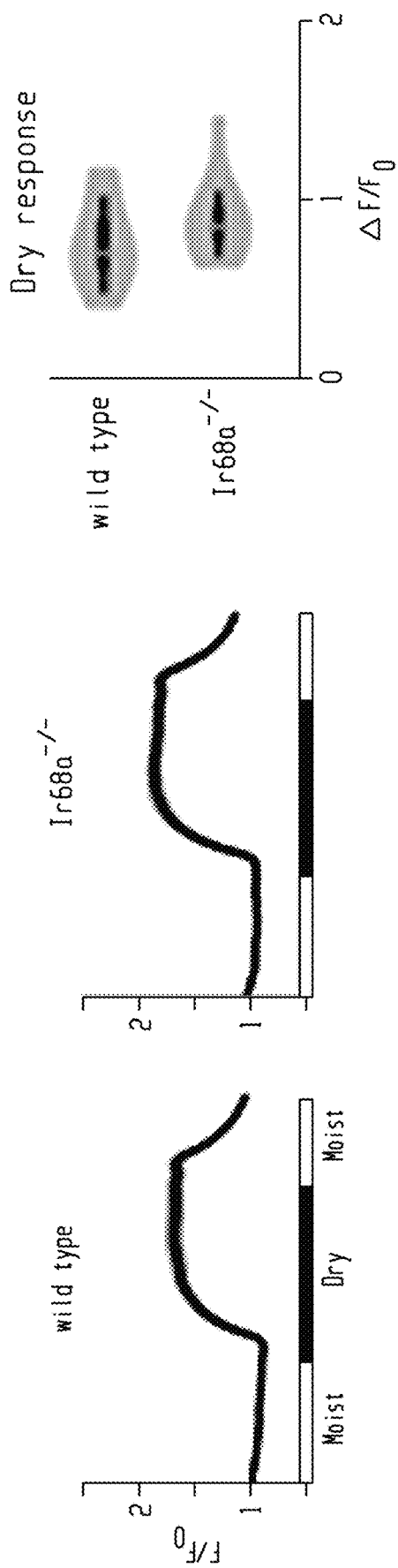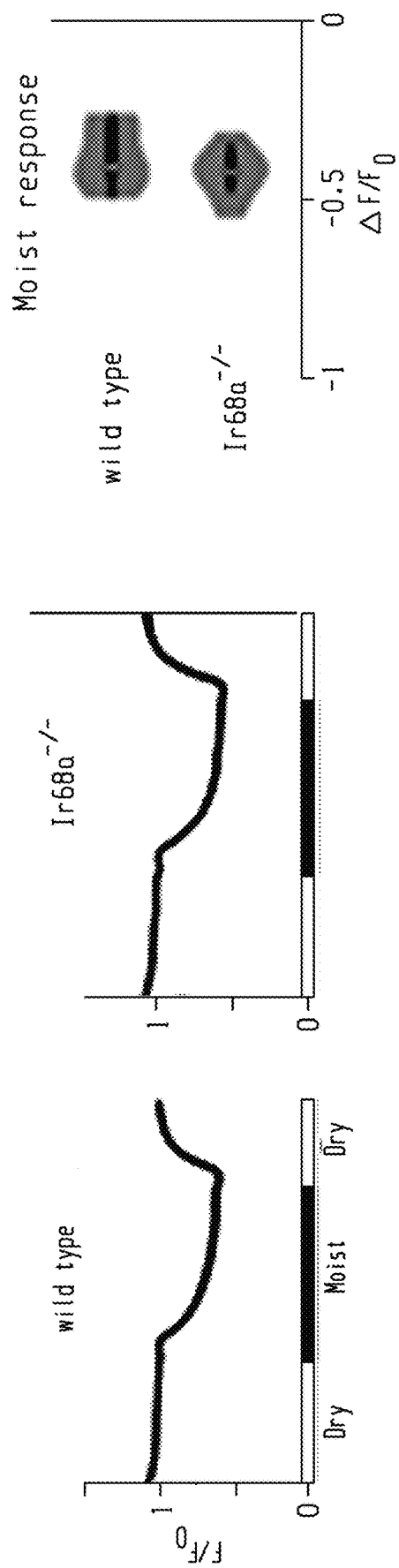
Fig. 41E Ir40a>GCaMP
Fig. 41F Ir40a>GCaMP

Fig. 44B

| | Ir92a | Ir76a | Ir84a | Ir87a | 100a | 68b/85a | |
|---|---|---|---|---|---|---|---|
| | ■ | ■ | ■ | 1 | 1,1p | 2 | Vinegar fly |
| | 1 | | | | | | Apple maggot (fly) |
| | ■ | | | 2 | 4,1p | | Yellow fever mosquito |
| | ■ | | | 1 | 2 | | Southern house mosquito |
| | | | | 1 | 3 | | Malaria mosquito |
| | | | | ■ | 0 | | Silkmoth |
| | | | | ■ | | | Tobacco hornworm (sphinx moth) |
| | | | | ■ | | | Cotton leafworm (moth) |
| | | | | ■ | 0 | | Monarch butterfly |
| | | | | ■ | | | Codling moth |
| | | | | | 2 | 7 | Red flour beetle |
| | | | | | | | Red harvester ant |
| | | | | | | | Argentine ant |
| | | | | | | | Parasitoid wasp |
| | | | | | | | Bee |
| | | | | | 0 | 2 | Pea aphid |
| | | | | | | | Body louse |
| | | | | | 0 | 3 | Termite |
| | | | | | | | Water flea |
| | | | | | | | Deer tick |
| | | | | | | | Nematode |
| | | | | | | | Polychaete worm |
| | | | | | | | Sea hare (sea slug) |
| | | | | | | | Owl limpet (mollusc/sea snail) |

MATCH TO FIG. 44B

*Fig. 44C*

Modified from Rytz and Benton, 2013

Molecular phylogeny of IR family members

FIG. 46

Amino acid identity

| | DmelIR25a | AaegIR25a | AgamIR25a |
|---|---|---|---|
| DmelIR25a | 100% | | |
| AaegIR25a | 71.33% | 100% | |
| AgamIR25a | 69.34% | 81.61% | 100% |
| CquiIR25a | 70.53% | 81.41% | 75.91% |

Amino acid similarity

| | DmelIR25a | AaegIR25a | AgamIR25a |
|---|---|---|---|
| DmelIR25a | 100% | | |
| AaegIR25a | 77% | 100% | |
| AgamIR25a | 77.92% | 83.36% | 100% |
| CquiIR25a | 65.91% | 75.66% | 68.89% |

Amino acid identity

| | DmelIR40a | AaegIR40a | AgamIR40a |
|---|---|---|---|
| DmelIR40a | 100% | | |
| AaegIR40a | 42.21% | 100% | |
| AgamIR40a | 41.39% | 62.77% | 100% |
| CquiIR40a | 41.39% | 74.05% | 63.91% |

Amino acid similarity

| | DmelIR40a | AaegIR40a | AgamIR40a |
|---|---|---|---|
| DmelIR40a | 100% | | |
| AaegIR40a | 48.54% | 100% | |
| AgamIR40a | 51.45% | 67.59% | 100% |
| CquiIR40a | 56.21% | 74.44% | 70.38% |

Amino acid identity

| | DmelIR68a | AaegIR68a | AgamIR68a |
|---|---|---|---|
| DmelIR68a | 100% | | |
| AaegIR68a | 41.95% | 100% | |
| AgamIR68a | 33.79% | 58.81% | 100% |
| CquiIR68a | 36.78% | 76.43% | 57.25% |

Amino acid similarity

| | DmelIR68a | AaegIR68a | AgamIR68a |
|---|---|---|---|
| DmelIR68a | 100% | | |
| AaegIR68a | 43.17% | 100% | |
| AgamIR68a | 43.91% | 58.67% | 100% |
| CquiIR68a | 46.24% | 60.39% | 58.05% |

Amino acid identity

| | DmelIR93a | AaegIR93a | AgamIR93a |
|---|---|---|---|
| DmelIR93a | 100% | | |
| AaegIR93a | 38.55% | 100% | |
| AgamIR93a | 36.43% | 58.07% | 100% |
| CquiIR93a | 36.54% | 74.21% | 57.73% |

Amino acid similarity

| | DmelIR93a | AaegIR93a | AgamIR93a |
|---|---|---|---|
| DmelIR93a | 100% | | |
| AaegIR93a | 53.13% | 100% | |
| AgamIR93a | 46.41% | 66.14% | 100% |
| CquiIR93a | 49.55% | 80.49% | 67.15% |

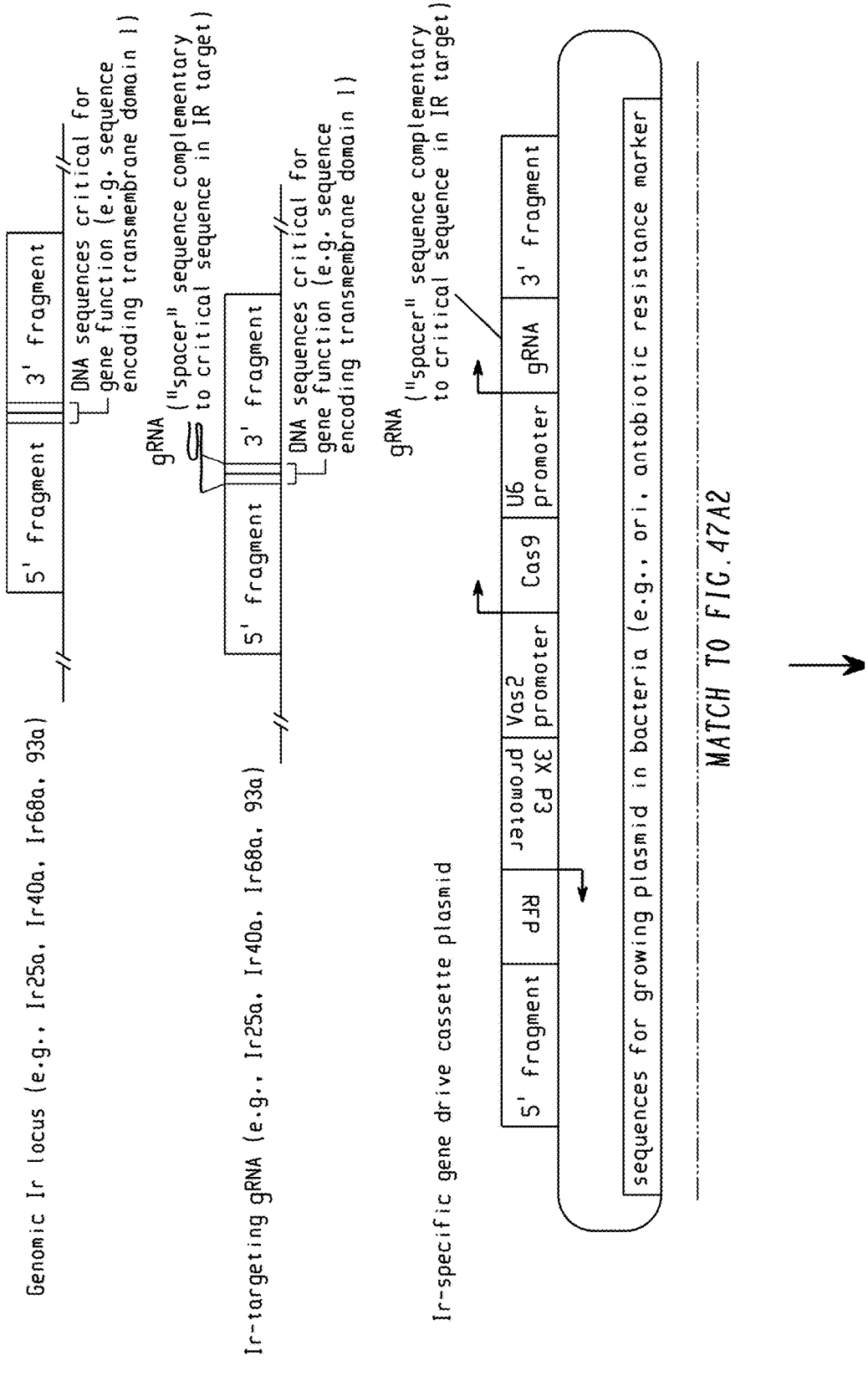
Fig. 47A1

MATCH TO FIG. 47A1

There are multiple possible approaches for integrating gene drive cassette using either homologous recombination or homology-independent transgene integration (HITI) which both result in the same modified locus. (Note that for HITI the gene drive cassette does not contain 5' fragment and 3' fragment flanking homology regions, but rather target sites for a second gRNA (which has no target site in the insect genome which is expressed from the gene drive cassette plasmid.

Shown here is a homologous recombination strategy using co-injection of:
+ recombinant Cas9 protein
+ IR-specific gRNA (either RNA or as DNA of plasmid that expresses gRNA)
+ targeting donor plasmid

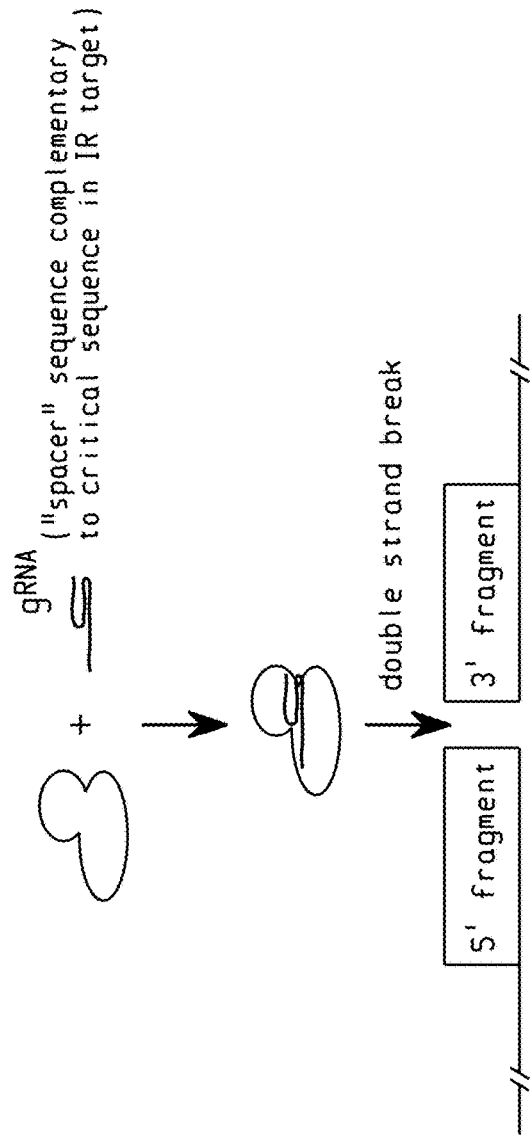

Fig. 47A2

MATCH TO FIG. 47A3

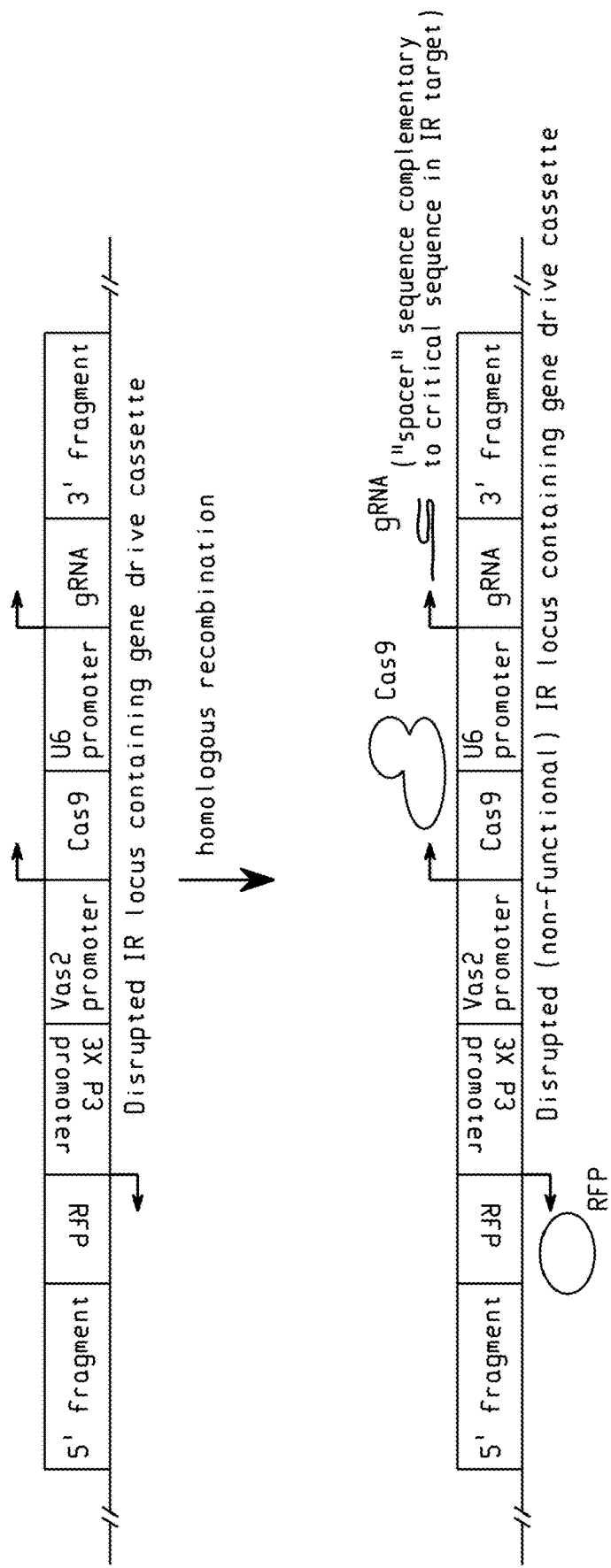
Fig. 47A3

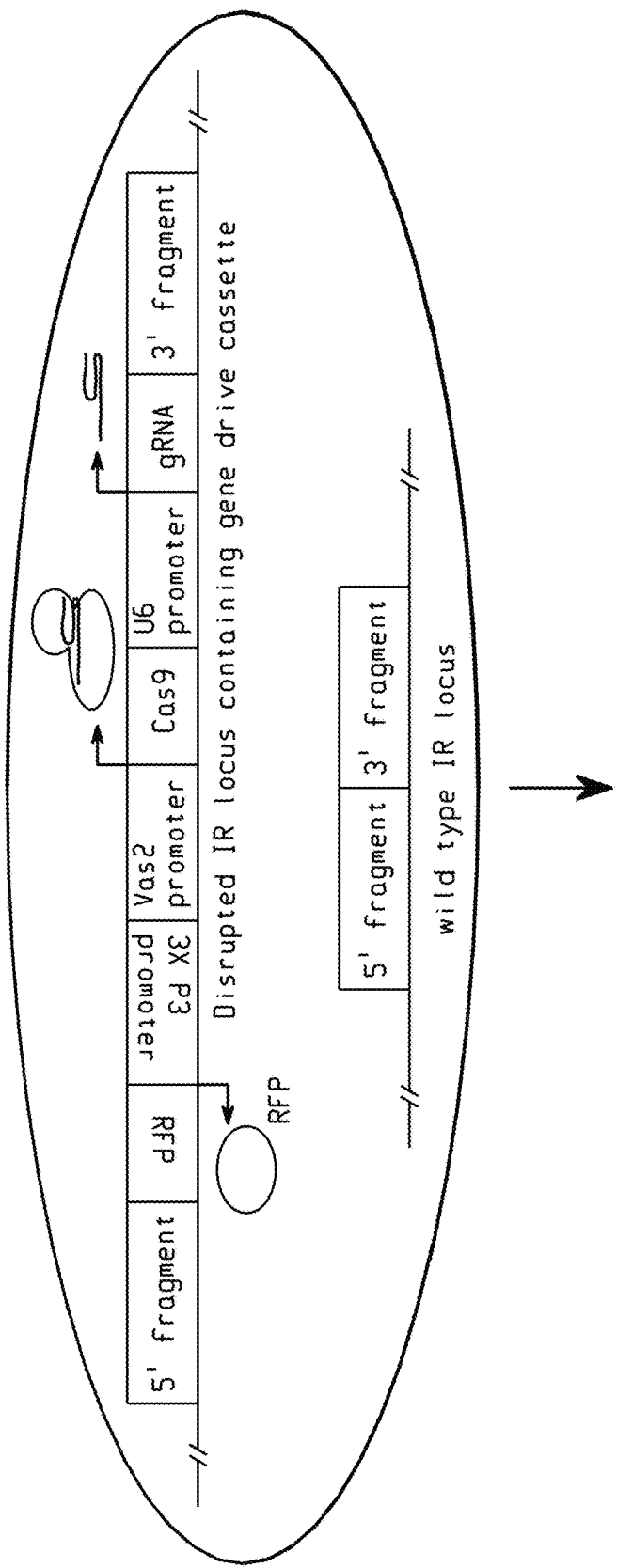
Fig. 47B1
Step 2: Allow "gene drive" locus to spread, inactivating IR loci population-wide.
Mate mosquitoes containing "gene drive" cassette to wild type mosquitoes, creating heterozygous adults. In the germ line of heterozygotes, the gene drive cassette will convert the wild type locus to a "gene drive" containing locus as shown below:

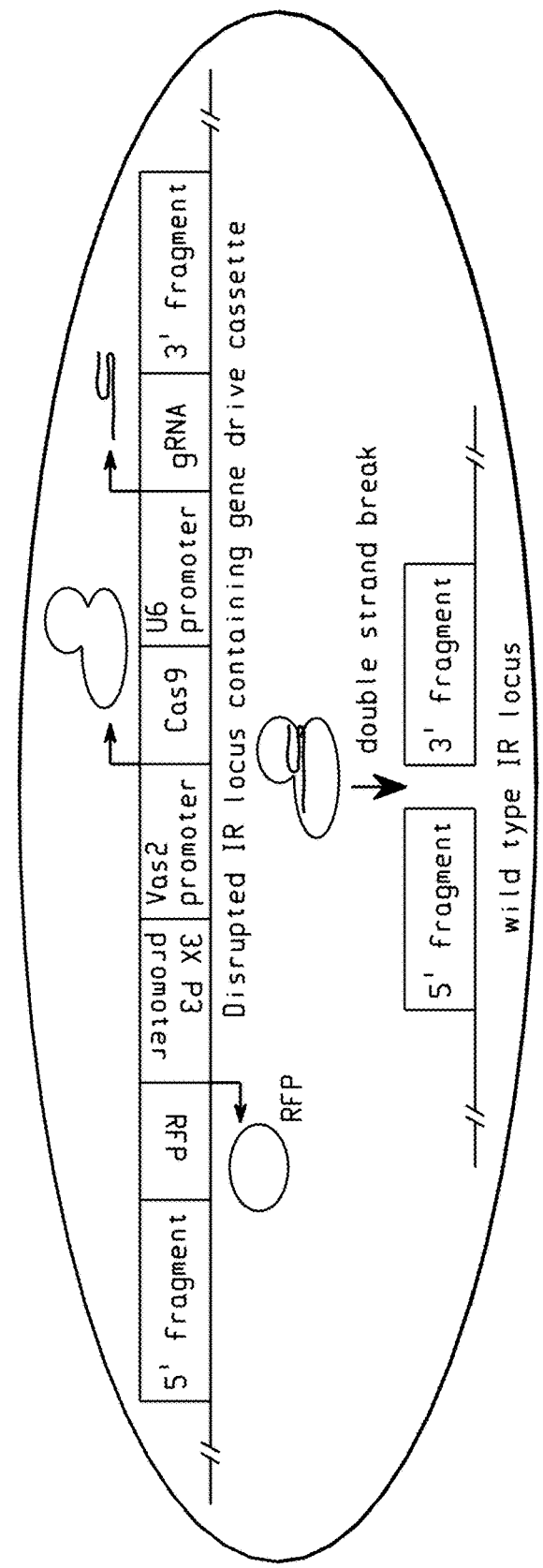
Fig. 47B2

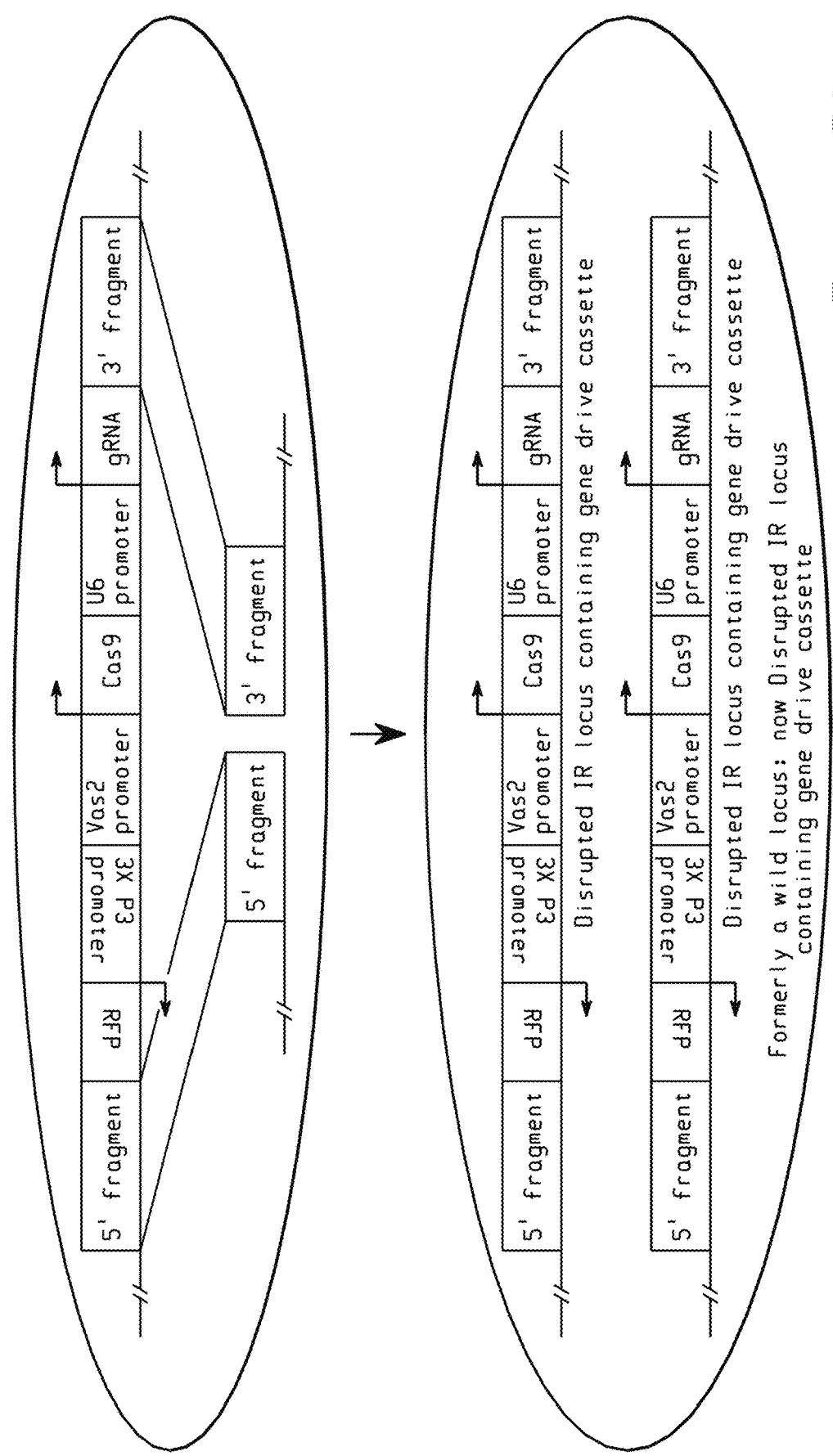
Fig. 47B3

METHODS FOR MODULATING INSECT HYGRO- AND/OR THERMOSENSATION

CROSS-REFERENCE TO RELATED APPLICATIONS

This application is the U.S. national phase application, pursuant to 35 U.S.C. § 371, of PCT International Application Ser. No.: PCT/US2017/031781, filed May 9, 2017, designating the United States and published in English, which claims priority to and benefit of provisional patent application No. 62/333,655, filed on May 9, 2016, the entire contents of which are hereby incorporated by reference in their entirety.

STATEMENT OF RIGHTS TO INVENTIONS MADE UNDER FEDERALLY SPONSORED RESEARCH

This invention was made with government support under Grant Nos. NIDCD: F31DC015155, NIAID: R01AI122802-01A1, and NIGMS: P01GM103770 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Sep. 30, 2020, is named BDV0006US2 Revised Sequence List_ST25.txt and is 381,952 bytes in size.

BACKGROUND OF THE INVENTION

Water is critical to the survival of all life on earth, and maintaining water balance is a key component of homeostasis. Humidity influences the tendency of water to evaporate, and acts as a cue for locating water sources, making awareness of humidity a critical component of survival. Insects are excellent morel organisms to study hygrosensation because their large surface area to volume ratio makes them especially vulnerable to changes in body water content. Insects therefore evolved a sensory system that allows them to respond to changes in environmental moisture levels. While desiccation is a threat to all animals, insects are particularly vulnerable to dehydration because of their small size, making water balance a key factor affecting the survival and distribution of insect vectors of disease. In addition, moisture is an important cue in host-seeking and oviposition site selection in mosquitoes, whose larval stages live in aquatic environments. Despite the importance of moisture sensing, the genetic, molecular, and mechanistic underpinnings of insect humidity remain largely unknown.

Insect vectors such as mosquitoes transmit human diseases including malaria, West Nile virus, chikungunya, yellow and dengue fever. Worldwide, malaria alone is estimated to have a direct cost of roughly $12 billion. About half the world's population lives within range of malaria, and in 2012 there were >200 million cases and >600,000 deaths from malaria. As insects serve as vectors for many human diseases, methods of controlling insect populations, particularly by disrupting insect survival, host-seeking, and/or reproductive capabilities, are urgently needed.

SUMMARY OF THE INVENTION

As described below, the present invention features methods of modulating hygrosensing and/or thermosensing in an animal, particularly in an invertebrate or an insect.

In one aspect, the invention provides a method of modulating hygrosensing and/or thermosensing in an animal, the method involving administering to the animal an effective amount of an agent that modulates the activity and/or expression of a polynucleotide or polypeptide of an ionotropic receptor (abbreviated Ir or IR herein) that is any one or more of Ir25a, Ir93a, Ir40a, Ir68a, and Ir21a.

In another aspect, the invention provides a method of reducing survival, host-seeking, and/or reproductive capability of an animal, the method involving administering to the animal an effective amount of an agent that modulates the activity and/or expression of a polynucleotide or polypeptide of an ionotropic receptor (Ir or IR herein) that is any one or more of Ir25a, Ir93a, Ir40a, Ir68a, and Ir21a.

In another aspect, the invention provides a method of identifying an agent that modulates hygrosensing and/or thermosensing in an animal, the method involving measuring activity (e.g., hygrosensing or thermosensing) of an ionotropic receptor that is any one or more of Ir25a, Ir93a, Ir40a, Ir68a, and Ir21a in an animal contacted with a candidate agent, wherein an alteration in the activity relative to a reference indicates the candidate agent modulates hygrosensing and/or thermosensing in the animal.

In another aspect, the invention provides a method of identifying an agent that modulates survival, host-seeking, and/or reproductive capability of an animal, the method involving measuring activity of an ionotropic receptor selected from the group consisting of Ir25a, Ir93a, Ir40a, Ir68a, and Ir21a in an animal contacted with a candidate agent, wherein an alteration in the activity relative to a reference indicates the candidate agent modulates survival, host-seeking, and/or reproductive capability of the animal.

In various embodiments of any of the above aspects, the animal is an invertebrate, a disease vector, or a mosquito. In one embodiment, the animal is *Drosophila melanogaster, Aedes aegypti, Culex quinquefasciatus, Anopheles gambiae, Bombyx mori, Tribolium castaneum, Apis mellifera, Nasonia vitripennis, Acyrthosiphon pisum, Pediculus humanus humanus* (lice), *Daphnia pulex, Caenorhabditis elegans, Capitella capitate, Aplysia californica*, or *Lottia gigantea* ionotropic receptor. In an embodiment, the animal is a disease-carrying insect. In an embodiment, the insect is a mosquito. In a particular embodiment, the mosquito is *Anopheles gambiae*. In another embodiment, the agent is a small molecule compound, polypeptide, or polynucleotide. In another embodiment, the agent is an inhibitory polynucleotide that reduces expression of the ionotropic receptor. In another embodiment, the agent is an inhibitory polynucleotide that increases expression of the ionotropic receptor. In another embodiment, the activity is hygrosensing or thermosensing. In one embodiment, the alteration in activity is a decrease in activity or expression. In one embodiment, the alteration in activity is an increase in activity or expression. In another embodiment, the agent decreases survival, host-seeking, and/or reproductive capability of the animal. In an embodiment, the ionotropic receptor is one or more of Ir25a, Ir93a, Ir40a, Ir68a, or Ir21a. In an embodiment, the ionotropic receptor is Ir25a. In an embodiment, the ionotropic receptor is Ir93a. In an embodiment, the ionotropic receptor is Ir40a. In an embodiment, the ionotropic receptor is Ir68a. In an embodiment, the ionotropic receptor is Ir21a. In another embodiment, the ionotropic receptor is Ir25a or Ir93a.

In an embodiment of the above methods, the ionotropic receptor is one or more of Ir68a or Ir40a. In an embodiment of the above methods, the ionotropic receptor is one or more of Ir25a, Ir93a, or Ir40a. In an embodiment of the above methods, the ionotropic receptor is one or more of Ir25a, Ir93a, or Ir68a. In an embodiment of the above methods, the ionotropic receptor is Ir68a so as to modulate moisture sensing in the animal, e.g., insect. In an embodiment of the above methods, the ionotropic receptor is Ir21a so as to modulate thermosensing in the animal, e.g., insect. In an embodiment of the above methods, the agent is a polynucleotide that overexpresses the ionotropic receptor polypeptide.

In various embodiments of the above aspects, the ionotropic receptor is one or more of Ir21a, Ir25a, Ir40a, Ir68a, or Ir93a. In various embodiments of the above aspects, the ionotropic receptor is one or more of Ir25a or Ir93a. In various embodiments of the above aspects, the ionotropic receptor is one or more of IR68a or Ir40a. In various embodiments of the above aspects, the ionotropic receptor is one or more of Ir25a, Ir93a, or Ir40a. In various embodiments of the above aspects, the ionotropic receptor is one or more of Ir25a, Ir93a, or Ir68a. In an embodiment of the above aspects, the ionotropic receptor is Ir68a so as to modulate moisture sensing in the animal. In an embodiment of the above aspects, the ionotropic receptor is Ir21a so as to modulate thermos-sensing in the animal.

In an aspect, the invention provides an expression vector for homology-dependent transgene insertion, in which the expression vector comprises: (a) two target nucleic acid sequences comprising 100 to 1000 bp 5' and 3' of an ionotropic receptor open reading frame selected from the group consisting of Ir25a, Ir93a, Ir40a, Ir68a, and Ir21a; (b) a nucleic acid sequence encoding a site-specific endonuclease or nickase; and (c) a nucleic acid sequence encoding two guide RNAs complementary to the target nucleic acid sequences. In an embodiment, the site-specific endonuclease or nickase is a Cas9 polypeptide or Cpf1 polypeptide. In an embodiment, expression of Cas9 is driven by a Vasa2 promoter. In an embodiment, expression of the guide RNA is driven by a U6 promoter.

In an aspect, the invention provides, an expression vector for homology independent transgene insertion, in which the expression vector comprises: (a) guide RNA binding sites flanking 5' and 3' an ionotropic receptor open reading frame selected from the group consisting of Ir25a, Ir93a, Ir40a, Ir68a, and Ir21a; (b) a nucleic acid sequence encoding a site-specific endonuclease or nickase; and (c) a nucleic acid sequence encoding two guide RNAs complementary to the target nucleic acid sequences. In an embodiment, the site-specific endonuclease or nickase is a Cas9 polypeptide or Cpf1 polypeptide. In an embodiment, expression of Cas9 is driven by a Vasa2 promoter. In an embodiment, expression of the guide RNA is driven by a U6 promoter.

In embodiments of the above aspects, the expression vector further comprises a nucleic acid sequence encoding an altered ionotropic receptor polypeptide selected from the group consisting of Ir25a, Ir93a, Ir40a, Ir68a, and Ir21a polypeptide. In an embodiment of the above aspects, the nucleic acid sequence encoding the altered ionotropic receptor polypeptide comprises a deletion, frame-shift, or point mutation.

In an aspect, the invention provides an invertebrate organism comprising the expression vector of any of the above aspects and embodiments. In another aspect, the invention provides an insect comprising the expression vector of any of the above aspects and embodiments. In embodiment, the insect is *Drosophila melanogaster, Aedes aegypti, Culex quinquefasciatus, Anopheles gambiae, Bombyx mori, Tribolium castaneum, Apis mellifera, Nasonia vitripennis, Acyrthosiphon pisum, Pediculus humanus humanus, Daphnia pulex, Caenorhabditis elegans, Capitella capitate, Aplysia californica*, or *Lottia gigantean*. In a particular embodiment, the insect is *Anopheles gambiae* or *Aedes aegypti*.

In an aspect, the invention provides a disease vector comprising the expression vector of any of the above aspects.

In an aspect, the invention provides a method for disrupting the expression or activity of an ionotropic receptor polypeptide in a wild-type population of invertebrate organisms, wherein the ionotropic receptor polypeptide is selected from the group consisting of Ir25a, Ir93a, Ir40a, Ir68a, and Ir21a, the method comprising introducing into a wild-type genome an expression vector for homology-dependent transgene insertion, the expression vector comprising the following: (a) two target nucleic acid sequences comprising 100 to 1000 bp 5' and 3' of an ionotropic receptor open reading frame selected from the group consisting of Ir25a, Ir93a, Ir40a, Ir68a, and Ir21a; (b) a nucleic acid sequence encoding a site-specific endonuclease or nickase; and (c) a nucleic acid sequence encoding two guide RNAs complementary to the target nucleic acid sequences.

In an aspect, the invention provides a method for disrupting the expression or activity of an ionotropic receptor polypeptide in a wild-type population of invertebrate organisms, wherein the ionotropic receptor polypeptide is selected from the group consisting of Ir25a, Ir93a, Ir40a, Ir68a, and Ir21a, the method comprising introducing into a wild-type genome an expression vector for homology independent transgene insertion, the expression vector comprising the following: (a) guide RNA binding sites flanking 5' and 3' an ionotropic receptor open reading frame selected from the group consisting of Ir25a, Ir93a, Ir40a, Ir68a, and Ir21a; (b) a nucleic acid sequence encoding a site-specific endonuclease or nickase; and (c) a nucleic acid sequence encoding two guide RNAs complementary to the target nucleic acid sequences.

In an embodiment of the above methods, the invertebrate organism is an insect. In an embodiment of the above methods, the invertebrate organism is a disease vector. In embodiments of the above methods, the insect is *Drosophila melanogaster, Aedes aegypti, Culex quinquefasciatus, Anopheles gambiae, Bombyx mori, Tribolium castaneum, Apis mellifera, Nasonia vitripennis, Acyrthosiphon pisum, Pediculus humanus humanus, Daphnia pulex, Caenorhabditis elegans, Capitella capitate, Aplysia californica*, or *Lottia gigantea*. In particular embodiments of the above methods, the insect is *Anopheles gambiae* or *Aedes aegypti*.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Genus/Species Abbreviations

Dmel=*Drosophila melanogaster*
Aaeg=*Aedes aegypti*
Agam=*Anopheles gambiae*
Cqui=*Culex quinquefasciatus*
Bmor=*Bombyx mori*
Dp=*Danaus plexippus*
Tcas=*Tribolium castaneum*
Nvit=*Nasonia vitripennis*
Amel=*Apis mellifera*
Znev=*Zooternopsis nevadensis*
Ccap=*Capitella capitata*
Lgig=*Lottia gigantia*

By "agent" is meant any small molecule chemical compound, antibody, nucleic acid molecule, or polypeptide, or fragments thereof.

By "alteration" is meant a change (increase or decrease) in the expression levels or activity of a gene or polypeptide as detected by standard art known methods such as those described herein. As used herein, an alteration includes a 10% change in expression levels, a 25% change, a 40% change, and a 50% or greater change in expression levels.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include insect vector-borne diseases, such as malaria, West Nile virus, chikungunya, Zika, yellow and dengue fever.

By "effective amount" is meant the amount of an agent required to alter a biological activity or function or behavior in an animal, particularly, an insect, relative to an untreated animal. In some embodiments, the biological activity, function, or behavior is ionotropic receptor (IR) activity, hygrosensing, or thermosensing. The effective amount of active compound(s) used to practice the present invention for control of animal, particularly, insect behavior and/or activity, varies depending upon the manner of administration and type of animal.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "hygrosensing" is meant sensing of humidity or changes in humidity.

By "inhibitory nucleic acid" or polynucleotide is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. The preparation can be at least 75%, at least 90%, and at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "mutation" is meant a change in a polypeptide or polynucleotide sequence relative to a reference sequence. In some embodiments, the reference sequence is a wild-type sequence. Exemplary mutations include point mutations, missense mutations, amino acid substitutions, and frameshift mutations. A "truncation mutation" refers to a mutation that results in expression of a polypeptide having a decreased number of amino acid residues relative to the wild-type polypeptide. A "loss-of-function mutation" refers to a mutation that decreases or abolishes an activity or function of a polypeptide. A "gain-of-function mutation" is a mutation that enhances or increases an activity or function of a polypeptide. In some embodiments, the IR mutation is a truncation mutation. In some embodiments, the IR truncation mutation is a gain-of-function mutation. In other embodiments, the IR truncation mutation is a loss-of-function mutation. In some embodiments, the IR mutation results in the total loss of activity or function of the ionotropic receptor or ortholog thereof.

As used herein, "obtaining" as in "obtaining an agent" includes synthesizing, purchasing, or otherwise acquiring the agent.

By "Ir25a polypeptide" is meant a polypeptide or fragment thereof having at least about 85% or greater amino acid identity to the amino acid sequence provided at GenBank or NCBI Accession No. ADU79032.1, NP_001260051.1 (isoform E), NP_001260050.1 (isoform D), NP_001260049.1 (isoform C), or NP_608863.2 (isoform B), AaegIR25a AAEL009813-PA, AgamIR25a AGAP010272-PA, CquiIR25a, BmorIR25a BGIBMGA011590-PA, DpIR25a Dappu|1313288, TcasIR25a XP_971258.2, NvitIR25a XP_001603703.1, NvitIR25b XP_001603675.1, ApisIR25a XP_001945524.1, DpuIIR25a Dappu|1313288, CcapIR25a Capcal|152072, LgigIR25b Lotgi|109845, LgigIR25a Lotgi|114647, AcalIR25a, ZnevIR25a KDR08634.1 L798_01536, and having ionotropic receptor activity. The sequences provided at provided at GenBank or NCBI Accession No. ADU79032.1, NP_001260051.1 (isoform E), NP_001260050.1 (isoform D), NP_001260049.1 (isoform C), and NP_608863.2 (isoform B) are reproduced below:

```
ADU79032.1
                                                                SEQ ID NO: 1
   1 milmnpktsk ilwllgflsl lssfsleiaa qttqninvlf inevdnepaa kavevvltyl 61 kkniryglsv qldsieanks dakvlleaic nkyatsiekk qtphlildtt ksgiasetvk 121 sftqalglpt isasygqqgd lrqwrdldea kqkyllqvmp padiipeair sivihmnitn 181 aailyddsfv mdhkyksllq niqtrhvita iakdgkrere eqieklrnld innffilgtl 241 qsirmvlesv kpayfernfa whaitqnege issqrdnati mfmkpmaytq yrdrlgllrt 301 tynlneepql ssafyfdlal rsfltikeml qsgawpkdme ylncddfqgg ntpqrnldlr 361 dyftkitept sygtfdlvtq stqpfnghsf mkfemdinvl qirggssvns ksigkwisgl 421 nselivkdee qmknltadtv yriftvvqap fimrdetapk gykgycidli neiaaivhfd 481 ytiqevedgk fgnmdengqw ngivkklmdk qadiglgsms vmaereivid ftvpyydlvg 541 itimmqrpss psslfkfltv letnvwlcil aayfftsflm wifdrwspys yqnnrekykd 601 deekrefnlk eclwfcmtsl tpqgggeapk nlsgrlvaat wwlfgfiiia sytanlaafl 661 tvsrldtpve slddlakqyk ilyaplngss amtyfermsn ieqmfyeiwk dlslndslta 721 versklavwd ypvsdkytkm wqamqeaklp atldeavarv rnstaatgfa flgdatdiry 781 lqltncdlqv vgeefsrkpy aiavqqgshl kdqfnnailt llnkrqlekl kekwwkndea 841 lakcdkpedq sdgisiqnig gvfivifvgi gmacitlvfe ywwyryrknp riidvaeana 901 ersnaadhpg klvdgvilgh sgekfekska alrprfnqyp atfkprf NP_001260051.1 (isoform E)
                                                                SEQ ID NO: 2
   1 mgsrldwgva dvalwaiadq idyhqvfine vdnepaakav evvltylkkn iryglsvqld 61 sieanksdak vlleaicnky atsiekkqtp hlildttksg iasetvksft qalglptisa 121 sygqqgdlrq wrdldeakqk yllqvmppad iipeairsiv ihmnitnaai lyddsfvmdh 181 kyksllqniq trhvitaiak dgkrereeqi eklrnldinn ffilgtlqsi rmvlesvkpa 241 yfernfawha itqnegeiss qrdnatimfm kpmaytqyrd rlgllrttyn lneepqlssa
```

-continued

```
301 fyfdlalrsf ltikemlqsg awpkdmeyln cddfqggntp qrnldlrdyf tkiteptsyg
361 tfdlvtqstq pfnghsfmkf emdinvlqir ggssvnsksi gkwisglnse livkdeeqmk
421 nltadtvyri ftvvqapfim rdetapkgyk gycidlinei aaivhfdyti qevedgkfgn
481 mdengqwngi vkklmdkqad iglgsmsvma ereividftv pyydlvgiti mmqrpsspss
541 lfkfltvlet nvwlcilaay fftsflmwif drwspysyqn nrekykddee krefnlkecl
601 wfcmtsltpq gggeapknls grlvaatwwl fgfiiiasyt anlaafltvs rldtpvesld
661 dlakqykily aplngssamt yfermsnieq mfyeiwkdls lndsltaver sklavwdypv
721 sdkytkmwqa mqeaklpatl deavarvrns taatgfaflg datdirylql tncdlqvvge
781 efsrkpyaia vqqgshlkdq fnnailtlln krqleklkek wwkndealak cdkpedqsdg
841 isiqniggvf ivifvgigma citlvfeyww yryrknprii dvaeanaers naadhpgklv
901 dgvilghsge kfekskaalr prfnqypatf kprf
```

NP_001260050.1 (isoform D)  SEQ ID NO: 3
```
  1 mprnafgqct ltdvipslwi vfinevdnep aakavevvlt ylkknirygl svqldsiean
 61 ksdakvllea icnkyatsie kkqtphlild ttksgiaset vksftqalgl ptisasygqq
121 gdlrqwrdld eakqkyllqv mppadiipea irsivihmni tnaailydds fvmdhkyksl
181 lqniqtrhvi taiakdgkre reeqieklrn ldinnffilg tlqsirmvle svkpayfern
241 fawhaitqne geissqrdna timfmkpmay tqyrdrlgll rttynlneep qlssafyfdl
301 alrsfltike mlqsgawpkd meylncddfq ggntpqrnld lrdyftkite ptsygtfdlv
361 tqstqpfngh sfmkfemdin vlqirggssv nsksigkwis glnselivkd eeqmknltad
421 tvyriftvvq apfimrdeta pkgykgycid lineiaaivh fdytiqeved gkfgnmdeng
481 qwngivkklm dkqadiglgs msvmaereiv idftvpyydl vgitimmqrp sspsslfkfl
541 tvletnvwlc ilaayfftsf lmwifdrwsp ysyqnnreky kddeekrefn lkeclwfcmt
601 sltpqgggea pknlsgrlva atwwlfgfii iasytanlaa fltvsrldtp veslddlakq
661 ykilyaplng ssamtyferm snieqmfyei wkdlslndsl taversklav wdypvsdkyt
721 kmwqamqeak lpatldeava rvrnstaatg faflgdatdi rylqltncdl qvvgeefsrk
781 pyaiavqqgs hlkdqfnnai ltllnkrqle klkekwwknd ealakcdkpe dqsdgisiqn
841 iggvfivifv gigmacitlv feywwyryrk npriidvaea naersnaadh pgklvdgvil
901 ghsgekfeks kaalrprfnq ypatfkprf
```

NP_001260049.1 (isoform C)  SEQ ID NO: 4
```
  1 milmnpktsk ilwllgflsl lssfsleiaa qttqninvlf inevdnepaa kavevvltyl
 61 kkniryglsv qldsieanks dakvlleaic nkyatsiekk qtphlildtt ksgiasetvk
121 sftqalglpt isasygqqgd lrqwrdldea kqkyllqvmp padiipeair sivihmnitn
181 aailyddsfv mdhkyksllq niqtrhvita iakdgkrere eqieklrnld innffilgtl
241 qsirmvlesv kpayfernfa whaitqnege issqrdnati mfmkpmaytq yrdrlgllrt
301 tynlneepql ssafyfdlal rsfltikeml qsgawpkdme ylncddfqgg ntpqrnldlr
361 dyftkitept sygtfdlvtq stqpfnghsf mkfemdinvl qirggssvns ksigkwisgl
421 nselivkdee qmknitadtv yriftvvqap fimrdetapk gykgycidli neiaaivhfd
481 ytiqevedgk fgnmdengqw ngivkklmdk qadiglgsms vmaereivid ftvpyydlvg
541 itimmqrpss psslfkfltv letnvwlcil aayfftsflm wifdrwspys yqnnrekykd
601 deekrefnlk eclwfcmtsl tpqgggeapk nlsgrlvaat wwlfgfiiia sytanlaafl
```

-continued

```
661 tvsrldtpve slddlakqyk ilyapingss amtyfermsn ieqmfyeiwk dlslndslta 721 verskiavwd ypvsdkytkm wqamqeaklp atldeavary rnstaatgfa flgdatdiry 781 lqltncdlqv vgeefsrkpy aiavqqgshl kdqfnnailt llnkrqlekl kekwwkndea 841 lakcdkpedg sdgisiqnig gvfivifvgi gmacitivfe ywwyryrknp riidvaeana 901 ersnaadhpg klvdgvilgh sgekfekska alrprfnqyp atfkprf
```

NP_608863.2 (isoform B)  SEQ ID NO: 5

```
  1 mgsrldwgva dvalwaiadq idyhqvfine vdnepaakav evvltylkkn iryglsvqld 61 sieanksdak vlleaicnky atsiekkqtp hlildttksg iasetvksft qalglptisa 121 sygqqgdlrq wrdldeakqk yllqvmppad iipeairsiv ihmnitnaai lyddsfvmdh 181 kyksllqniq trhvitaiak dgkrereeqi eklrnldinn ffilgtlqsi rmvlesvkpa 241 yfernfawha itqnegeiss qrdnatimfm kpmaytqyrd rlgllrttyn lneepqlssa 301 fyfdlalrsf ltikemlqsg awpkdmeyln cddfqggntp qrnldlrdyf tkiteptsyg 361 tfdlvtqstq pfnghsfmkf emdinvlqir ggssvnsksi gkwisglnse livkdeeqmk 421 nltadtvyri ftvvqapfim rdetapkgyk gycidlinei aaivhfdyti qevedgkfgn 481 mdengqwngi vkklmdkqad iglgsmsvma ereividftv pyydlvgiti mmqrpsspss 541 lfkfltvlet nvwlcilaay fftsflmwif drwspysyqn nrekykddee krefnlkecl 601 wfcmtsltpq gggeapknls grlvaatwwl fgfiiiasyt anlaafltvs rldtpvesld 661 dlakqykily apingssamt yfermsnieq mfyeiwkdls lndsltaver sklavwdypv 721 sdkytkmwqa mqeaklpatl deavarvrns taatgfaflg datdirylql tncdlqvvge 781 efsrkpyaia vqqgshlkdq fnnailtlln krqleklkek wwkndealak cdkpedqsdg 841 isiqniggvf ivifvgigma citlvfeyww yryrknprii dvaeanaers naadhpgklv 901 dgvilghsge kfekskaalr prfnqypatf kprf
```

>AaegIR25a AAEL009813-PA  SEQ ID NO: 6

```
MQISVFVNEVGNDLAQVAVDVALNYIRKNPSLGLSVELLTVEGNRTDSKGLLESLCSKYT

EAINTNRPPHVIFDTTLTGVSSETVKSISAALGIPTVSASTGQEGDLRQWRSLSNVKSNY

LLQVMPPIDIIPEVIRAIVTYMNITNAAILYDESFVMDHKYKALLQNFPTRHVITAIGND

RDRAEQIEKLRNLDINNFFILGSFASIKKVLESAKREFFERNFAWHAITQYQGELSSNIE

NATIMLLRPVSDSKSKDRLGVIRTTYNMKQEPQITTVFYFDLALRTFLAIKNILQVGAWP

PNMKYLTCDEYDGTNSPNHTIDLKSAFIEVTEPTTYGPFEFPKGKTPFNGHSFMKFDMDI

SAVTIRGGASVSTKNLGKWEASLDNALYVISEDDMKNLTADIVYRVYTVVQEPFIIRDPT

APKGFKGYCIDLLDEIAKIVKFDYEIKEVEDGKFGNMNEKGEWNGIVRKLIDKQADIGLG

SMSVMAERETVTDFTVPYYDLVGISIMMLLPSTPSSLFKFLTVLETNVWLCILAAYFFTS

FLMWIFDRYSPYSYQNNREKYKNDDEKREFNIKECLWFCMTSLTPQGGGEAPKNLSGRLV

AATWWLFGFIIIASYTANLAAFLTVSRLDTPVESLDDLSKQYKILYAPLNGSSAMTYFQR

MADIEARFYEIWKEMSLNDSLTPVERSKLAVWDYPVSDKYTKMWQAMQEAGLPNSLDEAV

ERIRNSTSASGFAFLGDATDIRYKVLTNCDLQMVGEEFSRKPYAIAVQQGSPLKDQFNNA

ILMLLNKRQLEKLKEQWWKNDDIQSKCEKPDDQSDGISIQNIGGVFIVIFVGIGMACITL

VFEFWYYKYRKNVKIIDVAEATEDKLAQKTSNLRLPNLKNEFGAMGQIKDDSQKTQSLRT

RTQTIDANNFKSRF
```

>AgamIR25a AGAP010272-PA

SEQ ID NO: 7

MDPKNGRRWLVLIPIQLASYAIIAIMGQTTQNINILFVNEVDNNLANVAVEVALNYVKKN

PQLGLSVDMMYVEGNRTDSKDLLQALCSKYGQSLSENRPPHLLLDTTLTGVSSETVKSFS

LALGIPTVSASFGQEGDLRQWRDLTPTKRGYLLQVMPPADMIPQVIRSIIIYMNITNAAI

LYDNTFVMDHKYKALLQNIPTRHVVTTIADDRDRASQIEKLRNLDINNFFILGSLASIKQ

VLESAKNEYFERNFAWHVITQEQKDLTCNVENATIMFLRPMSDSSSKDRLGSIRTTYNLK

QEPQITGFFYFDLTLRALIAIKNILQSGSWPSNMKYITCEDYDGTNTPNHTIDLKTAFIE

VTEPTTFGPFEIPKGGKMQFNGNTYMKEDMDINAVSIRSGASVNTRSLGTWEASLNAPIN

VANEAEIKNLTADVVYRVYTVVQAPFIMRDPTAPKGFKGYCIDLLNKIAEIVEFDYEIRE

VEDGKFGNMNENGEWNGIVRKLIDKQADIGLGSMSVMAERETVIDFTVPYYDLVGISIMM

QLPSTPSSLFKFLTVLETNVWLCILAAYFFTSFLMWIFDRYSPYSYQNNREKYKNDDEKR

EFNIKECLWFCMTSLIPQGGGEAPKNLSGRLVAATWWLFGFIIIASYTANLAAFLTVSRL

DTPVESLDDLSKQYKILYAPLNGSSAMTYFQRMADIEAKFYEIWKEMSLNDSLTAVERSK

LAVWDYPVSDKYTKMWQAMLEAGLPNSLEEAVQRIRNSTSASGFAFLGDATDIRYQVLIN

CDLQMVGEEFSRKPYAIAVQQGSPLKDQFNNAILMLLNRRELEKLKEQWWKNDDVQNKCE

KPDDQSDGISIQNIGGVFIVIFVGIGMACITLLFEFWYYKYRNNSKVIDVAESTDQQHGG

TIVKNVRPAGKLMKQDSLKDSTKGHNYQNLRTRTLMPNLSKFQPRF

>CquiIR25a DerivedFromBlastPof CpipJ2 Supercont3.1486

SEQ ID NO: 8

VCSKYSEALNTNRMPHVILDTTLTGVASETVKSISVALGIPTVSTSFGQEGDIRQWRSLS

PEKGNYLLQIMPPTDMIPEVIRSIIIYMNITNAAILYDDSFVMDHKYKALLQNIPTRHVI

TSIGNDKDRGEQIEKLRNLDINNFFILGSFPSIRKVLESAKREFFERNFAWHAITQFQGE

LSSNIENATIMLLRPVSDSKSKDRLGVIRTTYNMKQEPQTSSVFYFDIALRTFLAIKNLF

YDDAKNDYEYDPPYTMDQDFDRITIKVRDLREKLDNGFDGKCLSRLRAYFHRVMRLVTTN

DDEKVRKRELAEEMLQIFVTFNVNPDKQPDEISDGNPEKEETEKEEASLKKILLLINVYF

LQQEPFIFRDPSAPKGFKGYCIDLLDEIAKIVKFDYEIKAVEDGKEGNMNEKGEWNGIVR

KLIDKQADIGLGSMSVMAERETVIDFTVPYYDLVGISIMMQLPSTPSSLFKFLTVLETNV

WLCILAAYFFTSFLMWIFDRYSPYSYQNNREKYKNDDEKREFNIKECLWFCMTSLIPQGG

GEAPKNLSGRLVAATWWLFGFIIIASYTANLAAFLTVSRLDTPVESLDDLSKQYKILYAP

LNGSSAMTYFQRMADIESRFYEIWKEMSLNDSLTPVERSKLAVWDYPVSDKYTKMWQAMQ

EAGLPNSLDEAVERIRNSTSASGFAFLGDATDIRYKVLTNCDLQMVGEEFSRKPYAIAVQ

QGSPLKDQFNNAILMLLNKRQLEKLKEQWWKNDDIQSKCEKPDDQSDGISIQNIGGVFIV

IFVGIGMACITLVFEFWYYKYRKNIKIVDVMEANDENS

>BmorIR25a BGIBMGA011590-PA

SEQ ID NO: 9

MCRSSHIFQNSMPLFVVFLQFFIFRLIVSQTTQNINVLLINEENNALAEKSFEIAKEYVR

RNPSLGLAIEPVIVVGNRSDAKTFLENVCRKYNDMLSSKKTPHVVLDFTMTGVGSETIKS

FTAALALPTISGSFGQTGDLRQWRSLNANQTKFLLQVMPPADILPESIRAIVIKQDITNA

AIIFDELFVMDHKYKSLLQNIPTRHVITPVKSFNKEDIKTQLRSLRELDIVNFFIVGSLR

TIKNVLDAADENQYFGRKTAWFAFSLDKGDITCGCKDATIVYMRPTPDAKSRDRLGKIKT

TYSMNGEPEITSAFYFDLSLRTFLAVKSLLDSGKWPNNMKYITCDDYDGKNTPNRTLDLK

LAFQEVKETPTYAPFYIPGDDPMNGRSYMEFSTDLSAVTVKDGASIGSKALGTWKAGLNS

-continued

PLSLTDSDNMSDYSAQLVYRVVTVEQQPFIIRDDNAPKGFKGYCIDLIEEIRQIVKFDYE

VTLSPDGNFGTMDENGNWNGIIKELIEKRADIALTSLSVMAERENVVDFTVPYYDLVGIT

IMMKLPRTPTSLFKFLTVLENDVWLSILAAYFFTSFLMWVFDKWSPYSYQNNREKYKDDE

EKREFTLKECLWFCMTSLTPQGGGEAPKNLSGRLLAATWWLFGFIIIASYTANLAAFLTV

SRLDTPIESLDDLSKQYKIQYAPLNGSAAMTYFERMAAIEVRFYEIWKEMSLNDSLSDVE

RAKLAVWDYPVSDKYSKMWQAMKEAGLPNSIEEAVQRVRDSKSSSEGFAWLGDATDVRYY

VLTSCDLQMVGDEFSRKPYAIAVQQGSPLKDQFNNAILQLLNRRRLEKLKENWWNNNPKA

MKCEKQDDQSDGISIQNIGGVFIVIFMGIGLACITLGVEYWWYKWRRRPIVGDVTQVEPA

KSTRNNIGNFVKGEGFTFRSRNFGLSDLKQKF

>DpIR25a Dappu1|313288
SEQ ID NO: 10

MILLNVLLIYFFRIILSQTTQNINVLLINEENNALAERSFEVAKEYVRRNPGLGLAVNPV

IVVGNRSDAKVFLENVCRKYNDMISAKKTPHVVLDFTMTGVGSETIKSFTAALALPTISG

SFGQPGDLRQWRALVDNQTKYLLQVMPPADILPEAVRAIVMKQDITNAAIIFDEYFVMDH

KYKSLLQNIPTRHVITPVKSFSKDDIKTQLRSLRELDIVNFFIVGSLRTIKNVLDAANEN

QYFGRKTAWFALSLDKGEISCGCKDATIVHIKPTPDANSRDRLGKIKITYSMNGEPEITS

AFYFDLSLRTFLSIKSLLDSGKWQNDMNFITCDDYDGKNTPNRSLDLKTAFQEVKETPTY

ASFYIPEDDPMNGRSYMEFSTDLTAVTIKDGASIGSKTLGSWKAGLSSPLLLTDPDNMSD

YSAQLVYRIVTVEQQPFIIRDEEAPKGFKGYCIDLIEEIRQIVKFDYEITLAPDGSFGVM

DENGNWNGIIKELMEKRADIGLTSLSVMAERENVVDFTVPYYDLVGITILMKLPRTPTSL

FKFLTVLENDVWLSILAAYFFTSFLMWVFDKWSPYSYQNNREKYKDDEEKREFTLKECLW

FCMTSLTPQGGGEAPKNLSGRLLAATWWLFGFIIIASYTANLAAFLTVSRLDTPIESLDD

LSKQYKIQYAPLNGSAAMTYFERMANIEVRFYEIWKEMSLNDSLSDVERAKLAVWDYPVS

DKYSKMWQAMKEAGLPNSIEEAVDRVRASKSSSEGFAWLGDATDIRYHVLISCDLQMVGD

EFSRKPYAIAVQQGSPLKDQFNNAILQLLNKRKLEKLKEDWWNNNPNAIKCEKQDDQSDG

ISIQNIGGVFIVIFMGIGLACVTLGVEYWWYKWRRRPTISGVKQVEPAKSVRNNTESNTK

INDGFTFRARNLGLANLKQKF

>TcasIR25a XP_971258.2
SEQ ID NO: 11

MASSSAIIYRIAIYSRIATAHLNYSDFLNNVLTETHKMLKLVAFILYCTNLANGQTTQNI

NVLFVNEEGNLVAEKAVDVATNYIKKNNKLGVNADPVKVVGNRTDASGLLDSLCSSYNEM

IANSMNPHLVLDTTMTGLASETVKSFTAALGLPTISASFGQEGDLRQWRNIDENEKEYLV

QISPPADVIPEIIRSLVLSKNVTNAAILFDDSFVMDHKYKSLLQNVATRHVIAPIKEADK

IGDQLRQLRKLDIVNFFILGSFENIKRVLDAADSVGFFNRKFSWHAITQDKGELKCNCRN

ATITLAKPLIDAQYQDRLGLIKTSYQLNAEPEIAAAFYFDLALYSFLAVKEMIADGVWKR

NNATNYITCDDFDGKNTPRRAGLNLKKYFSKEVSETPTYGPISIVSNGYSFMEFTMQISA

VGVRESSSDKSVPLGSWKAGYDNNLTLVDPQIMKNYTADVVYRVVTVEQKPFIIKDETAP

KGYKGYCIDLIQRISEILNFDYEITPVGDQKFGNMDENGKWNGVVRELMEKRADIGLGSM

SVMAERENVIDETVPYYDLVGITILMKLPKTPTSLFKFLTVLENEVWLCILAAYFFTSFL

MWVFDRWSPYSYQNNREKYKDDEEKREFNLKECLWFCMTSLTPQGGGEAPKNLSGRLVAA

TWWLFGFIIIASYTANLAAFLTVSRLDTPIESLDDLSKQYKIQYAPLNGSSTMTYFERMA

NIEAKFYEIWKDMSLNDSLSEVERAKLAVWDYPVSDKYTKMWQAMKEAGLPNTLDEAVKR

VKDSRSSSEGFAYLGDATDIRYLEITSCDLQMVGEEFSRKPYAIAVQQGSPLKDQFNTAI

```
LQLLNRRELERLKEKWWSKNPEAKKCDKQEDQSDGISIQNIGGVFIVIFVGIGLACITLA

FEYWWYKYRKGGKVVDVQAKHSDVATKINDGFHAKINKLYPRSRF
```

>NvitIR25a XP_001603703.1                                         SEQ ID NO: 12

```
MYRRGCSKGLSLLLIGKLVLLVGGQQTTDTAANRPVNVFVINDANNDVANKSVINSLKAL

KEKSPDKLGQVYVAQINVSDSDQSLDAICSLWQSSIRENEADAPDFVLDTTTYGIGAESV

NRFTALLGIPTLSAQFGQEGDLLGWRDISEEQKRYLVQVMNPADLMPEVIRQQCSNFNIS

NAAILFDENFVMDHKYKSLLLNVPTRHVIVPAEPAGAPLQKQISKLRDLDIVNFFILGSE

STISSALIEANNLNFTGHKYGWEGITLNEEFQAQCQDCRNISLLLFKPKAESSQQLSELT

SKGSLPKPVISSAFYYDLTKLGVLAMKSALMSGEWHRPRFITCDEYNENATLPARNLNLR

QRLEQVANSSGFTRTYASFAWGRNGVSRAKFGVNGLLIRIRDSKLISSDPVETWEAGVDS

QLKVLDENKAGNHTAVTSYRVVTVIKPPFVMYDNETGNWTGYCIDLLDEIREHVKFEYEI

REVDDKEYGNMDEDGNWNGMVRELKEKKADIALGALAVMAERENVIDYTVPYYDLVGISI

LRKKPKTATSLFKFLTVLESDVWLCILGAYFFTSLLMWIFDKFSPYSYQNNMEKYKDDDE

KRLFTMKECLWFCMTSLTPQGGGEAPKNLSGRLVAATWWLFGFIIIASYTANLAAFLTVS

RLDAPVESLEDLSKQYKIQYAPILNSSEYRYFERMANIEKKFYEIWKDMSLNDSLSDVER

AKLAVWDYPVSDKYTKMFQTMQDAGFPNDMDEALRRVREGKPTEFAFIGDATDIKYLTMT

DCTFMQIGEEFSRKPYAIAVQQGSPLKDQFNNAILMMLNRRKLEKLKDTWWNKNPKRKRC

NKAEDQSDGISIQNIGGVFIVIFVGIGLACVTLIFEYFYYRRRPQIKKRHQESRTDKTKS

VQSVKSMKFNLRPAPTQSLENTNYRSRF
```

>NvitIR25b XP_001603675.1                                         SEQ ID NO: 13

```
MNATAKPTYRVITIPKPPFVIYDPDSNWYGGFLVDLLNEIARRLNFRYEIEMQNESEYGF

MDDQGNWNGLMRDLKEGKADIGLAAVSVMSERMKVVDFTEPIYKPTGISVLMQKPIPKTD

FYRFLTVLELDVWLCIIGAYIFTSLLLWIFDTWSPYSYRNCKAKYKDDTEKRIFGCKESL

WFCLTSLTPQGGGEAPKNLSGRLVAATWWLFGFIIIASYTANLAAFLTISKFEKTIETFD

DLISQYKYSYTCIQNSSTNRYFQRMNDIEYVCYEKWKDMTLNDSLSPYERAQLAVWEYPL

SDKFIKIYSAISHHGMVASLQDGLDKFNSTDSRFALITEASDVQYQAMIDCSVKEIGPEF

SKKPYAIVLQKNSPLTKQFNRIIYNMKNDNWLEALTDKWWKYNPLRQRCHDKDEMINGII

FENIGGVFVLIGVGILSAFSTLVYEYFYFKCLQDKFERIFEHKLKSIFRRQKNFARSISV

KP
```

>ApisIR25a XP_001945524.1                                         SEQ ID NO: 14

```
MYKPIRGITILLWINTLFNIGTSQNVQTVNILFINDRTNEVAEDTLNVALNYIRRNPRVG

LMIDGLYSVKIGGDDASAILETLCVNYNASIRNNKPPHLVIDTTINGVASEAVKSFTAAL

ALPTVSASYGQTGDIRQWRNLDGEQQKYLIQISPPADLIPEIVRSIVVAQNITNAGIMFD

DTFVMDHKYKSLLQNIPTRHIIAAIDDTTSIKLHLTRFRDVDIVNFFVLGKLSIIKSVLD

HANSNKLFGRKYAWHVITQDKGSLKCGCSNATILFVKPEPDAGSRERLSNLRTTYGLTST

PELKAAFYFDFYYRSLLAIRSMMNSGEWPTNVTYTTCDEYNEENPLPRRNVDLRRYLKDM

TEPPSYAPFLIDTNGHSYEEFTMRLEKVTVLNSQSVSAENVGSWKASLNSPIIVKDAANM

THFSAVTVYRVVTVLQNPFMIQIDDEDGKGVKFKGYCIDLIEEIRKLIGFEYEIYIAPDN

NFGNMDENGQWNGMVKELVEKRADIALGSLSVMAERENVVDFTVPYYDLVGITILMKKPQ

TPTSLFKFLTVLENDVWMCILGAYFFTSFLMWVFDRWSPYSYQNNRIKYKDDEEKREFNL
```

-continued

KECLWFCMTSLTPQGGGEAPKNLSGRLVAATWWLFGFIIIASYTANLAAFLTVSRLDTPV
ESLDDLSKQYKIQYAPLNGSSAMTYFQRMADIETRFYEIWKDMSLNDSLSEVERAKLAVW
DYPVSDKYTKMWQAMKEAKLPNTLEEAIERVQSSKSSSEGFAYLGDATDIRYQVMIDCHL
QMVGDEFSRKPYAIAVQQGSPLKDQFNNAILLLLNKRKLEKLKETWWNLNPERIQCEKQD
NQSDGISIHNIGGVFIVIFVGIGLACFTLAFEYWWYKYKKSSRIIDIAMVINENCIYPIG
YISVGTNLMANIQRVMHIGY

>DpulIR25a Dappu1|313288
SEQ ID NO: 15
MRSFQLLLVLGLAFAVQSADPIRVLLVYETNNVDADRAFTAVQSYLERTKVQGLSLGNVT
RVTLDSTQKYLTVDDVCSVYDKSIDAGTPPHIVLDLTWSGLSSEVMKALTRNLGLPTISG
SYGGIGDLKHWSNIDGNQTKYLVQVMPPSDIIPQLVALITSMQNMTNAAILYDDSFDMLN
KYKSLLKNRPIRHMFSKIETNINTQIRRLEDMDIVNFFVLGKIDRINQVLMSAAQENYFG
KKYSWTAISKDGSAEPFVRTENGSILFAVPTVNPDVANGILEKTSGLNNGYSVDTGFYFD
LILRAITTVKNMLDGNTWPVDMSYSKCSMTNITAVTRNNFDLRKAFADTNVGSTFANMIL
NGNGKSYPQVEMTINQMNFKNSRLESKNALGIWKAGMPGEISFSPGQSLRPFQVISVFKI
AVVVQAPFIMKRKANGTVTFYGYCVDLIKDIQAIMGFEYELYEVPDGKYGNMDSKMNWNG
MIKELMEKRADIGLGALAVMAERENVIDFTVPYYDLVGISILMAKPQVSTSLFKFLTVLE
NDVWGCILAAYFFTSILLWIFDRWSPYSYQNNKEKYADDPEEEKREFSLKESLWFCMTSL
TPQGGGESPKHLSGRLIAATWWLFGFIIIASYTANLAAFLTVSRLDSPVNSLDDLSTQYK
VQYAPQNGTDVATYFERMAYIEKRFYEIWKDMSLNDSMNEVERSKLAVWDYPVSDKYTKI
WQSMQDAGLPHTFDEALTRVRASNAENNDGFAFLGDATDIRYQVLVNCDLQMVGEEFSRK
PYAVAVQEGSPLRDLLNDAILRLLNQRRLETLKERWWTDNPEKQECGDTNDQSDGISIQN
IGGVFIVIFVGIFLACVTLAIEYCYFKVRRNPEGDEVVSTPESRNNAAGNRNKLDDAYVK
NSQKPFVLDDNSKDPYAGDYGYYGAKKELELEGDGPRPRKAW >CcapIR25a Capca1|152072
SEQ ID NO: 16
MTLLKVSAAFLFDLVAFIGETANSLLAAGDWHQISYPDCFTFEKTDKVAQDQAVRKDATS
GLRAPHNSVSQLGSWSAADGLVTLDGPITNKNAKKTYRIVIVHEPPFIFRSKELPKNEKL
DYYYYNEENQTYYYGYCVDLIHRISEIMDFEYVIYEPDDGAYGTMQEDGSWNGMVNELIH
DVSNEVCLVLSLLYLWHMFYQRADMSVATLSVMAERENVVDFTVPYYDLVGITILMQKPK
FEYSVFKFMSVLEDAVWGCILSAFIIVSVLLAVFDKFSPYSYQNNRSSWDGQGEEPRVFS
LKEGLWFCMTSLTPQGGGEAPRALSGRLVAATWWMFGFIMIATYTANLAAFLTVSRLDQP
IESLDDLAEQFKTKYAPQQSTSTETYFKRMKDIEEKFYSIWKSMSLNDSLDQVERAKLAV
WDYPVSDKFINMWVSMIESGFPKDFESAKKRILKQDGSTDEFAFIGDATQNKYATLTDCD
LWEVGEEFSRKPYALAVQEGSPLKNQLSSVILQLLNQRVLEDLKTTWWEFNRLKCPKIED
ESDGISIKNIGGVELVIFIGIGLGLITLAFEYYWYKWLQQKKAIRIIYKETYNTHTKPLF
VRSKILPLPKVTILQTAQILHQLHNNVLPPLIAACINHHSVAHLHHLRHIRPFRI >LgigIR25b Lotgi|109845
SEQ ID NO: 17
MIYVPICIHRIFEFLQEPPFVFRNTSGQEVMYEGYSIDVMNDVAERVGFTYTIRECDGGV
YGNLDSDQRWTGCVGNILKGDADIIVGAMTVTADRETVVDYTLPYYDFAGIQILMRKQKQ
QVNIFYFADVESNAAWLCLGGVIALTSILLLLFDKYSPGPGFSKNVEKREEFKFNLHESI
WFVVGSITMAGGGDPPRSFSARLLVAGFWFFSVIMMSTFTANLAAFLTVSRLGVTVSSLD
DLAEQSDIKYSVVAESSVANYFERMAAIEENFYSMWKEMSLGTAENGNSSFAVWDYPLGD -continued

KYVTIWKSIRKTGFIKTSDAAIDKVLSENFALLTDSPIIKYITSRNCELTAIGDQFSVRP

YAFALKEKSVYTKKISAAILDLQQDRKLETYKRKWWDDGKVSCPEDTSNQGLDLQSLTGS

FLVVVMGIVSGVIVLGIELLWIKAKVTKKVI

>LgigIR25a Lotgi|114647
SEQ ID NO: 18
LMTVLIAYLNCLLHVRSQTHRIVVVIDNTILEYNKNIEKILSNSDSLVDQGVNLAQTEFK

IIIADKNDSLVTLDNVCAEMKKGAVALIDMSIPSSAVLLRSYASSLGIAYISVVDKSYFR

YGSGDSTIHYQIEPTAVEILQIVADIVNFDDLNNVAIVYDETFDIQNTPRRILTNVPAQH

LYVRMSSDPTETKRQVEMLKRIEIKNIFIIGNSRKAPDFLEVANVISDEFDVNWFFLTKV

NIAIQILWYGVLMEFPVLISELLVYDSVQFRVAVLTFQYFVILHIHDLKSKLSQLVHYLT

PISTFSEEGVYGPLVEENDITRYKFTLLINQLTFKSGNNINNREVGNWTEAGEDGRRLVL

KPGITSLTKSNKKKLYRVVTVANMPPFVYKKVSGNTTNTNDMYDGYCIELLKRISYLLDF

DYILYDSPDGMYGSMDDDGNWNGAIKELIDKKADIAVGPISVMAERENVVDFTVPYYDLV

GLTILMKKPEFDYTLGKFLTVLDEDVWFCIIGAFFLFSILICVFDKLSPFSYQNNTVDWN

GEGTEPRVFTLKEGIWFCMMSLTPQGGGETPRALSGRLVAATWWLFGFIIIATYTANLAA

FLTVSRLETPIESLDDLSKQFKVKYAPMNGSNALIYFKRMQEIEHRFYGIWKNMSLDDNL

GAVERAKLAVWDYPVSDKYTKLWETMLESEFPSNKDEAVERVLTGEFAYIGDATVNKYAK

LTNCDLWEVGEEFSRKPYALAVQEGSPLRSQLSTIILQLINQRELEEYKTKWWKKDKRDC

PDIEDESNGISIKNIGGVFLVIVIGSALALITLAIECYWYKYKPKQKKKLYVISSKANLN

KLDTAPSGNNLSNLANGYQSSTQLCNGHVPEGETTSNGKIENDGHTNTGF

>AcalIR25a
SEQ ID NO: 19
LLHVYHLILLLLSYQTSIAPSSRSSCFYMFKPDIYTKIQIYIYIYIYIYNYYLLVTPLFF

GTYISPNCVASAVKRLLKQKTKKLFLFFISQVDEALAFDIGRIVTLALEAVPNVQNIVKV

SCDNGTDPTPASLKQSAELTNELTVVTRRPLSWSEQSQALRYNMTLLLSEMFFESGILKS

KDQVANWTQAGGLQLDVPTLQKANKKKRYRIVTVAGIPPFVYKEEPINSTGPPVYKGYCI

DLLERIAQDMNFDYEIHDVEIVGSMDDDGNWSGVIKELIDNKADIAVGPISVMAERENVI

DFTVPYYDLVGLTILMRKPRFDYSLVKFLNVLDEEVWGCIIGAFFLFSILICVFDKLSPF

SYQNRKNQWKSSGSEPRVFTLKEGVWFCMMSLTPQGGGETPKALSGRLIAATWWLFGFII

IATYTANLAAFLTVSRLETPIESLDDLSEQFKVQYAPMNGSTAMIYFKRMAHIEHRFYEI

WKNMSLNDNLAAVERAQLAVWDYPVSDKYTKLWQTMQDSHFPSNKTEAVHRVLNEDFAFI

SDATTNKYQTLINCDLWQVGEEFSRKPYALAVQEGSPLRSQLSNIILKLINQRALEEMKT

KWWKEDEKECPKLENETDGISIRNIGGVFLVIVIGSGLSLITLAFECYWYRLRPERKTLS

KMYNGRSKDTNSQGQLTTSGTATSVLASDSQMSKENQRNNKLETGGLDSGFVNIGFELNG

GGLDSGFTSDRASGIEISRMRTTILEF

>ZnevIR25a KDR08634.1 L798_01536
SEQ ID NO: 20
MRPRSLLVSLFLFITLDASQPVTAELMNILFLNEEGNKIGDEAFNVALDYVKKNPSLGVEIGEVIKAVGN

TTDAQTFLKSICSVYDAAIKAETRPHVVLDMTMSGVPSETAKSVTAALALPTISTSFGQEGDLRQWRSLE

EAEKNYLIQIMPPADIMPEIIRRIVIFQNITNAGILFDDSIVMNHKYKSLLQNLPTRHMIVEADEGNGEA

QLKRLRERDIFNYFILGRLSTIVSVLDSAEKCGFFDRQFAWHGITLDSGNLGCSCKNATVFFVKPKPNEE

YTETYTELTEKYNLQNLPEISAAFYFDVALRTLLATKEIMQGNDYRKNYVTCDDYDETKHVTRDVDLLTA

FKQVSQPESYGKLSITSNGESMMEFQMEMTAVKIRSSVPQTAIDMATWNASLTLPLDVKDSTTMVKHSAV

-continued

```
TVYRIVTVVQNPFVIYDGVDGKNRTKFKGYCIDLIDEIRNITKEDYEIYEAPDKKEGNMDENGNWNGMIK

ELMLKNADIALGSLSVMAERENVVDFTVPYYDLVGITILMKKPKAATSLFKFLTVLENEVWLCILGAYFF

TSFLMWVFDRWSPYSYQNNREKYKDDEEKREFNLKECLWFCMTSLTPQGGGEAPKNLSGRLVAATWWLFG

FIIIASYTANLAAFLTVSRLDTPVESLDDLAKQYKIQYAPLNNSASMIYFQRMSDIENRFYEIWKDMSLN

DSLSDVERAKLAVWDYPVSDKYTKIWQAMNEAKFPNTLEEAVNRVLDSKSSSEGFAYIGDATDVRYLVLT

SCNLQMVGEEFSRKPYAIATQQGSPLKDQFNNAILQLLNKRKLEKLKEQWWNQNPEKRRDCEKQDDQTDG

ISIQNIGGVFIVIFVGIGLACITLAFEYWWYKYKKIPKVVDTGKVVAHSRQIPTTGGGKLETGLKMQGFR

PRNPTFPTHSFRRNVGPMTGVKSPW
```

By "Ir25a polynucleotide" is meant a polynucleotide encoding an Ir25a polypeptide. An exemplary Ir25a polynucleotide sequence is provided at GenBank Accession No. HQ600588.1. The sequence is provided below:

```
                                                      SEQ ID NO: 21
   1 atgattttga tgaatccgaa aacttcgaaa atcctgtggc tgctgggatt tctatcgtta 61 ttaagcagct ttagtttgga gatcgctgcg caaaccactc aaaatatcaa tgtgttgttc 121 atcaacgagg tggacaatga gccggctgcg aaggctgtgg aggtggtgct cacctacttg 181 aagaagaaca tacgatatgg tctatcggtg caactggatt cgatagaggc gaacaagtcc 241 gatgccaagg tgctgctgga agctatttgc aataagtacg caacaagtat tgaaaagaaa 301 cagacgcctc atctgatcct ggacaccacc aaatcgggca tagcctcgga aacggtaaag 361 agcttcaccc aggctctggg tctgcccacc attagtgcct cctatggcca gcagggcgac 421 ttgaggcagt ggcgcgactt ggatgaggcg aagcagaagt atttgctgca ggtgatgccg 481 ccggcggata ttattcccga ggccattcga agtatagtga ttcacatgaa catcacgaat 541 gctgccattc tgtacgatga ttcctttgtc atggaccaca agtacaagtc cctgctgcag 601 aatatacaaa cccgtcatgt gatcaccgcc atagccaagg atggtaagcg ggagcgcgag 661 gagcaaatcg aaaagctgag gaacttggac atcaataact tctttattct gggcaccctg 721 caatcgatcc gcatggtcct ggagtcggtg aagccagcgt atttcgagcg caacttcgcc 781 tggcacgcca tcactcagaa cgaaggagag attagcagtc agcgggacaa tgcgaccatt 841 atgtttatga aacccatggc gtatacgcaa tatcgagatc gcttgggatt gctgcgaacc 901 acttacaatc tgaacgagga gccgcagttg tcatccgcgt tttacttcga tctggcactt 961 aggagtttcc ttaccatcaa agaaatgtta caatcgggcg cctggccaaa ggacatggag 1021 tatctgaatt gtgacgattt ccaaggtggc aacacacccc aaaggaactt ggatcttcga 1081 gattacttca ccaagattac cgaaccgact tcgtatggaa ccttcgatct cgtcacgcaa 1141 tccactcagc catttaatgg gcatagcttc atgaaattcg aaatggatat aaatgtgctg 1201 cagattcgtg gtggcagttc cgtgaacagc aagtccattg gcaaatggat atcgggtctg 1261 aactcggagc tcatcgtcaa agacgaggag cagatgaaga atctcactgc ggacactgtt 1321 tatcgaatct ttactgtagt gcaagctcct ttcataatgc gcgatgaaac ggctccgaaa 1381 ggatacaaag gatactgcat tgatctgatc aacgagatag ccgcaattgt ccacttcgat 1441 tacaccatcc aggaggtgga ggacggcaag tttggcaaca tggacgagaa tggccaatgg 1501 aatggcattg tgaagaagct gatggacaaa caggcggaca ttggccttgg cagcatgtcg 1561 gtgatggccg aacgggagat agtcattgac ttcaccgttc cgtactacga tctggtcggg 1621 attacgatca tgatgcagcg acccagttcg ccaagctcgc tgttcaagtt ccttaccgtg
```

-continued

```
1681 ctggaaacga acgtgtggct ttgcatcctg gctgcctact tctttaccag ctttctcatg
1741 tggatcttcg atcgctggag tccctatagc tatcagaaca atcgggagaa gtacaaggac
1801 gacgaggaga agcgcgagtt caatctgaag gagtgcctct ggttctgcat gacgtcattg
1861 acgcctcaag gcggtggcga ggctccaaag aatctgtctg gccgtttagt ggccgccacc
1921 tggtggctat tcggttttat cattattgct tcgtacacgg ccaatttggc tgccttcttg
1981 accgtatcac gtttggatac gcccgttgaa agcttggatg acctggcgaa gcagtacaag
2041 atcctgtacg ctccattgaa tggctcatct gcgatgacat atttcgagcg tatgtccaac
2101 atagagcaga tgttttacga gatttggaag gatctgtcgc tgaacgactc cctgaccgcc
2161 gtggagcgct ccaagctggc tgtttgggat tatccagtga gcgacaagta taccaagatg
2221 tgcaggcca tgcaggaggc gaagctaccg gccacctcg acgaagcagt ggcccgggtt
2281 agaaattcga cagcggccac gggttttgcc ttcctgggcg atgccaccga tatacgctac
2341 ctgcagttga ccaattgcga tctgcaggtg gttggcgagg agttctcccg gaaaccctat
2401 gccatagctg ttcagcaggg ctcgcatctt aaggatcagt tcaataatgc aatcctgacc
2461 ctgctcaaca aacgacagct ggagaagctc aaggagaagt ggtggaagaa cgacgaagct
2521 ctggccaagt gcgataagcc ggaggatcaa tcggatggca tctcgatcca gaacattggc
2581 ggcgtcttca ttgtcatatt cgtgggcatt ggaatggcct gcattacgct ggtctttgag
2641 tactggtggt acaggtaccg caagaatccg cggatcatcg atgtggccga agccaatgcg
2701 gagcgatcca atgctgctga ccatcctggc aagctggtcg atggtgtgat ccttggccac
2761 tcgggggaga agttcgagaa gtcaaaagct gcactgcgtc cgcgcttcaa tcagtatccg
2821 gccacgttta agcctcgttt ctag
```

By "Ir93a polypeptide" is meant a polypeptide or fragment thereof having at least about 85% or greater amino acid identity to the amino acid sequence provided at NCBI Accession No. NP_650924.3, AaegIR93a AAEL005012-PA, AgamIR93a AGAP000257-256-PA, CquiIR93a CPIJ009222, BmorIR93a BGIBMGA010960-PA, DpIR93a, TcasIR93a XP_974691.2, NvitIR93a XP_001604783.1, ApisIR93a, DpulIR93a Dappu|309629, ZnevIR93a KDR15941.1 L798_09868, and having ionotropic receptor activity. An exemplary sequence of Ir93a polypeptide is provided below (NP_650924.3):

```
                                                          SEQ ID NO: 22
  1 mnpgemrpsa cllllaglql silvpteand fssflsanas lavvvdheym tvhgenilah
 61 fekilsdvir enlrngginv kyfswnavrl kkdflaaitv tdcentwnfy kntqetsill
121 iaitdsdcpr lplnralmvp ivengdefpq lildakvqqi lnwktavvfv dqtileenal
181 lvksivhesi tnhitpisli lyeindslrg qqkrvalrqa lsqfapkkhe emrqqflvis
241 afhediieia etlnmfhvgn qwmifvldmv ardfdagtvt inldegania falnetdpnc
301 qdslnctise islalvnais kitveeesiy geisdeewea irftkqekqa eileymkefl
361 ktnakcssca rwrvetaitw gksqenrkfr stpqrdaknr nfefinigyw tpvlgfvcqe
421 lafphiehhf rnitmdiltv hnppwqiltk nsngvivehk givmeivkel sralnfsyyl
481 heasawkeed slstsaggne sdelvgsmtf ripyrvvemv qgnqffiaav aatvedpdqk
541 pfnytqpisv qkysfitrkp devsriylft apftvetwfc lmgiilltap tlyainrlap
601 lkemrivgls tvkscfwyif gallqqggmy lptadsgrlv vgfwwivviv lvttycgnlv
661 afltfpkfqp gvdylnqled hkdivqyglr ngtfferyvq sttredfkhy lerakiygsa
721 qeedieavkr gerinidwri nlqlivqrhf erekechfal gresfvdeqi amivpaqsay
781 lhlvnrhiks mfrmgfierw hqmnlpsagk cngksaqrqv tnhkvnmddm qgcflvlllg
841 ftlalliveg efwyrrfras rkrrqftn
```

-continued

>DmelIR93a NP_650924.3
SEQ ID NO: 23

MNPGEMRPSACLLLLAGLQLSILVPTEANDFSSFLSANASLAVVVDHEYMTVHGENILAH

FEKILSDVIRENLRNGGINVKYFSWNAVRLKKDFLAAITVTDCENTWNFYKNTQETSILL

IAITDSDCPRLPLNRALMTVECRINAVVFVDQTILEENALLVKSIVHESITNHITPISLI

LYEINDSLRGQQKRVALRQALSQFAPKKHEEMRQQFLVISAFHEDIIEIAETLNMFHVGN

QWMIFVLDMVARDFDAGTVTINLDEGANIAFALNETDPNCQDSLNCTISEISLALVNAIS

KITVEEESIYGEISDEEWEAIRFTKQEKQAEILEYMKEFLKTNAKCSSCARWRVETAITW

GKSQENRKFRSTPQRDAKNRNFEFINIGYWTPVLGFVCQELAFPHIEHHFRNITMDILTV

HNPPWQILTKNSNGVIVEHKGIVMEIVKELSRALNFSYYLHEASAWKEEDSLSTSAGGNE

SDELVGSMTFRIPYRVVEMVQGNQFFIAAVAATVEDPDQKPFNYTQPISVQKYSFITRKP

DEVSRIYLFTAPFTVETWFCLMGIILLTAPTLYAINRLAPLKEMRIVGLSTVKSCFWYIF

GALLQQGGMYLPTADSGRLVVGFWWIVVIVLVTTYCGNLVAFLTFPKFQPGVDYLNQLED

HKDIVQYGLRNGTFFERYVQSTTREDFKHYLERAKIYGSAQEEDIEAVKRGERINIDWRI

NLQLIVQRHFEREKECHFALGRESFVDEQIAMIVPAQSAYLHLVNRHIKSMFRMGFIERW

HQMNLPSAGKCNGKSAQRQVTNHKVNMDDMQGCFLVLLLGFTLALLIVCGEFWYRRFRAS

RKRRQFTN

>AaegIR93a AAEL005012-PA
SEQ ID NO: 24

MLPRLKWLVLVVCKLDHSRGDDFPSLISANASIAVILDREYLDAQYDDILEGTKRLFE

RILRDNFRNGGLIVKYFSWTSINLRRDFTAVLSISNCENTWDVYKNAAKENLVIMSITDS

DCLRLPLNNAIMVNLKSIVALSKESEDVRPLSLSLFRIESHTHMWEKRKAIRKVLVNLPT

RYIGRNFIAIITTQTMELVMEIAKELRMVTPLAQWLYVVSDTSADRNNISAVHPIISEGD

NIAFVYNLRRNAQSCESHMLCYVENLITSLVHGLSKLIREEKAVYGQIADEEWEVIRMTK

AERKDEILKIMRSDLIGKDSCNECSMWKVEAGETWGYTYQSAADELLTGVMSTHRKQISL

LDVGYWTPQDGFVMRDNMFPHVADGFRGVHLNFYSYHNPPWQFVTYNESGHLSLSRGVVM

DILTELSRKLNFTFNILISQTNLEYIGNMTDDANNTINRDAHSITTDIPNEILRSLMDNK

ILLAAVGATVSPKQKKYVNFTTPISIQTYSFIVSRPKELSRVFLFLSPFTIDTWLCLSAT

VLLMGPFLYVVNRLSPFYEHHGRSNTIGLGKLYNCFWYIYGALLQQGGLYLPYADSGRII

IGTWWLVVLVIVTTYCGNLVAFLTFPKIAIPITTVNQLIRNEQGVSWSIRRGTFLEQFLQ

ETDDPKYIKLHNHAGYVSEESEQMVERIRTGRHVHIDWRTNLKYLMKKEFLKNDRCDFAL

SVDEFLDEQIALAMPKNSPYLELINAELTKMHQFGFIQRWLGSYMPSEDKCSNARKSTEV

ENHTVNNDDMAGSYYVLMIGFSMGLFMFVLEYGWRWYKRSKEETLQPFTE

>AgamIR93a AGAP000257-256-PA
SEQ ID NO: 25

MVLRLVGLWSILLLLLLLLVLRPDPAVGDDFPSLLSTNASMGKLNITPLLSIILDREYLG

ADYERTLDETKNVVEKLIREHLKNGGLIVKYYSWTSINLKRDFSAVLSVSSCKNTWDIYQ

EAVRERLVMLSITDPDCPRLPTNNAIMIPRSDGSGSNAFDEVSQIILDMKSSRAINWHTA

TLLYDQVYDAEISRCILSLLEDREGIKPLTLTEFKINAPTHSWEKRKEIRRTLLGIPTAY

TGRNFIAIVNIATLTLLMEISKDLKLVNPFAQWLYLIPNTEKANSNFTTRSTLINEGDNV

AFVYNSGSKAQNCTVSVLCYIESYLLHFIRSLSKLIREEQVVFGQISDEEWEIIRPSKQE

RKTKFLQMIKAAITSKDECNKCSQWKIQSAETWGYVYRTDFLTDGADLQERRKYTMLDIG

YWSPQDGFMLTDALFPHTQYGFRGVQLIFYSYHNPPWQFVAYNDSGSPVISSGVVYDILN

```
ELSRKLNFTYTMVISQPAEINGSLVEGNTSSVYDLKTISSDIPQEIFSTLVNNKILLAAV

GATVNEKQKKFVSFTDPISIQTYSFVISRPRELSRVLLFLSPFGSDTWLCLAAAVALMGP

ILCAINKLSPYYEVHNKPTDTGLGKVNNCFWYIYGALLQQGLYLPYADSGRIIIGTWWLV

VLVIVTTYCGNLVAFLTFPKIDIPVNRVMQLLRNDRGMTWSIRRGTFLEEMLMDSTEPKY

MQLYKGSQIIGELTDELVERIEAGQHVHIDWRNNLRYLMKRQFLRTDRCDFALSTDEFLD

EQIALVMPKDSPYLELVNEEIKRMHQFGFIQRWVAQYLPAKDKCSGTGRVMDVQNHTVNS

SDMAGSYWILLLGFVSGLFVFVCEFAVAWYRKHRAARAATVAYRD
```

>CquiIR93a CPIJ009222                                  SEQ ID NO: 26
```
MAAVILDREYLDNQYEALLENTKRTFEQILRDNFKNGGLIVKYFSWTSINLRRDFTAVLS

VSNCENTWDVYRNAAKENLVIMAITDTDCPRLPSHNAIMIPKSIPASGIFEELPQVIMDM

KTMKAFSWKSAILLYDDSFDRDIVARSVLALSKESEDVLPLSLSLFRIESHTHMWEKRKA

VRKVLLGLPTRYIGTNFIAIVTATTMELVMDIAKELKMVNPLAQWLYVISDTTAEQNNIS

SVHSIISEGDNIAFVYNMRKTAASCESQTLCYIENLVNALVKGLSKLIREEKAVYGQIAD

EEWEVIRMTKVERKNDILQIIKEERVGKDTCNECSMWKVQSGETWGYTYQLPADDVLSGT

AVGRRKQVEMLDVGYWTPQDGFVMADFLFPHISHGFRGIHLNFYTYHNPPWQFVSFNESG

HPTLSGGVVMDILEELSRKLNFTYTVIVAQTNIEYVGNLTEDGNNTSIREIHTVTTDIPS

EIMKSLIDNKILLAAVGATVSEKQKKFINFTVPISIQTYSFIVSRPKELSRVFLFLSPFT

VDTWMCLGLTILMMAPLLYVVNRVSPFYEHHGKSNKLGLGKLNNCFWYLYGALLQQGGLY

LPYADSGRIIIGTWWLVVLVIVTTYCGNLVAFLTFPKIAVPITTISQLVRNNEGITWSIR

KGTFLEQFLRETDDAKYLKLSHGATFISDESDSMVQSIRNGHHVHIDWRTNLKYLLKREF

LKNDRCDFALSLDEFLDEQIALALPKASPYLDVINAEITKMHQFGFIHKWLSNYMPSEDK

CSKARKNTDVENHTVNNDDMAGSYYVLLIGFSSGMFLFLIEFGWRFYKKSKEQSLQPFTD
```

>BmorIR93a BGIBMGA010960-PA                            SEQ ID NO: 27
```
MKIWVLGVLCLAISVQGEDFPSLITANASIAVILDRQYLGDKYQTVLDELKDYIKELARV

ELKHGGVLVHYYSWTNISLNKGFLAVFSIASCEDTWELFSRTEEEDLLLFALTEVDCPRL

PQRSAITVTYSEPGEELPQLLLDLRSSNAISWKSAVILHDDTLGRDMVSRVVQSLTSQID

EESARPVSVTVFKMKHEMNEYLRRKEMHRVLSKLPVKYIGENFIAIVTSDVMTTMAEIAR

ELLMSHTMAQWLYVISDTNAHASNLSGFINTLNEGENVAFIYNITENGPDCKNGLMCYSQ

EMMSAFISALDAAIQAEFDVAAQVSDEEWEAIRPSKVQRRDILLKHMQQYILAKSVCGNC

TLWRALAADTWGVTYRQNDVPEQINEHANGSTGVIEHLELMNVGIWRPIDAMTFADLLFP

HVHHGFRGKELPIITYHNPPWTFLQANESGAIVKYSGLMFDIVNQLAKNKNFQRLPHPSN

RNALLLHGRNRQGGGTYPCGLTKGPITYNNIPLYFRAVFIAHQAGVNLKNNYYRCINYTI

PVSTQPHTFIVARPRELSRALLFLLPFTTDTWLCLGFAVILMGPMLYIVHRLSPYYEAME

ITREGGLATIHNCLWYIYGALLQQGGMYLPRADSGRLVIGTWWLVVLVIVTTYSGNLVAF

LTFPKLEAPVTTISELLKNSDAYTWSVTKGSYLEMELKNSEEPKYKRLIKEAELLKETGG

IEGTIHAARGTLDRVRGQRHLIFDWRLRLTYLMSADHIATETCDFALAVEDFMEEQVAMI

VPAGSPYLPVINKEINRMHKAGLISKWLSAYLPKPNRCLKISTVTQEVSNHTVNLSDMQG

SFFVLFLGNDKIYVYMYIAELI
```

>DpIR93a                                               SEQ ID NO: 28
```
MIYLTAVVLDHQFLGDEYQMMLEDLEDYIKELVRVELKHGGINVHYYSWTSINLKKGFLA

IFSIASCEDTWSLFLRAEEEDLLHIAVTEVDCPRLPSDSAITVTFADPGQELPQLVLDLR
```

```
TRKAFNWKSAIILHDETLNRDMVSRVVESLTSQIDDISSISVSVYKMRHENNEYLRRKEV
YRVLKKLPVKYIGENFIAIVTTDVMATIAEIARELRMSHTQAQWLYLVPDTDSHTGNVTN
LINDLYEGENIAYIFNFTDDRGCKNGLKCYAHEVLDSFISALEAAVLDELEAALQVSDEE
WEAVRPTKLQRRNSLLWHMQQYLSTRSVCGNCSSWRALSADTWGATYDRADENTSSLIEQ
VHLVQVGFWRPIDGVTFEDVLFPHIQHGFRGKQLPIMTYHTLYNTNRQLILSAIAKGHAA
LVAAPFTVSPDTHPGVNFTVPVSTQSYSFIIARPRELNRALLFLLPFTTDTWLCIAFAVV
LMGPTLYVVHRVSPYYEAMEITREGGLSTIYNCLWYIYGALLQQGGMYLPRADSGRLVVG
TWWLVVLVVVTTYSGNLVVFLTFPKLEIPVTTVSELLDSGTYSWSIRSGSFLESQLKNSN
EPKYEALLKRAELTSPSDGAENDAIVERVRIVERVRFSHHALFDWKLRLRYLMRADTEQT
DSCDFALSTEEFMDEQVAMILPAGSPYLPVINKEINRMKKAGLITKWLSAYLPKRDRCWK
TSAITQEVNNHTVNLSDMQGSFLVLFLGFFSALTVLLLEYFYNRRKNNEERTVIKPYVE

>TcasIR93a XP_974691.2                                    SEQ ID NO: 29
MLLELVLSSAFVCVIRGDSFPSLLTTNATLAVIIDREFLSNEYEVIKHAIESYLVFAKRE
ILKHGGVNVQYYSWTTINIKKDVTAIFSIASCPDTWRLFRQARDANLLHMAISESDCPRL
PPDEAITVPLITRGEELPQLLLDLRTRQTYNWNSAFILYDDTLSRDQVTRVVKSITAQYS
NLRVNAAAISFVKLETRLPMDEIRRQVKEILSSVSIKTVGGNFLAIIGYELVELLMEYAK
MFGLVNTRTQWLYIISNTHFRHKDINRFRQLLSEGDNIAFLYNNTVNNDTCTGGIQCHCE
EILSGFTRALDEAILFEWETSSQVSDEEWEAIRPSKLDRRNSLLQGIKTFLLQRGQCDNC
TSWLMKTGDTWGREYQQNGTDSGGLISVGNWRPSDGPSMSDELFPHIVHGFRKRNLPIVT
FHNPPWQIIRSNESGAVSEYAGVIFELIKELSKNLNFTYTVELAKIGQEFSANLTKNEAQ
VVTNFIPDSILDMIRNKSVAFGACAFTVTEESKRLINFTSPISTQTYTFLVSRPRELSRA
LLFMSPFTGDTWLCLSASIVSMGPILYYIHKYSPVYEYKGLSKRGLSSVQNCIWYMYGAL
LQQGGMHLPQADSARIIVGAWWLVVLVLATTYCGNLVAFLTFPKIDIPITTIDELLAHSG
TVTWSMPKGSYLERTLKYTTEPRFRYLFDKKVEVGNFKNMIEDIENGKHVHIDWKIKLQY
IMKQQYLDSDRCDLALGLDEFLNEQLAMVVSQDTPYLEIINDEIKKLHQVGLIQKWLTDY
LPKKDRCWKNNRHIVEVNNHTVNMDDMQGSFFVLFLGFLLSFFITIGEKLWHKYVTKKKM
KIIQPFTT >NvitIR93a XP_001604783.1                                 SEQ ID NO: 30
MLLALLVLLAGWIEIGTGYNDFPSLMTANATMAVIVEKGFFKSADNYRHTLDEISDVANA
VIRKNMEISGIALHVFGDADVNLARDYTVLLSVASCQTTWHLFKRAQKEKLVYLAVTDPD
CPRLPEDAGISLPLTNPGEELPQIFLDLRTTGSLSWPKVNLIHDDTFARDTISRVVKALS
LELPDKRVSLSAQALFSTRFEKNENAMRQRVHRILSNYHVDQLGSCFMVVVTVDMVSIVM
EVAKSLRLVHPGSQWLYVISDAAGREAKVTSFAELLAEGENVAFVHNATKHVANCNMGLM
CHVKELVRALAISLENSLLNELELYDRVTEEEFEVVRLSKAERKQEIVKSVNRELSYARA
HTSSCGKCVNWRFSSAITWGTSFASSEEKQRRESGEKRRRENSKRHSEDDLGEKSLGLGE
LLDAGTWSPGPGVNMSEPLFPHVEHGFRGRSLPVSTFHNPPWQIIKYSNTGAQEYGGLIF
DVLNYLSLKLNFTYTVRLASSPAAEAPTRLPSAGDSSKSMDLAAMSVAQKVPQEVVELVR
SKQVFIAASAFTVGKNSGGLNFTAAIVMQNYALLSAKPKPLSRALLFTAPYTNETWACLT
SVLIVIGPILYLTVKLSPRPRDIDNSLSLSTTWQCSWYVYGALLQQGGMSLPKADSARLV
IGTWWLVVMIVVATYSGNLIAFLTFPRIDAPIDNVDDLLARSDAFHWSFPNGSALESYLI
```

```
AAVNDDPKYKQLLDGAERQDPSKPKQILDRVKAGNQVLIDWRISLAFLMREDLIDTGGCH

FHVSAEDFMHENMAMIISGDSPYLPLINDAIERMHESGLMKKWITEKMPMKDKCWEIAKT

NQEATNHKVDMGDMQGIFFVLAIGFVIAAIAIGVEFAWHKRKEAFERSLIRPFVS
```

>ApisIR93a frameshift

SEQ ID NO: 31

```
LYIVLRLKYHKNITDGKPTIFLPLKFKFNNISIYFYNKFKRXRRRRVRICCLRLTHLSFR

QISFTNFNSILVCYTDCPRLPTDEAITIPLTVHHSELSQMILDLRMSNAFSWKSAVLMHD

NSIGDSVLQHIVTSLTKYYPSNIMSPSITIFEIYTQGSEWKRRKLFMEDLQHFLKMSEIN

SNYICIVSILYVPLILDVAKSLNLMTAENSWLIIIPDIDSSRNNTSSFTNLLSEGENISF

IYNSTKTGSKCIVRILCLVDELMSVFIMAFSALIQQEIELSQRVSEEEWDEIRPSKIDRR

QSMVSFIKFRLNESGVCETCPLWQIDSGVTWGQEHFGQGCYILPVGNWNTKTGLKLTEPL

FLHLANGFRGIALPIATFNFPPWQIVNFNRSGHLIGYSGLVFDIINQLAKTLNFTYNVIV

ISNTEQMNTTRTLFMQNNVLGEHDAVVSKPLWDKMIDLVRSEKVFIAAAAFAVKEANQIL

VNYTTHISLEPHQILVARPKELSRALLFTAPFTLLTWLCIAIVVGLMGPLLNVFHVLSPY

YEYHNIPRRGGLNSPLNCFWYVYGALLQQGGAHLPDADSGRLVVGTWWLFVLVIVTTYSG

NLVAYLTFPQMDSMVSNVADLMARKPQGYSWGIPKTSNLHSLLTTLPDDTMVKELIKNAE

HHEELSRSIIERVRSGKHAFIHRRTNLMYIMKNDFLKTNRCDFAIGNEDFAEEKLAMMLS

KESPYLSRINREIEKMHKVGLINKWLVDTLPKKDQCWTNTQLEVTNHKVNLDDMQGSFIV

LLLGVLSSLVSFVFEYILHKYINRRQIVITPFIN
```

>DpulIR93a Dappul|309629

SEQ ID NO: 32

```
MLLRVLLVLASAFIHVQSAHYELYSELRPDERWFLDDTKLIPVSCENGDCSALFNKHNKH

KIAKRAAVQVETMKDYIKFLLRGNKTKDDDTNTDPYRTANITLGVVMDKNLIGNLQTFTN

IFDVANMPSNPEIDYLRLQKFNVTYLNPQDKLPSNINAVLSILPCDVLTRFDKNLASLPI

LHIAITSDNCPRITRWAVLMVPVVKTGAELPQIFTDLRLSDTLNWKEAVVIAEEHANKEL

FDGLVDSLSRPVHKKDPLALTVVKLHGPVALRKKNFESQLLNLQVRPKGRNFILVSKQDT

ALWAFDAASHVGLVNPYSQWLFLITDSTDPAIFLPNVEDGQNISFLYNISDIETTANANS

SSERVNDLPCYTSNLLQVYVKALHQLIREEETHYFQTTEDDWIRSKPSAGDRRNNIFRTL

QNMWKDATKCSSWLNWAMKAVEIKETRKPTLLDVGVWDAAHGLVVYDDFFPHFTGGLRQR

VINVTTMEFPPWQIFERNSHGKVVRHTGLVLELTKELGNRLNFSVNVVEPADGKWGSRLS

FSRWTGMVEQVRTGSVAFAAAGFTVTADRMSAVNFSMSLDAQPYTFMFARPKQLSRAYLF

IQPYTPNAWITIFAMTIGAGPLIWAFNKITPFYDFYPDRPGSPIFSIWYNIWYCIGALLF

QGQREMPIALSGRMVVGFFWLFVIVVLTAYSGNLVAFLTFPTYTNPINTLQDLIDNKGSL

TWGILRGTALEDYLKTSDEKMYRELYEGAILHDTADDVLLDMIRNQQHVYIEWKTNLQWL

MKQDFMKTNSCDFSLGTENFFLQQVALAFPRDSPILERVNLEIIYMQRGGLIEHWRQEFW

PSADRCSETATGGSDGDTIQAISVADMQGSFYVLFFGKTKNLGTLYNLFINGKFMYE
```

>ZnevIR93a KDR15941.1 L798_09868

SEQ ID NO: 33

```
MMLLSWTTIVLFITFHQVSNAEADTDYSGTVAHLAVVIDKEFRGLDYKNLLRQMRHFLRNATHQHLTHGE

LITKFFTKTDIAVEKDITALFSILSCDDTWKIYRRYQDYHLLHLAITEADCPRLPRDDGLTVPLVAVNRV

ASQLMLDIKMSQLASWTTSILIYDESVDTETVQRIITSLSLPTLGRERSAAPVAVFKVNDTQREWERRAS

IMKLLKDEPVNRLGSNFIVAVSHEVVGVIMEVCKAVGLSHPETQWLYVIADSDAIINMSAFTSLLSEGEN

IAFVHNSRSSGVECEGGLLCHVHELLQSFVEALGVVIEDEEDFISQVSTEEWNAIQPSKRKRRSTLLDLM

KAQLIETGRCDSCLTWTLEAGDTWGLEYQEHEEEETGQKIVRRLNPVGRWSPRDGLSMSSHLEPHLRKGF
```

-continued

```
VGRDLTIISFHNPPWQIIKHNDTSQITEYKGLIFKIIDQLAENLNFRYTVIFPANNIPGWTNDSSLMKDS

EDNRTRAFLVTDRIIEILRRKKVFLAAGAFVVTPNRKTLVNFTMPVSIQTATLLTARPREVSRALIFMHP

FTYGTWACIATLIVMVTPVLNYFHRHSPYYEYYSKDNVKGGLSSHYNCLWYLYGALMQQGGMHLPEADSG

RIIVGAWWLVVLVIVTSYGGNLVAFLTFPKYEVAVTNLEELLTRRGTVSWGILKDTATEQHLKEMDYPKY

KSLFEGATIHEEQDDDLVSRVRSGSHVFIEWKLNLLKIMKKEFLSKNSCDFALGDEEFLEEQVAMMMQFG

SPYLGLVNRELRRMHQAGLIYKWYLEYLPRKDRCWTTNRLLQATTHTVNLDDMQGSFFVLGLGCAFAMVL

ICMEQCYHTYKISKEKRVIKPFAS
```

By "Ir93a polynucleotide" is meant a polynucleotide encoding an Ir93a polypeptide. An exemplary Ir93a polynucleotide sequence is provided at NCBI Accession No. NM_142667.3. The sequence is provided below:

```
                                                     SEQ ID NO: 34
   1 atgaatcctg gcgaaatgcg gccttcggct tgccttctgc tcctggctgg actgcagctc 61 tctatcctgg tacccactga ggccaatgac ttttcgtcct tcctgagcgc aatgcatcg 121 ctggccgttg tggtggatca cgagtatatg acggttcatg gcgagaatat attggctcat 181 ttcgagaaaa tcctgagcga cgtaatacgg gagaatctaa ggaacggtgg cataaacgta 241 aaatatttta gctggaatgc agtgcgattg aagaaggatt ttttggctgc cataactgtt 301 acggattgcg agaatacatg gaacttttac aagaacactc aggaaacttc aattctactg 361 atcgccatta cggattccga ctgtcccagg ctgcccctaa atagagctct aatggtaccc 421 atcgttgaga acggcgatga attcccccaa cttattctgg atgccaaggt ccagcagatt 481 ctaaattgga agaccgccgt tgttttttgtg atcaaaccca tattggagga aacgcactt 541 ctggtaaaat cgattgtgca cgaaagtata accaaccaca tcaccccaat ctccctgatc 601 ctttacgaga tcaacgactc cctgaggggc aacagaagc gagttgctct cgccaagct 661 ctgtctcaat tcgctcccaa aaagcacgag gagatgcgcc agcagttcct ggtcatatct 721 gcctttcacg aggacatcat cgaaatagcc gagaccctga acatgtttca cgtgggcaat 781 cagtggatga ttttcgtgct ggacatggtg gctcgggact tcgatgccgg cactgtgacc 841 ataaacctgg acgagggagc caacatagcc ttcgccctca cgaaacgga tcccaactgc 901 caggactcgc taaactgcac gatctcggaa attagtctcg ctctggtcaa cgctatttcc 961 aaaattaccg tcgaggagga gtccatatat ggtgagatct ccgatgagga atgggaggcc 1021 atccgcttta ccaagcagga aaagcaggcc gagattctgg agtacatgaa ggaattcctg 1081 aagaccaatg ccaagtgctc cagctgcgcg agatggcgcg tggagacggc cattacctgg 1141 ggcaaaagcc aggagaatcg caagtttcgc tcaactcccc aacgcgacgc taagaaccga 1201 aattttgagt tcatcaacat tggctattgg acaccgtgc tgggattcgt ctgccaggag 1261 ctcgcctttc cgcacatcga gcaccacttc cgcaacataa ccatggacat tctgaccgtg 1321 cacaatccac cctggcaaat ccttaccaag aacagcaatg gggtcatcgt ggagcacaag 1381 ggcattgtta tggagatcgt caaggagctg agtcgcgccc taaacttcag ctactacctt 1441 cacgaagcct ccgcatggaa ggaagaagat tcactcagca catcagcggg cggaaatgaa 1501 agcgacgagc tagttggttc catgaccttt cgtataccct atcgagtggt ggagatggtg 1561 cagggcaatc agttttttcat cgctgccgtg gcagccaccg ttgaggatcc gaccaaaag 1621 cccttcaatt atacccagcc catcagtgtg cagaagtact ccttcatcac ccgcaagccg 1681 gatgaggtgt cccgcatttta cttgttcacg gcaccttca ccgtggagac ttggttctgc
```

```
1741 ctaatgggca tcattctgct gactgctccc acgctgtacg ccattaatcg cctagctcct 1801 ctgaaggaga tgcgaatcgt gggcctgtcc acagttaaga gctgttttg gtatatattc 1861 ggggctttgt tacaacaggg aggcatgtac ttgcccacag cagacagtgg gcgcctagtg 1921 gtcggctttt ggtggatcgt ggttatcgtg ctggtgacca cctattgcgg caaccttgtg 1981 gccttcctca cgttccccaa atttcaaccg ggcgtggact atttgaatca actagaggac 2041 cacaaggaca ttgtacagta tggattgcga acggcacct tcttcgagcg gtacgttcag 2101 tcgacaacgc gggaggactt caaacactac ctggaacggg cgaaaatcta cggcagcgcc 2161 caagaggagg acatcgaggc ggtgaagcgt ggcgagcgca tcaacatcga ttggcggatc 2221 aatctgcagt tgattgttca gcggcacttc gagcgggaga aggagtgcca ctttgctttg 2281 ggcagggaga gcttcgtgga cgagcagatt gccatgattg tgccggccca gagtgcgtat 2341 ctgcacctgg taaaccgcca catcaagagc atgttccgga tgggcttcat cgagcgctgg 2401 caccagatga acttacccag cgcgggcaag tgcaacggga agagcgccca gcgccaggtt 2461 accaaccaca aggtgaacat ggacgacatg caagggtgct ttctggtcct gctcttgggc 2521 ttcacgttgg ctctttaat agtgtgcggc gagttctggt atcgtcgctt cgggccagt 2581 cgaaaacggg gtcagttcac caactgacca ctggggaatc ctaagagctc ttgccatgga 2641 atagtgtaat gaatgagcag taactggcat gtacaacgct gatgaaaatc gtatatagat 2701 ataaacattt aaataagcta tcaaatataa atatatcaat tg
```

By "Ir40a polypeptide" is meant a polypeptide or fragment thereof having at least about 85% or greater amino acid identity to the amino acid sequence provided at NCBI Accession No. NP_001260687.1 (isoform E), NP_610140.4 (isoform F), or NP_001286132.1 (isoform G), AaegIR40a AAEL014270-PA, AgamIR40a AGAP004021-PA, CquiIR40a CPIJ009722, BmorIR40a BGIBMGA010939_40-PA, DpIR40a, TcasIR40a XP_969561.1, ApisIR40a, and having ionotropic receptor activity. The sequences provided at NP_001260687.1 (isoform E), NP_610140.4 (isoform F), and NP_001286132.1 (isoform G) are reproduced below:

```
NP_001260687.1 (isoform E)
                                              SEQ ID NO: 35
  1 macnelhngy rakfltivyw iaatyvladv ysaqltsqfa rpareppint lqrlqaamih 61 dgyrlyveke ssslemleng telfrqlyal mrqqvindpq gffidsveag ikliaegged 121 kavlggretl ffnvqqygsn nfqlsqklyt rysavavqig cpflgslnnv lmqlfesgil 181 dkmtaaeyak qyqeveatri ykgsvqakns eaysrtesyd stvisplnlr mlqgafialg 241 vgslaagvil lleivfikld qarlwmlcsr lqwirydrkv NP_610140.4 (isoform F)
                                              SEQ ID NO: 36
  1 mhkflalgll pyllgllnst rltfigndes dtaialtqiv rglqqsslai lalpslalsd 61 gvcqkernvy lddflqrlhr snyksvvfsq telffqhiee nlqganecis lildepnqll 121 nslhdrhlgh rlslfifywg arwppssrvi rfreplrvvv vtrprkkafr iyynqarpcs 181 dsqlqlvnwy dgdnlglqri pllptalsvy anfkgrtfrv pvfhsppwfw vtycnnsfee 241 deefnsldsi ekrkvrvtgg rdhrllmlls khmnfrfkyi eapgrtqgsm rsedgkdsnd 301 sftggigllq sgqadfflgd vglswerrka iefsfftlad sgafathapr rlnealaimr 361 pfkqdiwphl iltiifsgpi fygiialpyi wrrrwansdv ehlgelyihm tylkeitprl 421 lklkprtvls ahqmphqlfq kciwftlrlf lkqscnelhn gyrakfltiv ywiaatyvla 481 dvysaqltsq farpareppi ntlqrlqaam ihdgyrlyve kessslemle ngtelfrqly 541 almrqqvind pqgffidsve agikliaegg edkavlggre tlffnvqqyg snnfqlsqkl 601 ytrysavavq igcpflgsln nvlmqlfesg ildkmtaaey akqyqeveat riykgsvqak
```

-continued

```
661 nseaysrtes ydstvispln lrmlqgafia lgvgslaagv illleivfik ldqarlwmlc 721 srlqwirydr kv
```

NP_001286132.1 (isoform G)

SEQ ID NO: 37
```
  1 mihdgyrlyv ekesssleml engtelfrql yalmrqqvin dpqgffidsv eagikliaeg 61 gedkavlggr etlffnvqqy gsnnfqlsqk lytrysavav qigcpflgsl nnvlmqlfes 121 gildkmtaae yakqyqevea triykgsvqa knseaysrte sydstvispl nlrmlqgafi 181 algvgslaag villleivfi kldqarlwml csrlqwiryd rkv
```

By "Ir40a polynucleotide" is meant a polynucleotide encoding an Ir40a polypeptide. An exemplary Ir40a polynucleotide sequence is provided at NCBI Accession No. NM_001273758.2. The sequence is provided below:

SEQ ID NO: 38
```
   1 atttaacata cggcaagctt acaggtgtag cttaaatatt gggatttatt gttctaatct 61 taacattatt gttcttaact cttagccctc taatttaagt ttgttctcaa gcggtatcta 121 gatgcagaat atgttgttaa actgatgtag gttagcgccc cctgagcaaa aattttggat 181 atgagatatt tggaaaacgg ttcgagcgag agctatggaa attttttttcc ctcaaaagtt 241 gaacatctct ataaataaaa agtgtatata ggatgcagtt tgttgtctat agatttttat 301 ttcaataaaa aagaaaaaca atcaataaat ggcatgcaat gaactacata acggataccg 361 agccaagttt ttgaccatag tgtattggat agcagcgacc tatgttttgg ccgatgtata 421 ttcagctcaa ctgaccagcc aatttgcacg tccagctcgc gagccaccaa tcaatactct 481 tcagcgcctg caagcagcga tgattcatga cggttaccgg ctatatgtgg agaaggaaag 541 cagttcattg gagatgttgg agaatgggac agaactgttt cgtcagcttt atgctctgat 601 gaggcagcag gtgatcaatg accctcaagg attttttatt gactctgtgg aagcgggaat 661 taaactaatt gcagagggcg gcgaggacaa ggcagtactc ggagggcgtg aaacactgtt 721 tttcaacgtt cagcaatacg gatcaaacaa ctttcagctc agtcaaaaac tttacactcg 781 ttattcggct gtggctgttc aaatcggatg tccctttcta ggtagcctca ataatgtctt 841 gatgcagttg tttgagagcg gaatcctaga taagatgacc gctgccgaat acgcaaagca 901 gtaccaggag gtagaagcca cgagaatata caagggcagc gtgcaggcga aaaacagtga 961 ggcttacagt cgaaccgaaa gctatgacag cacggttatc agtccgctta atctacgaat 1021 gctgcagggc gcttttatcg ctctcggagt tggttcattg gctgcaggtg taattttgct 1081 gttagagata gtatttataa aactggatca agcgcgattg tggatgctgt gctcacggct 1141 gcaatggatt agatatgaca ggaaagtgta agtcagtgta ttttatttgc tgcagccgct 1201 ttaaataata caataaacgt cagatcctt
```

>AaegIR40a AAEL014270-PA

SEQ ID NO: 39
```
MNKVLATPASKADKLESLISIGLVVQNLCSQLQSMRMEAHLSNPSLLQELVDKLPANIKL

HWALHQRQVPVVDFRAFTYHAHLAPLPDLSNHSGMVLGLSEMINLLAPKTLAILVLKETK

IDKIDRLTVMIHHHNIPTCIFNNQDEYFQYIGNNLKKSLETTSLLFCHPEEMLGELIDRR

LAHRLSLYIFYWGARKAPTNLDRSLMREPLRVAVITNPRKNIFRIFYNQAKPNNRGELLS

ANWFDGNDMTFQKVPLLPIPTTVYKNFEGRVFTIPVIHKPPWHFVTYRKVNESSLNETDV

DQLELSANGTDNEQLEVFEVTGGRDHNLIQLIAHRMNFSFKYVDQEDRIQGTAVGPPENA

IFTGALGMLQRREVDLFLGDVAVTWERMQAVEFSFFTLADSAAFVTHAPRKLSEALALVR
```

-continued

```
PFQVAVWPLVLLTIMMSGPILYMIIAMPYRLEDWARGTMARRRREKVQRGSAFYHMQYIQ

EMNYGTLPGGAEIAGTPRHPSLDRCIWYTINVYLRQSATIPYNGHVSRFFSILLWLCATY

VLGDVYSAQLTSQLARPAREGPIDTLGKLEVFMERDGYQLLVERQSAFQAALVNSTGILQ

RLYRITQRQSHNESYLVSSVEEGIRILVDNSKRAVFGGRETLYFNTKRYGAHRFQLSEKL

YTRYSAVAVQFGSPFLDSLNEVIMRLFEAGIIEKITIAEYERMFGSQLGQFGDESAKTTK

PESFETEGGKSKKSTESNEKLQPMNLRMLQGAFLALACGHSLGVLTLVLENKTKCIQISF

GWIKAWLHRIGLIFCKLGKVVWRSWRRLHNDD
```

>AgamIR40a AGAP004021-PA                                     SEQ ID NO: 40

```
MGVGSNSKYILALVLLRVALVWGAFPTQRNLIALYERSNQSGMIRGISEMVNLLAPKSLV

ILVQNETKIDRLDKLTVMIHHHNIPTCVYYDLEAYFSLIEENLKKSLEITSLIFCHPEDM

LQDITDRRLAHRLSLFIFYWGAAQLPPTLNPNLLMEPFRVAIITNPRRNIFRIFYNQAKP

NNRGDMLSVNWEDGNDMTFKRVPLLPSPTEVYKNFEGRIFTIPVIHKPPWHFIVYGNGSA

SVGDNQNSSSSDAAGGFELELDENVTVESDDTYFTVKGGRDHNLMQLIAERMNFTFQYVE

PPEKIQGIALGSEDNASFSGALGMLQRREVELYLGDVAVTWERMKAVEFSFFTLADSAAF

VTHAPRKLNEALALVRPFQITVWPPVIITILISGPILYIIISTPYRWRSAQTVHARNARW

RPTRSRLRKPAFYNLRYIEEMSYTRFRAERTSLINNHHHSRGQDYPSLDRCIWYTINVYL

RQSANIPFDGHLARFFSILLWLCATYVLGDVYSAQLTSQLARPARESPINTLGRLENRMN

REGYQLLVERQSAFHAALVNSTGVLQRLYRLTRQRSVNDSFLVKSVEEGIRVLQADPKYA

VFGGRETLYFNIKRYGANRFQLSEKLYTRYSAVAVQIGCPFLDSLNEVIMRLFEAGIVEK

ITIAEYEQMFGRQKGGVSHAEETVRTVKSTNSECDTDGIGSGKRKTDSNDKLQPMNLRML

QGAFLVLACGHLLGGICLFIERHMGMINPCGDILRQGWRHLNRVVRKLGRGGSFKTQSN
```

>CquiIR40a CPIJ009722                                         SEQ ID NO: 41

```
MKVGIVWCLFVLLGRSFVQAYHSQLVPIADPSNHSGMVTGLSEMINLLSPKTLVLLVLNE

TKIHKIDRLTVAIHSYNIPTCIFYDLEQYFEYIANNLKNSLDTTSLLLCHPADMLVDLVD

RRLAHRLSLYIFYWGARRLPAGFDRALLREPLRVAVITNPKKKIFRIFYNQAKPNNLGEL

LSANWFDGSDMTFKRVPLLPTPTEVYKNFEGRVFTIPVIHKPPWHFLTYTNLNESCNDTD

TEFDMANVTSFQVTGGRDHNLMQLIAARMNFTFRYIEPEEKIQGTAMGSGDNVSISGALG

MLQRREVDLFLGDVAVTWERMQAVEFSFFTLADSAAFVTHAPRKLSEALALVRPFQVTVW

PLVIFTIILSGPVLYLIIAMPFRLEDWMKGTLDKARRLQVRRGPPFYDMQYIREMGYGLV

PRADIAGTPQHPSLNRCVWYTINVYLRQSATIPYNGHVARFFSILLWLCATYVLGDVYSA

QLTSQLARPAREGPINTLGKLEELMESPGGGYQLLVERQSAFQVALANSTGILQRLYRIT

QRHPDNESYLVGSVEEGIQILLVNSKRAVEGGRETLYENTKRYGAHREQLSDNLYTRYSA

VAVQFGSPFLDSLNEVIMRLFEAGIIGKITVAEYERMFGSKSGGQFADETVESTKSDDGV

DATGKAKKSAESSEKLQPMNLRMLQGAFLALGFGHSVGAIILLVENQLKGIKSVYQRVLG

VLTRTGRVVRKIWTAIRRSL
```

>BmorIR40a BGIBMGA010939_40-PA                               SEQ ID NO: 42

```
MTKLPKDFNVAIKDIAESLPSKEMTVVRGNSTNIRSQDVFELLRLLCQHNIQVVNLDIAA

MENKEMYYGYLKKALDVSDERTNLILCEPYECENLLLELRENNLIHRTILYIFFWPYGSV

SDRELNTMVEAMRVAVITNPRESVERIYYNQATPNRLNHLSLVNWWAFRLYKSPLLPSAD

KVYKNFRGRVFDVPVLHAPPWHFVKYNNDSSINVTGGRDDKLLKLIANKLNFRYRYYDPP
```

-continued

DRSQGSGIIGNGTFKGTLGLIWKRQADFFLGDVTMTWERLQAVEFSFLTLADSGAFLTHA

PAKLSETLAIIRPFRWEVWPLVCATLFITGPALWIVIAAPSLWQRKKRDQMGLLNNCCWF

TVTLFLRQSSTKEPSSTHKARLVTVLISLGATYVIGDMYSANLTSLLARPAKEPPIGTLP

ALEEAMREHGYELVVESHSSSLSILENGTGVYGRLAKLMKRQRVQRVHNVEAGVRLVLNR

RRVAVLGGRETLYYDTERFGSHNFHLSEKLYTRYSAIAFQIGSPYLETINNVVMTLFEAG

ILGKMTTDEYKNLPEQSRRSEPVTESENLSTEKTGETAAVTQIQNETSKGLEPVSLTMLR

GAFCLLGIGHLLAGVTLLIETQLYRRARKRALPPQTRNPTNTFKAKAKKCILRGWRRIKA

AAILAIDRALAPDRGID

>DpIR40a Derived from BlastP against genomicsequence
SEQ ID NO: 43
MILTYIILLCVRDTQCLFEVRDSVDVNLKQLPKDFSKAVVDIAIGLPTNTITVVRGNSTD

VRDADIFELFCSLGDNNIQVTNLDLMTPESKDIYYKYLKEGLDNSEERTSLILCKPKECE

DLLLEVTSNNFIHRPILYIFFWSEDEVPKNFTTCIKEAVRVAVITNPRKGVERLYYNQAN

PNKPRHLKLVNWWAGQLYKSPSLPPANKVYEDFQGRILNVPVLHAPPWHEVRYMNDSTVN

VTGGRDHKLLSLLAKKLNFKYKYYDPPERSQGSRISGNGTFKGTLGQIWQRKADFFIGDV

TMTWERLQAVEFSFLTLADSGAFLTHAPDKLSETLAIIRPFRWEVWPLVFATILVTGPAL

WVVIATPYIWQRRERDQMELLNNCCWFTTSLFLRQTTRKEPSTSNKARLVSILISLGATY

VIGDMYSANLTSLMARPSKEQAIGTLVALEEAMRNDGYELVVESHSSSLAILQNGTDIYG

RLARLMRRQRTQRVKSVEVGVNMVLSKRRIAILGGRETLFYDTERFGSHNFHLSEKLYTR

YSAIALQIGCPYLETFNNVLMTLFEAGILTKMTSDEYRNLPEQSRRSEKVTESESKENND

VTENSPTAQIQPESTIGLEPVSLTMLRGAFCLLGIGYFIAAVVLATEIEIQRRKRSRAER

VMDTSLFPKSPRMYLRHYLIRIFRTMYNIVDGALRPEMKE

>TcasIR40a XP_969561.1
SEQ ID NO: 44
MRRDHGGDLVSASFDIVAGFLFEEICICFDKNININFLQHLLVRFVSNNIAIKLFNITTV

EVQDKYFAFLNYQVINHLGANTIFFSSHKFYEHVLLEINERDFIRRNLIYIFNWGRRPFS

RYFVRNIINVMKVFVITNPRNDTFRIFYNQAVPYKKHHLEMVNWWQHGVGLFNHPTLPAK

YNNVFKDFKENVFKIPVIHKPPWHFVQYGNDSIKVIGGRDDRILSLLSKKLNFRYDYFDP

PERIQGSSASENGTFKGVLGLIWKRQAEFFIGDVALSHERANYVEFSFITLADSGAFITH

APSKLNEALALLRPFQWQVWPAIGVIFVVVGPVLYAIIALPNAWRPRFRVRSHARLFFDC

TWFTTTVLLKQTGKEPSSSHKARFFIIILSISSTYVINDMYSANLTSLLAKPGREKAINN

LNQLEKAMATRGYDLYVERHSSSYSLFENGTGIYSRLWQMMNRRQTHFLLESVEEGVQLV

RDSTNKAVIAGRETLFFDIQRFGASNFHLSEKLNTAYSAIALQLGCPYIEEINKILMAIF

EAGIITKMTENEYEQLGKKKQTTSETEKELIPGVKKENRRVAKVSEDNEKLQPISIKMLQ

GTFYLLCIGNIFSGFILLAEILVYKHRKTYKHKKRRHRFVYLRKIRHSVASKFGAVVDAV

RRVYRRAMHDAFVATLEYLE

>ApisIR40a
SEQ ID NO: 45
IYIFFLIRSTIYYVSFSGRDIFKNTVASAICNEYSIVVLTNXNANIIMLILINIIFISLY

LSSSIILIDYNTYLIIQNLLVNVTIYINIYRLLGLHRDGDFLFFTQIRRSNLMSRNVVYV

FLWLRSSVSRTFKADILEAMRVCVITSPRPGFYQIYYSQASARPGYGSSLKMVNWWSAMD

GLVRFPLLPPPKQVYKNFEGRYFNVPVLHKPPWTFVEYLNDSFRVEGGRDDKLINLLADK

LHFQFKYIDPPDRYQGSGLDRGSSMQGVLGLIWQREADWFVGDLSITYERNLVVDFSFLT

LVDNEAFLTHAPGRLNEAFSLIRPFHWSVWPLLLITVIFAGPILYILVDTTDGHPQGKSM

```
LYWKCVWWSVTVFLQQAAIIPSENNKIRFVAGLLMLSVTYVIGDMYSASLTSILARPPKE

PPINTLKELSEAMRDSGLQLLVEVQSASQAMLENGTGVYEELSQLVTRQREYLIGSTEKG

MQLVRDNKNYAVIGGRETFYYDIKRFGAQHFHLSEKLNTRYSAIAFQRACPYRDNFDDVL

MRLFEGGILSKITEEEYQKLNDKLMGSEEFDSTSVVIEPVLEGSEPRQEDDDKQLTIAMS

MKTLQGAFYVLAIGSILAGLLLLIEMRSHDKLEKDKVIKLVEAPFVYKRKVPNKFQNRLY

DLK
```

By "Ir68a polypeptide" is meant a polypeptide or fragment thereof having at least about 85% or greater amino acid identity to the amino acid sequence provided at NCBI Accession No. NP_648455.2 (isoform A) or NP_001287031.1 (isoform B), AaegIR68a AAEL005039-PA, AgamIR68a AGAP007951-PA, CquiIR68a CPIJ001503-504, BmorIR68a BGIBMGA006657-PA, DpIR68a, TcasIR68a XP_968308.2, NvitIR68a XP_001606197.1, ApisIR68a XP_001945663.1, ZnevIR68a KDR18055.1 L798_07732, and having ionotropic receptor activity. The sequences provided at NCBI Accession No. NP_648455.2 (isoform A) and NP_001287031.1 (isoform B) are reproduced below:

```
NP_648455.2 (isoform A)
                                                   SEQ ID NO: 46
  1 mrclwiliva fislamatsi pipianpapl sgyemqlkil lqkilwvanv krcfavitdd 61 lhypiydrif fesvgrrvip ffvmrtnesd dlqrpsrqve lfvkaikssd celnvitiln 121 gwqvqrflgy iydnrslnmq kkfvllhdlr lfesdmihlw svfidaiflk rqldnkytis 181 tiafpgilsg vlvmknianw elgkglngri lfadktsnlf gtslpvaise hvpmvlwana 241 tksfqgveve imnalgkaln fkpvyykpnq tenmdwteld ggasvaygsg npdgyaqngt 301 hidsmlvdev aahsarfaig dlhlfqvylk lvelsaphnf ecltfltpes stdnswqtfi 361 lpfsagmwvg vllslfvvgt vfyaisflna iingnvssef frclrpnrnv pmdpkiyrri 421 sfriaisryr sskgdrmprd lfdgytncil ltysmllyva lprmprnwpl rvltgwywiy 481 cillvatyra sftailanpa arvtidtled llrshippst gatenrqffl eandevarkv 541 gekmevfgys ddltsriakg qcayydnefy lrylrvades gsalhimkec vlympvvlam 601 eknsalkprv dasiqhlaeg gliakwlkda iehlpaeala qqealmniqk fwssfvalli 661 gyvismltll aerwhfkhiv mkhpmydvyn pslyynfkri ypqh NP_001287031.1 (isoform B)
                                                   SEQ ID NO: 47
  1 mrclwiliva fislamatsi pipianpapl sgyemqlkil lqkilwvanv krcfavitdd 61 lhypiydrif fesvgrrvip ffvmrtnesd dlqrpsrqve lfvkaikssd celnvitiln 121 gwqvqrflgy iydnrslnmq kkfvllhdlr lfesdmihlw svfidaiflk rqldnkytis 181 tiafpgilsg vlvmknianw elgkglngri lfadktsnlf gtslpvaise hvpmvlwana 241 tksfqgveve imnalgkaln fkpvyykpnq tenmdwteld ggasvaygsg npdgyaqngt 301 hidsmlvdev aahsarfaig dlhlfqvylk lvelsaphnf ecltfltpes stdnswqtfi 361 lpfsagmwvg vllslfvvgt vfyaisflna iingnvssef frclrpnrnv pmdpkiyrri 421 sfriaisryr sskgdrmprd lfdgytncil ltysmllyva lprmprnwpl rvltgwywiy 481 cillvatyra sftailanpa arvtidtled llrshippst gatenrqffl eandevarkv 541 gekmevfgys ddltsriakg qcayydnefy lrylrvades gsalhimkec vlympvvlam 601 eknsalkprv dasiqhlaeg liakwlkdai ehlpaealaq qealmniqkf wssfvallig 661 yvismltlla erwhfkhivm khpmydvynp slyynfkriy pqh
```

-continued

\>AaegIR68a AAEL005039-PA

SEQ ID NO: 48

FPFPLRGVFISRRLDFWFNGKFRKGRKLFSDKTTNLDGQSMKVVVLEHTPAIFRTTHNET

DEHLKYYGLEVELLKAISEAMKFEMDFYESDDAAVAMWGTVTDGENATGLLGEMMSHKFL

HCFNYVFQNEGHADFALADLHHTQYHLEIMDLSIPYNTECLTFLTPEALTDNSWTTLILP

FTGGMWAGVLASLFSIGTVFYALSRLLMFVRHEQSYRSDLDMIAKRSRKRNRKVHFKIVC

GMVNSYKRALDPLPPRDIFDTFSGCIIYTYSMLLLVSLPRLPKGWPLRLLTGWYWIYCIL

LVVAYRASLTAILANPVARVTIDKLKDLADSPIRCGAWGEQNKLFFQSASDQVSMQIGQK

LEHTPKAEAAVERVVEGHFAYYDNVYMLKHLRATRKSAKARETLHIMEECAVHMPISIGL

EKNSPLKPKVDKYVRALVEAGLTKKWLADAIEEFQSNVEIPPQEATMDLQKLTAAFIALA

IGYGVSLLAFSAEKLYWRFVVEKHPAYDKYIVGSYRGKVVRF

\>AgamIR68a AGAP007951-PA

SEQ ID NO: 49

MCKTSRLVWILTAFVLILGVKHCANKQLNSATKGNDRKSSQSIHHEEYSTELHLEMLLLE

LAAKMDYGHCYVVLFDEVYESVLNAAFFRQIHRAARYIVKIEQDEDTFNPRPSLKCILES

TRKAGCGGYILLMANGIQMALYELSTAPFPMQIKGVFFSKILNFWQGGKFRLANSTFFDD

KTKDLRRQEMRVVVLEHTPAVFKSATTSNYYGLEIELLKAISKAMHFQMVFYETSDADKE

RWGRLGGNGTLTGIIKEMQEGKADFALADLHHTEYNLGFMDLSVPYNTECLTFLTPEALS

DNSWKTLILPFNGEMWAGVLLSLFAVGFVFYAFSNTLMLKWLRHKKPKTNMSKSSAYDRN

KLKKLRMIPFKRQPEPWHDPLPANDMFDTFSDCIIYTYSMLLLVSLPRIPEKWPLRMLTG

WYWVYCVLVVVAYRASFTAILANPIPRVTIDTLQDLAESSVRCGAWGEQNRLFFQMAQDQ

YSQTIGAKLEHAPNQNEAVEKVSEGLYAYYENIYSLRQLRSTRKSEKARQTLHIMQECAV

HMPISIGLGKNSPLKHQVDLYVRALIEGGLTRKWLSDAIEQFQSNVEIPPQEAIIDLKKM

YAGIVALCFGYVIALFAFVVEKIYWRYYIENNPAFDKYLHGIVFRGRG

\>CquiIR68a CPIJ001503-504

SEQ ID NO: 50

MEVVKICLVFALAIAIASAALNHTLFEDENDLVDFGRLIVDLVGKTKPGHCYAFVTDPIY

RVTLTDTLFKEIGGHPRFVVEIPEDEDTLRPGKQVRCMLEEIRKIGCGAYVVLIANGIQM

ERFLRYGDKTRILDTRAKFIILYDYRLFVPELHYLWKRIVNVVFVRTLTVENSHKRSHFE

LSTVPFPLPLKGVFVSKRLDFWHNGKFRYGRKLFSDKTASLDGQTMRVVVLEHTPAIFRT

TLNETSGERRQRIKYSGLEVELLKAVAQAMRFEMSLYETEDAGTEKWGTIMEDDNSTGLL

GDMNEGRADFALADLHYTLYHLQIMDLSIPYNTECLTFLTPEALTDNSWTTLILPFTGGM

WAGVLVSLFSIGTVFYALSRLMMYIRHEKIYRRDLELVAKRKKVKSAKRVRFGNLKFLAV

KIMITNKMKTSKISKLRTRINHVIKRKPVEKDTLDLSKLKMLKMVPFKRQALPWRDPLPP

RDIFDTFSGCIIYTYSMLLLVSLPRLPKGWPLRLLTGWYWIYCILLVVAYRASLTAILSK

PVARLTIDKLKDLAESPIRCGAWGEQNRLFFQTAQDKPSMIIGGKLEHTPDPDAAVERVV

RGNFAYYDNVYSLKHLRSTRKSEKARQTLHIMEECAVHMPISIGLEKNSPLKPKVDKYVR

ALVETGLTKKWLADAIEAFQSNVELPPQEATMDLQKLTAAFIGLALGYGISLLAFGVEKL

YWKCVIERDPAYDKYLTGTCHRRVIRR

\>BmorIR68a BGIBMGA006657-PA frameshift

SEQ ID NO: 51

TIMPLTLFSRSPRSGKTRAVSKASPILEDIYEQKDLEFVLVDLLNHAGRYHDFTCVAVIC

DAIYYNVFDGAFFKRIDTVPFVMIVVEEYDDLLSPNFDILEALREARRDGCNMYIILLAN

GLQAARLLKFGDRHRVLDTRAKYIILHDYRLFHSDLHYLWKRIVNVIFLKHHRKIGSVAK

-continued

SQAWFDLSTVPFPNPIKGVFVPRRVDLWKSGKFHYNTVPFDDKTSNLNDEVLHVVYLDHV

PSVVVVNSNETGQIGGVEIEIINTLSEKMNFRPKLYQPMNVELHKWGQKQPNGSFSGLLG

EMVNGRADLALGNLQYTPYHLELIDLSIPYTSQCWTFLTPEALTDNSWKTLLLPFKLYMW

IAVLLVLXITGTIFYGLARYQTYLHGLKRQEEMKKPVYSKPVGLYLFGEIINSILYTYGM

LLVVSLPKLPTGWSIRFLTGWYWLYCILLVVSYRASMTAILANPAPRVTIDTLVELAASK

LTCGGWGIETKNFFQDSLDEIGQKISDRFEISNDPNIAADKVAQGTFAYYDNKNFLKYIT

VRRQNGFIMETIDNTTNFTSISTKSNNERNLHIMSDCVVNIPISIGFHKNSPLKPLTDIY

ITRIVEVGLVEKWLNDAMYTIKTLETNEEEIKALMNLKKLYGAFIALAIGYFLSVMCLIG

ELAHWNCVVKKDPNYDKYALHKYYEKINKK

>DpIR68a
SEQ ID NO: 52
SVMSYPGAMSRPRWWKDVVFWESYVQTRADTSRIIKNIEISKDLQDLVADLINYLVRRDD

VTCLTVVSDPVYLNVFEGALFKGIYTVPNIMIVVEEREDLLSPNFNTLESLRQARNDGCN

VYLIILANGLQVTRLLKFGYKHRLLDTRAKYIMLHDVRLFHSANHYLWKSIVNVIFLKYH

SKVIGDVKSKAWFDLSTVPFPNIIKEIFIPRRVDIWRRNKFHYGRDLFADKTGNLYDEVL

NVVYVDHVPSVVVTKSNATNKVGGVEIEILKTLAQKMHFKPKLYEPINAESQKWGHKQDN

GSFSGLLGEMVNSGADVALGNLQYTPSHLEMTDLSIPYTSQCWTFLTPEALTDNSWKTLI

LPFKLNMWIAVLLVLLVTGSIFYGLAIYYMNLLNYKGVSEGFEANDRKMSYTKPVGLYLF

GEISNSILYTYGMLVVVSLPKLPTGWSIRLLTGWYWLYCILLVVSYRASMTAILANPTPR

VTIDTLQELVDSKIACGGWGSETKNFFLESLDEMGQKIGEMFENVDDPEQATNKIAQGIF

AYYDSENFLKHLTVKRKNMVLMTSPENNTRDRNLHIMKDCVVNIPISIGFHKNSPLKPLA

DVYLRRIVEVGLVEKWLNDAMYKIRTREKNEEEVKALINLKKLYCAFVALSIGYTLSSIC

LFLEFMHWHFVVKRDPGFDKYAMNEYYMHKNKKK

>TcasIR68a XP_968308.2
SEQ ID NO: 53
MIKNLLPYKCVVLISDDIYGGTFTKSWYRRFGPFITFVVIRVDEYEDLLSPFEETQACLD

TAKNEGCQMYLILLSNALQVSRLLRFGDKYRVINTRAKFVLLYDNRLFDKPLFYLWKRII

NVIFIRRYSGQKSDTKKNMPWYEITTVPFPTQITSILIPRRLDIWTKSKFRKGIDLFRDK

TSDLRNQTLKVAAFSHIPGTTKSLQEKTARTVIGNFSGTEVEILQTVSAAMNFHCELYEP

VNVDVDLWGGKQSSGKYTGLVGEMVSTNADIALGDLYYTPYILDLMDLSIPYNTECLTFL

TPESLTDNSWKTLILPFKYFRPAMWAAVLVCLLICGAVFHALARFHETISQNKSQVLEIH

TKRKKIIILSICPEIEKLDSNLKYTKMREQYKPPRFEGQSIGLYQFSEPFNSVLYTYSML

LLVSLPKLPTGWSLRMLTGWYWLYCLLLVVAYRASMTAILARPTPRVTIDTLQELVNSRL

KCGGWGEINRQFFKSSLDPITKLIGENFELVNDSNEAVDRVAQGVFAFYENSYYLKEALV

KRQLRFQIARTTQNQSEREMRDIAREDRNLHIMTDCVIKMPISIGLQKNSPIKPRVDKYI

RRVLEAGLIKKWLQDVMASILNAEVQSTQEEMKAIMNMKKFFGAIVALFIGYFISVVVLI

VENVYFHFFVKRNPHYNKYTRSIHHVKKAE

>NvitIR68a XP_001606197.1
SEQ ID NO: 54
MYFLIVLIICLGTSLSVTDNRRLIYPASNKQLQTLVKLLIEEVAENSRCIVSMVDTYYRR

KVDISQIKANKFLPTYRVLIRENEEFSPPRRRLLRILKESKHLGCDVYLIMMANGLQVAS

LLRYAEEERLMNVQGKFLFVYDFRIFHVEMLYLWNRIINVIFIRRYVEFKRRSSNRQLQK

YEWYDLNTIPFPARKKGLIVTRYIDTWYQNRFRYGINHFTAKTDDLRRQKLQVAVFEHVP

AVTEDAQAYYKSQKDVGSNSKPLGIEFEMILIIANALNFKPYFYQPDNIQTERWGDSKND

-continued

```
TYTGLFGEAKEGKAVFYLGDLHYTSRHIQILDLSWPYNTECLTFLTLESLTENSWKLLIL

PFRLNTWLAVLFTLVFACATSFVFSRFYMRHVNVGENNDSDARKVFSKSKTMKVLEKRPV

QAEEWKGLYLFTDPQNSVLYTYSMLLQVSLPSLPRAWSLRVFIGWWWIFSILIAVTYRAS

MTATLANAIDRVTIDTIPELGKSNVAVGSWNDETREFFINSSDPYLQKLSRRYVVTKDEQ

SALAAVANGTLCYYENVYVLQRERVKRQILEDELQKNGSQGKHKFQDHNLHIMEECVVNM

PISLGMDKHSPLKHHVDKLVKRIIEAGFVEKWLSDITQQSKILELRGEGIADKALIDLDK

LQGAVVALGIGYLFSLLALAAETWHWRYIVMRHPNFNKY

>ApisIR68a XP_001945663.1
                                                         SEQ ID NO: 55
SYKEIKWNSEFENLAVDITYKWKDTATCLNLILDNFHNGILDKAFYRAVSGIPLFKTLVD

ESEDLMSPNFQTWQILNHVRKEGCNMNIIFILNADQTMRLLKFSDKHRMLDSRTKFILLH

DRRLFTKQHHTIWTKIINVVFIRKYRLKDMYELSTVPYPAPIKGALVTLRLDIWNKRNFQ

KKTDLYTDKVSDLQGNLLKVVTFNYIPSAIKNSVINENEENSGYKKGLEIEVLKSLGSAM

NFIPVIYEPINWRTEQWGKKQINGTISGLLGEVWSARADLALGNLHYTPYHLNILDLSIP

YNTECLTFLTFESKTDNSWKTLILPFRLNMWVGVLITLLIGGFLFYALATAHKHIEDSEN

SIKMIQCDTMKTKILEKKPELLTKNKGITKRNSILYTFGMLVAVSLPKVPSGWAIRILTG

WWWMYCLLVVVAYKASMTAILANPDTRVTIDTLDALADSNINCGGWGEQSKEFFMTSLDK

TGQRVGQKFQEVYEVDKAIDLVSKGQFAYYDNIHFLRYVKVMQNTKTYEKNSQFINDFTL

HIMSKCIINMPISLGLQKNSPLKPAVDRFLRRVIEAGLVKKWLNDVMLDTVILEEPQQIE

EVKALMDLKKLYGAFVVLVAGYILSILVLLIEIGYWYGVVKKDPLFDEYSLNCYYAQQ

>ZnevIR68a KDR18055.1 L798_07732
                                                         SEQ ID NO: 56
MLSDLNCLVIMNDNIQQDIFEGHFFKKLGSVPYYKVLVKEKEDLQSPNYKTLSVIRHVKRAGCQVYILMI

SNGGKVSRFLKFGDRHRVLDTRAKFILLHDHRLFHSSLHYLWRKIVNVVFLHQQGRHHGSVITRQKIHPW

YDISTVPFPSPIDSTFVPLHLDTWHQGKFRSGADLFRKKTSDLRGQQLRVVTFQHLPASVKMASPSLRID

SVVEGNGPVGFGGLEIEVLRTLATVMNFHPDVYEAENADVEQWGRRQLNGSYSGLLGEVMSGQADIALGN

LYYTPYYLELIDLTIPYTTECLTFLTPESLTNNSWMTLILPFRPLMWAAVFVALILAGFVFYALANYHIH

IVSTAMNLQTNNAIMVQERSKINDSKVIHIQEERNKTGDGLYLFSKLENGILYTYGMLLLISLPKFPSDW

SLRVLTGWWWIYCILLVVAYRASMTAILANPTPRVTIDTMEQLVDNHITCGGWGEEIKQFFLTSLDISGQ

KIGLKFEVIYDTDLAVEKVAKGEFAYYENIYFLQYLRVRRQLIVKEVGTKKDVNTNEESGGNRNLHIMHD

CVIHMPVSIGLQKNSPLKPHMDRFLRRIVEAGLIKKWLKDVMLSIVSVDNTDKEDGNKPLMNLQKLYGAF

VALGVGYLISICAFAGEKIHWQCVVKKSPLFDKYAINIYYDHQKSSKAIKK
```

By "Ir68a polynucleotide" is meant a polynucleotide encoding an Ir68a polypeptide. An exemplary Ir68a polynucleotide sequence is provided at NCBI Accession No. NM_140198.3. The sequence is provided below:

```
                                                         SEQ ID NO: 57
  1 cattatctgg ttaaacttat taacccctgg ccgcaaaac tttaattagt taaccctgtg 61 cccgctggaa actcggaatg cgagtaaatc aggttgatga gtgactgact gactggctgg 121 ctgactaacc gacagtccgt tggctaccgg ttcacgagt tcggacaact ttaattagat 181 ctgcatatgc aatgaggact cgagggttcg ttccggtaaa caggttaacg aactgccgga 241 acggacaagt ggccaacagt ttgcgtttgg cggcgaaagg atgcgctgtc tgtggattct 301 gattgtggct ttcatatccc tggcgatggc cacctcaatt cccattccca ttgccaaccc
```

-continued

```
 361 agcaccactc agtggatatg agatgcaact gaaatattg ctacagaaaa tcctgtgggt 421 ggccaatgtg aagagatgct ttgccgtcat tacggatgat ctgcattatc ccatatacga 481 tcgaatattt ttcgaatcgg tgggtcgacg agtgataccc ttctttgtga tgcgaactaa 541 tgaaagtgat gatctacagc gaccttccag acaagttgaa ctctttgtta aggccatcaa 601 atccagtgat tgtgaactaa atgtgatcac catactgaat ggctggcagg tccaacgatt 661 tcttggctat atatacgata acagatcttt gaatatgcag aaaagtttg tattattaca 721 tgatttgcga cttttgaga gcgatatgat tcacctatgg agcgttttta tcgatgccat 781 tttcctcaaa aggcagctgg acaacaagta taccatttct accatagcct ttccgggcat 841 tttaagtggc gttttggtaa tgaaaaatat tgctaattgg gagttgggaa aaggtctgaa 901 tggaaggatt ctatttgcgg acaaaacaag caacttattc ggaacctctt tgccagttgc 961 catttccgag cacgtgccca tggttctatg gcaaatgca accaagagct tccaaggagt 1021 cgaggttgag attatgaatg ccctgggcaa ggcacttaat ttcaagcccg tttactacaa 1081 gcccaatcaa acggagaata tggactggac ggagctggat ggtggtgcta gtgttgccta 1141 tggaagtggt aatccggatg gatatgcaca gaatgggaca cacattgact cgatgcttgt 1201 ggatgaggtg gctgcgcaca gtgcccgctt tgccattggg gatttgcatc tgttccaggt 1261 gtaccttaaa ttagtggagc taagtgcgcc gcataatttc gaatgcctga cctttctcac 1321 accggaatcg tcgacggata actcctggca gacctttatc ctgcccttca gcgctggaat 1381 gtgggtgggg gtgctgctct ccctttttcgt ggtgggcact gttttctatg ccatcagttt 1441 tttgaatgcc attatcaacg gcaatgtgtc ctctgagttt tttcgttgcc tacgaccaaa 1501 tcgcaacgtg cccatggatc caaagatcta tcgtcgcatt agttttcgca ttgccatcag 1561 tcggtatcgt tcatctaaag gagatcgaat gcctcgcgat cttttcgatg gctataccaa 1621 ctgcatcctc tcacgtata gtatgctcct atatgtggcc ctaccccgaa tgcctcgaaa 1681 ttggcccctg agggtactca ctggttggta ctggatctac tgcatcctct tggtggccac 1741 atatagggcc agcttcactg ccattttggc caatccagct gccagggtca ctatagacac 1801 actggaggat ctgctgcgat ctcatatacc gccatccacc ggggcaactg agaatagaca 1861 gtttttcctg gaggccaatg atgaggttgc tcgaaaagtt ggcgaaaaga tggaggtgtt 1921 cggctacagc gatgatttga cctctcgcat agccaaggga cagtgcgcct actacgacaa 1981 cgagttctat ctgcgctact tacgagtggc agacgaatcc ggatcagctc tccacatcat 2041 gaaggaatgt gtcctctata tgcccgtagt gctggccatg gagaagaact cggctctgaa 2101 gccacgggta gatgcctcca ttcaacatct ggcggagggt ggtctgatag ccaagtggct 2161 caaggatgcc atagagcatc taccggcgga ggcacttgct caacaggagg ccctaatgaa 2221 tattcaaaaa ttctggagct cttttgtggc cttgctgatt ggttacgtaa tctcaatgct 2281 tacactgctc gctgaaagat ggcatttcaa gcacatagtt atgaaacatc ccatgtatga 2341 tgtgtacaac ccaagcttgt attataattt taagcgaata tatccgcagc attaatgtca 2401 aggtttctgc ctagaaatat atatattttt ttttgcacat cac
```

By "Ir21a polypeptide" is meant a polypeptide or fragment thereof having at least about 85% or greater amino acid identity to the amino acid sequence provided at NCBI Accession No. NP_001097043.1, and having ionotropic receptor activity. An exemplary sequence of Ir21a polypeptide is provided below (NP_001097043.1):

SEQ ID NO: 58

```
   1 msyywvalvl ftaqafsieg drsasyqekc isrrlinhyq lnkeifgvgm cdgnnenefr
  61 qkrrivptfq gnprprgell askfhvnsyn feqtnslvgl vnkiaqeyln kcppviyyds
 121 fveksdglil enlfktipit fyhgeinady eaknkrftsh idcncksyil flsdplmtrk
 181 ilgpqtesrv vlvsrstqwr lrdflssels snivnllvig eslmadpmre rpyvlythkl
 241 yadglgsntp vvltswikga lsrphinlfp skfqfgfagh rfqisaanqp pfifrirtld
 301 ssgmgqlrwd gvefrlltmi skrlnfsidi tetptrsntr gvvdtiqeqi iertvdigms
 361 giyitqerlm dsamsvghsp dcaafitlas kalpkyraim gpfqwpvwva licvylggif
 421 pivftdrltl shlmgnwgev enmfwyvfgm ftnafsftgk yswsntrkns trlligaywl
 481 ftiiitscyt gsiiafvtlp afpdtvdsvl dllglffrvg tlnnggwetw fqnsthipts
 541 rlykkmefvg svdegignvt qsffwnyafl gskaqleylv qsnfsdenis rrsalhlsee
 601 cfalfqigfl fpresvykik idsmillaqq sgliakinne vswvmqrsss grllqasssn
 661 slreiiqeer qlttadtegm fllmalgyfl gatalvseiv ggitnkcrqi ikrsrksaas
 721 swssassgsm lrtnaeqlsh dkrkanrrea aevaqkmsfg mrelnltrat lreiygsyga
 781 petdhgqldi vhtefpnssa klnniedees realeslqrl defmdqmdnd gnpsshtfri
 841 dn
```

By "Ir21a polynucleotide" is meant a polynucleotide encoding an Ir21a polypeptide. An exemplary Ir21a polynucleotide sequence is provided at NCBI Accession No. NM_001103573.2. The sequence is provided below:

SEQ ID NO: 59

```
    1 cgatatgtca tattattggg tagctctggt cttatttacc gcgcaagcct tttcaattga
   61 aggggataga tccgctagtt atcaagagaa gtgtattagc cgacggctta tcaaccatta
  121 tcaattaaac aaagaaattt ttggtgtggg aatgtgcgat ggtaataatg aaaacgagtt
  181 ccgtcaaaaa cgccgtattg tccctacatt tcaaggcaat ccaaggccac gaggtgaact
  241 tttggccagt aagtttcacg taaattccta taacttcgag cagactaact cattggttgg
  301 gttggttaac aaaattgccc aagagtacct caataaatgc ccaccggtca tatattatga
  361 tagctttgtg gaaaaatctg acggattaat tctagagaat ttgttcaaga ctattcctat
  421 tactttctac cacggggaaa tcaatgcaga ctacgaagca aaaaataaac gttttacgag
  481 ccatatagat tgcaattgca aaagctacat tcttttcctt tcggacccat taatgacgcg
  541 aaagatttta ggcccgcaaa ctgaaagtcg tgtagttctt gtctcaaggt ccacccaatg
  601 gagacttcgt gattttttgt cttcggagct atcctcaaac attgtaaatt tactagttat
  661 tggggaatcg ctcatggctg acccgatgcg cgagcgccca tacgtactct acacccacaa
  721 gctctatgca gatggacttg gctcaaacac tccggtagtg ctaaccagct ggataaaggg
  781 agctttgtca cgtccacata taatctttt cccatcgaag tttcaatttg ggtttgcggg
  841 acacagattt caaatttcag ccgcaaatca gccgccgttt attttcgaa ttcgcacttt
  901 agattcctca ggaatgggcc agttgcgttg ggacggagtt gaatttcgtc tgctgacaat
  961 gatatctaag cggctaaact tttcgataga tatcactgag acccccaacac ggtcgaatac
 1021 gcgcggggta gtagacacca tccaggaaca gattatagaa agaacagtag acattggtat
 1081 gtccggtata tatataacac aggaacggct gatggactca gccatgtcgg tggggcactc
```

-continued

```
1141 acccgattgt gcagctttca taacacttgc atcgaaggcg ctgccgaaat acagagccat 1201 aatgggaccg ttccaatggc cagtctgggt cgctctgatt tgcgtttacc tcggtggaat 1261 atttccgata gtttttaccg accgtttgac acttagccat ttaatgggta attggggtga 1321 ggtagaaaac atgttctggt atgtatttgg catgttcaca aacgctttct ccttcaccgg 1381 aaaatactcg tggagcaaca cgcggaaaaa ttccacacgc cttctaattg gagcatattg 1441 gctctttaca attatcatta catcttgcta cacaggttcc atcatagcat tcgtaacgtt 1501 gccagctttt ccggacaccg ttgactctgt gttggatctg ctgggattgt tctttcgcgt 1561 tggaaccctg aacaatggtg gctgggagac ctggttccag aactcgaccc atataccgac 1621 gtctagattg tacaagaaaa tggagtttgt cgggtccgta gatgagggca ttggcaacgt 1681 tacccagagc ttcttttgga actatgcctt tcttggctca aaggctcagc tcgaatacct 1741 ggtgcagtca aatttttcag atgaaaatat ttcccgccga tcggcgcttc atttgagtga 1801 agagtgtttt gctcttttcc aaataggatt tctgtttccc cgagagtcag tgtataaaat 1861 caaaatcgac tcgatgatat tacttgccca gcaaagtggt cttattgcaa aaatcaataa 1921 cgaggtaagc tgggtcatgc agcgatcatc ttcaggacgc ctgctccagg caagttcttc 1981 gaattcctta cgcgaaataa ttcaggaaga gcgccaattg actacagcgg acacagaagg 2041 aatgttcctg ctcatggcac tgggctactt tctaggagcc acagccctgg tatccgagat 2101 cgtcggtggg attaccaaca agtgccgcca aataatcaag cgctcccgca agtcggccgc 2161 ctcctcttgg tcgtcggcgt caagtgggtc aatgcttcgc actaatgccg agcaactttc 2221 ccatgataag cgaaaggcca atagacgcga ggctgctgag gttgctcaaa aaatgagttt 2281 tggaatgcgc gagttaaatc ttacccgcgc aacgcttcgg gaaatatacg gaagctacgg 2341 ggcacctgaa acagatcatg gtcagctaga catcgtccac actgagtttc caaacagttc 2401 tgcaaaatta aataatattg aagacgaaga atctcgggaa gctcttgaat ctctgcagcg 2461 tttagacgaa tttatggacc agatggataa cgacggcaat ccttcctcac atacattccg 2521 tattgacaat taatcacaga aattttaaa tgcaaataca aaataatcac tttagtgcac 2581 atgaaattat atgtattgaa ataaaaagtt tgatgcaaca acaaatttt
```

The amino acid sequences of the IR25a, IR40a, IR68a and IR93a orthologs in multiple insect species (*Drosophila melanogaster* (DmeI); *Aedes aegypti* (Aaeg); *Anopheles gambiae* (Agam); *Culex quinquefasciatus* (Cqui); *Bombyx mori* (Bmor); *Danaus plexippus* (Dp); *Tribolium castaneum* (Tcas); *Nasonia vitripennis* (Nvit); *Apis mellifera* (Amel); a *Zooternopsis nevadensis* (Znev); *Capitella capitata* (Ccap); and *Lottia gigantia* (Lgig) are presented herein above. In an embodiment, the invention encompasses a polypeptide or fragment thereof having at least about 85% or greater amino acid identity to the aforementioned amino acid sequences. In an embodiment, the invention encompasses a polypeptide or fragment thereof having at least about 90% or greater amino acid identity to the aforementioned amino acid sequences. In an embodiment, the invention encompasses a polypeptide or fragment thereof having at least about 95% or greater amino acid identity to the aforementioned amino acid sequences.

A "nickase" refers to an enzyme (endonuclease) that introduces nicks (breaks) in one strand of a nucleic acid molecule or polynucleotide (e.g., double stranded DNA). A Cas9 nickase enzyme (e.g., a mutated form of Cas9) generates a single-strand DNA break (nick) at a specific location based on a co-expressed gRNA-defined target sequence, rather than a double-strand DNA break (cut) produced by the wild type enzyme. Nicks are typically repaired in the cell by homology directed repair (HDR), using the intact strand as the template, as described herein. HDR has high fidelity and rarely results in errors. Two adjacent, opposite strand nicks can cause a double strand break (DSB) and trigger error-prone, non-homologous end joining (NHEJ) repair; however, in the presence of a repair template, the double nicks can be repaired by HDR. Double nicking can greatly reduce unwanted off-target effects. (e.g., as described in Shen, B. et al., 2014, *Nature Methods*, 11:399-402; Ann Ran, F. et al., 2013, *Cell*, 154(6):1380-4389; Chiang, T.-W. W. et al., 2016, *Scientific Reports*, 6, Art. No. 24456).

"Modulate" as used herein refers to changing (e.g., increasing, such as over-expressing, decreasing, reducing, or eliminating), modifying, or regulating the expression, activity, or function (or level or amount thereof) of an ionotropic receptor polynucleotide or polypeptide as described herein, e.g., one of more of IR25a, IR40a, IR68a, IR93a, IR21a, or a combination thereof. Such modulation may occur through the effects of one or more agents and/or carried out by a gene drive system as described herein and as shown in FIGS. 47A and 47B.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition. In some embodiments, a control or reference animal behavior is behavior of a normal, healthy animal or an animal not treated with a test agent. In some embodiments, a control or reference hygrosensing or thermosensing is hygrosensing or thermosensing in an untreated animal. In some embodiments, the control or reference hygrosensing or thermosensing is hygrosensing or thermosensing in a normal, healthy animal.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, or at least about 25 amino acids. The length of the reference polypeptide sequence can be about 35 amino acids, about 50 amino acids, or about 100 amino acids. For nucleic acids, the length of the reference nucleic acid sequence will generally be at least about 50 nucleotides, at least about 60 nucleotides, or at least about 75 nucleotides. The length of the reference nucleic acid sequence can be about 100 nucleotides, about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987), Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions will ordinarily include temperatures of at least about 30° C., at least about 37° C., and at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 µg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will be less than about 30 mM NaCl and 3 mM trisodium citrate, or less than about 15 mM NaCl and 1.5 mM trisodium citrate. Stringent temperature conditions for the wash steps will ordinarily include a temperature of at least about 25° C., at least about 42° C., and at least about 68° C. In one embodiment, wash steps will occur at 25° C. in 30 mM NaCl, 3 mM trisodium citrate, and 0.1% SDS. In another embodiment, wash steps will occur at 42 C in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence is at least 60%, at least 80%, at least 85%, at least 90%, at least 95% or even at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "thermosensing" is meant sensing of temperature or changes in temperature.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a schematic of a two-choice apparatus used to screen for hygropreference in the studies described herein. The screen for hygropreference uses a two-choice apparatus. The files are given 5 minutes to choose between a 100% and 3% relative humidity chamber. FIG. 1B is a plot showing dry preference index (DPI) in various fly mutants. N=6-26 assays, except antennal ablation n=3. (alpha=*0.05, **0.01, Differ from wild type, Tukey HSD.).

FIG. 2A shows antennal IR mutants. FIG. 2B shows Ir25a and Ir93a rescues. FIG. 2C shows additional Ir25a and Ir93a alleles. n=6-26 assays (alpha=**0.01, Tukey HSD, differ from wild type and rescues).

FIG. 3A shows Ir25a and Ir40a expression in the sacculus. FIG. 3B shows Ir93a and Ir40a expression in the sacculus. FIG. 3C shows no expression of Ir40a in the arista. FIG. 3D shows dendritic localization of Ir93a.

FIG. 4A shows that silencing of Ir40a expressing cells disrupts hygrosensing. FIG. 4B shows that silencing Ir40a cells has no effect on thermal preference. FIG. 4C shows that dehydrated Ir93a mutants are moisture blind.

FIG. 5A shows pseudo-color images of moisture-responsive fluorescence changes in the axons of wild type Ir40a-Gal4(+) neurons expressing GCaMP6, pseudo-colored to reflect ΔF/F. FIG. 5B shows time-course of fluorescence changes (ΔF/F) in Ir40a-Gal4; UASGCaMP6-labeled axons. Note that hygroresponses are reduced in Ir93a mutants and restored by expression of an Ir93a cDNA under Ir40a-Gal4 control. Wild type and mutant traces are mean+/−SEM (n=3-5); for rescues (n=2) individual traces shown. Power calculations indicate n~8 required to statistically resolve responses between genotypes. The data indicate that responses are reduced in Ir93a mutants and restored by expression of an Ir93a cDNA under Ir40a-Gal4 control. Wild type and mutant traces are mean+/−SEM (n=3-5); for rescues (n=2) individual traces shown.

FIG. 6B shows loss of Ir25a and Ir93a decreases cold avoidance. Each of FIG. 6C and FIG. 6D shows loss of Ir21a decreases cold avoidance. Double asterisk (**) denotes statistically distinct from wild type (Tukey HSD, alpha=0.01).

FIG. 7A shows larval cool sensors labeled with Ir21a-Gal4; UAS-CD8: GFP and anti-IR93a. In Ir21a and Ir25a mutants, Ir93a localization to sensory endings decreases. Ir93aMIC mutants lack Ir93a protein. FIG. 7B shows quantification of IR93a sensory ending enrichment. CD8:GFP is used as an internal control membrane protein to normalize anti-IR93a staining intensity. Intensities quantified using ImageJ Measure tool. n>4 each. *P<0.05, differ from wild type, Tukey HSD. FIG. 7C shows that Ir93a protein is enriched in sensory endings of adult arista thermoreceptors. Asterisks: cell bodies; arrowheads: sensory endings.

FIG. 11A shows that the electrophysiology of hygrosensilla suggests the presence of "moist" and "dry" cells (Tichy and Kallina 2013, *PLoS One*, 8(1), e53998.). FIG. 11B shows hygrosensilla have distinct morphology and contain a triad of neurons: "moist cell" fires when humidity increases (moist cell is indicated by "M"); "dry cell" first when humidity decreases (dry cell is indicated by "D"); and, "cold cell" fires when temperature decreases. FIG. 11C shows possible mechanisms for how the moist, dry, or cold cells signal evaporative conditions. In one model ("mechanical hygrometer"), the cells sense evaporative conditions by sensing relative humidity changes that causes shrinking or swelling of the sensillum. Such cells function as a mechanoreceptor. In another model ("psychrometer"), the cells sense evaporative conditions by sensing changes in temperature caused by evaporative cooling. Thus, the cells in such a model function as a thermosensor. In still another model ("evaporation rate"), evaporation changes ion concentration of lymph, and the concentration of lymph is sensed by the cells. Cells in such a model function as a chemosensor.

FIG. 12C is a schematic showing expression Ir93a, Ir25a, and IR40a in the sacculus. FIG. 12A is a schematic representation of structures showing various domains of Ir93a and Ir25a. FIG. 12B shows a three-dimensional structure of an AMPA receptor (left) (Sobolevsky, *Nature*. 2009 Dec. 10; 462(7274):745-56)) and a model of an IR hetero-tetramer (2 IR25a's and 2 odor-specific IR's) (Rytz et al. 2013, Chemosensory ionotropic glutamate receptors in *Drosophila* and beyond. *Insect biochemistry and molecular biology*).

FIG. 13 is a set of schematics and plots summarizing background information relevant to the studies herein to elucidate humidity and temperature sensing in the genetically and behaviorally tractable model organism *D. melanogaster*.

FIGS. 17A-17D are images, plots, and schematics showing a behavioral assay to examine IR hygrosensitivity used in the studies herein. FIG. 17A is a schematic showing saturation pressure of pure water and a salt solution. FIG. 17B is an image showing the "hygro gradient" device used in the studies described herein. FIG. 17C is a plot showing the temperature and relative humidity in the "hygro gradient" device. The device maintains a stable gradient and temperature. FIG. 17D is a set of schematics showing how the Dry Preference Index (DPI) is computed.

FIGS. 19A-19D are plots, images, and schematics showing investigation of three antennal IRs: Ir25a, Ir8a, and Ir76b. FIG. 19A shows that three antennal IRs that are known co-receptors (Ir25a, Ir8a, and Ir74b). FIG. 19B shows exemplary IRs forming heteromeric complexes to sense odorants such as phenylethylamine (left) or 1,4-diaminobutane (right). FIG. 19C shows that a mutation in Ir25a, but not other broadly expressed IRs (Ir8a or Ir76b), eliminates hygrosensory choice. FIG. 19D shows immunostaining for IR25a and a cilia base marker (mAb 21A6) in antennal sections from wildtype (left) and IR25a null mutant (IR25a$^1$/IR25a$^2$) animals (Benton et al. Cell. 2009 Jan. 9; 136(1):149-62).

FIGS. 20A-20D are images, schematics, and plots showing investigation of IRs Ir93a and Ir25a. FIG. 20A shows that Ir93a expression is limited to the arista and sacculus. FIG. 20B shows results of a screen of conserved IRs, which reveals Ir93a is also required for dry preference behavior. FIG. 20C is a set of images showing immunostaining of Ir25a in WT and Ir93a$^{MIC}$ (left) and Ir93a in WT/Ir25a$^2$ (right). FIG. 20D is a schematic showing a working model of Ir93a and Ir25a function. Ir93a may act as an Ir76b-like coreceptor.

FIGS. 21A-21C are images, plots and tracings showing investigation of IRs Ir40a and Ir93a. FIG. 21A shows immunostaining for Ir40a and Ir93a in sacculus cells. FIG. 21B shows Ir40a$^+$ neurons are activated by dry and silenced by moist air. FIG. 21C shows that Ir40a mutants show reduced dry preference.

FIG. 25 is a schematic showing a working model of hygrosensation involving IRs Ir25a, Ir93a, Ir68a, Ir21a, and Ir40a.

FIG. 28 shows codependence of Ir40a/Ir93a/Ir25a.

FIG. 30 is a diagram showing response of cell types ("C"=cold cells; "M"=moist cells; "D"=dry cells) to various stimuli (T=temperature; VP=vapor pressure; RH=relative humidity). C, M, and D cells respond to vapor pressure and temperature. Relative humidity is affect by both temperature and vapor pressure. C and M cells respond differently to changes in temperature and vapor pressure.

FIG. 31A illustrates that two areas of identical relative humidity (RH) can have different evaporative conditions. Thus, RH is not indicative of evaporative conditions. The higher the temperature, the more water vapor a space can contain. For example, 1 m$^3$ at 18° C. can contain 15 mL; 1 m$^3$ at 29° C. can hold 29 mL. RH only explains the "wetness" and "dryness" of the air in two places if the temperature is constant between them. The saturation/vapor pressure deficit is more informative of evaporative conditions. The saturation/vapor pressure deficit is the difference between vapor pressure (Vp) and saturation vapor pressure (Vp*) at a particular temperature. The saturation deficit has an almost linear relationship with evaporation rate. FIG. 31B shows that two areas with the same RH can have difference saturation deficits (SD). Additionally, temperature depression also indicates evaporative conditions. FIG. 31C shows temperatures measured with two thermometers, one moist and one dry. The temperature difference measured is due to evaporative cooling.

FIG. 32A: Gene structure of the Ir93a locus; sequences encoding the transmembrane (TM) domains and channel pore are colored. The triangle denotes site of MIMIC insertion in Ir93a$^{MI05555}$, and the CRISPR/Cas9-generated deletion in the Ir93a$^{122}$ allele is shown below. Sequences are SEQ ID NOs: 63 and 67 in order of appearance. FIG. 32B shows a schematic of the larval anterior showing the bilaterally symmetric Dorsal Organ Ganglia within which three Dorsal Organ Cool Cells (DOCCs) are located. FIG. 32C shows immunofluorescence images of the larval anterior (corresponding to the boxed region in the schematic) showing expression of IR93a protein in DOCCs (Ir21a-Gal4; UAS-GFP [Ir21a>GFP]), as well as additional sensory neurons. Ir93a$^{MI05555}$ mutants lack IR93a immunostaining. The arrow and arrowhead label the soma and dendritic bulb of one of the DOCCs. Scale bar is 10 μm. FIG. 32D shows cool avoidance behavior assessed as navigational bias (movement toward warmth/total path length) of individual larval trajectories on an ~0.36° C./cm gradient extending from ~13.5° C. to ~21.5° C., with a midpoint of ~17.5° C. Letters denote statistically distinct categories (alpha=0.05; Tukey HSD). wild type (Canton-S), n=37 animals. Ir93a$^{MI05555}$, n=132. Ir21a-Gal4/+; Ir93a$^{MI05555}$, n=72. Ir93a$^{MI05555}$, UAS-Ir93a/Ir93a$^{MI05555}$, n=80. Ir21a-Gal4/+; Ir93a$^{MI05555}$, UAS-Ir93a/Ir93a$^{MI05555}$, n=45. Ir93a$^{122}$, n=101.

FIGS. 33A-33E show graphs, violin plots and images illustrating results showing cool-responsive calcium and voltage changes in DOCCs require IR93a. FIG. 33A: Left: DOCC responses monitored using R11F02>GCaMP6m. DOCC cool-responsive increases in fluorescence are dramatically reduced in Ir93a$^{MI05555}$, and responses are rescued by expression of a wild-type Ir93a cDNA under R11F02-Gal4 control. Traces, average±SEM. Right: Ratio of fluorescence at 14° C. versus 20° C. depicted using a violin plot (internal white circles show median; black boxes denote 25th to 75th percentiles; whiskers extend 1.5 times interquartile range). Letters denote statistically distinct categories, $p<0.01$, Steel-Dwass test. wild type, n=12 cells. Ir93a$^{MI05555}$, n=44. Ir93a$^{MI05555}$; R11F02>Ir93a, n=46. FIG. 33B: Temperature-dependent DOCC voltage responses in the sensory endings of wild-type (upper panels) or Ir93a$^{MI05555}$ mutant (lower panels) larvae monitored using R11F02>Arclight. Arrowheads denote DOCC dendritic bulbs. Note that Arclight fluorescence decreases upon depolarization. Asterisks denote cuticular autofluorescence from adjacent sensory structures. FIG. 33C: Robust cool-responsive depolarization of DOCC sensory endings was observed in otherwise wild-type animals using either R11F02>Arclight or Ir21a>Arclight. Depolarization response was eliminated in Ir93a$^{MI05555}$, Ir25a$^2$, and Ir21a$^{A1}$ mutants. Traces, average±SEM. Violin plot depicts ratio of fluorescence at 14° C. versus 20° C. ** denotes distinct from wild-type control, $p<0.01$ compared to control, Steel-Dwass test. R11F02-Gal4; UAS-Arclight, n=57 cells. R11F02-Gal4; UAS-Arclight; Ir93a$^{MI05555}$, n=24. R11F02-Gal4; UAS-Arclight; Ir25a$^2$, n=30. Ir21a-Gal4; UAS-Arclight, n=18. Ir21a-Gal4; UAS-Arclight; Ir21a$^{A1}$, n=23.

FIG. 34A Left: schematic of the adult Drosophila antenna, illustrating the location of the sacculus in the interior of this appendage. Right: the sacculus is composed of three main chambers (I, II, III), which are lined with sensilla of various morphologies (schematic adapted from Shanbhag et al., 1995, Cell and Tissue Research, 282:237-249). FIG. 34B Top: immunofluorescence on a whole-mount wild-type antenna showing expression of IR93a protein in two groups of soma (arrows) around sacculus chambers I and II; these chambers were visualized by cuticle autofluorescence shown in the images on the right. The arrowhead marks the concentration of IR93a in the dendritic endings that innervate the sensilla in chamber I. Note that the dendrites of chamber II neurons are not visible in this image; sensilla localization of IR93a in these cells was more easily detected in antennal sections; see panel FIG. 34D, Bottom: Ir93a$^{MI05555}$ mutants lack detectable IR93a protein. Scale bar is 20 μm. (FIGS. 34C-34E): Double immunofluorescence with the indicated antibodies on antennal cryosections revealing co-expression of these IRs in sacculus neurons; the arrows point to the cluster of neurons innervating chamber II. Scale bar is 10 μm. IR25a is expressed in additional neurons that do not express IR93a or IR40a because of IR25a's broader role as an olfactory IR co-receptor (Abuin et al., 2011, Neuron, 69:44-60).

FIGS. 35A-35D show graphic depictions of assays, graphs and violin plots illustrating results demonstrating the hygrosensory behavior requires IR93a, IR25a and IR40a. FIG. 35A shows a schematic of the hygrosensory behavior assays. ~67% to ~96% RH gradients were generated by filling wells with either a saturated solution of ammonium nitrate in water or pure water. ~89% to ~96% RH gradients were generated by pairing empty wells with wells filled with pure water. Nylon mesh prevented fly contact with solutions. Dry preference was quantified by counting flies on either side of chamber midline. 25-35 flies were used per assay. FIG. 35B shows mean±SD of RH and temperature measured at indicated gradient positions. ~67% to ~96% RH, n=58 gradients. ~89% to ~96% RH, n=28. FIGS. 35C and 35D show dry preference assessed on ~67% vs. ~96% (FIG. 35C) and ~89% vs. ~96% (FIG. 35D) gradients. Asterisks denote statistically distinct from wild type (**$p<0.01$; *$p<0.05$, Steel with control). wild type, n=16 assays. Ir8a mutant (Ir8a$^1$), n=8. Ir76b mutant (Ir76b$^2$), n=14. Ir21a mutant (Ir21a$^{123}$), n=14. Ir25a mutant (Ir26a$^2$), n=11. Ir25a rescue (Ir25a$^2$; UAS-Ir25a), n=15. Ir40a mutant (Ir40a$^1$), n=15. Ir40a rescue (Ir40a$^1$; UAS-Ir40a), n=9. Ir40a CRISPR mutant (Ir40a$^{134}$), n=10. Ir93a mutant (Ir93a$^{MI05555}$), n=11. Ir93a rescue (Ir93a$^{MI05555}$, UAS-Ir93a), n=14. Ir40a mutant alleles and thermosensory behavior are shown in FIGS. 36A and 36B. Note that UAS-cDNA rescues were observed in the absence of Gal4 drivers, reflecting Gal4-independent expression of UAS transgenes (FIGS. 36C and 36D).

FIGS. 36A-36D show a schematic, a bar graph, RT-PCR gels and images describing Ir40a mutants and the analysis of Gal4-independent transgene expression. FIG. 36A shows gene structure and sequence alterations in Ir40a alleles. Regions encoding transmembrane domains (TMs) and pore region are shown. The Ir40a promoter region present in Ir40a-Gal4 is indicated. Sequences are SEQ ID NOs: 68-71 in order of appearance. FIG. 36B shows larval cool avoidance behavior (assayed as in FIG. 32D) is unaffected by mutation of Ir40a. wild type, n=37 animals. Ir40a1,n=55. FIG. 36C shows an RT-PCR analysis of Gal4-independent expression of UAS-Ir transgenes in adult heads in the indicated genotypes. Upper panels: IR-specific RT-PCR products. Lower panels: RpL32 (a ribosomal protein gene) as a cDNA synthesis control. Asterisk indicates a background amplification product observed in some Ir25a PCR reactions. The mechanism underlying Gal4-independent UAS-transgene expression is unknown, but is a phenomenon that has been previously reported (Mao et al., 2014). FIG. 36D: Top: IR25a protein expression in the sacculus of wild-type, Ir25a2 and Ir25a2; UAS-Ir25a animals. Bottom: IR93a protein expression in the sacculus of wild-type, Ir93aMI05555 and Ir93aMI05555; UAS-mCherry:IR93a animals. Gal4-independent expression of UAS transgenes restores expression of IR25a and IR93a in the dendrites of sacculus neurons (arrowhead).

FIG. 37A shows a schematic of the *Drosophila* head (viewed from above) illustrating the projection of IR40a/IR93a/IR25a-expressing neurons (labeled using Ir40a-Gal4 (Silbering et al., 2011) from the sacculus to the antennal lobes in the brain, visualized through a hole in the head cuticle. FIG. 37B shows raw fluorescence image of Ir40a axons (in Ir40a-Gal4; UAS-GCaMP6m animals) innervating the arm and column in the antennal lobe. The dashed circle indicates the position of the ROI used for quantification in panels (FIGS. 37D-37G). FIG. 37C shows images (reflecting GCaMP6m fluorescence intensity changes) of IR40a neuron responses to a switch from 90% to 7% RH ('Dry response') and to a switch from 7% to 90% RH ('Moist response'). FIGS. 37D and 37F show moisture-responsive fluorescence changes in the arm (moist=90% RH, dry=7% RH). Traces represent average±SEM. FIGS. 37E and 37G show quantification of changes in ΔF/F (mean fluorescence change in the ROI shown in (FIG. 37B) upon shift from moist to dry (FIG. 37E) or dry to moist (FIG. 37G). Dry responses were quantified as [ΔF/F at 7% RH (average from 4.5 to 6.5 s after shift to 7% RH)]−[ΔF/F at 90% RH (average from 3.5 to 1 s prior to shift to 7% RH)], and moist responses quantified by performing the converse calculation. Genotypes: control: n=17 animals (pooled data from Ir40a-Gal4, Ir40a$^1$/Ir40a-Gal4, +; UAS-GCaMP6m/+, n=9; IR40a-Gal4; UAS-GCaMP6m, Ir93a$^{MI05555}$/+, n=8). Ir93a mutant (Ir40a-Gal4; UAS-GCaMP6m, Ir93a$^{MI05555}$/Ir93a$^{MI05555}$), n=10. Ir93a rescue (Ir40a-Gal4; UAS-GCaMP6m, Ir93a$^{MI05555}$/UAS-mcherry:Ir93a, Ir93a$^{MI05555}$), n=8. Ir40a mutant (Ir40a-Gal4, Ir40a$^1$; UAS-GCaMP6m/+), n=8. Ir40a rescue (Ir40a-Gal4, Ir40a$^1$; UAS-GCaMP6m/UAS-Ir40a), n=6. **p<0.01, distinct from controls and rescues, Steel-Dwass test.

FIG. 38A shows dry preference assessed on ~67% to ~96% gradient. Asterisks denote statistically different responses from wild type (**p<0.01; Steel with control). wild type, n=016 assays. nan mutant (nan$^{36a}$), n=9. wtrw mutant (wtrw$^2$), n=9. FIGS. 38B-38E show moisture-responsive fluorescence changes of IR40a neurons recorded and quantified as described in FIGS. 37D-37G. Genotypes: control: n=5 animals (Ir40a-Gal4, UAS-GCaMP6m/+). nan mutant (Ir40a-Gal4, UAS-GCaMP6m/+; nan$^{36a}$), n=5. wtrw mutant (Ir40a-Gal4, UAS-GCaMP6m/+; wtrw$^2$), n=7. (All P>0.4 versus control, Steel with control).

FIG. 39A, Left, presents a schematic of the adult *Drosophila* antenna, showing the location of the sacculus inside the antenna. FIG. 39A, Right, presents an enlargement of the sacculus (shown in (a)), which contains three chambers (I, II, III) lined with sensilla of various morphologies (modified from (Shanbhag et al., 1995, *Cell and Tissue Research*, 282, 237-249) and as described herein. FIG. 39B shows immunostaining of the antenna of a Ir68a-Gal4/UAS-myr:GFP (Ir68a>GFP) fly (left). Ir68a is expressed in neurons that send processes to sacculus chamber II (9.8±0.4 neurons (mean±SEM); n=8 antennae). Arrowheads denote sensory endings. Scale bar in all panels indicates 10 μm. Cuticle autofluorescence outlines sacculus chambers in the right panel. FIG. 39C shows immunostaining of LexAop-RFP(II); Ir68a-Gal4/Ir40a-LexA, UAS-myr:GFP (Ir68a>GFP, Ir40a>RFP) flies reveals non-overlapping expression in cells adjacent to chamber II. Arrows indicate select cell bodies. Arrowhead marks an Ir68a>GFP-labelled dendrite projecting into a chamber II sensillum. Cuticle autofluorescence outlines sensilla of the sacculus in the GFP channel. FIGS. 39D and 39E show images of immunofluorescence on antennal cryosections which reveals overlapping expression of Ir68a>GFP with IR25a protein (FIG. 39D) and IR93a protein (FIG. 39E) in sacculus neurons. Arrows denote cells which detectably coexpress Ir68a>GFP and IR25a (FIG. 39D) or Ir68a>GFP and IR93a (FIG. 39E). Arrows denote cells expressing only IR25a or IR93a, reflecting their broader expression in the sacculus, including co-expression with IR40a. FIGS. 39F and 39G show that Ir68a>GFP-labeled and Ir40a>RFP-labeled axons project to distinct regions of the antennal lobe. In FIG. 39G, the antennal lobe neuropil is labeled using nc82. FIG. 39H shows a scheme indicating the relative position of Ir40a neuron and Ir68a neuron projections; glomerular nomenclature is from (Grabe et al., 2015, *J. Comparative Neurology*, 523, 530-544). D, dorsal. V, ventral. L, lateral. M, medial.

FIG. 41A shows a schematic of the *Drosophila* head (viewed from above) illustrating the projection of Ir68a-Gal4 labeled neurons from the sacculus to the antennal lobes in the brain, visualized through a hole cut in the head cuticle. FIG. 41B, Left panel, shows a raw fluorescence image of Ir68a-labeled axons (in Ir68a-Gal4; UAS-GCaMP6m animals) innervating the antennal lobe. The circle indicates the position of the ROI used for quantification. The middle and right panels of FIG. 41B show images (reflecting GCaMP6m relative fluorescence intensity changes) of responses to a switch from 7% to 90% RH ("Moist response") and to a switch from 90% to 7% RH ("Dry response"). Scale bar is 10 μm. FIGS. 41C and 41D are traces showing moist-elicited (FIG. 41C) and dry-elicited (FIG. 41D) fluorescence changes in the region of interest in FIG. 41B (moist=90% RH, dry=7% RH). Left panels: Traces represent mean±SEM. Right panels: Quantification of responses. Letters denote statistically distinct groups (p=0.05) Steel-Dwass. Moist-response was calculated as [F/F$_0$ at 90% RH (average F/F$_0$ from 4.5 to 6.5 s after shift to 90% RH)]−[F/F$_0$ at 7% RH (average F/F$_0$ from 3.5 to 1 s prior to shift to 90% RH)]. Dry-response was quantified using the converse calculation. Violin plots: internal white circles show median; black boxes denote 25th to 75th percentiles; whiskers extend 1.5 times interquartile range. Genotypes: wild type: Ir68a-Gal4, UAS-GCaMP6m (n=10 animals). Ir68a$^{-/-}$: UAS-GCaMP6m(II); Ir68a-Gal4, Ir68a$^{c04139}$/Ir68a$^{c04139}$ (n=9). Ir68a rescue: Ir68a$^+$ rescue transgene(II)/UAS-GCaMP6m; Ir68a-Gal4, Ir68a$^{c04139}$/Ir68a$^{c04139}$ (n=8). Ir40$^{-/-}$: Ir40a$^1$; Ir68a-Gal4, UAS-GCaMP6m (n=8). Ir25a$^{-/-}$: Ir25a$^2$; Ir68a-Gal4, UAS-GCaMP6m (n=8). Ir25a rescue: Ir25a$^2$, Ir25aBAC/Ir25a$^2$; Ir68a-Gal4, UAS-GCaMP6m (n=8). Ir93a$^{-/-}$: UAS-GCaMP6m(II); Ir68a-Gal4, Ir93a$^{MI05555}$/Ir93a$^{MI05555}$ (n=8). Ir93a rescue: UAS-GCaMP6m(II); Ir68a-Gal4, Ir93a$^{MI05555}$/UAS-mcherry:Ir93a, Ir93a$^{MI05555}$) (n=6). FIGS. 41E and 41F show moist-elicited (FIG. 41E) and dry-elicited (FIG. 41F) fluorescence changes in Ir40a-Gal4-labeled dry receptors, as in the panels in FIGS. 41C and 41D. Genotypes: wild type: Ir40a-Gal4/+; UAS-GCaMP6m/+ (n=8). Ir68a$^{-/-}$: Ir40aGal4/UAS-GCaMP6m; Ir68a$^{c04139}$ (n=10). Ir68a mutant alleles and genomic rescue fragment are shown in FIGS. 39A-H and 40.

FIG. 42A depicts a schematic of a hygrotaxis assay. Approximately 67% to approximately 96% RH gradients were generated as described herein. Dry preference was quantified by counting flies on either side of chamber midline. 25-35 flies were used per assay. FIG. 42B presents a graph illustrating the dry preference of hydrated flies. Asterisks denote values that are statistically distinct from wild type (**p<0.01, Steel with control). wild type, n=12 assays. Ir25a$^2$, n=12. Ir93a$^{MI05555}$, n=11. Ir40a$^1$, n=15. Ir68a$^{c04139}$, n=16. Ir68a$^{MB05565}$, n=14. Ir68a$^{MB05565}$+rescue (Ir68a$^+$ rescue transgene(II); Ir68a$^{MB05565}$), n=12. Ir40a$^1$; Ir68a$^{MB05565}$, n=15.

FIG. 43A depicts a schematic of the hygrotaxis assay using dehydrated flies. FIG. 43B shows a graphic representation of hygrotaxis behavior in dehydrated flies. Letters denote statistically distinct groups (p<0.01, Tukey HSD). Genotypes: wild type, n=15 assays. Ir25a$^2$, n=13. Ir93a$^{MI05555}$, n=14. Ir40a$^1$, n=12. Ir68a$^{MB05565}$, n=11. Ir40a$^1$; Ir68a$^{MB05565}$, n=12.

FIG. 46 presents a table showing the amino acid identity and similarity matrices comparing the *Drosophila melanogaster* (Dmel) IR25a, IR40a, IR68a and IR93a polypeptide sequences to their orthologs in *Aedes aegypti*, *Anopheles gambiae* and *Culex quinquefasciatus*. Multiple Sequence Alignments were generated using T-COFFEE. Identity matrices created using SIAS (http://imed.med.ucm.es/Tools/sias.html). Amino acid identity and similarity were calculated using "Y=F=W; V=I=L; R=K=H; D=E; S=T; N=Q".

FIGS. 47A and 47B present a gene drive strategy for disrupting (e.g., inactivating) gene function of IR polypeptides in vector insects. A gene drive for disrupting IR function in *Anopheles gambiae* is presented in this figure. FIG. 47A presents Step 1 of the procedure, i.e., the creation of a transgenic mosquito with targeted integration of a gene drive cassette. FIG. 47B presents Step 2 of the procedure, i.e., allowing the gene drive locus to spread, thus inactivating the IR loci population-wide. This conversion of a wild type to a mutant locus as detailed in Steps 1 and 2 of FIGS. 47A and 47B means that the frequency of disrupted "gene drive" allele rises. As the frequency of the disrupted allele rises, the population contains increasing proportions of homozygous mutant mosquitos, mosquitos that lack IR gene function. Such mutants would be expected to be unable to host-seek and seek moisture, thus adversely affecting behavior(s) on which they rely for survival.

DETAILED DESCRIPTION OF THE INVENTION

Figure 1A:
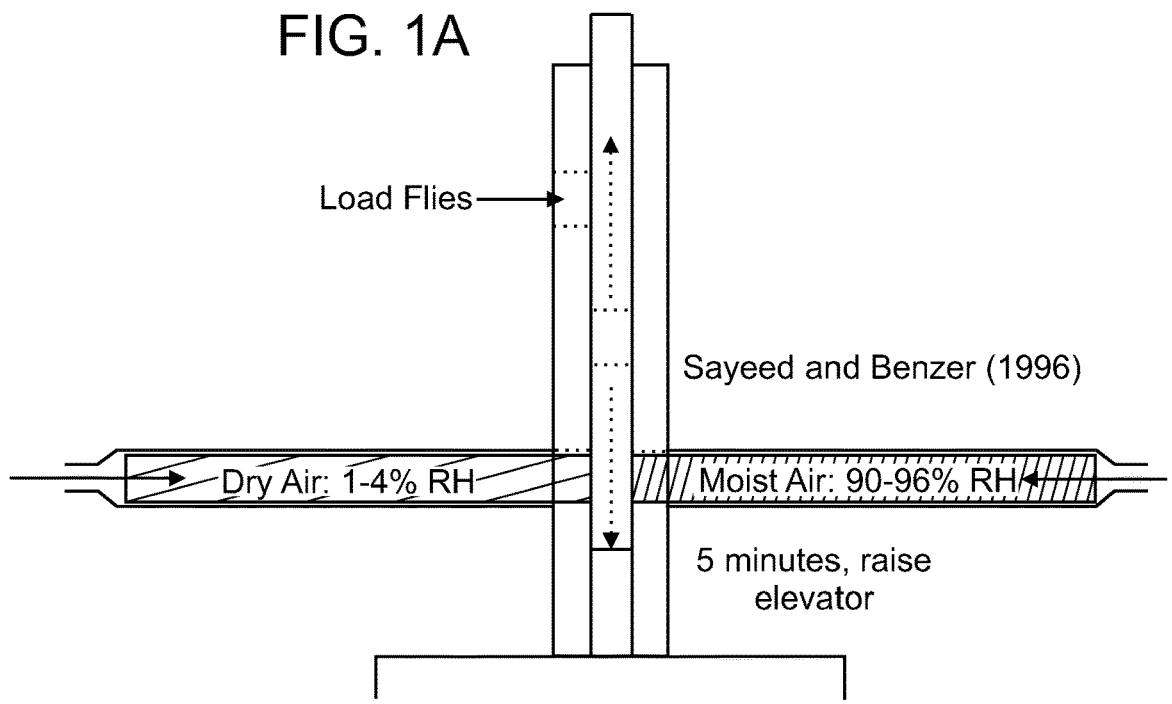
FIGS. 1A-1B are a schematic and plot showing that Ir25a function is required for hygrosensation.

The invention features methods that are useful for modulating hygrosensation and/or thermosensation in insects. Modulation of hygrosensation and/or thermosensation in insects is highly desirable, since insects use hygrosensation to avoid desiccation and, in vectors such as mosquitos, to locate vertebrate hosts.

The invention is based, at least in part, on the discovery of multiple members of the Ionotropic Receptor (IR) family of ionotropic glutamate receptors, which mediate a combination of insect thermo- and hygrosensory responses. These receptors are conserved across diverse arthropods. These receptors, individually and in combination, constitute potential targets for control of arthropod disease vectors (insects) and pests, as thermo- and hygrosensory responses are important for their survival, host-seeking, and reproduction.

As insects serve as vectors for many human diseases and infection, it is critical to understand the sensory mechanisms they use to navigate their environment, select suitable habitats, and locate prey. Humidity is both a critical habitat feature that will be impacted by climate change, and an important host-seeking cue for mosquitos that transmit disease and cause millions of human deaths each year. This work is therefore advantageous and of importance from the standpoint of both public health and human industry, as humidity will influence insect ecology in the wake of climate change, as well as impact the pathology of insect-borne diseases.

Maintaining appropriate water balance is critical for physiological homeostasis. For land animals, humidity impacts water balance by helping determine evaporation rates and by serving as a cue for locating water sources. Insects in particular are vulnerable to shifts in body water content because of their small sizes and their large surface area to volume ratios, and so they have evolved sophisticated hygrosensory systems. Despite detailed study of these systems, the fundamental cellular and molecular mechanisms involved in insect hygrosensation are still uncertain.

The Ionotropic Receptors (IRs) include a large family of sensory receptors that mediate a range of chemosensory responses, but have not been previously implicated in hygrosensation. Results described herein show that IRs are critical mediators of hygrosensation. Studies herein found that loss-of-function mutations in multiple IRs strongly disrupted hygrosensory behavior. At the cellular level, expression of these IR proteins is detected in sensory neurons of the sacculus, in association with sensilla that resemble the well-characterized hygro-responsive sensilla of larger insects. Cell-type specific inhibition and rescue experiments support the importance of these neurons in mediating hygrosensory behavior. Furthermore, these neurons exhibit IR-dependent physiological responses to humidity, consistent with a role of the IRs and these neurons in humidity detection. Interestingly, prior work implicated the Transient Receptor Potential channels Nanchung and Water witch and sensory sensilla on the antennal surface in mediating hygrosensation (Liu et al., 2007, *Nature*, 450, 294-298). Thus, the involvement of IRs and the sacculus in hygrosensation indicates both a previously unanticipated function for IRs and a modified view of hygrosensing.

Molecular Basis of Hygrosensation

Water is an essential component of all life, and maintaining water balance is a key component of physiological homeostasis. The humidity of the air determines how rapidly water evaporates, and is thus a critical environmental variable. Insects are particularly vulnerable to changes in body water from evaporation because of their small size and large surface area to volume ratio, and so possess sensitive hygro-sensory systems that allow them to seek out environments of appropriate moisture and avoid excessively dry or moist regions. From a human health perspective, insect disease vectors use hygrosensing to locate hosts. Field studies indicate that moisture can be as powerful an attractive cue for *Aedes* females, as temperature and carbon dioxide. Despite the importance of hygrosensing to human health and insect biology, its molecular and cellular basis remains poorly understood.

While humidity is a function of the concentration of water vapor, the key humidity-dependent parameter that governs hygrosensory responses has remained elusive. Three distinct humidity-dependent stimuli: evaporation rate, moisture-dependent pressure changes and evaporative cooling have each been proposed to underlie hygrosensation. In each model, the stimulus would activate a distinct sensory modality, evaporation rate activating chemoreceptors, pressure activating mechanoreceptors and cooling activating thermoreceptors. However, the precise stimulus or combination of stimuli involved is unclear.

Data described herein indicate functional overlap between the molecular sensors required for sensing moisture and cold temperatures. The work herein not only provides a foundation for identification of molecular cold and moisture sensors, but also indicates that awareness of cooling may be critical to hygrosensing. Identification of the underlying basis of hygrosensing and further elucidation of the critical receptors for moisture in *Drosophila melanogaster* as a representative insect are performed using the molecular genetic tools of the fly to probe their molecular and cellular properties. The work described herein addresses basic questions in neuroscience and sensory biology, with relevance to the survival of insect vectors of human disease and their ability to seek hosts.

Hygrosensation is Important for Insect Disease Vector Physiology, Host-Seeking and Reproduction Hygrosensation is a critical sensory modality for all animals, particularly for insects, whose small bodies and large surface area to volume ratios make dehydration a constant threat. Environmental humidity levels are therefore a key determinant of where and when a given species of insect will thrive (Chown et al., 2011, *Journal of Insect Physiology*, 57, 1070-1084,). Hygrosensory cues are also fundamental for host-seeking by disease-transmitting mosquitoes (Brown, A. W. A., 1966, *JAMA*, 196(3):249-252).

Electrophysiological studies in larger insects suggest that hygrosensation also involves sensory neurons activated by high humidity levels ("moist cells") (Tichy and Gingl, 2001, Problems in hygro- and thermoreception. In: *Ecology of sensing* (pp. 271-287), Springer Berlin Heidelberg) in a manner that varies with the hydration state of the animal.

Hygrosensing in insects is significant from two perspectives. First, from a basic science perspective, hygrosensing is an important sensory modality whose molecular basis is unknown. Second, hygrosensing is relevant to human health because of its important role in the ecology and host-seeking behavior of insect vectors such as mosquitos, which transmit human diseases including malaria, West Nile virus, chikungunya, yellow and dengue fever (Komar, 2003, *Advances in Virus Research*, 61, 185-234; World Health Organization (2009): *Dengue: guidelines for diagnosis, treatment, prevention and control*; Takken et al., 1999, *Annu Rev Entomol*, 44, 131-157). Worldwide, malaria alone is estimated to have a direct cost of roughly $12 billion (World Health Organization (2014). World malaria report 2013. *World Health Organization*). About half the world's population lives in range of malaria, and in 2012 there were >200 million cases and >600,000 deaths from malaria (World Health Organization (2014), World malaria report 2013, *World Health Organization*).

Humidity is critical because maintaining water balance and locating water are vital to organismal homeostasis (Anderson, 1936, Ecology, 17(2), 277-282). Insects are especially vulnerable to dehydration because of their small size and have evolved sensitive mechanisms to sense and react to moisture (Benoit et al., 2010, *J Insect Physiol*, 56(10), 1366-1376; Chown et al., 2011, *Journal of insect physiology*, 57(8), 1070-1084; Gibbs et al., 1997, *Journal of Experimental Biology*, 12, 1821-1832). Humidity is also a key determinant of an insect's geographic range (Chown et al., 2011, *Journal of insect physiology*, 57(8), 1070-1084, Yamana et al., 2013, *Environ Health Perspect*, 121(10), 1179-1186) and is used by mosquitoes both for host-seeking and, after feeding, for locating oviposition sites suitable for their aquatic offspring (Bar-Zeev, 1967, *Nature*, 213(5077), 737-738; Brown, 1951, *Bulletin of Entomological Research*, 42(3), 575-582; Okal et al., 2013, *Malaria Journal*, 12, 365; Parker, 1952, *Bulletin of Entomological Research*, 43(1), 221-229; Zwiebel et al., 2004, *Insect biochemistry and molecular biology*, 34(7), 645-652. Understanding the mechanisms by which insects sense humidity can provide insights of potential relevance to understanding the ability of insect vectors to survive, locate breeding sites and target human hosts.

Humidity Presents a Challenge for Sensory Detection

Humidity is a complex stimulus comprised of two parameters that together determine evaporation rates, temperature and vapor pressure (Anderson, 1936, *Ecology*, 17(2), 277-282). In humans and *C. elegans*, hygrosensation has been proposed to depend on the integration of thermal and vapor-pressure-dependent mechanical stimuli but the precise mechanisms involved remain unclear and may not apply to insects (Russell et al., 2014, *Proc Natl Acad Sci USA*, 111(22), 8269-8274; Filingeri et al., 2014, *J Neurophysiol*, 112(6), 1457-1469).

A critical obstacle to studying insect hygrosensation is that few molecules associated with humidity detection have been identified and their mechanisms are unknown (Liu et al., 2007, *Nature*, 450(7167), 294-298). However, the structure and response characteristics of hygroreceptive sensilla in many insect species, have been studied in detail (Altner et al., 1985, *Annu Rev Entomol*, 30, 273-295). These contain a pair of cells with antagonistic response properties. One increases firing in response to rising humidity (the "moist cell"), and one increases firing in response to falling humidity (the "dry cell"). A third cell is thermoreceptive, and is deemed a "cold cell" (Altner et al., 1985, *Annu Rev Entomol*, 30, 273-295; Tichy et al., 2010, *Neurophysiol*, 103(6), 3274-3286; Tichy et al., 2001, Problems in hygro- and thermoreception. In *Ecology of sensing* (pp. 271-287), Springer Berlin Heidelberg; Tichy et al., 2013, *PLoS One*, 8(1), e53998). Importantly, these thermo-/hygro-sensors occur in poreless sensilla with stiff, inflexible sockets (Altner et al., 1985, *Annu Rev Entomol*, 30, 273-295; Tichy et al., 2001, Problems in hygro- and thermoreception. In *Ecology of sensing* (pp. 271-287), Springer Berlin Heidelberg; Tichy et al., 2013, *PLoS One*, 8(1), e53998; Shanbhag et al., 1995, *Cell and tissue research*, 282(2), 237-249). Despite extensive physiological analyses, however, the roles of these cells in driving behavior has been uncertain. Furthermore, the sensory receptors that mediate their responsiveness to moisture have been unknown.

Drosophila as a Model Organism to Study Humidity Sensing

*Drosophila melanogaster* exhibit robust humidity preferences. These behavioral responses depend upon the physiological state of the fly, as hydrated flies prefer drier environments and dehydrated flies moister environments (Lin et al., 2014, *Drosophila Nat. Neurosci*, 17(11), 1536-1542; Perttunen et al., 1956, *Ann. Entomol. Fenn*, 22, 36-45). Anatomically these responses require the third segment of the antenna (Ji et al., 2015, *PLoS One*, 10(3), e0119162; Sayeed et al., 1996, *Proc Natl Acad Sci*, 93(12), 6079-6084). This portion of the antenna contains the sacculus, a pit-like structure that contains poreless sensilla morphologically identical to the hygroresponsive sensilla identified by electrophysiology in other insects (Altner et al., 1985, *Annu Rev Entomol*, 30, 273-295; Shanbhag et al., 1995, *Cell and tissue research*, 282(2), 237-249). In addition, coeloconic sensilla on the antennal surface show humidity-dependent changes in firing rate (Yao et al., 2005, *J Neurosci*, 25(37), 8359-8367). At the molecular level, a prior study implicated the Transient Receptor Potential (TRP) channels waterwitch (wtrw) and nanchung (nan) in moisture avoidance in *Drosophila* (Liu et al., 2007, *Nature*, 450(7167), 294-298), although analysis of wtrw relied on RNA interference. Surprisingly, in preliminary experiments, hygrosensory behavior defects in null mutants for either nan or wtrw were not observed, a finding consistent with a recently published study that also saw no hygrosensory defects in nan or wtrw animals (Ji et al., 2015, *PLoS One*, 10(3), e0119162). This suggested that other receptors mediate moisture sensing. The neurons innervating the sacculus express several ionotropic receptor (IR) family receptors (Rytz et al., 2013, Ionotropic Receptors (IRs): Chemosensory ionotropic glutamate receptors in *Drosophila* and beyond. *Insect biochemistry and molecular biology*; Benton et al., 2009, *Cell*, 136(1), 149-162.

Figure 44A:
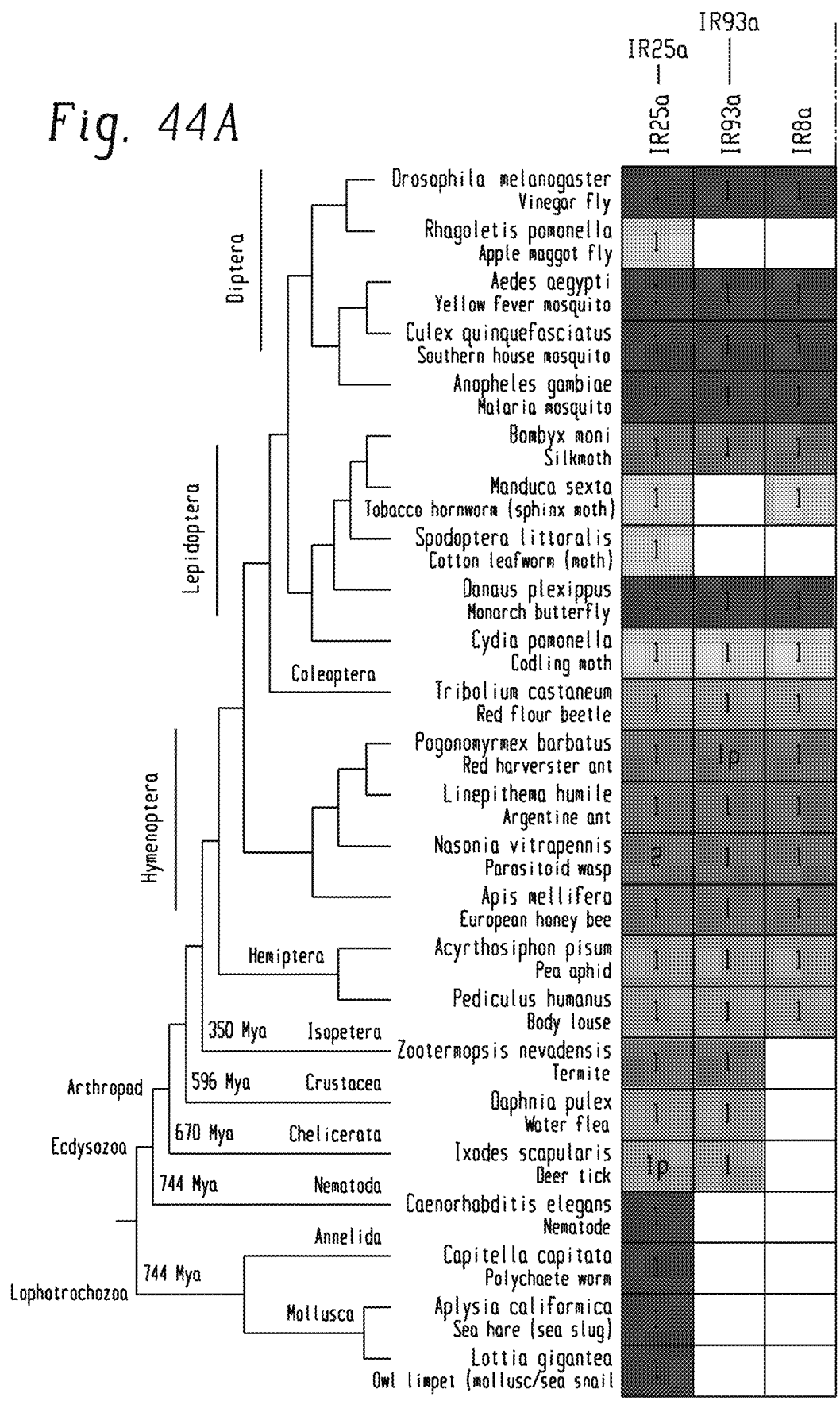
FIG. 44 shows a chart and related dendogram showing the number of orthologs of each IR (IR25a, (IR93a, IR68a and IR40a) that is present in various invertebrates, including insects. (Modified from Rytz, R. et al., 2013, *Insect Biochemistry and Molecular Biology*, 43:888-897).
Figure 44B:
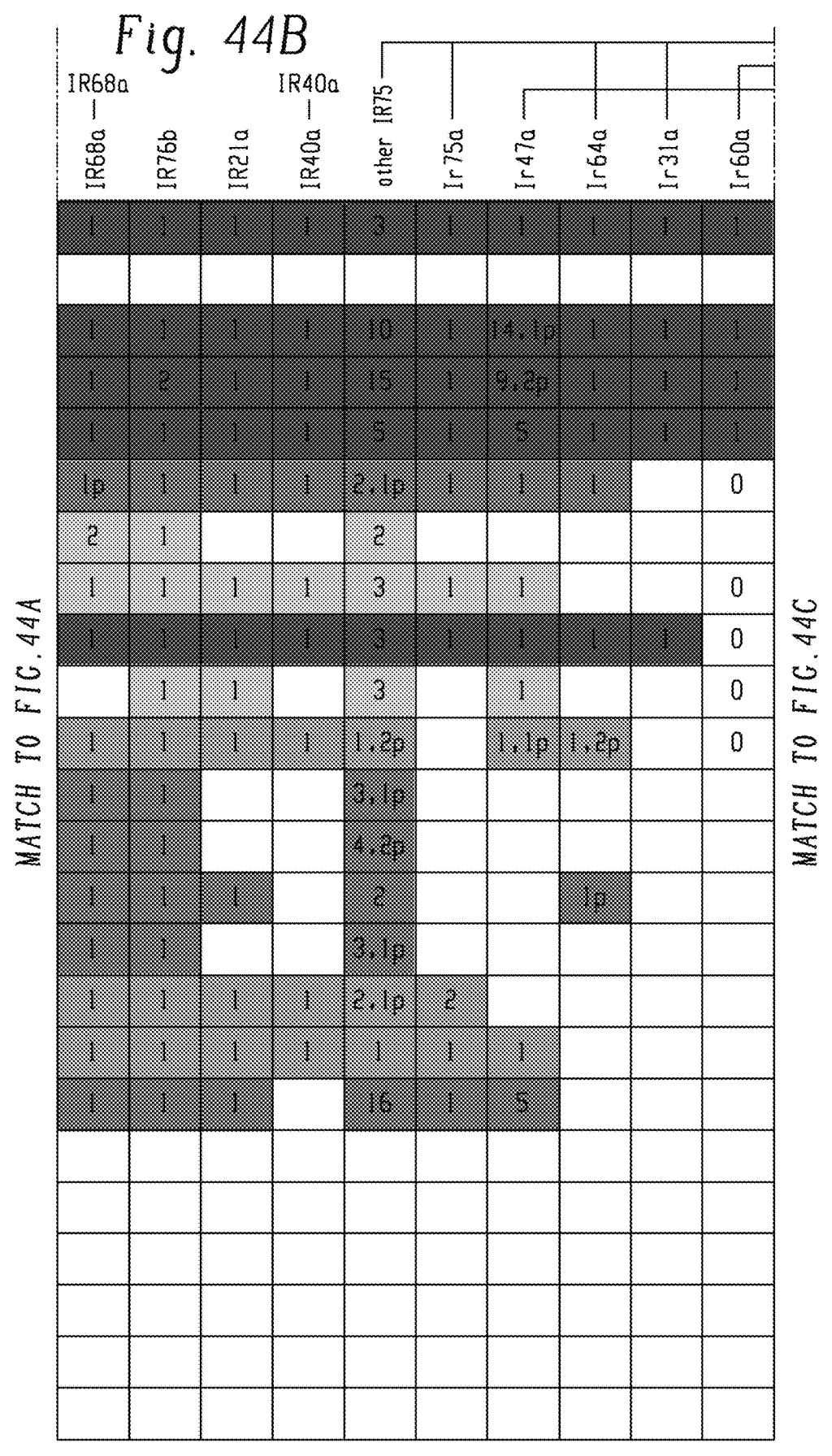
Figure 44:
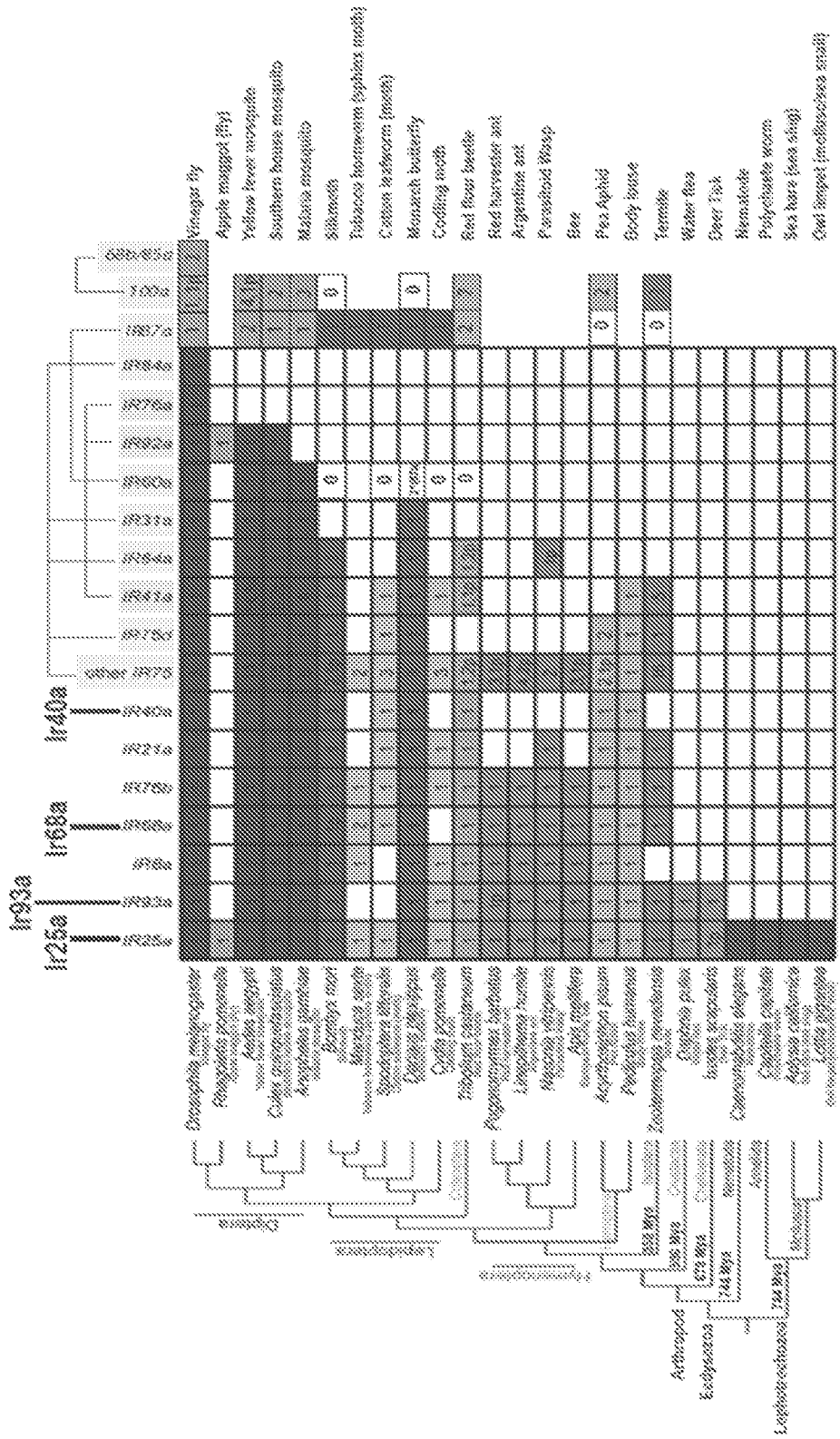
Figure 45:
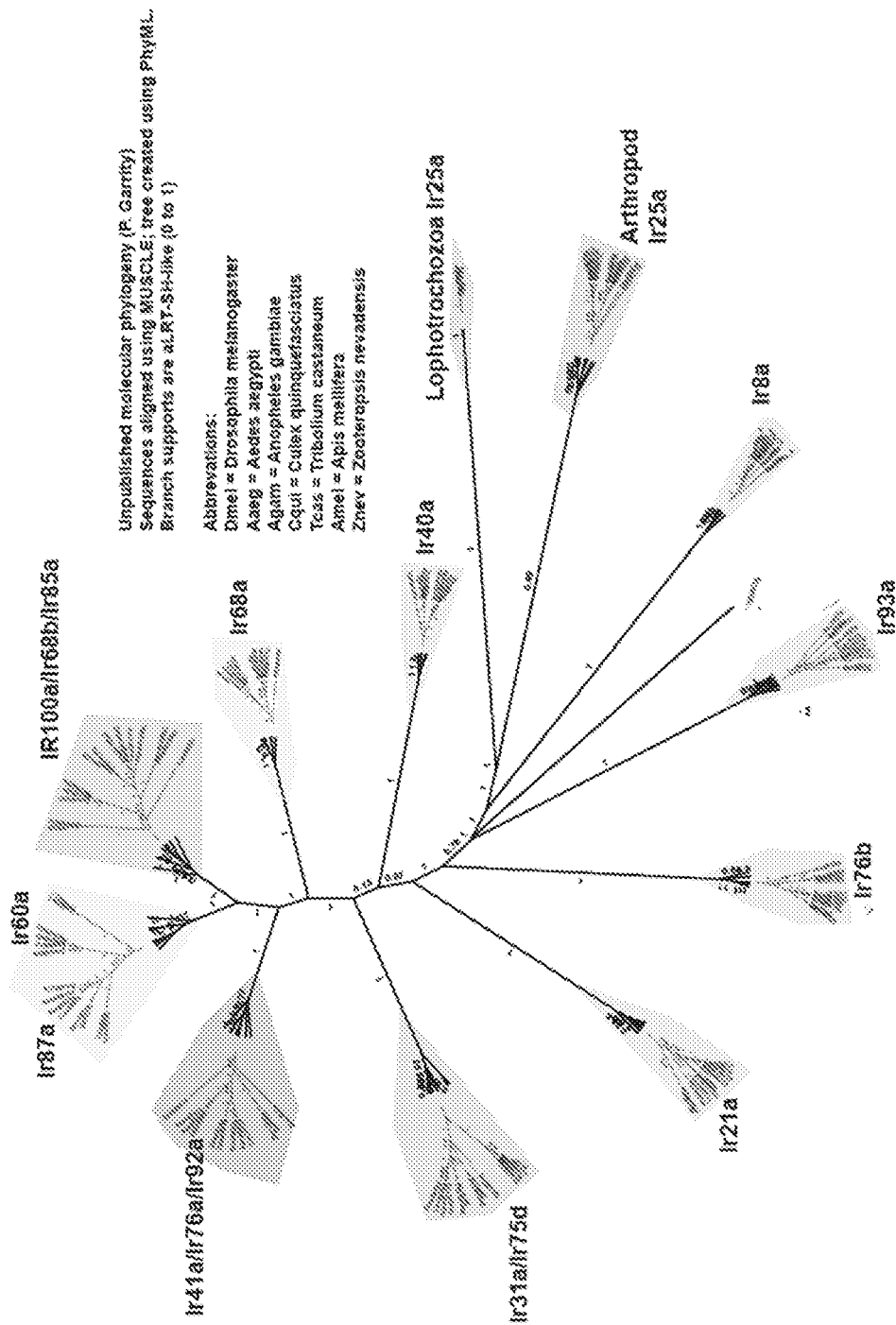
FIG. 45 presents a schematic showing the molecular phylogeny of IR family members, illustrating the true ortholog nature of the IRs among species. (Modified from Rytz, R. et al., 2013, Ibid.).

IRs are a large family of cation channels distantly related to Ionotropic Glutamate Receptors. IRs have been widely studied in insect olfaction and taste (Rytz et al., 2013, Ionotropic Receptors (IRs): Chemosensory ionotropic glutamate receptors in *Drosophila* and beyond. *Insect biochemistry and molecular biology*), but not previously implicated in thermo- or hygro-sensation. Data herein indicate that a subset of variant IRs (Ir21a, Ir25a, Ir93a and possibly Ir40a) constitute previously unknown classes of hygro- and thermo-receptors. While Ir21a and Ir93a have been reported as orphan receptors, Ir25a is known to act as a co-receptor for other, stimulus-specific IRs (Rytz et al., 2013, Ibid.; Benton et al., 2009, *Cell*, 136(1), 149-162; Abuin et al., 2011, *Neuron*, 69(1), 44-60). Ir40a has been proposed as a possible DEET receptor (Kain et al., 2013, *Nature*, 502 (7472), 507-512), although this claim is controversial (Xu et al., 2014, Proc Natl Acad Sci USA, 111(46), 16592-16597). All four of these IRs have close orthologs in biting flies and mosquitoes (Croset et al., 2010, *PLoS Genet*, 6(8), e1001064; Silbering et al., 2011, *J Neurosci*, 31(38), 13357-13375) (FIGS. 44, 45, 46) and are expressed in both fly and mosquito antennae (Silbering et al., 2011, *J Neurosci*, 31(38), 13357-13375; Pitts et al., 2011, BMC Genomics, 12, 271) consistent with sensory roles of these receptors.

Ionotropic Receptors and Hygrosensing

Water is essential for survival. While desiccation is a threat to all animals, insects are particularly vulnerable to dehydration because of their small size, making water balance a key factor affecting the survival and distribution of insect vectors of disease (Benoit et al., 2010, *J Insect Physiol*, 56(10), 1366-1376). In addition, moisture is an important cue in host-seeking and oviposition site selection in mosquitoes, whose larval stages live in aquatic environments (Bentley et al., 1989, *Annu Rev Entomol*, 34, 401-421; Brown, 1966, *JAMA* 4, 196(3), 249-252). Despite the importance of moisture sensing, the genetic, molecular, and mechanistic underpinnings of insect humidity sensation remain largely unknown.

The mechanism by which insects detect humidity presents an interesting puzzle because the sensilla housing insect hygrosensors lack pores, limiting direct contact between sensory neurons and the environment (Altner et al., 1985, *Annu Rev Entomol*, 30, 273-295). Thus hygrosensing is thought to involve the detection of a humidity-dependent stimulus, rather than water vapor itself. While prevailing theories favor mechanical pressure due to changing humidity, the molecular receptors involved have remained unclear, preventing detailed analysis.

Studies herein found two receptors required for hygrosensing. Strikingly, both are also required for the detection of cooling in other sets of neurons, indicating that insect hygrosensation could have a thermosensory basis. Understanding cooling and hygrosensing in insects can enhance basic understanding of sensory transduction and potentially reveal insights relevant to host-seeking behavior, pest control and insect responses to climate change.

Figure 48:
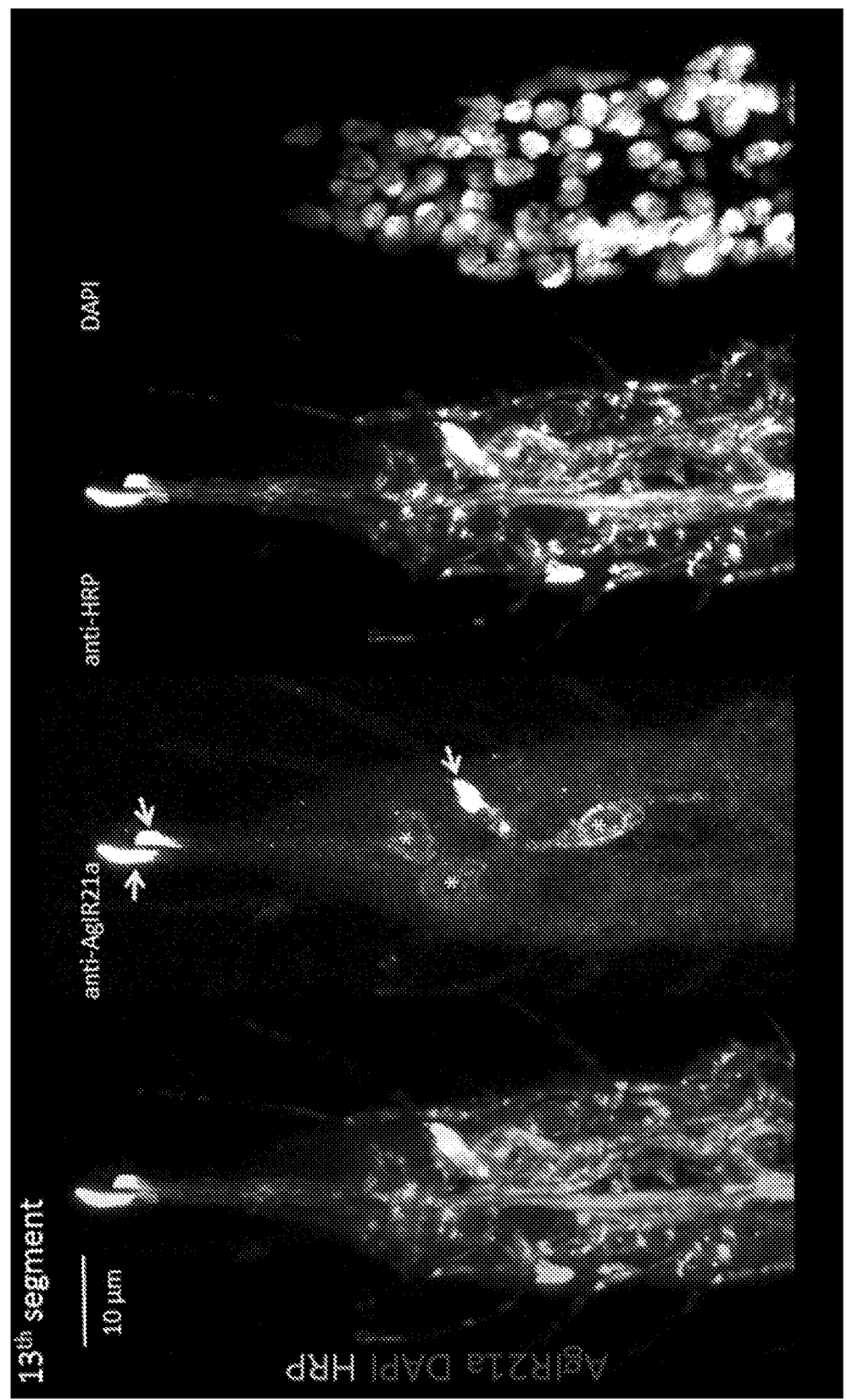
FIG. 48 shows microscopic images of the tip of the antenna (13th segment) of a mated female *Anopheles gambiae* mosquito stained for *Anopheles gambiae* Ir21a along with anti-HRP (a marker for neuronal membranes) and DAPI (nuclei). Ir21a labels sensory neuron dendrites of the putative thermoreceptor neurons in the 13th antennal segment, located at the distal tip of the antenna as well as in the middle of the 13th antennal segment. Left-most panel shows merge image, second panel from left shows anti-AgIR21a antibody staining (asterisks indicate cell bodies; arrows indicate sensory endings), third panel indicates anti-HRP staining (outlines all neurons), and right-most panel indicates DAPI (DNA). These data indicate that IR21a is expressed in the proper location for participating in temperature-responsive host-seeking behavior.

Data herein show that two Ionotropic Receptors (IRs), Ir25a and Ir93a, act in distinct cell populations to mediate moisture and cool avoidance. These findings are novel as IRs have previously been studied as chemoreceptors, but not as thermoreceptors or hygroreceptors (Rytz et al., 2013, Ibid.). In an embodiment, humidity detection by insect moist cells and hygrosensory behavior in insects particularly involve IR68a (Example 4). In an embodiment, IR25a, IR93a and IR40a comprise a population of dry-activated hygroreceptors whose activity is particularly involved in insect dry sensing and dry cell function. In an embodiment, IR25a, IR93a and IR68a comprise a population of moist-activated hygroreceptors whose activity is particularly involved in insect moisture sensing and moist cell function. In an embodiment, the activity of IR25a and IR93a is involved in insect hygrosensation and thermosensation. In an embodiment, the activity of IR21a is involved in insect thermosensation. In a particular embodiment, IR21a is involved in thermosensation of the mosquito, such as *Anopheles gambiae*. By way of example, IR21a protein expression was detected in sensory neuron dendrites of thermoreceptor neurons in antennal segments (the distal tip and middle of the antenna) in *Anopheles gambiae*. (See, e.g., FIG. 48). The involvement of IRs, e.g., IR25a and IR93a, in both temperature and moisture sensation in an insect suggests that thermos- and hygro-sensation may share common mechanisms of sensory detection. By way of example, hygrosensation may involve a thermosensory component based on evaporative cooling. Temperature and moisture detection could involve mechanosensation based on swelling or shrinking of sensory structures.

Methods of Insect Control

In some aspects, the invention provides a method of modulating thermosensation and/or hygrosensation of an animal, particularly, an insect, by modulating activity of an ionotropic receptor (IR) of the animal, such IRs Ir25a, Ir93a, Ir40a, Ir68a, or Ir21a. In an embodiment, activity of IR25a or IR93a is modulated. In another embodiment, activity of both IR40a and IR68a is modulated. In another embodiment, activity of IR25a, IR93a and IR40a, which are involved in insect dry sensing, is modulated. In another embodiment, activity of IR25a, IR93a and IR68a, which are involved in insect moisture sensing, is modulated. Without being bound by theory, either preventing or forcing activation of these receptors, via chemical or genetic means, could provide a targeted means of disrupting the survival, host-seeking, and/or reproductive abilities of arthropod disease vectors and pests. Present control strategies largely rely on either the introduction of sterile insects (which often have reduced fitness), the use of lethal chemicals that lack species-specificity and exert strong selection for development of resistance, or target chemical receptors that prompt repulsion from specific targets or alter the seeking of specific targets. However, thermal and moisture cues are critical for so many different aspects of insect physiology that interdictions targeting these receptors provides an approach to potentially simultaneously disrupt multiple processes critical for insect survival: these include physiological homeostasis, host-seeking, and reproduction. It is believed that no strategies have ever been developed to exploit these multi-functional systems.

Thus, in some embodiments, the method of modulating thermosensation and/or hygrosensation contains the step of administering to an animal an effective amount of an agent that modulates the activity of an ionotropic receptor (IR) of the animal. In some embodiments, the animal is an invertebrate. In some embodiments, the animal is an insect. In some embodiments, the animal is a vector for a human disease. In some other embodiments, the IR is Ir25a, Ir93a, Ir40a, Ir68a, or Ir21a. In an embodiment, the IR is IR25a or IR93a. In another embodiment, the IRs are IR40a and IR68a. In another embodiment, the IRs are IR25a, IR93a and IR40a (e.g., receptors involved in insect dry sensing). In another embodiment, the IRs are IR25a, IR93a and IR68a (e.g., receptors involved in insect moisture sensing). In some embodiments, the agent decreases activity of the IR. In some other embodiments, the agent increases activity of the IR.

An effective amount of the agent can be an amount that alters behavior of the animal relative to a reference or control. The control can be, for example, the behavior of a normal, healthy animal not treated with the agent. Exemplary behavior(s) altered include, without limitation, dry preference of an animal. Methods of assaying dry preference of an animal are described elsewhere herein. In some embodiments, the agent alters survival, host-seeking, and/or reproductive abilities of an animal. In particular embodiments, the agent reduces survival, host-seeking, and/or reproductive abilities of an animal.

In some embodiments, the agent that modulates activity of an IR is a small molecule compound, polypeptide, or polynucleotide. In some embodiments the agent is an inhibitory polynucleotide, such as interfering RNA, e.g., siRNA, RNAi, that reduces expression of an ionotropic receptor (IR) herein (e.g., Ir25a, Ir93a, Ir40a, Ir68a, Ir21a). In an embodiment, the inhibitory polynucleotide reduces expression of the ionotropic receptor IR25a or IR93a. In another embodiment, the inhibitory polynucleotide reduces expression of the ionotropic receptors IR40a and IR68a. In another embodiment, the inhibitory polynucleotide reduces expression of the ionotropic receptors IR25a, IR93a and IR40a, (e.g., receptors involved in insect dry sensing). In another embodiment, the inhibitory polypeptide reduces expression of the ionotropic receptors IR25a, IR93a and IR68a (e.g., receptors involved in insect moisture sensing).

The inhibitory polynucleotide can be administered to an insect for example by injection into the hemolymph or feeding. Microinjection, for example, was used in a successful application of RNAi in an insect, to obtain knockdown of frizzled in *Drosophila melanogaster* (Kennerdell and Carthew, 1998, *Cell*. 1998 Dec. 23; 95(7):1017-26). This method was transferred to *T. castaneum* (Brown et al., 1999, *Evol Dev.* 1999 July-August; 1(1):11-5) and subsequently applied to adult insects in *An. gambiae* (Blandin et al., 2002, *EMBO Rep.* 2002 September; 3(9):852-6). Microinjection has been applied to all life stages in hemi- and holometabolous insects. Protocols are in place for injection for various taxa, including *Tribolium, B. mori*, several genera of *Diptera*, the honey bee, cockroaches and orthopterans (Belles (2010, *Annu Rev Entomol*. 2010; 55:111-28).

An important barrier to the use of microinjection in some insects is non-specific damage caused by mechanical damage, which is most often pronounced when targeting embryos. Experimental variables that influence survivorship include methods of immobilization (cold, CO2, adherence to a substrate), injection volume, site of injection, and diluents. Although water or physiologic saline work well for most species, the diluent may require adjustment to the particular osmotic pressure of the hemolymph.

Oral delivery is a less-invasive and a high-throughput method for RNAi delivery. It has particular value for insects that are intolerant of injection and for field applications for RNAi-mediated pest control. Protocols for administration of dsRNA synthesized in vitro and incorporated into the diet are available for honey bees, aphids, whiteflies and psyllids (Aronstein et al., 2006, *Journal of Apicultural Research*. 2006; 45:20-24; Wuriyanghan et al., 2011, *PLoS One*. 2011; 6(11):e27736; Ghanim et al., 2007, *Insect Biochem Mol Biol*. 2007 July; 37(7):732-8.; Whyard et al., 2009, *Insect Biochem Mol Biol*. 2009 November; 39(11):824-32.). RNAi delivery to phytophagous insects can also be achieved by engineering plants to express dsRNAs in plant systems for which transgene introduction technologies are available. Two complementary methods are in use: stable transformation by hairpin dsRNAs that target insect genes (Baum et al., 2007, *Nat Biotechnol.* 2007 November; 25(11):1322-6) and transient virus-induced gene silencing (VIGS), in which engineered viral vectors carrying the gene sequence of interest are transformed into *Agrobacterium tumefaciens* and infiltrated into the plant tissue (Burch-Smith et al., 2004, *Plant J.* 2004 September; 39(5):734-46). Both approaches have been exploited, to achieve transcript suppression in *Coleoptera* (Baum et al., 2007, *Nat Biotechnol.* 2007 November; 25(11):1322-6), *Lepidoptera* (Baum et al., 2007, *Nat Biotechnol.* 2007 November; 25(11):1322-6; Kumar et al., 2012, *PLoS One.* 2012; 7(2):e31347) and *Hemiptera* (Pitino et al. 2011, *PLoS One.* 2011; 6(10):e25709.; Zha et al., 2011, *PLoS One.* 2011; 6(5):e20504.). In some species, notably dipterans, oral delivery of RNAi triggers has yielded less consistent results than microinjection (Zhang et al., 2011, *PLoS One.* 2011 Apr. 11; 6(4):e18644). Further, in *Lepidoptera*, feeding as a mode of delivery necessitates the provision of high doses of RNAi trigger (Terenius et al., 2011, *J Insect Physiol.* 2011 February; 57(2):231-45). This can be attributed to a variety of factors. The efficacy of RNAi of midgut transcripts may be reduced due to low or inconsistent doses taken up by individual insects, frequency and size of feeding, plus GI tract morphology and physiology will affect the actual dose of RNAi that reaches the midgut epithelium.

Other routes for dsRNA delivery include electroporation, soaking or ectopic application, incorporation into nanoparticles, expression in bacteria, topical application, injection into woody plants, direct absorption of dsRNA in water solution into plant cuttings, or rooted seedlings and trees and solubilization using transfection agents, such as Lipofectamine™ (Wang et al., 2011, *PLoS One.* 2011 Apr. 11; 6(4):e18644.; Karim et al., 2010, *BMC Biotechnol.* 2010 Jan. 14; 100:1.; Zhang et al., 2010, *Insect Mol Biol.* 2010 October; 19(5):683-93; Pridgeon et al., 2008, *J Med Entomol.* 2008 May; 45(3):414-20; Lopez-Martinez et al., 2012, *J Med Entomol.* 2012 January; 49(1):215-8; Hunter et al., 2012, *Southwestern Entomologist.* 2012; 37:85-87; Yu et al. (2013), *Insect Sci.* 2013 February; 20(1):4-14).

Genome Editing

Genome editing is a major focus of biomedical research. The development of novel "gene editing" tools provides the ability to manipulate the DNA sequence of a cell at a specific chromosomal locus, without introducing mutations at other sites of the genome. This technology effectively enables the researcher to manipulate the genome of a subject's (e.g., a mammal or invertebrate, such as an insect, subject) cells in vitro or in vivo.

In one embodiment, gene editing involves targeting an endonuclease (an enzyme that causes DNA breaks internally within a DNA molecule) to a specific site of the genome and thereby triggering formation of a chromosomal double strand break (DSB) at the chosen site. An endonuclease is an enzyme that cleaves the phosphodiester bond within a polynucleotide chain, such as DNA. If, concomitant with the introduction of the chromosome breaks, a donor DNA molecule is introduced (for example, by plasmid or oligonucleotide introduction), interactions between the broken chromosome (DNA) and the introduced DNA can occur, especially if the two sequences share homology. In this instance, a process termed "gene targeting" can occur, in which the DNA ends of the chromosome invade homologous sequences of the donor DNA by homologous recombination (HR). By using the donor plasmid sequence as a template for HR, a seamless repair of the chromosomal DSB can be accomplished. Importantly, if the donor DNA molecule differs slightly in sequence from the chromosomal sequence, HR-mediated DSB repair will introduce the donor sequence into the chromosome, resulting in gene conversion/gene correction of the chromosomal locus. By targeting the nuclease to a genomic site of interest, the concept is to use DSB formation to stimulate HR and to thereby replace target sequence with a desired sequence, which might include a gene having a deletion or mutation (e.g., insertion, point mutation, frame shift).

Current genome editing tools use the induction of double strand breaks (DSBs) to enhance gene manipulation of cells. Such methods include zinc finger nucleases (ZFNs; described for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, and U.S. Pat. Publ. Nos. 20030232410 and US2009020314, which are incorporated herein by reference), Transcription Activator-Like Effector Nucleases (TALENs; described for example in U.S. Pat. Nos. 8,440,431, 8,440,432, 8,450,471, 8,586,363, and 8,697,853, and U.S. Pat. Publ. Nos. 20110145940, 20120178131, 20120178169, 20120214228, 20130122581, 20140335592, and 20140335618, which are incorporated herein by reference), and the CRISPR (Clustered Regularly Interspaced Short Palindromic Repeats)/Cas9 system (described for example in U.S. Pat. Nos. 8,697,359, 8,771,945, 8,795,965, 8,871,445, 8,889,356, 8,906,616, 8,932,814, 8,945,839, 8,993,233, and 8,999,641, and U.S. Pat. Publ. Nos. 20140170753, 20140227787, 20140179006, 20140189896, 20140273231, 20140242664, 20140273232, 20150184139, 20150203872, 20150031134, 20150079681, 20150232882, and 20150247150, which are incorporated herein by reference). For example, ZFN DNA sequence recognition capabilities and specificity can be unpredictable. Similarly, TALENs and CRISPR/Cas9 cleave not only at the desired site, but often at other "off-target" sites, as well. These methods have significant issues connected with off-target double-stranded break induction and the potential for deleterious mutations, including indels, genomic rearrangements, and chromosomal rearrangements, associated with these off-target effects. ZFNs and TALENs entail the use of modular sequence-specific DNA binding proteins to generate specificity for ~18 bp sequences in the genome.

RNA-guided nuclease-mediated genome editing, based on Type 2 CRISPR (Clustered Regularly Interspaced Short Palindromic Repeat)/Cas (CRISPR Associated) systems, offers a valuable approach to alter the genome. In brief, Cas9, a nuclease guided by single-guide RNA (sgRNA), binds to a targeted genomic locus next to the protospacer adjacent motif (PAM) and generates a double-strand break (DSB). The DSB is then repaired either by non-homologous end joining (NHEJ), which leads to insertion/deletion (indel) mutations, or by homology-directed repair (HDR), which requires an exogenous template and can generate a precise modification at a target locus (Mali et al., *Science.* 2013 Feb. 15; 339(6121):823-6). Unlike other gene editing methods, which add a functional, or partially functional, copy of a gene to a subject's cells but retain the original copy of the gene, this system can remove and replace the target gene. Genetic editing using engineered nucleases has been demonstrated in tissue culture cells and rodent models of rare diseases.

CRISPR has been used in a wide range of organisms including baker's yeast (*S. cerevisiae*), zebra fish, nematodes (*C. elegans*), plants, mice, and several other organisms. Additionally, CRISPR has been modified to make programmable transcription factors that allow scientists to target and activate or silence specific genes. Libraries of tens of thousands of guide RNAs are now available.

Since 2012, the CRISPR/Cas system has been used for gene editing (silencing, enhancing or changing specific genes) that even works in eukaryotes like mice and primates. By inserting a plasmid containing cas genes and specifically designed CRISPRs, an organism's genome can be cut at any desired location. CRISPR repeats range in size from 24 to 48 base pairs. They usually show some dyad symmetry, implying the formation of a secondary structure such as a hairpin, but are not truly palindromic. Repeats are separated by spacers of similar length. Some CRISPR spacer sequences exactly match sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define 8 CRISPR subtypes (E. coli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (about 30 base pairs in length), which are then inserted into the CRISPR locus near the leader sequence. RNAs from the CRISPR loci are constitutively expressed and are processed by Cas proteins to small RNAs composed of individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype E. coli) proteins (called CasA-E in E. coli) form a functional complex, Cascade, that processes CRISPR RNA transcripts into spacer-repeat units that Cascade retains. In other prokaryotes, Cas6 processes the CRISPR transcripts. Interestingly, CRISPR-based phage inactivation in E. coli requires Cascade and Cas3, but not Cas1 and Cas2. The Cmr (Cas RAMP module) proteins found in Pyrococcus furiosus and other prokaryotes form a functional complex with small CRISPR RNAs that recognizes and cleaves complementary target RNAs. RNA-guided CRISPR enzymes are classified as type V restriction enzymes. See also U.S. Patent Publication 2014/0068797, which is incorporated by reference in its entirety.

Cas9

Cas9 is a nuclease, an enzyme specialized for cutting DNA, with two active cutting sites, one for each strand of the double helix. It has been demonstrated that one or both sites could be disabled while preserving Cas9's ability to home locate its target DNA. Jinek et al., (2012, Science. 2012, Aug. 7; 337(6096):816-21) combined tracrRNA and spacer RNA into a "single-guide RNA" molecule that, mixed with Cas9, could find and cut the correct DNA targets. It has been proposed that such synthetic guide RNAs might be able to be used for gene editing (Jinek et al., 2012, Ibid).

Cas9 proteins are highly enriched in pathogenic and commensal bacteria. CRISPR/Cas-mediated gene regulation may contribute to the regulation of endogenous bacterial genes, particularly during bacterial interaction with eukaryotic hosts. For example, Cas protein Cas9 of Francisella novicida uses a unique, small, CRISPR/Cas-associated RNA (scaRNA) to repress an endogenous transcript encoding a bacterial lipoprotein that is critical for F. novicida to dampen host response and promote virulence. Coinjection of Cas9 mRNA and sgRNAs into the germline (zygotes) generated mice with mutations. Delivery of Cas9 DNA sequences is also contemplated.

gRNA

As an RNA guided protein, Cas9 requires a short RNA to direct the recognition of DNA targets. Though Cas9 preferentially interrogates DNA sequences containing a PAM sequence, NGG, it can bind here without a protospacer target. However, the Cas9-gRNA complex requires a close match to the gRNA to create a double strand break. CRISPR sequences in bacteria are expressed in multiple RNAs and then processed to create guide strands for RNA. Because Eukaryotic systems lack some of the proteins required to process CRISPR RNAs, the synthetic construct gRNA was created to combine the essential pieces of RNA for Cas9 targeting into a single RNA expressed with the RNA polymerase type 21 promoter (U6). Synthetic gRNAs are slightly over 100 bp at the minimum length and contain a portion which targets the 20 protospacer nucleotides immediately preceding the PAM sequence NGG; gRNAs do not contain a PAM sequence.

In one approach, one or more cells of a subject (e.g., insect) are altered to express a wild-type form of an IR using a CRISPR-Cas system. Cas9 can be used to target an IR comprising a mutation. Upon target recognition, Cas9 induces double strand breaks in the IR target gene. Homology-directed repair (HDR) at the double-strand break site can allow insertion of a desired wild-type IR sequence.

The following US patents and patent publications are incorporated herein by reference: U.S. Pat. No. 8,697,359, 20140170753, 20140179006, 20140179770, 20140186843, 20140186958, 20140189896, 20140227787, 20140242664, 20140248702, 20140256046, 20140273230, 20140273233, 20140273234, 20140295556, 20140295557, 20140310830, 20140356956, 20140356959, 20140357530, 20150020223, 20150031132, 20150031133, 20150031134, 20150044191, 20150044192, 20150045546, 20150050699, 20150056705, 20150071898, 20150071899, 20150071903, 20150079681, 20150159172, 20150165054, 20150166980, and 20150184139.

Gene Drives

In an aspect, genes encoding one or more of the IR variant proteins described herein (e.g., one or more of Ir25a, Ir93a, Ir40a, Ir68a, or Ir21a) can be targeted in synthetic, RNA-guided gene drive systems based on CRISPR/Cas9 gene technology to alter behavior in or eliminate populations of undesired pests and vector organisms, for example, without limitation, various species of mosquitos (e.g., Anopheles gambiae, the insect vector of human malaria), lice, termites, aphids, for example, in natural populations in the wild. (Core Working Group on Guidance for Contained Field Trials, Vector-borne and zoonotic diseases, Vol. 8(2): 127-168) (FIGS. 47A and 47B). CRISPR/Cas9 gene drives which can spread in a population and alter insect populations have been reported, and thus are known and can be practiced by those having skill in the art. See, for example, Hammond, A. et al., 2016, Nature Biotechnology, 34(1):78-83; Esvelt, K. M. et al., 2014, eLife; 3; e03401; doi: 10.7554/eLife.03401; Isaacs, A. T. et al., 2011, PLoS Pathogens, 7(4): e1002017. doi:10.1371/journal.ppat.1002017; Gantz, V. M. et al., 2015, Proc. Natl. Acad. Sci. USA, 112(49), E6736-E6743; Gantz, V. M. and Bier, E., 2015, *Science,* 348(6233):442-444, each of which is incorporated herein in its entirety. Accordingly, an endonuclease-based gene drive system that interferes with the normal functioning of the IR genes required for the insect's hygrosensing (and/or thermosensing) provides a molecular genetics-based control of the survival of the insect vector. Gene drives that involve the IR genes required for hygrosensation and/or thermosensation in insect pests offers a key target for controlling or destroying harmful human pests because of their vulnerabilty to dehydration and their need to maintain water balance for their survival, as moisture plays a critical role in host-seeking and oviposition site selection by mosquitoes, whose larval stages live in aquatic environments.

CRISPR/Cas9 endonuclease constructs engineered for specificity toward one or more of Ir25a, Ir93a, Ir40a, Ir68a, or Ir21a genes, are advantageous for controlling insect vectors of disease. In a particular embodiment, IR25a and IR93a genes are highly suitable targets as they are required for humidity detection by moist and dry cells and well as cold detection by cool receptors in insects, as shown in the examples herein. In another particular embodiment, the IR68a gene, which encodes the IR68a receptor that is required for moist cell function in the insect, and the IR40a gene, which encodes the IR40a receptor that is required for dry cell function in the insect, are highly suitable targets. Gene drives targeting the genes encoding receptors that are essential for driving hygrotaxis provide an advantageous system for controlling an insect population such vector mosquitos, as the loss of either IR25a or IR93a, or the combined loss of IR40a and IR68a, in insect sensory neurons completely eliminates the animal's responses to humidity as described and exemplified herein.

In an aspect, CRISPR/Cas9-mediated homology-independent targeted integration (HITI) can be employed for in vivo genome editing of organisms, including insects. See, e.g., FIGS. 47A and 47B. HITI can be used for DNA knock-in in both dividing and non-dividing cells in vitro and in vivo. HITI-mediated in vivo genome editing in neurons has been reported by Suzuki, K. et al., 2016, *Nature,* 540:144-167.

Screening Assays

In some aspects, the invention provides methods for identifying modulators, i.e., candidate or test compounds or agents (e.g., proteins, peptides, peptidomimetics, peptoids, polynucleotides, small molecules or other drugs) that are useful for disrupting survival, host-seeking, and/or reproductive abilities of an animal, particularly, an invertebrate or an insect. The methods contain the steps of contacting an ionotropic receptor (IR) of an animal or administering to an animal a candidate agent, and measuring a biological activity of the IR. In some embodiments, the candidate agent increases or decreases a biological activity of the IR. In some embodiments, an increase or decrease in biological activity of the IR indicates the candidate agent modulates hygrosensing and/or thermosensing in the animal. In some other embodiments, an increase or decrease in biological activity of the IR indicates the candidate agent alters survival, host-seeking, and/or reproductive capabilities of the animal. In some embodiments, the candidate agent decreases survival, host-seeking, and/or reproductive capabilities of the animal. In particular embodiments, the ionotropic receptor is Ir25a, Ir93a, Ir40a, Ir68a, or Ir21a. In a particular embodiment, the ionotropic receptor is IR25a or IR93a. In another particular embodiment, the ionotropic receptors are IR40a and IR68a. In another particular embodiment, the ionotropic receptors are IR25a, IR93a and IR40a, (e.g., receptors involved in insect dry sensing). In another particular embodiment, the ionotropic receptors are IR25a, IR93a and IR68a (e.g., receptors involved in insect moisture sensing).

The test agents of the present invention can be obtained singly or using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. (1994) et al., *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) Proc. Natl. Acad. Sci. U.S.A. 90:6909; Erb et al. (1994) *Proc. Natl. Acad. Sci. USA* 91:11422; Zuckermann et al. (1994) *J. Med. Chem.* 37:2678; Cho et al. (1993) *Science,* 261:1303; Carrell et al. (1994) *Angew. Chem. Int. Ed. Engl.* 33:2059; Carell et al (1994) *Angew. Chem. Int. Ed. Engl.* 33:2061; and Gallop et al. (1994) *J. Med. Chem.* 37:1233.

Libraries of compounds may be presented in solution (e.g., Houghten (1992), *Biotechniques,* 13:412-421), or on beads (Lam (1991), *Nature,* 354:82-84), chips (Fodor (1993) *Nature,* 364:555-556), bacteria (Ladner, U.S. Pat. No. 5,223,409), spores (Ladner U.S. Pat. No. 5,223,409), plasmids (Cull et al. (1992) *Proc Natl Acad Sci USA,* 89:1865-1869) or on phage (Scott and Smith (1990) *Science,* 249:386-390; Devlin (1990) *Science,* 249:404-406; Cwirla et al. (1990) *Proc. Natl. Acad. Sci. USA,* 87:6378-6382; Felici (1991) *J. Mol. Biol.,* 222:301-310; Ladner supra.).

Chemical compounds to be used as test agents (i.e., potential inhibitor, antagonist, agonist) can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock (1989) *Comprehensive Organic Transformations,* VCH Publishers; T. W. Greene and P. G. M. Wuts, *Protective Groups in Organic Synthesis,* 2nd ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

Combinations of substituents and variables in compounds envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., transport, storage, assaying, therapeutic administration to a subject).

The compounds described herein can contain one or more asymmetric centers and thus occur as racemates and racemic mixtures, single enantiomers, individual diastereomers and diastereomeric mixtures. All such isomeric forms of these compounds are expressly included in the present invention. The compounds described herein can also be represented in multiple tautomeric forms, all of which are included herein. The compounds can also occur in cis- or trans- or E- or Z-double bond isomeric forms. All such isomeric forms of such compounds are expressly included in the present invention.

Test agents of the invention can also be peptides (e.g., growth factors, cytokines, receptor ligands) or polynucleotides encoding such peptides.

Screening methods of the invention identify agents that increase or decrease a biological activity of an ionotropic receptor (IR) of the invention, such as Ir25a, Ir93a, Ir40a, Ir68a, or Ir21a. In some embodiments, an animal is administered a candidate agent or an IR of an animal is contacted with a candidate agent, and an effect of the candidate agent on a biological activity or function of IR is assayed. Exemplary biological effects of the candidate agent that can be assayed include hygrosensing and thermosensing. In some embodiments, alteration in hygrosensing and/thermosensing alters survival, proliferation, host-seeking abilities, and/or reproductive capabilities of the animal. Assays of measuring such biological activities or animal behavior are known to one skilled in the art. In some embodiments, the animal is an invertebrate. In some embodiments, the animal is an insect.

Agents useful in the methods of the invention can also be detected by identifying an increase or decrease in expression of an ionotropic receptor (IR) (e.g., Ir25a, Ir93a, Ir40a, Ir68a, Ir21a). The level of expression can be measured in a number of ways, including, but not limited to: measuring the IR mRNA; and, measuring the amount and/or activity of IR polypeptide.

The level of mRNA corresponding to an IR can be determined both by in situ and by in vitro formats. The isolated mRNA can be used in hybridization or amplification assays that include, but are not limited to, Southern or Northern analyses, polymerase chain reaction analyses and probe arrays. In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA of the IRs described herein.

The level of mRNA in a sample can be evaluated with nucleic acid amplification, e.g., by rtPCR (Mullis (1987) U.S. Pat. No. 4,683,202), ligase chain reaction (Barany (1991) *Proc. Natl. Acad. Sci. USA*, 88:189-193), self sustained sequence replication (Guatelli et al. (1990) *Proc. Natl. Acad. Sci. USA*, 87:1874-1878), transcriptional amplification system (Kwoh et al. (1989) *Proc. Natl. Acad. Sci. USA*, 86:1173-1177), Q-Beta Replicase (Lizardi et al. (1988) *Bio/Technology*, 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the IR being analyzed.

The practice of the present invention generally employs, unless otherwise indicated, conventional techniques of molecular biology (including recombinant techniques), microbiology, cell biology, biochemistry and immunology, which are well within the purview of the skilled artisan. Such techniques are explained fully in the literature, such as, *Molecular Cloning: A Laboratory Manual*, second edition (Sambrook, 1989); *Oligonucleotide Synthesis* (Gait, 1984); *Animal Cell Culture* (Freshney, 1987); *Methods in Enzymology, Handbook of Experimental Immunology* (Weir, 1996); *Gene Transfer Vectors for Mammalian Cells* (Miller and Calos, 1987); *Current Protocols in Molecular Biology* (Ausubel, 1987); *PCR: The Polymerase Chain Reaction*, (Mullis, 1994); *Current Protocols in Immunology* (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Hygrosensation in Insects

Humidity is a key environmental variable. Water is the solvent of living cells. Humidity determines the tendency of water to evaporate and signals the presence/absence of water. Absolute humidity is the amount of water vapor in a given volume of air. In other words, absolute humidity is the mass of water vapor divided by the total volume of the air/water mixture. Humidity is linked to evaporation and condensation. The amount of water vapor in the air has little influence on the "wetness" or "dryness" of the air. Absolute humidity does not account for temperature.

Figure 31A:
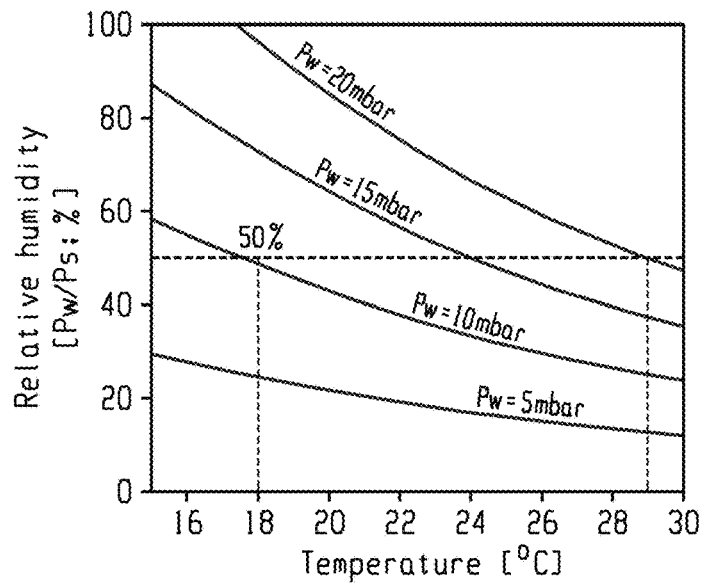
FIGS. 31A-31C are plots illustrating that saturation/vapor pressure deficit is more informative of evaporative conditions.
Figure 31B:
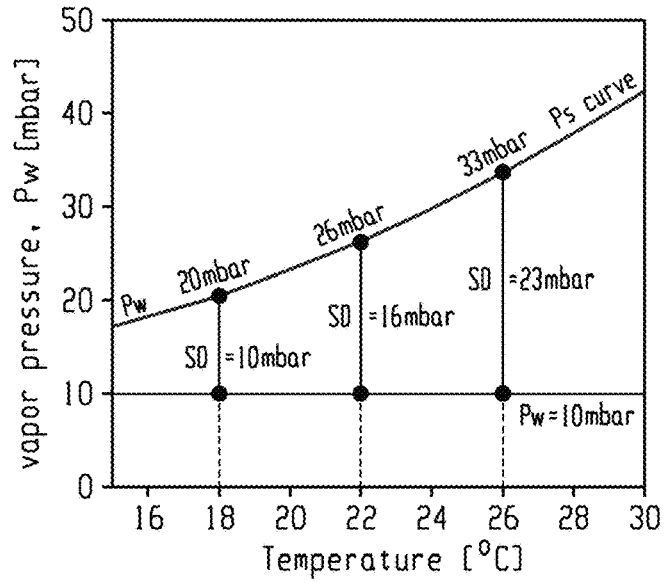
Figure 31C:
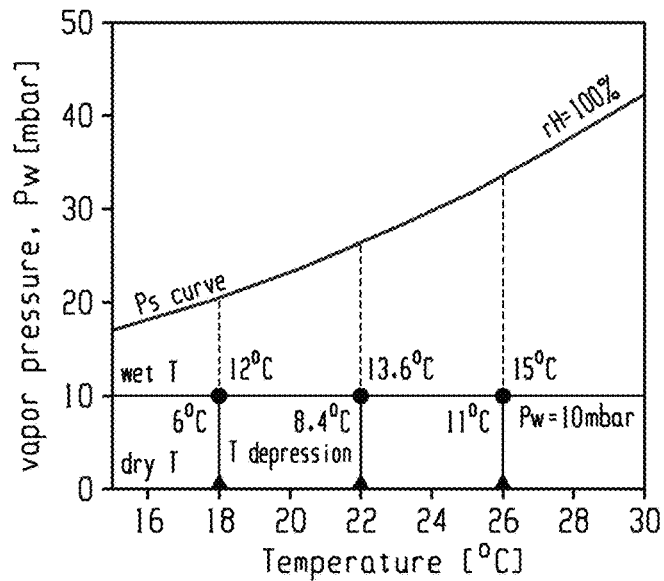

Relative humidity helps account for temperature. Relative humidity (RH) is the ratio of partial pressure of water vapor (Vp) to saturated vapor pressure (Vp*). However, relative humidity is not necessarily indicative of evaporative conditions. As shown in FIGS. 31A-31B, evaporative conditions are better indicated by saturation deficit, which is the difference between the vapor pressure and saturation vapor pressure at a given temperature. Alternatively, evaporative conditions can be indicated by temperature depression. FIG. 31C shows temperatures measured with two thermometers, one moist and one dry. The temperature difference measured is due to evaporative cooling.

Figure 30:
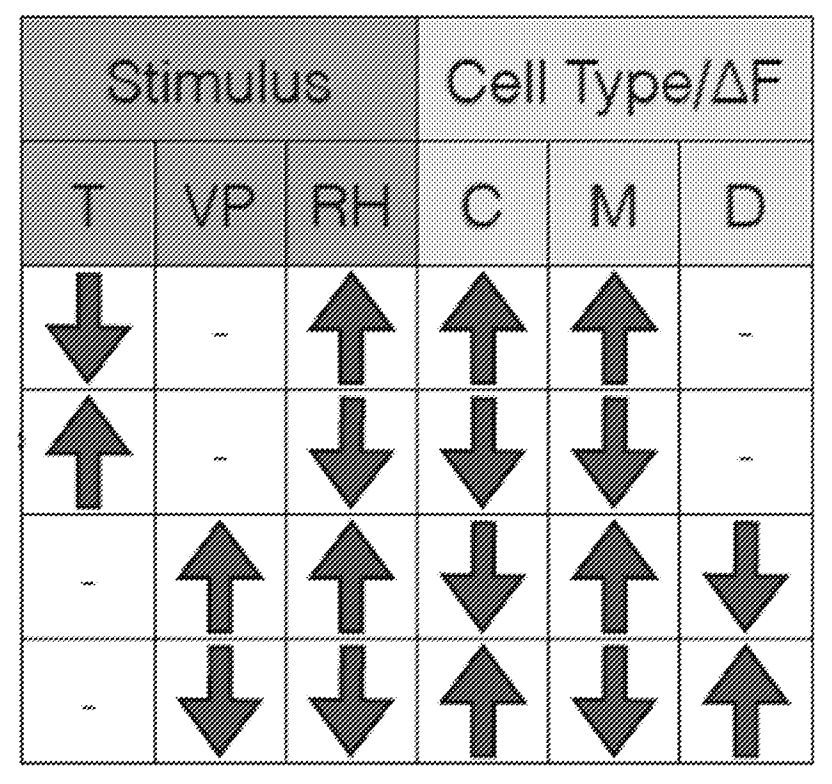

An insect's awareness of evaporative conditions depends on multiple parameters (FIG. 30). The studies herein focus on investigating how a "biological hygrometer" would function. Mosquitoes, for example, rely on hygrosensation. This is needed to locate water sources for breeding, and is important for host seeking.

Figure 11A:
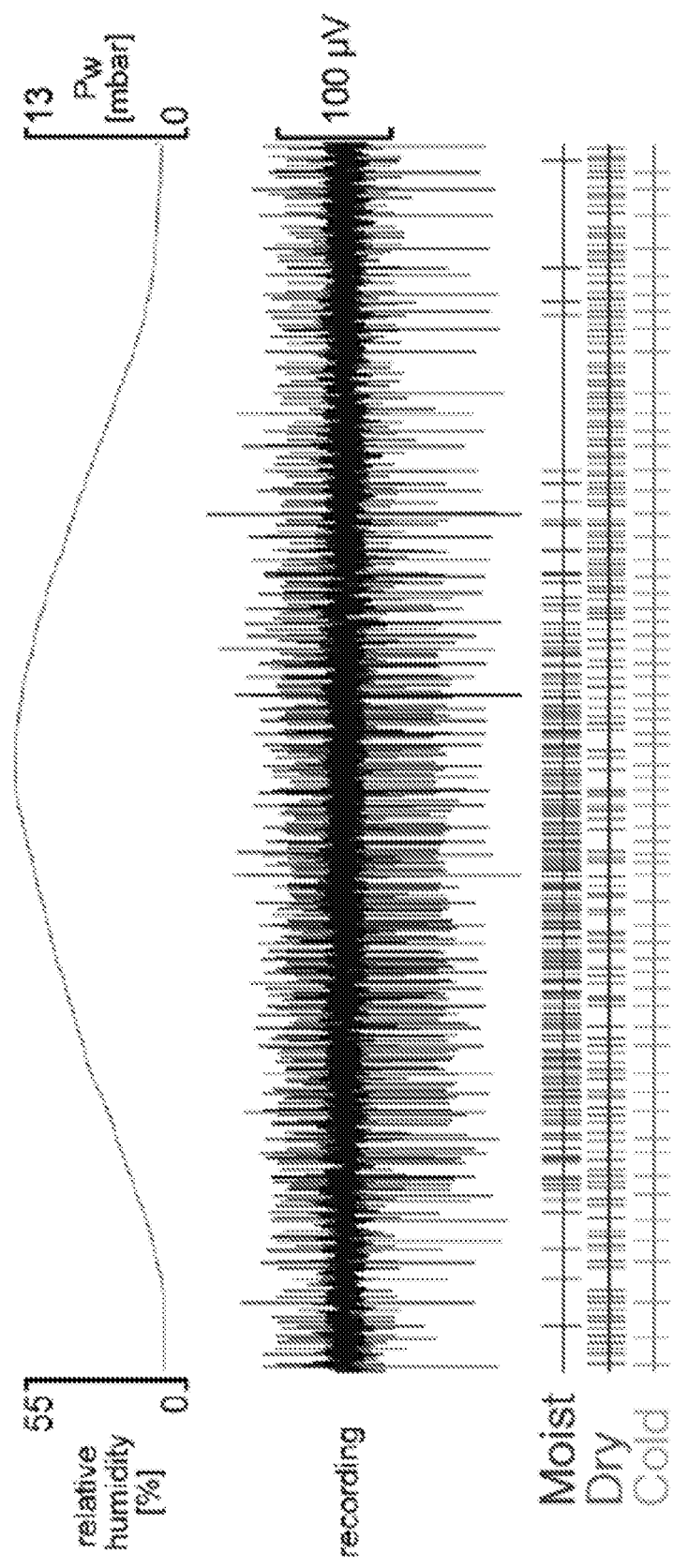
FIGS. 11A-11C are traces, plots and schematics illustrating that moist and dry cells sense humidity change through unknown mechanisms.
Figure 11B:
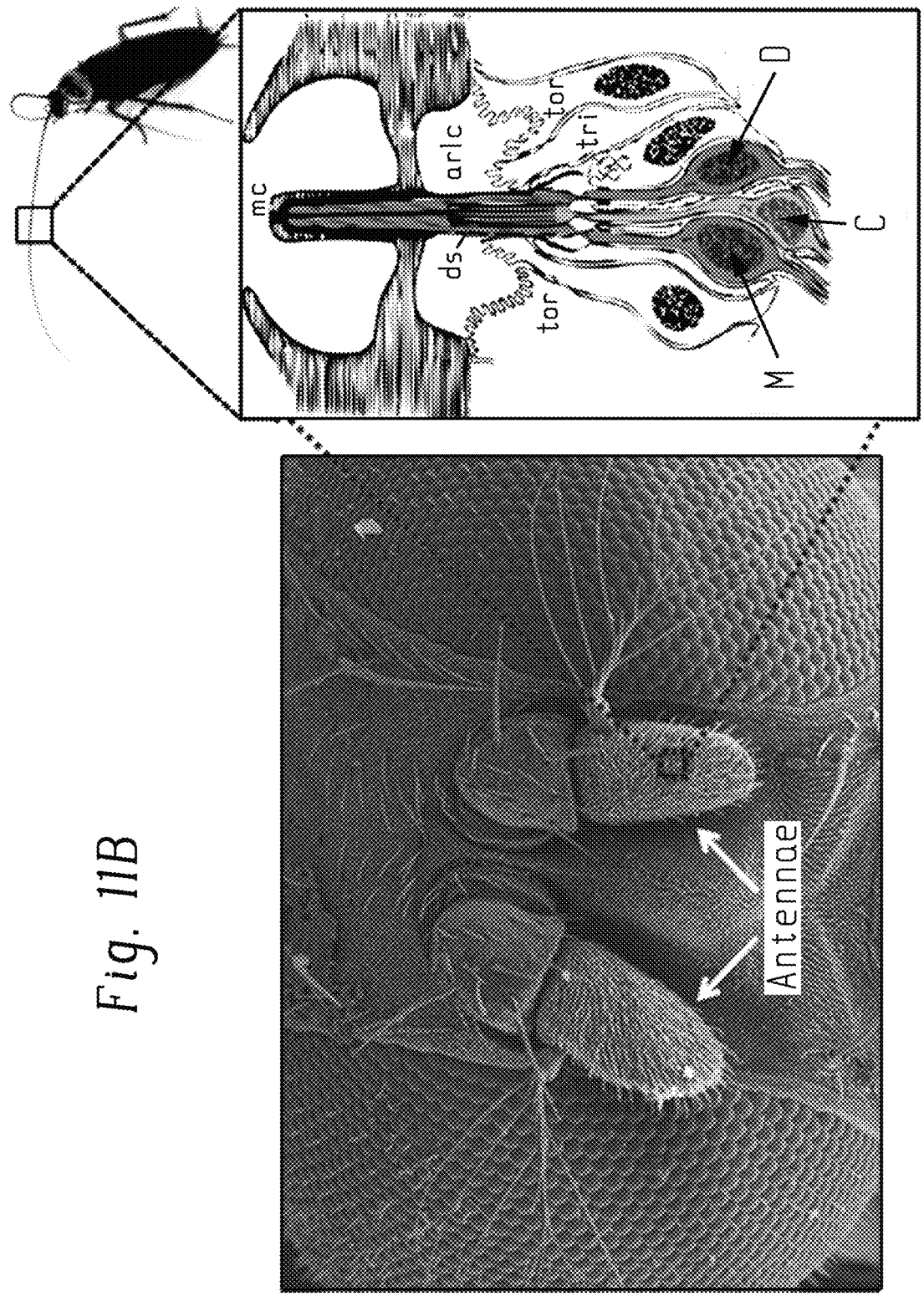
Figure 11C:
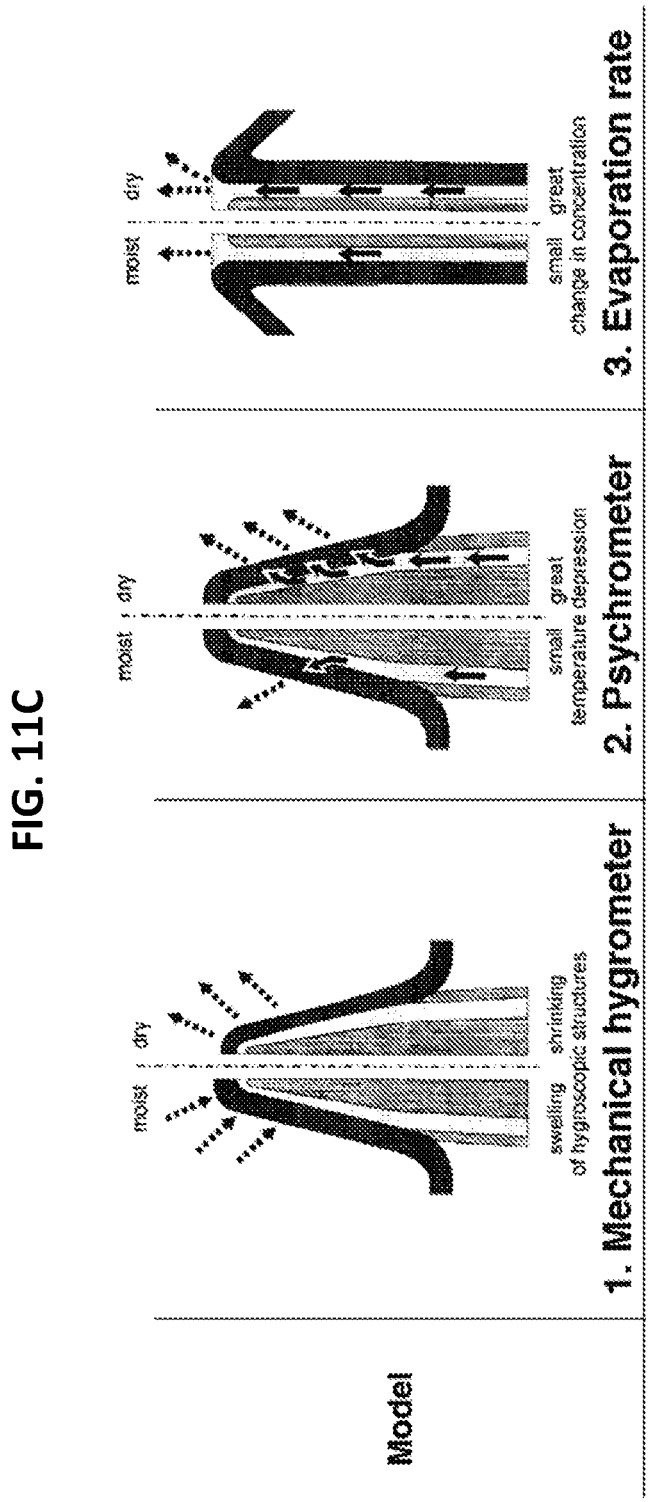

Currently, there are three models of insect hygrosensation (FIG. 11C). In the "mechanical hygrometer" or mechanoreceptor model, evaporative conditions are sensed through shrinking or swelling due to equilibrium changes. In the "evaporative rate" or chemoreceptor model, lymph concentration changes are sensed. In the "psychrometer" or thermoreceptor model, changes in temperature indicative of evaporative conditions are sensed.

Hygrosensation in insects raises challenging questions. Insects sense stimuli through innervated hair-like structures called sensilla (FIG. 11B). Insects have dedicated hygrosensing sensilla. Electrophysiology suggests these contain a triad of "moist," "dry," and "cold" cells (FIG. 11A). The behavioral significance of these cells is unknown. The molecular basis of their function is unknown. The aim of the work described herein is to answer questions regarding the behavioral significance and molecular basis of the function of these cells using genetically and behaviorally tractable D. melanogaster. In particular, Drosophila genetics is used to determine the molecular receptors required for hygrosensing. The behavioral relevance of these receptors with regard to moist and dry cells and the mechanism of activation for these receptors are determined. The goal of the study herein is to use Drosophila melanogaster to identify and characterize genes required for responding to changing humidity.

Previous work showed that hygrotactic behavior in Drosophila requires the third antennal segment and arista (FIG. 13). Coeloconic sensilla on the antennal surface and the TRP channels waterwitch and nanchung were implicated in hygrosensing (FIG. 13) (Liu et al. 2007, Nature, 450 (7167), 294-298; Sayeed and Benzer 1996, Proc Natl Acad Sci USA, 93(12), 6079-6084; Ji and Zhu 2015, PLoS One, 10(3), e0119162). Data described elsewhere herein implicate other sensory neurons and receptors in the response.

Figure 14:
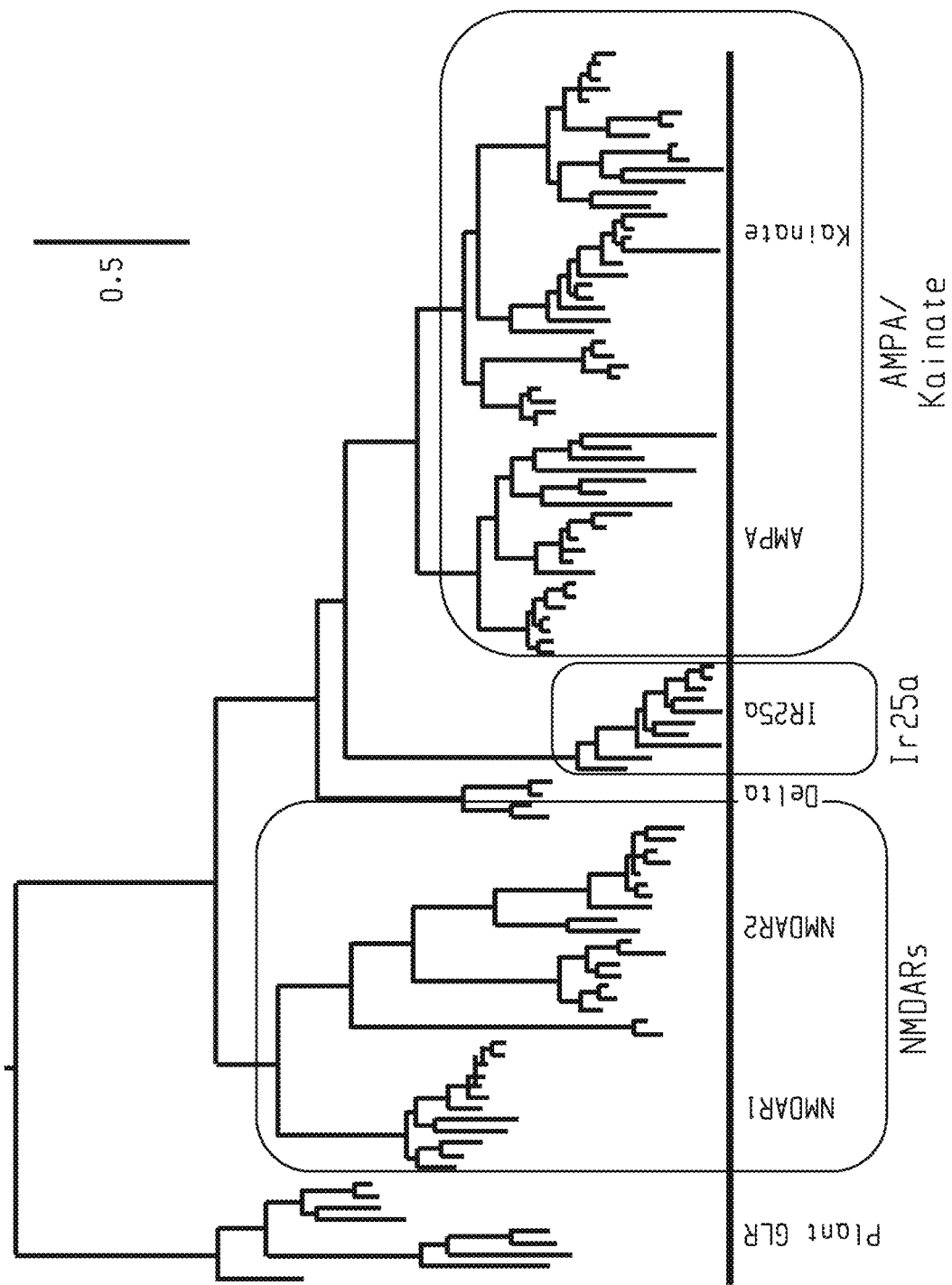
FIG. 14 is a dendogram showing that the "Ionotropic Receptor" (IR) family is related to ionotropic glutamate receptors (iGluRs) (Croset, Rytz, et al. 2010, *PLoS Genet*, 6(8), e1001064).
Figure 15:
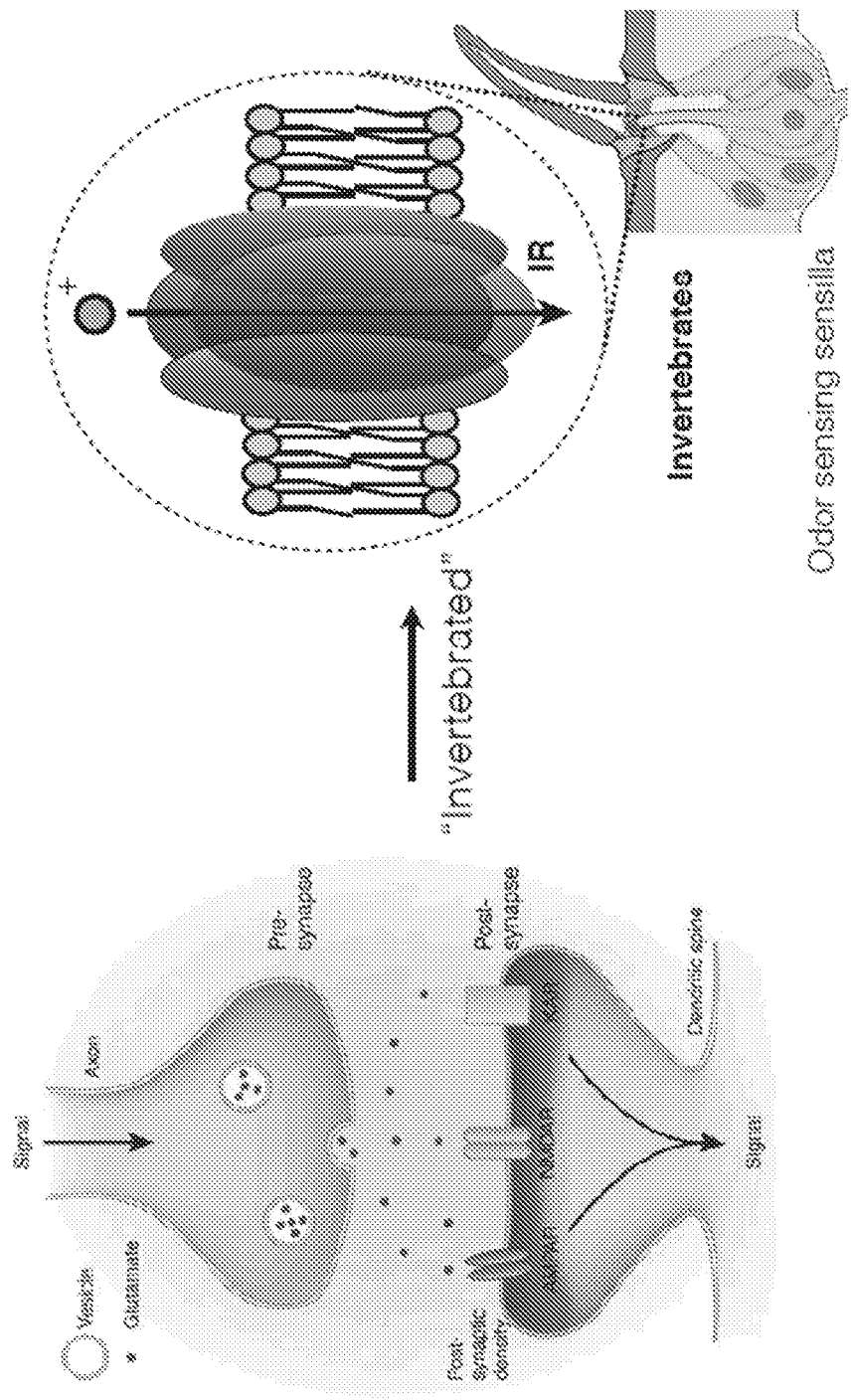
FIG. 15 is a schematic showing that iGluRs function in synaptic transmission (left) and invertebrate IRs localize to the dendrites of sensory neurons (right). Invertebrate IRs function equivalently or analogously to iGluRs.
Figure 16:
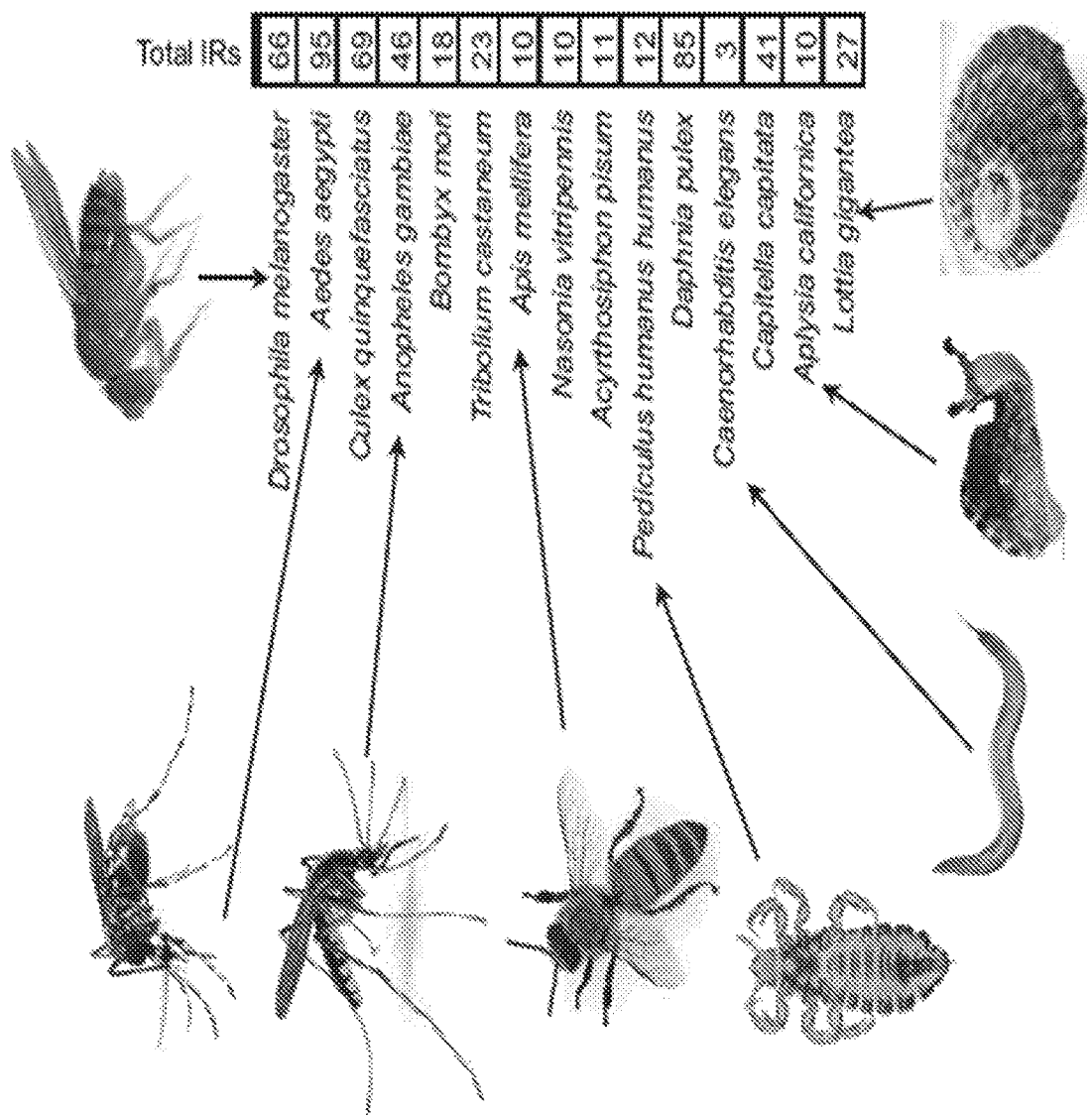
FIG. 16. is a diagram showing that numerous ionotropic receptors (IRs) are found in diverse invertebrate species (Croset et al., 2010, *PLoS Genet*, 6(8), e1001064).
Figure 18:
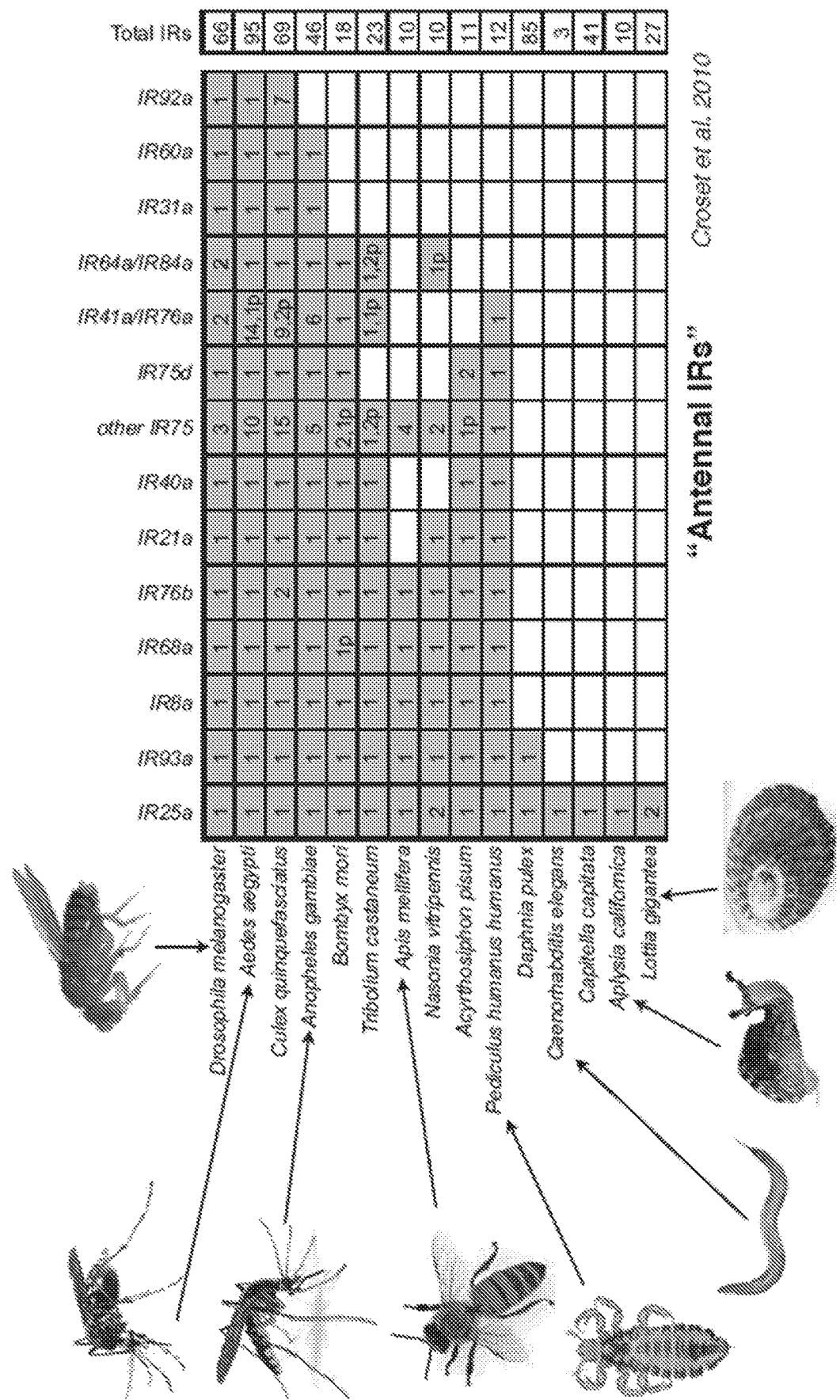
FIG. 18 is a diagram showing only the antennal IRs are highly conserved across invertebrate species.

Previous work conducting a behavioral screen of many receptor candidates showed the invertebrate Ionotropic Receptor (IR) family participates in hygrosensing. The invertebrate Ionotropic Receptor (IR) family is related to invertebrate glutamate receptors (iGluRs) (FIG. 14). Invertebrate glutamate receptors (iGluRs) function in synaptic transmission; invertebrate IRs localize to the dendrites of sensory neurons (FIG. 15). Numerous IRs are found in diverse invertebrate species (FIG. 16). However, only the antennal IRs are highly conserved across invertebrate species (FIG. 18). Three of the most highly conserved IRs are "orphan" receptors.

Figure 12C:
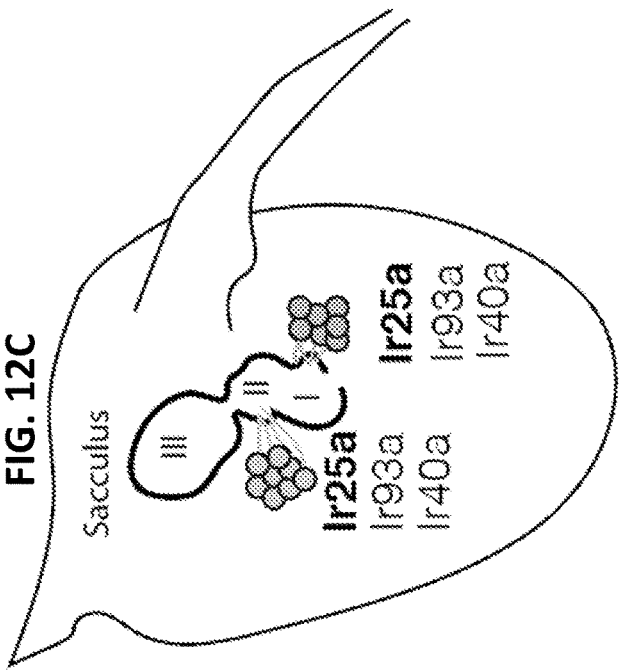
FIGS. 12A-12C are schematics showing that several highly conserved ionotropic receptors (IRs) are expressed in the sacculus.
Figure 12A:
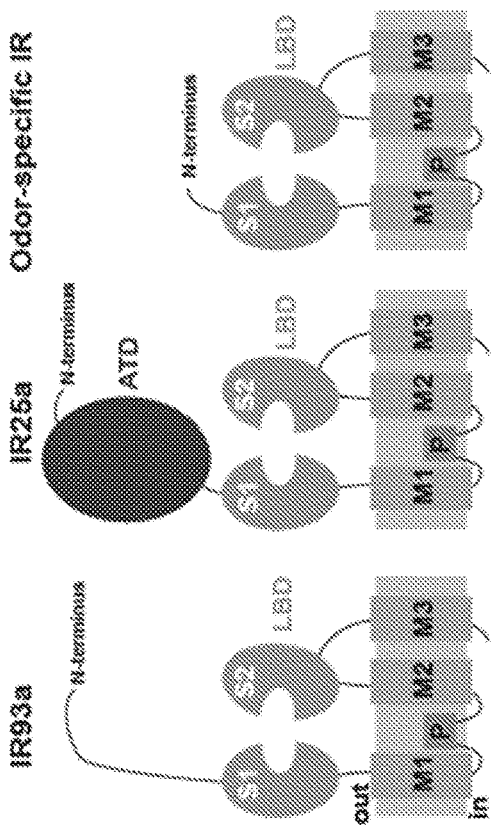
Figure 12B:
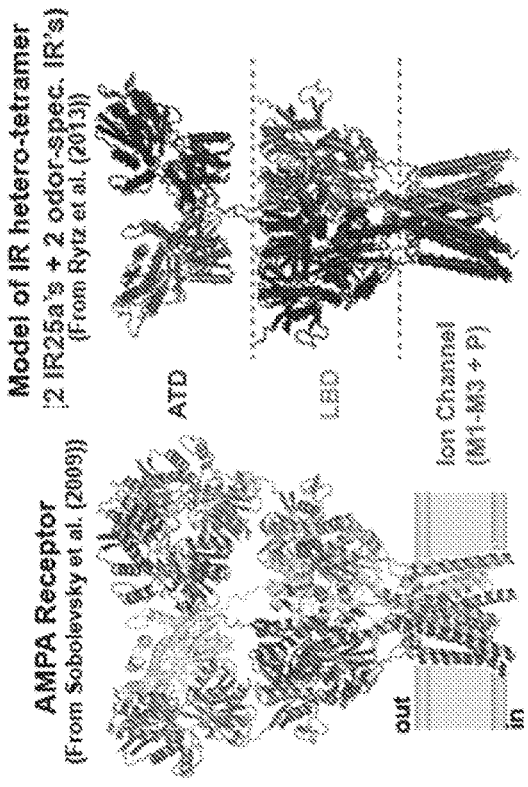

Several highly conserved IRs are expressed in the sacculus (FIGS. 12A-12C). Sacculus cells do not express odorant or gustatory receptors, but do express several IRs. IRs have been implicated as chemoreceptors, but not thermo or hygrosensors. Ir25a is previously implicated as a broadly expressed coreceptor for other IRs.

FIGS. 17A-17D illustrate the behavioral assay used in the studies herein to examine IR hygrosensitivity. The saturation of a solution with pure salt reduces the ability of water molecules to evaporate. Hence, the saturation pressure is decreased, and relative humidity (RH) is decreased. FIG. 17B shows the "hygro gradient" device used in the studies described herein. FIG. 17C shows the temperature and relative humidity in the "hygro gradient" device. The device maintains a stable gradient and temperature. FIG. 17D shows how the Dry Preference Index (DPI) is computed. The DPI is the difference in the number of flies on the "dry" (low RH) and "wet" (high RH) side of the hydro gradient device, normalized to the total number of flies. The DPI ranges from −1 (all flies on the "wet" side and none on the "dry" side) to 1 (all flies on the "dry" side and none on the "wet" side). A DPI of 0 indicates an equal number of flies on the "wet" and "dry" side, thus indicating no preference for either side. The larger the number of flies on the dry side relative to the wet side, the closer the DPI is to 1; conversely, the larger the number of flies on the wet side relative to the dry side, the closer the DPI is to −1.

Figure 19D:
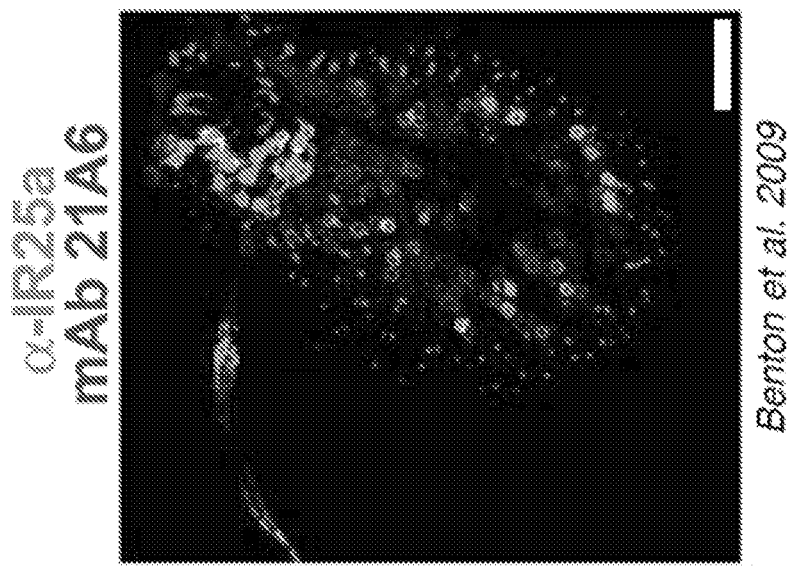
Figure 19C:
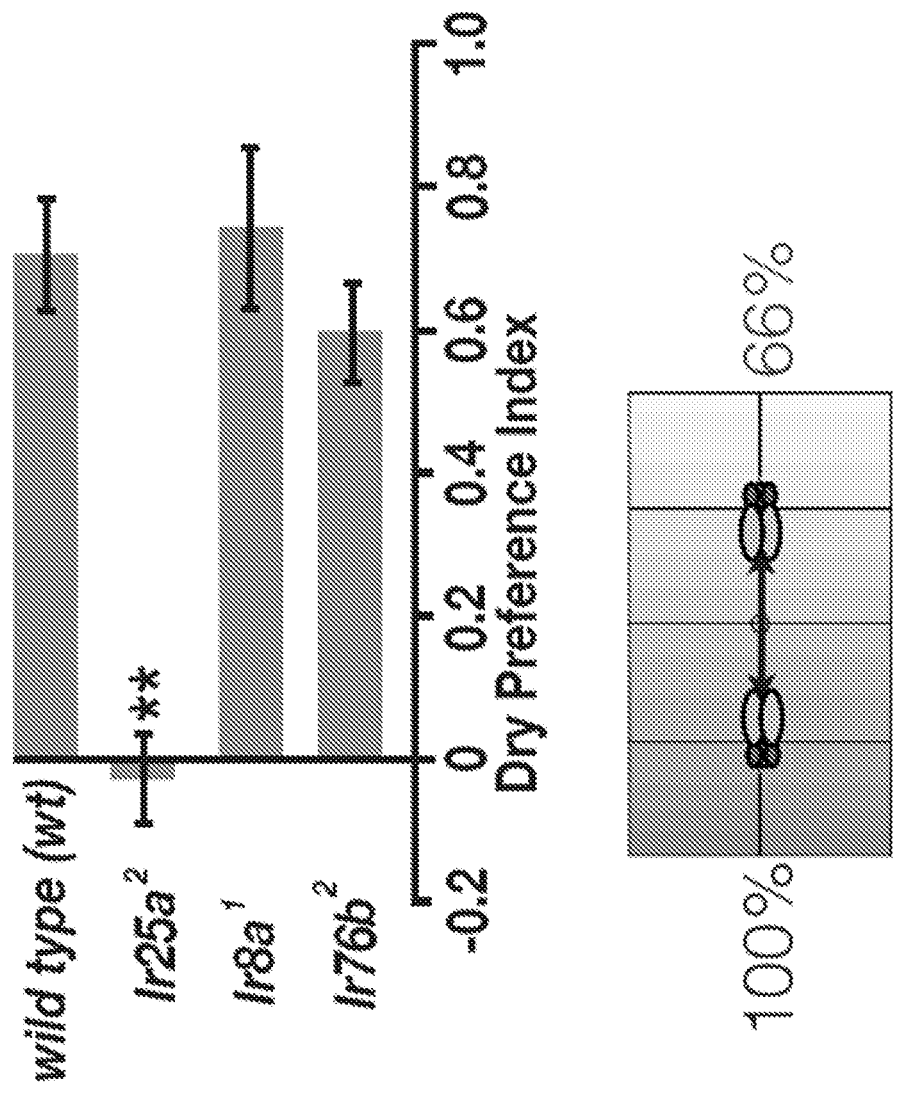

FIG. 19A shows that three antennal IRs that are known co-receptors (Ir25a, Ir8a, and Ir74b). IRs form heteromeric complexes to sense odorants. Examples of such include phenylethylamine or 1,4-diaminobutane (FIG. 19B). Stimulus specific IRs pair with more broadly expressed coreceptors. IRs have never been shown to function as anything other than odorant receptors. Mutation in Ir25a, but not other broadly expressed IRs (Ir8a or Ir76b), eliminates hygrosensory choice (FIG. 19C). Ir25a is expressed in antennal sections of Drosophila (FIG. 19D).

Figure 20D:
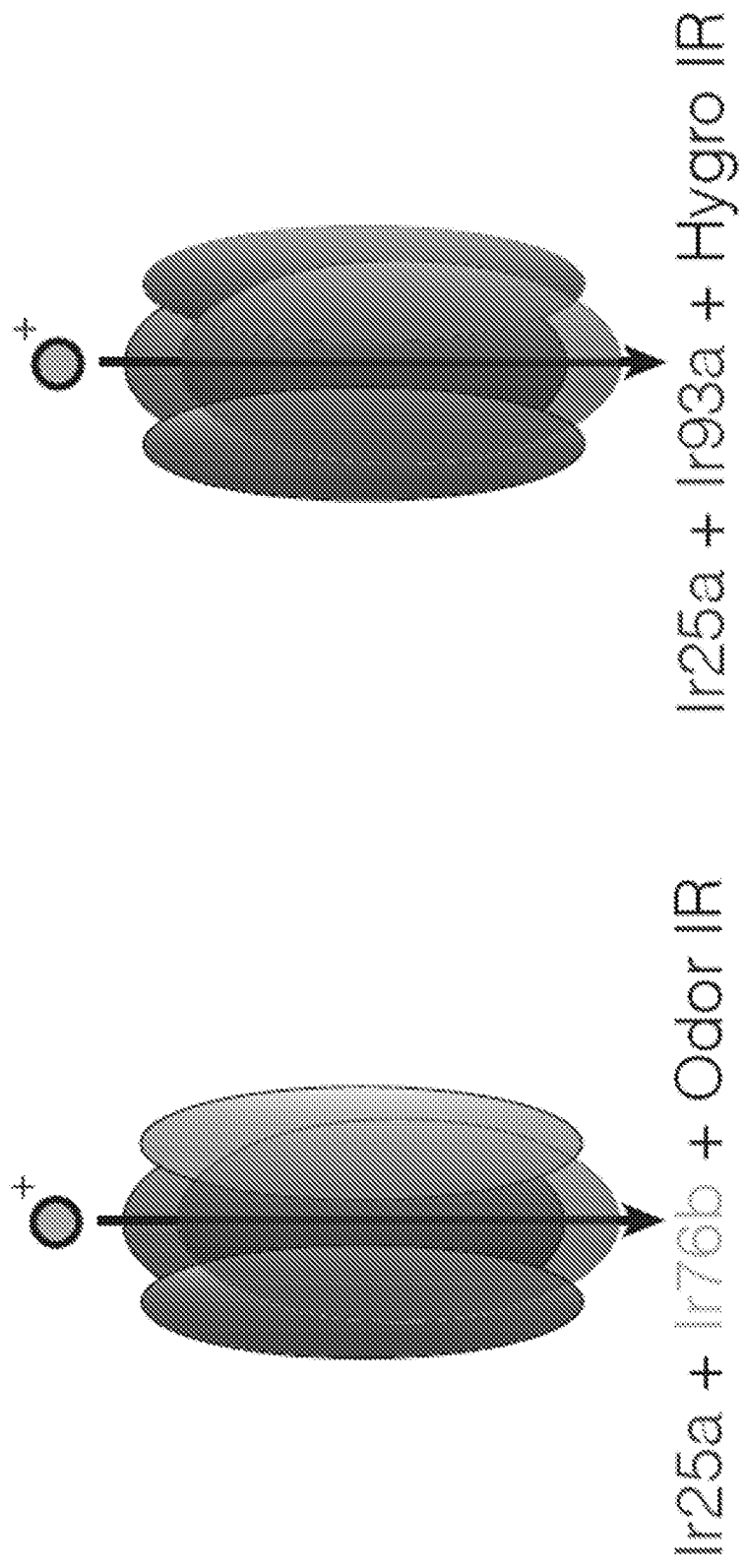

Ir93a expression is limited to the arista and sacculus (FIG. 20A). Ir25a expresses in the arista and sacculus, but also more broadly in the antenna. Ir93a expression is more limited. Ir93a is required for cold cell (CC) function. A screen of conserved IRs, which reveals Ir93a is also required for dry preference behavior (FIG. 20B). Ir93a and Ir25a are codependent for proper localization (FIG. 20C). FIG. 20D is a schematic showing a working model of Ir93a and Ir25a function. Ir93a may act as an Ir76b-like coreceptor.

Ir40a and Ir93a coexpress in some sacculus cells (FIG. 21A). Ir40a$^+$ neurons are activated by dry and silenced by moist air (FIG. 21B). Ir40a mutants show reduced dry preference (FIG. 21C).

Figure 22:
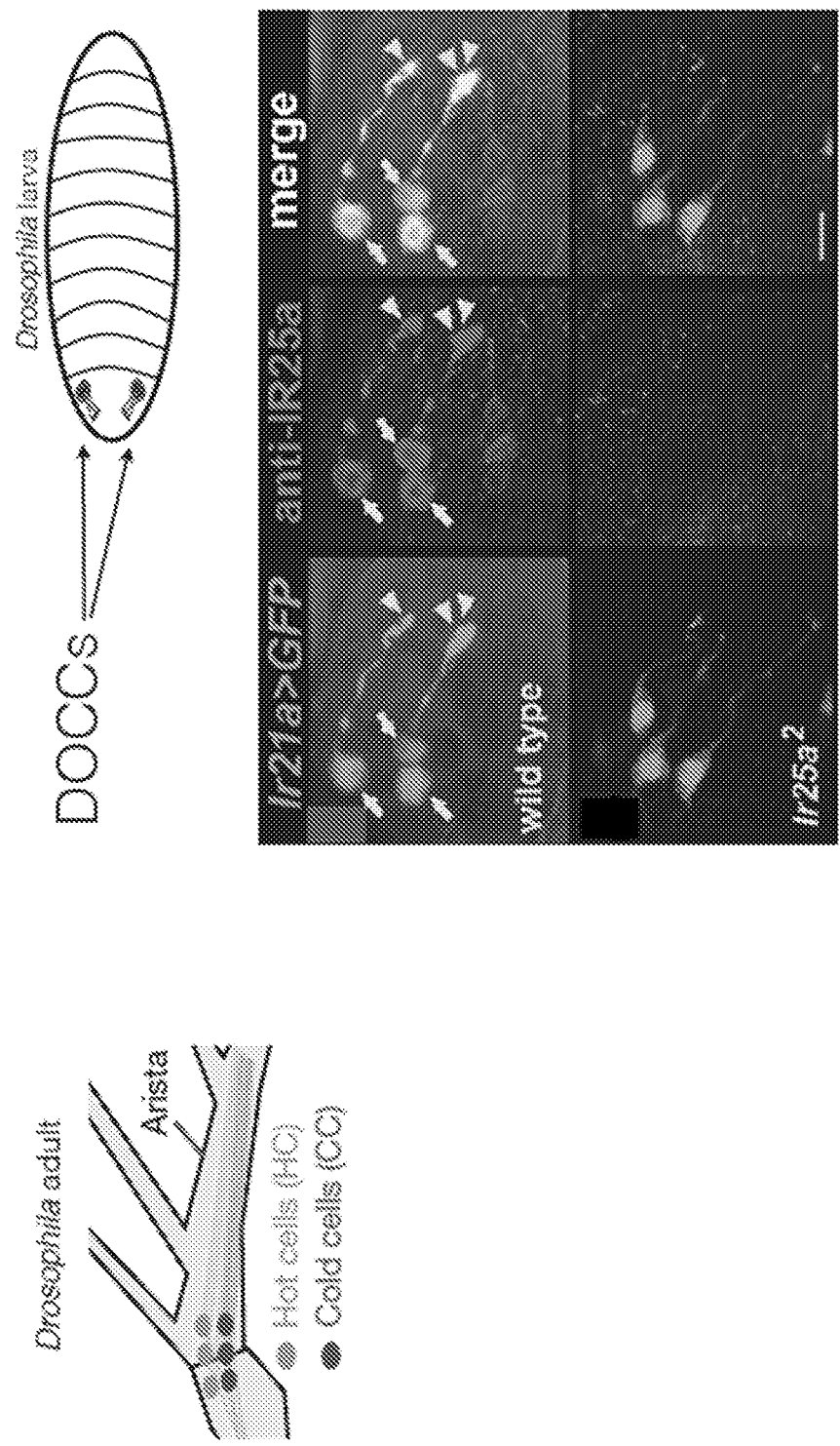
FIG. 22 is a set of schematics and images showing Ir93a and Ir25a are also involved in larval thermosensing.
Figure 23:
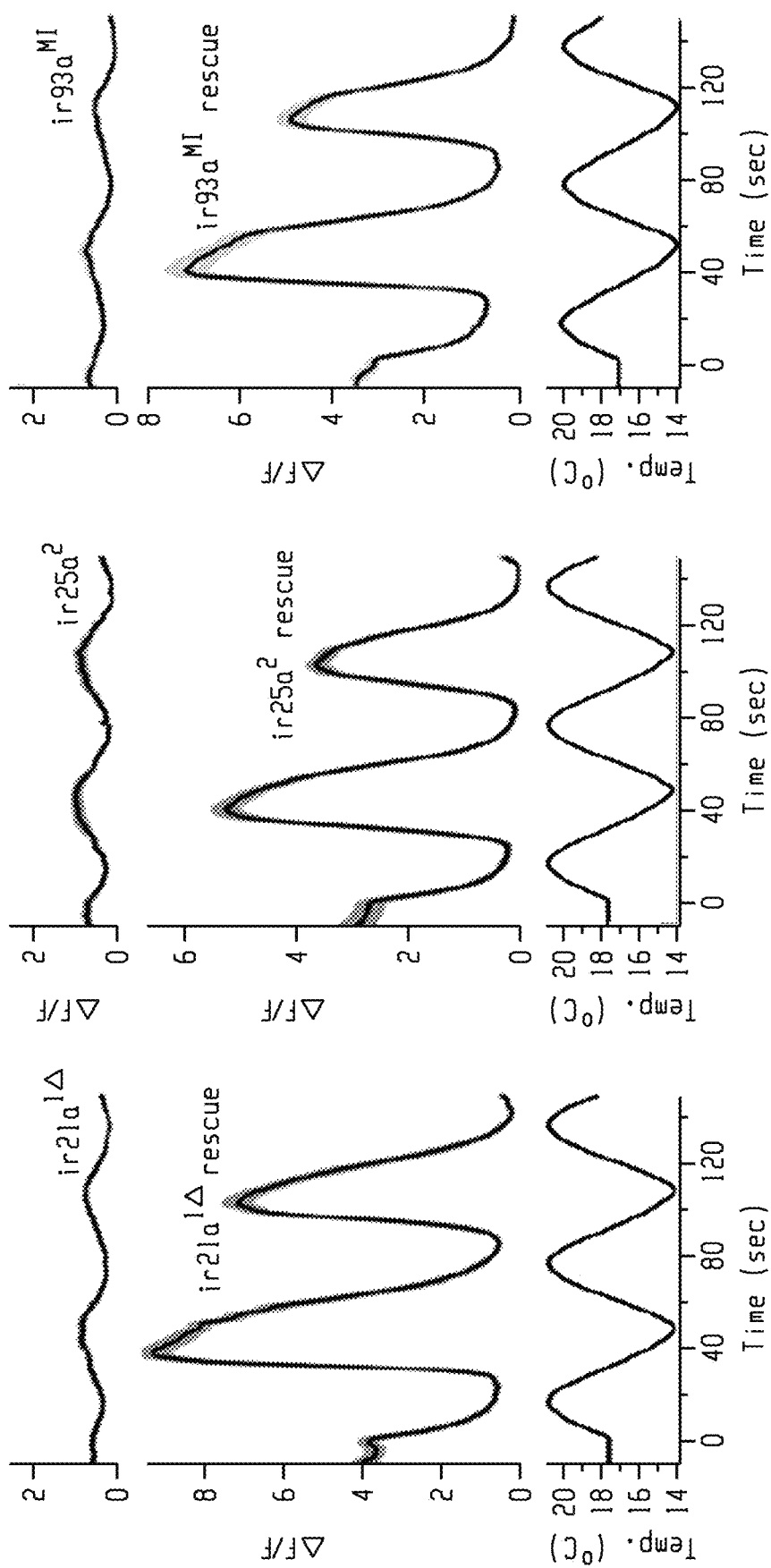
FIG. 23 is a set of plots and tracings showing that Ir93a, Ir25a, and Ir21a are involved in larval thermosensing.
Figure 24:
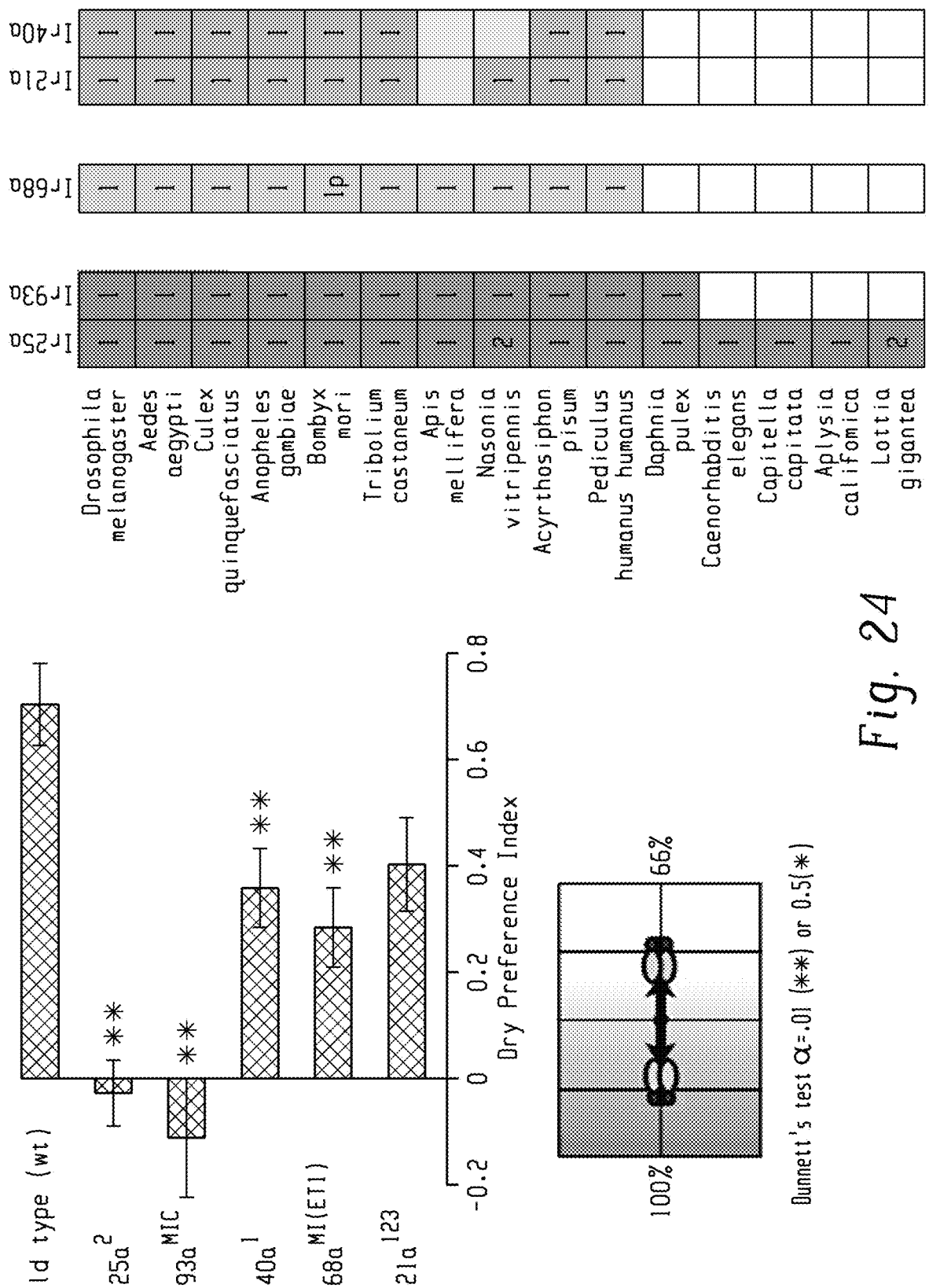
FIG. 24 is a plot and diagram showing that remaining antennal IRs (Ir25a, Ir93a, Ir68a, Ir21a, and Ir40a) show reduced dry preference.

Ir93a and Ir25a are also involved in larval thermosensing (FIG. 22). Larval dorsal organ cold cells (DOCCs) expressed Ir93a and Ir25a. DOCCs and cold cells (CCs) also expressed Ir21a. Ir93a, Ir25a, and Ir21a are involved in larval thermosensing (FIG. 23). FIG. 24 shows that remaining antennal IRs (Ir25a, Ir93a, Ir68a, Ir21a, and Ir40a) show reduced dry preference.

Figure 25:
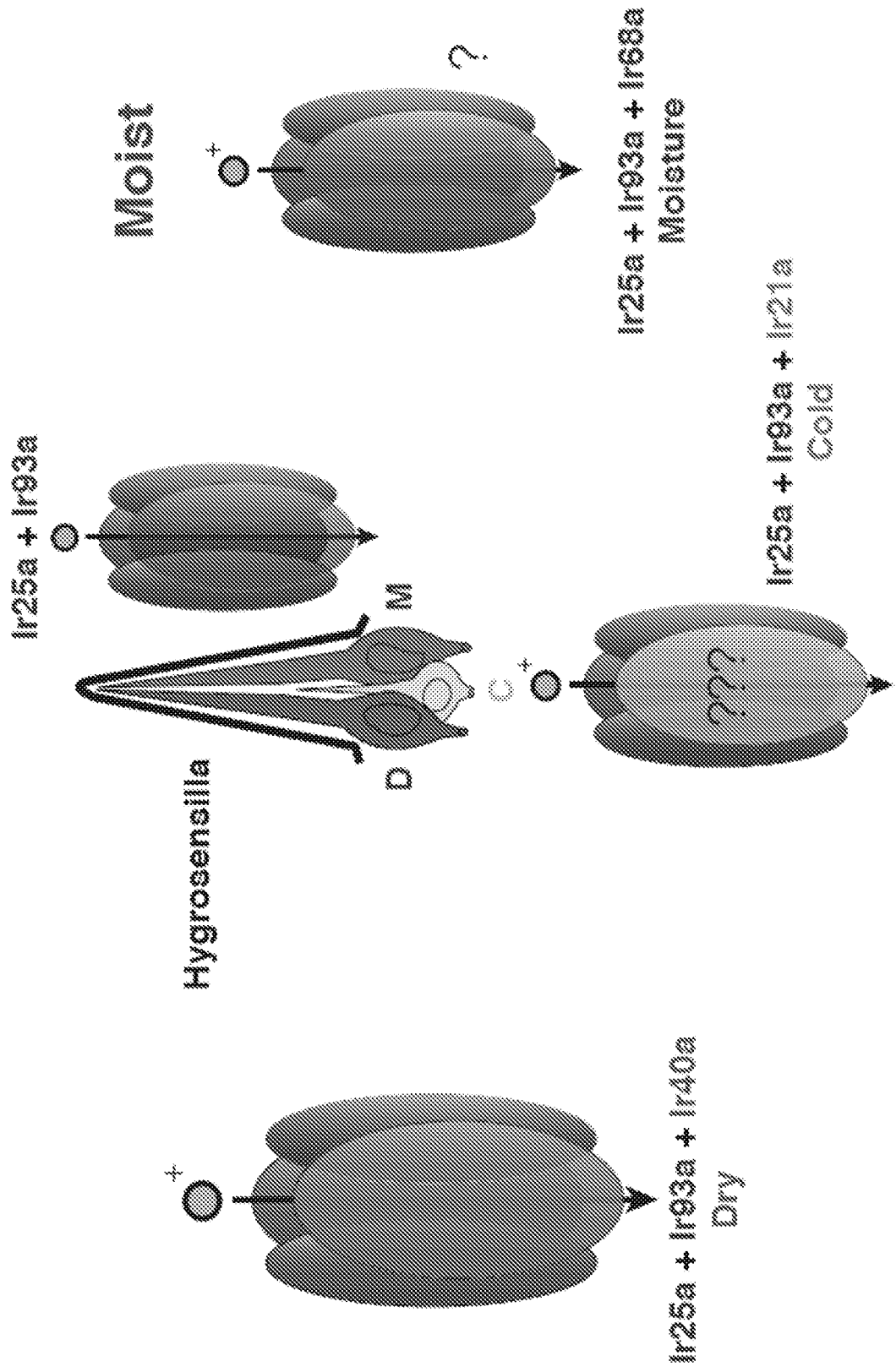
Figure 27:
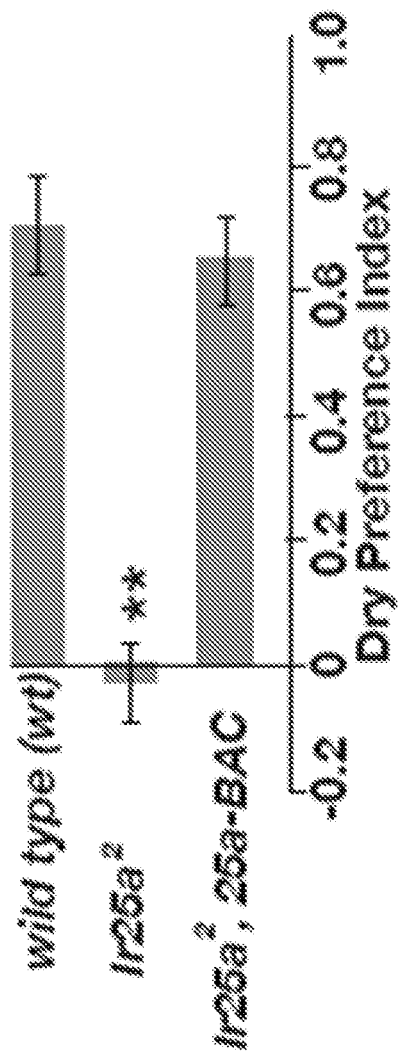
FIG. 27 is a plot showing dry preference index of wild-type, Ir25a mutant (Ir25a$^2$) and Ir25a$^2$ expressing 25a-BAC.

FIG. 25 is a schematic showing a working model of hygrosensation involving IRs Ir25a, Ir93a, Ir68a, Ir21a, and Ir40a. Multiple independent alleles of Ir21a, Ir25a, Ir93a, Ir40a, and Ir68a are to be further analyzed. Using CRISPR-Cas9 editing methods, multiple alleles of Ir21a, Ir25a, Ir93a, Ir40a, and Ir68a are constructed. Complete cell type specific rescue/ectopic expression is performed. FIG. 27 shows characterization of dry preference index of Ir25a$^2$ expressing Ir25a-BAC, which restored wild type dry preference.

Further, Ir93a and Ir25a each encode multiple protein isoforms. The role of Ir93a and Ir25a isoforms are determined using isoform specific mutations generated using CRISPR-Cas9 editing methods. Isoform specific cDNA constructs are created. The role of Ir93a and Ir25a are also investigated in Anopheles gambiae by examining hygrosensory behavior/electrophysiology.

Figure 28:
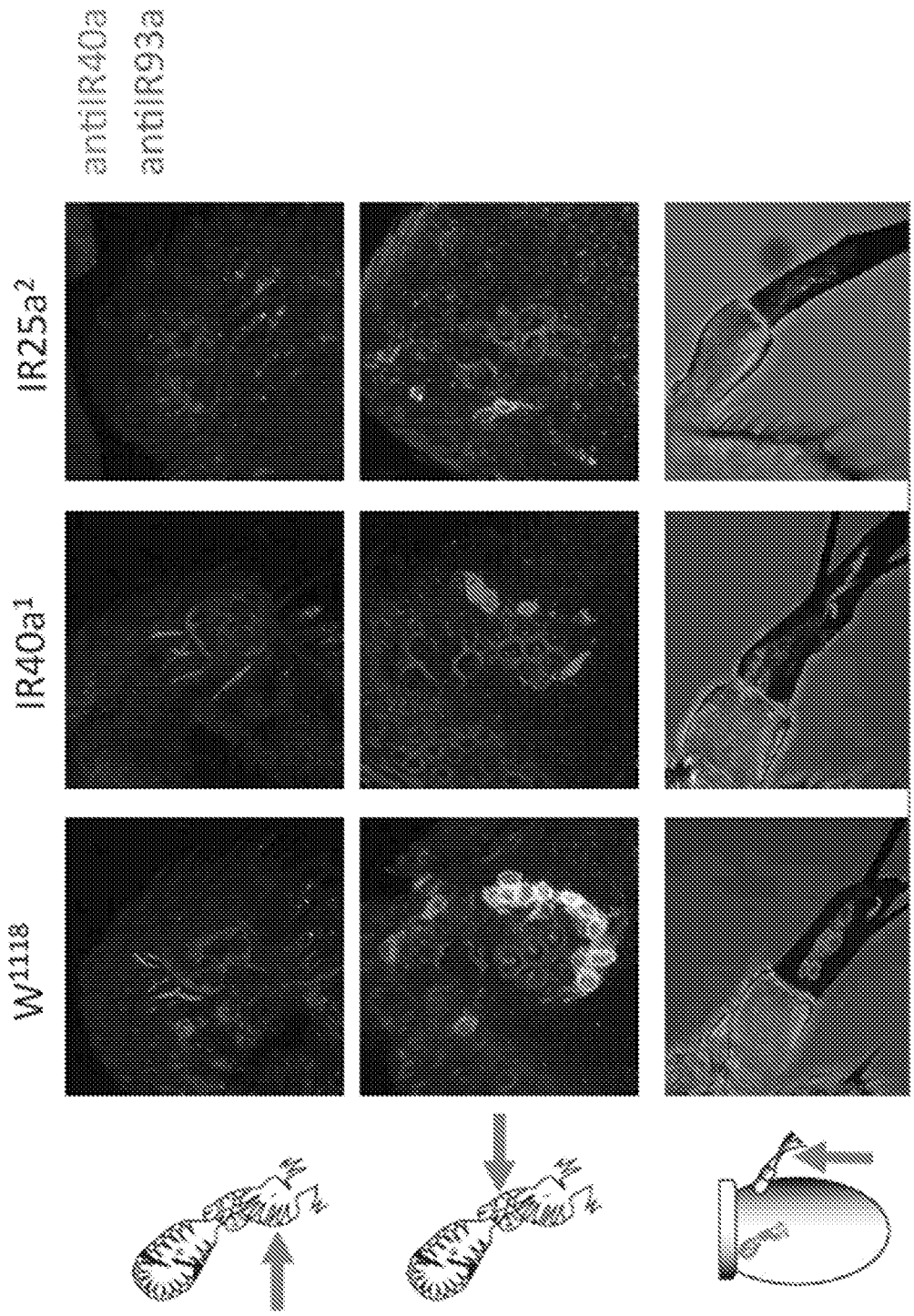
FIG. 28 is a set of micrographs showing immunostaining for Ir40a and Ir93a in various backgrounds (W1118, IR40a1, and IR25a2) in the indicated regions of the antenna.
Figure 29:
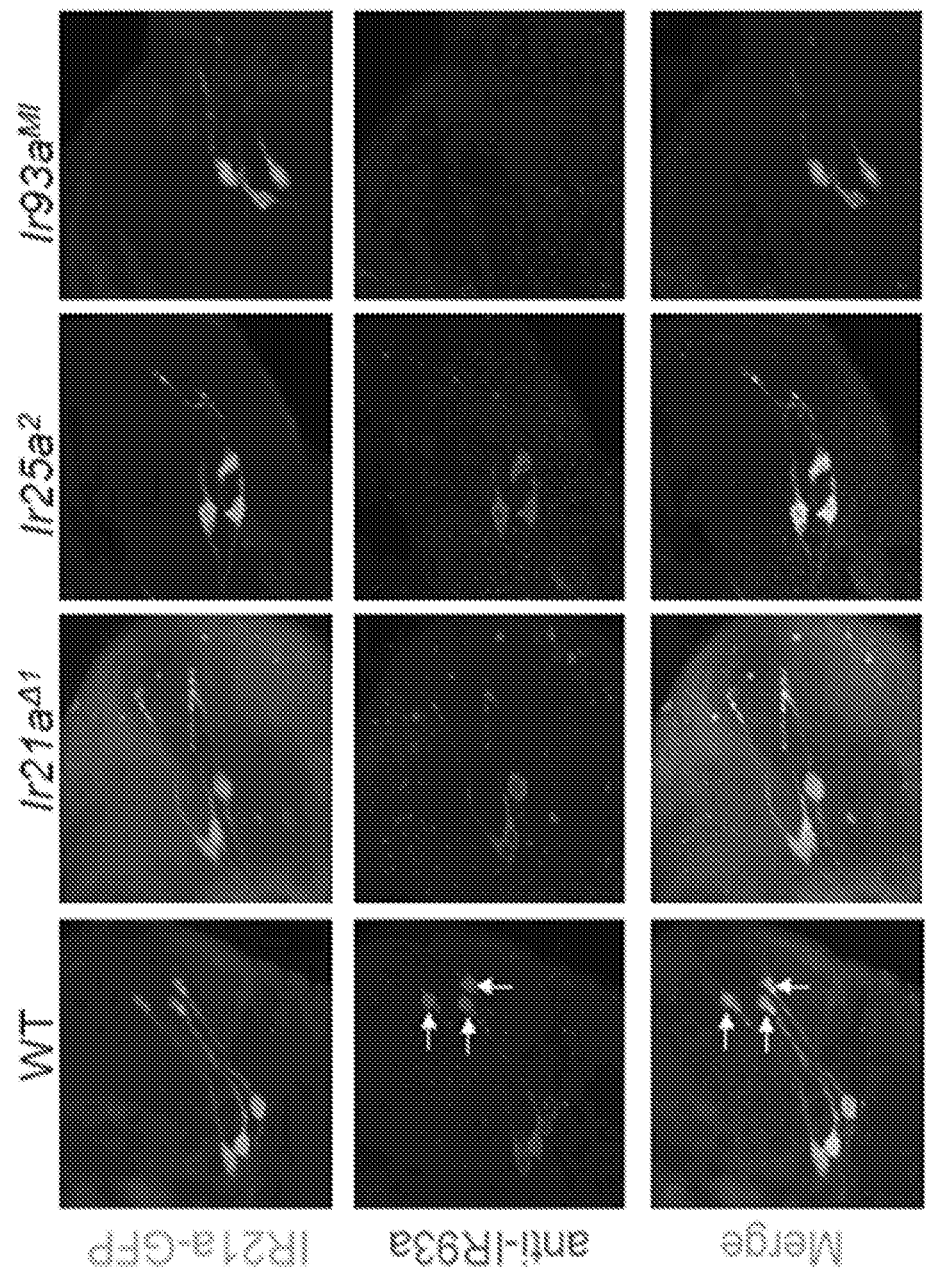
FIG. 29 is a set of micrographs showing dorsal organ cold cells (DOCCs) morphology in wild-type and mutant flies.

FIG. 28 is a set of micrographs showing immunostaining for Ir40a and Ir93a in various backgrounds (W1118, IR40a1, and IR25a2) in the indicated regions of the antenna. FIG. 28 shows codependence of Ir40a/Ir93a/Ir25a. FIG. 29 is a set of micrographs showing dorsal organ cold cells (DOCCs) morphology in mutants.

Example 2: Role of Ionotropic Receptors (IRs) in Hygroreception

It was hypothesized herein that hygroreception might involve receptor families implicated in other sensory modalities. Thus, hygrosensory behavior of flies mutant for receptors implicated in thermal and chemical sensation was examined. In the hygrosensory behavior assay, flies (about 25) were placed in a T-maze, poised between tubes filled with either humidified (90-95%) or dried (1-4%) air at 25°

Figure 1B:
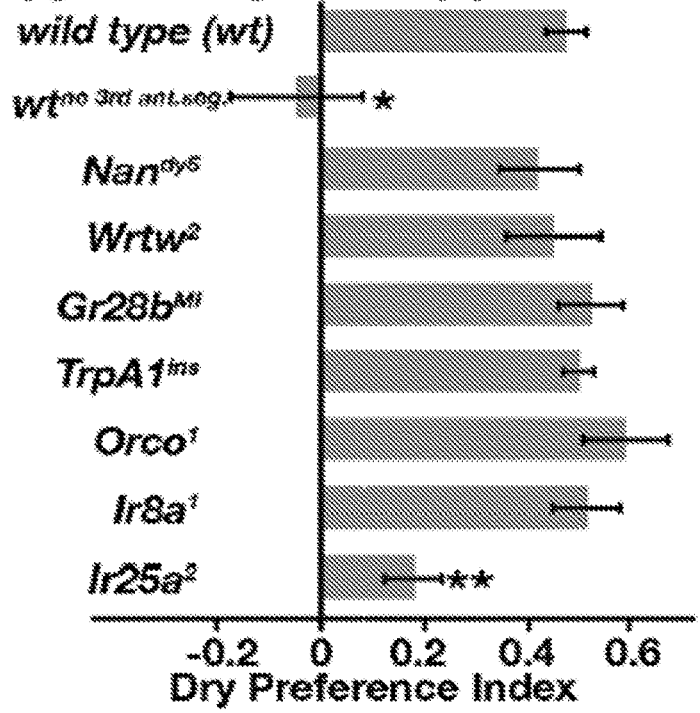
Figure 2A:
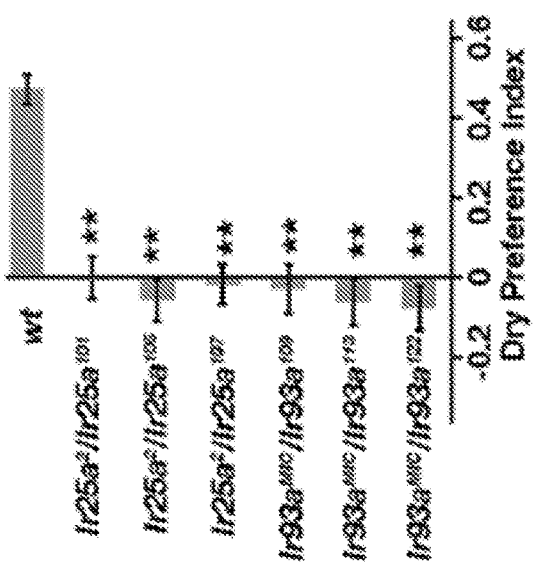
FIGS. 2A-2C are bar graphs showing that Ir25a and Ir93a mediate dry preference in hydrated flies.
Figure 2B:
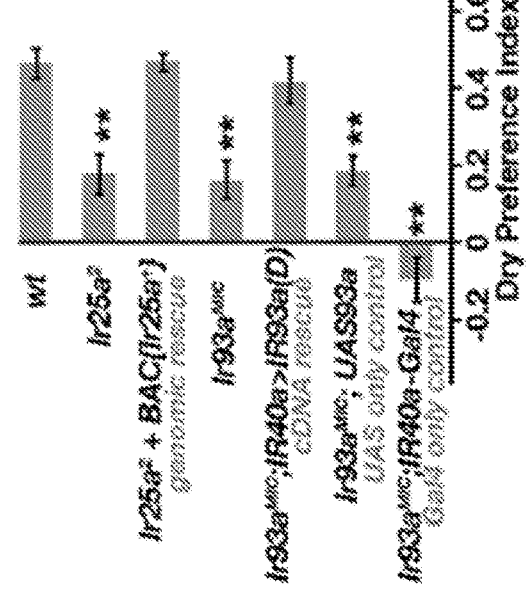
Figure 2C:
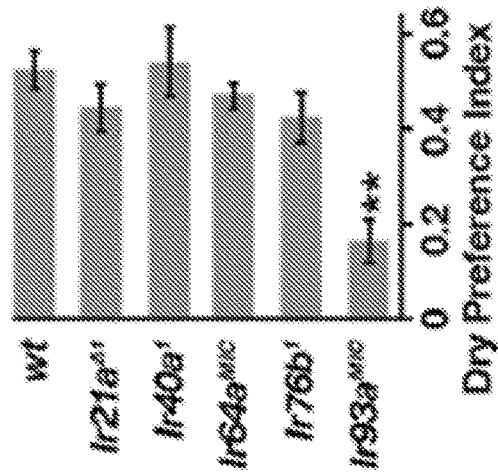

C. (Sayeed et al., 1996, *Proc Natl Acad Sci USA*, 93(12), 6079-6084) (FIG. 1A). After 5 minutes, a barrier was placed between the tubes, and the flies in each tube were counted and a dry preference index (DPI) calculated (FIG. 1B). In this assay, wild type flies prefer the dry tube (Lin et al., 2014, *Nat Neurosci*, 17(11), 1536-1542) (FIGS. 1A-1B). The analysis yielded one candidate regulator of hygrosensation, Ir25a (FIG. 1B). As Ir25a normally acts as a co-receptor for other IRs (Abuin et al., 2011, *Neuron*, 69(1), 44-60), mutants lacking other IRs expressed in the antenna were tested, and Ir93a was identified as a second regulator of the response (FIG. 2A). Both the Ir25a and Ir93a mutant phenotypes were rescued with corresponding wild type transgenes (FIG. 2B), and created multiple additional loss-of-function alleles of Ir25a and of Ir93a using CRISPR, observing that all loss-of-function allelic combinations strongly reduced dry preference (FIG. 2A; FIG. 2C). Together these data firmly establish the importance of Ir25a and Ir93a in hygrosensation.

Figure 3D:
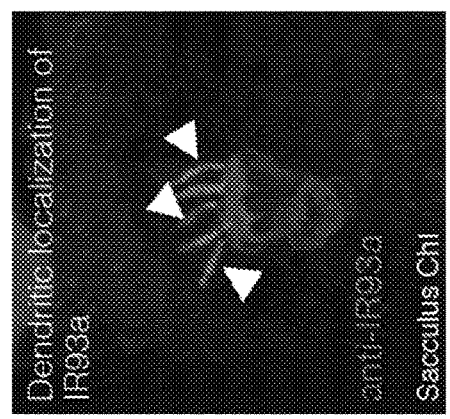
FIGS. 3A-3D are micrographs showing that Ir40a is co-expressed with Ir25a and Ir93a in sacculus, but not arista.
Figure 3A:
Figure 3B:
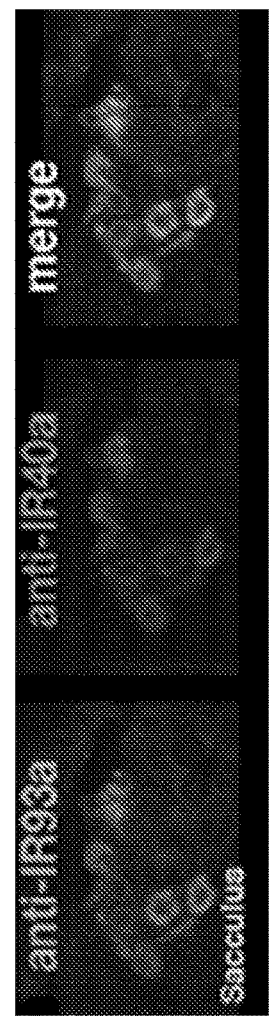
Figure 3C:
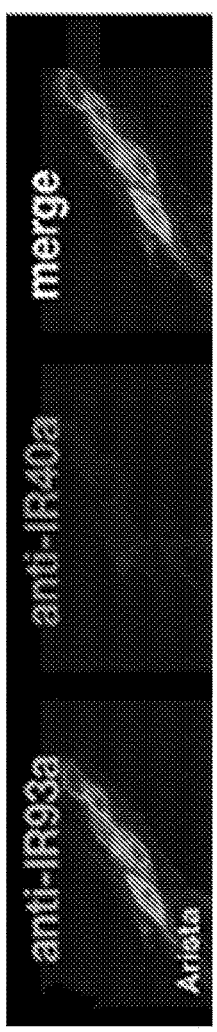
Figure 4B:
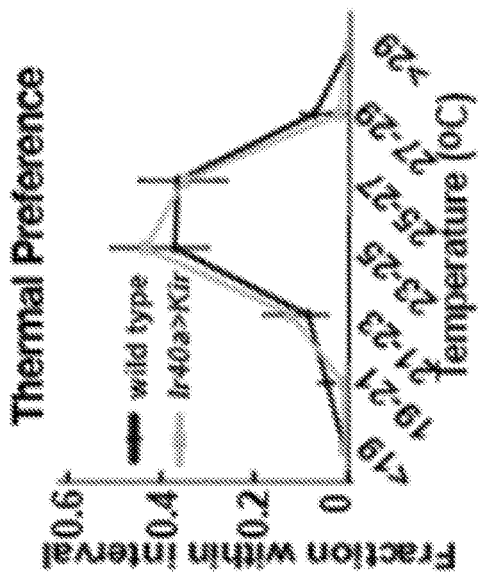
FIGS. 4A-4C are bar graphs and plots showing that Ir40a-Gal4 cells regulate hygrosensory behavior and moisture preference of Ir93a mutants. n=13-26 assays (alpha=**0.01, Tukey HSD, differ from controls).
Figure 4A:
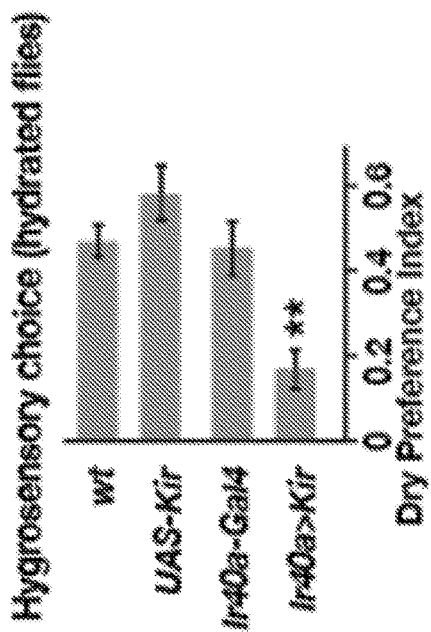
Figure 4C:
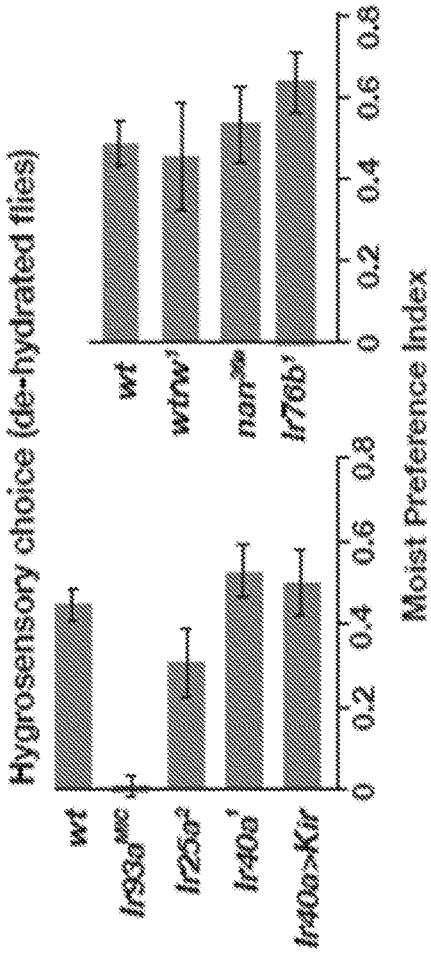

At the cellular level, IR93a is expressed by neurons in the first and second chambers of the sacculus, which house "no-pore" sensilla suspected to house hygroreceptors (Silbering, 2011, *J Neurosci*, 31(38), 13357-13375). In addition, Ir93a is also expressed in all six neurons of the arista, an antennal extension that contains just six neurons, three cool and three warm receptors (FIG. 3B). FIG. 3D shows dendritic localization of Ir93a. IR25a is co-expressed with IR93a in the sacculus and arista, as well as more broadly in the 3rd antennal segment, reflecting its role as a co-receptor for multiple IRs (Benton et al., 2009, *Cell*, 136(1), 149-162) (FIG. 3A). In the sacculus, Ir93a is also co-expressed with a third member of the IR family, Ir40a (FIG. 3B, 3C; note all staining is specific as it is absent in corresponding mutant animals). Consistent with a hygrosensory role for these cells, it was found that inhibition of Ir40a-Gal4-positive neurons by expression of the Kir potassium channel disrupts hygrosensory behavior (FIG. 4A). FIG. 4C shows dehydrated Ir93a mutants are moisture blind.

Figure 5B:
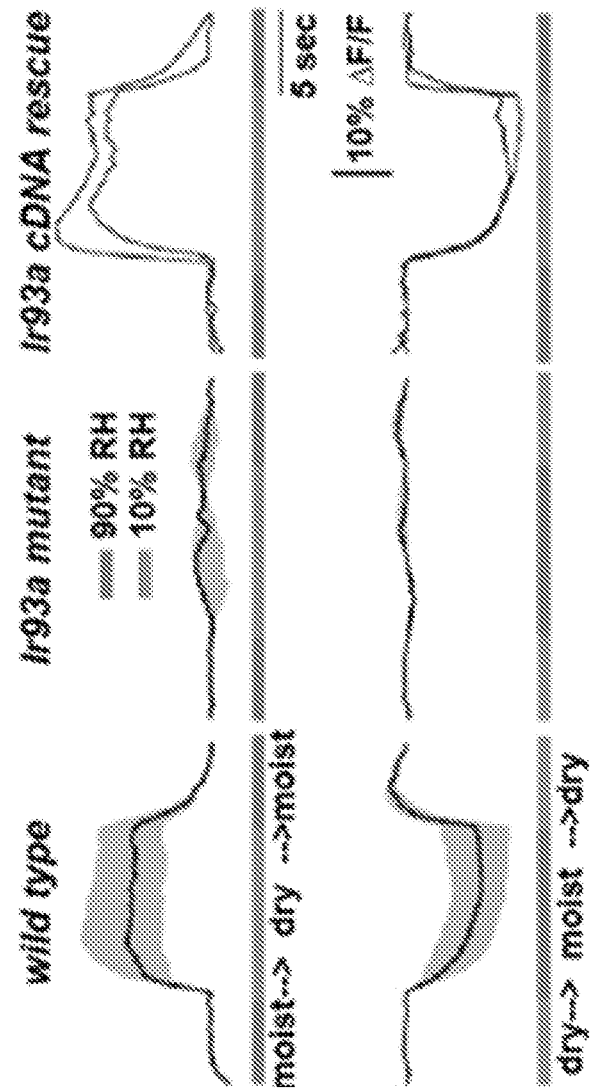
FIGS. 5A-5B are images and tracings showing physiological responses of Ir40-Gal4(+)neurons to humidity changes.
Figure 5A:
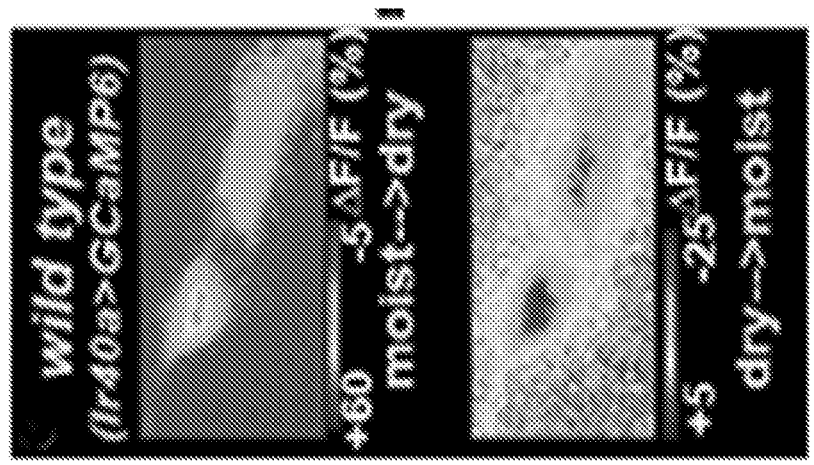
Figure 6B:
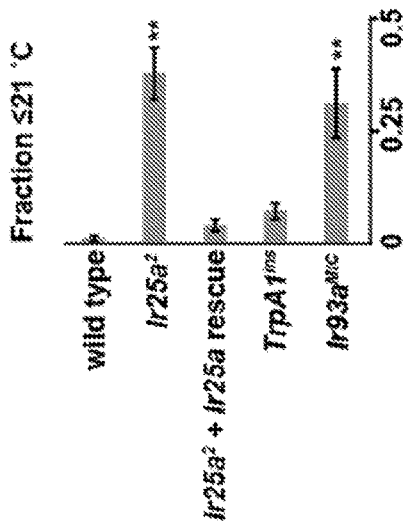
FIGS. 6A-6D are plots and graphs showing loss of Ir25a, Ir93a or Ir21a decreases cold avoidance (for comparison, loss of TrpA1 decreases warmth avoidance in FIGS. 6A-6B). Each of FIG. 6A
Figure 6D:
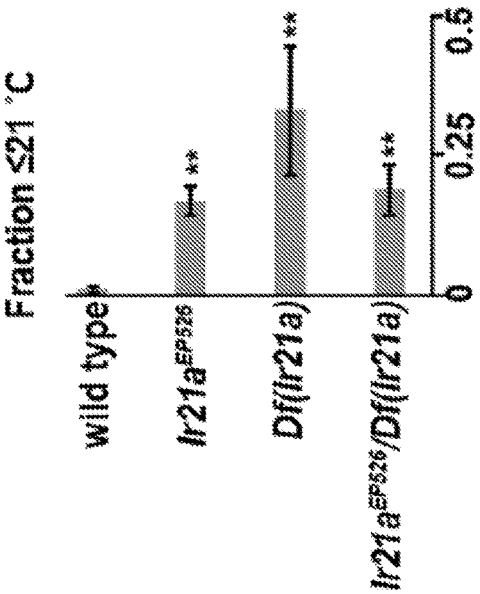
Figure 6A:
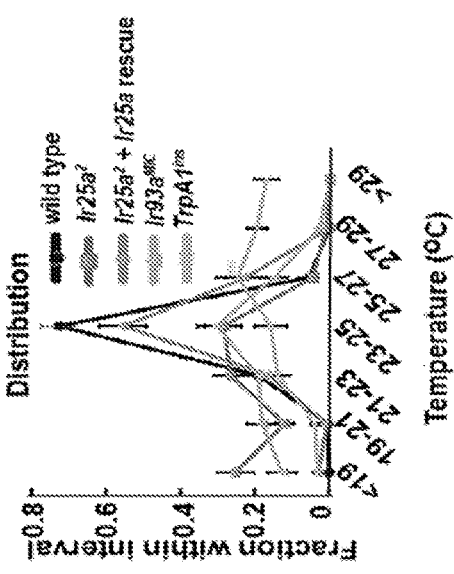
Figure 7B:
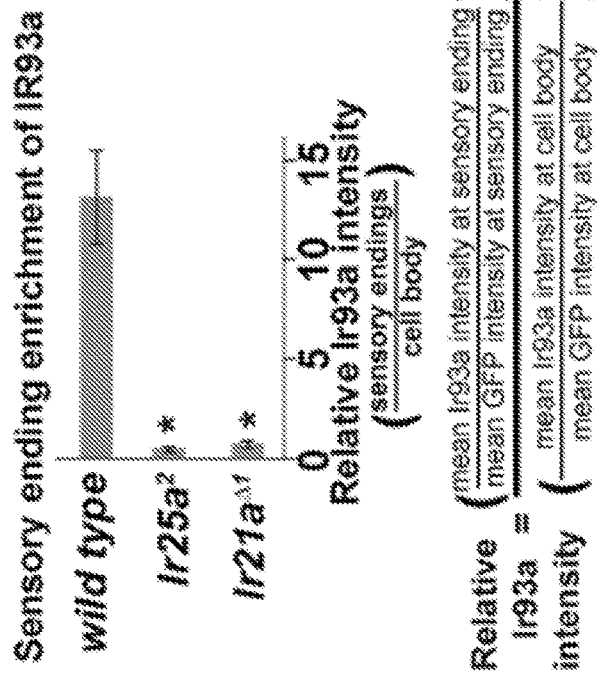
FIGS. 7A-7C are micrographs and plots showing Ir93a protein concentrates in thermoreceptor sensory endings.
Figure 7C:
Figure 7A:
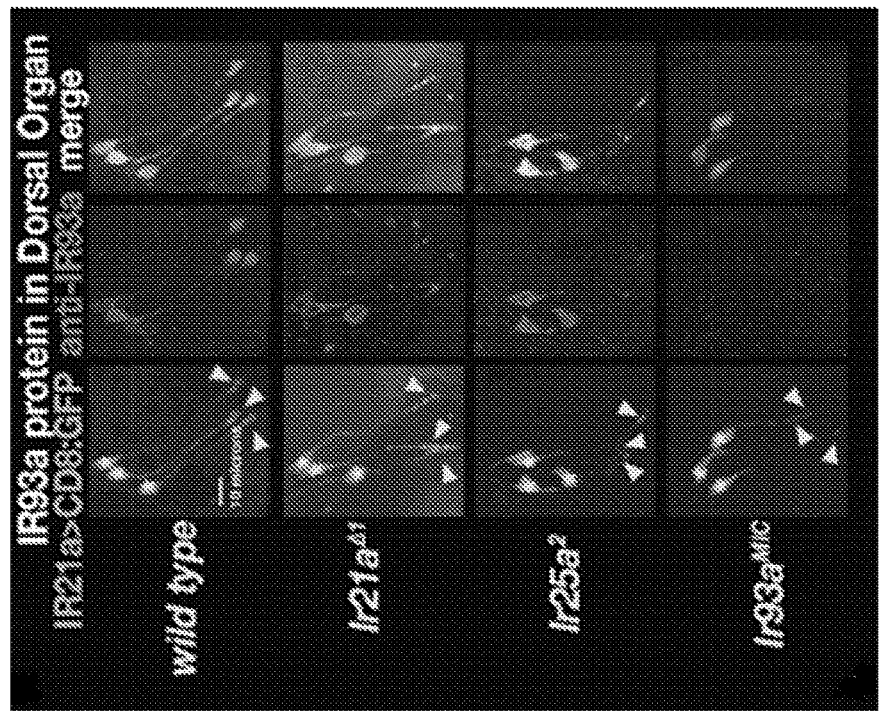
Figure 26:
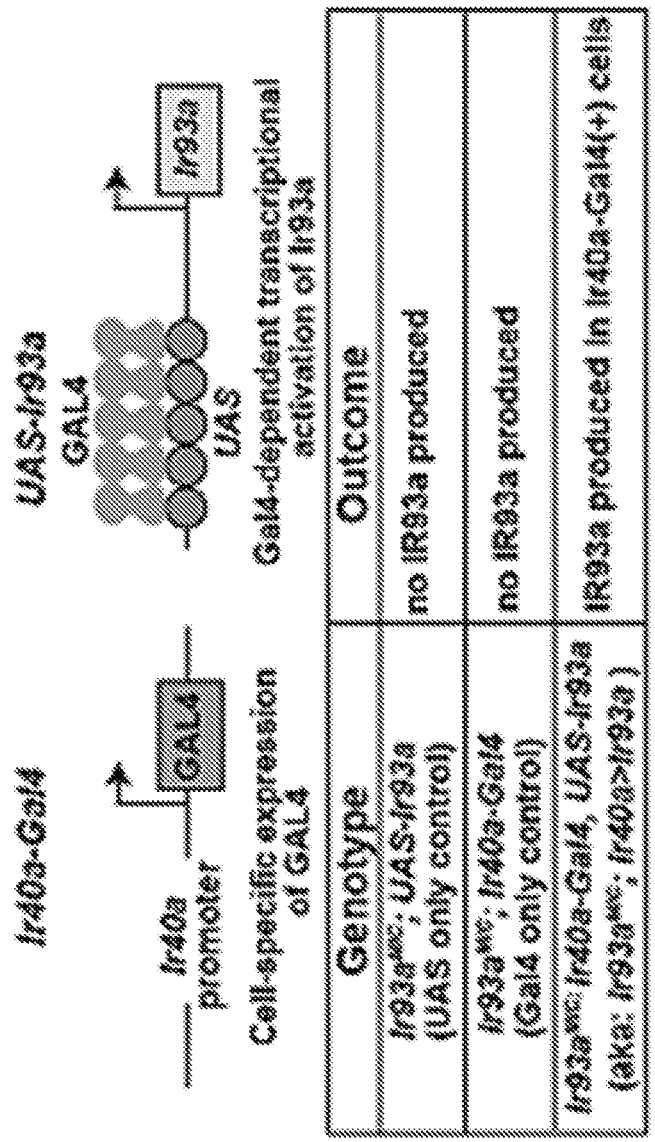
FIG. 26 is a schematic showing genotypes and production of Ir93a in various mutant strains used in the studies herein.

Furthermore, expression of an Ir93a cDNA in these cells (using Ir40a-Gal4) rescued the Ir93a defect (FIG. 2B), indicating Ir93a functions in these cells FIG. 26 is a schematic showing genotypes and production of Ir93a in various mutant strains used in the studies herein. In addition, calcium imaging of Ir40a-Gal4-positive axons in the fly a brain indicates these neurons are dry-responsive, and that Ir93a function is required for this response (FIGS. 5A-5B). These data provide physiological evidence that Ir40a-Gal4(+) neurons in the sacculus are hygrosensors and strongly support the notion that Ir93a is involved in moisture detection. The role of the IR40a receptor itself is yet to be determined, as Ir40a mutants have only recently been isolated from a study of Ir40a in another context. The expression of Ir93a in the arista suggested Ir93a might also act in thermosensation (FIG. 7C). Thus, thermal preference behavior was examined by allowing groups of flies (~50) 30 minutes to settle on a thermal gradient (17° C.-30° C.). Consistent with a role in cool sensing, Ir93a mutant adults are cold-shifted compared to wild type (FIGS. 6A-6B). Inhibition of the IR40a-Gal4 neurons of the sacculus had no effect on thermal preference, suggesting distinct sets of cells mediate cool and moisture sensing (FIG. 4B). In the larva, it was found that IR93a is specifically expressed in coolresponsive thermoreceptors in the larval dorsal organ (FIGS. 7A-7B). Consistent with a role in sensory transduction, IR93a is concentrated in the sensory dendrites of these cool receptors (FIGS. 7A-7B). These neurons no longer respond to cooling in an Ir93a mutant (FIG. 8), and Ir93a mutant larvae show robust defects in cool avoidance behavior. These data demonstrate Ir93a participates in cool sensing as well as hygrosensing.

Figure 6C:
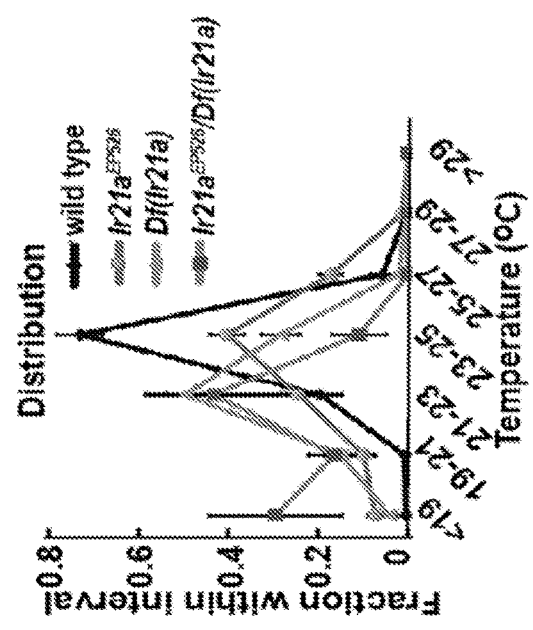
Figure 8:
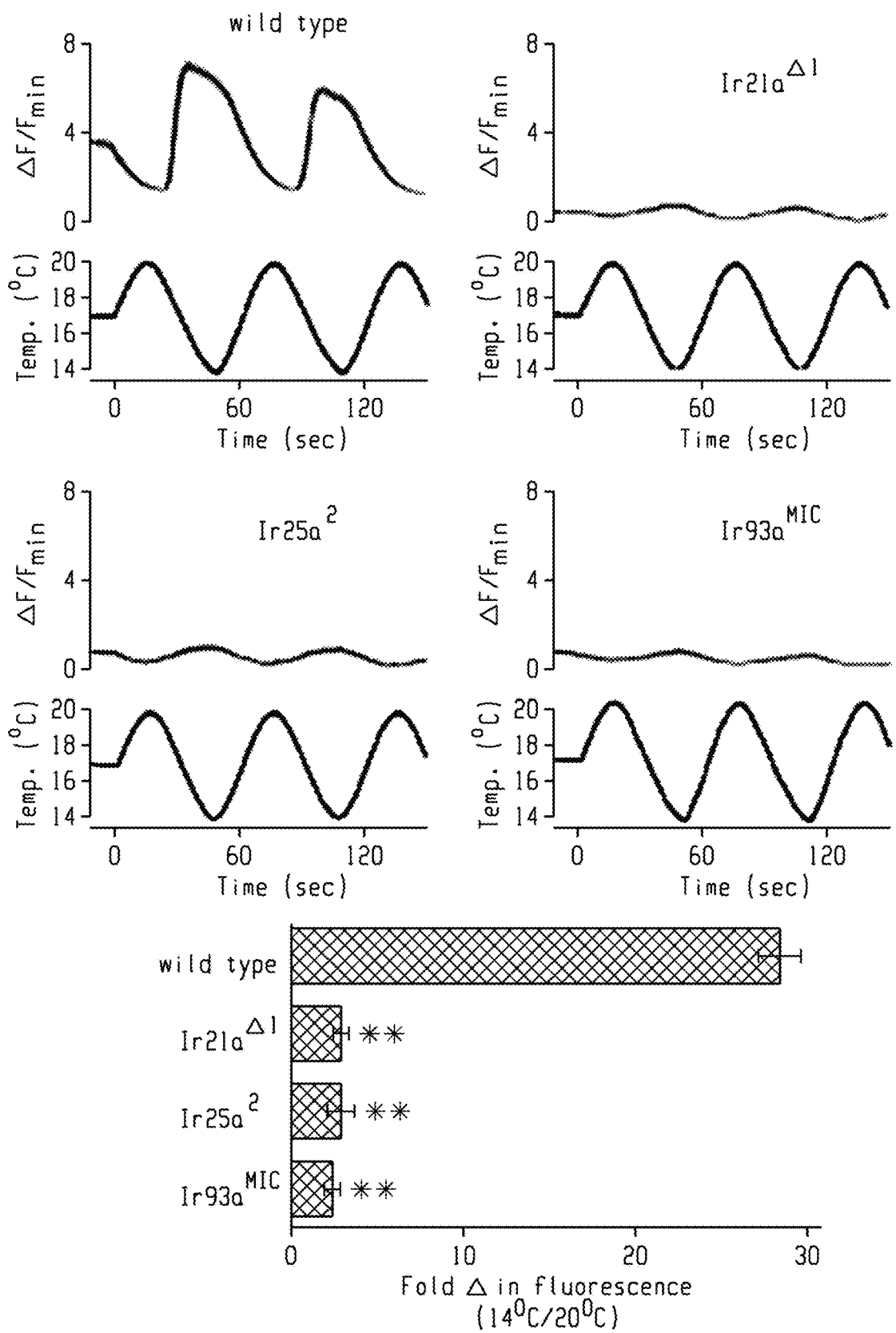
FIG. 8 is a set of plots showing thermosensitivity of larval cool sensors is reduced in Ir21a, Ir25a and Ir93a mutants. AF/F, fold (not %) change in 11F02>GCaMP6 signal. Traces: ave.+/−SEM; n>9 cells each. Temperature varies as sine wave. Graph: Ratio of fluorescence at 14° C. vs 20° C. **differ from wild type, P=0.01, t-test, Bonferroni correction.
Figure 9:
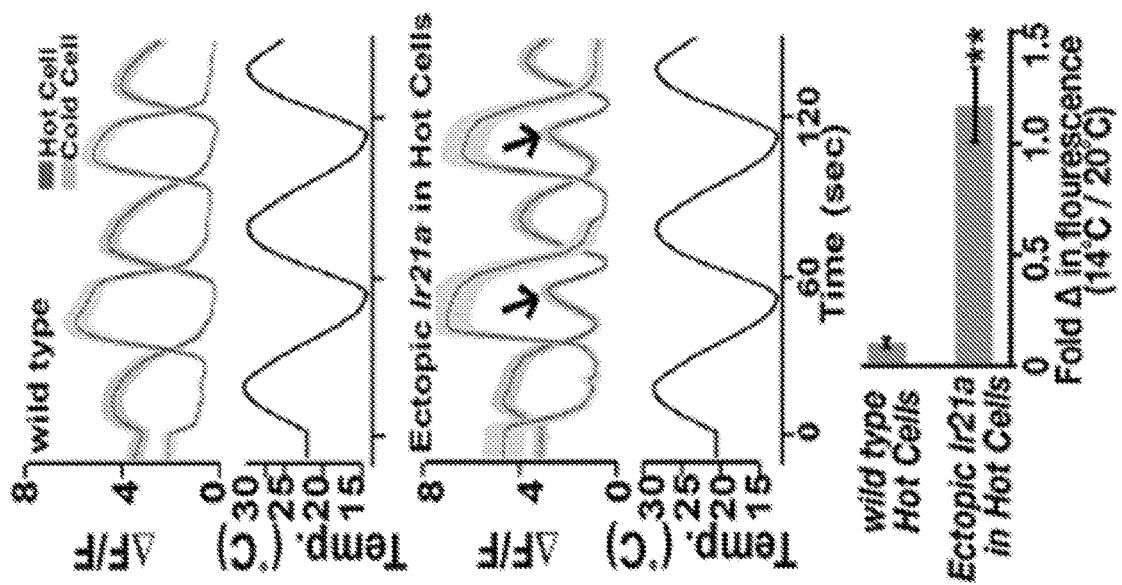
FIG. 9 is a set of plots showing Adult Hot Cell and Cold Cell responses to temperature. Ectopic Ir21a expression makes Hot Cells coolresponsive (arrows). AF/F, fold change in 11F02>GCaMP6 signal. Traces/Graph are as described in FIG. 8.

As in hygrosensing, Ir25a is co-expressed with Ir93a in adult and larval thermosensors, and Ir25a mutants show defects in cool-responsive behavior and physiology similar to Ir93a mutants (FIGS. 6A-6B; FIG. 8). One difference between hygrosensing and thermosensing, however, is that cool responses also depended on a third IR encoded by Ir21a. Ir21a is co-expressed with Ir93a in cool-responsive neurons, and Ir21a mutants show behavioral and physiological cool-response deficits similar to Ir93a and Ir25a mutants in both the larva and adult, suggesting these three IRs act together in cool sensing (FIGS. 6C-6D and FIG. 8). Further supporting an interaction between these three IRs, loss-of-function mutations in either Ir21a or Ir25a disrupt the localization of IR93a to the tip of the thermosensor dendrite. In addition, the misexpression of Ir21a in the "Hot Cells" of the arista, which normally respond only to warming, causes these cells to become strongly cool-responsive (FIG. 9). Importantly, the "Hot Cells" normally express both Ir93a and Ir25a, suggesting that Ir21a may complex with these proteins to form a cool receptor. As Ir21a is not expressed in the first or second chambers of the sacculus (Silbering, 2011, *J Neurosci*, 31(38), 13357-13375), these data suggest a working model in which Ir21a/Ir25a/Ir93a act together in the arista to mediate cool sensitivity and Ir25a/Ir93a or Ir25a/Ir40a/Ir93a act in the sacculus to mediate hygrosensation.

In sum, results herein show that Ir25a, Ir40a, and Ir93a are expressed in overlapping populations of cells in the sacculus. In hydrated animals, mutations in Ir25a and Ir93a and the silencing of Ir40$^+$ a cells disrupted dry preference. In dehydrated animals, Ir93a mutants disrupted moist preference.

Example 3: Role of Ir93a and Ir25a Isoforms in Forming Cool/Moist Sensors

Figure 10:
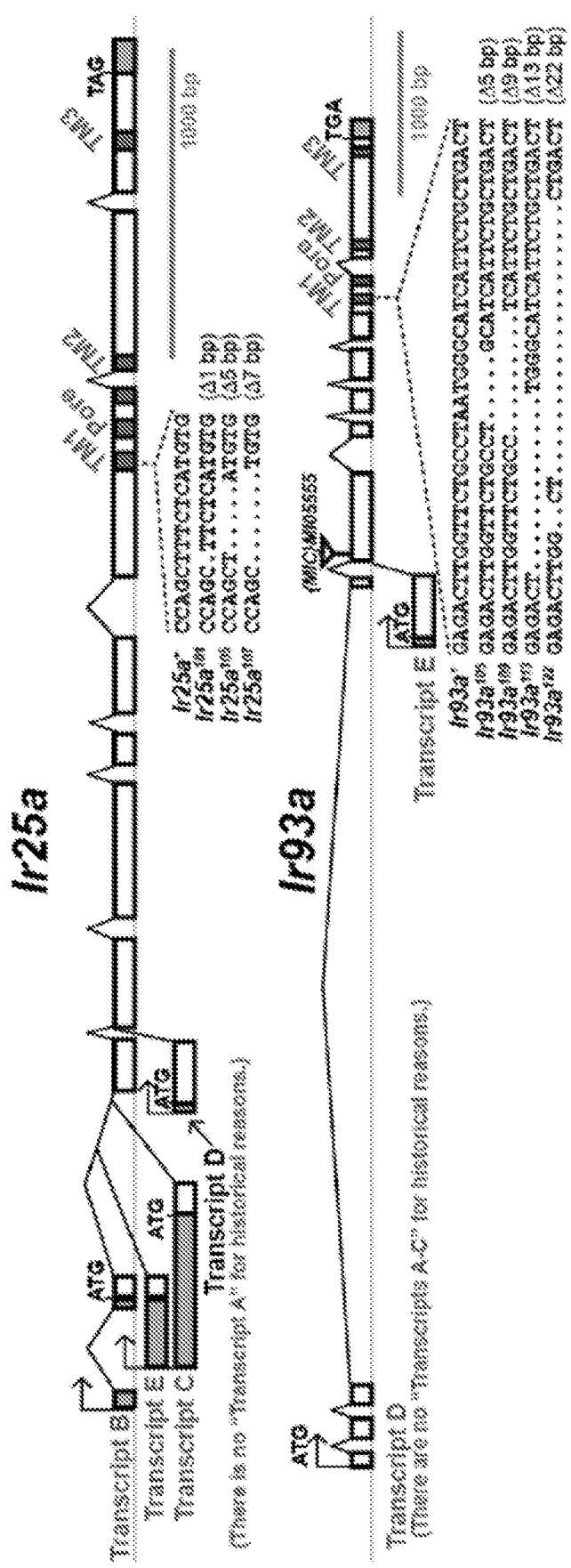
FIG. 10 is a schematic showing Ir25a and Ir93a genes. TM1-TM3 denote transmembrane sequences, pore denotes ion pore sequence. Triangle, Ir93a$^{MIC}$ transposon insert site. Gray, untranslated regions. Sequences depict base pairs deleted in CRISPR-generated alleles. Sequences are SEQ ID NOs: 60-67 in order of appearance.

Data herein show that Ir25a and Ir93a are involved in both temperature and moisture detection. Interestingly, both Ir25a and Ir93a encode multiple receptors with different amino termini, and these receptors could each have different functions. Ir25a encodes three alternative receptors (two transcripts encode identical proteins) and Ir93a encodes two alternative receptors (FIG. 10). Thus, even though the same genes mediate both thermo- and hygro-sensation, the actual receptors involved may differ (for example, Ir93a-D might mediate hygrosensation and the Ir93a-E thermosensation). Different isoforms of *Drosophila* TRPA1 mediate thermal and chemical sensing, providing clear precedent for such functional distinctions among isoforms.

Whether or not different classes of sensory neurons require different isoforms of Ir25a and Ir93a, is tested and whether the different isoforms of Ir25a and Ir93a help endow stimulus specificity to sensory neurons is tested. The hypotheses are tested through isoform-specific knockouts and isoform-specific cDNA rescue experiments.

Ir25a and Ir93a are required for both hygro- and thermo-sensation, performing these roles in distinct neurons and with different IR co-factors. It is unclear whether hygro- and thermo-sensation involve the same or different isoforms of Ir25a and Ir93a. Functions of different IR93a and IR25a isoforms are assessed.

Role of Ir25a and Ir93a Isoforms in Mediating Hygro- and Thermo-Sensory Responses To address which isoforms are normally involved in hygrosensing and which in thermosensing, isoform-selective alleles that specifically disrupt a subset of the isoforms encoded by each gene are created. These isoform selective alleles are then tested for their ability to support hygro- and thermo-sensory behavior, revealing which isoform of each gene mediates responses to moisture and/or cooling.

Established methods for fully transgenic CRISPR-based genome editing (Port et al., 2014, *Proc Natl Acad Sci USA*, 111(29), E2967-E2976) are used to specifically mutate coding regions unique to subsets of isoforms. For Ir25a, Ir25a^BE alleles, Ir25a^C alleles, and Ir25a^D alleles are created, each with small translation-disrupting deletions in the coding sequences unique to each. Similarly, Ir93a^D and Ir93a^E alleles are created, each with translation disrupting deletions in isoform-unique coding regions. To date, analogous lesions in other exons of both Ir25a and Ir93a were successfully generated (FIG. 10). If difficulties with generating additional alleles are encountered, additional guide RNAs can be used. Adult hygrosensory behavior and larval and adult thermosensory behavior are assessed as in the foregoing section, using established methods (Sayeed et al., 1996, *Proc Natl Acad Sci USA*, 93(12), 6079-6084; Klein et al., 2015, *Proc Natl Acad Sci USA*, 112(2), E220-E229; Ni et al., 2013, *Nature*, 500(7464), 580-584).

In one scenario, different isoforms of Ir25a and/or Ir93a mediate hygro- and thermosensation, in which case trans alleles would show deficits in one but not both behaviors. One can also imagine more complex scenarios in which different isoforms mediate larval versus adult thermosensation or even a case where isoforms are functionally redundant and no single isoform-specific allele disrupts a behavior.

To test isoform-redundancy, an additional round of CRISPR would be performed to create alleles in which multiple isoform-specific exons are simultaneously disrupted. Finally, mutations in a single isoform might affect both hygro- and thermo-sensing. This would suggest that the same isoform mediates both responses. In all cases, these findings would be further probed by isoform-specific rescue experiments.

Use Isoform-Specific cDNA Constructs to Probe the Role of IR93a and IR25a Variants To determine which receptors isoforms can mediate hygro- and/or thermo-sensation (irrespective of their normal expression), rescue experiments using cDNAs encoding each isoform in the appropriate null mutant are performed in order to test whether Ir25a and/or Ir93a isoforms have distinct functional abilities.

cDNAs are expressed under IR40a-Gal4 control to test hygrosensation, Ir21a-Gal4 to test larval thermosensation, and R11F02-Gal4 (expressed in all arista neurons) to test adult thermosensation. Larval and adult thermosensory behavior and adult hygrosensory behavior are assessed as in preliminary data, using established methods (Sayeed et al., 1996, Proc Natl Acad Sci, 93(12), 6079-6084; Klein et al., 2015, *Proc Natl Acad Sci USA*, 112(2), E220-E229; Ni et al., 2013, *Nature*, 500(7464), 580-584). Optical imaging of neuronal responses are performed using established approaches (Silbering et al., 2011, J Neurosci, 31(38), 13357-13375; Klein et al., 2015, *Proc Natl Acad Sci USA*, 112(2), E220-E229), expressing GCaMP6 (Chen et al., 2013, *Nature*, 499(7458), 295-300) under control of the appropriate Gal4 (i.e., Ir4oa-Gal4, Ir2ia-Gal4 and IR11F02-Gal4). Briefly, thermosensory imaging is performed using a spinning disc confocal with temperature-controlled stage (Pitts et al., 2011, *BMC Genomics*, 12, 271), with larval thermosensors imaged in intact larvae and adult thermosensors in antennae dissociated from the head (see FIGS. 8-9). Hygrosensory imaging is performed using an imaging approach widely used to study olfaction (Xu et al., 2014, *Proc Natl Acad Sci USA*, 111(46), 16592-16597); briefly, antennal neuron responses are imaged in their target regions in the brain through a small hole cut in the head cuticle (as in FIG. 5). The antennae remain dry, permitting stimulation with airborne cues. Moisture is provided using streams of dry (10% RH, 25° C.) and moist (90% RH, 25° C.) air provided through two parallel 500 ml/min flow meters.

In one scenario, some isoforms may support only one modality, thermo- or hygro-sensation, indicating functional differences between the proteins. In this case, whether this difference reflects isoform-specific limits on assembling with other is tested. Alternatively, individual isoforms may support both responses, suggesting overlap in function between isoforms. At the physiological level, whether expression of individual isoforms can restore the normal sensory response (hygro- and/or thermo-sensory) and/or confer novel sensitivity, such as turning a cell into a thermoreceptor that normally does not function as such, is tested. Together with the experiments described in the foregoing section, these experiments determine which isoforms of Ir25a and Ir93a are necessary for detection of cold and moisture, and show the degree to which each isoform is capable of conferring responsiveness to a given stimulus.

The Ir25a and Ir93a genes each encode multiple receptor isoforms with potentially distinct properties. Whether the same or different receptor isoforms mediate hygro- and thermo-sensing, and establish their cellular sites of action is tested. CRISPR is used to create isoform-specific alleles of Ir25a and Ir93a, and then test which isoforms of each are required to confer behavioral and physiological responsiveness to cooling and to moisture. This tests if the same or distinct receptor isoforms mediate these distinct functions. Whether the same or distinct isoforms mediate hygrosensory responses in hydrated and de-hydrated flies, which show opposite moisture preferences, is also tested. Isoform-specific cDNA rescue is used to determine the isoforms of Ir25a and Ir93a capable of supporting behavioral and physiological responses to cooling and moisture, and establish the cells through which they support each modality so as to determine the nature and extent to which distinct isoforms and sensory neurons differ in their ability to support cold and moisture sensing.

Example 4: Contribution of Ir21a and Ir40a to Hygro- and Thermo-Sensor Formation IRs frequently function as multimeric complexes, with a broadly expressed co-receptor combining with one or more stimulus specific subunits (Ai et al., 2013, *Neurosci*, 33(26), 10741-10749; Abuin et al., 2011, *Neuron*, 69(1), 44-60). It is hypothesized that Ir93a and Ir25a pair with additional subunits that help specify the receptor as a hygro- or thermo-sensor.

In addition to Ir25a and Ir93a, the neurons of the sacculus express Ir40a, and the larval and adult cool sensors express Ir21a. Thus, Ir40a and Ir21a may help confer specificity upon an IR complex, with Ir25a/Ir40a/Ir93a mediating hygrosensing in the sacculus and Ir21a/Ir25a/Ir93a mediating thermosensing in larval and adult thermosensors. This model is tested in three ways: testing Ir40a's importance for hygrosensory behavior, examining the extent to which IR expression requires coexpressed IRs, and testing the ability of Ir40a and Ir21a to functionally substitute for one another. Ir40a's Role in Hygro- and Thermo-Sensation by Examining Ir40a Null Mutants An Ir40a null allele (Ir40a1) was recently generated in a study investigating Ir40a's proposed role in DEET detection (Kain et al., 2013, Nature, 502(7472), 507-512). However, subsequent studies have demonstrated that neurons expressing IR40a are not DEET detectors (Silbering, A. F. et al., 2016, Nature, 534, online publication doi:10. 1038/nature 18321), leading to a retraction of the original report of this finding (Kain, P. et al., 2013, Nature, 502:507-512). This mutant can be used to test how the loss of Ir40a affects behavioral and physiological responses to hygro- and thermo-sensory responses, and cell-specific cDNA rescue is used to assess the cells in which Ir40a acts. These results test the functional significance of Ir40a expression in the sacculus. In addition, the thermosensory responsiveness of Ir40a-Gal4 cells in the sacculus are also examined using the genetically encoded calcium sensor GCaMP6.

Hygrosensory and thermosensory behavior, and physiological responses of hygrosensory and thermosensory neurons can be assessed, using established procedures (Sayeed et al., 1996, Proc Natl Acad Sci, 93(12), 6079-6084; Silbering et al., 2011, Neurosci, 31(38), 13357-13375; Klein et al., 2015, Proc Natl Acad Sci USA, 112(2), E220-E229; Ni et al., 2013, Nature, 500(7464), 580-584).

The co-expression of Ir40a in the sacculus with Ir25a and Ir93a makes it a strong candidate to participate in hygro-sensing, suggesting that Ir40a mutants are likely to show Ir25a- and Ir93a-like hygrosensory defects. In addition, if there is indeed an Ir25a/Ir40a/Ir93a complex, loss of Ir40a should disrupt Ir25a and Ir93a expression. In addition, response of the Ir40a-Gal4 cells to thermal stimulation in wild type animals would suggest a thermosensory mechanism for the sacculus' role in hygrosensing. It is also formally possible that Ir25a and Ir93a act without Ir40a despite their co-expression, in which case the investigation can explore the role of Ir25a and Ir93a in hygro-responses, and of Ir21a, Ir25a and Ir93a in cool responses. This would raise the possibility that Ir25a and Ir93a together are sufficient for hygrosensing without a third IR.

Contribution of IR Cofactors to Formation of Functional Receptor Complexes

IRs that act in heteromeric complexes frequently depend on IR partners for robust expression and localization. The interdependence of Ir21a, Ir25a, Ir40a and/or Ir93a expression and localization is tested by examining Ir21a expression in Ir25a and Ir93a mutants, Ir40a expression in Ir25a and Ir93a mutants, and Ir93a expression in Ir25a and Ir40a mutants. Similarly, the interdependence Ir21a, Ir25a, and Ir93a expression in thermoreceptors is tested by examining Ir21a expression in Ir25a and Ir93a mutants, Ir25a expression in Ir21a and Ir93a mutants, and Ir93a expression in Ir21a and Ir25a mutants. To probe whether such interdependence may reflect physical interactions, CRISPR-based homologous recombination is used to incorporate unique epitope tags into each of the four endogenous IR loci, facilitating co-immunoprecipitation (co-IP) analysis of IR complexes from the large quantities of fly tissue required to observe the endogenously expressed IRs. In parallel, the Gal4/UAS system is used to express epitope-tagged cDNAs of the four IRs in combinations, both in fly neurons and in cultured S2 cells. Together these studies can be used to assess heteromeric complex formation among different IR combinations.

Larval cool cells and the adult arista and sacculus are stained using available anti-Ir25a, anti-Ir40a and anti-Ir93a antisera, as well as anti-Ir21a antisera currently being generated. Each endogenous IR loci is also modified, incorporating an epitope tag via CRISPR-mediated homologous gene targeting (Chen et al., 2015, Genetics, 199(3), 683-694). This permits co-IPs using commercially available antisera (quantities of IR-specific antisera are limited). Epitope-tagged IR cDNAs under UAS control are also created. Each IR is tagged with a distinct epitope (e.g., Ir21a with myc, Ir25a with V5, Ir93a with HA, Ir40a with FLAG) at its C-terminus, as other IRs retain function when tagged at this location (Abuin et al., 2011, Neuron, 69(1), 44-60; Ai et al., 2013, J Neurosci, 33(26), 10741-10749). The functionality of epitope-tagged IRs is confirmed by testing their ability to rescue mutant behavior; should tagging disrupt function, alternative tags and locations are used. Epitope tagging of endogenous IR loci has been used to successfully co-IP other IRs1.

If specific IRs show a change in localization or expression in mutants for other IRs, this would suggest functional interactions between these receptors. In preliminary experiments, it was found that Ir93a location is reduced in larval thermoreceptors mutant for Ir21a and Ir25a, supporting such a notion. Results of co-precipitation (Co-IP) experiments permit assessment of which IR combinations form heteromeric complexes.

Stimulus Response Specificity Conferred by Ir21a and Ir40a Expression

The hypothesis that Ir21a and Ir40a expression determines the specificity of Ir25a/Ir93a expressing neurons for mediating hygro- and thermo-sensation, respectively, is tested. First the ability of Ir21a and Ir40a to carry out similar functions by examining their ability to functionally replace one another is tested. This is done by examining whether Ir40a expression can substitute for that of Ir21a in cool receptors and whether Ir21a expression can substitute for Ir40a in the sacculus. Ir25a and Ir93a alone and with either Ir21a or Ir40a are ectopically expressed in the fly, and the ability of these ectopically expressed IRs to mediate thermosensitivity, a stimulus that can be reliably applied to all cells, is tested.

The ability of Ir21a and Ir40a to substitute for one another is tested by expressing Ir40a cDNA in thermoreceptors (using Ir21a-Gal4 and R11F02-Gal4) in an Ir21a mutant, and an Ir21a cDNA in the sacculus (using Ir40a-Gal4) in an Ir40a mutant. Hygro- and thermo-sensory behavior and sensory neuron physiology are assessed. Ectopic expression (in otherwise wild type animals) is performed using Gal4 sources expressed in neurons whose physiology is readily examined, including arista neurons (RiiF02-Gal4), motor neurons (OK3yi-Gal4), chemosensors (Gr66a-Gal4 and Gr5a-Gal4), and all neurons (Nsyb-Gal4). Motor neuron activity is monitored by recording from target muscles in third instar larvae and chemosensor activity by tip-recording on the labellum, as our lab previously described (Croset et al., 2010, PLoS Genet, 6(8), e1001064). Arista responses are monitored using calcium imaging as described elsewhere herein, and pan-neuronal activation assessed as previously described (Pitts et al., 2011, BMC Genomics, 12, 271) by calcium imaging in larvae.

If Ir21a and Ir40a can substitute for one another, shared functional properties between the two receptors are indicated. If they cannot, it would suggest that each is specifically suited to their normal role. In the ectopic expression experiments, successful ectopic expression establishes that a particular set of IRs is sufficient to confer sensitivity for a given stimulus upon a sensory neuron. In preliminary experiments, ectopic Ir21a expression conferred cool-sensitivity upon hot cell (HC) neurons in the arista (see FIG. 9). As the HC's also express Ir25a and Ir93a this is consistent with the formation of an Ir21a/Ir25a/Ir93a cool receptor complex. Thus, without being bound by theory, it is expected that combinations of IR's can confer cool sensitivity. The properties conferred by ectopic expression of Ir40a have not yet been tested, but if it also confers thermosensitivity, this would suggest a thermosensory basis for sacculus hygrosensing.

Data herein show that Ir25a/Ir93a-expressing thermosensors also express Ir21a, while the Ir25a/Ir93a-expressing candidate hygrosensors also express Ir40a. Thus, the contributions of these additional IRs to the formation of moisture and cooling sensors with Ir25a and Ir93a are probed. The contribution of Ir40a to hygro-sensing by examining hygrosensory behavior and physiology in Ir40a mutant animals is tested. Whether Ir93a and Ir25a show functional interactions with Ir40a and with Ir21a is determined by co-immunoprecipitation and by immunostaining for each Ir protein in mutants lacking their potential partners. Whether Ir21a and Ir40a confer stimulus specificity to Ir93a and Ir25a expressing cells by ectopic expression of combinations of Ir cDNAs in fly neurons and heterologous cells is probed. These experiments further assess the molecular components required to form sensors for moisture and cold.

Related studies demonstrated that IR25a, IR93a and IR40a in dry air-activated neurons ("dry cells") in the sacculus were needed for the insect to sense changes in humidity, as well as to respond behaviorally in humidity gradients.

Example 5: IR93a is Expressed in Larval Thermosensory Neurons and is Essential for Cool Avoidance This Example describes a study of the orphan receptor, IR93a, which has orthologs across arthropods (Corey, E. A. et al., 2013, PloS One 8, e60551; Groh-Lunow et al., 2014, Frontiers in Cellular Neuroscience, 8:448; Rytz, R. et al., 2013, Insect Biochemistry and Molecular Biology, 43:888-897). RNA expression analysis in several insects and crustaceans indicates that this receptor gene is transcribed in peripheral sensory organs (Benton, R. et al., 2009, Cell, 136:149-162; Corey et al., 2013; Groh-Lunow et al., 2014; Rytz et al., 2013), but its role(s) is/are unknown. The study utilized Drosophila as a model and found that IR93a acts with different combinations of IRs in distinct populations of neurons to mediate physiological and behavioral responses to both thermosensory and hygrosensory cues.

To investigate the expression and function of IR93a, antibodies were generated against a C-terminal peptide sequence of this receptor, and two Ir93a mutant alleles were obtained: Ir93a$^{MI05555}$, which contains a transposon insertion in the fifth coding exon, and Ir93a$^{122}$, which was generated using CRISPR/Cas9 to delete 22 bases within the sequence encoding the first transmembrane domain (FIG. 32A).

Figures 32A, 32B, 32C, 32D:
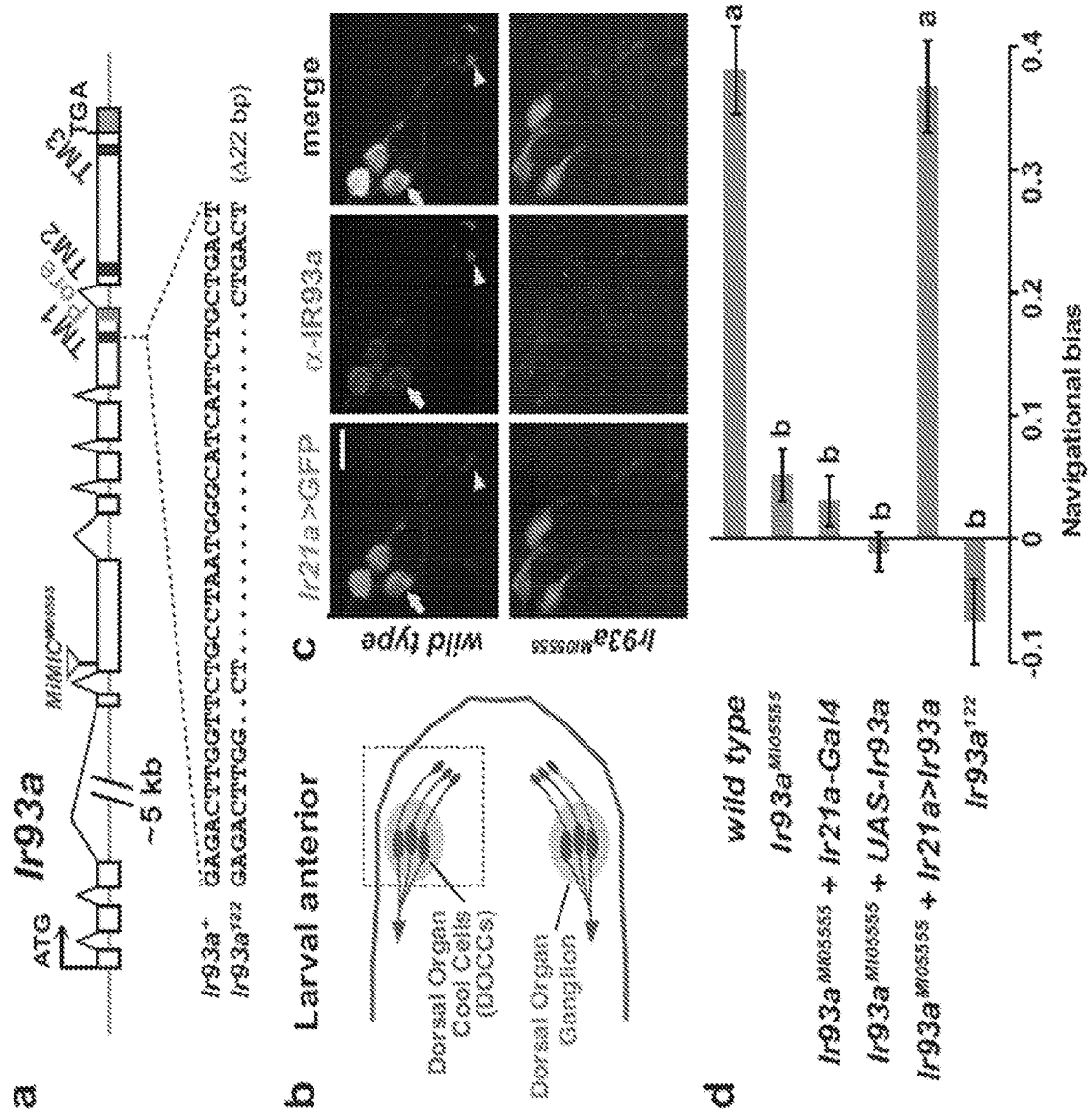
FIGS. 32A-32D show schematics, fluorescent microscopic images and a graph illustrating that IR93a is expressed in Dorsal Organ Cool Cells (DOCCs) and is required for cool avoidance.

In larvae, IR93a protein is expressed in several neurons in the dorsal organ ganglion, one of the main sensory organs in the larval head (Stocker, 1994, Cell and Tissue Research, 275, 3-26) (FIGS. 32B and 32C). These neurons encompass the DOCCs (labeled by an Ir21a promoter-Gal4-driven GFP reporter), and the protein localized prominently to the dendritic bulb at the tip of the sensory processes of these cells (FIG. 32C). All expression was absent in Ir93a mutants, confirming antiserum specificity (FIG. 32C).

These observations indicated that IR93a might function in cool sensing. Indeed, when larval thermotaxis was assessed on a thermal gradient (Klein et al., 2015, Ibid.), both Ir93a mutant alleles were found to exhibit strong defects in cool avoidance (FIG. 32D). Cell-specific expression of an Ir93a cDNA in the DOCCs under Ir21a-Gal4 control fully rescued this mutant phenotype (FIG. 32D). These data demonstrate an essential role for IR93a in DOCCs in larval thermotaxis.

Figures 33A, 33B, 33C:
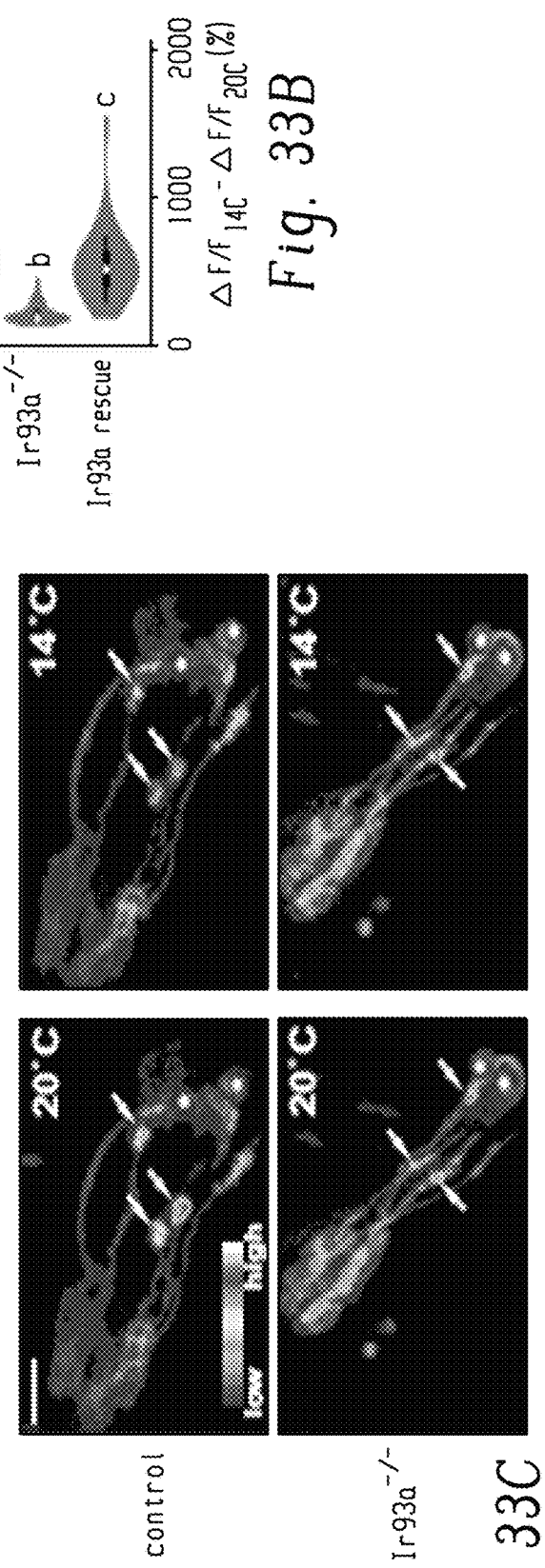

Example 6: IR93a is Required, Together with IR21a and IR25a, for Cool-Dependent Physiological Responses of DOCCs IR93a was assessed to determine if it was required for the physiological responses of DOCCs to cooling by optical imaging of these neurons using the genetically encoded calcium indicator, GCaMP6m (Chen et al., 2013, Nature, 499:295-300). Wild-type DOCCs exhibit robust increases in intracellular calcium in response to cooling (FIG. 33A), (Klein et al., 2015, Proc. Natl. Acad. Sci. USA, 112:E220-E229; Ni et al., 2016, eLife 5, e13254). These responses were dramatically reduced in Ir93a mutants, and could be rescued by cell-specific expression of an Ir93a cDNA (using the R11F02-Gal4 DOCC driver (FIGS. 33A, 33B). This dramatic loss of DOCC temperature sensitivity resembled that observed in both Ir21a and Ir25a mutants (Ni et al., 2016, Ibid.), and was consistent with IR21a, IR25a and IR93a functioning together to mediate cool activation of the DOCCs.

To provide a more direct readout of thermotransduction in these neurons than soma calcium measurements, the requirement for IR93a, IR21a and IR25a was tested in cool-evoked membrane voltage changes using the genetically encoded voltage sensor, Arclight (Jin et al., 2012, Neuron, 75, 779-785). In wild-type animals, cool-dependent voltage changes were observed in the DOCC sensory dendritic bulbs (FIGS. 33C-33D), where IRs are localized (FIG. 32C). This response was completely eliminated in Ir21a, Ir25a and Ir93a mutants (FIGS. 33C-33E), indicating that each of these IRs is required for temperature-dependent voltage changes in this sensory compartment.

Example 7: IR93a is Co-Expressed with IR25a and IR40a in the Antennal Sacculus

Figures 34A, 34B, 34C, 34D, 34E:
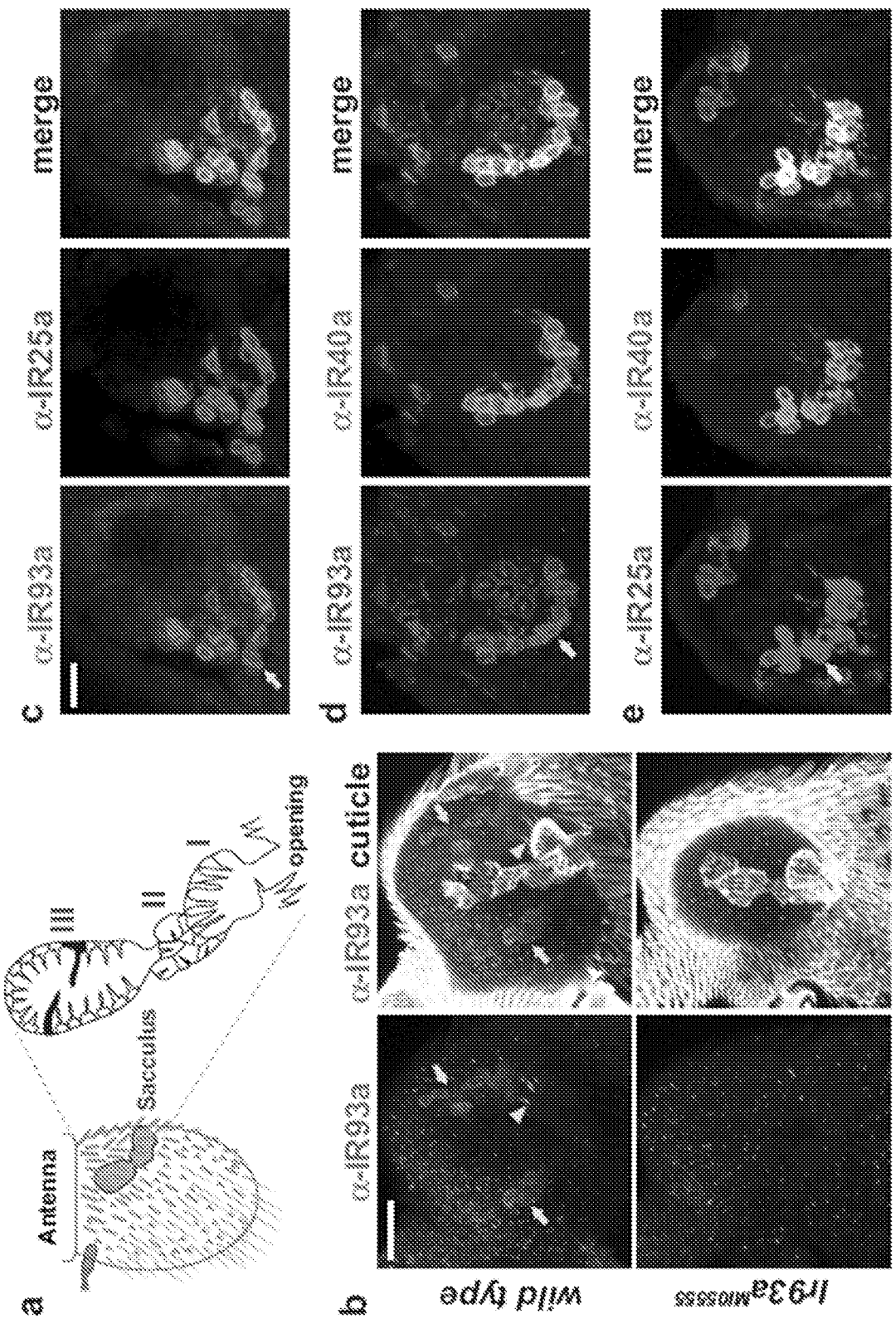
FIGS. 34A-34E show schematics and microscope images illustrating that IR93a is co-expressed with IR25a and IR40a in sacculus neurons.

In adults, Ir93a transcripts were previously weakly detected in a set of neurons in the third antennal segment surrounding the sacculus, a three-chambered pouch whose opening lies on the posterior surface of the antenna (Benton, R. et al., 2009, Ibid.) (FIG. 34A). With anti-IR93a antibody, IR93a expression was detected in neurons innervating sacculus chamber I (11.0±0.5 neurons, n=48 animals; mean±SEM) and chamber II (13.9±0.7 neurons, n=23), with signal detected both in the soma and in the sensory cilia that project into cuticular sensory hairs (sensilla) (FIG. 34B). As in larval DOCCs, IR25a was expressed in IR93a-expressing cells in the sacculus (FIG. 34C). By contrast, no expression was detected in these cells when using a Ir21a promoter driver. Instead, it was found that the IR93a/IR25a sacculus neurons expressed a distinct receptor, IR40a (FIGS. 34D and 34E).

Example 8: IR93a, IR25a and IR40a are Necessary for Hygrosensory Behavior

Figure 35A:
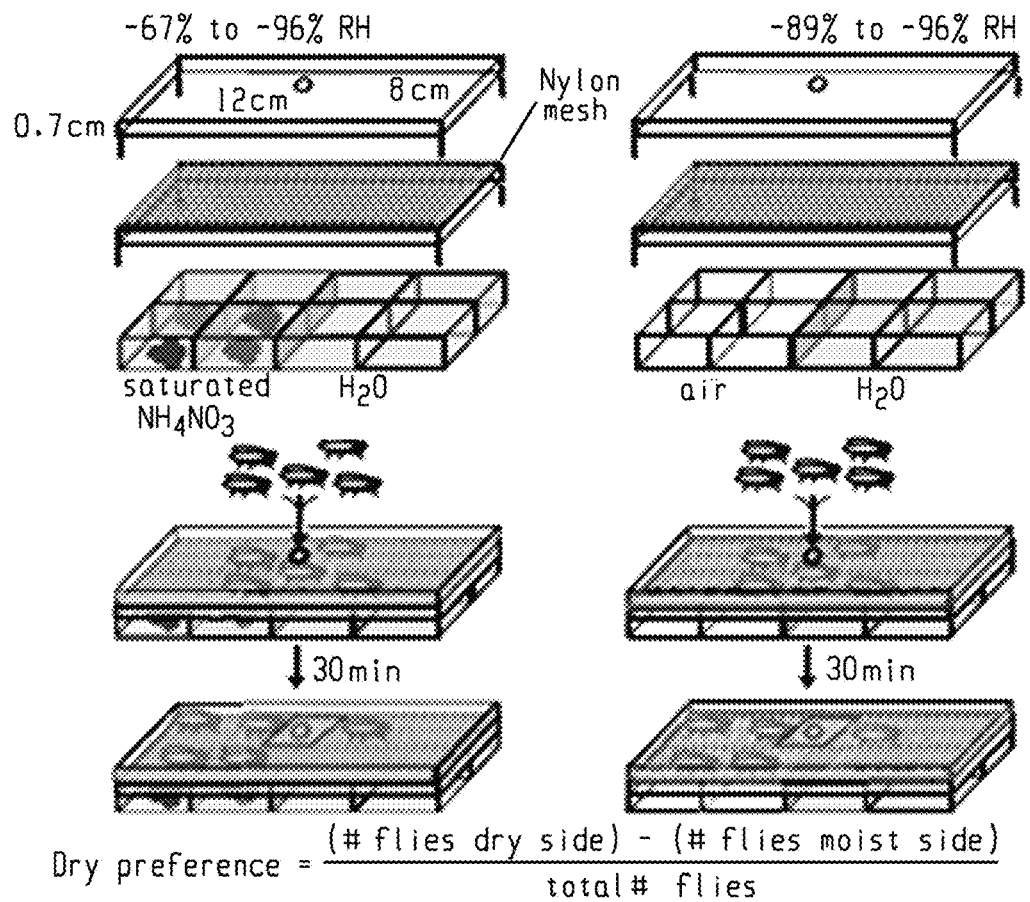
Figure 35B:
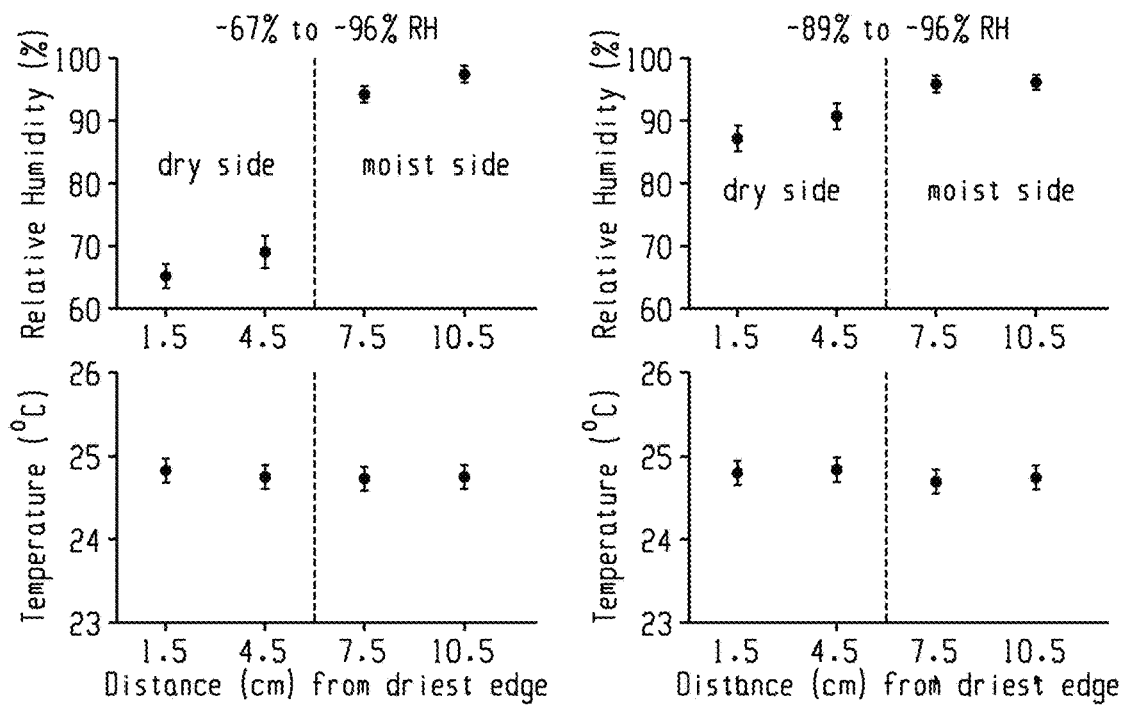
Figure 35C:
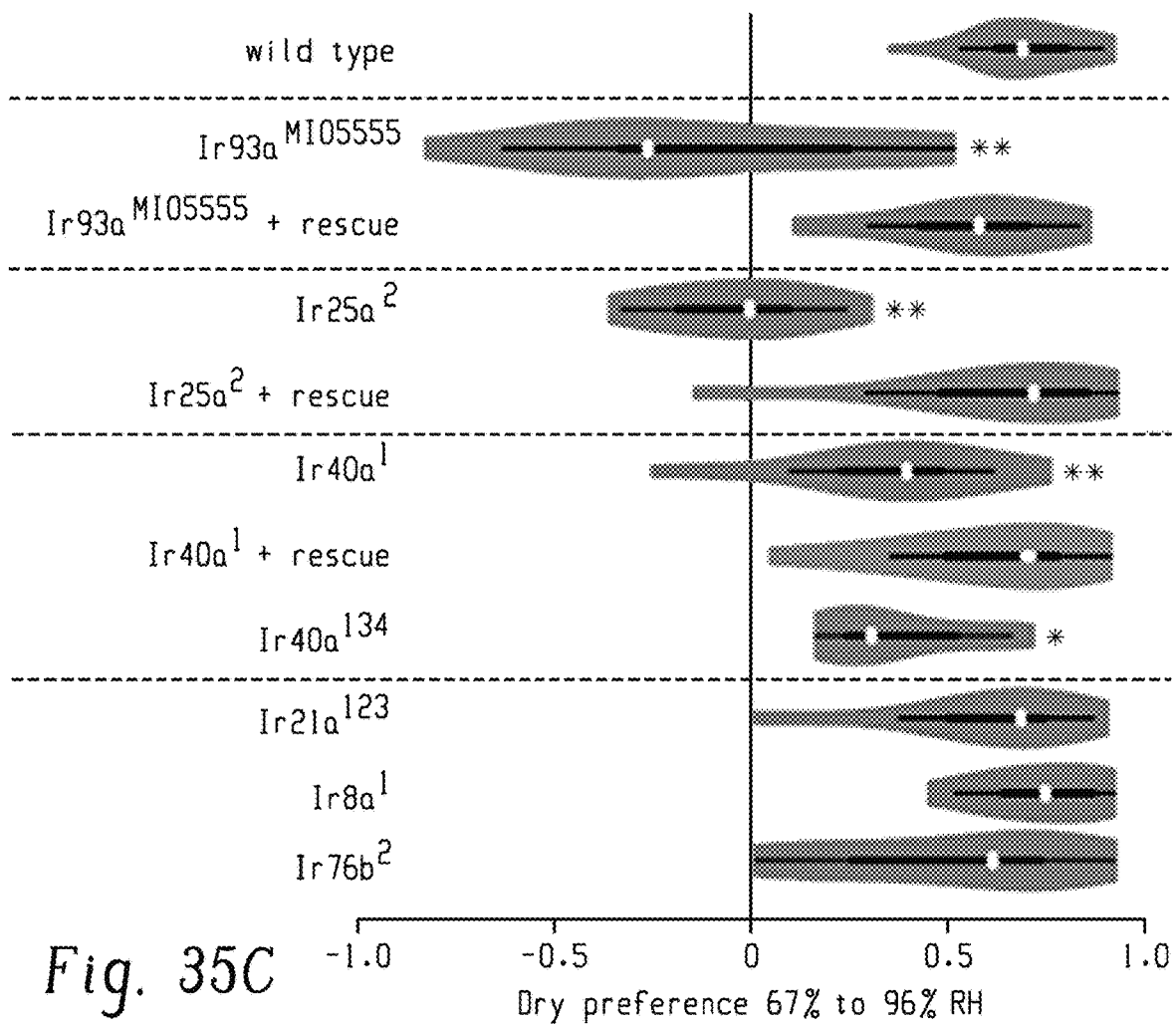
Figure 35D:
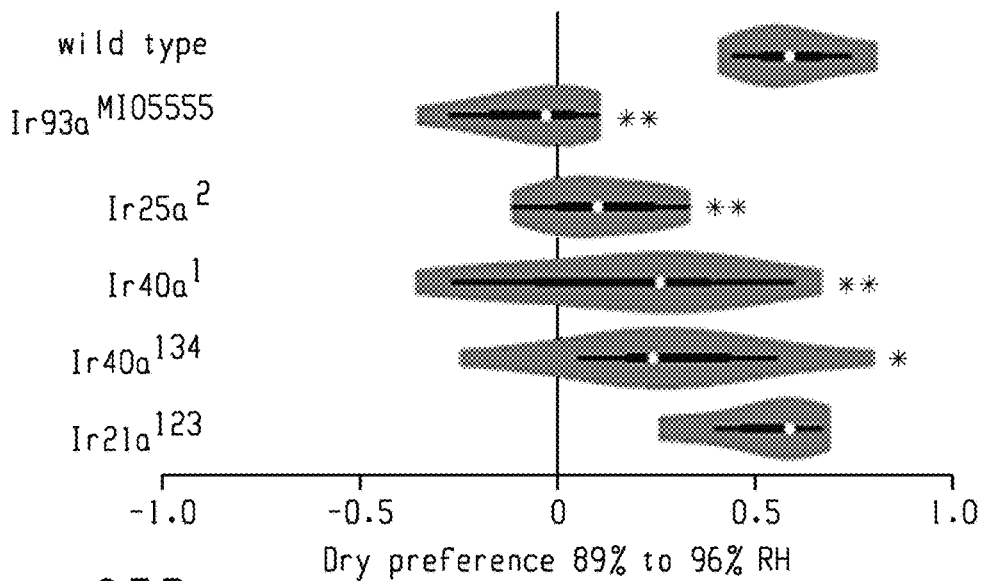
Figure 36C:
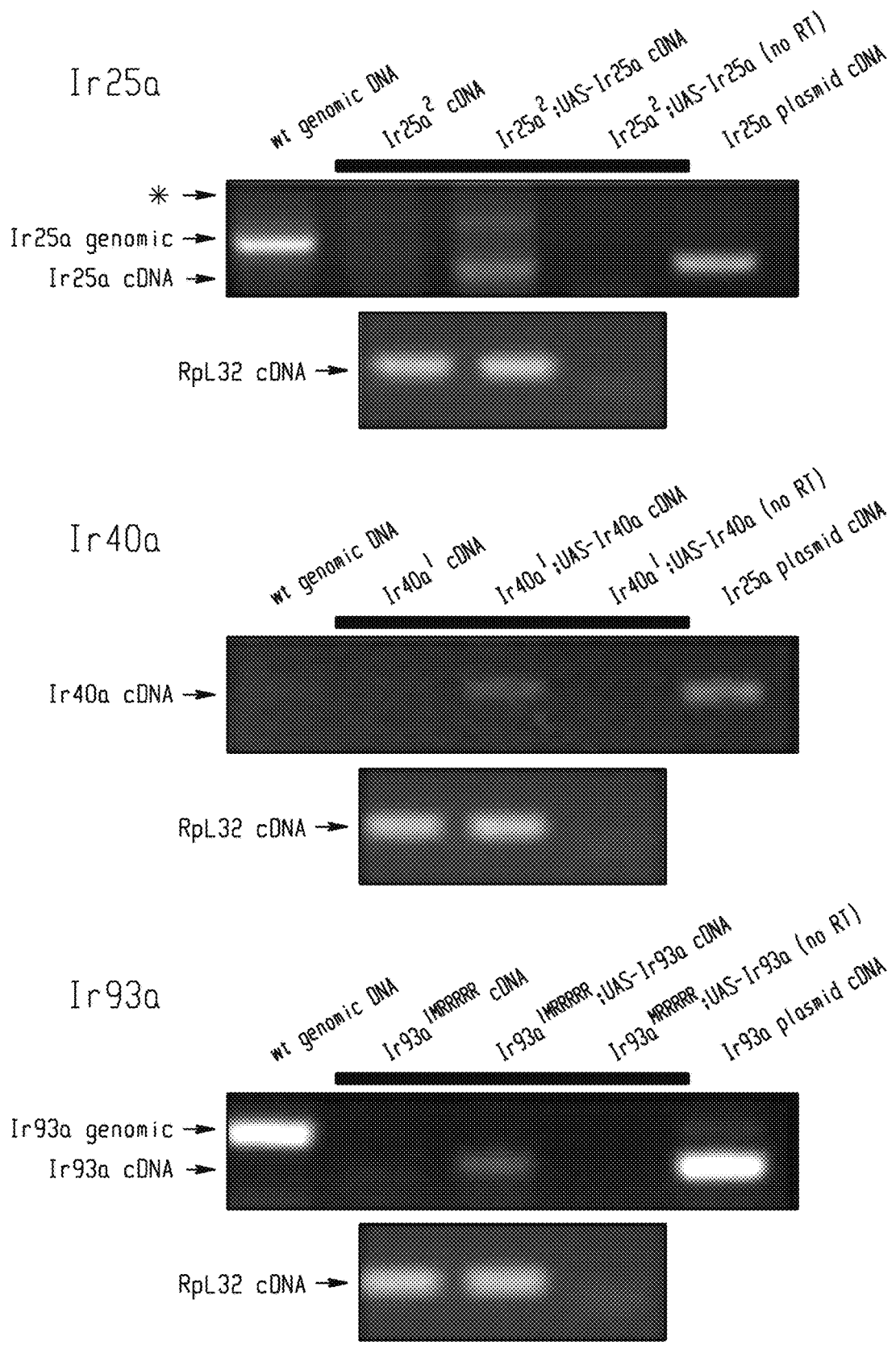

To test whether IR93a, IR25a, and IR40a were required for hygrosensory behavior, an experimental paradigm (Perttunen and Salmi, 1956, Suomen Hyonteistieteellinen Aikakauskirja. Annales Entomologici Fennici, 22, 36-45) was adapted in this experiment, in which flies chose between regions of differing humidity generated by two underlying chambers: one containing deionized water and the other containing water saturated with a non-volatile solute (ammonium nitrate) to lower its vapor pressure (FIG. 35A). This assay design created a humidity gradient of ~96% relative humidity (RH) to ~67% RH, with negligible variation in temperature (FIG. 35B). Consistent with previous observations, wild-type flies exhibited a strong preference for lower humidity (FIG. 35C). This preference was completely eliminated in Ir93a and Ir25a mutant flies, and significantly reduced, but not abolished, in Ir40a mutants (FIG. 35C and FIG. 36A). All of these behavioral defects were robustly rescued by the corresponding cDNAs, confirming the specificity of the mutant defects (FIG. 35C). Importantly, the loss of Ir21a (or other antennal-expressed IR co-receptors, Ir8a and Ir76b) did not disrupt dry preference. To exclude any potential contribution of the non-volatile solute to the behavior observed, flies were also tested in a humidity gradient (~89% to ~96% RH) generated using underlying chambers of deionized water alone and air (FIG. 35A). Even in this very shallow gradient, wild type flies displayed a strong preference for the side with lower humidity (FIG. 35D), and this preference was dependent on IR93a, IR25a and IR40a, but independent of IR21a (FIG. 35D). The distinction between the functions of IR21a and IR40a extended to thermotaxis, as Ir40a mutants exhibited no defects in this IR21a-dependent behavior (FIGS. 36A and 36B), consistent with lack of expression of IR40a in the larval DOCCs.

Example 9: IRs Mediate Dry Detection by Sacculus Neurons

To test whether the IR40a/IR93a/IR25a-expressing sacculus neurons are physiological hygrosensors, calcium responses of these neurons to changes in the RH of an airstream (of constant temperature) directed toward the antenna were monitored. Ir40a-Gal4 was used to express UAS-GCaMP6m selectively in these neurons, and GCaMP6m fluorescence was measured in their axon termini, which innervate two regions of the antennal lobe, the 'arm' and the 'column' (Silbering et al., 2016, *Nature*, 534:E5-E7; Silbering et al., 2011, *J. Neuroscience*, 31:13357-13375) (FIGS. 37A and 37B).

Figures 37A, 37B, 37C, 37D, 37E, 37F, 37G:
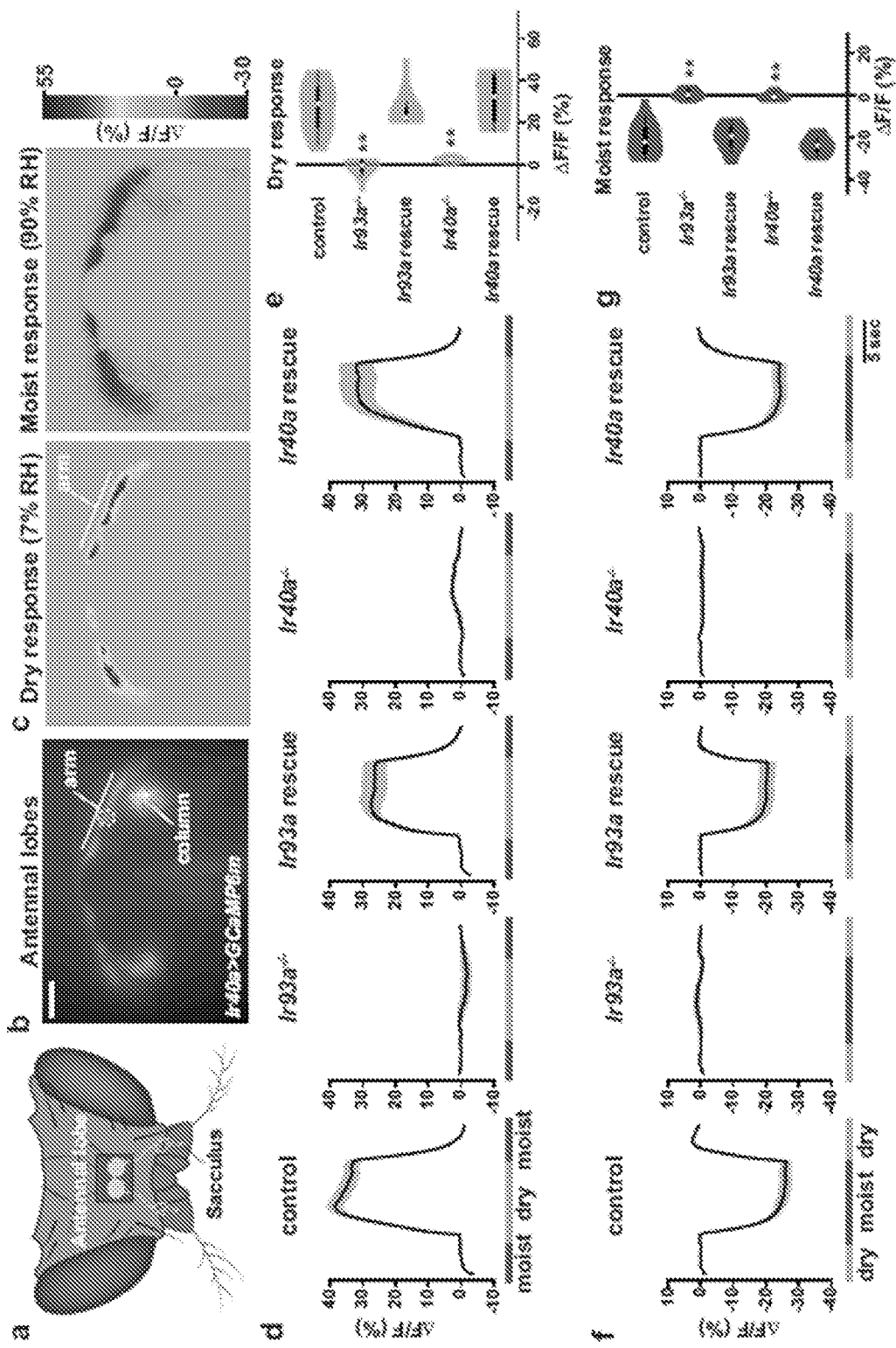
FIGS. 37A-37G show a schematic, fluorescence microscope images, traces and violin plot graphs illustrating IR-dependent physiological responses to dry air.

These sacculus neurons were found to behave as dry-activated hygrosensors: decreasing the RH from ~90% to ~7% RH elicited an increase in GCaMP6m fluorescence, while increasing RH from ~7% to ~90% elicited a decrease (FIGS. 37C-37G). Calcium changes were most apparent in the 'arm' (FIG. 37C). Importantly, these physiological responses were IR-dependent, as mutations in either Ir93a or Ir40a eliminated the dry response (Ir25a mutants were not tested), and these defects were restored with corresponding cDNA rescue transgenes (FIG. 37D-37G). These data corroborate the requirement for IRs in behavioral preference for lower humidity.

Figures 38A, 38B, 38C, 38D, 38E:
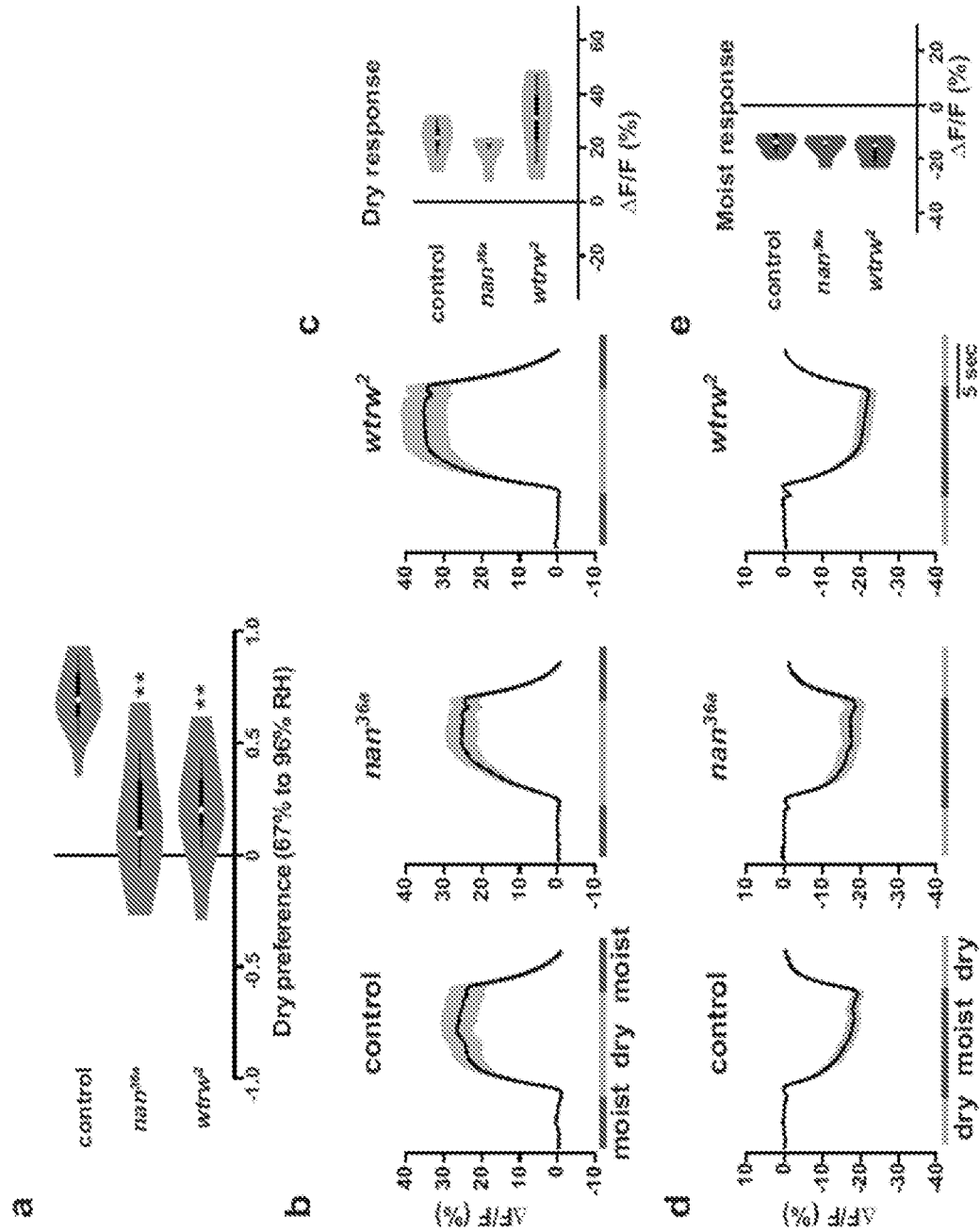
FIGS. 38A-38E show violin plots and traces illustrating that the TRP channels Nanchung and Water witch do not mediate IR-dependent dry sensation.

Example 10: The TRP Channels Nanchung and Water Witch do not Mediate IR-Dependent Dry Sensation While it has been reported that two Transient Receptor Potential (TRP) channels, Nanchung and Water witch, are involved in in hygrosensation (Liu et al., 2007, *Nature*, 450, 294-298), it was unclear whether they have an essential function in this modality (Enjin et al., 2016, *Current Biology*, 26, 1352-1358; Ji and Zhu, 2015, *PLOS One*, 10) and the cells in which these proteins act are unknown (Jourjine et al., 2016, *Cell*, 166, 855-866; Liu et al., 2007, Ibid.). In the gradient assay, it was found that animals mutant for nanchung or water witch displayed partially diminished dry preference behavior (FIG. 38A). However, neither nan nor wtrw was required for the dry responsiveness of IR40a-expressing sacculus neurons (FIGS. 38B-38E). Thus, these TRP channels are not essential for IR-dependent dry sensing, suggesting that they contribute to hygrotaxis through other mechanisms.

From their ancestral origins within the synaptic iGluR family, IRs are widely appreciated to have evolved functionally diverse roles in environmental chemosensory detection (Croset et al., 2010, *PLoS Genetics*, 6; Rytz et al., 2013, *Insect Biochemistry and Molecular Biology*, 43, 888-897). The experiments described in this Example provide evidence that a previously uncharacterized member of this repertoire, IR93a, functions in two critical non-chemosensory modalities, namely, thermosensation and hygrosensation. In both of these roles, IR93a acts with the broadly expressed co-receptor IR25a. However, these IRs mediate these two modalities in different populations of neurons in conjunction with a third, distinct IR—with IR21a in cool sensation, but not dry sensation, and with IR40a in dry sensation, but not cool sensation. All of these receptors are widely conserved in insects, indicating that these sensory pathways likely underlie behavioral responses of diverse species to these important environmental stimuli.

The identification of an IR21a/IR25a/IR93a-dependent cool-sensing system provides a molecular counterpart to the TRP channel and 'Gustatory' Receptor GR28B(D) warmth-sensing systems (Barbagallo and Garrity, 2015, *Current Opinion in Neurobiology*, 34, 8-13; Ni et al., 2013). By contrast, despite the importance of hygrosensation in helping insects to avoid desiccation or inundation (Chown et al., 2011, *Journal of Insect Physiology*, 57, 1070-1084) and—in blood-feeding species such as mosquitoes—to locate mammalian hosts (Brown, 1966, *JAMA*, 196, 249-162; Olanga et al., 2010, *Malaria Journal*, 9,), the neuronal and molecular basis of this sensory modality is poorly understood. Hygrosensitive neurons have been identified electrophysiologically in large insects (Tichy and Gingl, 2001, *Problems in Hygro-and Thermoreception*, Springer, New York, 271-287; Tichy and Kallina, 2010, *Journal of Neurophysiology*, 103, 3274-3286), but their behavioral role has been hard to determine to date. In *Drosophila*, the antenna has long been suspected to be an important hygrosensory organ (Perttunen and Syrjamaki, 1958; Sayeed and Benzer, 1996, *PNAS*, 93, 6079-6084), but there has been little consensus on the relevant populations of neurons and sensory receptors. As described herein, a discrete population of dry-activated hygroreceptors has been identified in the sacculus that express IR40a/IR93a/IR25a. The described experimental data provide physiological and behavioral evidence supporting these as one pathway that enables flies to distinguish external humidity levels, as supported by an independent study (Enjin et al., 2016, *Current Biology*, 26, 1352-1358).

In addition to the roles of IR93a in cool and dry sensing, it is very likely that this receptor defines additional sensory pathways. The expression analysis described herein has identified IR93a-positive cells that do not express IR21a or IR40a, such as non-DOCCs in the larval dorsal organ (FIG. 32C).

Figure 36D:
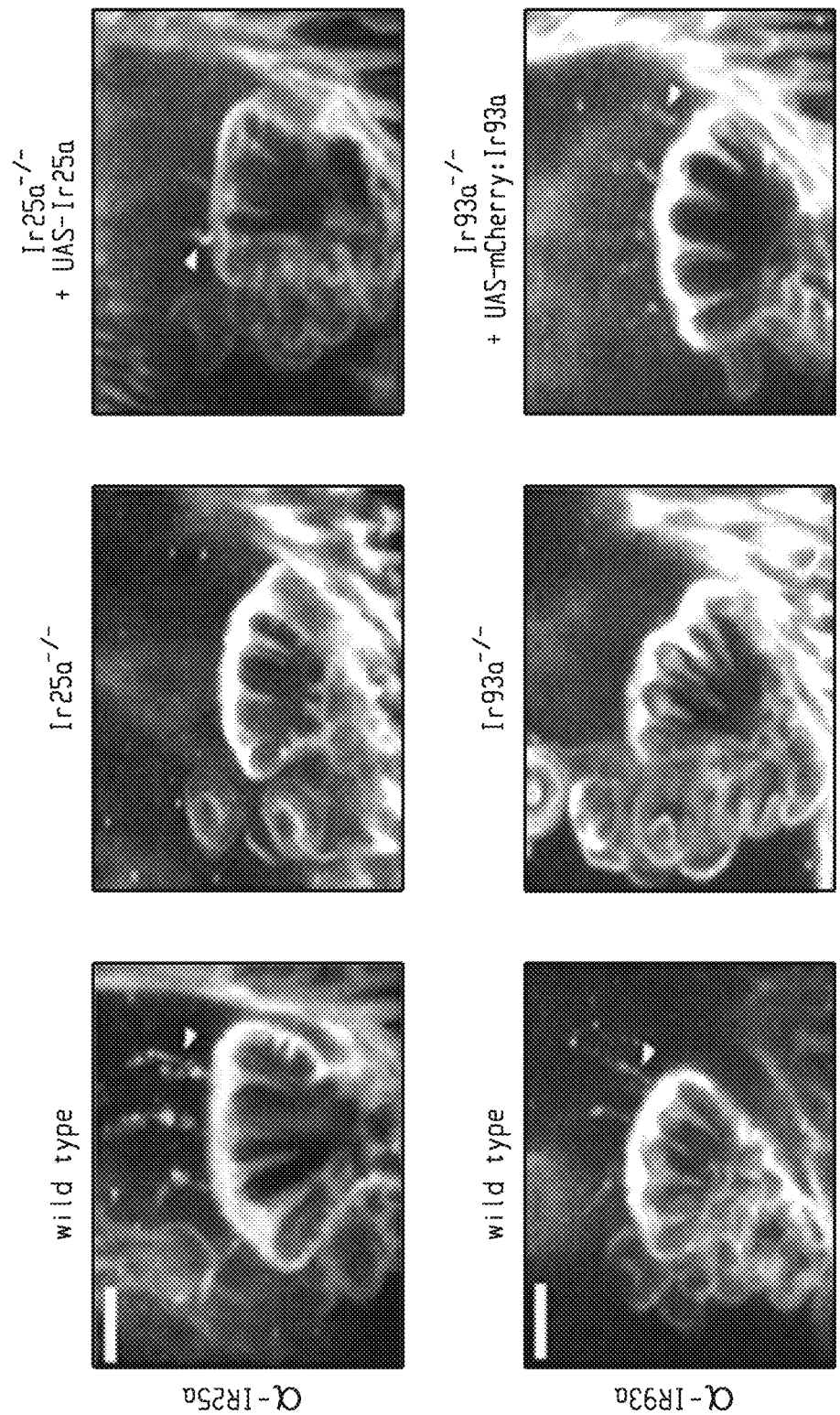

Moreover, the milder hygrosensory behavior phenotype of the protein null Ir40a mutants described herein compared to Ir93a (or Ir25a) mutants suggests that IR93a may have broader roles in this sensory modality than acting exclusively with IR40a. (e.g, FIGS. 36C and 36D). The populations of IR93a-expressing neurons characterized in this study are themselves heterogeneous. For example, IR40a/IR93a/IR25a-expressing sacculus neurons belong to two morphologically and physiologically distinct subpopulations. Arm neurons have contralateral projections (Silbering et al., 2011 *Journal of Neuroscience*, 31, 13357-13375) and respond robustly to low humidity, while column neurons are exclusively ipsilateral (Silbering et al., 2011, Ibid.) and respond more weakly to humidity, as well as displaying mild thermosensitivity (Enjin et al., 2016, *Current Biology*, 26, 1352-1358). IR40a-expressing neurons also respond to ammonia (Silbering et al., 2016). Given that these neurons are housed in apparently poreless sensilla (Shanbhag et al., 1995), the ammonia chemical is likely to activate these cells indirectly, for example, through modification of the humidity of the air, or the temperature of the cuticular surface, within the sacculus.

Concerning possible mechanisms by which IRs contribute to the sensation of thermal and humidity cues, ectopically-expressed IR21a were found to be capable of conferring cool sensitivity to other IR-expressing neurons, consistent with IR21a acting as a sensory specificity determinant (Ni et al., 2016, *eLife*, 5). IR40a may also serve a more permissive role or function in a similar capacity in dry sensing. The potential contribution of the Venus flytrap-like ligand-binding domains of these receptors is of particular interest. Although this domain recognizes glutamate in iGluRs, and diverse organic molecules in chemosensory IRs, these domains may mediate thermo- and hygrosensory detection in these receptors in a ligand-independent manner. For example, IR21a could transduce information via temperature-dependent conformational changes. The requirement for IR93a (and IR25a) in both thermosensation and hygrosensation also indicates that these modalities could share common mechanisms of sensory detection. For example, hygrosensation may involve a thermosensory component, based on evaporative cooling. Alternatively, both temperature and moisture detection could involve mechanosensation, based on swelling or shrinkage of sensory structures, as reported for mammals and *C. elegans* (Filingeri, 2015, *Journal of Neurophysiology*, 114, 763-767; Russell et al., 2014, *PNAS USA*, 111, 8269-8274). Defining how IRs mediate temperature and moisture detection can be carried out by reconstituting thermosensory or hygrosensory responses in heterologous systems by expressing the known combinations of IRs. IRs, like iGluRs, are thought to form heterotetrameric complexes (Abuin et al., 2011, *Neuron*, 69, 44-60). Thus, additional IR subunits may be required. For animals (insects) to be able to monitor such ubiquitous and ever-changing environmental stimuli as moisture and dryness in their surroundings, other types of accessory signaling molecules could act with IRs and/or cellular and cuticular specializations of the thermosensory and hygrosensory structures of the animals could be involved.

IR25a, IR93a and IR68a are Required for Hygrosensitivity

The involvement of sensory neurons activated by high humidity levels ("moist cells") was determined by electrophysiological studies in larger insects. (Tichy, H. and Gingl, E., 2001, *Problems in hygro-and thermo-reception*. In: *The Ecology of Sensing*, F. G. Barth and A. Schimd, Eds., New York, Springer, pp. 271-287). The Examples below describe studies in which moist cells identified in the sacculus of *D. melanogaster* were shown to require IR25a, IR93a and IR68a for hygrosensitivity in the insect. Hygrosensory behavior was shown to be driven by a combination of IR68a-dependent moist sensing and IR40a-dependent dry sensing in a manner that varies with the hydration state of the animal.

Example 11: An Ir68a Reporter is Expressed in Candidate Moist Cells in the *Drosophila* Sacculus To identify cells and receptors involved in moist sensing, the inventors hypothesized that moist sensing, like dry sensing, could involve a conserved IR for which no chemical ligand had been identified. IR68a was an excellent candidate, as this receptor has been conserved across ~350 million years of insect evolution (Rytz, R. et al., 2013, *Ionotropic receptors (IRs): chemosensory ionotropic glutamate receptors in Drosophila and beyond. Insect biochemistry and molecular biology* 43, 888-897. doi: 10.1016/j.ibmb.2013.02.007). Moreover, previous RT-PCR studies (Croset, V. et al., 2010, *PLoS Genetics* 6, e1001064. doi: 10.1371/journal.pgen.1001064), as well as transcriptomic analyses (Menuz, K. et al., 2014, *PLoS genetics* 10, e1004810. doi: 10.1371/journal.pgen.1004810; Shiao, M. S. et al., 2013, *Zool Studies* 52, 42. doi: 10.1186/1810-522X-52-42), detected Ir68a expression in the antenna.

Figures 39A, 39B, 39C, 39D, 39E, 39F, 39G, 39H:
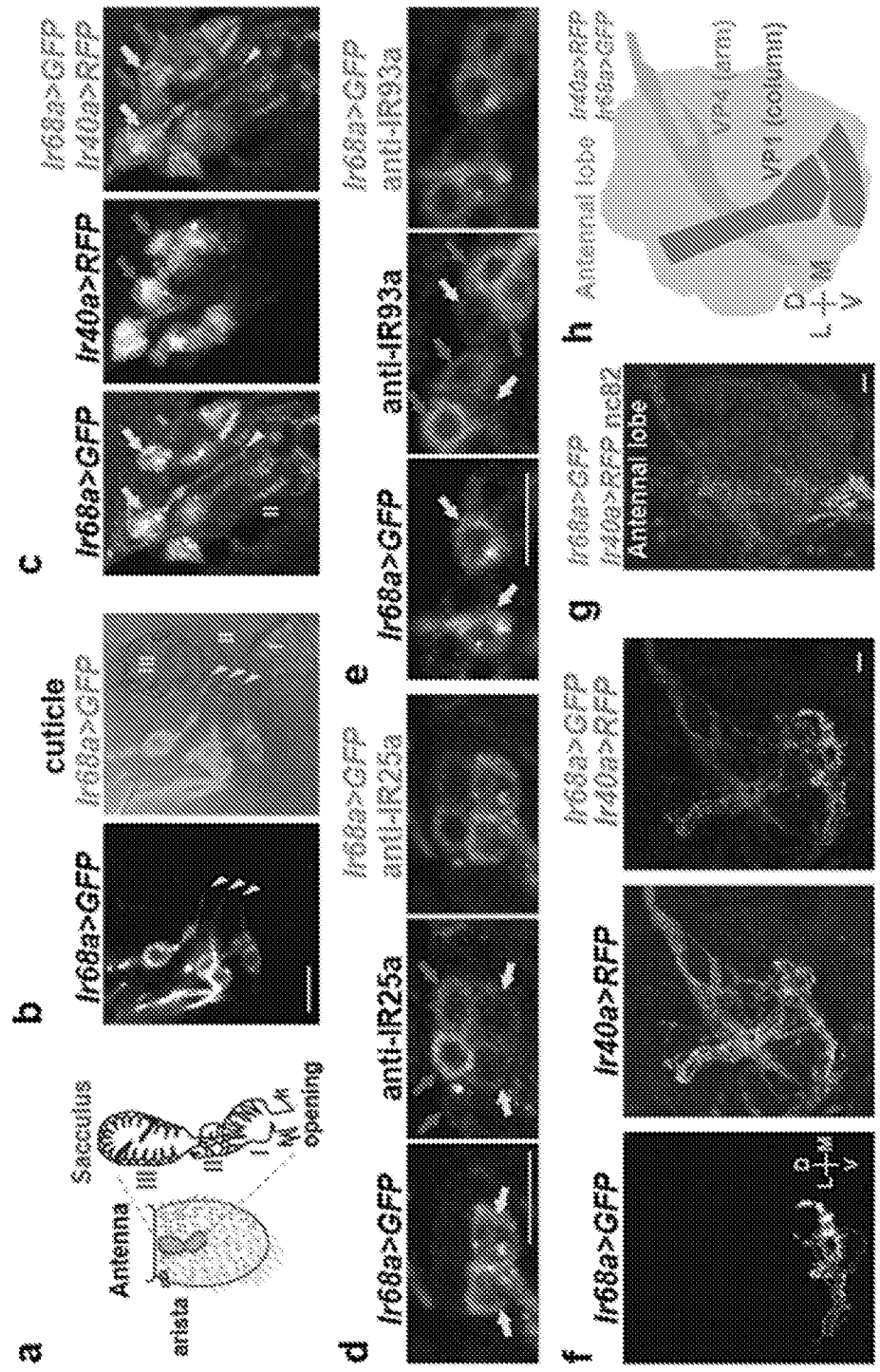
FIGS. 39A-39H show schematics and immunostained images illustrating that Ir68a and Ir40a reporters are expressed by neighboring neurons in the sacculus of *Drosophila*.
Figure 40:
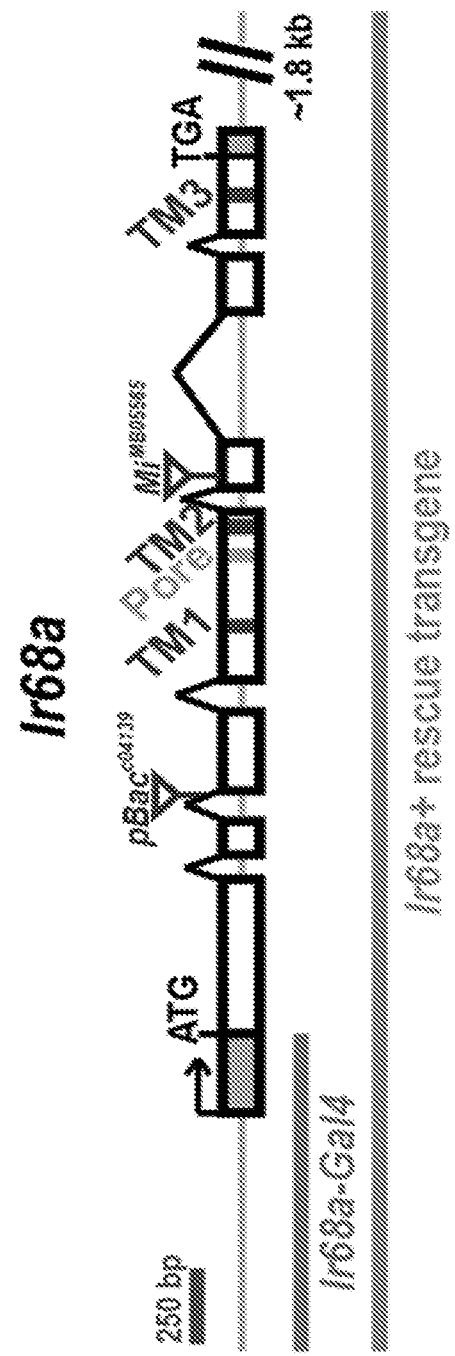
FIG. 40 is a schematic depiction of the organization of the Ir68a locus. In the schematic, exons are illustrated as boxes; shaded regions correspond to the UTRs. Sequences encoding the transmembrane (TM) domains (TM1 and TM2) and channel pore (PORE) of IR68a are labeled. The upside down triangles denote transposon insertions in Ir68a$^{c04139}$ and Ir68a$^{MB05565}$. The promoter region in the Ir68a-Gal4 transgene is indicated as (Ir68a-Gal4). Sequences included in the Ir68a' rescue transgene are indicated by the bottom bar.

As moist and dry cells are housed in the same sensilla in other species (Altner, H. and Loftus, R., 1985, *Ann. Rev. Entomol.*, 30:273-295), the studies herein determined that moist cells in *Drosophila* were located in the antennal sacculus adjacent to the IR40a-expressing dry cells. While attempts to generate IR68a antisera were unsuccessful, an Ir68a-Gal4 transgene containing the putative Ir68a promoter was successfully used to drive expression in a population of neurons that innervate chamber II of the sacculus (FIGS. 39A-B and FIG. 40). Importantly, these Ir68a-Gal4-expressing cells were intermingled with, but distinct from, Ir40a-expressing neurons (FIG. 39C), consistent with a role as moist cells in the sensilla of chamber II.

IR40a-positive neurons also express two co-receptors, IR25a and IR93a as described herein. Immunostaining revealed that IR25a and IR93a proteins are also present in Ir68a-Gal4-expressing neurons (FIGS. 39D-E). The cell bodies of sacculus neurons showed heterogeneous levels of IR25a and IR93a, with generally lower levels detected in Ir68a-Gal4-positive cells, which could reflect differences in the overall IR expression between cells or the efficiency of IR transport to sensory processes.

In the brain, Ir68a-Gal4-labelled neurons project to the antennal lobe, terminating in a discrete region near its ventrolateral edge (FIG. 39F). This region is distinct from the one innervated by IR40a-positive neurons (FIGS. 39G and 39H), and does not appear to correspond to any previously characterized glomerulus (Grabe et al., 2015, *J. Comparative Neurology*, 523, 530-544;)(Munch, D., and Galizia, C. G. (2016). DoOR 2.0—Comprehensive Mapping of *Drosophila melanogaster* Odorant Responses. Scientific reports 6, 21841. doi: 10.1038/srep21841), a finding that is consistent with a novel sensory function for these neurons.

Example 12: Ir68a-Gal4 Neurons are Activated by Moist Air

Figure 41A:
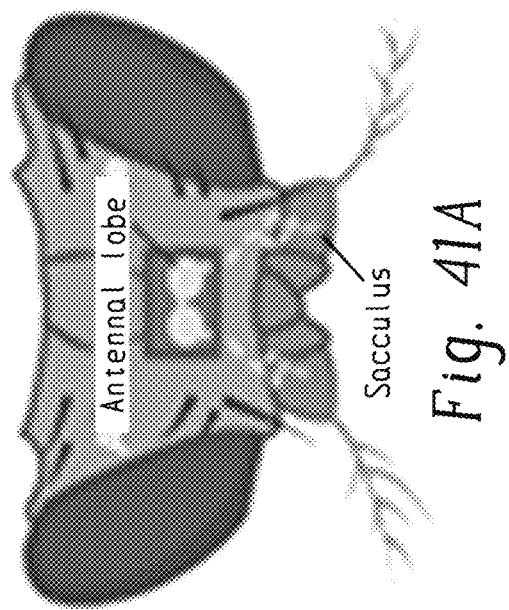
FIG. 41A-41F show a schematic drawing, microscope images, traces and violin plot graphs demonstrating that Ir68a is required for humidity detection by moist cells.
Figure 41B:
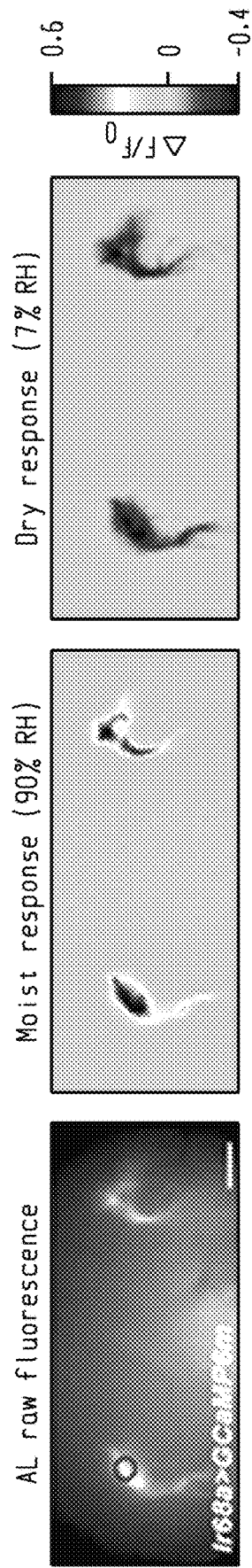
Figures 41A, 41B, 41C, 41D, 41E, 41F:
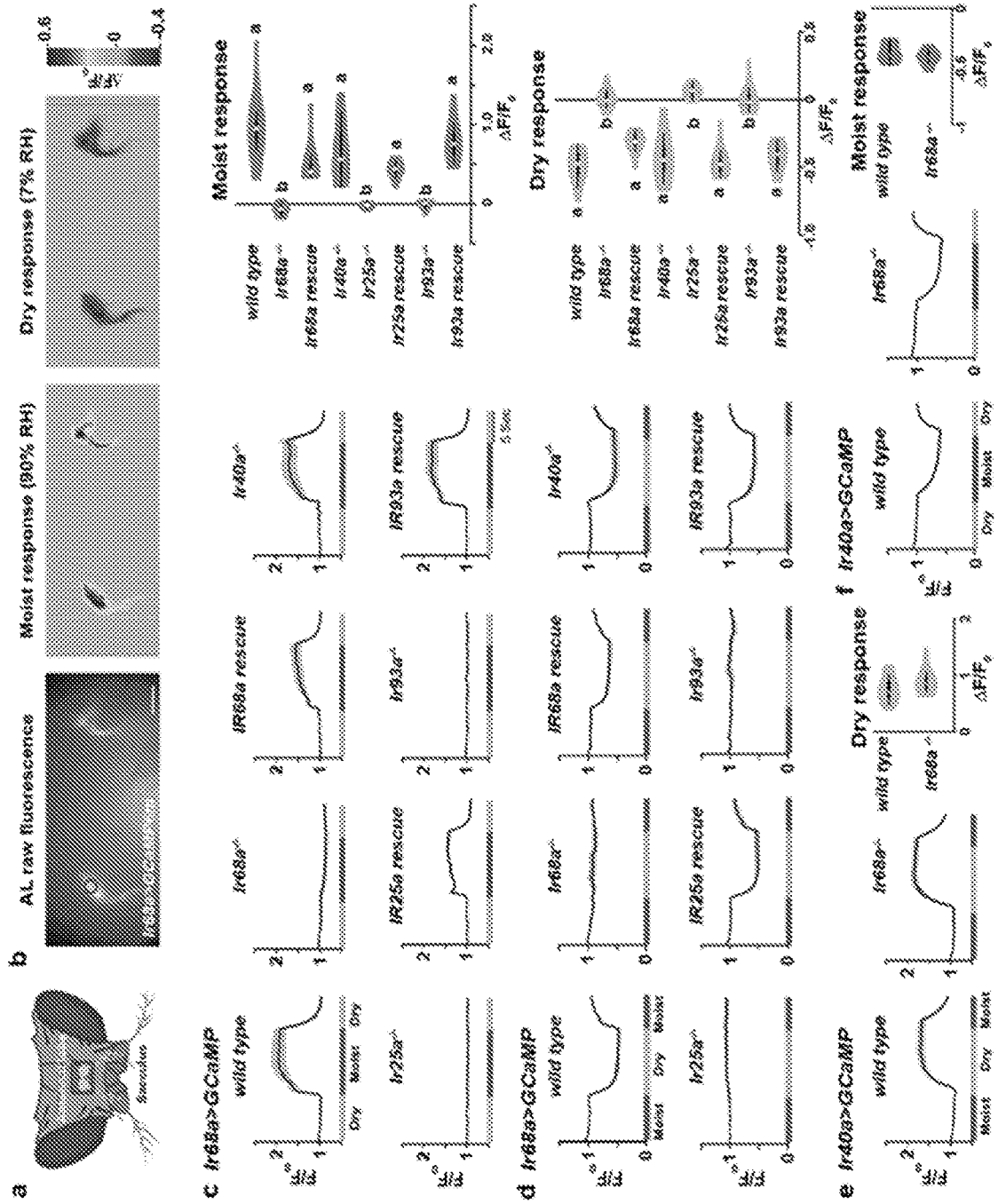

To examine the physiological sensitivity of Ir68a-Gal4-expressing neurons to humidity changes, calcium imaging analyses were performed in their axon termini using GCaMP6m (FIGS. 41A-B). Robust, non-adapting increases in GCaMP fluorescence were observed upon switching from low to high humidity air (7% to 90% relative humidity (RH)), and robust, non-adapting decreases in fluorescence were observed upon switching from high to low humidity air (FIGS. 41B-41D). These humidity-dependent calcium responses were opposite of those of IR40a-expressing dry cells (Enjin, A. et al., 2016, Current Biology, CB 26, 1352-1358. doi: 10.1016/j.cub.2016.03.049), and as described herein, indicating that Ir68a-Gal4 neurons correspond to moist cells.

Example 13: Moist Cell Responses Require IR68a, IR25a and IR93a, but not IR40a

To examine the function of IR68a, Ir68a mutants were employed (FIG. 40). Calcium imaging in this mutant background revealed a complete loss of sensitivity of Ir68a neurons to humidity changes (FIGS. 41C and 41D), which was restored by a wild-type Ir68a transgene, (FIG. 40 and FIGS. 41C and 41D). IR68a was therefore determined to be essential for hygrosensory transduction in moist cells.

IR25a and IR93a are required for hygrosensing by dry cells. Consistent with the expression of these receptors in Ir68a-Gal4 neurons, moist cell responses were also eliminated in Ir25a and Ir93a mutants, and these defects were restored by the corresponding rescue construct (FIGS. 41C and 41D). By contrast, IR40a, which is required for dry cell responses, was dispensable for the responses of moist cells (FIGS. 41C and 41D). Similarly, loss of IR68a had no effect on dry cell responses to humidity changes (FIGS. 41E and 41F). Together these data define two distinct classes of hygrosensory neurons in the sacculus, namely, IR68a-dependent moist cells and IR40a-dependent dry cells.

Example 14: IR68a is Required for Hygrosensory Behavior

Figures 42A, 42B:
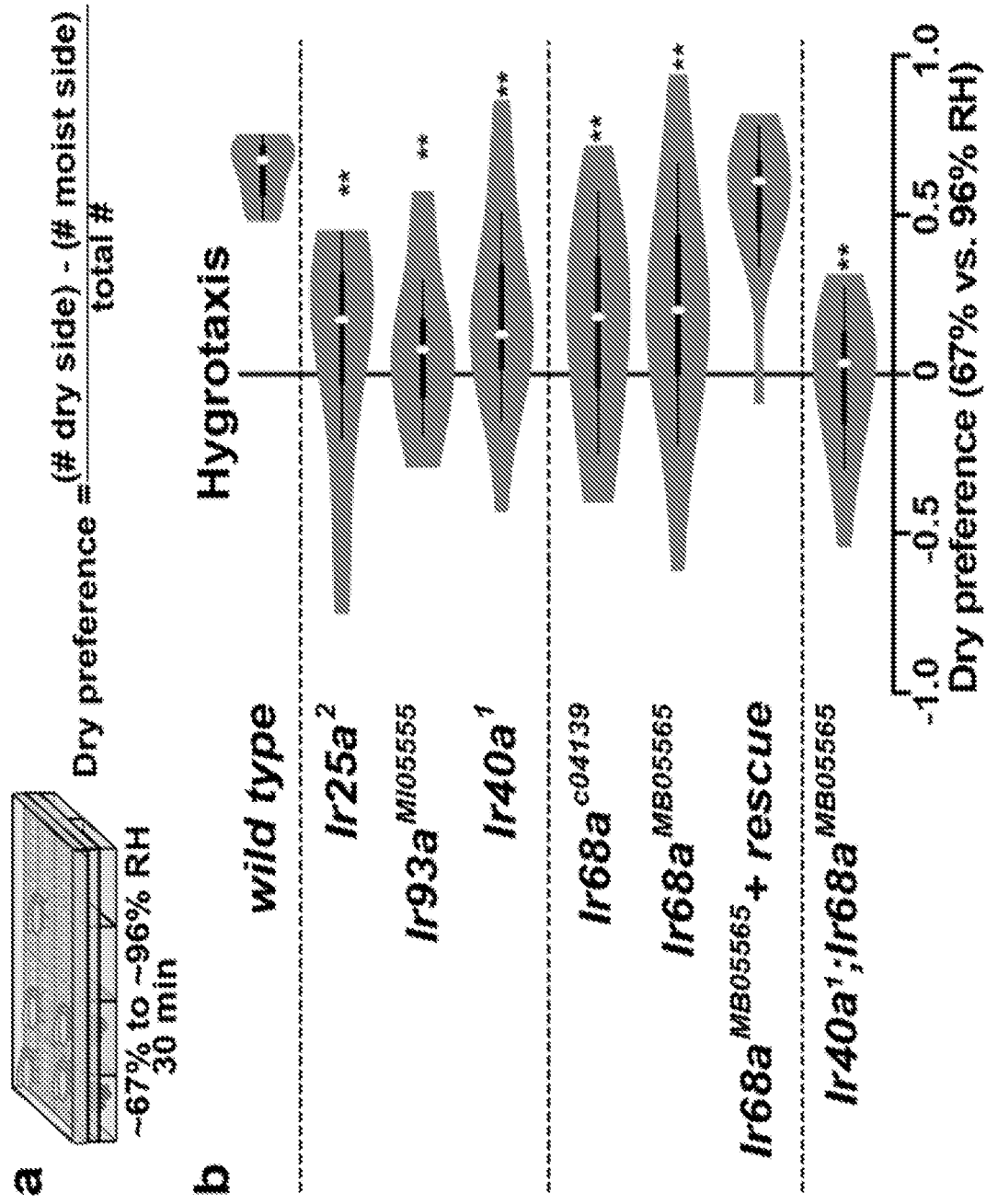
FIGS. 42A and 42B show a schematic and graphic violin plot representation demonstrating that Ir68a is required for hygrosensory behavior.

The role of IR68a in behavioral responses to humidity differences was assessed by quantifying the distribution of flies in a humidity gradient (~67% to ~96% RH) (FIG. 42A). Wild-type flies exhibited robust dry-seeking behavior, and loss of function mutations in Ir25a, Ir93a and Ir40a significantly reduced this response (FIG. 42B). Loss of function mutations in Ir68a caused a similar decrease in dry preference, a defect rescued by the introduction of a wild-type Ir68a transgene (FIG. 42B). Thus, the experiments showed that IR68a was critical for behavioral responses to humidity. Notably, because IR40a-dependent dry cell responses persist in Ir68a mutants (FIGS. 41E and 41F), dry-sensing neurons appeared to be insufficient to guide hygrotaxis, at least in this assay. Similarly, moist cell function alone was insufficient to support normal hygrotaxis, because Ir40a mutants displayed hygrosensory behavioral impairment (FIG. 42B), despite having physiologically-active moist cells (FIGS. 41C and 41D). Flies lacking both Ir68a and Ir40a displayed defects similar to the single mutants (as well as Ir25a or Ir93a mutants in which both moist and dry pathways were eliminated) (FIG. 42B). These results indicate that intact IR40a- and IR68a-dependent pathways are required for wild-type hygrotaxis.

Figures 43A, 43B:
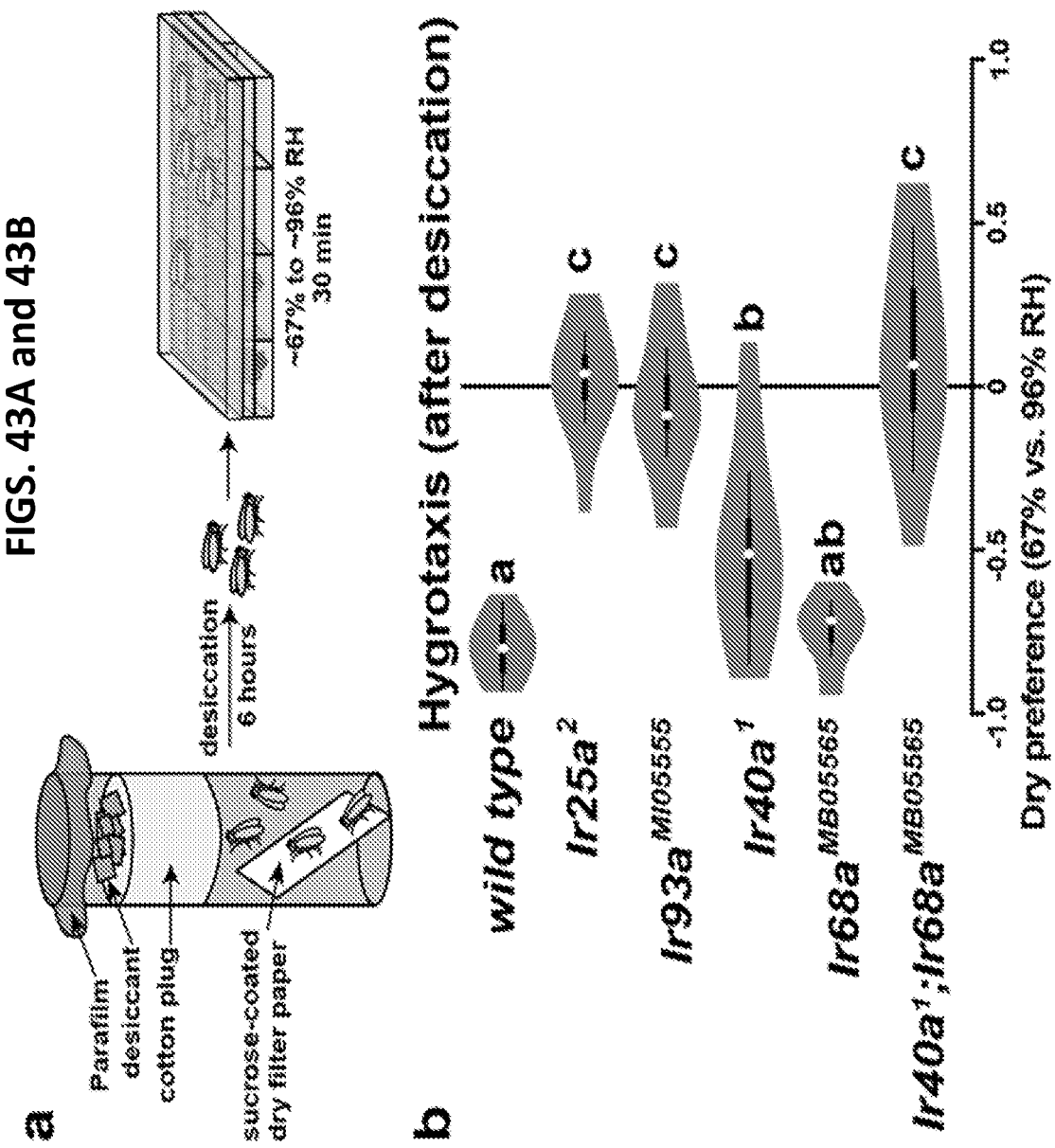
FIGS. 43A and 43B show schematics and a graphic violin plot representation demonstrating that Ir40a and Ir68a each contribute to hygrotaxis in dehydrated flies.

Example 15: Hydration State Alters the Impact of IR-Dependent Moist and Dry Sensing on Behavior The behavioral requirement for both IR40a and IR68a raised the question of whether their combined activity was an obligate feature of the hygrosensory system or whether the function of a single pathway suffices under some conditions. Hydration state dramatically alters insect responses to humidity (Chown, S. L. et al., 2011, *J. Insect Physiol.*, 57:1070-1084), and *Drosophila* prefer significantly moister environments when dehydrated (Perttunen, V. and Erkkila, H., 1952, *Nature*, 169:78). Consistent with those observations, animals previously subjected to desiccation stress became strongly moist-seeking in the assays described in this Example, as reflected in the shift of Dry Preference to negative values (FIGS. 43A and 43B). Null mutations in either Ir25a or Ir93a (which disrupt both dry and moist cell function) abolished this moist preference, indicating that dehydrated flies still rely on IR-dependent hygrosensing (FIG. 43B). By contrast, moist-seeking behavior persisted in dehydrated Ir40a and Ir68a single mutants, although it was slightly reduced in Ir40a mutants (FIG. 43B). However, in Ir40a; Ir68a double mutant animals, moist-seeking was completely abolished (FIG. 43B). Thus, while hydrated flies were dependent on both Ir40a- and Ir68a-dependent signaling, flies experiencing desiccation stress exhibited significant moist-seeking as long as one pathway was operative.

The results of the experiments described in this Example demonstrate a central role for an evolutionarily conserved set of IRs in physiological and behavioral responses to humidity in *Drosophila*. IR25a and IR93a are required for humidity detection by both moist and dry cells, while IR68a and IR40a are specifically required for moist or dry cell function, respectively. Together, these receptors are essential for driving hygrotaxis, as the loss of either IR25a or IR93a, or the combined loss of IR40a and IR68a, completely eliminated responses to humidity in the assays described herein. This work reinforces a model in which the broadly-expressed co-receptors IR25a and IR93a act with more selectively-expressed IRs that determine the specificity for different chemo-, thermo-, or hygrosensory cues (Abuin, L. et al., 2011, *Neuron*, 69:44-60) and as described herein. The mechanism(s) involved in humidity detection by IRs may be investigated through reconstitution of IR-dependent hygrosensory responses in expression systems that permit structure/function analyses.

It is notable that the same IRs mediate hygrotaxis regardless of the hydration state of the insect, even though dehydration switches the valence of behavioral responses in a humidity gradient. These observations suggest that the moist and dry hygrosensory pathways do not simply promote attraction or aversion when activated. An explanation is that the information conveyed by these peripheral neurons is combined in the brain with signals from internal hydration sensors to determine how the animal responds to moisture. Internal osmolarity-sensing neurons that influence water consumption have been identified in *Drosophila* (Jourjine, N. et al., 2016, *Cell*, 166:855-866) and similar classes of internal sensors of water balance are likely to be involved in setting the preference for moist-seeking versus dry-seeking. Central mapping of the pathways that influence water-seeking behaviors may reveal how the animal monitors and adjusts its hydration state to maintain an optimal concentration of this essential biological solvent.

Example 16: Materials and Methods Used in the Above-Described Experimental Studies and Results (Examples 11-15)

Fly strains: The fly strains, namely, Ir25a$^2$ (Benton et al., 2009, Cell, 136, 149-162), UAS-Ir25a (Abuin et al., 2011, Neuron, 69, 44-60), Ir8a$^1$ (Abuin et al., 2011, Ibid,), Ir21a$^{123}$ (Ni et al., 2016, eLife, 5, 2016, .doi.org/10.7554/eLife.13254), Ir76b$^2$ (Zhang et al., 2013, *Science*, 340, 1334-1338), R11F02-Gal4 (Klein et al., 2015, *PNAS*, 112, E220-E229), Ir40a-Gal4 (Silbering et al., 2011, *Journal of Neuroscience*, 31, 13357-13375), Ir40a$^1$ (Silbering et al., 2016, *Nature*, 534, E5-E7), UAS-Ir40a (Silbering et al., 2016, Ibid.), Ir93a$^{MI05555}$ (Venken et al., 2011, *Nature Methods*, 8, 737-743), UAS-GCaMP6m (P[20XUAS-IVS- GCaMP6m]attp2 and P[20XUAS-IVS-GCaMP6m]attp2attP40 (Chen et al., 2013, *Nature*, 499, 295-300), UAS-Arclight (Cao et al., 2013, *Cell*, 154, 904-913) UAS-GFP (P[10XUAS-IVS-Syn21-GFP-p10]attP2 (Pfeiffer et al., 2012, *PNAS*, 109, 6626-6631), nan[36a] (Gong et al., 2004, *Journal of Neuroscience*, 24, 9059-9066), wtrw[2] (Kwon et al., 2010, *Journal of Neuroscience*, 30, 10465-10471) and y[1] P(act5c-cas9, w) M(3xP3-RFP.attP)ZH-2A w* (Port et al., 2014, PNAS, 111, E2967-E2976) were as previously described.

Ir40a[134] (FIG. 36A) and Ir93a[122] (FIG. 32A) were generated by transgene-based CRISPR/Cas9-mediated genome engineering (Port et al., 2014, Ibid), using either an Ir40a-targeting gRNA (5'-GCCCGTTTAAGCAAGACATC; SEQ ID NO: 72) or an Ir93a-targeting gRNA (5'-TCAGCAGAATGATGCCCATT; SEQ ID NO: 73) expressed under U6-3 promoter control (dU6-3:gRNA) in the presence of act-cas9. UAS-mCherry:Ir93a contains codons 29-869 of the Ir93a ORF (corresponding to Ir93a-PD [flybase.org], without the sequence encoding the predicted endogenous signal peptide), which were PCR amplified from Oregon R antennal cDNA and subcloned into pUAST-mCherry attB (Abuin et al., 2011, *Neuron*, 69, 44-60) (which encodes the calreticulin signal sequence upstream of the mCherry ORF). This construct was integrated into VK00027 by phiC31-mediated transgenesis (Genetic Services, Inc.). Sensory Behavior: Thermotaxis of early second instar larvae was assessed over a 15 min period on a temperature gradient extending from 13.5 to 21.5° C. over 22 cm (~0.36° C./cm) as described (Klein et al., 2015, *PNAS*, 112, E220-E229). As thermotaxis data were normally distributed (as assessed by Shapiro-Wilk test), statistical comparisons were performed by Tukey HSD test, which corrects for multiple comparisons.

To assay hygrosensory behavior, 8 well rectangular dishes (12.8×8.55×1.5 cm; ThermoFisher #267060) were modified to serve as humidity preference chambers. The lids of two 8 well plates were used. A heated razor blade was used to cut out the middle of one lid, and a nylon mesh was glued into place around the edges, providing a surface for the animals to walk on which separated them from contact with any liquid. A soldering iron was used to melt a small hole in a second culture plate lid, which could then be placed over the screen, creating a chamber ~0.7 cm in height in which the flies could move freely. To monitor the gradients formed, an additional chamber was constructed with four holes equally spaced along its length to allow the insertion of humidity sensors (Sensirion EK-H4 evaluation kit) for monitoring the humidity and temperature.

Prior to the start of each experiment, 4 wells on one side of the culture dish were filled with purified water, while the opposite 4 were filled with ~4 ml water and sufficient ammonium nitrate to obtain a saturated solution (~3 g). The gradient was assembled with the screen and lid piece, and the whole apparatus wrapped in food service film to avoid any transfer of air between the inside and outside of the device. Gradients were transferred to an environmental room that maintained at constant external temperature and humidity (25° C. and 70% RH). Ammonium nitrate gradients were permitted to equilibrate for approximately 1 hr and were stable over many hours. For the water and air only gradients, the air only side humidified over time. These gradients were incubated for 25 min prior to use to allow the temperature to equilibrate; the humidity of the dry side typically rose by ~2% RH during the 30 min assay (values shown are at the 30 min time point). A small hole was poked through the food service film covering the device to allow animals to be transferred to the gradient. This hole was sealed using transparent scotch tape once the animals were inside. Experiments used 1-4 day old adult flies that had been sorted under light $CO_2$ anesthesia into groups of 30 (15 male and 15 female) animals 24 hr before testing, and transferred to fresh tubes. Flies were allowed 30 min to settle on the gradient, at which point a photograph was taken of their position, and the number of animals on each side counted, allowing calculation of a dry preference index as follows:

$$\text{Dry Preference} = \frac{\text{\# animals of dry side} - \text{\# animals on moist side}}{\text{total number of animals}}$$

As moisture preference data did not conform to normal distributions (as assessed by Shapiro-Wilk test, p<0.01), statistical comparisons to wild-type control were performed by Steel test, a non-parametric test that corrects for multiple comparisons, using JMP11 (SAS).

Calcium and Arclight imaging: Calcium and Arclight imaging of larval thermosensors was performed as previously described (Klein et al., 2015, Ibid.). Pseudocolor images were created using the 16-colors lookup table in ImageJ 1.43r. Adult antennal lobe calcium imaging was performed as described for olfactory imaging (Silbering et al., 2012, *Journal of Visualized Experiments*, 61), with slight modifications to sample preparation and stimulation. Briefly, 3-7 day old flies were fixed to a Plexiglas stage using UV-glue (Al Tetric Evoflow, Ivoclar Vivadent), the antennae were pulled forward and a small opening was made in the head capsule to allow visual access to the antennal lobes. For the stimulation compressed air from a tank was passed through activated charcoal and then either through an empty gas washing bottle or a gas washing bottle filled with distilled water producing either a dry airstream of ~7% RH or a humid airstream of ~90% RH. A computer controlled solenoid valve (The Lee Company, Westbrook, Conn.) was used to switch the airflow between the two gas washing bottles. The flow was kept constant at 1l/min with a parallel arrangement of two 500 ml/min mass flow controllers (PKM SA, www.pkmsa.ch) placed before the gas washing bottles. Activating the solenoid valve resulted in a complete reversal of RH from low to high or high to low within less than 10 s. For each animal tested, both high to low and low to high RH transitions were applied in random order. Following humidity stimulation, a final pulse of 10% ammonia was applied as a control to confirm cellular activity (Silbering et al., 2016, *Nature*, 534, E5-E7) (animals showing no response to this positive control were excluded from the analysis). Data were processed using Stackreg (ImageJ) (Thevenaz et al., 1998, *IEEE Transactions on Image Processing*, 7, 27-41) to correct for movement artifacts (animals with movement artifacts that could not be corrected with Stackreg were excluded from the analysis) and custom scripts in Matlab and R as previously described (Silbering et al., 2011, *Journal of Neuroscience*, 31, 13357-13375). As quantified imaging data did not conform to normal distributions (as assessed by Shapiro-Wilk test, p<0.01), statistical comparisons were performed by Steel-Dwass test, a non-parametric test that corrects for multiple comparisons, using JMP11 (SAS).

Immunohistochemistry: Larval immunostaining was performed as described (Kang et al., 2012, *Nature*, 481, 76-80). Immunofluorescence on antennal cryosections or whole-mount antennae was performed essentially as described (Saina and Benton, 2013, *Methods in Molecular Biology*, 1003, 211-228), except that whole-mount antennae were placed in Vectashield immediately after the final washes without dehydration. The following antibodies were used: rabbit anti-IR25a (1:1000; Benton et al., 2009, *Cell*, 136, 149-162), guinea pig anti-IR40a (1:200), (Silbering et al., 2016, *Nature*, 534, E5-E7), rabbit anti-IR93a (peptide immunogen CGEFWYRRFRASRKRRQFTN (SEQ ID NO: 74), Proteintech, Rosemont, Ill., USA, 1:4000 for tissue sections and 1:500 for whole-mount tissue), guinea pig anti-IR25a (peptide immunogen SKAALRPRFNQYPATFKPRF (SEQ ID NO: 75), Proteintech, Rosemont, Ill., USA, 1:200), mouse anti-GFP (1:200; Roche), goat anti-rabbit Cy3 (1:100 larva, 1:1000 sections; Jackson ImmunoResearch), goat anti-rabbit Alexa488 (1:100 antenna whole-mount, 1:1000 antennal sections, A11034 Invitrogen AG), goat anti-guinea pig (1:1000, A11073 Invitrogen AG) and donkey anti-mouse FITC (1:100; Jackson ImmunoResearch).

RT-PCR: cDNA for each genotype was purified from 20 fly heads (RETROscript, Ambion) for RT-PCR. Primers used:

```
Ir25a forward, 5'-TAGCAGTCAGCGGGACAATG;    (SEQ ID NO: 76)

Ir25a reverse, 5'-GAGTGGATTGCGTGACGAGA;    (SEQ ID NO: 77)

Ir40a forward, 5'-GGCGAGGACAAGGCAGTA;     (SEQ ID NO: 78)

Ir40a reverse, 5'-CGGCAGCGGTCATCTTATCT;    (SEQ ID NO: 79)

Ir93a forward, 5'-TGCCAAGGTCCAGCAGATTC;    (SEQ ID NO: 80)

Ir93a reverse, 5'-AACATGTTCAGGGTCTCGGC.    (SEQ ID NO: 81)

RpL32 forward, 5'-GCTAAGCTGTCGCACAAATG;   (SEQ ID NO: 82)

RpL32 reverse 5'-GTTCGATCCGTAACCCGATGT.   (SEQ ID NO: 83)
```

*Drosophila* strains and molecular biology: *Drosophila* strains Ir25a$^2$ (Benton, R. et al., 2009, *Cell*, 136:149-162); Ir25aBAC (Chen, C. et al., 2015, *Nature*, 527, 516-520); Ir40a-Gal4 (Silbering, A. F. et al., 2011, *J. Neurosci*, 31:13357-13375), Ir40a-LexA (Silbering, A. J. et al., 2016, *Nature*, 534, E5-7, doi: 10.1038/nature18321), Ir40a$^1$ (Silbering et al., 2016, Ibid), Ir93a$^{MI05555}$ and UAS-Ir93a as described above, UAS-GCaMP6m (P[20XUAS-IVS-GCaMP6m]attp2 and P[20XUAS-IVS-GCaMP6m] attp2attP40 (Chen, T. W. et al., 2013, *Nature*, 499, 295-300. doi: 10.1038/nature12354), and UAS-myr: GFP (P[10UAS-IVS-myr::GFP]attp1) (Pfeiffer, B. D. et al., 2012, *Proc. Natl. Acad. Sci. USA*, 109, 6626-6631. doi: 10.1073/pnas.1204520109) were as previously described. LexAop-RFP (P[lexA-2xmRFP.nls]2) was obtained from the Bloomington *Drosophila* Stock Center (stock #29956).

Ir68a-Gal4 was generated by PCR amplification of a 1040 bp genomic sequence directly upstream of the Ir68a translation start site (using 5'-cggccgcCACGTCGTCGTCCG-CATTAC (SEQ ID NO: 84) and 5'-gcggccgcCCTTTCGCCGCCAAACGCAA (SEQ ID NO: 85)), which was cloned into pGEM-T Easy (Promega), sequenced, and subcloned as a NotI fragment into pGal4 attB (Croset, V. et al., 2010, *PLoS Genetics*, 6, e100164. doi:10.1371/journal.pgen. 1001064); this construct was integrated into attP2 (Markstein, M. et al., 2008, *Nat. Genet.*, 40:476-483). The Ir68a$^+$ rescue transgene contains Ir68a genomic sequence from −1040 bp to +4751 bp (+1 denotes Ir68a translation start site), which was PCR amplified using 5'-cgttacacgcatgcCACGTCGTCGTCCGCATTACAATATC (SEQ ID NO: 86) and 5'-acggaccactctagaT-GAAGTGTGGGTGTTTCTCCAACCA (SEQ ID NO: 87). This PCR product was digested with SbhI and XbaI and used to replace the UAS-hsp70 promoter sequences of pUAST-attB, which had been excised by SbhI and XbaI digest. This Ir68a$^+$-attB construct was integrated into attP40 (Markstein et al., 2008, Ibid).

Immunohistochemistry Whole mount antennal stainings (FIG. 39B) were performed as described herein. Immunostaining of antennal cryosections (FIGS. 39C-E) was performed largely as described (Saina and Benton, 2013, In: *Olfactory Receptors: Methods and Protocols*, C. Crasto, Ed., New York, Humana Press, pp. 211-228). Male and female 1-3 week old flies were mounted in OCT (Sakura #4583); 12 µm or 16 µm frozen sections were cut and then fixed in 4% paraformaldehyde at room temperature for 7-10 minutes. For brains (FIGS. 39F-I), female flies were freshly dissected in 1×PBS before either ~2 min of fixation and immediate mounting, or 5 min of fixation and staining in primary antibody. All samples were mounted in Vectashield (Vector Labs) for confocal microscopy (Leica SP5 or Zeiss LSM710). The following antibodies were used: FIG. 39B: chicken anti-GFP (1:1000, Abcam 13970) and goat anti-Chicken Alexa488 (1:1000, Abcam 150169); FIG. 39E: mouse anti-GFP (1:1000, Invitrogen A11120), rabbit anti-IR93a (1:3000), as described above, goat anti-mouse Alexa488 (1:1000, A11029 Invitrogen), goat anti-rabbit Cy3 (1:1000, 111-165-144 0 Milan Analytica); FIGS. 39C, 39D, 39F and 39G: chicken anti-GFP (1:200 brains or 1:1000 cryosections, Ayes Labs GFP-1020), rabbit anti-DsRed (1:200 brains or 1:1000 cryosections, Clontech #632496), rabbit anti-IR25a (1:100, (Benton, R. et al., 2009, *Cell* 136:149-162), goat anti-chicken Alexa488 (1:200, Life Technologies A-11039), goat anti-rabbit Alexa594 (1:200, Life Technologies A-11037), mouse anti-nc82 (1:500, Developmental Studies Hybridoma Bank) and goat anti-mouse Cy5 (1:200, Jackson Labs #115-176-0030).

Calcium imaging: Calcium imaging was performed as described above. Data were processed largely as described hereinabove, but using a different custom Matlab script. For analysis, the average pixel intensity of a nearby background region (BGR) was subtracted from the average pixel intensity of a polygon drawn around the labeled glomerulus (ROI). The first twenty frames (5 sec) were used to define baseline fluorescence ($F_0$). $F/F_0$ was calculated using $F_i/F_0$ (frame i)=$(ROI_i-BGR_i)/F_0$. As quantified imaging data did not conform to normal distribution (assessed by Shapiro-Wilk test, $p<0.1$), statistical comparisons were performed by Steel-Dwass test using JMP11 (SAS). Samples unresponsive to humidity change were subsequently depolarized by bath application of 0.7 mM KCl to confirm their physiological integrity; animals unresponsive to this positive control were excluded from analysis. Animals were also excluded if movement artifacts could not be corrected using Stackreg in ImageJ (Schneider, C. A. et al., 2012, *Nature Methods*, 9:671-675).

Behavior: Hygrosensory behavior in the insect animals was assayed as described hereinabove. Desiccation prior to analysis was performed using a modification of (Lin, S. et al., 2014, *Nature Neuroscience*, 17:1536-1542). Flies were sorted and placed in tubes containing a strip of filter paper soaked in 3% sucrose and let to dry. The vial stopper was pushed down below the vial lip, ~0.5 g Drierite spread over it, and Parafilm was placed over the top to seal the vial. Vials were kept in an incubator (25° C., 70% RH) for 6 hr before hygrosensory behavior was assessed as described above. Humidity preference data in FIGS. 42A-B did not conform to normal distributions (assessed by Shapiro-Wilk test, p<0.01) and were analyzed by Steel with control test using JMP11 (SAS). Humidity preference data in FIGS. 43A-43B did conform to normal distributions and were analyzed using Tukey HSD using JMP11 (SAS).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

---

What is claimed is:

1. A method of modulating survival, host-seeking, and/or reproductive capability of an invertebrate organism, or hygrosensing and/or thermosensing in an invertebrate organism, the method comprising administering to the invertebrate organism an effective amount of an agent that reduces the expression of a polynucleotide encoding an ionotropic receptor, wherein the ionotropic receptor comprises ionotropic receptor 68a (Ir68a) and/or ionotropic receptor 21a (Ir21a), wherein the agent is an inhibitory polynucleotide that is an siRNA or antisense RNA.

2. The method of claim 1, wherein the invertebrate organism is an insect.

3. The method of claim 2, wherein the invertebrate organism is a disease vector.

4. The method of claim 2, wherein the insect is a mosquito.

5. The method of claim 1, wherein the invertebrate organism is *Drosophila melanogaster, Aedes aegypti, Culex quinquefasciatus, Anopheles gambiae, Bombyx mori, Tribolium castaneum, Apis mellifera, Nasonia vitripennis, Acyrthosiphon pisum, Pediculus humanus, Daphnia pulex, Caenorhabditis elegans, Capitella capitate, Aplysia californica,* or *Lottia gigantea.*

6. The method of claim 5, wherein the invertebrate organism is *Anopheles gambiae* or *Aedes aegypti.*

7. The method of claim 1, wherein the ionotropic receptor comprises IR68a and further comprises ionotropic receptor 25a (Ir25a) and/or ionotropic receptor 93a (Ir93a).

8. The method of claim 1, wherein the ionotropic receptor comprises IR68a and further comprises ionotropic receptor 40a (IR40a).

* * * * *

SEQUENCE LISTING

<160> NUMBER OF SEQ ID NOS: 87

<210> SEQ ID NO 1
<211> LENGTH: 947
<212> TYPE: PRT
<213> ORGANISM: Drosophila melanogaster

<400> SEQUENCE: 1

```
Met Ile Leu Met Asn Pro Lys Thr Ser Lys Ile Leu Trp Leu Leu Gly
1               5                   10                  15

Phe Leu Ser Leu Leu Ser Ser Phe Ser Leu Glu Ile Ala Ala Gln Thr
            20                  25                  30

Thr Gln Asn Ile Asn Val Leu Phe Ile Asn Glu Val Asp Asn Glu Pro
        35                  40                  45

Ala Ala Lys Ala Val Glu Val Val Leu Thr Tyr Leu Lys Lys Asn Ile
    50                  55                  60

Arg Tyr Gly Leu Ser Val Gln Leu Asp Ser Ile Glu Ala Asn Lys Ser
65                  70                  75                  80

Asp Ala Lys Val Leu Leu Glu Ala Ile Cys Asn Lys Tyr Ala Thr Ser
                85                  90                  95

Ile Glu Lys Lys Gln Thr Pro His Leu Ile Leu Asp Thr Thr Lys Ser
            100                 105                 110

Gly Ile Ala Ser Glu Thr Val Lys Ser Phe Thr Gln Ala Leu Gly Leu
        115                 120                 125

Pro Thr Ile Ser Ala Ser Tyr Gly Gln Gln Gly Asp Leu Arg Gln Trp
    130                 135                 140

Arg Asp Leu Asp Glu Ala Lys Gln Lys Tyr Leu Leu Gln Val Met Pro
145                 150                 155                 160

Pro Ala Asp Ile Ile Pro Glu Ala Ile Arg Ser Ile Val Ile His Met
                165                 170                 175

Asn Ile Thr Asn Ala Ala Ile Leu Tyr Asp Asp Ser Phe Val Met Asp
            180                 185                 190

His Lys Tyr Lys Ser Leu Leu Gln Asn Ile Gln Thr Arg His Val Ile
        195                 200                 205

Thr Ala Ile Ala Lys Asp Gly Lys Arg Glu Arg Glu Glu Gln Ile Glu
    210                 215                 220

Lys Leu Arg Asn Leu Asp Ile Asn Asn Phe Phe Ile Leu Gly Thr Leu
225                 230                 235                 240

Gln Ser Ile Arg Met Val Leu Glu Ser Val Lys Pro Ala Tyr Phe Glu
                245                 250                 255

Arg Asn Phe Ala Trp His Ala Ile Thr Gln Asn Glu Gly Glu Ile Ser
            260                 265                 270
```

```
Ser Gln Arg Asp Asn Ala Thr Ile Met Phe Met Lys Pro Met Ala Tyr
        275                 280                 285

Thr Gln Tyr Arg Asp Arg Leu Gly Leu Leu Arg Thr Thr Tyr Asn Leu
        290                 295                 300

Asn Glu Glu Pro Gln Leu Ser Ser Ala Phe Tyr Phe Asp Leu Ala Leu
305                 310                 315                 320

Arg Ser Phe Leu Thr Ile Lys Glu Met Leu Gln Ser Gly Ala Trp Pro
                325                 330                 335

Lys Asp Met Glu Tyr Leu Asn Cys Asp Asp Phe Gln Gly Gly Asn Thr
                340                 345                 350

Pro Gln Arg Asn Leu Asp Leu Arg Asp Tyr Phe Thr Lys Ile Thr Glu
                355                 360                 365

Pro Thr Ser Tyr Gly Thr Phe Asp Leu Val Thr Gln Ser Thr Gln Pro
        370                 375                 380

Phe Asn Gly His Ser Phe Met Lys Phe Glu Met Asp Ile Asn Val Leu
385                 390                 395                 400

Gln Ile Arg Gly Gly Ser Ser Val Asn Ser Lys Ser Ile Gly Lys Trp
                405                 410                 415

Ile Ser Gly Leu Asn Ser Glu Leu Ile Val Lys Asp Glu Glu Gln Met
                420                 425                 430

Lys Asn Leu Thr Ala Asp Thr Val Tyr Arg Ile Phe Thr Val Val Gln
                435                 440                 445

Ala Pro Phe Ile Met Arg Asp Glu Thr Ala Pro Lys Gly Tyr Lys Gly
        450                 455                 460

Tyr Cys Ile Asp Leu Ile Asn Glu Ile Ala Ala Ile Val His Phe Asp
465                 470                 475                 480

Tyr Thr Ile Gln Glu Val Glu Asp Gly Lys Phe Gly Asn Met Asp Glu
                485                 490                 495

Asn Gly Gln Trp Asn Gly Ile Val Lys Lys Leu Met Asp Lys Gln Ala
                500                 505                 510

Asp Ile Gly Leu Gly Ser Met Ser Val Met Ala Glu Arg Glu Ile Val
        515                 520                 525

Ile Asp Phe Thr Val Pro Tyr Tyr Asp Leu Val Gly Ile Thr Ile Met
        530                 535                 540

Met Gln Arg Pro Ser Ser Pro Ser Ser Leu Phe Lys Phe Leu Thr Val
545                 550                 555                 560

Leu Glu Thr Asn Val Trp Leu Cys Ile Leu Ala Ala Tyr Phe Phe Thr
                565                 570                 575

Ser Phe Leu Met Trp Ile Phe Asp Arg Trp Ser Pro Tyr Ser Tyr Gln
                580                 585                 590

Asn Asn Arg Glu Lys Tyr Lys Asp Asp Glu Glu Lys Arg Glu Phe Asn
                595                 600                 605

Leu Lys Glu Cys Leu Trp Phe Cys Met Thr Ser Leu Thr Pro Gln Gly
        610                 615                 620

Gly Gly Glu Ala Pro Lys Asn Leu Ser Gly Arg Leu Val Ala Ala Thr
625                 630                 635                 640

Trp Trp Leu Phe Gly Phe Ile Ile Ile Ala Ser Tyr Thr Ala Asn Leu
                645                 650                 655

Ala Ala Phe Leu Thr Val Ser Arg Leu Asp Thr Pro Val Glu Ser Leu
                660                 665                 670

Asp Asp Leu Ala Lys Gln Tyr Lys Ile Leu Tyr Ala Pro Leu Asn Gly
                675                 680                 685
```

```
Ser Ser Ala Met Thr Tyr Phe Glu Arg Met Ser Asn Ile Glu Gln Met
    690                 695                 700

Phe Tyr Glu Ile Trp Lys Asp Leu Ser Leu Asn Asp Ser Leu Thr Ala
705                 710                 715                 720

Val Glu Arg Ser Lys Leu Ala Val Trp Asp Tyr Pro Val Ser Asp Lys
                725                 730                 735

Tyr Thr Lys Met Trp Gln Ala Met Gln Glu Ala Lys Leu Pro Ala Thr
                740                 745                 750

Leu Asp Glu Ala Val Ala Arg Val Arg Asn Ser Thr Ala Ala Thr Gly
            755                 760                 765

Phe Ala Phe Leu Gly Asp Ala Thr Asp Ile Arg Tyr Leu Gln Leu Thr
770                 775                 780

Asn Cys Asp Leu Gln Val Val Gly Glu Glu Phe Ser Arg Lys Pro Tyr
785                 790                 795                 800

Ala Ile Ala Val Gln Gln Gly Ser His Leu Lys Asp Gln Phe Asn Asn
                805                 810                 815

Ala Ile Leu Thr Leu Leu Asn Lys Arg Gln Leu Glu Lys Leu Lys Glu
                820                 825                 830

Lys Trp Trp Lys Asn Asp Glu Ala Leu Ala Lys Cys Asp Lys Pro Glu
            835                 840                 845

Asp Gln Ser Asp Gly Ile Ser Ile Gln Asn Ile Gly Gly Val Phe Ile
850                 855                 860

Val Ile Phe Val Gly Ile Gly Met Ala Cys Ile Thr Leu Val Phe Glu
865                 870                 875                 880

Tyr Trp Trp Tyr Arg Tyr Arg Lys Asn Pro Arg Ile Ile Asp Val Ala
                885                 890                 895

Glu Ala Asn Ala Glu Arg Ser Asn Ala Ala Asp His Pro Gly Lys Leu
                900                 905                 910

Val Asp Gly Val Ile Leu Gly His Ser Gly Glu Lys Phe Glu Lys Ser
            915                 920                 925

Lys Ala Ala Leu Arg Pro Arg Phe Asn Gln Tyr Pro Ala Thr Phe Lys
930                 935                 940

Pro Arg Phe
945

<210> SEQ ID NO 2
<211> LENGTH: 934
<212> TYPE: PRT
<213> ORGANISM: Drosophila melanogaster

<400> SEQUENCE: 2

Met Gly Ser Arg Leu Asp Trp Gly Val Ala Asp Val Ala Leu Trp Ala
1               5                   10                  15

Ile Ala Asp Gln Ile Asp Tyr His Gln Val Phe Ile Asn Glu Val Asp
                20                  25                  30

Asn Glu Pro Ala Ala Lys Ala Val Glu Val Val Leu Thr Tyr Leu Lys
            35                  40                  45

Lys Asn Ile Arg Tyr Gly Leu Ser Val Gln Leu Asp Ser Ile Glu Ala
        50                  55                  60

Asn Lys Ser Asp Ala Lys Val Leu Leu Glu Ala Ile Cys Asn Lys Tyr
65                  70                  75                  80

Ala Thr Ser Ile Glu Lys Lys Gln Thr Pro His Leu Ile Leu Asp Thr
                85                  90                  95

Thr Lys Ser Gly Ile Ala Ser Glu Thr Val Lys Ser Phe Thr Gln Ala
            100                 105                 110
```

```
Leu Gly Leu Pro Thr Ile Ser Ala Ser Tyr Gly Gln Gln Gly Asp Leu
            115                 120                 125

Arg Gln Trp Arg Asp Leu Asp Glu Ala Lys Gln Lys Tyr Leu Leu Gln
130                 135                 140

Val Met Pro Pro Ala Asp Ile Ile Pro Glu Ala Ile Arg Ser Ile Val
145                 150                 155                 160

Ile His Met Asn Ile Thr Asn Ala Ala Ile Leu Tyr Asp Asp Ser Phe
                165                 170                 175

Val Met Asp His Lys Tyr Lys Ser Leu Leu Gln Asn Ile Gln Thr Arg
            180                 185                 190

His Val Ile Thr Ala Ile Ala Lys Asp Gly Lys Arg Glu Arg Glu Glu
        195                 200                 205

Gln Ile Glu Lys Leu Arg Asn Leu Asp Ile Asn Asn Phe Phe Ile Leu
    210                 215                 220

Gly Thr Leu Gln Ser Ile Arg Met Val Leu Glu Ser Val Lys Pro Ala
225                 230                 235                 240

Tyr Phe Glu Arg Asn Phe Ala Trp His Ala Ile Thr Gln Asn Glu Gly
                245                 250                 255

Glu Ile Ser Ser Gln Arg Asp Asn Ala Thr Ile Met Phe Met Lys Pro
            260                 265                 270

Met Ala Tyr Thr Gln Tyr Arg Asp Arg Leu Gly Leu Leu Arg Thr Thr
        275                 280                 285

Tyr Asn Leu Asn Glu Glu Pro Gln Leu Ser Ser Ala Phe Tyr Phe Asp
    290                 295                 300

Leu Ala Leu Arg Ser Phe Leu Thr Ile Lys Glu Met Leu Gln Ser Gly
305                 310                 315                 320

Ala Trp Pro Lys Asp Met Glu Tyr Leu Asn Cys Asp Asp Phe Gln Gly
                325                 330                 335

Gly Asn Thr Pro Gln Arg Asn Leu Asp Leu Arg Asp Tyr Phe Thr Lys
            340                 345                 350

Ile Thr Glu Pro Thr Ser Tyr Gly Thr Phe Asp Leu Val Thr Gln Ser
        355                 360                 365

Thr Gln Pro Phe Asn Gly His Ser Phe Met Lys Phe Glu Met Asp Ile
    370                 375                 380

Asn Val Leu Gln Ile Arg Gly Gly Ser Ser Val Asn Ser Lys Ser Ile
385                 390                 395                 400

Gly Lys Trp Ile Ser Gly Leu Asn Ser Glu Leu Ile Val Lys Asp Glu
                405                 410                 415

Glu Gln Met Lys Asn Leu Thr Ala Asp Thr Val Tyr Arg Ile Phe Thr
            420                 425                 430

Val Val Gln Ala Pro Phe Ile Met Arg Asp Glu Thr Ala Pro Lys Gly
        435                 440                 445

Tyr Lys Gly Tyr Cys Ile Asp Leu Ile Asn Glu Ile Ala Ala Ile Val
    450                 455                 460

His Phe Asp Tyr Thr Ile Gln Glu Val Glu Asp Gly Lys Phe Gly Asn
465                 470                 475                 480

Met Asp Glu Asn Gly Gln Trp Asn Gly Ile Val Lys Lys Leu Met Asp
                485                 490                 495

Lys Gln Ala Asp Ile Gly Leu Gly Ser Met Ser Val Met Ala Glu Arg
            500                 505                 510

Glu Ile Val Ile Asp Phe Thr Val Pro Tyr Tyr Asp Leu Val Gly Ile
        515                 520                 525
```

```
Thr Ile Met Met Gln Arg Pro Ser Ser Pro Ser Ser Leu Phe Lys Phe
530                 535                 540

Leu Thr Val Leu Glu Thr Asn Val Trp Leu Cys Ile Leu Ala Ala Tyr
545                 550                 555                 560

Phe Phe Thr Ser Phe Leu Met Trp Ile Phe Asp Arg Trp Ser Pro Tyr
            565                 570                 575

Ser Tyr Gln Asn Asn Arg Glu Lys Tyr Lys Asp Asp Glu Glu Lys Arg
        580                 585                 590

Glu Phe Asn Leu Lys Glu Cys Leu Trp Phe Cys Met Thr Ser Leu Thr
    595                 600                 605

Pro Gln Gly Gly Gly Glu Ala Pro Lys Asn Leu Ser Gly Arg Leu Val
610                 615                 620

Ala Ala Thr Trp Trp Leu Phe Gly Phe Ile Ile Ala Ser Tyr Thr
625                 630                 635                 640

Ala Asn Leu Ala Ala Phe Leu Thr Val Ser Arg Leu Asp Thr Pro Val
            645                 650                 655

Glu Ser Leu Asp Asp Leu Ala Lys Gln Tyr Lys Ile Leu Tyr Ala Pro
            660                 665                 670

Leu Asn Gly Ser Ser Ala Met Thr Tyr Phe Glu Arg Met Ser Asn Ile
        675                 680                 685

Glu Gln Met Phe Tyr Glu Ile Trp Lys Asp Leu Ser Leu Asn Asp Ser
690                 695                 700

Leu Thr Ala Val Glu Arg Ser Lys Leu Ala Val Trp Asp Tyr Pro Val
705                 710                 715                 720

Ser Asp Lys Tyr Thr Lys Met Trp Gln Ala Met Gln Glu Ala Lys Leu
            725                 730                 735

Pro Ala Thr Leu Asp Glu Ala Val Ala Arg Val Arg Asn Ser Thr Ala
            740                 745                 750

Ala Thr Gly Phe Ala Phe Leu Gly Asp Ala Thr Asp Ile Arg Tyr Leu
        755                 760                 765

Gln Leu Thr Asn Cys Asp Leu Gln Val Val Gly Glu Glu Phe Ser Arg
770                 775                 780

Lys Pro Tyr Ala Ile Ala Val Gln Gln Gly Ser His Leu Lys Asp Gln
785                 790                 795                 800

Phe Asn Asn Ala Ile Leu Thr Leu Leu Asn Lys Arg Gln Leu Glu Lys
            805                 810                 815

Leu Lys Glu Lys Trp Trp Lys Asn Asp Glu Ala Leu Ala Lys Cys Asp
            820                 825                 830

Lys Pro Glu Asp Gln Ser Asp Gly Ile Ser Ile Gln Asn Ile Gly Gly
        835                 840                 845

Val Phe Ile Val Ile Phe Val Gly Ile Gly Met Ala Cys Ile Thr Leu
850                 855                 860

Val Phe Glu Tyr Trp Trp Tyr Arg Tyr Arg Lys Asn Pro Arg Ile Ile
865                 870                 875                 880

Asp Val Ala Glu Ala Asn Ala Glu Arg Ser Asn Ala Ala Asp His Pro
            885                 890                 895

Gly Lys Leu Val Asp Gly Val Ile Leu Gly His Ser Gly Glu Lys Phe
            900                 905                 910

Glu Lys Ser Lys Ala Ala Leu Arg Pro Arg Phe Asn Gln Tyr Pro Ala
        915                 920                 925

Thr Phe Lys Pro Arg Phe
930
```

<210> SEQ ID NO 3
<211> LENGTH: 929
<212> TYPE: PRT
<213> ORGANISM: Drosophila melanogaster

<400> SEQUENCE: 3

```
Met Pro Arg Asn Ala Phe Gly Gln Cys Thr Leu Thr Asp Val Ile Pro
 1               5                  10                  15

Ser Leu Trp Ile Val Phe Ile Asn Glu Val Asp Asn Glu Pro Ala Ala
            20                  25                  30

Lys Ala Val Glu Val Val Leu Thr Tyr Leu Lys Lys Asn Ile Arg Tyr
        35                  40                  45

Gly Leu Ser Val Gln Leu Asp Ser Ile Glu Ala Asn Lys Ser Asp Ala
    50                  55                  60

Lys Val Leu Leu Glu Ala Ile Cys Asn Lys Tyr Ala Thr Ser Ile Glu
65                  70                  75                  80

Lys Lys Gln Thr Pro His Leu Ile Leu Asp Thr Thr Lys Ser Gly Ile
                85                  90                  95

Ala Ser Glu Thr Val Lys Ser Phe Thr Gln Ala Leu Gly Leu Pro Thr
            100                 105                 110

Ile Ser Ala Ser Tyr Gly Gln Gln Gly Asp Leu Arg Gln Trp Arg Asp
        115                 120                 125

Leu Asp Glu Ala Lys Gln Lys Tyr Leu Leu Gln Val Met Pro Pro Ala
    130                 135                 140

Asp Ile Ile Pro Glu Ala Ile Arg Ser Ile Val Ile His Met Asn Ile
145                 150                 155                 160

Thr Asn Ala Ala Ile Leu Tyr Asp Asp Ser Phe Val Met Asp His Lys
                165                 170                 175

Tyr Lys Ser Leu Leu Gln Asn Ile Gln Thr Arg His Val Ile Thr Ala
            180                 185                 190

Ile Ala Lys Asp Gly Lys Arg Glu Arg Glu Glu Gln Ile Glu Lys Leu
        195                 200                 205

Arg Asn Leu Asp Ile Asn Asn Phe Phe Ile Leu Gly Thr Leu Gln Ser
    210                 215                 220

Ile Arg Met Val Leu Glu Ser Val Lys Pro Ala Tyr Phe Glu Arg Asn
225                 230                 235                 240

Phe Ala Trp His Ala Ile Thr Gln Asn Glu Gly Glu Ile Ser Ser Gln
                245                 250                 255

Arg Asp Asn Ala Thr Ile Met Phe Met Lys Pro Met Ala Tyr Thr Gln
            260                 265                 270

Tyr Arg Asp Arg Leu Gly Leu Arg Thr Thr Tyr Asn Leu Asn Glu
        275                 280                 285

Glu Pro Gln Leu Ser Ser Ala Phe Tyr Phe Asp Leu Ala Leu Arg Ser
    290                 295                 300

Phe Leu Thr Ile Lys Glu Met Leu Gln Ser Gly Ala Trp Pro Lys Asp
305                 310                 315                 320

Met Glu Tyr Leu Asn Cys Asp Asp Phe Gln Gly Gly Asn Thr Pro Gln
                325                 330                 335

Arg Asn Leu Asp Leu Arg Asp Tyr Phe Thr Lys Ile Thr Glu Pro Thr
            340                 345                 350

Ser Tyr Gly Thr Phe Asp Leu Val Thr Gln Ser Thr Gln Pro Phe Asn
        355                 360                 365

Gly His Ser Phe Met Lys Phe Glu Met Asp Ile Asn Val Leu Gln Ile
    370                 375                 380
```

```
Arg Gly Gly Ser Ser Val Asn Ser Lys Ser Ile Gly Lys Trp Ile Ser
385                 390                 395                 400

Gly Leu Asn Ser Glu Leu Ile Val Lys Asp Glu Glu Gln Met Lys Asn
            405                 410                 415

Leu Thr Ala Asp Thr Val Tyr Arg Ile Phe Thr Val Val Gln Ala Pro
        420                 425                 430

Phe Ile Met Arg Asp Glu Thr Ala Pro Lys Gly Tyr Lys Gly Tyr Cys
    435                 440                 445

Ile Asp Leu Ile Asn Glu Ile Ala Ala Ile Val His Phe Asp Tyr Thr
450                 455                 460

Ile Gln Glu Val Glu Asp Gly Lys Phe Gly Asn Met Asp Glu Asn Gly
465                 470                 475                 480

Gln Trp Asn Gly Ile Val Lys Lys Leu Met Asp Lys Gln Ala Asp Ile
            485                 490                 495

Gly Leu Gly Ser Met Ser Val Met Ala Glu Arg Glu Ile Val Ile Asp
        500                 505                 510

Phe Thr Val Pro Tyr Tyr Asp Leu Val Gly Ile Thr Ile Met Met Gln
    515                 520                 525

Arg Pro Ser Ser Pro Ser Ser Leu Phe Lys Phe Leu Thr Val Leu Glu
530                 535                 540

Thr Asn Val Trp Leu Cys Ile Leu Ala Ala Tyr Phe Phe Thr Ser Phe
545                 550                 555                 560

Leu Met Trp Ile Phe Asp Arg Trp Ser Pro Tyr Ser Tyr Gln Asn Asn
            565                 570                 575

Arg Glu Lys Tyr Lys Asp Asp Glu Glu Lys Arg Glu Phe Asn Leu Lys
        580                 585                 590

Glu Cys Leu Trp Phe Cys Met Thr Ser Leu Thr Pro Gln Gly Gly Gly
    595                 600                 605

Glu Ala Pro Lys Asn Leu Ser Gly Arg Leu Val Ala Ala Thr Trp Trp
610                 615                 620

Leu Phe Gly Phe Ile Ile Ile Ala Ser Tyr Thr Ala Asn Leu Ala Ala
625                 630                 635                 640

Phe Leu Thr Val Ser Arg Leu Asp Thr Pro Val Glu Ser Leu Asp Asp
            645                 650                 655

Leu Ala Lys Gln Tyr Lys Ile Leu Tyr Ala Pro Leu Asn Gly Ser Ser
        660                 665                 670

Ala Met Thr Tyr Phe Glu Arg Met Ser Asn Ile Glu Gln Met Phe Tyr
    675                 680                 685

Glu Ile Trp Lys Asp Leu Ser Leu Asn Asp Ser Leu Thr Ala Val Glu
690                 695                 700

Arg Ser Lys Leu Ala Val Trp Asp Tyr Pro Val Ser Asp Lys Tyr Thr
705                 710                 715                 720

Lys Met Trp Gln Ala Met Gln Glu Ala Lys Leu Pro Ala Thr Leu Asp
            725                 730                 735

Glu Ala Val Ala Arg Val Arg Asn Ser Thr Ala Thr Gly Phe Ala
        740                 745                 750

Phe Leu Gly Asp Ala Thr Asp Ile Arg Tyr Leu Gln Leu Thr Asn Cys
    755                 760                 765

Asp Leu Gln Val Val Gly Glu Phe Ser Arg Lys Pro Tyr Ala Ile
770                 775                 780

Ala Val Gln Gln Gly Ser His Leu Lys Asp Gln Phe Asn Asn Ala Ile
785                 790                 795                 800

Leu Thr Leu Leu Asn Lys Arg Gln Leu Glu Lys Leu Lys Glu Lys Trp
```

```
                 805                 810                 815

Trp Lys Asn Asp Glu Ala Leu Ala Lys Cys Asp Lys Pro Glu Asp Gln
            820                 825                 830

Ser Asp Gly Ile Ser Ile Gln Asn Ile Gly Gly Val Phe Ile Val Ile
            835                 840                 845

Phe Val Gly Ile Gly Met Ala Cys Ile Thr Leu Val Phe Glu Tyr Trp
        850                 855                 860

Trp Tyr Arg Tyr Arg Lys Asn Pro Arg Ile Ile Asp Val Ala Glu Ala
865                 870                 875                 880

Asn Ala Glu Arg Ser Asn Ala Ala Asp His Pro Gly Lys Leu Val Asp
                885                 890                 895

Gly Val Ile Leu Gly His Ser Gly Glu Lys Phe Glu Lys Ser Lys Ala
            900                 905                 910

Ala Leu Arg Pro Arg Phe Asn Gln Tyr Pro Ala Thr Phe Lys Pro Arg
            915                 920                 925

Phe

<210> SEQ ID NO 4
<211> LENGTH: 947
<212> TYPE: PRT
<213> ORGANISM: Drosophila melanogaster

<400> SEQUENCE: 4

Met Ile Leu Met Asn Pro Lys Thr Ser Lys Ile Leu Trp Leu Leu Gly
1               5                   10                  15

Phe Leu Ser Leu Leu Ser Ser Phe Ser Leu Glu Ile Ala Ala Gln Thr
            20                  25                  30

Thr Gln Asn Ile Asn Val Leu Phe Ile Asn Glu Val Asp Asn Glu Pro
        35                  40                  45

Ala Ala Lys Ala Val Glu Val Val Leu Thr Tyr Leu Lys Lys Asn Ile
    50                  55                  60

Arg Tyr Gly Leu Ser Val Gln Leu Asp Ser Ile Glu Ala Asn Lys Ser
65                  70                  75                  80

Asp Ala Lys Val Leu Leu Glu Ala Ile Cys Asn Lys Tyr Ala Thr Ser
                85                  90                  95

Ile Glu Lys Lys Gln Thr Pro His Leu Ile Leu Asp Thr Thr Lys Ser
            100                 105                 110

Gly Ile Ala Ser Glu Thr Val Lys Ser Phe Thr Gln Ala Leu Gly Leu
        115                 120                 125

Pro Thr Ile Ser Ala Ser Tyr Gly Gln Gln Gly Asp Leu Arg Gln Trp
    130                 135                 140

Arg Asp Leu Asp Glu Ala Lys Gln Lys Tyr Leu Leu Gln Val Met Pro
145                 150                 155                 160

Pro Ala Asp Ile Ile Pro Glu Ala Ile Arg Ser Ile Val Ile His Met
                165                 170                 175

Asn Ile Thr Asn Ala Ala Ile Leu Tyr Asp Asp Ser Phe Val Met Asp
            180                 185                 190

His Lys Tyr Lys Ser Leu Leu Gln Asn Ile Gln Thr Arg His Val Ile
        195                 200                 205

Thr Ala Ile Ala Lys Asp Gly Lys Arg Glu Arg Glu Gln Ile Glu
    210                 215                 220

Lys Leu Arg Asn Leu Asp Ile Asn Asn Phe Phe Ile Leu Gly Thr Leu
225                 230                 235                 240

Gln Ser Ile Arg Met Val Leu Glu Ser Val Lys Pro Ala Tyr Phe Glu
```

-continued

```
                245                 250                 255
Arg Asn Phe Ala Trp His Ala Ile Thr Gln Asn Glu Gly Glu Ile Ser
            260                 265                 270

Ser Gln Arg Asp Asn Ala Thr Ile Met Phe Met Lys Pro Met Ala Tyr
            275                 280                 285

Thr Gln Tyr Arg Asp Arg Leu Gly Leu Leu Arg Thr Thr Tyr Asn Leu
            290                 295                 300

Asn Glu Glu Pro Gln Leu Ser Ser Ala Phe Tyr Phe Asp Leu Ala Leu
305                 310                 315                 320

Arg Ser Phe Leu Thr Ile Lys Glu Met Leu Gln Ser Gly Ala Trp Pro
                325                 330                 335

Lys Asp Met Glu Tyr Leu Asn Cys Asp Asp Phe Gln Gly Gly Asn Thr
                340                 345                 350

Pro Gln Arg Asn Leu Asp Leu Arg Asp Tyr Phe Thr Lys Ile Thr Glu
                355                 360                 365

Pro Thr Ser Tyr Gly Thr Phe Asp Leu Val Thr Gln Ser Thr Gln Pro
                370                 375                 380

Phe Asn Gly His Ser Phe Met Lys Phe Glu Met Asp Ile Asn Val Leu
385                 390                 395                 400

Gln Ile Arg Gly Gly Ser Ser Val Asn Ser Lys Ser Ile Gly Lys Trp
                405                 410                 415

Ile Ser Gly Leu Asn Ser Glu Leu Ile Val Lys Asp Glu Gln Met
                420                 425                 430

Lys Asn Leu Thr Ala Asp Thr Val Tyr Arg Ile Phe Thr Val Val Gln
                435                 440                 445

Ala Pro Phe Ile Met Arg Asp Glu Thr Ala Pro Lys Gly Tyr Lys Gly
                450                 455                 460

Tyr Cys Ile Asp Leu Ile Asn Glu Ile Ala Ala Ile Val His Phe Asp
465                 470                 475                 480

Tyr Thr Ile Gln Glu Val Glu Asp Gly Lys Phe Gly Asn Met Asp Glu
                485                 490                 495

Asn Gly Gln Trp Asn Gly Ile Val Lys Lys Leu Met Asp Lys Gln Ala
                500                 505                 510

Asp Ile Gly Leu Gly Ser Met Ser Val Met Ala Glu Arg Glu Ile Val
                515                 520                 525

Ile Asp Phe Thr Val Pro Tyr Tyr Asp Leu Val Gly Ile Thr Ile Met
                530                 535                 540

Met Gln Arg Pro Ser Ser Pro Ser Ser Leu Phe Lys Phe Leu Thr Val
545                 550                 555                 560

Leu Glu Thr Asn Val Trp Leu Cys Ile Leu Ala Ala Tyr Phe Phe Thr
                565                 570                 575

Ser Phe Leu Met Trp Ile Phe Asp Arg Trp Ser Pro Tyr Ser Tyr Gln
                580                 585                 590

Asn Asn Arg Glu Lys Tyr Lys Asp Asp Glu Glu Lys Arg Glu Phe Asn
                595                 600                 605

Leu Lys Glu Cys Leu Trp Phe Cys Met Thr Ser Leu Thr Pro Gln Gly
                610                 615                 620

Gly Gly Glu Ala Pro Lys Asn Leu Ser Gly Arg Leu Val Ala Ala Thr
625                 630                 635                 640

Trp Trp Leu Phe Gly Phe Ile Ile Ile Ala Ser Tyr Thr Ala Asn Leu
                645                 650                 655

Ala Ala Phe Leu Thr Val Ser Arg Leu Asp Thr Pro Val Glu Ser Leu
                660                 665                 670
```

Asp Asp Leu Ala Lys Gln Tyr Lys Ile Leu Tyr Ala Pro Leu Asn Gly
            675                 680                 685

Ser Ser Ala Met Thr Tyr Phe Glu Arg Met Ser Asn Ile Glu Gln Met
    690                 695                 700

Phe Tyr Glu Ile Trp Lys Asp Leu Ser Leu Asn Asp Ser Leu Thr Ala
705                 710                 715                 720

Val Glu Arg Ser Lys Leu Ala Val Trp Asp Tyr Pro Val Ser Asp Lys
                725                 730                 735

Tyr Thr Lys Met Trp Gln Ala Met Gln Glu Ala Lys Leu Pro Ala Thr
                740                 745                 750

Leu Asp Glu Ala Val Ala Arg Val Arg Asn Ser Thr Ala Ala Thr Gly
            755                 760                 765

Phe Ala Phe Leu Gly Asp Ala Thr Asp Ile Arg Tyr Leu Gln Leu Thr
770                 775                 780

Asn Cys Asp Leu Gln Val Val Gly Glu Glu Phe Ser Arg Lys Pro Tyr
785                 790                 795                 800

Ala Ile Ala Val Gln Gln Gly Ser His Leu Lys Asp Gln Phe Asn Asn
                805                 810                 815

Ala Ile Leu Thr Leu Leu Asn Lys Arg Gln Leu Glu Lys Leu Lys Glu
            820                 825                 830

Lys Trp Trp Lys Asn Asp Glu Ala Leu Ala Lys Cys Asp Lys Pro Glu
            835                 840                 845

Asp Gln Ser Asp Gly Ile Ser Ile Gln Asn Ile Gly Gly Val Phe Ile
            850                 855                 860

Val Ile Phe Val Gly Ile Gly Met Ala Cys Ile Thr Leu Val Phe Glu
865                 870                 875                 880

Tyr Trp Trp Tyr Arg Tyr Arg Lys Asn Pro Arg Ile Ile Asp Val Ala
                885                 890                 895

Glu Ala Asn Ala Glu Arg Ser Asn Ala Ala Asp His Pro Gly Lys Leu
            900                 905                 910

Val Asp Gly Val Ile Leu Gly His Ser Gly Glu Lys Phe Glu Lys Ser
            915                 920                 925

Lys Ala Ala Leu Arg Pro Arg Phe Asn Gln Tyr Pro Ala Thr Phe Lys
            930                 935                 940

Pro Arg Phe
945

<210> SEQ ID NO 5
<211> LENGTH: 934
<212> TYPE: PRT
<213> ORGANISM: Drosophila melanogaster

<400> SEQUENCE: 5

Met Gly Ser Arg Leu Asp Trp Gly Val Ala Asp Val Ala Leu Trp Ala
1               5                   10                  15

Ile Ala Asp Gln Ile Asp Tyr His Gln Val Phe Ile Asn Glu Val Asp
                20                  25                  30

Asn Glu Pro Ala Ala Lys Ala Val Glu Val Val Leu Thr Tyr Leu Lys
            35                  40                  45

Lys Asn Ile Arg Tyr Gly Leu Ser Val Gln Leu Asp Ser Ile Glu Ala
        50                  55                  60

Asn Lys Ser Asp Ala Lys Val Leu Leu Glu Ala Ile Cys Asn Lys Tyr
65                  70                  75                  80

Ala Thr Ser Ile Glu Lys Lys Gln Thr Pro His Leu Ile Leu Asp Thr

```
                85                  90                  95
Thr Lys Ser Gly Ile Ala Ser Glu Thr Val Lys Ser Phe Thr Gln Ala
            100                 105                 110

Leu Gly Leu Pro Thr Ile Ser Ala Ser Tyr Gly Gln Gln Gly Asp Leu
            115                 120                 125

Arg Gln Trp Arg Asp Leu Asp Glu Ala Lys Gln Lys Tyr Leu Leu Gln
            130                 135                 140

Val Met Pro Pro Ala Asp Ile Ile Pro Glu Ala Ile Arg Ser Ile Val
145                 150                 155                 160

Ile His Met Asn Ile Thr Asn Ala Ala Ile Leu Tyr Asp Asp Ser Phe
                165                 170                 175

Val Met Asp His Lys Tyr Lys Ser Leu Leu Gln Asn Ile Gln Thr Arg
                180                 185                 190

His Val Ile Thr Ala Ile Ala Lys Asp Gly Lys Arg Glu Arg Glu Glu
                195                 200                 205

Gln Ile Glu Lys Leu Arg Asn Leu Asp Ile Asn Asn Phe Phe Ile Leu
            210                 215                 220

Gly Thr Leu Gln Ser Ile Arg Met Val Leu Glu Ser Val Lys Pro Ala
225                 230                 235                 240

Tyr Phe Glu Arg Asn Phe Ala Trp His Ala Ile Thr Gln Asn Glu Gly
                245                 250                 255

Glu Ile Ser Ser Gln Arg Asp Asn Ala Thr Ile Met Phe Met Lys Pro
                260                 265                 270

Met Ala Tyr Thr Gln Tyr Arg Asp Arg Leu Gly Leu Leu Arg Thr Thr
                275                 280                 285

Tyr Asn Leu Asn Glu Glu Pro Gln Leu Ser Ser Ala Phe Tyr Phe Asp
            290                 295                 300

Leu Ala Leu Arg Ser Phe Leu Thr Ile Lys Glu Met Leu Gln Ser Gly
305                 310                 315                 320

Ala Trp Pro Lys Asp Met Glu Tyr Leu Asn Cys Asp Asp Phe Gln Gly
                325                 330                 335

Gly Asn Thr Pro Gln Arg Asn Leu Asp Leu Arg Asp Tyr Phe Thr Lys
                340                 345                 350

Ile Thr Glu Pro Thr Ser Tyr Gly Thr Phe Asp Leu Val Thr Gln Ser
                355                 360                 365

Thr Gln Pro Phe Asn Gly His Ser Phe Met Lys Phe Glu Met Asp Ile
            370                 375                 380

Asn Val Leu Gln Ile Arg Gly Gly Ser Val Asn Ser Lys Ser Ile
385                 390                 395                 400

Gly Lys Trp Ile Ser Gly Leu Asn Ser Glu Leu Ile Val Lys Asp Glu
                405                 410                 415

Glu Gln Met Lys Asn Leu Thr Ala Asp Thr Val Tyr Arg Ile Phe Thr
                420                 425                 430

Val Val Gln Ala Pro Phe Ile Met Arg Asp Glu Thr Ala Pro Lys Gly
                435                 440                 445

Tyr Lys Gly Tyr Cys Ile Asp Leu Ile Asn Glu Ile Ala Ala Ile Val
                450                 455                 460

His Phe Asp Tyr Thr Ile Gln Glu Val Glu Asp Gly Lys Phe Gly Asn
465                 470                 475                 480

Met Asp Glu Asn Gly Gln Trp Asn Gly Ile Val Lys Lys Leu Met Asp
                485                 490                 495

Lys Gln Ala Asp Ile Gly Leu Gly Ser Met Ser Val Met Ala Glu Arg
                500                 505                 510
```

```
Glu Ile Val Ile Asp Phe Thr Val Pro Tyr Tyr Asp Leu Val Gly Ile
    515                 520                 525

Thr Ile Met Met Gln Arg Pro Ser Ser Pro Ser Ser Leu Phe Lys Phe
530             535                 540

Leu Thr Val Leu Glu Thr Asn Val Trp Leu Cys Ile Leu Ala Ala Tyr
545                 550                 555                 560

Phe Phe Thr Ser Phe Leu Met Trp Ile Phe Asp Arg Trp Ser Pro Tyr
            565                 570                 575

Ser Tyr Gln Asn Asn Arg Glu Lys Tyr Lys Asp Asp Glu Glu Lys Arg
        580                 585                 590

Glu Phe Asn Leu Lys Glu Cys Leu Trp Phe Cys Met Thr Ser Leu Thr
    595                 600                 605

Pro Gln Gly Gly Gly Glu Ala Pro Lys Asn Leu Ser Gly Arg Leu Val
    610                 615                 620

Ala Ala Thr Trp Trp Leu Phe Gly Phe Ile Ile Ile Ala Ser Tyr Thr
625             630                 635                 640

Ala Asn Leu Ala Ala Phe Leu Thr Val Ser Arg Leu Asp Thr Pro Val
                645                 650                 655

Glu Ser Leu Asp Asp Leu Ala Lys Gln Tyr Lys Ile Leu Tyr Ala Pro
            660                 665                 670

Leu Asn Gly Ser Ser Ala Met Thr Tyr Phe Glu Arg Met Ser Asn Ile
        675                 680                 685

Glu Gln Met Phe Tyr Glu Ile Trp Lys Asp Leu Ser Leu Asn Asp Ser
    690                 695                 700

Leu Thr Ala Val Glu Arg Ser Lys Leu Ala Val Trp Asp Tyr Pro Val
705             710                 715                 720

Ser Asp Lys Tyr Thr Lys Met Trp Gln Ala Met Gln Glu Ala Lys Leu
            725                 730                 735

Pro Ala Thr Leu Asp Glu Ala Val Ala Arg Val Arg Asn Ser Thr Ala
        740                 745                 750

Ala Thr Gly Phe Ala Phe Leu Gly Asp Ala Thr Asp Ile Arg Tyr Leu
    755                 760                 765

Gln Leu Thr Asn Cys Asp Leu Gln Val Val Gly Glu Glu Phe Ser Arg
    770                 775                 780

Lys Pro Tyr Ala Ile Ala Val Gln Gln Gly Ser His Leu Lys Asp Gln
785             790                 795                 800

Phe Asn Asn Ala Ile Leu Thr Leu Leu Asn Lys Arg Gln Leu Glu Lys
            805                 810                 815

Leu Lys Glu Lys Trp Trp Lys Asn Glu Ala Leu Ala Lys Cys Asp
        820                 825                 830

Lys Pro Glu Asp Gln Ser Asp Gly Ile Ser Ile Gln Asn Ile Gly Gly
    835                 840                 845

Val Phe Ile Val Ile Phe Val Gly Ile Gly Met Ala Cys Ile Thr Leu
850             855                 860

Val Phe Glu Tyr Trp Trp Tyr Arg Tyr Arg Lys Asn Pro Arg Ile Ile
865             870                 875                 880

Asp Val Ala Glu Ala Asn Ala Glu Arg Ser Asn Ala Ala Asp His Pro
            885                 890                 895

Gly Lys Leu Val Asp Gly Val Ile Leu Gly His Ser Gly Glu Lys Phe
        900                 905                 910

Glu Lys Ser Lys Ala Ala Leu Arg Pro Arg Phe Asn Gln Tyr Pro Ala
    915                 920                 925
```

Thr Phe Lys Pro Arg Phe
    930

<210> SEQ ID NO 6
<211> LENGTH: 914
<212> TYPE: PRT
<213> ORGANISM: Aedes aegypti

<400> SEQUENCE: 6

Met Gln Ile Ser Val Phe Val Asn Glu Val Gly Asn Asp Leu Ala Gln
1               5                   10                  15

Val Ala Val Asp Val Ala Leu Asn Tyr Ile Arg Lys Asn Pro Ser Leu
            20                  25                  30

Gly Leu Ser Val Glu Leu Leu Thr Val Glu Gly Asn Arg Thr Asp Ser
        35                  40                  45

Lys Gly Leu Leu Glu Ser Leu Cys Ser Lys Tyr Thr Glu Ala Ile Asn
50                  55                  60

Thr Asn Arg Pro Pro His Val Ile Phe Asp Thr Thr Leu Thr Gly Val
65                  70                  75                  80

Ser Ser Glu Thr Val Lys Ser Ile Ser Ala Ala Leu Gly Ile Pro Thr
                85                  90                  95

Val Ser Ala Ser Thr Gly Gln Glu Gly Asp Leu Arg Gln Trp Arg Ser
            100                 105                 110

Leu Ser Asn Val Lys Ser Asn Tyr Leu Leu Gln Val Met Pro Pro Thr
        115                 120                 125

Asp Ile Ile Pro Glu Val Ile Arg Ala Ile Val Thr Tyr Met Asn Ile
130                 135                 140

Thr Asn Ala Ala Ile Leu Tyr Asp Glu Ser Phe Val Met Asp His Lys
145                 150                 155                 160

Tyr Lys Ala Leu Leu Gln Asn Phe Pro Thr Arg His Val Ile Thr Ala
                165                 170                 175

Ile Gly Asn Asp Arg Asp Arg Ala Glu Gln Ile Glu Lys Leu Arg Asn
            180                 185                 190

Leu Asp Ile Asn Asn Phe Phe Ile Leu Gly Ser Phe Ala Ser Ile Lys
        195                 200                 205

Lys Val Leu Glu Ser Ala Lys Arg Glu Phe Phe Glu Arg Asn Phe Ala
210                 215                 220

Trp His Ala Ile Thr Gln Tyr Gln Gly Glu Leu Ser Ser Asn Ile Glu
225                 230                 235                 240

Asn Ala Thr Ile Met Leu Leu Arg Pro Val Ser Asp Ser Lys Ser Lys
                245                 250                 255

Asp Arg Leu Gly Val Ile Arg Thr Thr Tyr Asn Met Lys Gln Glu Pro
            260                 265                 270

Gln Ile Thr Thr Val Phe Tyr Phe Asp Leu Ala Leu Arg Thr Phe Leu
        275                 280                 285

Ala Ile Lys Asn Ile Leu Gln Val Gly Ala Trp Pro Pro Asn Met Lys
290                 295                 300

Tyr Leu Thr Cys Asp Glu Tyr Asp Gly Thr Asn Ser Pro Asn His Thr
305                 310                 315                 320

Ile Asp Leu Lys Ser Ala Phe Ile Glu Val Thr Glu Pro Thr Thr Tyr
                325                 330                 335

Gly Pro Phe Glu Phe Pro Lys Gly Lys Thr Pro Phe Asn Gly His Ser
            340                 345                 350

Phe Met Lys Phe Asp Met Asp Ile Ser Ala Val Thr Ile Arg Gly Gly
        355                 360                 365

```
Ala Ser Val Ser Thr Lys Asn Leu Gly Lys Trp Glu Ala Ser Leu Asp
    370                 375                 380
Asn Ala Leu Tyr Val Thr Ser Glu Asp Met Lys Asn Leu Thr Ala
385                 390                 395                 400
Asp Ile Val Tyr Arg Val Tyr Thr Val Val Gln Glu Pro Phe Ile Ile
                    405                 410                 415
Arg Asp Pro Thr Ala Pro Lys Gly Phe Lys Gly Tyr Cys Ile Asp Leu
            420                 425                 430
Leu Asp Glu Ile Ala Lys Ile Val Lys Phe Asp Tyr Glu Ile Lys Glu
        435                 440                 445
Val Glu Asp Gly Lys Phe Gly Asn Met Asn Lys Gly Glu Trp Asn
    450                 455                 460
Gly Ile Val Arg Lys Leu Ile Asp Lys Gln Ala Asp Ile Gly Leu Gly
465                 470                 475                 480
Ser Met Ser Val Met Ala Glu Arg Glu Thr Val Ile Asp Phe Thr Val
                485                 490                 495
Pro Tyr Tyr Asp Leu Val Gly Ile Ser Ile Met Met Leu Leu Pro Ser
            500                 505                 510
Thr Pro Ser Ser Leu Phe Lys Phe Leu Thr Val Leu Glu Thr Asn Val
        515                 520                 525
Trp Leu Cys Ile Leu Ala Ala Tyr Phe Phe Thr Ser Phe Leu Met Trp
    530                 535                 540
Ile Phe Asp Arg Tyr Ser Pro Tyr Ser Tyr Gln Asn Asn Arg Glu Lys
545                 550                 555                 560
Tyr Lys Asn Asp Asp Glu Lys Arg Glu Phe Asn Ile Lys Glu Cys Leu
                565                 570                 575
Trp Phe Cys Met Thr Ser Leu Thr Pro Gln Gly Gly Gly Glu Ala Pro
            580                 585                 590
Lys Asn Leu Ser Gly Arg Leu Val Ala Ala Thr Trp Trp Leu Phe Gly
        595                 600                 605
Phe Ile Ile Ile Ala Ser Tyr Thr Ala Asn Leu Ala Ala Phe Leu Thr
    610                 615                 620
Val Ser Arg Leu Asp Thr Pro Val Glu Ser Leu Asp Asp Leu Ser Lys
625                 630                 635                 640
Gln Tyr Lys Ile Leu Tyr Ala Pro Leu Asn Gly Ser Ser Ala Met Thr
                645                 650                 655
Tyr Phe Gln Arg Met Ala Asp Ile Glu Ala Arg Phe Tyr Glu Ile Trp
            660                 665                 670
Lys Glu Met Ser Leu Asn Asp Ser Leu Thr Pro Val Glu Arg Ser Lys
        675                 680                 685
Leu Ala Val Trp Asp Tyr Pro Val Ser Asp Lys Tyr Thr Lys Met Trp
    690                 695                 700
Gln Ala Met Gln Glu Ala Gly Leu Pro Asn Ser Leu Asp Glu Ala Val
705                 710                 715                 720
Glu Arg Ile Arg Asn Ser Thr Ser Ala Ser Gly Phe Ala Phe Leu Gly
                725                 730                 735
Asp Ala Thr Asp Ile Arg Tyr Lys Val Leu Thr Asn Cys Asp Leu Gln
            740                 745                 750
Met Val Gly Glu Glu Phe Ser Arg Lys Pro Tyr Ala Ile Ala Val Gln
        755                 760                 765
Gln Gly Ser Pro Leu Lys Asp Gln Phe Asn Asn Ala Ile Leu Met Leu
    770                 775                 780
```

```
Leu Asn Lys Arg Gln Leu Glu Lys Leu Lys Glu Gln Trp Trp Lys Asn
785                 790                 795                 800

Asp Asp Ile Gln Ser Lys Cys Glu Lys Pro Asp Asp Gln Ser Asp Gly
            805                 810                 815

Ile Ser Ile Gln Asn Ile Gly Gly Val Phe Ile Val Ile Phe Val Gly
            820                 825                 830

Ile Gly Met Ala Cys Ile Thr Leu Val Phe Glu Phe Trp Tyr Tyr Lys
            835                 840                 845

Tyr Arg Lys Asn Val Lys Ile Ile Asp Val Ala Glu Ala Thr Glu Asp
            850                 855                 860

Lys Leu Ala Gln Lys Thr Ser Asn Leu Arg Leu Pro Asn Leu Lys Asn
865                 870                 875                 880

Glu Phe Gly Ala Met Gly Gln Ile Lys Asp Asp Ser Gln Lys Thr Gln
            885                 890                 895

Ser Leu Arg Thr Arg Thr Gln Thr Ile Asp Ala Asn Asn Phe Lys Ser
            900                 905                 910

Arg Phe

<210> SEQ ID NO 7
<211> LENGTH: 946
<212> TYPE: PRT
<213> ORGANISM: Anopheles gambiae

<400> SEQUENCE: 7

Met Asp Pro Lys Asn Gly Arg Arg Trp Leu Val Leu Ile Pro Ile Gln
1               5                   10                  15

Leu Ala Ser Tyr Ala Ile Ile Ala Ile Met Gly Gln Thr Thr Gln Asn
            20                  25                  30

Ile Asn Ile Leu Phe Val Asn Glu Val Asp Asn Asn Leu Ala Asn Val
            35                  40                  45

Ala Val Glu Val Ala Leu Asn Tyr Val Lys Lys Asn Pro Gln Leu Gly
        50                  55                  60

Leu Ser Val Asp Met Met Tyr Val Glu Gly Asn Arg Thr Asp Ser Lys
65                  70                  75                  80

Asp Leu Leu Gln Ala Leu Cys Ser Lys Tyr Gly Gln Ser Leu Ser Glu
            85                  90                  95

Asn Arg Pro Pro His Leu Leu Leu Asp Thr Thr Leu Thr Gly Val Ser
            100                 105                 110

Ser Glu Thr Val Lys Ser Phe Ser Leu Ala Leu Gly Ile Pro Thr Val
        115                 120                 125

Ser Ala Ser Phe Gly Gln Glu Gly Asp Leu Arg Gln Trp Arg Asp Leu
    130                 135                 140

Thr Pro Thr Lys Arg Gly Tyr Leu Leu Gln Val Met Pro Pro Ala Asp
145                 150                 155                 160

Met Ile Pro Gln Val Ile Arg Ser Ile Ile Tyr Met Asn Ile Thr
            165                 170                 175

Asn Ala Ala Ile Leu Tyr Asp Asn Thr Phe Val Met Asp His Lys Tyr
            180                 185                 190

Lys Ala Leu Leu Gln Asn Ile Pro Thr Arg His Val Val Thr Thr Ile
        195                 200                 205

Ala Asp Asp Arg Asp Arg Ala Ser Gln Ile Glu Lys Leu Arg Asn Leu
    210                 215                 220

Asp Ile Asn Asn Phe Phe Ile Leu Gly Ser Leu Ala Ser Ile Lys Gln
225                 230                 235                 240
```

```
Val Leu Glu Ser Ala Lys Asn Glu Tyr Phe Arg Asn Phe Ala Trp
                245                 250                 255

His Val Ile Thr Gln Glu Gln Lys Asp Leu Thr Cys Asn Val Glu Asn
            260                 265                 270

Ala Thr Ile Met Phe Leu Arg Pro Met Ser Asp Ser Ser Lys Asp
                275                 280                 285

Arg Leu Gly Ser Ile Arg Thr Thr Tyr Asn Leu Lys Gln Glu Pro Gln
            290                 295                 300

Ile Thr Gly Phe Phe Tyr Phe Asp Leu Thr Leu Arg Ala Leu Ile Ala
305                 310                 315                 320

Ile Lys Asn Ile Leu Gln Ser Gly Ser Trp Pro Ser Asn Met Lys Tyr
                325                 330                 335

Ile Thr Cys Glu Asp Tyr Asp Gly Thr Asn Thr Pro Asn His Thr Ile
                340                 345                 350

Asp Leu Lys Thr Ala Phe Ile Glu Val Thr Glu Pro Thr Thr Phe Gly
            355                 360                 365

Pro Phe Glu Ile Pro Lys Gly Gly Lys Met Gln Phe Asn Gly Asn Thr
            370                 375                 380

Tyr Met Lys Phe Asp Met Asp Ile Asn Ala Val Ser Ile Arg Ser Gly
385                 390                 395                 400

Ala Ser Val Asn Thr Arg Ser Leu Gly Thr Trp Glu Ala Ser Leu Asn
                405                 410                 415

Ala Pro Ile Asn Val Ala Asn Glu Ala Glu Ile Lys Asn Leu Thr Ala
                420                 425                 430

Asp Val Val Tyr Arg Val Tyr Thr Val Gln Ala Pro Phe Ile Met
            435                 440                 445

Arg Asp Pro Thr Ala Pro Lys Gly Phe Lys Gly Tyr Cys Ile Asp Leu
    450                 455                 460

Leu Asn Lys Ile Ala Glu Ile Val Glu Phe Asp Tyr Glu Ile Arg Glu
465                 470                 475                 480

Val Glu Asp Gly Lys Phe Gly Asn Met Asn Glu Asn Gly Glu Trp Asn
                485                 490                 495

Gly Ile Val Arg Lys Leu Ile Asp Lys Gln Ala Asp Ile Gly Leu Gly
                500                 505                 510

Ser Met Ser Val Met Ala Glu Arg Glu Thr Val Ile Asp Phe Thr Val
                515                 520                 525

Pro Tyr Tyr Asp Leu Val Gly Ile Ser Ile Met Met Gln Leu Pro Ser
                530                 535                 540

Thr Pro Ser Ser Leu Phe Lys Phe Leu Thr Val Leu Glu Thr Asn Val
545                 550                 555                 560

Trp Leu Cys Ile Leu Ala Ala Tyr Phe Phe Thr Ser Phe Leu Met Trp
                565                 570                 575

Ile Phe Asp Arg Tyr Ser Pro Tyr Ser Tyr Gln Asn Asn Arg Glu Lys
                580                 585                 590

Tyr Lys Asn Asp Asp Glu Lys Arg Glu Phe Asn Ile Lys Glu Cys Leu
            595                 600                 605

Trp Phe Cys Met Thr Ser Leu Thr Pro Gln Gly Gly Gly Glu Ala Pro
            610                 615                 620

Lys Asn Leu Ser Gly Arg Leu Val Ala Ala Thr Trp Trp Leu Phe Gly
625                 630                 635                 640

Phe Ile Ile Ile Ala Ser Tyr Thr Ala Asn Leu Ala Ala Phe Leu Thr
                645                 650                 655

Val Ser Arg Leu Asp Thr Pro Val Glu Ser Leu Asp Asp Leu Ser Lys
```

```
                    660                 665                 670
Gln Tyr Lys Ile Leu Tyr Ala Pro Leu Asn Gly Ser Ser Ala Met Thr
            675                 680                 685

Tyr Phe Gln Arg Met Ala Asp Ile Glu Ala Lys Phe Tyr Glu Ile Trp
        690                 695                 700

Lys Glu Met Ser Leu Asn Asp Ser Leu Thr Ala Val Glu Arg Ser Lys
705                 710                 715                 720

Leu Ala Val Trp Asp Tyr Pro Val Ser Asp Lys Tyr Thr Lys Met Trp
                725                 730                 735

Gln Ala Met Leu Glu Ala Gly Leu Pro Asn Ser Leu Glu Glu Ala Val
            740                 745                 750

Gln Arg Ile Arg Asn Ser Thr Ser Ala Ser Gly Phe Ala Phe Leu Gly
        755                 760                 765

Asp Ala Thr Asp Ile Arg Tyr Gln Val Leu Thr Asn Cys Asp Leu Gln
    770                 775                 780

Met Val Gly Glu Glu Phe Ser Arg Lys Pro Tyr Ala Ile Ala Val Gln
785                 790                 795                 800

Gln Gly Ser Pro Leu Lys Asp Gln Phe Asn Asn Ala Ile Leu Met Leu
                805                 810                 815

Leu Asn Arg Arg Glu Leu Glu Lys Leu Lys Glu Gln Trp Trp Lys Asn
            820                 825                 830

Asp Asp Val Gln Asn Lys Cys Glu Lys Pro Asp Gln Ser Asp Gly
        835                 840                 845

Ile Ser Ile Gln Asn Ile Gly Gly Val Phe Ile Val Ile Phe Val Gly
    850                 855                 860

Ile Gly Met Ala Cys Ile Thr Leu Leu Phe Glu Phe Trp Tyr Tyr Lys
865                 870                 875                 880

Tyr Arg Asn Asn Ser Lys Val Ile Asp Val Ala Glu Ser Thr Asp Gln
                885                 890                 895

Gln His Gly Gly Thr Ile Val Lys Asn Val Arg Pro Ala Gly Lys Leu
            900                 905                 910

Met Lys Gln Asp Ser Leu Lys Asp Ser Thr Lys Gly His Asn Tyr Gln
        915                 920                 925

Asn Leu Arg Thr Arg Thr Leu Met Pro Asn Leu Ser Lys Phe Gln Pro
    930                 935                 940

Arg Phe
945

<210> SEQ ID NO 8
<211> LENGTH: 818
<212> TYPE: PRT
<213> ORGANISM: Culex quinquefasciatus

<400> SEQUENCE: 8

Val Cys Ser Lys Tyr Ser Glu Ala Leu Asn Thr Asn Arg Met Pro His
1               5                   10                  15

Val Ile Leu Asp Thr Thr Leu Thr Gly Val Ala Ser Glu Thr Val Lys
                20                  25                  30

Ser Ile Ser Val Ala Leu Gly Ile Pro Thr Val Ser Thr Ser Phe Gly
            35                  40                  45

Gln Glu Gly Asp Ile Arg Gln Trp Arg Ser Leu Ser Pro Glu Lys Gly
        50                  55                  60

Asn Tyr Leu Leu Gln Ile Met Pro Pro Thr Asp Met Ile Pro Glu Val
65                  70                  75                  80
```

Ile Arg Ser Ile Ile Ile Tyr Met Asn Ile Thr Asn Ala Ala Ile Leu
            85                  90                  95

Tyr Asp Asp Ser Phe Val Met Asp His Lys Tyr Lys Ala Leu Leu Gln
        100                 105                 110

Asn Ile Pro Thr Arg His Val Ile Thr Ser Ile Gly Asn Asp Lys Asp
        115                 120                 125

Arg Gly Glu Gln Ile Glu Lys Leu Arg Asn Leu Asp Ile Asn Asn Phe
        130                 135                 140

Phe Ile Leu Gly Ser Phe Pro Ser Ile Arg Lys Val Leu Glu Ser Ala
145                 150                 155                 160

Lys Arg Glu Phe Phe Glu Arg Asn Phe Ala Trp His Ala Ile Thr Gln
                165                 170                 175

Phe Gln Gly Glu Leu Ser Ser Asn Ile Glu Asn Ala Thr Ile Met Leu
        180                 185                 190

Leu Arg Pro Val Ser Asp Ser Lys Ser Lys Asp Arg Leu Gly Val Ile
        195                 200                 205

Arg Thr Thr Tyr Asn Met Lys Gln Glu Pro Gln Thr Ser Ser Val Phe
        210                 215                 220

Tyr Phe Asp Ile Ala Leu Arg Thr Phe Leu Ala Ile Lys Asn Leu Phe
225                 230                 235                 240

Tyr Asp Asp Ala Lys Asn Asp Tyr Glu Tyr Asp Pro Pro Tyr Thr Met
                245                 250                 255

Asp Gln Asp Phe Asp Arg Ile Thr Ile Lys Val Arg Asp Leu Arg Glu
        260                 265                 270

Lys Leu Asp Asn Gly Phe Asp Gly Lys Cys Leu Ser Arg Leu Arg Ala
        275                 280                 285

Tyr Phe His Arg Val Met Arg Leu Val Thr Thr Asn Asp Asp Glu Lys
        290                 295                 300

Val Arg Lys Arg Glu Leu Ala Glu Glu Met Leu Gln Ile Phe Val Thr
305                 310                 315                 320

Phe Asn Val Asn Pro Asp Lys Gln Pro Asp Glu Ile Ser Asp Gly Asn
                325                 330                 335

Pro Glu Lys Glu Glu Thr Glu Lys Glu Glu Ala Ser Leu Lys Lys Ile
        340                 345                 350

Leu Leu Leu Ile Asn Val Tyr Phe Leu Gln Gln Glu Pro Phe Ile Phe
        355                 360                 365

Arg Asp Pro Ser Ala Pro Lys Gly Phe Lys Gly Tyr Cys Ile Asp Leu
        370                 375                 380

Leu Asp Glu Ile Ala Lys Ile Val Lys Phe Asp Tyr Glu Ile Lys Ala
385                 390                 395                 400

Val Glu Asp Gly Lys Phe Gly Asn Met Asn Glu Lys Gly Glu Trp Asn
                405                 410                 415

Gly Ile Val Arg Lys Leu Ile Asp Lys Gln Ala Asp Ile Gly Leu Gly
        420                 425                 430

Ser Met Ser Val Met Ala Glu Arg Glu Thr Val Ile Asp Phe Thr Val
        435                 440                 445

Pro Tyr Tyr Asp Leu Val Gly Ile Ser Ile Met Met Gln Leu Pro Ser
        450                 455                 460

Thr Pro Ser Ser Leu Phe Lys Phe Leu Thr Val Leu Glu Thr Asn Val
465                 470                 475                 480

Trp Leu Cys Ile Leu Ala Ala Tyr Phe Phe Thr Ser Phe Leu Met Trp
                485                 490                 495

Ile Phe Asp Arg Tyr Ser Pro Tyr Ser Tyr Gln Asn Asn Arg Glu Lys

```
                500             505             510
Tyr Lys Asn Asp Asp Glu Lys Arg Glu Phe Asn Ile Lys Glu Cys Leu
            515                 520                 525

Trp Phe Cys Met Thr Ser Leu Thr Pro Gln Gly Gly Gly Glu Ala Pro
        530                 535                 540

Lys Asn Leu Ser Gly Arg Leu Val Ala Ala Thr Trp Trp Leu Phe Gly
545                 550                 555                 560

Phe Ile Ile Ile Ala Ser Tyr Thr Ala Asn Leu Ala Ala Phe Leu Thr
                565                 570                 575

Val Ser Arg Leu Asp Thr Pro Val Glu Ser Leu Asp Asp Leu Ser Lys
            580                 585                 590

Gln Tyr Lys Ile Leu Tyr Ala Pro Leu Asn Gly Ser Ser Ala Met Thr
        595                 600                 605

Tyr Phe Gln Arg Met Ala Asp Ile Glu Ser Arg Phe Tyr Glu Ile Trp
    610                 615                 620

Lys Glu Met Ser Leu Asn Asp Ser Leu Thr Pro Val Glu Arg Ser Lys
625                 630                 635                 640

Leu Ala Val Trp Asp Tyr Pro Val Ser Asp Lys Tyr Thr Lys Met Trp
                645                 650                 655

Gln Ala Met Gln Glu Ala Gly Leu Pro Asn Ser Leu Asp Glu Ala Val
            660                 665                 670

Glu Arg Ile Arg Asn Ser Thr Ser Ala Ser Gly Phe Ala Phe Leu Gly
        675                 680                 685

Asp Ala Thr Asp Ile Arg Tyr Lys Val Leu Thr Asn Cys Asp Leu Gln
    690                 695                 700

Met Val Gly Glu Glu Phe Ser Arg Lys Pro Tyr Ala Ile Ala Val Gln
705                 710                 715                 720

Gln Gly Ser Pro Leu Lys Asp Gln Phe Asn Asn Ala Ile Leu Met Leu
                725                 730                 735

Leu Asn Lys Arg Gln Leu Glu Lys Leu Lys Glu Gln Trp Trp Lys Asn
            740                 745                 750

Asp Asp Ile Gln Ser Lys Cys Glu Lys Pro Asp Asp Gln Ser Asp Gly
        755                 760                 765

Ile Ser Ile Gln Asn Ile Gly Gly Val Phe Ile Val Ile Phe Val Gly
    770                 775                 780

Ile Gly Met Ala Cys Ile Thr Leu Val Phe Glu Phe Trp Tyr Tyr Lys
785                 790                 795                 800

Tyr Arg Lys Asn Ile Lys Ile Val Asp Val Met Glu Ala Asn Asp Glu
                805                 810                 815

Asn Ser

<210> SEQ ID NO 9
<211> LENGTH: 932
<212> TYPE: PRT
<213> ORGANISM: Bombyx mori

<400> SEQUENCE: 9

Met Cys Arg Ser Ser His Ile Phe Gln Asn Ser Met Pro Leu Phe Val
1               5                   10                  15

Val Phe Leu Gln Phe Phe Ile Phe Arg Leu Ile Val Ser Gln Thr Thr
                20                  25                  30

Gln Asn Ile Asn Val Leu Leu Ile Asn Glu Glu Asn Asn Ala Leu Ala
            35                  40                  45

Glu Lys Ser Phe Glu Ile Ala Lys Glu Tyr Val Arg Arg Asn Pro Ser
```

-continued

```
               50                  55                  60
Leu Gly Leu Ala Ile Glu Pro Val Ile Val Val Gly Asn Arg Ser Asp
 65                  70                  75                  80

Ala Lys Thr Phe Leu Glu Asn Val Cys Arg Lys Tyr Asn Asp Met Leu
                 85                  90                  95

Ser Ser Lys Lys Thr Pro His Val Val Leu Asp Phe Thr Met Thr Gly
            100                 105                 110

Val Gly Ser Glu Thr Ile Lys Ser Phe Thr Ala Ala Leu Ala Leu Pro
            115                 120                 125

Thr Ile Ser Gly Ser Phe Gly Gln Thr Gly Asp Leu Arg Gln Trp Arg
        130                 135                 140

Ser Leu Asn Ala Asn Gln Thr Lys Phe Leu Leu Gln Val Met Pro Pro
145                 150                 155                 160

Ala Asp Ile Leu Pro Glu Ser Ile Arg Ala Ile Val Thr Lys Gln Asp
                165                 170                 175

Ile Thr Asn Ala Ala Ile Ile Phe Asp Glu Leu Phe Val Met Asp His
            180                 185                 190

Lys Tyr Lys Ser Leu Leu Gln Asn Ile Pro Thr Arg His Val Ile Thr
        195                 200                 205

Pro Val Lys Ser Phe Asn Lys Glu Asp Ile Lys Thr Gln Leu Arg Ser
210                 215                 220

Leu Arg Glu Leu Asp Ile Val Asn Phe Phe Ile Val Gly Ser Leu Arg
225                 230                 235                 240

Thr Ile Lys Asn Val Leu Asp Ala Ala Asp Glu Asn Gln Tyr Phe Gly
                245                 250                 255

Arg Lys Thr Ala Trp Phe Ala Phe Ser Leu Asp Lys Gly Asp Ile Thr
            260                 265                 270

Cys Gly Cys Lys Asp Ala Thr Ile Val Tyr Met Arg Pro Thr Pro Asp
        275                 280                 285

Ala Lys Ser Arg Asp Arg Leu Gly Lys Ile Lys Thr Thr Tyr Ser Met
            290                 295                 300

Asn Gly Glu Pro Glu Ile Thr Ser Ala Phe Tyr Phe Asp Leu Ser Leu
305                 310                 315                 320

Arg Thr Phe Leu Ala Val Lys Ser Leu Leu Asp Ser Gly Lys Trp Pro
                325                 330                 335

Asn Asn Met Lys Tyr Ile Thr Cys Asp Asp Tyr Asp Gly Lys Asn Thr
            340                 345                 350

Pro Asn Arg Thr Leu Asp Leu Lys Leu Ala Phe Gln Glu Val Lys Glu
        355                 360                 365

Thr Pro Thr Tyr Ala Pro Phe Tyr Ile Pro Gly Asp Asp Pro Met Asn
    370                 375                 380

Gly Arg Ser Tyr Met Glu Phe Ser Thr Asp Leu Ser Ala Val Thr Val
385                 390                 395                 400

Lys Asp Gly Ala Ser Ile Gly Ser Lys Ala Leu Gly Thr Trp Lys Ala
                405                 410                 415

Gly Leu Asn Ser Pro Leu Ser Leu Thr Asp Ser Asp Asn Met Ser Asp
            420                 425                 430

Tyr Ser Ala Gln Leu Val Tyr Arg Val Val Thr Val Glu Gln Gln Pro
        435                 440                 445

Phe Ile Ile Arg Asp Asp Asn Ala Pro Lys Gly Phe Lys Gly Tyr Cys
    450                 455                 460

Ile Asp Leu Ile Glu Glu Ile Arg Gln Ile Val Lys Phe Asp Tyr Glu
465                 470                 475                 480
```

```
Val Thr Leu Ser Pro Asp Gly Asn Phe Gly Thr Met Asp Glu Asn Gly
                485                 490                 495

Asn Trp Asn Gly Ile Ile Lys Glu Leu Ile Glu Lys Arg Ala Asp Ile
                500                 505                 510

Ala Leu Thr Ser Leu Ser Val Met Ala Glu Arg Glu Asn Val Val Asp
                515                 520                 525

Phe Thr Val Pro Tyr Tyr Asp Leu Val Gly Ile Thr Ile Met Met Lys
                530                 535                 540

Leu Pro Arg Thr Pro Thr Ser Leu Phe Lys Phe Leu Thr Val Leu Glu
545                 550                 555                 560

Asn Asp Val Trp Leu Ser Ile Leu Ala Ala Tyr Phe Phe Thr Ser Phe
                565                 570                 575

Leu Met Trp Val Phe Asp Lys Trp Ser Pro Tyr Ser Tyr Gln Asn Asn
                580                 585                 590

Arg Glu Lys Tyr Lys Asp Asp Glu Glu Lys Arg Glu Phe Thr Leu Lys
                595                 600                 605

Glu Cys Leu Trp Phe Cys Met Thr Ser Leu Thr Pro Gln Gly Gly Gly
                610                 615                 620

Glu Ala Pro Lys Asn Leu Ser Gly Arg Leu Leu Ala Ala Thr Trp Trp
625                 630                 635                 640

Leu Phe Gly Phe Ile Ile Ile Ala Ser Tyr Thr Ala Asn Leu Ala Ala
                645                 650                 655

Phe Leu Thr Val Ser Arg Leu Asp Thr Pro Ile Glu Ser Leu Asp Asp
                660                 665                 670

Leu Ser Lys Gln Tyr Lys Ile Gln Tyr Ala Pro Leu Asn Gly Ser Ala
                675                 680                 685

Ala Met Thr Tyr Phe Glu Arg Met Ala Ala Ile Glu Val Arg Phe Tyr
                690                 695                 700

Glu Ile Trp Lys Glu Met Ser Leu Asn Asp Ser Leu Ser Asp Val Glu
705                 710                 715                 720

Arg Ala Lys Leu Ala Val Trp Asp Tyr Pro Val Ser Asp Lys Tyr Ser
                725                 730                 735

Lys Met Trp Gln Ala Met Lys Glu Ala Gly Leu Pro Asn Ser Ile Glu
                740                 745                 750

Glu Ala Val Gln Arg Val Arg Asp Ser Lys Ser Ser Glu Gly Phe
                755                 760                 765

Ala Trp Leu Gly Asp Ala Thr Asp Val Arg Tyr Tyr Val Leu Thr Ser
                770                 775                 780

Cys Asp Leu Gln Met Val Gly Asp Glu Phe Ser Arg Lys Pro Tyr Ala
785                 790                 795                 800

Ile Ala Val Gln Gln Gly Ser Pro Leu Lys Asp Gln Phe Asn Asn Ala
                805                 810                 815

Ile Leu Gln Leu Leu Asn Arg Arg Leu Glu Lys Leu Lys Glu Asn
                820                 825                 830

Trp Trp Asn Asn Asn Pro Lys Ala Met Lys Cys Glu Lys Gln Asp Asp
                835                 840                 845

Gln Ser Asp Gly Ile Ser Ile Gln Asn Ile Gly Gly Val Phe Ile Val
                850                 855                 860

Ile Phe Met Gly Ile Gly Leu Ala Cys Ile Thr Leu Gly Val Glu Tyr
865                 870                 875                 880

Trp Trp Tyr Lys Trp Arg Arg Arg Pro Ile Val Gly Asp Val Thr Gln
                885                 890                 895
```

-continued

```
Val Glu Pro Ala Lys Ser Thr Arg Asn Asn Ile Gly Asn Phe Val Lys
                900                 905                 910

Gly Glu Gly Phe Thr Phe Arg Ser Arg Asn Phe Gly Leu Ser Asp Leu
            915                 920                 925

Lys Gln Lys Phe
        930

<210> SEQ ID NO 10
<211> LENGTH: 921
<212> TYPE: PRT
<213> ORGANISM: Danaus plexippus

<400> SEQUENCE: 10

Met Ile Leu Leu Asn Val Leu Leu Ile Tyr Phe Phe Arg Ile Ile Leu
1               5                   10                  15

Ser Gln Thr Thr Gln Asn Ile Asn Val Leu Leu Ile Asn Glu Glu Asn
            20                  25                  30

Asn Ala Leu Ala Glu Arg Ser Phe Glu Val Ala Lys Glu Tyr Val Arg
        35                  40                  45

Arg Asn Pro Gly Leu Gly Leu Ala Val Asn Pro Val Ile Val Val Gly
    50                  55                  60

Asn Arg Ser Asp Ala Lys Val Phe Leu Glu Asn Val Cys Arg Lys Tyr
65                  70                  75                  80

Asn Asp Met Ile Ser Ala Lys Lys Thr Pro His Val Val Leu Asp Phe
                85                  90                  95

Thr Met Thr Gly Val Gly Ser Glu Thr Ile Lys Ser Phe Thr Ala Ala
            100                 105                 110

Leu Ala Leu Pro Thr Ile Ser Gly Ser Phe Gly Gln Pro Gly Asp Leu
        115                 120                 125

Arg Gln Trp Arg Ala Leu Val Asp Asn Gln Thr Lys Tyr Leu Leu Gln
    130                 135                 140

Val Met Pro Pro Ala Asp Ile Leu Pro Glu Ala Val Arg Ala Ile Val
145                 150                 155                 160

Met Lys Gln Asp Ile Thr Asn Ala Ala Ile Ile Phe Asp Glu Tyr Phe
                165                 170                 175

Val Met Asp His Lys Tyr Lys Ser Leu Leu Gln Asn Ile Pro Thr Arg
            180                 185                 190

His Val Ile Thr Pro Val Lys Ser Phe Ser Lys Asp Ile Lys Thr
        195                 200                 205

Gln Leu Arg Ser Leu Arg Glu Leu Asp Ile Val Asn Phe Phe Ile Val
    210                 215                 220

Gly Ser Leu Arg Thr Ile Lys Asn Val Leu Asp Ala Ala Asn Glu Asn
225                 230                 235                 240

Gln Tyr Phe Gly Arg Lys Thr Ala Trp Phe Ala Leu Ser Leu Asp Lys
                245                 250                 255

Gly Glu Ile Ser Cys Gly Cys Lys Asp Ala Thr Ile Val His Ile Lys
            260                 265                 270

Pro Thr Pro Asp Ala Asn Ser Arg Asp Arg Leu Gly Lys Ile Lys Thr
        275                 280                 285

Thr Tyr Ser Met Asn Gly Glu Pro Glu Ile Thr Ser Ala Phe Tyr Phe
    290                 295                 300

Asp Leu Ser Leu Arg Thr Phe Leu Ser Ile Lys Ser Leu Leu Asp Ser
305                 310                 315                 320

Gly Lys Trp Gln Asn Asp Met Asn Phe Ile Thr Cys Asp Tyr Asp
                325                 330                 335
```

```
Gly Lys Asn Thr Pro Asn Arg Ser Leu Asp Leu Lys Thr Ala Phe Gln
            340                 345                 350

Glu Val Lys Glu Thr Pro Thr Tyr Ala Ser Phe Tyr Ile Pro Glu Asp
            355                 360                 365

Asp Pro Met Asn Gly Arg Ser Tyr Met Glu Phe Ser Thr Asp Leu Thr
            370                 375                 380

Ala Val Thr Ile Lys Asp Gly Ala Ser Ile Gly Ser Lys Thr Leu Gly
385                 390                 395                 400

Ser Trp Lys Ala Gly Leu Ser Ser Pro Leu Leu Thr Asp Pro Asp
            405                 410                 415

Asn Met Ser Asp Tyr Ser Ala Gln Leu Val Tyr Arg Ile Val Thr Val
            420                 425                 430

Glu Gln Gln Pro Phe Ile Ile Arg Asp Glu Glu Ala Pro Lys Gly Phe
            435                 440                 445

Lys Gly Tyr Cys Ile Asp Leu Ile Glu Glu Ile Arg Gln Ile Val Lys
            450                 455                 460

Phe Asp Tyr Glu Ile Thr Leu Ala Pro Asp Gly Ser Phe Gly Val Met
465                 470                 475                 480

Asp Glu Asn Gly Asn Trp Asn Gly Ile Ile Lys Glu Leu Met Glu Lys
            485                 490                 495

Arg Ala Asp Ile Gly Leu Thr Ser Leu Ser Val Met Ala Glu Arg Glu
            500                 505                 510

Asn Val Val Asp Phe Thr Val Pro Tyr Tyr Asp Leu Val Gly Ile Thr
            515                 520                 525

Ile Leu Met Lys Leu Pro Arg Thr Pro Thr Ser Leu Phe Lys Phe Leu
            530                 535                 540

Thr Val Leu Glu Asn Asp Val Trp Leu Ser Ile Leu Ala Ala Tyr Phe
545                 550                 555                 560

Phe Thr Ser Phe Leu Met Trp Val Phe Asp Lys Trp Ser Pro Tyr Ser
            565                 570                 575

Tyr Gln Asn Asn Arg Glu Lys Tyr Lys Asp Asp Glu Lys Arg Glu
            580                 585                 590

Phe Thr Leu Lys Glu Cys Leu Trp Phe Cys Met Thr Ser Leu Thr Pro
            595                 600                 605

Gln Gly Gly Gly Glu Ala Pro Lys Asn Leu Ser Gly Arg Leu Leu Ala
            610                 615                 620

Ala Thr Trp Trp Leu Phe Gly Phe Ile Ile Ile Ala Ser Tyr Thr Ala
625                 630                 635                 640

Asn Leu Ala Ala Phe Leu Thr Val Ser Arg Leu Asp Thr Pro Ile Glu
            645                 650                 655

Ser Leu Asp Asp Leu Ser Lys Gln Tyr Lys Ile Gln Tyr Ala Pro Leu
            660                 665                 670

Asn Gly Ser Ala Ala Met Thr Tyr Phe Glu Arg Met Ala Asn Ile Glu
            675                 680                 685

Val Arg Phe Tyr Glu Ile Trp Lys Glu Met Ser Leu Asn Asp Ser Leu
            690                 695                 700

Ser Asp Val Glu Arg Ala Lys Leu Ala Val Trp Asp Tyr Pro Val Ser
705                 710                 715                 720

Asp Lys Tyr Ser Lys Met Trp Gln Ala Met Lys Glu Ala Gly Leu Pro
            725                 730                 735

Asn Ser Ile Glu Glu Ala Val Asp Arg Val Arg Ala Ser Lys Ser Ser
            740                 745                 750
```

```
Ser Glu Gly Phe Ala Trp Leu Gly Asp Ala Thr Asp Ile Arg Tyr His
            755                 760                 765

Val Leu Thr Ser Cys Asp Leu Gln Met Val Gly Asp Glu Phe Ser Arg
        770                 775                 780

Lys Pro Tyr Ala Ile Ala Val Gln Gln Gly Ser Pro Leu Lys Asp Gln
785                 790                 795                 800

Phe Asn Asn Ala Ile Leu Gln Leu Leu Asn Lys Arg Lys Leu Glu Lys
                805                 810                 815

Leu Lys Glu Asp Trp Trp Asn Asn Pro Asn Ala Ile Lys Cys Glu
            820                 825                 830

Lys Gln Asp Asp Gln Ser Asp Gly Ile Ser Ile Gln Asn Ile Gly Gly
        835                 840                 845

Val Phe Ile Val Ile Phe Met Gly Ile Gly Leu Ala Cys Val Thr Leu
850                 855                 860

Gly Val Glu Tyr Trp Trp Tyr Lys Trp Arg Arg Pro Thr Ile Ser
865                 870                 875                 880

Gly Val Lys Gln Val Glu Pro Ala Lys Ser Val Arg Asn Asn Thr Glu
                885                 890                 895

Ser Asn Thr Lys Ile Asn Asp Gly Phe Thr Phe Arg Ala Arg Asn Leu
            900                 905                 910

Gly Leu Ala Asn Leu Lys Gln Lys Phe
            915                 920

<210> SEQ ID NO 11
<211> LENGTH: 945
<212> TYPE: PRT
<213> ORGANISM: Tribolium castaneum

<400> SEQUENCE: 11

Met Ala Ser Ser Ser Ala Ile Ile Tyr Arg Ile Ala Ile Tyr Ser Arg
1               5                   10                  15

Ile Ala Thr Ala His Leu Asn Tyr Ser Asp Phe Leu Asn Asn Val Leu
            20                  25                  30

Thr Glu Thr His Lys Met Leu Lys Leu Val Ala Phe Ile Leu Tyr Cys
        35                  40                  45

Thr Asn Leu Ala Asn Gly Gln Thr Thr Gln Asn Ile Asn Val Leu Phe
50                  55                  60

Val Asn Glu Glu Gly Asn Leu Val Ala Glu Lys Ala Val Asp Val Ala
65                  70                  75                  80

Thr Asn Tyr Ile Lys Lys Asn Asn Lys Leu Gly Val Asn Ala Asp Pro
                85                  90                  95

Val Lys Val Val Gly Asn Arg Thr Asp Ala Ser Gly Leu Leu Asp Ser
            100                 105                 110

Leu Cys Ser Ser Tyr Asn Glu Met Ile Ala Asn Ser Met Asn Pro His
        115                 120                 125

Leu Val Leu Asp Thr Thr Met Thr Gly Leu Ala Ser Glu Thr Val Lys
    130                 135                 140

Ser Phe Thr Ala Ala Leu Gly Leu Pro Thr Ile Ser Ala Ser Phe Gly
145                 150                 155                 160

Gln Glu Gly Asp Leu Arg Gln Trp Arg Asn Ile Asp Glu Asn Glu Lys
                165                 170                 175

Glu Tyr Leu Val Gln Ile Ser Pro Pro Ala Asp Val Ile Pro Glu Ile
            180                 185                 190

Ile Arg Ser Leu Val Leu Ser Lys Asn Val Thr Asn Ala Ala Ile Leu
        195                 200                 205
```

Phe Asp Asp Ser Phe Val Met Asp His Lys Tyr Lys Ser Leu Leu Gln
    210                 215                 220

Asn Val Ala Thr Arg His Val Ile Ala Pro Ile Lys Glu Ala Asp Lys
225                 230                 235                 240

Ile Gly Asp Gln Leu Arg Gln Leu Arg Lys Leu Asp Ile Val Asn Phe
                245                 250                 255

Phe Ile Leu Gly Ser Phe Glu Asn Ile Lys Arg Val Leu Asp Ala Ala
                260                 265                 270

Asp Ser Val Gly Phe Phe Asn Arg Lys Phe Ser Trp His Ala Ile Thr
            275                 280                 285

Gln Asp Lys Gly Glu Leu Lys Cys Asn Cys Arg Asn Ala Thr Ile Thr
    290                 295                 300

Leu Ala Lys Pro Leu Ile Asp Ala Gln Tyr Gln Asp Arg Leu Gly Leu
305                 310                 315                 320

Ile Lys Thr Ser Tyr Gln Leu Asn Ala Glu Pro Glu Ile Ala Ala Ala
                325                 330                 335

Phe Tyr Phe Asp Leu Ala Leu Tyr Ser Phe Leu Ala Val Lys Glu Met
                340                 345                 350

Ile Ala Asp Gly Val Trp Lys Arg Asn Asn Ala Thr Asn Tyr Ile Thr
            355                 360                 365

Cys Asp Asp Phe Asp Gly Lys Asn Thr Pro Arg Arg Ala Gly Leu Asn
    370                 375                 380

Leu Lys Lys Tyr Phe Ser Lys Glu Val Ser Glu Thr Pro Thr Tyr Gly
385                 390                 395                 400

Pro Ile Ser Ile Val Ser Asn Gly Tyr Ser Phe Met Glu Phe Thr Met
                405                 410                 415

Gln Ile Ser Ala Val Gly Val Arg Glu Ser Ser Ser Asp Lys Ser Val
            420                 425                 430

Pro Leu Gly Ser Trp Lys Ala Gly Tyr Asp Asn Asn Leu Thr Leu Val
            435                 440                 445

Asp Pro Gln Ile Met Lys Asn Tyr Thr Ala Asp Val Val Tyr Arg Val
    450                 455                 460

Val Thr Val Glu Gln Lys Pro Phe Ile Ile Lys Asp Glu Thr Ala Pro
465                 470                 475                 480

Lys Gly Tyr Lys Gly Tyr Cys Ile Asp Leu Ile Gln Arg Ile Ser Glu
                485                 490                 495

Ile Leu Asn Phe Asp Tyr Glu Ile Thr Pro Val Gly Asp Gln Lys Phe
                500                 505                 510

Gly Asn Met Asp Glu Asn Gly Lys Trp Asn Gly Val Val Arg Glu Leu
            515                 520                 525

Met Glu Lys Arg Ala Asp Ile Gly Leu Gly Ser Met Ser Val Met Ala
    530                 535                 540

Glu Arg Glu Asn Val Ile Asp Phe Thr Val Pro Tyr Tyr Asp Leu Val
545                 550                 555                 560

Gly Ile Thr Ile Leu Met Lys Leu Pro Lys Thr Pro Thr Ser Leu Phe
                565                 570                 575

Lys Phe Leu Thr Val Leu Glu Asn Glu Val Trp Leu Cys Ile Leu Ala
            580                 585                 590

Ala Tyr Phe Phe Thr Ser Phe Leu Met Trp Val Phe Asp Arg Trp Ser
            595                 600                 605

Pro Tyr Ser Tyr Gln Asn Asn Arg Glu Lys Tyr Lys Asp Asp Glu Glu
    610                 615                 620

Lys Arg Glu Phe Asn Leu Lys Glu Cys Leu Trp Phe Cys Met Thr Ser
625                 630                 635                 640

Leu Thr Pro Gln Gly Gly Glu Ala Pro Lys Asn Leu Ser Gly Arg
            645                 650                 655

Leu Val Ala Ala Thr Trp Trp Leu Phe Gly Phe Ile Ile Ile Ala Ser
        660                 665                 670

Tyr Thr Ala Asn Leu Ala Ala Phe Leu Thr Val Ser Arg Leu Asp Thr
        675                 680                 685

Pro Ile Glu Ser Leu Asp Asp Leu Ser Lys Gln Tyr Lys Ile Gln Tyr
690                 695                 700

Ala Pro Leu Asn Gly Ser Ser Thr Met Thr Tyr Phe Glu Arg Met Ala
705                 710                 715                 720

Asn Ile Glu Ala Lys Phe Tyr Glu Ile Trp Lys Asp Met Ser Leu Asn
            725                 730                 735

Asp Ser Leu Ser Glu Val Glu Arg Ala Lys Leu Ala Val Trp Asp Tyr
            740                 745                 750

Pro Val Ser Asp Lys Tyr Thr Lys Met Trp Gln Ala Met Lys Glu Ala
        755                 760                 765

Gly Leu Pro Asn Thr Leu Asp Glu Ala Val Lys Arg Val Lys Asp Ser
770                 775                 780

Arg Ser Ser Ser Glu Gly Phe Ala Tyr Leu Gly Asp Ala Thr Asp Ile
785                 790                 795                 800

Arg Tyr Leu Glu Ile Thr Ser Cys Asp Leu Gln Met Val Gly Glu Glu
            805                 810                 815

Phe Ser Arg Lys Pro Tyr Ala Ile Ala Val Gln Gln Gly Ser Pro Leu
        820                 825                 830

Lys Asp Gln Phe Asn Thr Ala Ile Leu Gln Leu Leu Asn Arg Arg Glu
        835                 840                 845

Leu Glu Arg Leu Lys Glu Lys Trp Trp Ser Lys Asn Pro Glu Ala Lys
850                 855                 860

Lys Cys Asp Lys Gln Glu Asp Gln Ser Asp Gly Ile Ser Ile Gln Asn
865                 870                 875                 880

Ile Gly Gly Val Phe Ile Val Ile Phe Val Gly Ile Gly Leu Ala Cys
            885                 890                 895

Ile Thr Leu Ala Phe Glu Tyr Trp Trp Tyr Lys Tyr Arg Lys Gly Gly
        900                 905                 910

Lys Val Val Asp Val Gln Ala Lys His Ser Asp Val Ala Thr Lys Ile
        915                 920                 925

Asn Asp Gly Phe His Ala Lys Ile Asn Lys Leu Tyr Pro Arg Ser Arg
930                 935                 940

Phe
945

<210> SEQ ID NO 12
<211> LENGTH: 928
<212> TYPE: PRT
<213> ORGANISM: Nasonia vitripennis

<400> SEQUENCE: 12

Met Tyr Arg Arg Gly Cys Ser Lys Gly Leu Ser Leu Leu Leu Ile Gly
1               5                   10                  15

Lys Leu Val Leu Leu Val Gly Gly Gln Gln Thr Thr Asp Thr Ala Ala
            20                  25                  30

Asn Arg Pro Val Asn Val Phe Val Ile Asn Asp Ala Asn Asn Asp Val
        35                  40                  45

```
Ala Asn Lys Ser Val Thr Asn Ser Leu Lys Ala Leu Lys Glu Lys Ser
     50                  55                  60

Pro Asp Lys Leu Gly Gln Val Tyr Val Ala Gln Ile Asn Val Ser Asp
 65                  70                  75                  80

Ser Asp Gln Ser Leu Asp Ala Ile Cys Ser Leu Trp Gln Ser Ser Ile
                 85                  90                  95

Arg Glu Asn Glu Ala Asp Ala Pro Asp Phe Val Leu Asp Thr Thr Thr
            100                 105                 110

Tyr Gly Ile Gly Ala Glu Ser Val Asn Arg Phe Thr Ala Leu Leu Gly
        115                 120                 125

Ile Pro Thr Leu Ser Ala Gln Phe Gly Gln Glu Gly Asp Leu Leu Gly
    130                 135                 140

Trp Arg Asp Ile Ser Glu Glu Gln Lys Arg Tyr Leu Val Gln Val Met
145                 150                 155                 160

Asn Pro Ala Asp Leu Met Pro Glu Val Ile Arg Gln Gln Cys Ser Asn
                165                 170                 175

Phe Asn Ile Ser Asn Ala Ala Ile Leu Phe Asp Glu Asn Phe Val Met
                180                 185                 190

Asp His Lys Tyr Lys Ser Leu Leu Leu Asn Val Pro Thr Arg His Val
            195                 200                 205

Ile Val Pro Ala Glu Pro Ala Gly Ala Pro Leu Gln Lys Gln Ile Ser
    210                 215                 220

Lys Leu Arg Asp Leu Asp Ile Val Asn Phe Phe Ile Leu Gly Ser Glu
225                 230                 235                 240

Ser Thr Ile Ser Ser Ala Leu Ile Glu Ala Asn Asn Leu Asn Phe Thr
                245                 250                 255

Gly His Lys Tyr Gly Trp Phe Gly Ile Thr Leu Asn Glu Glu Phe Gln
            260                 265                 270

Ala Gln Cys Gln Asp Cys Arg Asn Ile Ser Leu Leu Leu Phe Lys Pro
        275                 280                 285

Lys Ala Glu Ser Ser Gln Gln Leu Ser Glu Leu Thr Ser Lys Gly Ser
    290                 295                 300

Leu Pro Lys Pro Val Ile Ser Ser Ala Phe Tyr Tyr Asp Leu Thr Lys
305                 310                 315                 320

Leu Gly Val Leu Ala Met Lys Ser Ala Leu Met Ser Gly Glu Trp His
                325                 330                 335

Arg Pro Arg Phe Ile Thr Cys Asp Glu Tyr Asn Glu Asn Ala Thr Leu
            340                 345                 350

Pro Ala Arg Asn Leu Asn Leu Arg Gln Arg Leu Glu Gln Val Ala Asn
        355                 360                 365

Ser Ser Gly Phe Thr Arg Thr Tyr Ala Ser Phe Ala Trp Gly Arg Asn
    370                 375                 380

Gly Val Ser Arg Ala Lys Phe Gly Val Asn Gly Leu Leu Ile Arg Ile
385                 390                 395                 400

Arg Asp Ser Lys Leu Ile Ser Ser Asp Pro Val Glu Thr Trp Glu Ala
                405                 410                 415

Gly Val Asp Ser Gln Leu Lys Val Leu Asp Glu Asn Lys Ala Gly Asn
            420                 425                 430

His Thr Ala Val Thr Ser Tyr Arg Val Val Thr Val Ile Lys Pro Pro
        435                 440                 445

Phe Val Met Tyr Asp Asn Glu Thr Gly Asn Trp Thr Gly Tyr Cys Ile
    450                 455                 460
```

Asp Leu Leu Asp Glu Ile Arg Glu His Val Lys Phe Glu Tyr Glu Ile
465                 470                 475                 480

Arg Glu Val Asp Asp Lys Glu Tyr Gly Asn Met Asp Glu Asp Gly Asn
            485                 490                 495

Trp Asn Gly Met Val Arg Glu Leu Lys Glu Lys Lys Ala Asp Ile Ala
        500                 505                 510

Leu Gly Ala Leu Ala Val Met Ala Glu Arg Glu Asn Val Ile Asp Tyr
    515                 520                 525

Thr Val Pro Tyr Tyr Asp Leu Val Gly Ile Ser Ile Leu Arg Lys Lys
530                 535                 540

Pro Lys Thr Ala Thr Ser Leu Phe Lys Phe Leu Thr Val Leu Glu Ser
545                 550                 555                 560

Asp Val Trp Leu Cys Ile Leu Gly Ala Tyr Phe Phe Thr Ser Leu Leu
                565                 570                 575

Met Trp Ile Phe Asp Lys Phe Ser Pro Tyr Ser Tyr Gln Asn Asn Met
                580                 585                 590

Glu Lys Tyr Lys Asp Asp Asp Lys Arg Leu Phe Thr Met Lys Glu
            595                 600                 605

Cys Leu Trp Phe Cys Met Thr Ser Leu Thr Pro Gln Gly Gly Gly Glu
    610                 615                 620

Ala Pro Lys Asn Leu Ser Gly Arg Leu Val Ala Ala Thr Trp Trp Leu
625                 630                 635                 640

Phe Gly Phe Ile Ile Ile Ala Ser Tyr Thr Ala Asn Leu Ala Ala Phe
                645                 650                 655

Leu Thr Val Ser Arg Leu Asp Ala Pro Val Glu Ser Leu Glu Asp Leu
                660                 665                 670

Ser Lys Gln Tyr Lys Ile Gln Tyr Ala Pro Ile Leu Asn Ser Ser Glu
    675                 680                 685

Tyr Arg Tyr Phe Glu Arg Met Ala Asn Ile Glu Lys Lys Phe Tyr Glu
    690                 695                 700

Ile Trp Lys Asp Met Ser Leu Asn Asp Ser Leu Ser Asp Val Glu Arg
705                 710                 715                 720

Ala Lys Leu Ala Val Trp Asp Tyr Pro Val Ser Asp Lys Tyr Thr Lys
                725                 730                 735

Met Phe Gln Thr Met Gln Asp Ala Gly Phe Pro Asn Asp Met Asp Glu
                740                 745                 750

Ala Leu Arg Arg Val Arg Glu Gly Lys Pro Thr Glu Phe Ala Phe Ile
    755                 760                 765

Gly Asp Ala Thr Asp Ile Lys Tyr Leu Thr Met Thr Asp Cys Thr Phe
770                 775                 780

Met Gln Ile Gly Glu Glu Phe Ser Arg Lys Pro Tyr Ala Ile Ala Val
785                 790                 795                 800

Gln Gln Gly Ser Pro Leu Lys Asp Gln Phe Asn Asn Ala Ile Leu Met
            805                 810                 815

Met Leu Asn Arg Arg Lys Leu Glu Lys Leu Lys Asp Thr Trp Trp Asn
            820                 825                 830

Lys Asn Pro Lys Arg Lys Arg Cys Asn Lys Ala Glu Asp Gln Ser Asp
            835                 840                 845

Gly Ile Ser Ile Gln Asn Ile Gly Gly Val Phe Ile Val Ile Phe Val
            850                 855                 860

Gly Ile Gly Leu Ala Cys Val Thr Leu Ile Phe Glu Tyr Phe Tyr Tyr
865                 870                 875                 880

Arg Arg Arg Pro Gln Ile Lys Lys Arg His Gln Glu Ser Arg Thr Asp

```
                        885                 890                 895
Lys Thr Lys Ser Val Gln Ser Val Lys Ser Met Lys Phe Asn Leu Arg
                    900                 905                 910

Pro Ala Pro Thr Gln Ser Leu Glu Asn Thr Asn Tyr Arg Ser Arg Phe
                915                 920                 925

<210> SEQ ID NO 13
<211> LENGTH: 482
<212> TYPE: PRT
<213> ORGANISM: Nasonia vitripennis

<400> SEQUENCE: 13

Met Asn Ala Thr Ala Lys Pro Thr Tyr Arg Val Ile Thr Ile Pro Lys
 1               5                  10                  15

Pro Pro Phe Val Ile Tyr Asp Pro Asp Ser Asn Trp Tyr Gly Gly Phe
                20                  25                  30

Leu Val Asp Leu Leu Asn Glu Ile Ala Arg Arg Leu Asn Phe Arg Tyr
             35                  40                  45

Glu Ile Glu Met Gln Asn Glu Ser Glu Tyr Gly Phe Met Asp Asp Gln
 50                  55                  60

Gly Asn Trp Asn Gly Leu Met Arg Asp Leu Lys Glu Gly Lys Ala Asp
 65                  70                  75                  80

Ile Gly Leu Ala Ala Val Ser Val Met Ser Glu Arg Met Lys Val Val
                 85                  90                  95

Asp Phe Thr Glu Pro Ile Tyr Lys Pro Thr Gly Ile Ser Val Leu Met
                100                 105                 110

Gln Lys Pro Ile Pro Lys Thr Asp Phe Tyr Arg Phe Leu Thr Val Leu
            115                 120                 125

Glu Leu Asp Val Trp Leu Cys Ile Ile Gly Ala Tyr Ile Phe Thr Ser
        130                 135                 140

Leu Leu Leu Trp Ile Phe Asp Thr Trp Ser Pro Tyr Ser Tyr Arg Asn
145                 150                 155                 160

Cys Lys Ala Lys Tyr Lys Asp Asp Thr Glu Lys Arg Ile Phe Gly Cys
                165                 170                 175

Lys Glu Ser Leu Trp Phe Cys Leu Thr Ser Leu Thr Pro Gln Gly Gly
            180                 185                 190

Gly Glu Ala Pro Lys Asn Leu Ser Gly Arg Leu Val Ala Ala Thr Trp
        195                 200                 205

Trp Leu Phe Gly Phe Ile Ile Ile Ala Ser Tyr Thr Ala Asn Leu Ala
210                 215                 220

Ala Phe Leu Thr Ile Ser Lys Phe Glu Lys Thr Ile Glu Thr Phe Asp
225                 230                 235                 240

Asp Leu Ile Ser Gln Tyr Lys Tyr Ser Tyr Thr Cys Ile Gln Asn Ser
                245                 250                 255

Ser Thr Asn Arg Tyr Phe Gln Arg Met Asn Asp Ile Glu Tyr Val Cys
            260                 265                 270

Tyr Glu Lys Trp Lys Asp Met Thr Leu Asn Asp Ser Leu Ser Pro Tyr
        275                 280                 285

Glu Arg Ala Gln Leu Ala Val Trp Glu Tyr Pro Leu Ser Asp Lys Phe
    290                 295                 300

Ile Lys Ile Tyr Ser Ala Ile Ser His His Gly Met Val Ala Ser Leu
305                 310                 315                 320

Gln Asp Gly Leu Asp Lys Phe Asn Ser Thr Asp Ser Arg Phe Ala Leu
                325                 330                 335
```

-continued

```
Ile Thr Glu Ala Ser Asp Val Gln Tyr Gln Ala Met Ile Asp Cys Ser
            340                 345                 350

Val Lys Glu Ile Gly Pro Glu Phe Ser Lys Lys Pro Tyr Ala Ile Val
        355                 360                 365

Leu Gln Lys Asn Ser Pro Leu Thr Lys Gln Phe Asn Arg Ile Ile Tyr
    370                 375                 380

Asn Met Lys Asn Asp Asn Trp Leu Glu Ala Leu Thr Asp Lys Trp Trp
385                 390                 395                 400

Lys Tyr Asn Pro Leu Arg Gln Arg Cys His Asp Lys Asp Glu Met Thr
                405                 410                 415

Asn Gly Ile Ile Phe Glu Asn Ile Gly Gly Val Phe Val Leu Ile Gly
            420                 425                 430

Val Gly Ile Leu Ser Ala Phe Ser Thr Leu Val Tyr Glu Tyr Phe Tyr
        435                 440                 445

Phe Lys Cys Leu Gln Asp Lys Phe Glu Arg Ile Phe Glu His Lys Leu
    450                 455                 460

Lys Ser Ile Phe Arg Arg Gln Lys Asn Phe Ala Arg Ser Ile Ser Val
465                 470                 475                 480

Lys Pro

<210> SEQ ID NO 14
<211> LENGTH: 920
<212> TYPE: PRT
<213> ORGANISM: Apis mellifera

<400> SEQUENCE: 14

Met Tyr Lys Pro Ile Arg Gly Ile Thr Ile Leu Leu Trp Ile Asn Thr
1               5                   10                  15

Leu Phe Asn Ile Gly Thr Ser Gln Asn Val Gln Thr Val Asn Ile Leu
            20                  25                  30

Phe Ile Asn Asp Arg Thr Asn Glu Val Ala Glu Asp Thr Leu Asn Val
        35                  40                  45

Ala Leu Asn Tyr Ile Arg Arg Asn Pro Arg Val Gly Leu Met Ile Asp
    50                  55                  60

Gly Leu Tyr Ser Val Lys Ile Gly Gly Asp Ala Ser Ala Ile Leu
65                  70                  75                  80

Glu Thr Leu Cys Val Asn Tyr Asn Ala Ser Ile Arg Asn Asn Lys Pro
                85                  90                  95

Pro His Leu Val Ile Asp Thr Thr Ile Asn Gly Val Ala Ser Glu Ala
            100                 105                 110

Val Lys Ser Phe Thr Ala Ala Leu Ala Leu Pro Thr Val Ser Ala Ser
        115                 120                 125

Tyr Gly Gln Thr Gly Asp Ile Arg Gln Trp Arg Asn Leu Asp Gly Glu
    130                 135                 140

Gln Gln Lys Tyr Leu Ile Gln Ile Ser Pro Pro Ala Asp Leu Ile Pro
145                 150                 155                 160

Glu Ile Val Arg Ser Ile Val Val Ala Gln Asn Ile Thr Asn Ala Gly
                165                 170                 175

Ile Met Phe Asp Asp Thr Phe Val Met Asp His Lys Tyr Lys Ser Leu
            180                 185                 190

Leu Gln Asn Ile Pro Thr Arg His Ile Ile Ala Ala Ile Asp Asp Thr
        195                 200                 205

Thr Ser Ile Lys Leu His Leu Thr Arg Phe Arg Asp Val Asp Ile Val
    210                 215                 220
```

```
Asn Phe Phe Val Leu Gly Lys Leu Ser Ile Ile Lys Ser Val Leu Asp
225                 230                 235                 240

His Ala Asn Ser Asn Lys Leu Phe Gly Arg Lys Tyr Ala Trp His Val
            245                 250                 255

Ile Thr Gln Asp Lys Gly Ser Leu Lys Cys Gly Cys Ser Asn Ala Thr
                260                 265                 270

Ile Leu Phe Val Lys Pro Glu Pro Asp Ala Gly Ser Arg Glu Arg Leu
            275                 280                 285

Ser Asn Leu Arg Thr Thr Tyr Gly Leu Thr Ser Thr Pro Glu Leu Lys
        290                 295                 300

Ala Ala Phe Tyr Phe Asp Phe Tyr Arg Ser Leu Leu Ala Ile Arg
305                 310                 315                 320

Ser Met Met Asn Ser Gly Glu Trp Pro Thr Asn Val Thr Tyr Thr Thr
                325                 330                 335

Cys Asp Glu Tyr Asn Glu Glu Asn Pro Leu Pro Arg Arg Asn Val Asp
                340                 345                 350

Leu Arg Arg Tyr Leu Lys Asp Met Thr Glu Pro Pro Ser Tyr Ala Pro
            355                 360                 365

Phe Leu Ile Asp Thr Asn Gly His Ser Tyr Glu Glu Phe Thr Met Arg
370                 375                 380

Leu Glu Lys Val Thr Val Leu Asn Ser Gln Ser Val Ser Ala Glu Asn
385                 390                 395                 400

Val Gly Ser Trp Lys Ala Ser Leu Asn Ser Pro Ile Ile Val Lys Asp
                405                 410                 415

Ala Ala Asn Met Thr His Phe Ser Ala Val Thr Val Tyr Arg Val Val
                420                 425                 430

Thr Val Leu Gln Asn Pro Phe Met Ile Gln Ile Asp Asp Glu Asp Gly
            435                 440                 445

Lys Gly Val Lys Phe Lys Gly Tyr Cys Ile Asp Leu Ile Glu Glu Ile
            450                 455                 460

Arg Lys Leu Ile Gly Phe Glu Tyr Glu Ile Tyr Ile Ala Pro Asp Asn
465                 470                 475                 480

Asn Phe Gly Asn Met Asp Glu Asn Gly Gln Trp Asn Gly Met Val Lys
                485                 490                 495

Glu Leu Val Glu Lys Arg Ala Asp Ile Ala Leu Gly Ser Leu Ser Val
            500                 505                 510

Met Ala Glu Arg Glu Asn Val Val Asp Phe Thr Val Pro Tyr Tyr Asp
            515                 520                 525

Leu Val Gly Ile Thr Ile Leu Met Lys Lys Pro Gln Thr Pro Thr Ser
        530                 535                 540

Leu Phe Lys Phe Leu Thr Val Leu Glu Asn Asp Val Trp Met Cys Ile
545                 550                 555                 560

Leu Gly Ala Tyr Phe Phe Thr Ser Phe Leu Met Trp Val Phe Asp Arg
                565                 570                 575

Trp Ser Pro Tyr Ser Tyr Gln Asn Asn Arg Ile Lys Tyr Lys Asp Asp
            580                 585                 590

Glu Glu Lys Arg Glu Phe Asn Leu Lys Glu Cys Leu Trp Phe Cys Met
            595                 600                 605

Thr Ser Leu Thr Pro Gln Gly Gly Gly Glu Ala Pro Lys Asn Leu Ser
            610                 615                 620

Gly Arg Leu Val Ala Ala Thr Trp Trp Leu Phe Gly Phe Ile Ile Ile
625                 630                 635                 640

Ala Ser Tyr Thr Ala Asn Leu Ala Ala Phe Leu Thr Val Ser Arg Leu
```

```
                645                 650                 655
Asp Thr Pro Val Glu Ser Leu Asp Leu Ser Lys Gln Tyr Lys Ile
            660                 665                 670
Gln Tyr Ala Pro Leu Asn Gly Ser Ala Met Thr Tyr Phe Gln Arg
            675                 680                 685
Met Ala Asp Ile Glu Thr Arg Phe Tyr Glu Ile Trp Lys Asp Met Ser
        690                 695                 700
Leu Asn Asp Ser Leu Ser Glu Val Glu Arg Ala Lys Leu Ala Val Trp
705                 710                 715                 720
Asp Tyr Pro Val Ser Asp Lys Tyr Thr Lys Met Trp Gln Ala Met Lys
                725                 730                 735
Glu Ala Lys Leu Pro Asn Thr Leu Glu Glu Ala Ile Glu Arg Val Gln
            740                 745                 750
Ser Ser Lys Ser Ser Glu Gly Phe Ala Tyr Leu Gly Asp Ala Thr
            755                 760                 765
Asp Ile Arg Tyr Gln Val Met Ile Asp Cys His Leu Gln Met Val Gly
        770                 775                 780
Asp Glu Phe Ser Arg Lys Pro Tyr Ala Ile Ala Val Gln Gln Gly Ser
785                 790                 795                 800
Pro Leu Lys Asp Gln Phe Asn Asn Ala Ile Leu Leu Leu Asn Lys
                805                 810                 815
Arg Lys Leu Glu Lys Leu Lys Glu Thr Trp Trp Asn Leu Asn Pro Glu
            820                 825                 830
Arg Ile Gln Cys Glu Lys Gln Asp Asn Gln Ser Asp Gly Ile Ser Ile
        835                 840                 845
His Asn Ile Gly Gly Val Phe Ile Val Ile Phe Val Gly Ile Gly Leu
850                 855                 860
Ala Cys Phe Thr Leu Ala Phe Glu Tyr Trp Trp Tyr Lys Tyr Lys Lys
865                 870                 875                 880
Ser Ser Arg Ile Ile Asp Ile Ala Met Val Ile Asn Glu Asn Cys Ile
                885                 890                 895
Tyr Pro Ile Gly Tyr Ile Ser Val Gly Thr Asn Leu Met Ala Asn Ile
            900                 905                 910
Gln Arg Val Met His Ile Gly Tyr
            915                 920

<210> SEQ ID NO 15
<211> LENGTH: 942
<212> TYPE: PRT
<213> ORGANISM: Daphnia pulex

<400> SEQUENCE: 15

Met Arg Ser Phe Gln Leu Leu Val Leu Gly Leu Ala Phe Ala Val
1               5                   10                  15
Gln Ser Ala Asp Pro Ile Arg Val Leu Leu Val Tyr Glu Thr Asn Asn
            20                  25                  30
Val Asp Ala Asp Arg Ala Phe Thr Ala Val Gln Ser Tyr Leu Glu Arg
        35                  40                  45
Thr Lys Val Gln Gly Leu Ser Leu Gly Asn Val Thr Arg Val Thr Leu
    50                  55                  60
Asp Ser Thr Gln Lys Tyr Leu Thr Val Asp Asp Val Cys Ser Val Tyr
65                  70                  75                  80
Asp Lys Ser Ile Asp Ala Gly Thr Pro Pro His Ile Val Leu Asp Leu
                85                  90                  95
```

```
Thr Trp Ser Gly Leu Ser Ser Glu Val Met Lys Ala Leu Thr Arg Asn
            100                 105                 110

Leu Gly Leu Pro Thr Ile Ser Gly Ser Tyr Gly Gly Ile Gly Asp Leu
        115                 120                 125

Lys His Trp Ser Asn Ile Asp Gly Asn Gln Thr Lys Tyr Leu Val Gln
    130                 135                 140

Val Met Pro Pro Ser Asp Ile Ile Pro Gln Leu Val Ala Leu Ile Thr
145                 150                 155                 160

Ser Met Gln Asn Met Thr Asn Ala Ala Ile Leu Tyr Asp Asp Ser Phe
                165                 170                 175

Asp Met Leu Asn Lys Tyr Lys Ser Leu Leu Lys Asn Arg Pro Ile Arg
            180                 185                 190

His Met Phe Ser Lys Ile Glu Thr Asn Ile Asn Thr Gln Ile Arg Arg
        195                 200                 205

Leu Glu Asp Met Asp Ile Val Asn Phe Phe Val Leu Gly Lys Ile Asp
    210                 215                 220

Arg Ile Asn Gln Val Leu Met Ser Ala Ala Gln Glu Asn Tyr Phe Gly
225                 230                 235                 240

Lys Lys Tyr Ser Trp Thr Ala Ile Ser Lys Asp Gly Ser Ala Glu Pro
                245                 250                 255

Phe Val Arg Thr Glu Asn Gly Ser Ile Leu Phe Ala Val Pro Thr Val
            260                 265                 270

Asn Pro Asp Val Ala Asn Gly Ile Leu Phe Lys Thr Ser Gly Leu Asn
        275                 280                 285

Asn Gly Tyr Ser Val Asp Thr Gly Phe Tyr Phe Asp Leu Ile Leu Arg
    290                 295                 300

Ala Ile Thr Thr Val Lys Asn Met Leu Asp Gly Asn Thr Trp Pro Val
305                 310                 315                 320

Asp Met Ser Tyr Ser Lys Cys Ser Met Thr Asn Ile Thr Ala Val Thr
                325                 330                 335

Arg Asn Asn Phe Asp Leu Arg Lys Ala Phe Ala Asp Thr Asn Val Gly
            340                 345                 350

Ser Thr Phe Ala Asn Met Ile Leu Asn Gly Asn Gly Lys Ser Tyr Pro
        355                 360                 365

Gln Val Glu Met Thr Ile Asn Gln Met Asn Phe Lys Asn Ser Arg Leu
    370                 375                 380

Glu Ser Lys Asn Ala Leu Gly Ile Trp Lys Ala Gly Met Pro Gly Glu
385                 390                 395                 400

Ile Ser Phe Ser Pro Gly Gln Ser Leu Arg Pro Phe Gln Val Ile Ser
                405                 410                 415

Val Phe Lys Ile Ala Val Val Gln Ala Pro Phe Ile Met Lys Arg
            420                 425                 430

Lys Ala Asn Gly Thr Val Thr Phe Tyr Gly Tyr Cys Val Asp Leu Ile
        435                 440                 445

Lys Asp Ile Gln Ala Ile Met Gly Phe Glu Tyr Glu Leu Tyr Glu Val
    450                 455                 460

Pro Asp Gly Lys Tyr Gly Asn Met Asp Ser Lys Met Asn Trp Asn Gly
465                 470                 475                 480

Met Ile Lys Glu Leu Met Glu Lys Arg Ala Asp Ile Gly Leu Gly Ala
                485                 490                 495

Leu Ala Val Met Ala Glu Arg Glu Asn Val Ile Asp Phe Thr Val Pro
            500                 505                 510

Tyr Tyr Asp Leu Val Gly Ile Ser Ile Leu Met Ala Lys Pro Gln Val
```

-continued

```
            515                 520                 525
Ser Thr Ser Leu Phe Lys Phe Leu Thr Val Leu Glu Asn Asp Val Trp
        530                 535                 540
Gly Cys Ile Leu Ala Ala Tyr Phe Phe Thr Ser Ile Leu Leu Trp Ile
545                 550                 555                 560
Phe Asp Arg Trp Ser Pro Tyr Ser Tyr Gln Asn Asn Lys Glu Lys Tyr
                565                 570                 575
Ala Asp Asp Pro Glu Glu Lys Arg Glu Phe Ser Leu Lys Glu Ser
            580                 585                 590
Leu Trp Phe Cys Met Thr Ser Leu Thr Pro Gln Gly Gly Glu Ser
        595                 600                 605
Pro Lys His Leu Ser Gly Arg Leu Ile Ala Ala Thr Trp Trp Leu Phe
    610                 615                 620
Gly Phe Ile Ile Ile Ala Ser Tyr Thr Ala Asn Leu Ala Ala Phe Leu
625                 630                 635                 640
Thr Val Ser Arg Leu Asp Ser Pro Val Asn Ser Leu Asp Asp Leu Ser
                645                 650                 655
Thr Gln Tyr Lys Val Gln Tyr Ala Pro Gln Asn Gly Thr Asp Val Ala
            660                 665                 670
Thr Tyr Phe Glu Arg Met Ala Tyr Ile Glu Lys Arg Phe Tyr Glu Ile
        675                 680                 685
Trp Lys Asp Met Ser Leu Asn Asp Ser Met Asn Glu Val Glu Arg Ser
    690                 695                 700
Lys Leu Ala Val Trp Asp Tyr Pro Val Ser Asp Lys Tyr Thr Lys Ile
705                 710                 715                 720
Trp Gln Ser Met Gln Asp Ala Gly Leu Pro His Thr Phe Asp Glu Ala
                725                 730                 735
Leu Thr Arg Val Arg Ala Ser Asn Ala Glu Asn Asp Gly Phe Ala
            740                 745                 750
Phe Leu Gly Asp Ala Thr Asp Ile Arg Tyr Gln Val Leu Val Asn Cys
        755                 760                 765
Asp Leu Gln Met Val Gly Glu Glu Phe Ser Arg Lys Pro Tyr Ala Val
    770                 775                 780
Ala Val Gln Glu Gly Ser Pro Leu Arg Asp Leu Leu Asn Asp Ala Ile
785                 790                 795                 800
Leu Arg Leu Leu Asn Gln Arg Arg Leu Glu Thr Leu Lys Glu Arg Trp
                805                 810                 815
Trp Thr Asp Asn Pro Glu Lys Gln Glu Cys Gly Asp Thr Asn Asp Gln
            820                 825                 830
Ser Asp Gly Ile Ser Ile Gln Asn Ile Gly Gly Val Phe Ile Val Ile
        835                 840                 845
Phe Val Gly Ile Phe Leu Ala Cys Val Thr Leu Ala Ile Glu Tyr Cys
    850                 855                 860
Tyr Phe Lys Val Arg Arg Asn Pro Glu Gly Asp Glu Val Val Ser Thr
865                 870                 875                 880
Pro Glu Ser Arg Asn Asn Ala Ala Gly Asn Arg Asn Lys Leu Asp Asp
                885                 890                 895
Ala Tyr Val Lys Asn Ser Gln Lys Pro Phe Val Leu Asp Asp Asn Ser
            900                 905                 910
Lys Asp Pro Tyr Ala Gly Asp Tyr Gly Tyr Tyr Gly Ala Lys Lys Glu
        915                 920                 925
Leu Glu Leu Glu Gly Asp Gly Pro Arg Pro Arg Lys Ala Trp
    930                 935                 940
```

<210> SEQ ID NO 16
<211> LENGTH: 655
<212> TYPE: PRT
<213> ORGANISM: Capitella capitata

<400> SEQUENCE: 16

| | | | | | | | | | | | | | | |
|---|---|---|---|---|---|---|---|---|---|---|---|---|---|---|
| Met | Thr | Leu | Leu | Lys | Val | Ser | Ala | Ala | Phe | Leu | Phe | Asp | Leu | Val | Ala |
| 1 | | | | 5 | | | | | 10 | | | | | 15 | |
| Phe | Ile | Gly | Glu | Thr | Ala | Asn | Ser | Leu | Leu | Ala | Ala | Gly | Asp | Trp | His |
| | | | 20 | | | | | 25 | | | | | 30 | | |
| Gln | Ile | Ser | Tyr | Pro | Asp | Cys | Phe | Thr | Phe | Glu | Lys | Thr | Asp | Lys | Val |
| | | | 35 | | | | | 40 | | | | | 45 | | |
| Ala | Gln | Asp | Gln | Ala | Val | Arg | Lys | Asp | Ala | Thr | Ser | Gly | Leu | Arg | Ala |
| | 50 | | | | | 55 | | | | | 60 | | | | |
| Pro | His | Asn | Ser | Val | Ser | Gln | Leu | Gly | Ser | Trp | Ser | Ala | Ala | Asp | Gly |
| 65 | | | | | 70 | | | | | 75 | | | | | 80 |
| Leu | Val | Thr | Leu | Asp | Gly | Pro | Ile | Thr | Asn | Lys | Asn | Ala | Lys | Lys | Thr |
| | | | | 85 | | | | | 90 | | | | | 95 | |
| Tyr | Arg | Ile | Val | Thr | Val | His | Glu | Pro | Pro | Phe | Ile | Phe | Arg | Ser | Lys |
| | | | 100 | | | | | 105 | | | | | 110 | | |
| Glu | Leu | Pro | Lys | Asn | Glu | Lys | Leu | Asp | Tyr | Tyr | Tyr | Asn | Glu | Glu |
| | | 115 | | | | | 120 | | | | | 125 | | | |
| Asn | Gln | Thr | Tyr | Tyr | Tyr | Gly | Tyr | Cys | Val | Asp | Leu | Ile | His | Arg | Ile |
| | 130 | | | | | 135 | | | | | 140 | | | | |
| Ser | Glu | Ile | Met | Asp | Phe | Glu | Tyr | Val | Ile | Tyr | Glu | Pro | Asp | Asp | Gly |
| 145 | | | | | 150 | | | | | 155 | | | | | 160 |
| Ala | Tyr | Gly | Thr | Met | Gln | Glu | Asp | Gly | Ser | Trp | Asn | Gly | Met | Val | Asn |
| | | | | 165 | | | | | 170 | | | | | 175 | |
| Glu | Leu | Ile | His | Asp | Val | Ser | Asn | Glu | Val | Cys | Leu | Val | Leu | Ser | Leu |
| | | | 180 | | | | | 185 | | | | | 190 | | |
| Leu | Tyr | Leu | Trp | His | Met | Phe | Tyr | Gln | Arg | Ala | Asp | Met | Ser | Val | Ala |
| | | 195 | | | | | 200 | | | | | 205 | | | |
| Thr | Leu | Ser | Val | Met | Ala | Glu | Arg | Glu | Asn | Val | Val | Asp | Phe | Thr | Val |
| | 210 | | | | | 215 | | | | | 220 | | | | |
| Pro | Tyr | Tyr | Asp | Leu | Val | Gly | Ile | Thr | Ile | Leu | Met | Gln | Lys | Pro | Lys |
| 225 | | | | | 230 | | | | | 235 | | | | | 240 |
| Phe | Glu | Tyr | Ser | Val | Phe | Lys | Phe | Met | Ser | Val | Leu | Glu | Asp | Ala | Val |
| | | | | 245 | | | | | 250 | | | | | 255 | |
| Trp | Gly | Cys | Ile | Leu | Ser | Ala | Phe | Ile | Ile | Val | Ser | Val | Leu | Leu | Ala |
| | | | 260 | | | | | 265 | | | | | 270 | | |
| Val | Phe | Asp | Lys | Phe | Ser | Pro | Tyr | Ser | Tyr | Gln | Asn | Asn | Arg | Ser | Ser |
| | | 275 | | | | | 280 | | | | | 285 | | | |
| Trp | Asp | Gly | Gln | Gly | Glu | Glu | Pro | Arg | Val | Phe | Ser | Leu | Lys | Glu | Gly |
| | 290 | | | | | 295 | | | | | 300 | | | | |
| Leu | Trp | Phe | Cys | Met | Thr | Ser | Leu | Thr | Pro | Gln | Gly | Gly | Gly | Glu | Ala |
| 305 | | | | | 310 | | | | | 315 | | | | | 320 |
| Pro | Arg | Ala | Leu | Ser | Gly | Arg | Leu | Val | Ala | Ala | Thr | Trp | Trp | Met | Phe |
| | | | | 325 | | | | | 330 | | | | | 335 | |
| Gly | Phe | Ile | Met | Ile | Ala | Thr | Tyr | Thr | Ala | Asn | Leu | Ala | Ala | Phe | Leu |
| | | | 340 | | | | | 345 | | | | | 350 | | |
| Thr | Val | Ser | Arg | Leu | Asp | Gln | Pro | Ile | Glu | Ser | Leu | Asp | Asp | Leu | Ala |
| | | 355 | | | | | 360 | | | | | 365 | | | |
| Glu | Gln | Phe | Lys | Thr | Lys | Tyr | Ala | Pro | Gln | Gln | Ser | Thr | Ser | Thr | Glu |

```
                370                 375                 380
Thr Tyr Phe Lys Arg Met Lys Asp Ile Glu Glu Lys Phe Tyr Ser Ile
385                 390                 395                 400

Trp Lys Ser Met Ser Leu Asn Asp Ser Leu Asp Gln Val Glu Arg Ala
                405                 410                 415

Lys Leu Ala Val Trp Asp Tyr Pro Val Ser Asp Lys Phe Thr Asn Met
                420                 425                 430

Trp Val Ser Met Ile Glu Ser Gly Phe Pro Lys Asp Phe Glu Ser Ala
                435                 440                 445

Lys Lys Arg Ile Leu Lys Gln Asp Gly Ser Thr Asp Glu Phe Ala Phe
                450                 455                 460

Ile Gly Asp Ala Thr Gln Asn Lys Tyr Ala Thr Leu Thr Asp Cys Asp
465                 470                 475                 480

Leu Trp Glu Val Gly Glu Glu Phe Ser Arg Lys Pro Tyr Ala Leu Ala
                485                 490                 495

Val Gln Glu Gly Ser Pro Leu Lys Asn Gln Leu Ser Ser Val Ile Leu
                500                 505                 510

Gln Leu Leu Asn Gln Arg Val Leu Glu Asp Leu Lys Thr Thr Trp Trp
                515                 520                 525

Glu Phe Asn Arg Leu Lys Cys Pro Lys Ile Glu Asp Glu Ser Asp Gly
                530                 535                 540

Ile Ser Ile Lys Asn Ile Gly Gly Val Phe Leu Val Ile Phe Ile Gly
545                 550                 555                 560

Ile Gly Leu Gly Leu Ile Thr Leu Ala Phe Glu Tyr Tyr Trp Tyr Lys
                565                 570                 575

Trp Leu Gln Gln Lys Lys Ala Ile Arg Ile Ile Tyr Lys Glu Thr Tyr
                580                 585                 590

Asn Thr His Thr Lys Pro Leu Phe Val Arg Ser Lys Ile Leu Pro Leu
                595                 600                 605

Pro Lys Val Thr Ile Leu Gln Thr Ala Gln Ile Leu His Gln Leu His
                610                 615                 620

Asn Asn Val Leu Pro Pro Leu Ile Ala Ala Cys Ile Asn His His Ser
625                 630                 635                 640

Val Ala His Leu His His Leu Arg His Ile Arg Pro Phe Arg Ile
                645                 650                 655

<210> SEQ ID NO 17
<211> LENGTH: 451
<212> TYPE: PRT
<213> ORGANISM: Lottia gigantia

<400> SEQUENCE: 17

Met Ile Tyr Val Pro Ile Cys Ile His Arg Ile Phe Glu Phe Leu Gln
1               5                   10                  15

Glu Pro Pro Phe Val Phe Arg Asn Thr Ser Gly Gln Glu Val Met Tyr
                20                  25                  30

Glu Gly Tyr Ser Ile Asp Val Met Asn Asp Val Ala Glu Arg Val Gly
                35                  40                  45

Phe Thr Tyr Thr Ile Arg Glu Cys Asp Gly Gly Val Tyr Gly Asn Leu
                50                  55                  60

Asp Ser Asp Gln Arg Trp Thr Gly Cys Val Gly Asn Ile Leu Lys Gly
65                  70                  75                  80

Asp Ala Asp Ile Ile Val Gly Ala Met Thr Val Thr Ala Asp Arg Glu
                85                  90                  95
```

```
Thr Val Val Asp Tyr Thr Leu Pro Tyr Tyr Asp Phe Ala Gly Ile Gln
            100                 105                 110

Ile Leu Met Arg Lys Gln Lys Gln Val Asn Ile Phe Tyr Phe Ala
        115                 120                 125

Asp Val Phe Ser Asn Ala Ala Trp Leu Cys Leu Gly Val Ile Ala
        130                 135                 140

Leu Thr Ser Ile Leu Leu Leu Phe Asp Lys Tyr Ser Pro Gly Pro
145                 150                 155                 160

Gly Phe Ser Lys Asn Val Glu Lys Arg Glu Phe Lys Phe Asn Leu
                165                 170                 175

His Glu Ser Ile Trp Phe Val Val Gly Ser Ile Thr Met Ala Gly Gly
            180                 185                 190

Gly Asp Pro Pro Arg Ser Phe Ser Ala Arg Leu Leu Val Ala Gly Phe
            195                 200                 205

Trp Phe Phe Ser Val Ile Met Met Ser Thr Phe Thr Ala Asn Leu Ala
210                 215                 220

Ala Phe Leu Thr Val Ser Arg Leu Gly Val Thr Val Ser Ser Leu Asp
225                 230                 235                 240

Asp Leu Ala Glu Gln Ser Asp Ile Lys Tyr Ser Val Val Ala Glu Ser
            245                 250                 255

Ser Val Ala Asn Tyr Phe Glu Arg Met Ala Ala Ile Glu Glu Asn Phe
            260                 265                 270

Tyr Ser Met Trp Lys Glu Met Ser Leu Gly Thr Ala Glu Asn Gly Asn
            275                 280                 285

Ser Ser Phe Ala Val Trp Asp Tyr Pro Leu Gly Asp Lys Tyr Val Thr
            290                 295                 300

Ile Trp Lys Ser Ile Arg Lys Thr Gly Phe Ile Lys Thr Ser Asp Ala
305                 310                 315                 320

Ala Ile Asp Lys Val Leu Ser Glu Asn Phe Ala Leu Leu Thr Asp Ser
            325                 330                 335

Pro Ile Ile Lys Tyr Ile Thr Ser Arg Asn Cys Glu Leu Thr Ala Ile
            340                 345                 350

Gly Asp Gln Phe Ser Val Arg Pro Tyr Ala Phe Ala Leu Lys Glu Lys
            355                 360                 365

Ser Val Tyr Thr Lys Lys Ile Ser Ala Ala Ile Leu Asp Leu Gln Gln
370                 375                 380

Asp Arg Lys Leu Glu Thr Tyr Lys Arg Lys Trp Trp Asp Asp Gly Lys
385                 390                 395                 400

Val Ser Cys Pro Glu Asp Thr Ser Asn Gln Gly Leu Asp Leu Gln Ser
            405                 410                 415

Leu Thr Gly Ser Phe Leu Val Val Met Gly Ile Val Ser Gly Val
            420                 425                 430

Ile Val Leu Gly Ile Glu Leu Leu Trp Ile Lys Ala Lys Val Thr Lys
            435                 440                 445

Lys Val Ile
    450

<210> SEQ ID NO 18
<211> LENGTH: 890
<212> TYPE: PRT
<213> ORGANISM: Lottia gigantia

<400> SEQUENCE: 18

Leu Met Thr Val Leu Ile Ala Tyr Leu Asn Cys Leu Leu His Val Arg
1               5                   10                  15
```

```
Ser Gln Thr His Arg Ile Val Val Ile Asp Asn Thr Ile Leu Glu
            20                  25                  30

Tyr Asn Lys Asn Ile Glu Lys Ile Leu Ser Asn Ser Asp Ser Leu Val
        35                  40                  45

Asp Gln Gly Val Asn Leu Ala Gln Thr Glu Phe Lys Ile Ile Ala
50                  55                  60

Asp Lys Asn Asp Ser Leu Val Thr Leu Asp Asn Val Cys Ala Glu Met
65                  70                  75                  80

Lys Lys Gly Ala Val Ala Leu Ile Asp Met Ser Ile Pro Ser Ser Ala
                85                  90                  95

Val Leu Leu Arg Ser Tyr Ala Ser Ser Leu Gly Ile Ala Tyr Ile Ser
            100                 105                 110

Val Val Asp Lys Ser Tyr Phe Arg Tyr Gly Ser Gly Asp Ser Thr Ile
            115                 120                 125

His Tyr Gln Ile Glu Pro Thr Ala Val Glu Ile Leu Gln Ile Val Ala
    130                 135                 140

Asp Ile Val Asn Phe Asp Asp Leu Asn Asn Val Ala Ile Val Tyr Asp
145                 150                 155                 160

Glu Thr Phe Asp Ile Gln Asn Thr Pro Arg Arg Ile Leu Thr Asn Val
                165                 170                 175

Pro Ala Gln His Leu Tyr Val Arg Met Ser Ser Asp Pro Thr Glu Thr
                180                 185                 190

Lys Arg Gln Val Glu Met Leu Lys Arg Ile Glu Ile Lys Asn Ile Phe
            195                 200                 205

Ile Ile Gly Asn Ser Arg Lys Ala Pro Asp Phe Leu Glu Val Ala Asn
            210                 215                 220

Val Ile Ser Asp Glu Phe Asp Val Asn Trp Phe Phe Leu Thr Lys Val
225                 230                 235                 240

Asn Ile Ala Ile Gln Ile Leu Trp Tyr Gly Val Leu Met Glu Phe Pro
                245                 250                 255

Val Leu Ile Ser Glu Leu Leu Val Tyr Asp Ser Val Gln Phe Arg Val
            260                 265                 270

Ala Val Leu Thr Phe Gln Tyr Phe Val Ile Leu His Ile His Asp Leu
            275                 280                 285

Lys Ser Lys Leu Ser Gln Leu Val His Tyr Leu Thr Pro Ile Ser Thr
    290                 295                 300

Phe Ser Glu Glu Gly Val Tyr Gly Pro Leu Val Glu Glu Asn Asp Ile
305                 310                 315                 320

Thr Arg Tyr Lys Phe Thr Leu Leu Ile Asn Gln Leu Thr Phe Lys Ser
                325                 330                 335

Gly Asn Asn Ile Asn Asn Arg Gly Val Gly Asn Trp Thr Glu Ala Gly
            340                 345                 350

Glu Asp Gly Arg Arg Leu Val Leu Lys Pro Gly Ile Thr Ser Leu Thr
            355                 360                 365

Lys Ser Asn Lys Lys Leu Tyr Arg Val Val Thr Val Ala Asn Met
    370                 375                 380

Pro Pro Phe Val Tyr Lys Lys Val Ser Gly Asn Thr Thr Asn Thr Asn
385                 390                 395                 400

Asp Met Tyr Asp Gly Tyr Cys Ile Glu Leu Leu Lys Arg Ile Ser Tyr
                405                 410                 415

Leu Leu Asp Phe Asp Tyr Ile Leu Tyr Asp Ser Pro Asp Gly Met Tyr
            420                 425                 430
```

Gly Ser Met Asp Asp Gly Asn Trp Asn Gly Ala Ile Lys Glu Leu
             435                 440                 445

Ile Asp Lys Lys Ala Asp Ile Ala Val Gly Pro Ile Ser Val Met Ala
450                 455                 460

Glu Arg Glu Asn Val Val Asp Phe Thr Val Pro Tyr Tyr Asp Leu Val
465                 470                 475                 480

Gly Leu Thr Ile Leu Met Lys Lys Pro Glu Phe Asp Tyr Thr Leu Gly
             485                 490                 495

Lys Phe Leu Thr Val Leu Asp Glu Asp Val Trp Phe Cys Ile Ile Gly
             500                 505                 510

Ala Phe Phe Leu Phe Ser Ile Leu Ile Cys Val Phe Asp Lys Leu Ser
             515                 520                 525

Pro Phe Ser Tyr Gln Asn Asn Thr Val Asp Trp Asn Gly Glu Gly Thr
             530                 535                 540

Glu Pro Arg Val Phe Thr Leu Lys Glu Gly Ile Trp Phe Cys Met Met
545                 550                 555                 560

Ser Leu Thr Pro Gln Gly Gly Glu Thr Pro Arg Ala Leu Ser Gly
             565                 570                 575

Arg Leu Val Ala Ala Thr Trp Trp Leu Phe Gly Phe Ile Ile Ala
             580                 585                 590

Thr Tyr Thr Ala Asn Leu Ala Ala Phe Leu Thr Val Ser Arg Leu Glu
             595                 600                 605

Thr Pro Ile Glu Ser Leu Asp Asp Leu Ser Lys Gln Phe Lys Val Lys
             610                 615                 620

Tyr Ala Pro Met Asn Gly Ser Asn Ala Leu Ile Tyr Phe Lys Arg Met
625                 630                 635                 640

Gln Glu Ile Glu His Arg Phe Tyr Gly Ile Trp Lys Asn Met Ser Leu
             645                 650                 655

Asp Asp Asn Leu Gly Ala Val Glu Arg Ala Lys Leu Ala Val Trp Asp
             660                 665                 670

Tyr Pro Val Ser Asp Lys Tyr Thr Lys Leu Trp Glu Thr Met Leu Glu
             675                 680                 685

Ser Glu Phe Pro Ser Asn Lys Asp Glu Ala Val Glu Arg Val Leu Thr
             690                 695                 700

Gly Glu Phe Ala Tyr Ile Gly Asp Ala Thr Val Asn Lys Tyr Ala Lys
705                 710                 715                 720

Leu Thr Asn Cys Asp Leu Trp Glu Val Gly Glu Phe Ser Arg Lys
             725                 730                 735

Pro Tyr Ala Leu Ala Val Gln Glu Gly Ser Pro Leu Arg Ser Gln Leu
             740                 745                 750

Ser Thr Ile Ile Leu Gln Leu Ile Asn Gln Arg Glu Leu Glu Glu Tyr
             755                 760                 765

Lys Thr Lys Trp Trp Lys Lys Asp Lys Arg Asp Cys Pro Asp Ile Glu
             770                 775                 780

Asp Glu Ser Asn Gly Ile Ser Ile Lys Asn Ile Gly Gly Val Phe Leu
785                 790                 795                 800

Val Ile Val Ile Gly Ser Ala Leu Ala Leu Ile Thr Leu Ala Ile Glu
             805                 810                 815

Cys Tyr Trp Tyr Lys Tyr Lys Pro Lys Gln Lys Lys Lys Leu Tyr Val
             820                 825                 830

Ile Ser Ser Lys Ala Asn Leu Asn Lys Leu Asp Thr Ala Pro Ser Gly
             835                 840                 845

Asn Asn Leu Ser Asn Leu Ala Asn Gly Tyr Gln Ser Ser Thr Gln Leu

```
                  850              855              860
Cys Asn Gly His Val Pro Glu Gly Glu Thr Thr Ser Asn Gly Lys Ile
865                  870              875              880

Glu Asn Asp Gly His Thr Asn Thr Gly Phe
                  885              890

<210> SEQ ID NO 19
<211> LENGTH: 747
<212> TYPE: PRT
<213> ORGANISM: Aplysia californica

<400> SEQUENCE: 19

Leu Leu His Val Tyr His Leu Ile Leu Leu Leu Ser Tyr Gln Thr
1               5                   10                  15

Ser Ile Ala Pro Ser Ser Arg Ser Ser Cys Phe Tyr Met Phe Lys Pro
                20                  25                  30

Asp Ile Tyr Thr Lys Ile Gln Ile Tyr Ile Tyr Ile Tyr Ile
                35                  40                  45

Tyr Asn Tyr Tyr Leu Leu Val Thr Pro Leu Phe Phe Gly Thr Tyr Ile
        50                  55                  60

Ser Pro Asn Cys Val Ala Ser Ala Val Lys Arg Leu Leu Lys Gln Lys
65                  70                  75                  80

Thr Lys Lys Leu Phe Leu Phe Phe Ile Ser Gln Val Asp Glu Ala Leu
                85                  90                  95

Ala Phe Asp Ile Gly Arg Ile Val Thr Leu Ala Leu Glu Ala Val Pro
                100                 105                 110

Asn Val Gln Asn Ile Val Lys Val Ser Cys Asp Asn Gly Thr Asp Pro
                115                 120                 125

Thr Pro Ala Ser Leu Lys Gln Ser Ala Glu Leu Thr Asn Glu Leu Thr
                130                 135                 140

Val Val Thr Arg Arg Pro Leu Ser Trp Ser Glu Gln Ser Gln Ala Leu
145                 150                 155                 160

Arg Tyr Asn Met Thr Leu Leu Ser Glu Met Phe Phe Glu Ser Gly
                165                 170                 175

Ile Leu Lys Ser Lys Asp Gln Val Ala Asn Trp Thr Ala Gly Gly
                180                 185                 190

Leu Gln Leu Asp Val Pro Thr Leu Gln Lys Ala Asn Lys Lys Arg
                195                 200                 205

Tyr Arg Ile Val Thr Val Ala Gly Ile Pro Pro Phe Val Tyr Lys Glu
                210                 215                 220

Glu Pro Ile Asn Ser Thr Gly Pro Pro Val Tyr Lys Gly Tyr Cys Ile
225                 230                 235                 240

Asp Leu Leu Glu Arg Ile Ala Gln Asp Met Asn Phe Asp Tyr Glu Ile
                245                 250                 255

His Asp Val Glu Ile Val Gly Ser Met Asp Asp Gly Asn Trp Ser
                260                 265                 270

Gly Val Ile Lys Glu Leu Ile Asp Asn Lys Ala Asp Ile Ala Val Gly
                275                 280                 285

Pro Ile Ser Val Met Ala Glu Arg Glu Asn Val Ile Asp Phe Thr Val
                290                 295                 300

Pro Tyr Tyr Asp Leu Val Gly Leu Thr Ile Leu Met Arg Lys Pro Arg
305                 310                 315                 320

Phe Asp Tyr Ser Leu Val Lys Phe Leu Asn Val Leu Asp Glu Glu Val
                325                 330                 335
```

```
Trp Gly Cys Ile Ile Gly Ala Phe Phe Leu Phe Ser Ile Leu Ile Cys
            340                 345                 350

Val Phe Asp Lys Leu Ser Pro Phe Ser Tyr Gln Asn Arg Lys Asn Gln
        355                 360                 365

Trp Lys Ser Ser Gly Ser Glu Pro Arg Val Phe Thr Leu Lys Glu Gly
    370                 375                 380

Val Trp Phe Cys Met Met Ser Leu Thr Pro Gln Gly Gly Glu Thr
385                 390                 395                 400

Pro Lys Ala Leu Ser Gly Arg Leu Ile Ala Ala Thr Trp Trp Leu Phe
                405                 410                 415

Gly Phe Ile Ile Ile Ala Thr Tyr Thr Ala Asn Leu Ala Ala Phe Leu
                420                 425                 430

Thr Val Ser Arg Leu Glu Thr Pro Ile Glu Ser Leu Asp Asp Leu Ser
            435                 440                 445

Glu Gln Phe Lys Val Gln Tyr Ala Pro Met Asn Gly Ser Thr Ala Met
        450                 455                 460

Ile Tyr Phe Lys Arg Met Ala His Ile Glu His Arg Phe Tyr Glu Ile
465                 470                 475                 480

Trp Lys Asn Met Ser Leu Asn Asp Asn Leu Ala Ala Val Glu Arg Ala
                485                 490                 495

Gln Leu Ala Val Trp Asp Tyr Pro Val Ser Asp Lys Tyr Thr Lys Leu
            500                 505                 510

Trp Gln Thr Met Gln Asp Ser His Phe Pro Ser Asn Lys Thr Glu Ala
        515                 520                 525

Val His Arg Val Leu Asn Glu Asp Phe Ala Phe Ile Ser Asp Ala Thr
    530                 535                 540

Thr Asn Lys Tyr Gln Thr Leu Ile Asn Cys Asp Leu Trp Gln Val Gly
545                 550                 555                 560

Glu Glu Phe Ser Arg Lys Pro Tyr Ala Leu Ala Val Gln Glu Gly Ser
                565                 570                 575

Pro Leu Arg Ser Gln Leu Ser Asn Ile Ile Leu Lys Leu Ile Asn Gln
            580                 585                 590

Arg Ala Leu Glu Glu Met Lys Thr Lys Trp Trp Lys Glu Asp Glu Lys
        595                 600                 605

Glu Cys Pro Lys Leu Glu Asn Glu Thr Asp Gly Ile Ser Ile Arg Asn
    610                 615                 620

Ile Gly Gly Val Phe Leu Val Ile Val Ile Gly Ser Gly Leu Ser Leu
625                 630                 635                 640

Ile Thr Leu Ala Phe Glu Cys Tyr Trp Tyr Arg Leu Arg Pro Glu Arg
                645                 650                 655

Lys Thr Leu Ser Lys Met Tyr Asn Gly Arg Ser Lys Asp Thr Asn Ser
            660                 665                 670

Gln Gly Gln Leu Thr Thr Ser Gly Thr Ala Thr Ser Val Leu Ala Ser
        675                 680                 685

Asp Ser Gln Met Ser Lys Glu Asn Gln Arg Asn Lys Leu Glu Thr
    690                 695                 700

Gly Gly Leu Asp Ser Gly Phe Val Asn Thr Gly Phe Glu Leu Asn Gly
705                 710                 715                 720

Gly Gly Leu Asp Ser Gly Phe Thr Ser Asp Arg Ala Ser Gly Ile Glu
                725                 730                 735

Ile Ser Arg Met Arg Thr Thr Ile Leu Glu Phe
            740                 745
```

<210> SEQ ID NO 20
<211> LENGTH: 935
<212> TYPE: PRT
<213> ORGANISM: Zooternopsis nevadensis

<400> SEQUENCE: 20

Met Arg Pro Arg Ser Leu Leu Val Ser Leu Phe Leu Phe Ile Thr Leu
1               5                   10                  15

Asp Ala Ser Gln Pro Val Thr Ala Glu Leu Met Asn Ile Leu Phe Leu
            20                  25                  30

Asn Glu Glu Gly Asn Lys Ile Gly Asp Glu Ala Phe Asn Val Ala Leu
        35                  40                  45

Asp Tyr Val Lys Lys Asn Pro Ser Leu Gly Val Glu Ile Gly Glu Val
    50                  55                  60

Ile Lys Ala Val Gly Asn Thr Thr Asp Ala Gln Thr Phe Leu Lys Ser
65                  70                  75                  80

Ile Cys Ser Val Tyr Asp Ala Ala Ile Lys Ala Glu Thr Arg Pro His
                85                  90                  95

Val Val Leu Asp Met Thr Met Ser Gly Val Pro Ser Glu Thr Ala Lys
            100                 105                 110

Ser Val Thr Ala Ala Leu Ala Leu Pro Thr Ile Ser Thr Ser Phe Gly
        115                 120                 125

Gln Glu Gly Asp Leu Arg Gln Trp Arg Ser Leu Glu Glu Ala Glu Lys
    130                 135                 140

Asn Tyr Leu Ile Gln Ile Met Pro Pro Ala Asp Ile Met Pro Glu Ile
145                 150                 155                 160

Ile Arg Arg Ile Val Ile Phe Gln Asn Ile Thr Asn Ala Gly Ile Leu
                165                 170                 175

Phe Asp Asp Ser Ile Val Met Asn His Lys Tyr Lys Ser Leu Leu Gln
            180                 185                 190

Asn Leu Pro Thr Arg His Met Ile Val Glu Ala Asp Glu Gly Asn Gly
        195                 200                 205

Glu Ala Gln Leu Lys Arg Leu Arg Glu Arg Asp Ile Phe Asn Tyr Phe
    210                 215                 220

Ile Leu Gly Arg Leu Ser Thr Ile Val Ser Val Leu Asp Ser Ala Glu
225                 230                 235                 240

Lys Cys Gly Phe Phe Asp Arg Gln Phe Ala Trp His Gly Ile Thr Leu
                245                 250                 255

Asp Ser Gly Asn Leu Gly Cys Ser Cys Lys Asn Ala Thr Val Phe Phe
            260                 265                 270

Val Lys Pro Lys Pro Asn Glu Glu Tyr Thr Glu Thr Tyr Thr Glu Leu
        275                 280                 285

Thr Glu Lys Tyr Asn Leu Gln Asn Leu Pro Glu Ile Ser Ala Ala Phe
    290                 295                 300

Tyr Phe Asp Val Ala Leu Arg Thr Leu Leu Ala Thr Lys Glu Ile Met
305                 310                 315                 320

Gln Gly Asn Asp Tyr Arg Lys Asn Tyr Val Thr Cys Asp Asp Tyr Asp
                325                 330                 335

Glu Thr Lys His Val Thr Arg Asp Val Asp Leu Leu Thr Ala Phe Lys
            340                 345                 350

Gln Val Ser Gln Pro Glu Ser Tyr Gly Lys Leu Ser Ile Thr Ser Asn
        355                 360                 365

Gly Glu Ser Met Met Glu Phe Gln Met Glu Met Thr Ala Val Lys Ile
    370                 375                 380

```
Arg Ser Ser Val Pro Gln Thr Ala Ile Asp Met Ala Thr Trp Asn Ala
385                 390                 395                 400

Ser Leu Thr Leu Pro Leu Asp Val Lys Asp Ser Thr Thr Met Val Lys
            405                 410                 415

His Ser Ala Val Thr Val Tyr Arg Ile Val Thr Val Val Gln Asn Pro
        420                 425                 430

Phe Val Ile Tyr Asp Gly Val Asp Gly Lys Asn Arg Thr Lys Phe Lys
        435                 440                 445

Gly Tyr Cys Ile Asp Leu Ile Asp Glu Ile Arg Asn Ile Thr Lys Phe
        450                 455                 460

Asp Tyr Glu Ile Tyr Glu Ala Pro Asp Lys Lys Phe Gly Asn Met Asp
465                 470                 475                 480

Glu Asn Gly Asn Trp Asn Gly Met Ile Lys Glu Leu Met Leu Lys Asn
            485                 490                 495

Ala Asp Ile Ala Leu Gly Ser Leu Ser Val Met Ala Glu Arg Glu Asn
        500                 505                 510

Val Val Asp Phe Thr Val Pro Tyr Tyr Asp Leu Val Gly Ile Thr Ile
        515                 520                 525

Leu Met Lys Lys Pro Lys Ala Ala Thr Ser Leu Phe Lys Phe Leu Thr
        530                 535                 540

Val Leu Glu Asn Glu Val Trp Leu Cys Ile Leu Gly Ala Tyr Phe Phe
545                 550                 555                 560

Thr Ser Phe Leu Met Trp Val Phe Asp Arg Trp Ser Pro Tyr Ser Tyr
            565                 570                 575

Gln Asn Asn Arg Glu Lys Tyr Lys Asp Asp Glu Glu Lys Arg Glu Phe
            580                 585                 590

Asn Leu Lys Glu Cys Leu Trp Phe Cys Met Thr Ser Leu Thr Pro Gln
            595                 600                 605

Gly Gly Gly Glu Ala Pro Lys Asn Leu Ser Gly Arg Leu Val Ala Ala
        610                 615                 620

Thr Trp Trp Leu Phe Gly Phe Ile Ile Ile Ala Ser Tyr Thr Ala Asn
625                 630                 635                 640

Leu Ala Ala Phe Leu Thr Val Ser Arg Leu Asp Thr Pro Val Glu Ser
            645                 650                 655

Leu Asp Asp Leu Ala Lys Gln Tyr Lys Ile Gln Tyr Ala Pro Leu Asn
            660                 665                 670

Asn Ser Ala Ser Met Ile Tyr Phe Gln Arg Met Ser Asp Ile Glu Asn
        675                 680                 685

Arg Phe Tyr Glu Ile Trp Lys Asp Met Ser Leu Asn Asp Ser Leu Ser
        690                 695                 700

Asp Val Glu Arg Ala Lys Leu Ala Val Trp Asp Tyr Pro Val Ser Asp
705                 710                 715                 720

Lys Tyr Thr Lys Ile Trp Gln Ala Met Asn Glu Ala Lys Phe Pro Asn
            725                 730                 735

Thr Leu Glu Glu Ala Val Asn Arg Val Leu Asp Ser Lys Ser Ser Ser
            740                 745                 750

Glu Gly Phe Ala Tyr Ile Gly Asp Ala Thr Asp Val Arg Tyr Leu Val
        755                 760                 765

Leu Thr Ser Cys Asn Leu Gln Met Val Gly Glu Phe Ser Arg Lys
        770                 775                 780

Pro Tyr Ala Ile Ala Thr Gln Gln Gly Ser Pro Leu Lys Asp Gln Phe
785                 790                 795                 800

Asn Asn Ala Ile Leu Gln Leu Leu Asn Lys Arg Lys Leu Glu Lys Leu
```

|       | 805 |     |     |     | 810 |     |     |     |     | 815 |     |     |
|-------|-----|-----|-----|-----|-----|-----|-----|-----|-----|-----|-----|-----|
| Lys   | Glu | Gln | Trp | Trp | Asn | Gln | Asn | Pro | Glu | Lys | Arg | Arg | Asp | Cys | Glu |
|       |     |     | 820 |     |     |     |     | 825 |     |     |     | 830 |

Lys Gln Asp Asp Gln Thr Asp Gly Ile Ser Ile Gln Asn Ile Gly Gly
            835                 840                 845

Val Phe Ile Val Ile Phe Val Gly Ile Gly Leu Ala Cys Ile Thr Leu
    850                 855                 860

Ala Phe Glu Tyr Trp Trp Tyr Lys Tyr Lys Lys Ile Pro Lys Val Val
865             870                 875                     880

Asp Thr Gly Lys Val Val Ala His Ser Arg Gln Ile Pro Thr Thr Gly
                885                 890                 895

Gly Gly Lys Leu Glu Thr Gly Leu Lys Met Gln Gly Phe Arg Pro Arg
            900                 905                 910

Asn Pro Thr Phe Pro Thr His Ser Phe Arg Arg Asn Val Gly Pro Met
            915                 920                 925

Thr Gly Val Lys Ser Pro Trp
            930         935

<210> SEQ ID NO 21
<211> LENGTH: 2844
<212> TYPE: DNA
<213> ORGANISM: Drosophila melanogaster

<400> SEQUENCE: 21

```
atgattttga tgaatccgaa aacttcgaaa atcctgtggc tgctgggatt tctatcgtta      60
ttaagcagct ttagtttgga gatcgctgcg caaaccactc aaaatatcaa tgtgttgttc     120
atcaacgagg tggacaatga gccggctgcg aaggctgtgg aggtggtgct cacctacttg     180
aagaagaaca tacgatatgg tctatcggtg caactggatt cgatagaggc gaacaagtcc     240
gatgccaagg tgctgctgga agctatttgc aataagtacg caacaagtat tgaaaagaaa     300
cagacgcctc atctgatcct ggacaccacc aaatcgggca tagcctcgga aacggtaaag     360
agcttcaccc aggctctggg tctgcccacc attagtgcct cctatggcca gcagggcgac     420
ttgaggcagt ggcgcgactt ggatgaggcg aagcagaagt atttgctgca ggtgatgccg     480
ccggcggata ttattcccga ggccattcga agtatagtga ttcacatgaa catcacgaat     540
gctgccattc tgtacgatga ttcctttgtc atggaccaca gtacaagtc cctgctgcag     600
aatatacaaa cccgtcatgt gatcaccgcc atagccaagg atggtaagcg ggagcgcgag     660
gagcaaatcg aaaagctgag gaacttggac atcaataact tctttattct gggcaccctg     720
caatcgatcc gcatggtcct ggagtcggtg aagccagcgt atttcgagcg caacttcgcc     780
tggcacgcca tcactcagaa cgaaggagag attagcagtc agcgggacaa tgcgaccatt     840
atgtttatga aacccatggc gtatacgcaa tatcgagatc gcttgggatt gctgcgaacc     900
acttacaatc tgaacgagga gccgcagttg tcatccgcgt tttacttcga tctggcactt     960
aggagtttcc ttaccatcaa agaaatgtta caatcgggcg cctggccaaa ggacatggag    1020
tatctgaatt gtgacgattt ccaaggtggc aacacacccc aaaggaactt ggatcttcga    1080
gattacttca ccaagattac cgaaccgact tcgtatggaa ccttcgatct cgtcacgcaa    1140
tccactcagc catttaatgg gcatagcttc atgaaattcg aaatggatat aaatgtgctg    1200
cagattcgtg gtggcagttc cgtgaacagc aagtccattg caaatggat  atcgggtctg    1260
aactcggagc tcatcgtcaa agacgaggag cagatgaaga atctcactgc ggacactgtt    1320
tatcgaatct ttactgtagt gcaagctcct ttcataatgc gcgatgaaac ggctccgaaa    1380
```

-continued

```
ggatacaaag gatactgcat tgatctgatc aacgagatag ccgcaattgt ccacttcgat      1440
tacaccatcc aggaggtgga ggacggcaag tttggcaaca tggacgagaa tggccaatgg      1500
aatggcattg tgaagaagct gatggacaaa caggcggaca ttggccttgg cagcatgtcg      1560
gtgatggccg aacgggagat agtcattgac ttcaccgttc cgtactacga tctggtcggg      1620
attacgatca tgatgcagcg acccagttcg ccaagctcgc tgttcaagtt ccttaccgtg      1680
ctggaaacga acgtgtggct ttgcatcctg gctgcctact tctttaccag ctttctcatg      1740
tggatcttcg atcgctggag tccctatagc tatcagaaca atcgggagaa gtacaaggac      1800
gacgaggaga agcgcgagtt caatctgaag gagtgcctct ggttctgcat gacgtcattg      1860
acgcctcaag gcggtggcga ggctccaaag aatctgtctg ccgtttagt ggccgccacc       1920 tggtggctat tcggttttat cattattgct tcgtacacgg ccaatttggc tgccttcttg      1980
accgtatcac gtttggatac gcccgttgaa agcttggatg acctggcgaa gcagtacaag      2040
atcctgtacg ctccattgaa tggctcatct gcgatgacat atttcgagcg tatgtccaac      2100
atagagcaga tgttttacga gatttggaag gatctgtcgc tgaacgactc cctgaccgcc      2160
gtggagcgct ccaagctggc tgtttgggat tatccagtga cgacaagta taccaagatg       2220 tggcaggcca tgcaggaggc gaagctaccg gccaccctcg acgaagcagt ggcccgggtt      2280
agaaattcga cagcggccac gggttttgcc ttcctgggcg atgccaccga tatacgctac      2340
ctgcagttga ccaattgcga tctgcaggtg gttggcgagg agttctcccg gaaaccctat      2400
gccatagctg ttcagcaggg ctcgcatctt aaggatcagt tcaataatgc aatcctgacc      2460
ctgctcaaca aacgacagct ggagaagctc aaggagaagt ggtggaagaa cgacgaagct      2520
ctggccaagt gcgataagcc ggaggatcaa tcggatggca tctcgatcca gaacattggc      2580
ggcgtcttca ttgtcatatt cgtgggcatt ggaatggcct gcattacgct ggtctttgag      2640
tactggtggt acaggtaccg caagaatccg cggatcatcg atgtggccga agccaatgcg      2700
gagcgatcca atgctgctga ccatcctggc aagctggtcg atggtgtgat ccttggccac      2760
tcggggagga agttcgagaa gtcaaaagct gcactgcgtc cgcgcttcaa tcagtatccg      2820
gccacgttta agcctcgttt ctag                                             2844
```

<210> SEQ ID NO 22
<211> LENGTH: 868
<212> TYPE: PRT
<213> ORGANISM: Drosophila melanogaster

<400> SEQUENCE: 22

```
Met Asn Pro Gly Glu Met Arg Pro Ser Ala Cys Leu Leu Leu Leu Ala
1               5                   10                  15

Gly Leu Gln Leu Ser Ile Leu Val Pro Thr Glu Ala Asn Asp Phe Ser
            20                  25                  30

Ser Phe Leu Ser Ala Asn Ala Ser Leu Ala Val Val Val Asp His Glu
        35                  40                  45

Tyr Met Thr Val His Gly Glu Asn Ile Leu Ala His Phe Glu Lys Ile
    50                  55                  60

Leu Ser Asp Val Ile Arg Glu Asn Leu Arg Asn Gly Gly Ile Asn Val
65                  70                  75                  80

Lys Tyr Phe Ser Trp Asn Ala Val Arg Leu Lys Lys Asp Phe Leu Ala
                85                  90                  95

Ala Ile Thr Val Thr Asp Cys Glu Asn Thr Trp Asn Phe Tyr Lys Asn
            100                 105                 110
```

```
Thr Gln Glu Thr Ser Ile Leu Leu Ile Ala Ile Thr Asp Ser Asp Cys
        115                 120                 125

Pro Arg Leu Pro Leu Asn Arg Ala Leu Met Val Pro Ile Val Glu Asn
130                 135                 140

Gly Asp Glu Phe Pro Gln Leu Ile Leu Asp Ala Lys Val Gln Gln Ile
145                 150                 155                 160

Leu Asn Trp Lys Thr Ala Val Val Phe Val Asp Gln Thr Ile Leu Glu
                165                 170                 175

Glu Asn Ala Leu Leu Val Lys Ser Ile Val His Glu Ser Ile Thr Asn
            180                 185                 190

His Ile Thr Pro Ile Ser Leu Ile Leu Tyr Glu Ile Asn Asp Ser Leu
        195                 200                 205

Arg Gly Gln Gln Lys Arg Val Ala Leu Arg Gln Ala Leu Ser Gln Phe
    210                 215                 220

Ala Pro Lys Lys His Glu Glu Met Arg Gln Gln Phe Leu Val Ile Ser
225                 230                 235                 240

Ala Phe His Glu Asp Ile Ile Glu Ile Ala Glu Thr Leu Asn Met Phe
                245                 250                 255

His Val Gly Asn Gln Trp Met Ile Phe Val Leu Asp Met Val Ala Arg
            260                 265                 270

Asp Phe Asp Ala Gly Thr Val Thr Ile Asn Leu Asp Glu Gly Ala Asn
        275                 280                 285

Ile Ala Phe Ala Leu Asn Glu Thr Asp Pro Asn Cys Gln Asp Ser Leu
    290                 295                 300

Asn Cys Thr Ile Ser Glu Ile Ser Leu Ala Leu Val Asn Ala Ile Ser
305                 310                 315                 320

Lys Ile Thr Val Glu Glu Glu Ser Ile Tyr Gly Glu Ile Ser Asp Glu
                325                 330                 335

Glu Trp Glu Ala Ile Arg Phe Thr Lys Gln Glu Lys Gln Ala Glu Ile
            340                 345                 350

Leu Glu Tyr Met Lys Glu Phe Leu Lys Thr Asn Ala Lys Cys Ser Ser
        355                 360                 365

Cys Ala Arg Trp Arg Val Glu Thr Ala Ile Thr Trp Gly Lys Ser Gln
    370                 375                 380

Glu Asn Arg Lys Phe Arg Ser Thr Pro Gln Arg Asp Ala Lys Asn Arg
385                 390                 395                 400

Asn Phe Glu Phe Ile Asn Ile Gly Tyr Trp Thr Pro Val Leu Gly Phe
                405                 410                 415

Val Cys Gln Glu Leu Ala Phe Pro His Ile Glu His His Phe Arg Asn
            420                 425                 430

Ile Thr Met Asp Ile Leu Thr Val His Asn Pro Pro Trp Gln Ile Leu
        435                 440                 445

Thr Lys Asn Ser Asn Gly Val Ile Val Glu His Lys Gly Ile Val Met
    450                 455                 460

Glu Ile Val Lys Glu Leu Ser Arg Ala Leu Asn Phe Ser Tyr Tyr Leu
465                 470                 475                 480

His Glu Ala Ser Ala Trp Lys Glu Glu Asp Ser Leu Ser Thr Ser Ala
                485                 490                 495

Gly Gly Asn Glu Ser Asp Glu Leu Val Gly Ser Met Thr Phe Arg Ile
            500                 505                 510

Pro Tyr Arg Val Val Glu Met Val Gln Gly Asn Gln Phe Phe Ile Ala
        515                 520                 525
```

Ala Val Ala Ala Thr Val Glu Asp Pro Asp Gln Lys Pro Phe Asn Tyr
530                 535                 540

Thr Gln Pro Ile Ser Val Gln Lys Tyr Ser Phe Ile Thr Arg Lys Pro
545                 550                 555                 560

Asp Glu Val Ser Arg Ile Tyr Leu Phe Thr Ala Pro Phe Thr Val Glu
            565                 570                 575

Thr Trp Phe Cys Leu Met Gly Ile Ile Leu Thr Ala Pro Thr Leu
            580                 585                 590

Tyr Ala Ile Asn Arg Leu Ala Pro Leu Lys Glu Met Arg Ile Val Gly
            595                 600                 605

Leu Ser Thr Val Lys Ser Cys Phe Trp Tyr Ile Phe Gly Ala Leu Leu
610                 615                 620

Gln Gln Gly Gly Met Tyr Leu Pro Thr Ala Asp Ser Gly Arg Leu Val
625                 630                 635                 640

Val Gly Phe Trp Trp Ile Val Ile Val Leu Val Thr Thr Tyr Cys
            645                 650                 655

Gly Asn Leu Val Ala Phe Leu Thr Phe Pro Lys Phe Gln Pro Gly Val
            660                 665                 670

Asp Tyr Leu Asn Gln Leu Glu Asp His Lys Asp Ile Val Gln Tyr Gly
            675                 680                 685

Leu Arg Asn Gly Thr Phe Phe Glu Arg Tyr Val Gln Ser Thr Thr Arg
690                 695                 700

Glu Asp Phe Lys His Tyr Leu Glu Arg Ala Lys Ile Tyr Gly Ser Ala
705                 710                 715                 720

Gln Glu Glu Asp Ile Glu Ala Val Lys Arg Gly Glu Arg Ile Asn Ile
            725                 730                 735

Asp Trp Arg Ile Asn Leu Gln Leu Ile Val Gln Arg His Phe Glu Arg
            740                 745                 750

Glu Lys Glu Cys His Phe Ala Leu Gly Arg Glu Ser Phe Val Asp Glu
755                 760                 765

Gln Ile Ala Met Ile Val Pro Ala Gln Ser Ala Tyr Leu His Leu Val
            770                 775                 780

Asn Arg His Ile Lys Ser Met Phe Arg Met Gly Phe Ile Glu Arg Trp
785                 790                 795                 800

His Gln Met Asn Leu Pro Ser Ala Gly Lys Cys Asn Gly Lys Ser Ala
            805                 810                 815

Gln Arg Gln Val Thr Asn His Lys Val Asn Met Asp Met Gln Gly
            820                 825                 830

Cys Phe Leu Val Leu Leu Gly Phe Thr Leu Ala Leu Leu Ile Val
            835                 840                 845

Cys Gly Glu Phe Trp Tyr Arg Arg Phe Arg Ala Ser Arg Lys Arg Arg
850                 855                 860

Gln Phe Thr Asn
865

<210> SEQ ID NO 23
<211> LENGTH: 848
<212> TYPE: PRT
<213> ORGANISM: Drosophila melanogaster

<400> SEQUENCE: 23

Met Asn Pro Gly Glu Met Arg Pro Ser Ala Cys Leu Leu Leu Leu Ala
1               5                   10                  15

Gly Leu Gln Leu Ser Ile Leu Val Pro Thr Glu Ala Asn Asp Phe Ser
            20                  25                  30

```
Ser Phe Leu Ser Ala Asn Ala Ser Leu Ala Val Val Asp His Glu
        35                  40                  45
Tyr Met Thr Val His Gly Glu Asn Ile Leu Ala His Phe Glu Lys Ile
 50                  55                  60
Leu Ser Asp Val Ile Arg Glu Asn Leu Arg Asn Gly Gly Ile Asn Val
 65                  70                  75                  80
Lys Tyr Phe Ser Trp Asn Ala Val Arg Leu Lys Lys Asp Phe Leu Ala
                 85                  90                  95
Ala Ile Thr Val Thr Asp Cys Glu Asn Thr Trp Asn Phe Tyr Lys Asn
                100                 105                 110
Thr Gln Glu Thr Ser Ile Leu Leu Ile Ala Ile Thr Asp Ser Asp Cys
            115                 120                 125
Pro Arg Leu Pro Leu Asn Arg Ala Leu Met Thr Val Glu Cys Arg Ile
130                 135                 140
Asn Ala Val Val Phe Val Asp Gln Thr Ile Leu Glu Glu Asn Ala Leu
145                 150                 155                 160
Leu Val Lys Ser Ile Val His Glu Ser Ile Thr Asn His Ile Thr Pro
                165                 170                 175
Ile Ser Leu Ile Leu Tyr Glu Ile Asn Asp Ser Leu Arg Gly Gln Gln
            180                 185                 190
Lys Arg Val Ala Leu Arg Gln Ala Leu Ser Gln Phe Ala Pro Lys Lys
        195                 200                 205
His Glu Glu Met Arg Gln Gln Phe Leu Val Ile Ser Ala Phe His Glu
            210                 215                 220
Asp Ile Ile Glu Ile Ala Glu Thr Leu Asn Met Phe His Val Gly Asn
225                 230                 235                 240
Gln Trp Met Ile Phe Val Leu Asp Met Val Ala Arg Asp Phe Asp Ala
                245                 250                 255
Gly Thr Val Thr Ile Asn Leu Asp Glu Gly Ala Asn Ile Ala Phe Ala
                260                 265                 270
Leu Asn Glu Thr Asp Pro Asn Cys Gln Asp Ser Leu Asn Cys Thr Ile
            275                 280                 285
Ser Glu Ile Ser Leu Ala Leu Val Asn Ala Ile Ser Lys Ile Thr Val
        290                 295                 300
Glu Glu Glu Ser Ile Tyr Gly Glu Ile Ser Asp Glu Glu Trp Glu Ala
305                 310                 315                 320
Ile Arg Phe Thr Lys Gln Glu Lys Gln Ala Glu Ile Leu Glu Tyr Met
                325                 330                 335
Lys Glu Phe Leu Lys Thr Asn Ala Lys Cys Ser Ser Cys Ala Arg Trp
            340                 345                 350
Arg Val Glu Thr Ala Ile Thr Trp Gly Lys Ser Gln Gly Asn Arg Lys
        355                 360                 365
Phe Arg Ser Thr Pro Gln Arg Asp Ala Lys Asn Arg Asn Phe Glu Phe
    370                 375                 380
Ile Asn Ile Gly Tyr Trp Thr Pro Val Leu Gly Phe Val Cys Gln Glu
385                 390                 395                 400
Leu Ala Phe Pro His Ile Glu His His Phe Arg Asn Ile Thr Met Asp
                405                 410                 415
Ile Leu Thr Val His Asn Pro Pro Trp Gln Ile Leu Thr Lys Asn Ser
            420                 425                 430
Asn Gly Val Ile Val Glu His Lys Gly Ile Val Met Glu Ile Val Lys
        435                 440                 445
```

-continued

Glu Leu Ser Arg Ala Leu Asn Phe Ser Tyr Tyr Leu His Glu Ala Ser
    450                 455                 460

Ala Trp Lys Glu Glu Asp Ser Leu Ser Thr Ser Ala Gly Gly Asn Glu
465                 470                 475                 480

Ser Asp Glu Leu Val Gly Ser Met Thr Phe Arg Ile Pro Tyr Arg Val
                485                 490                 495

Val Glu Met Val Gln Gly Asn Gln Phe Phe Ile Ala Ala Val Ala Ala
            500                 505                 510

Thr Val Glu Asp Pro Asp Gln Lys Pro Phe Asn Tyr Thr Gln Pro Ile
        515                 520                 525

Ser Val Gln Lys Tyr Ser Phe Ile Thr Arg Lys Pro Asp Glu Val Ser
    530                 535                 540

Arg Ile Tyr Leu Phe Thr Ala Pro Phe Val Glu Thr Trp Phe Cys
545                 550                 555                 560

Leu Met Gly Ile Ile Leu Leu Thr Ala Pro Thr Leu Tyr Ala Ile Asn
                565                 570                 575

Arg Leu Ala Pro Leu Lys Glu Met Arg Ile Val Gly Leu Ser Thr Val
                580                 585                 590

Lys Ser Cys Phe Trp Tyr Ile Phe Gly Ala Leu Leu Gln Gln Gly Gly
            595                 600                 605

Met Tyr Leu Pro Thr Ala Asp Ser Gly Arg Leu Val Val Gly Phe Trp
610                 615                 620

Trp Ile Val Val Ile Val Leu Val Thr Thr Tyr Cys Gly Asn Leu Val
625                 630                 635                 640

Ala Phe Leu Thr Phe Pro Lys Phe Gln Pro Gly Val Asp Tyr Leu Asn
                645                 650                 655

Gln Leu Glu Asp His Lys Asp Ile Val Gln Tyr Gly Leu Arg Asn Gly
                660                 665                 670

Thr Phe Phe Glu Arg Tyr Val Gln Ser Thr Thr Arg Glu Asp Phe Lys
            675                 680                 685

His Tyr Leu Glu Arg Ala Lys Ile Tyr Gly Ser Ala Gln Glu Glu Asp
        690                 695                 700

Ile Glu Ala Val Lys Arg Gly Glu Arg Ile Asn Ile Asp Trp Arg Ile
705                 710                 715                 720

Asn Leu Gln Leu Ile Val Gln Arg His Phe Glu Arg Lys Glu Cys
                725                 730                 735

His Phe Ala Leu Gly Arg Glu Ser Phe Val Asp Glu Gln Ile Ala Met
            740                 745                 750

Ile Val Pro Ala Gln Ser Ala Tyr Leu His Leu Val Asn Arg His Ile
        755                 760                 765

Lys Ser Met Phe Arg Met Gly Phe Ile Glu Arg Trp His Gln Met Asn
770                 775                 780

Leu Pro Ser Ala Gly Lys Cys Asn Gly Lys Ser Ala Gln Arg Gln Val
785                 790                 795                 800

Thr Asn His Lys Val Asn Met Asp Asp Met Gln Gly Cys Phe Leu Val
                805                 810                 815

Leu Leu Leu Gly Phe Thr Leu Ala Leu Leu Ile Val Cys Gly Glu Phe
            820                 825                 830

Trp Tyr Arg Arg Phe Arg Ala Ser Arg Lys Arg Gln Phe Thr Asn
        835                 840                 845

<210> SEQ ID NO 24
<211> LENGTH: 830
<212> TYPE: PRT

<213> ORGANISM: Aedes aegypti

<400> SEQUENCE: 24

```
Met Leu Pro Arg Leu Lys Trp Leu Val Leu Val Val Cys Lys
1               5                   10                  15
Leu Asp His Ser Arg Gly Asp Asp Phe Pro Ser Leu Ile Ser Ala Asn
                20                  25                  30
Ala Ser Ile Ala Val Ile Leu Asp Arg Glu Tyr Leu Asp Ala Gln Tyr
            35                  40                  45
Asp Asp Ile Leu Glu Gly Thr Lys Arg Leu Phe Glu Arg Ile Leu Arg
    50                  55                  60
Asp Asn Phe Arg Asn Gly Gly Leu Ile Val Lys Tyr Phe Ser Trp Thr
65                  70                  75                  80
Ser Ile Asn Leu Arg Arg Asp Phe Thr Ala Val Leu Ser Ile Ser Asn
                85                  90                  95
Cys Glu Asn Thr Trp Asp Val Tyr Lys Asn Ala Ala Lys Glu Asn Leu
            100                 105                 110
Val Ile Met Ser Ile Thr Asp Ser Asp Cys Leu Arg Leu Pro Leu Asn
        115                 120                 125
Asn Ala Ile Met Val Asn Leu Lys Ser Ile Val Ala Leu Ser Lys Glu
    130                 135                 140
Ser Glu Asp Val Arg Pro Leu Ser Leu Ser Leu Phe Arg Ile Glu Ser
145                 150                 155                 160
His Thr His Met Trp Glu Lys Arg Lys Ala Ile Arg Lys Val Leu Val
                165                 170                 175
Asn Leu Pro Thr Arg Tyr Ile Gly Arg Asn Phe Ile Ala Ile Ile Thr
            180                 185                 190
Thr Gln Thr Met Glu Leu Val Met Glu Ile Ala Lys Glu Leu Arg Met
        195                 200                 205
Val Thr Pro Leu Ala Gln Trp Leu Tyr Val Val Ser Asp Thr Ser Ala
    210                 215                 220
Asp Arg Asn Asn Ile Ser Ala Val His Pro Ile Ile Ser Glu Gly Asp
225                 230                 235                 240
Asn Ile Ala Phe Val Tyr Asn Leu Arg Arg Asn Ala Gln Ser Cys Glu
                245                 250                 255
Ser His Met Leu Cys Tyr Val Glu Asn Leu Ile Thr Ser Leu Val His
            260                 265                 270
Gly Leu Ser Lys Leu Ile Arg Glu Glu Lys Ala Val Tyr Gly Gln Ile
        275                 280                 285
Ala Asp Glu Glu Trp Glu Val Ile Arg Met Thr Lys Ala Glu Arg Lys
    290                 295                 300
Asp Glu Ile Leu Lys Ile Met Arg Ser Asp Leu Ile Gly Lys Asp Ser
305                 310                 315                 320
Cys Asn Glu Cys Ser Met Trp Lys Val Glu Ala Gly Glu Thr Trp Gly
                325                 330                 335
Tyr Thr Tyr Gln Ser Ala Ala Asp Glu Leu Leu Thr Gly Val Met Ser
            340                 345                 350
Thr His Arg Lys Gln Ile Ser Leu Leu Asp Val Gly Tyr Trp Thr Pro
        355                 360                 365
Gln Asp Gly Phe Val Met Arg Asp Asn Met Phe Pro His Val Ala Asp
    370                 375                 380
Gly Phe Arg Gly Val His Leu Asn Phe Tyr Ser Tyr His Asn Pro Pro
385                 390                 395                 400
```

```
Trp Gln Phe Val Thr Tyr Asn Glu Ser Gly His Leu Ser Leu Ser Arg
                405                 410                 415
Gly Val Val Met Asp Ile Leu Thr Glu Leu Ser Arg Lys Leu Asn Phe
            420                 425                 430
Thr Phe Asn Ile Leu Ile Ser Gln Thr Asn Leu Glu Tyr Ile Gly Asn
        435                 440                 445
Met Thr Asp Asp Ala Asn Asn Thr Ile Asn Arg Asp Ala His Ser Ile
    450                 455                 460
Thr Thr Asp Ile Pro Asn Glu Ile Leu Arg Ser Leu Met Asp Asn Lys
465                 470                 475                 480
Ile Leu Leu Ala Ala Val Gly Ala Thr Val Ser Pro Lys Gln Lys Lys
                485                 490                 495
Tyr Val Asn Phe Thr Thr Pro Ile Ser Ile Gln Thr Tyr Ser Phe Ile
            500                 505                 510
Val Ser Arg Pro Lys Glu Leu Ser Arg Val Phe Leu Phe Leu Ser Pro
        515                 520                 525
Phe Thr Ile Asp Thr Trp Leu Cys Leu Ser Ala Thr Val Leu Leu Met
    530                 535                 540
Gly Pro Phe Leu Tyr Val Val Asn Arg Leu Ser Pro Phe Tyr Glu His
545                 550                 555                 560
His Gly Arg Ser Asn Thr Ile Gly Leu Gly Lys Leu Tyr Asn Cys Phe
                565                 570                 575
Trp Tyr Ile Tyr Gly Ala Leu Leu Gln Gln Gly Gly Leu Tyr Leu Pro
            580                 585                 590
Tyr Ala Asp Ser Gly Arg Ile Ile Ile Gly Thr Trp Trp Leu Val Val
        595                 600                 605
Leu Val Ile Val Thr Thr Tyr Cys Gly Asn Leu Val Ala Phe Leu Thr
    610                 615                 620
Phe Pro Lys Ile Ala Ile Pro Ile Thr Thr Val Asn Gln Leu Ile Arg
625                 630                 635                 640
Asn Glu Gln Gly Val Ser Trp Ser Ile Arg Arg Gly Thr Phe Leu Glu
                645                 650                 655
Gln Phe Leu Gln Glu Thr Asp Asp Pro Lys Tyr Ile Lys Leu His Asn
            660                 665                 670
His Ala Gly Tyr Val Ser Glu Glu Ser Glu Gln Met Val Glu Arg Ile
        675                 680                 685
Arg Thr Gly Arg His Val His Ile Asp Trp Arg Thr Asn Leu Lys Tyr
    690                 695                 700
Leu Met Lys Lys Glu Phe Leu Lys Asn Asp Arg Cys Asp Phe Ala Leu
705                 710                 715                 720
Ser Val Asp Glu Phe Leu Asp Glu Gln Ile Ala Leu Ala Met Pro Lys
                725                 730                 735
Asn Ser Pro Tyr Leu Glu Leu Ile Asn Ala Glu Leu Thr Lys Met His
            740                 745                 750
Gln Phe Gly Phe Ile Gln Arg Trp Leu Gly Ser Tyr Met Pro Ser Glu
        755                 760                 765
Asp Lys Cys Ser Asn Ala Arg Lys Ser Thr Glu Val Glu Asn His Thr
    770                 775                 780
Val Asn Asn Asp Asp Met Ala Gly Ser Tyr Tyr Val Leu Met Ile Gly
785                 790                 795                 800
Phe Ser Met Gly Leu Phe Met Phe Val Leu Glu Tyr Gly Trp Arg Trp
                805                 810                 815
Tyr Lys Arg Ser Lys Glu Glu Thr Leu Gln Pro Phe Thr Glu
```

<210> SEQ ID NO 25
<211> LENGTH: 885
<212> TYPE: PRT
<213> ORGANISM: Anopheles gambiae

<400> SEQUENCE: 25

```
Met Val Leu Arg Leu Val Gly Leu Trp Ser Ile Leu Leu Leu Leu
1               5                   10                  15

Leu Leu Leu Val Leu Arg Pro Asp Pro Ala Val Gly Asp Asp Phe Pro
            20                  25                  30

Ser Leu Leu Ser Thr Asn Ala Ser Met Gly Lys Leu Asn Ile Thr Pro
        35                  40                  45

Leu Leu Ser Ile Ile Leu Asp Arg Glu Tyr Leu Gly Ala Asp Tyr Glu
    50                  55                  60

Arg Thr Leu Asp Glu Thr Lys Asn Val Val Glu Lys Leu Ile Arg Glu
65                  70                  75                  80

His Leu Lys Asn Gly Gly Leu Ile Val Lys Tyr Tyr Ser Trp Thr Ser
                85                  90                  95

Ile Asn Leu Lys Arg Asp Phe Ser Ala Val Leu Ser Val Ser Ser Cys
            100                 105                 110

Lys Asn Thr Trp Asp Ile Tyr Gln Glu Ala Val Arg Glu Arg Leu Val
        115                 120                 125

Met Leu Ser Ile Thr Asp Pro Asp Cys Pro Arg Leu Pro Thr Asn Asn
    130                 135                 140

Ala Ile Met Ile Pro Arg Ser Asp Gly Ser Gly Ser Asn Ala Phe Asp
145                 150                 155                 160

Glu Val Ser Gln Ile Ile Leu Asp Met Lys Ser Ser Arg Ala Ile Asn
                165                 170                 175

Trp His Thr Ala Thr Leu Leu Tyr Asp Gln Val Tyr Asp Ala Glu Ile
            180                 185                 190

Ser Arg Cys Ile Leu Ser Leu Leu Glu Asp Arg Glu Gly Ile Lys Pro
        195                 200                 205

Leu Thr Leu Thr Glu Phe Lys Ile Asn Ala Pro Thr His Ser Trp Glu
    210                 215                 220

Lys Arg Lys Glu Ile Arg Arg Thr Leu Leu Gly Ile Pro Thr Ala Tyr
225                 230                 235                 240

Thr Gly Arg Asn Phe Ile Ala Ile Val Asn Ile Ala Thr Leu Thr Leu
                245                 250                 255

Leu Met Glu Ile Ser Lys Asp Leu Lys Leu Val Asn Pro Phe Ala Gln
            260                 265                 270

Trp Leu Tyr Leu Ile Pro Asn Thr Glu Lys Ala Asn Ser Asn Phe Thr
        275                 280                 285

Thr Arg Ser Thr Leu Ile Asn Glu Gly Asp Asn Val Ala Phe Val Tyr
    290                 295                 300

Asn Ser Gly Ser Lys Ala Gln Asn Cys Thr Val Ser Val Leu Cys Tyr
305                 310                 315                 320

Ile Glu Ser Tyr Leu Leu His Phe Ile Arg Ser Leu Ser Lys Leu Ile
                325                 330                 335

Arg Glu Glu Gln Val Val Phe Gly Gln Ile Ser Asp Glu Glu Trp Glu
            340                 345                 350

Ile Ile Arg Pro Ser Lys Gln Glu Arg Lys Thr Lys Phe Leu Gln Met
        355                 360                 365
```

```
Ile Lys Ala Ala Ile Thr Ser Lys Asp Glu Cys Asn Lys Cys Ser Gln
    370                 375                 380

Trp Lys Ile Gln Ser Ala Glu Thr Trp Gly Tyr Val Tyr Arg Thr Asp
385                 390                 395                 400

Phe Leu Thr Asp Gly Ala Asp Leu Gln Glu Arg Arg Lys Tyr Thr Met
                405                 410                 415

Leu Asp Ile Gly Tyr Trp Ser Pro Gln Asp Gly Phe Met Leu Thr Asp
                420                 425                 430

Ala Leu Phe Pro His Thr Gln Tyr Gly Phe Arg Gly Val Gln Leu Ile
            435                 440                 445

Phe Tyr Ser Tyr His Asn Pro Pro Trp Gln Phe Val Ala Tyr Asn Asp
450                 455                 460

Ser Gly Ser Pro Val Ile Ser Ser Gly Val Val Tyr Asp Ile Leu Asn
465                 470                 475                 480

Glu Leu Ser Arg Lys Leu Asn Phe Thr Tyr Thr Met Val Ile Ser Gln
                485                 490                 495

Pro Ala Glu Ile Asn Gly Ser Leu Val Glu Gly Asn Thr Ser Ser Val
                500                 505                 510

Tyr Asp Leu Lys Thr Ile Ser Ser Asp Ile Pro Gln Glu Ile Phe Ser
                515                 520                 525

Thr Leu Val Asn Asn Lys Ile Leu Leu Ala Ala Val Gly Ala Thr Val
            530                 535                 540

Asn Glu Lys Gln Lys Lys Phe Val Ser Phe Thr Asp Pro Ile Ser Ile
545                 550                 555                 560

Gln Thr Tyr Ser Phe Val Ile Ser Arg Pro Arg Glu Leu Ser Arg Val
                565                 570                 575

Leu Leu Phe Leu Ser Pro Phe Gly Ser Asp Thr Trp Leu Cys Leu Ala
            580                 585                 590

Ala Val Ala Leu Met Gly Pro Ile Leu Cys Ala Ile Asn Lys Leu
            595                 600                 605

Ser Pro Tyr Tyr Glu Val His Asn Lys Pro Thr Asp Thr Gly Leu Gly
            610                 615                 620

Lys Val Asn Asn Cys Phe Trp Tyr Ile Tyr Gly Ala Leu Leu Gln Gln
625                 630                 635                 640

Gly Leu Tyr Leu Pro Tyr Ala Asp Ser Gly Arg Ile Ile Gly Thr
                645                 650                 655

Trp Trp Leu Val Val Leu Val Ile Val Thr Thr Tyr Cys Gly Asn Leu
                660                 665                 670

Val Ala Phe Leu Thr Phe Pro Lys Ile Asp Ile Pro Val Asn Arg Val
                675                 680                 685

Met Gln Leu Leu Arg Asn Asp Arg Gly Met Thr Trp Ser Ile Arg Arg
    690                 695                 700

Gly Thr Phe Leu Glu Glu Met Leu Met Asp Ser Thr Glu Pro Lys Tyr
705                 710                 715                 720

Met Gln Leu Tyr Lys Gly Ser Gln Ile Ile Gly Glu Leu Thr Asp Glu
                725                 730                 735

Leu Val Glu Arg Ile Glu Ala Gly Gln His Val His Ile Asp Trp Arg
                740                 745                 750

Asn Asn Leu Arg Tyr Leu Met Lys Arg Gln Phe Leu Arg Thr Asp Arg
            755                 760                 765

Cys Asp Phe Ala Leu Ser Thr Asp Glu Phe Leu Asp Glu Gln Ile Ala
770                 775                 780

Leu Val Met Pro Lys Asp Ser Pro Tyr Leu Glu Leu Val Asn Glu Glu
```

```
                785                 790                 795                 800
Ile Lys Arg Met His Gln Phe Gly Phe Ile Gln Arg Trp Val Ala Gln
                    805                 810                 815

Tyr Leu Pro Ala Lys Asp Lys Cys Ser Gly Thr Gly Arg Val Met Asp
                    820                 825                 830

Val Gln Asn His Thr Val Asn Ser Ser Asp Met Ala Gly Ser Tyr Trp
                    835                 840                 845

Ile Leu Leu Leu Gly Phe Val Ser Gly Leu Phe Val Phe Val Cys Glu
                850                 855                 860

Phe Ala Val Ala Trp Tyr Arg Lys His Arg Ala Ala Arg Ala Ala Thr
865                 870                 875                 880

Val Ala Tyr Arg Asp
                885

<210> SEQ ID NO 26
<211> LENGTH: 840
<212> TYPE: PRT
<213> ORGANISM: Culex quinquefasciatus

<400> SEQUENCE: 26

Met Ala Ala Val Ile Leu Asp Arg Glu Tyr Leu Asp Asn Gln Tyr Glu
1               5                   10                  15

Ala Leu Leu Glu Asn Thr Lys Arg Thr Phe Glu Gln Ile Leu Arg Asp
                20                  25                  30

Asn Phe Lys Asn Gly Gly Leu Ile Val Lys Tyr Phe Ser Trp Thr Ser
                35                  40                  45

Ile Asn Leu Arg Arg Asp Phe Thr Ala Val Leu Ser Val Ser Asn Cys
            50                  55                  60

Glu Asn Thr Trp Asp Val Tyr Arg Asn Ala Ala Lys Glu Asn Leu Val
65              70                  75                  80

Ile Met Ala Ile Thr Asp Thr Asp Cys Pro Arg Leu Pro Ser His Asn
                85                  90                  95

Ala Ile Met Ile Pro Lys Ser Ile Pro Ala Ser Gly Ile Phe Glu Glu
                100                 105                 110

Leu Pro Gln Val Ile Met Asp Met Lys Thr Met Lys Ala Phe Ser Trp
            115                 120                 125

Lys Ser Ala Ile Leu Leu Tyr Asp Asp Ser Phe Asp Arg Asp Ile Val
130                 135                 140

Ala Arg Ser Val Leu Ala Leu Ser Lys Glu Ser Glu Asp Val Leu Pro
145                 150                 155                 160

Leu Ser Leu Ser Leu Phe Arg Ile Glu Ser His Thr His Met Trp Glu
                165                 170                 175

Lys Arg Lys Ala Val Arg Lys Val Leu Leu Gly Leu Pro Thr Arg Tyr
            180                 185                 190

Ile Gly Thr Asn Phe Ile Ala Ile Val Thr Ala Thr Met Glu Leu
            195                 200                 205

Val Met Asp Ile Ala Lys Glu Leu Lys Met Val Asn Pro Leu Ala Gln
            210                 215                 220

Trp Leu Tyr Val Ile Ser Asp Thr Thr Ala Glu Gln Asn Asn Ile Ser
225                 230                 235                 240

Ser Val His Ser Ile Ile Ser Glu Gly Asp Asn Ile Ala Phe Val Tyr
                245                 250                 255

Asn Met Arg Lys Thr Ala Ala Ser Cys Glu Ser Gln Thr Leu Cys Tyr
            260                 265                 270
```

-continued

```
Ile Glu Asn Leu Val Asn Ala Leu Val Lys Gly Leu Ser Lys Leu Ile
            275                 280                 285
Arg Glu Glu Lys Ala Val Tyr Gly Gln Ile Ala Asp Glu Glu Trp Glu
        290                 295                 300
Val Ile Arg Met Thr Lys Val Glu Arg Lys Asn Asp Ile Leu Gln Ile
305                 310                 315                 320
Ile Lys Glu Glu Arg Val Gly Lys Asp Thr Cys Asn Glu Cys Ser Met
                325                 330                 335
Trp Lys Val Gln Ser Gly Glu Thr Trp Gly Tyr Thr Tyr Gln Leu Pro
            340                 345                 350
Ala Asp Asp Val Leu Ser Gly Thr Ala Val Gly Arg Arg Lys Gln Val
        355                 360                 365
Glu Met Leu Asp Val Gly Tyr Trp Thr Pro Gln Asp Gly Phe Val Met
    370                 375                 380
Ala Asp Phe Leu Phe Pro His Ile Ser His Gly Phe Arg Gly Ile His
385                 390                 395                 400
Leu Asn Phe Tyr Thr Tyr His Asn Pro Pro Trp Gln Phe Val Ser Phe
                405                 410                 415
Asn Glu Ser Gly His Pro Thr Leu Ser Gly Gly Val Val Met Asp Ile
            420                 425                 430
Leu Glu Glu Leu Ser Arg Lys Leu Asn Phe Thr Tyr Thr Val Ile Val
        435                 440                 445
Ala Gln Thr Asn Ile Glu Tyr Val Gly Asn Leu Thr Glu Asp Gly Asn
    450                 455                 460
Asn Thr Ser Ile Arg Glu Ile His Thr Val Thr Thr Asp Ile Pro Ser
465                 470                 475                 480
Glu Ile Met Lys Ser Leu Ile Asp Asn Lys Ile Leu Leu Ala Ala Val
                485                 490                 495
Gly Ala Thr Val Ser Glu Lys Gln Lys Lys Phe Ile Asn Phe Thr Val
            500                 505                 510
Pro Ile Ser Ile Gln Thr Tyr Ser Phe Ile Val Ser Arg Pro Lys Glu
        515                 520                 525
Leu Ser Arg Val Phe Leu Phe Leu Ser Pro Phe Thr Val Asp Thr Trp
    530                 535                 540
Met Cys Leu Gly Leu Thr Ile Leu Met Met Ala Pro Leu Leu Tyr Val
545                 550                 555                 560
Val Asn Arg Val Ser Pro Phe Tyr Glu His His Gly Lys Ser Asn Lys
                565                 570                 575
Leu Gly Leu Gly Lys Leu Asn Asn Cys Phe Trp Tyr Leu Tyr Gly Ala
            580                 585                 590
Leu Leu Gln Gln Gly Gly Leu Tyr Leu Pro Tyr Ala Asp Ser Gly Arg
        595                 600                 605
Ile Ile Ile Gly Thr Trp Trp Leu Val Val Leu Val Ile Val Thr Thr
    610                 615                 620
Tyr Cys Gly Asn Leu Val Ala Phe Leu Thr Phe Pro Lys Ile Ala Val
625                 630                 635                 640
Pro Ile Thr Thr Ile Ser Gln Leu Val Arg Asn Asn Glu Gly Ile Thr
                645                 650                 655
Trp Ser Ile Arg Lys Gly Thr Phe Glu Gln Phe Leu Arg Glu Thr
            660                 665                 670
Asp Asp Ala Lys Tyr Leu Lys Leu Ser His Gly Ala Thr Phe Ile Ser
        675                 680                 685
Asp Glu Ser Asp Ser Met Val Gln Ser Ile Arg Asn Gly His His Val
```

```
              690                 695                 700
His Ile Asp Trp Arg Thr Asn Leu Lys Tyr Leu Leu Lys Arg Glu Phe
705                 710                 715                 720

Leu Lys Asn Asp Arg Cys Asp Phe Ala Leu Ser Leu Asp Glu Phe Leu
                725                 730                 735

Asp Glu Gln Ile Ala Leu Ala Leu Pro Lys Ala Ser Pro Tyr Leu Asp
                740                 745                 750

Val Ile Asn Ala Glu Ile Thr Lys Met His Gln Phe Gly Phe Ile His
            755                 760                 765

Lys Trp Leu Ser Asn Tyr Met Pro Ser Glu Asp Lys Cys Ser Lys Ala
        770                 775                 780

Arg Lys Asn Thr Asp Val Glu Asn His Thr Val Asn Asn Asp Asp Met
785                 790                 795                 800

Ala Gly Ser Tyr Tyr Val Leu Leu Ile Gly Phe Ser Ser Gly Met Phe
                805                 810                 815

Leu Phe Leu Ile Glu Phe Gly Trp Arg Phe Tyr Lys Lys Ser Lys Glu
                820                 825                 830

Gln Ser Leu Gln Pro Phe Thr Asp
            835                 840

<210> SEQ ID NO 27
<211> LENGTH: 862
<212> TYPE: PRT
<213> ORGANISM: Bombyx mori

<400> SEQUENCE: 27

Met Lys Ile Trp Val Leu Gly Val Leu Cys Leu Ala Ile Ser Val Gln
1               5                   10                  15

Gly Glu Asp Phe Pro Ser Leu Ile Thr Ala Asn Ala Ser Ile Ala Val
                20                  25                  30

Ile Leu Asp Arg Gln Tyr Leu Gly Asp Lys Tyr Gln Thr Val Leu Asp
            35                  40                  45

Glu Leu Lys Asp Tyr Ile Lys Glu Leu Ala Arg Val Glu Leu Lys His
        50                  55                  60

Gly Gly Val Leu Val His Tyr Tyr Ser Trp Thr Asn Ile Ser Leu Asn
65                  70                  75                  80

Lys Gly Phe Leu Ala Val Phe Ser Ile Ala Ser Cys Glu Asp Thr Trp
                85                  90                  95

Glu Leu Phe Ser Arg Thr Glu Glu Asp Leu Leu Leu Phe Ala Leu
                100                 105                 110

Thr Glu Val Asp Cys Pro Arg Leu Pro Gln Arg Ser Ala Ile Thr Val
            115                 120                 125

Thr Tyr Ser Glu Pro Gly Glu Glu Leu Pro Gln Leu Leu Leu Asp Leu
        130                 135                 140

Arg Ser Ser Asn Ala Ile Ser Trp Lys Ser Ala Val Ile Leu His Asp
145                 150                 155                 160

Asp Thr Leu Gly Arg Asp Met Val Ser Arg Val Gln Ser Leu Thr
                165                 170                 175

Ser Gln Ile Asp Glu Glu Ser Ala Arg Pro Val Ser Val Thr Val Phe
            180                 185                 190

Lys Met Lys His Glu Met Asn Glu Tyr Leu Arg Arg Lys Glu Met His
        195                 200                 205

Arg Val Leu Ser Lys Leu Pro Val Lys Tyr Ile Gly Glu Asn Phe Ile
    210                 215                 220
```

```
Ala Ile Val Thr Ser Asp Val Met Thr Thr Met Ala Glu Ile Ala Arg
225                 230                 235                 240

Glu Leu Leu Met Ser His Thr Met Ala Gln Trp Leu Tyr Val Ile Ser
            245                 250                 255

Asp Thr Asn Ala His Ala Ser Asn Leu Ser Gly Phe Ile Asn Thr Leu
        260                 265                 270

Asn Glu Gly Glu Asn Val Ala Phe Ile Tyr Asn Ile Thr Glu Asn Gly
    275                 280                 285

Pro Asp Cys Lys Asn Gly Leu Met Cys Tyr Ser Gln Glu Met Met Ser
290                 295                 300

Ala Phe Ile Ser Ala Leu Asp Ala Ala Ile Gln Ala Glu Phe Asp Val
305                 310                 315                 320

Ala Ala Gln Val Ser Asp Glu Glu Trp Glu Ala Ile Arg Pro Ser Lys
            325                 330                 335

Val Gln Arg Arg Asp Ile Leu Leu Lys His Met Gln Gln Tyr Ile Leu
        340                 345                 350

Ala Lys Ser Val Cys Gly Asn Cys Thr Leu Trp Arg Ala Leu Ala Ala
    355                 360                 365

Asp Thr Trp Gly Val Thr Tyr Arg Gln Asn Asp Val Pro Glu Gln Ile
370                 375                 380

Asn Glu His Ala Asn Gly Ser Thr Gly Val Ile Glu His Leu Glu Leu
385                 390                 395                 400

Met Asn Val Gly Ile Trp Arg Pro Ile Asp Ala Met Thr Phe Ala Asp
            405                 410                 415

Leu Leu Phe Pro His Val His Gly Phe Arg Gly Lys Glu Leu Pro
        420                 425                 430

Ile Ile Thr Tyr His Asn Pro Pro Trp Thr Phe Leu Gln Ala Asn Glu
    435                 440                 445

Ser Gly Ala Ile Val Lys Tyr Ser Gly Leu Met Phe Asp Ile Val Asn
450                 455                 460

Gln Leu Ala Lys Asn Lys Asn Phe Gln Arg Leu Pro His Pro Ser Asn
465                 470                 475                 480

Arg Asn Ala Leu Leu Leu His Gly Arg Asn Arg Gln Gly Gly Thr
            485                 490                 495

Tyr Pro Cys Gly Leu Thr Lys Gly Pro Ile Thr Tyr Asn Asn Ile Pro
        500                 505                 510

Leu Tyr Phe Arg Ala Val Phe Ile Ala His Gln Ala Gly Val Asn Leu
    515                 520                 525

Lys Asn Asn Tyr Tyr Arg Cys Ile Asn Tyr Thr Ile Pro Val Ser Thr
530                 535                 540

Gln Pro His Thr Phe Ile Val Ala Arg Pro Arg Glu Leu Ser Arg Ala
545                 550                 555                 560

Leu Leu Phe Leu Leu Pro Phe Thr Thr Asp Thr Trp Leu Cys Leu Gly
            565                 570                 575

Phe Ala Val Ile Leu Met Gly Pro Met Leu Tyr Ile Val His Arg Leu
        580                 585                 590

Ser Pro Tyr Tyr Glu Ala Met Glu Ile Thr Arg Glu Gly Gly Leu Ala
    595                 600                 605

Thr Ile His Asn Cys Leu Trp Tyr Ile Tyr Gly Ala Leu Leu Gln Gln
610                 615                 620

Gly Gly Met Tyr Leu Pro Arg Ala Asp Ser Gly Arg Leu Val Ile Gly
625                 630                 635                 640

Thr Trp Trp Leu Val Val Leu Val Ile Val Thr Thr Tyr Ser Gly Asn
```

```
                      645                 650                 655
Leu Val Ala Phe Leu Thr Phe Pro Lys Leu Glu Ala Pro Val Thr Thr
                660                 665                 670

Ile Ser Glu Leu Leu Lys Asn Ser Asp Ala Tyr Thr Trp Ser Val Thr
            675                 680                 685

Lys Gly Ser Tyr Leu Glu Met Glu Leu Lys Asn Ser Glu Glu Pro Lys
        690                 695                 700

Tyr Lys Arg Leu Ile Lys Glu Ala Glu Leu Leu Lys Glu Thr Gly Gly
705                 710                 715                 720

Ile Glu Gly Thr Ile His Ala Ala Arg Gly Thr Leu Asp Arg Val Arg
                725                 730                 735

Gly Gln Arg His Leu Ile Phe Asp Trp Arg Leu Arg Leu Thr Tyr Leu
            740                 745                 750

Met Ser Ala Asp His Ile Ala Thr Glu Thr Cys Asp Phe Ala Leu Ala
        755                 760                 765

Val Glu Asp Phe Met Glu Gln Val Ala Met Ile Val Pro Ala Gly
    770                 775                 780

Ser Pro Tyr Leu Pro Val Ile Asn Lys Glu Ile Asn Arg Met His Lys
785                 790                 795                 800

Ala Gly Leu Ile Ser Lys Trp Leu Ser Ala Tyr Leu Pro Lys Pro Asn
                805                 810                 815

Arg Cys Leu Lys Ile Ser Thr Val Thr Gln Glu Val Ser Asn His Thr
            820                 825                 830

Val Asn Leu Ser Asp Met Gln Gly Ser Phe Phe Val Leu Phe Leu Gly
        835                 840                 845

Asn Asp Lys Ile Tyr Val Tyr Met Tyr Ile Ala Glu Leu Ile
    850                 855                 860

<210> SEQ ID NO 28
<211> LENGTH: 779
<212> TYPE: PRT
<213> ORGANISM: Danaus plexippus

<400> SEQUENCE: 28

Met Ile Tyr Leu Thr Ala Val Val Leu Asp His Gln Phe Leu Gly Asp
1               5                   10                  15

Glu Tyr Gln Met Met Leu Glu Asp Leu Glu Asp Tyr Ile Lys Glu Leu
            20                  25                  30

Val Arg Val Glu Leu Lys His Gly Gly Ile Asn Val His Tyr Tyr Ser
        35                  40                  45

Trp Thr Ser Ile Asn Leu Lys Lys Gly Phe Leu Ala Ile Phe Ser Ile
    50                  55                  60

Ala Ser Cys Glu Asp Thr Trp Ser Leu Phe Leu Arg Ala Glu Glu Glu
65              70                  75                  80

Asp Leu Leu His Ile Ala Val Thr Glu Val Asp Cys Pro Arg Leu Pro
            85                  90                  95

Ser Asp Ser Ala Ile Thr Val Thr Phe Ala Asp Pro Gly Gln Glu Leu
        100                 105                 110

Pro Gln Leu Val Leu Asp Leu Arg Thr Arg Lys Ala Phe Asn Trp Lys
    115                 120                 125

Ser Ala Ile Ile Leu His Asp Glu Thr Leu Asn Arg Asp Met Val Ser
    130                 135                 140

Arg Val Val Glu Ser Leu Thr Ser Gln Ile Asp Asp Ile Ser Ser Ile
145                 150                 155                 160
```

```
Ser Val Ser Val Tyr Lys Met Arg His Glu Asn Asn Glu Tyr Leu Arg
                165                 170                 175
Arg Lys Glu Val Tyr Arg Val Leu Lys Lys Leu Pro Val Lys Tyr Ile
            180                 185                 190
Gly Glu Asn Phe Ile Ala Ile Val Thr Thr Asp Val Met Ala Thr Ile
        195                 200                 205
Ala Glu Ile Ala Arg Glu Leu Arg Met Ser His Thr Gln Ala Gln Trp
    210                 215                 220
Leu Tyr Leu Val Pro Asp Thr Asp Ser His Thr Gly Asn Val Thr Asn
225                 230                 235                 240
Leu Ile Asn Asp Leu Tyr Glu Gly Glu Asn Ile Ala Tyr Ile Phe Asn
                245                 250                 255
Phe Thr Asp Asp Arg Gly Cys Lys Asn Gly Leu Lys Cys Tyr Ala His
            260                 265                 270
Glu Val Leu Asp Ser Phe Ile Ser Ala Leu Glu Ala Ala Val Leu Asp
        275                 280                 285
Glu Leu Glu Ala Ala Leu Gln Val Ser Asp Glu Trp Glu Ala Val
    290                 295                 300
Arg Pro Thr Lys Leu Gln Arg Arg Asn Ser Leu Leu Trp His Met Gln
305                 310                 315                 320
Gln Tyr Leu Ser Thr Arg Ser Val Cys Gly Asn Cys Ser Ser Trp Arg
                325                 330                 335
Ala Leu Ser Ala Asp Thr Trp Gly Ala Thr Tyr Asp Arg Ala Asp Glu
            340                 345                 350
Asn Thr Ser Ser Leu Ile Glu Gln Val His Leu Val Gln Val Gly Phe
        355                 360                 365
Trp Arg Pro Ile Asp Gly Val Thr Phe Glu Asp Val Leu Phe Pro His
    370                 375                 380
Ile Gln His Gly Phe Arg Gly Lys Gln Leu Pro Ile Met Thr Tyr His
385                 390                 395                 400
Thr Leu Tyr Asn Thr Asn Arg Gln Leu Ile Leu Ser Ala Ile Ala Lys
                405                 410                 415
Gly His Ala Ala Leu Val Ala Ala Pro Phe Thr Val Ser Pro Asp Thr
            420                 425                 430
His Pro Gly Val Asn Phe Thr Val Pro Val Ser Thr Gln Ser Tyr Ser
        435                 440                 445
Phe Ile Ile Ala Arg Pro Arg Glu Leu Asn Arg Ala Leu Leu Phe Leu
    450                 455                 460
Leu Pro Phe Thr Thr Asp Thr Trp Leu Cys Ile Ala Phe Ala Val Val
465                 470                 475                 480
Leu Met Gly Pro Thr Leu Tyr Val Val His Arg Val Ser Pro Tyr Tyr
                485                 490                 495
Glu Ala Met Glu Ile Thr Arg Glu Gly Gly Leu Ser Thr Ile Tyr Asn
            500                 505                 510
Cys Leu Trp Tyr Ile Tyr Gly Ala Leu Leu Gln Gln Gly Gly Met Tyr
        515                 520                 525
Leu Pro Arg Ala Asp Ser Gly Arg Leu Val Gly Thr Trp Trp Leu
    530                 535                 540
Val Val Leu Val Val Val Thr Thr Tyr Ser Gly Asn Leu Val Val Phe
545                 550                 555                 560
Leu Thr Phe Pro Lys Leu Glu Ile Pro Val Thr Val Ser Glu Leu
                565                 570                 575
Leu Asp Ser Gly Thr Tyr Ser Trp Ser Ile Arg Ser Gly Ser Phe Leu
```

-continued

```
                580             585             590
        Glu Ser Gln Leu Lys Asn Ser Asn Glu Pro Lys Tyr Glu Ala Leu Leu
                    595                 600                 605

Lys Arg Ala Glu Leu Thr Ser Pro Ser Asp Gly Ala Glu Asn Asp Ala
        610                 615                 620

Ile Val Glu Arg Val Arg Ile Val Glu Arg Val Arg Phe Ser His His
        625                 630                 635                 640

Ala Leu Phe Asp Trp Lys Leu Arg Leu Arg Tyr Leu Met Arg Ala Asp
                        645                 650                 655

Thr Glu Gln Thr Asp Ser Cys Asp Phe Ala Leu Ser Thr Glu Glu Phe
                    660                 665                 670

Met Asp Glu Gln Val Ala Met Ile Leu Pro Ala Gly Ser Pro Tyr Leu
                675                 680                 685

Pro Val Ile Asn Lys Glu Ile Asn Arg Met Lys Lys Ala Gly Leu Ile
            690                 695                 700

Thr Lys Trp Leu Ser Ala Tyr Leu Pro Lys Arg Asp Arg Cys Trp Lys
        705                 710                 715                 720

Thr Ser Ala Ile Thr Gln Glu Val Asn Asn His Thr Val Asn Leu Ser
                        725                 730                 735

Asp Met Gln Gly Ser Phe Leu Val Leu Phe Leu Gly Phe Phe Ser Ala
                    740                 745                 750

Leu Thr Val Leu Leu Glu Tyr Phe Tyr Asn Arg Arg Lys Asn Asn
                755                 760                 765

Glu Glu Arg Thr Val Ile Lys Pro Tyr Val Glu
            770                 775

<210> SEQ ID NO 29
<211> LENGTH: 848
<212> TYPE: PRT
<213> ORGANISM: Tribolium castaneum

<400> SEQUENCE: 29

Met Leu Leu Glu Leu Val Leu Ser Ser Ala Phe Val Cys Val Ile Arg
1               5                   10                  15

Gly Asp Ser Phe Pro Ser Leu Leu Thr Thr Asn Ala Thr Leu Ala Val
            20                  25                  30

Ile Ile Asp Arg Glu Phe Leu Ser Asn Glu Tyr Glu Val Ile Lys His
        35                  40                  45

Ala Ile Glu Ser Tyr Leu Val Phe Ala Lys Arg Glu Ile Leu Lys His
    50                  55                  60

Gly Gly Val Asn Val Gln Tyr Tyr Ser Trp Thr Ile Asn Ile Lys
65                  70                  75                  80

Lys Asp Val Thr Ala Ile Phe Ser Ile Ala Ser Cys Pro Asp Thr Trp
                85                  90                  95

Arg Leu Phe Arg Gln Ala Arg Asp Ala Asn Leu Leu His Met Ala Ile
            100                 105                 110

Ser Glu Ser Asp Cys Pro Arg Leu Pro Pro Asp Glu Ala Ile Thr Val
        115                 120                 125

Pro Leu Ile Thr Arg Gly Glu Glu Leu Pro Gln Leu Leu Leu Asp Leu
    130                 135                 140

Arg Thr Arg Gln Thr Tyr Asn Trp Asn Ser Ala Phe Ile Leu Tyr Asp
145                 150                 155                 160

Asp Thr Leu Ser Arg Asp Gln Val Thr Arg Val Val Lys Ser Ile Thr
                165                 170                 175
```

```
Ala Gln Tyr Ser Asn Leu Arg Val Asn Ala Ala Ile Ser Phe Val
            180                 185                 190

Lys Leu Glu Thr Arg Leu Pro Met Asp Glu Ile Arg Arg Gln Val Lys
        195                 200                 205

Glu Ile Leu Ser Ser Val Ser Ile Lys Thr Val Gly Gly Asn Phe Leu
    210                 215                 220

Ala Ile Ile Gly Tyr Glu Leu Val Glu Leu Leu Met Glu Tyr Ala Lys
225                 230                 235                 240

Met Phe Gly Leu Val Asn Thr Arg Thr Gln Trp Leu Tyr Ile Ile Ser
            245                 250                 255

Asn Thr His Phe Arg His Lys Asp Ile Asn Arg Phe Arg Gln Leu Leu
        260                 265                 270

Ser Glu Gly Asp Asn Ile Ala Phe Leu Tyr Asn Asn Thr Val Asn Asn
    275                 280                 285

Asp Thr Cys Thr Gly Gly Ile Gln Cys His Cys Glu Glu Ile Leu Ser
290                 295                 300

Gly Phe Thr Arg Ala Leu Asp Glu Ala Ile Leu Phe Gly Trp Glu Thr
305                 310                 315                 320

Ser Ser Gln Val Ser Asp Glu Glu Trp Glu Ala Ile Arg Pro Ser Lys
            325                 330                 335

Leu Asp Arg Arg Asn Ser Leu Leu Gln Gly Ile Lys Thr Phe Leu Leu
        340                 345                 350

Gln Arg Gly Gln Cys Asp Asn Cys Thr Ser Trp Leu Met Lys Thr Gly
    355                 360                 365

Asp Thr Trp Gly Arg Glu Tyr Gln Gln Asn Gly Thr Asp Ser Gly Gly
370                 375                 380

Leu Ile Ser Val Gly Asn Trp Arg Pro Ser Asp Gly Pro Ser Met Ser
385                 390                 395                 400

Asp Glu Leu Phe Pro His Ile Val His Gly Phe Arg Lys Arg Asn Leu
            405                 410                 415

Pro Ile Val Thr Phe His Asn Pro Pro Trp Gln Ile Ile Arg Ser Asn
        420                 425                 430

Glu Ser Gly Ala Val Ser Glu Tyr Ala Gly Val Ile Phe Glu Leu Ile
    435                 440                 445

Lys Glu Leu Ser Lys Asn Leu Asn Phe Thr Tyr Thr Val Glu Leu Ala
450                 455                 460

Lys Ile Gly Gln Glu Phe Ser Ala Asn Leu Thr Lys Asn Glu Ala Gln
465                 470                 475                 480

Val Val Thr Asn Phe Ile Pro Asp Ser Ile Leu Asp Met Ile Arg Asn
            485                 490                 495

Lys Ser Val Ala Phe Gly Ala Cys Ala Phe Thr Val Thr Glu Glu Ser
        500                 505                 510

Lys Arg Leu Ile Asn Phe Thr Ser Pro Ile Ser Thr Gln Thr Tyr Thr
    515                 520                 525

Phe Leu Val Ser Arg Pro Arg Glu Leu Ser Arg Ala Leu Leu Phe Met
530                 535                 540

Ser Pro Phe Thr Gly Asp Thr Trp Leu Cys Leu Ser Ala Ser Ile Val
545                 550                 555                 560

Ser Met Gly Pro Ile Leu Tyr Tyr Ile His Lys Tyr Ser Pro Val Tyr
            565                 570                 575

Glu Tyr Lys Gly Leu Ser Lys Arg Gly Leu Ser Ser Val Gln Asn Cys
        580                 585                 590

Ile Trp Tyr Met Tyr Gly Ala Leu Leu Gln Gln Gly Gly Met His Leu
```

```
            595                 600                 605
Pro Gln Ala Asp Ser Ala Arg Ile Ile Val Gly Ala Trp Trp Leu Val
            610                 615                 620
Val Leu Val Leu Ala Thr Thr Tyr Cys Gly Asn Leu Val Ala Phe Leu
625                 630                 635                 640
Thr Phe Pro Lys Ile Asp Ile Pro Ile Thr Thr Ile Asp Glu Leu Leu
                    645                 650                 655
Ala His Ser Gly Thr Val Thr Trp Ser Met Pro Lys Gly Ser Tyr Leu
                660                 665                 670
Glu Arg Thr Leu Lys Tyr Thr Thr Glu Pro Arg Phe Arg Tyr Leu Phe
            675                 680                 685
Asp Lys Lys Val Glu Val Gly Asn Phe Lys Asn Met Ile Glu Asp Ile
        690                 695                 700
Glu Asn Gly Lys His Val His Ile Asp Trp Lys Ile Lys Leu Gln Tyr
705                 710                 715                 720
Ile Met Lys Gln Gln Tyr Leu Asp Ser Asp Arg Cys Asp Leu Ala Leu
                    725                 730                 735
Gly Leu Asp Glu Phe Leu Asn Glu Gln Leu Ala Met Val Val Ser Gln
                740                 745                 750
Asp Thr Pro Tyr Leu Glu Ile Ile Asn Asp Glu Ile Lys Lys Leu His
            755                 760                 765
Gln Val Gly Leu Ile Gln Lys Trp Leu Thr Asp Tyr Leu Pro Lys Lys
        770                 775                 780
Asp Arg Cys Trp Lys Asn Asn Arg His Ile Val Glu Val Asn Asn His
785                 790                 795                 800
Thr Val Asn Met Asp Asp Met Gln Gly Ser Phe Phe Val Leu Phe Leu
                    805                 810                 815
Gly Phe Leu Leu Ser Phe Phe Ile Thr Ile Gly Glu Lys Leu Trp His
                820                 825                 830
Lys Tyr Val Thr Lys Lys Met Lys Ile Ile Gln Pro Phe Thr Thr
            835                 840                 845

<210> SEQ ID NO 30
<211> LENGTH: 895
<212> TYPE: PRT
<213> ORGANISM: Nasonia vitripennis

<400> SEQUENCE: 30

Met Leu Leu Ala Leu Leu Val Leu Ala Gly Trp Ile Glu Ile Gly
1               5                   10                  15
Thr Gly Tyr Asn Asp Phe Pro Ser Leu Met Thr Ala Asn Ala Thr Met
                20                  25                  30
Ala Val Ile Val Glu Lys Gly Phe Phe Lys Ser Ala Asp Asn Tyr Arg
            35                  40                  45
His Thr Leu Asp Glu Ile Ser Asp Val Ala Asn Ala Val Ile Arg Lys
        50                  55                  60
Asn Met Glu Ile Ser Gly Ile Ala Leu His Val Phe Gly Asp Ala Asp
65                  70                  75                  80
Val Asn Leu Ala Arg Asp Tyr Thr Val Leu Leu Ser Val Ala Ser Cys
                85                  90                  95
Gln Thr Thr Trp His Leu Phe Lys Arg Ala Gln Lys Glu Lys Leu Val
                100                 105                 110
Tyr Leu Ala Val Thr Asp Pro Asp Cys Pro Arg Leu Pro Glu Asp Ala
            115                 120                 125
```

```
Gly Ile Ser Leu Pro Leu Thr Asn Pro Gly Glu Glu Leu Pro Gln Ile
    130                 135                 140

Phe Leu Asp Leu Arg Thr Thr Gly Ser Leu Ser Trp Pro Lys Val Asn
145                 150                 155                 160

Leu Ile His Asp Asp Thr Phe Ala Arg Asp Thr Ile Ser Arg Val Val
                165                 170                 175

Lys Ala Leu Ser Leu Glu Leu Pro Asp Lys Arg Val Ser Leu Ser Ala
            180                 185                 190

Gln Ala Leu Phe Ser Thr Arg Phe Glu Lys Asn Glu Asn Ala Met Arg
        195                 200                 205

Gln Arg Val His Arg Ile Leu Ser Asn Tyr His Val Asp Gln Leu Gly
    210                 215                 220

Ser Cys Phe Met Val Val Thr Val Asp Met Val Ser Ile Val Met
225                 230                 235                 240

Glu Val Ala Lys Ser Leu Arg Leu Val His Pro Gly Ser Gln Trp Leu
                245                 250                 255

Tyr Val Ile Ser Asp Ala Ala Gly Arg Glu Ala Lys Val Thr Ser Phe
                260                 265                 270

Ala Glu Leu Leu Ala Glu Gly Glu Asn Val Ala Phe Val His Asn Ala
        275                 280                 285

Thr Lys His Val Ala Asn Cys Asn Met Gly Leu Met Cys His Val Lys
    290                 295                 300

Glu Leu Val Arg Ala Leu Ala Ile Ser Leu Glu Asn Ser Leu Leu Asn
305                 310                 315                 320

Glu Leu Glu Leu Tyr Asp Arg Val Thr Glu Glu Phe Glu Val Val
                325                 330                 335

Arg Leu Ser Lys Ala Glu Arg Lys Gln Glu Ile Val Lys Ser Val Asn
            340                 345                 350

Arg Glu Leu Ser Tyr Ala Arg Ala His Thr Ser Ser Cys Gly Lys Cys
        355                 360                 365

Val Asn Trp Arg Phe Ser Ser Ala Ile Thr Trp Gly Thr Ser Phe Ala
    370                 375                 380

Ser Ser Glu Glu Lys Gln Arg Arg Glu Ser Gly Glu Lys Arg Arg Arg
385                 390                 395                 400

Glu Asn Ser Lys Arg His Ser Glu Asp Asp Leu Gly Glu Lys Ser Leu
                405                 410                 415

Gly Leu Gly Glu Leu Leu Asp Ala Gly Thr Trp Ser Pro Gly Pro Gly
                420                 425                 430

Val Asn Met Ser Glu Pro Leu Phe Pro His Val Glu His Gly Phe Arg
        435                 440                 445

Gly Arg Ser Leu Pro Val Ser Thr Phe His Asn Pro Pro Trp Gln Ile
    450                 455                 460

Ile Lys Tyr Ser Asn Thr Gly Ala Gln Glu Tyr Gly Gly Leu Ile Phe
465                 470                 475                 480

Asp Val Leu Asn Tyr Leu Ser Leu Lys Leu Asn Phe Thr Tyr Thr Val
                485                 490                 495

Arg Leu Ala Ser Ser Pro Ala Ala Glu Ala Pro Thr Arg Leu Pro Ser
            500                 505                 510

Ala Gly Asp Ser Ser Lys Ser Met Asp Leu Ala Ala Met Ser Val Ala
        515                 520                 525

Gln Lys Val Pro Gln Glu Val Val Glu Leu Val Arg Ser Lys Gln Val
    530                 535                 540

Phe Ile Ala Ala Ser Ala Phe Thr Val Gly Lys Asn Ser Gly Gly Leu
```

```
                545                 550                 555                 560
Asn Phe Thr Ala Ala Ile Val Met Gln Asn Tyr Ala Leu Leu Ser Ala
                        565                 570                 575

Lys Pro Lys Pro Leu Ser Arg Ala Leu Leu Phe Thr Ala Pro Tyr Thr
            580                 585                 590

Asn Glu Thr Trp Ala Cys Leu Thr Ser Val Leu Ile Val Ile Gly Pro
        595                 600                 605

Ile Leu Tyr Leu Thr Val Lys Leu Ser Pro Arg Pro Arg Asp Ile Asp
    610                 615                 620

Asn Ser Leu Ser Leu Ser Thr Thr Trp Gln Cys Ser Trp Tyr Val Tyr
625                 630                 635                 640

Gly Ala Leu Leu Gln Gln Gly Gly Met Ser Leu Pro Lys Ala Asp Ser
                        645                 650                 655

Ala Arg Leu Val Ile Gly Thr Trp Trp Leu Val Val Met Ile Val Val
            660                 665                 670

Ala Thr Tyr Ser Gly Asn Leu Ile Ala Phe Leu Thr Phe Pro Arg Ile
        675                 680                 685

Asp Ala Pro Ile Asp Asn Val Asp Asp Leu Leu Ala Arg Ser Asp Ala
    690                 695                 700

Phe His Trp Ser Phe Pro Asn Gly Ser Ala Leu Glu Ser Tyr Leu Ile
705                 710                 715                 720

Ala Ala Val Asn Asp Asp Pro Lys Tyr Lys Gln Leu Leu Asp Gly Ala
                        725                 730                 735

Glu Arg Gln Asp Pro Ser Lys Pro Lys Gln Ile Leu Asp Arg Val Lys
            740                 745                 750

Ala Gly Asn Gln Val Leu Ile Asp Trp Arg Ile Ser Leu Ala Phe Leu
        755                 760                 765

Met Arg Glu Asp Leu Ile Asp Thr Gly Gly Cys His Phe His Val Ser
    770                 775                 780

Ala Glu Asp Phe Met His Glu Asn Met Ala Met Ile Ile Ser Gly Asp
785                 790                 795                 800

Ser Pro Tyr Leu Pro Leu Ile Asn Asp Ala Ile Glu Arg Met His Glu
                        805                 810                 815

Ser Gly Leu Met Lys Lys Trp Ile Thr Glu Lys Met Pro Met Lys Asp
            820                 825                 830

Lys Cys Trp Glu Ile Ala Lys Thr Asn Gln Glu Ala Thr Asn His Lys
        835                 840                 845

Val Asp Met Gly Asp Met Gln Gly Ile Phe Phe Val Leu Ala Ile Gly
    850                 855                 860

Phe Val Ile Ala Ala Ile Ala Ile Gly Val Glu Phe Ala Trp His Lys
865                 870                 875                 880

Arg Lys Glu Ala Phe Glu Arg Ser Leu Ile Arg Pro Phe Val Ser
                        885                 890                 895

<210> SEQ ID NO 31
<211> LENGTH: 814
<212> TYPE: PRT
<213> ORGANISM: Apis mellifera
<220> FEATURE:
<221> NAME/KEY: misc_feature
<222> LOCATION: (42)..(42)
<223> OTHER INFORMATION: Xaa can be any naturally occurring amino acid

<400> SEQUENCE: 31

Leu Tyr Ile Val Leu Arg Leu Lys Tyr His Lys Asn Ile Thr Asp Gly
1               5                   10                  15
```

```
Lys Pro Thr Ile Phe Leu Pro Leu Lys Phe Lys Phe Asn Asn Ile Ser
         20                  25                  30

Ile Tyr Phe Tyr Asn Lys Phe Lys Arg Xaa Arg Arg Arg Arg Val Arg
             35                  40                  45

Ile Cys Cys Leu Arg Leu Thr His Leu Ser Phe Arg Gln Ile Ser Phe
 50                  55                  60

Thr Asn Phe Asn Ser Ile Leu Val Cys Tyr Thr Asp Cys Pro Arg Leu
 65                  70                  75                  80

Pro Thr Asp Glu Ala Ile Thr Ile Pro Leu Thr Val His His Ser Glu
                 85                  90                  95

Leu Ser Gln Met Ile Leu Asp Leu Arg Met Ser Asn Ala Phe Ser Trp
                100                 105                 110

Lys Ser Ala Val Leu Met His Asp Asn Ser Ile Gly Asp Ser Val Leu
                115                 120                 125

Gln His Ile Val Thr Ser Leu Thr Lys Tyr Tyr Pro Ser Asn Ile Met
130                 135                 140

Ser Pro Ser Ile Thr Ile Phe Glu Ile Tyr Thr Gln Gly Ser Glu Trp
145                 150                 155                 160

Lys Arg Arg Lys Leu Phe Met Glu Asp Leu Gln His Phe Leu Lys Met
                165                 170                 175

Ser Glu Ile Asn Ser Asn Tyr Ile Cys Ile Val Ser Ile Leu Tyr Val
                180                 185                 190

Pro Leu Ile Leu Asp Val Ala Lys Ser Leu Asn Leu Met Thr Ala Glu
                195                 200                 205

Asn Ser Trp Leu Ile Ile Pro Asp Ile Asp Ser Ser Arg Asn Asn
                210                 215                 220

Thr Ser Ser Phe Thr Asn Leu Leu Ser Glu Gly Glu Asn Ile Ser Phe
225                 230                 235                 240

Ile Tyr Asn Ser Thr Lys Thr Gly Ser Lys Cys Ile Val Arg Ile Leu
                245                 250                 255

Cys Leu Val Asp Glu Leu Met Ser Val Phe Ile Met Ala Phe Ser Ala
                260                 265                 270

Leu Ile Gln Gln Glu Ile Glu Leu Ser Gln Arg Val Ser Glu Glu
                275                 280                 285

Trp Asp Glu Ile Arg Pro Ser Lys Ile Asp Arg Arg Gln Ser Met Val
290                 295                 300

Ser Phe Ile Lys Phe Arg Leu Asn Glu Ser Gly Val Cys Glu Thr Cys
305                 310                 315                 320

Pro Leu Trp Gln Ile Asp Ser Gly Val Thr Trp Gly Gln Glu His Phe
                325                 330                 335

Gly Gln Gly Cys Tyr Ile Leu Pro Val Gly Asn Trp Asn Thr Lys Thr
                340                 345                 350

Gly Leu Lys Leu Thr Glu Pro Leu Phe Leu His Leu Ala Asn Gly Phe
                355                 360                 365

Arg Gly Ile Ala Leu Pro Ile Ala Thr Phe Asn Phe Pro Pro Trp Gln
                370                 375                 380

Ile Val Asn Phe Asn Arg Ser Gly His Leu Ile Gly Tyr Ser Gly Leu
385                 390                 395                 400

Val Phe Asp Ile Ile Asn Gln Leu Ala Lys Thr Leu Asn Phe Thr Tyr
                405                 410                 415

Asn Val Ile Val Ile Ser Asn Thr Glu Gln Met Asn Thr Thr Arg Thr
                420                 425                 430
```

```
Leu Phe Met Gln Asn Asn Val Leu Gly Glu His Asp Ala Val Val Ser
            435                 440                 445

Lys Pro Leu Trp Asp Lys Met Ile Asp Leu Val Arg Ser Glu Lys Val
450                 455                 460

Phe Ile Ala Ala Ala Phe Ala Val Lys Glu Ala Asn Gln Ile Leu
465                 470                 475                 480

Val Asn Tyr Thr Thr His Ile Ser Leu Glu Pro His Gln Ile Leu Val
                485                 490                 495

Ala Arg Pro Lys Glu Leu Ser Arg Ala Leu Leu Phe Thr Ala Pro Phe
                500                 505                 510

Thr Leu Leu Thr Trp Leu Cys Ile Ala Ile Val Val Gly Leu Met Gly
            515                 520                 525

Pro Leu Leu Asn Val Phe His Val Leu Ser Pro Tyr Tyr Glu Tyr His
        530                 535                 540

Asn Ile Pro Arg Arg Gly Gly Leu Asn Ser Pro Leu Asn Cys Phe Trp
545                 550                 555                 560

Tyr Val Tyr Gly Ala Leu Leu Gln Gln Gly Gly Ala His Leu Pro Asp
                565                 570                 575

Ala Asp Ser Gly Arg Leu Val Val Gly Thr Trp Trp Leu Phe Val Leu
                580                 585                 590

Val Ile Val Thr Thr Tyr Ser Gly Asn Leu Val Ala Tyr Leu Thr Phe
            595                 600                 605

Pro Gln Met Asp Ser Met Val Ser Asn Val Ala Asp Leu Met Ala Arg
        610                 615                 620

Lys Pro Gln Gly Tyr Ser Trp Gly Ile Pro Lys Thr Ser Asn Leu His
625                 630                 635                 640

Ser Leu Leu Thr Thr Leu Pro Asp Asp Thr Met Val Lys Glu Leu Ile
                645                 650                 655

Lys Asn Ala Glu His His Glu Glu Leu Ser Arg Ser Ile Ile Glu Arg
                660                 665                 670

Val Arg Ser Gly Lys His Ala Phe Ile His Arg Thr Asn Leu Met
            675                 680                 685

Tyr Ile Met Lys Asn Asp Phe Leu Lys Thr Asn Arg Cys Asp Phe Ala
690                 695                 700

Ile Gly Asn Glu Asp Phe Ala Glu Glu Lys Leu Ala Met Met Leu Ser
705                 710                 715                 720

Lys Glu Ser Pro Tyr Leu Ser Arg Ile Asn Arg Glu Ile Glu Lys Met
                725                 730                 735

His Lys Val Gly Leu Ile Asn Lys Trp Leu Val Asp Thr Leu Pro Lys
                740                 745                 750

Lys Asp Gln Cys Trp Thr Asn Thr Gln Leu Glu Val Thr Asn His Lys
            755                 760                 765

Val Asn Leu Asp Asp Met Gln Gly Ser Phe Ile Val Leu Leu Leu Gly
        770                 775                 780

Val Leu Ser Ser Leu Val Ser Phe Val Phe Glu Tyr Ile Leu His Lys
785                 790                 795                 800

Tyr Ile Asn Arg Arg Gln Ile Val Ile Thr Pro Phe Ile Asn
                805                 810
```

<210> SEQ ID NO 32
<211> LENGTH: 897
<212> TYPE: PRT
<213> ORGANISM: Daphnia pulex

<400> SEQUENCE: 32

```
Met Leu Leu Arg Val Leu Leu Val Leu Ala Ser Ala Phe Ile His Val
1               5                   10                  15

Gln Ser Ala His Tyr Glu Leu Tyr Ser Glu Leu Arg Pro Asp Glu Arg
                20                  25                  30

Trp Phe Leu Asp Asp Thr Lys Leu Ile Pro Val Ser Cys Glu Asn Gly
            35                  40                  45

Asp Cys Ser Ala Leu Phe Asn Lys His Asn Lys His Lys Ile Ala Lys
        50                  55                  60

Arg Ala Ala Val Gln Val Glu Thr Met Lys Asp Tyr Ile Lys Phe Leu
65                  70                  75                  80

Leu Arg Gly Asn Lys Thr Lys Asp Asp Thr Asn Thr Asp Pro Tyr
                85                  90                  95

Arg Thr Ala Asn Ile Thr Leu Gly Val Val Met Asp Lys Asn Leu Ile
                100                 105                 110

Gly Asn Leu Gln Thr Phe Thr Asn Ile Phe Asp Val Ala Asn Met Pro
            115                 120                 125

Ser Asn Pro Glu Ile Asp Tyr Leu Arg Leu Gln Lys Phe Asn Val Thr
    130                 135                 140

Tyr Leu Asn Pro Gln Asp Lys Leu Pro Ser Asn Ile Asn Ala Val Leu
145                 150                 155                 160

Ser Ile Leu Pro Cys Asp Val Leu Thr Arg Phe Asp Lys Asn Leu Ala
                165                 170                 175

Ser Leu Pro Ile Leu His Ile Ala Ile Thr Ser Asp Asn Cys Pro Arg
            180                 185                 190

Ile Thr Arg Trp Ala Val Leu Met Val Pro Val Val Lys Thr Gly Ala
        195                 200                 205

Glu Leu Pro Gln Ile Phe Thr Asp Leu Arg Leu Ser Asp Thr Leu Asn
    210                 215                 220

Trp Lys Glu Ala Val Val Ile Ala Glu His Ala Asn Lys Glu Leu
225                 230                 235                 240

Phe Asp Gly Leu Val Asp Ser Leu Ser Arg Pro Val His Lys Lys Asp
            245                 250                 255

Pro Leu Ala Leu Thr Val Val Lys Leu His Gly Pro Val Ala Leu Arg
            260                 265                 270

Lys Lys Asn Phe Glu Ser Gln Leu Leu Asn Leu Gln Val Arg Pro Lys
        275                 280                 285

Gly Arg Asn Phe Ile Leu Val Ser Lys Gln Asp Thr Ala Leu Trp Ala
    290                 295                 300

Phe Asp Ala Ala Ser His Val Gly Leu Val Asn Pro Tyr Ser Gln Trp
305                 310                 315                 320

Leu Phe Leu Ile Thr Asp Ser Thr Asp Pro Ala Ile Phe Leu Pro Asn
            325                 330                 335

Val Glu Asp Gly Gln Asn Ile Ser Phe Leu Tyr Asn Ile Ser Asp Ile
            340                 345                 350

Glu Thr Thr Ala Asn Ala Asn Ser Ser Glu Arg Val Asn Asp Leu
            355                 360                 365

Pro Cys Tyr Thr Ser Asn Leu Leu Gln Val Tyr Val Lys Ala Leu His
    370                 375                 380

Gln Leu Ile Arg Glu Glu Thr His Tyr Phe Gln Thr Thr Glu Asp
385                 390                 395                 400

Asp Trp Ile Arg Ser Lys Pro Ser Ala Gly Asp Arg Arg Asn Asn Ile
                405                 410                 415
```

```
Phe Arg Thr Leu Gln Asn Met Trp Lys Asp Ala Thr Lys Cys Ser Ser
            420                 425                 430

Trp Leu Asn Trp Ala Met Lys Ala Val Glu Ile Lys Glu Thr Arg Lys
        435                 440                 445

Pro Thr Leu Leu Asp Val Gly Val Trp Asp Ala His Gly Leu Val
            450                 455                 460

Val Tyr Asp Asp Phe Phe Pro His Phe Thr Gly Gly Leu Arg Gln Arg
465                 470                 475                 480

Val Ile Asn Val Thr Thr Met Glu Phe Pro Pro Trp Gln Ile Phe Glu
                485                 490                 495

Arg Asn Ser His Gly Lys Val Val Arg His Thr Gly Leu Val Leu Glu
            500                 505                 510

Leu Thr Lys Glu Leu Gly Asn Arg Leu Asn Phe Ser Val Asn Val Val
        515                 520                 525

Glu Pro Ala Asp Gly Lys Trp Gly Ser Arg Leu Ser Phe Ser Arg Trp
    530                 535                 540

Thr Gly Met Val Glu Gln Val Arg Thr Gly Ser Val Ala Phe Ala Ala
545                 550                 555                 560

Ala Gly Phe Thr Val Thr Ala Asp Arg Met Ser Ala Val Asn Phe Ser
                565                 570                 575

Met Ser Leu Asp Ala Gln Pro Tyr Thr Phe Met Phe Ala Arg Pro Lys
            580                 585                 590

Gln Leu Ser Arg Ala Tyr Leu Phe Ile Gln Pro Tyr Thr Pro Asn Ala
        595                 600                 605

Trp Ile Thr Ile Phe Ala Met Thr Ile Gly Ala Gly Pro Leu Ile Trp
    610                 615                 620

Ala Phe Asn Lys Ile Thr Pro Phe Tyr Asp Phe Tyr Pro Asp Arg Pro
625                 630                 635                 640

Gly Ser Pro Ile Phe Ser Ile Trp Tyr Asn Ile Trp Tyr Cys Ile Gly
                645                 650                 655

Ala Leu Leu Phe Gln Gly Gln Arg Glu Met Pro Ile Ala Leu Ser Gly
            660                 665                 670

Arg Met Val Val Gly Phe Phe Trp Leu Phe Val Ile Val Val Leu Thr
        675                 680                 685

Ala Tyr Ser Gly Asn Leu Val Ala Phe Leu Thr Phe Pro Thr Tyr Thr
    690                 695                 700

Asn Pro Ile Asn Thr Leu Gln Asp Leu Ile Asp Asn Lys Gly Ser Leu
705                 710                 715                 720

Thr Trp Gly Ile Leu Arg Gly Thr Ala Leu Glu Asp Tyr Leu Lys Thr
                725                 730                 735

Ser Asp Glu Lys Met Tyr Arg Glu Leu Tyr Glu Gly Ala Ile Leu His
            740                 745                 750

Asp Thr Ala Asp Asp Val Leu Leu Asp Met Ile Arg Asn Gln Gln His
        755                 760                 765

Val Tyr Ile Glu Trp Lys Thr Asn Leu Gln Trp Leu Met Lys Gln Asp
    770                 775                 780

Phe Met Lys Thr Asn Ser Cys Asp Phe Ser Leu Gly Thr Glu Asn Phe
785                 790                 795                 800

Phe Leu Gln Gln Val Ala Leu Ala Phe Pro Arg Asp Ser Pro Ile Leu
                805                 810                 815

Glu Arg Val Asn Leu Glu Ile Ile Tyr Met Gln Arg Gly Gly Leu Ile
            820                 825                 830

Glu His Trp Arg Gln Glu Phe Trp Pro Ser Ala Asp Arg Cys Ser Glu
```

```
                835                 840                 845
Thr Ala Thr Gly Gly Ser Asp Gly Asp Thr Ile Gln Ala Ile Ser Val
        850                 855                 860

Ala Asp Met Gln Gly Ser Phe Tyr Val Leu Phe Phe Gly Lys Thr Lys
865                 870                 875                 880

Asn Leu Gly Thr Leu Tyr Asn Leu Phe Ile Asn Gly Lys Phe Met Tyr
                885                 890                 895

Glu

<210> SEQ ID NO 33
<211> LENGTH: 864
<212> TYPE: PRT
<213> ORGANISM: Zooternopsis nevadensis

<400> SEQUENCE: 33

Met Met Leu Leu Ser Trp Thr Thr Ile Val Leu Phe Ile Thr Phe His
1               5                   10                  15

Gln Val Ser Asn Ala Glu Ala Asp Thr Asp Tyr Ser Gly Thr Val Ala
            20                  25                  30

His Leu Ala Val Val Ile Asp Lys Glu Phe Arg Gly Leu Asp Tyr Lys
        35                  40                  45

Asn Leu Leu Arg Gln Met Arg His Phe Leu Arg Asn Ala Thr His Gln
    50                  55                  60

His Leu Thr His Gly Glu Leu Ile Thr Lys Phe Thr Lys Thr Asp
65                  70                  75                  80

Ile Ala Val Glu Lys Asp Ile Thr Ala Leu Phe Ser Ile Leu Ser Cys
                85                  90                  95

Asp Asp Thr Trp Lys Ile Tyr Arg Arg Tyr Gln Asp Tyr His Leu Leu
            100                 105                 110

His Leu Ala Ile Thr Glu Ala Asp Cys Pro Arg Leu Pro Arg Asp Asp
        115                 120                 125

Gly Leu Thr Val Pro Leu Val Ala Val Asn Arg Val Ala Ser Gln Leu
    130                 135                 140

Met Leu Asp Ile Lys Met Ser Gln Leu Ala Ser Trp Thr Thr Ser Ile
145                 150                 155                 160

Leu Ile Tyr Asp Glu Ser Val Asp Thr Glu Thr Val Gln Arg Ile Ile
                165                 170                 175

Thr Ser Leu Ser Leu Pro Thr Leu Gly Arg Glu Arg Ser Ala Ala Pro
            180                 185                 190

Val Ala Val Phe Lys Val Asn Asp Thr Gln Arg Glu Trp Glu Arg Arg
        195                 200                 205

Ala Ser Ile Met Lys Leu Leu Lys Asp Phe Pro Val Asn Arg Leu Gly
    210                 215                 220

Ser Asn Phe Ile Val Ala Val Ser His Glu Val Val Gly Val Ile Met
225                 230                 235                 240

Glu Val Cys Lys Ala Val Gly Leu Ser His Pro Glu Thr Gln Trp Leu
                245                 250                 255

Tyr Val Ile Ala Asp Ser Asp Ala Ile Ile Asn Met Ser Ala Phe Thr
            260                 265                 270

Ser Leu Leu Ser Glu Gly Glu Asn Ile Ala Phe Val His Asn Ser Arg
        275                 280                 285

Ser Ser Gly Val Glu Cys Glu Gly Gly Leu Leu Cys His Val His Glu
    290                 295                 300

Leu Leu Gln Ser Phe Val Glu Ala Leu Gly Val Val Ile Glu Asp Glu
```

```
                305                 310                 315                 320
        Glu Asp Phe Ile Ser Gln Val Ser Thr Glu Glu Trp Asn Ala Ile Gln
                        325                 330                 335
        Pro Ser Lys Arg Lys Arg Ser Thr Leu Leu Asp Leu Met Lys Ala
                        340                 345                 350
        Gln Leu Ile Glu Thr Gly Arg Cys Asp Ser Cys Leu Thr Trp Thr Leu
                        355                 360                 365
        Glu Ala Gly Asp Thr Trp Gly Leu Glu Tyr Gln Glu His Glu Glu Glu
                        370                 375                 380
        Glu Thr Gly Gln Lys Ile Val Arg Arg Leu Asn Pro Val Gly Arg Trp
        385                 390                 395                 400
        Ser Pro Arg Asp Gly Leu Ser Met Ser Ser His Leu Phe Pro His Leu
                        405                 410                 415
        Arg Lys Gly Phe Val Gly Arg Asp Leu Thr Ile Ile Ser Phe His Asn
                        420                 425                 430
        Pro Pro Trp Gln Ile Ile Lys His Asn Asp Thr Ser Gln Ile Thr Glu
                        435                 440                 445
        Tyr Lys Gly Leu Ile Phe Lys Ile Ile Asp Gln Leu Ala Glu Asn Leu
                        450                 455                 460
        Asn Phe Arg Tyr Thr Val Ile Phe Pro Ala Asn Asn Ile Pro Gly Trp
        465                 470                 475                 480
        Thr Asn Asp Ser Ser Leu Met Lys Asp Ser Glu Asp Asn Arg Thr Arg
                        485                 490                 495
        Ala Phe Leu Val Thr Asp Arg Ile Ile Glu Ile Leu Arg Arg Lys Lys
                        500                 505                 510
        Val Phe Leu Ala Ala Gly Ala Phe Val Val Thr Pro Asn Arg Lys Thr
                        515                 520                 525
        Leu Val Asn Phe Thr Met Pro Val Ser Ile Gln Thr Ala Thr Leu Leu
                        530                 535                 540
        Thr Ala Arg Pro Arg Glu Val Ser Arg Ala Leu Ile Phe Met His Pro
        545                 550                 555                 560
        Phe Thr Tyr Gly Thr Trp Ala Cys Ile Ala Thr Leu Ile Val Met Val
                        565                 570                 575
        Thr Pro Val Leu Asn Tyr Phe His Arg His Ser Pro Tyr Tyr Glu Tyr
                        580                 585                 590
        Tyr Ser Lys Asp Asn Val Lys Gly Gly Leu Ser Ser His Tyr Asn Cys
                        595                 600                 605
        Leu Trp Tyr Leu Tyr Gly Ala Leu Met Gln Gln Gly Gly Met His Leu
                        610                 615                 620
        Pro Glu Ala Asp Ser Gly Arg Ile Ile Val Gly Ala Trp Trp Leu Val
        625                 630                 635                 640
        Val Leu Val Ile Val Thr Ser Tyr Gly Gly Asn Leu Val Ala Phe Leu
                        645                 650                 655
        Thr Phe Pro Lys Tyr Glu Val Ala Val Thr Asn Leu Glu Glu Leu Leu
                        660                 665                 670
        Thr Arg Arg Gly Thr Val Ser Trp Gly Ile Leu Lys Asp Thr Ala Thr
                        675                 680                 685
        Glu Gln His Leu Lys Glu Met Asp Tyr Pro Lys Tyr Lys Ser Leu Phe
                        690                 695                 700
        Glu Gly Ala Thr Ile His Glu Glu Gln Asp Asp Leu Val Ser Arg
        705                 710                 715                 720
        Val Arg Ser Gly Ser His Val Phe Ile Glu Trp Lys Leu Asn Leu Leu
                        725                 730                 735
```

```
Lys Ile Met Lys Lys Glu Phe Leu Ser Lys Asn Ser Cys Asp Phe Ala
            740                 745                 750
Leu Gly Asp Glu Glu Phe Leu Glu Glu Gln Val Ala Met Met Met Gln
        755                 760                 765
Phe Gly Ser Pro Tyr Leu Gly Leu Val Asn Arg Glu Leu Arg Arg Met
    770                 775                 780
His Gln Ala Gly Leu Ile Tyr Lys Trp Tyr Leu Glu Tyr Leu Pro Arg
785                 790                 795                 800
Lys Asp Arg Cys Trp Thr Thr Asn Arg Leu Leu Gln Ala Thr Thr His
            805                 810                 815
Thr Val Asn Leu Asp Asp Met Gln Gly Ser Phe Phe Val Leu Gly Leu
        820                 825                 830
Gly Cys Ala Phe Ala Met Val Leu Ile Cys Met Glu Gln Cys Tyr His
    835                 840                 845
Thr Tyr Lys Ile Ser Lys Glu Lys Arg Val Ile Lys Pro Phe Ala Ser
    850                 855                 860

<210> SEQ ID NO 34
<211> LENGTH: 2742
<212> TYPE: DNA
<213> ORGANISM: Drosophila melanogaster

<400> SEQUENCE: 34
atgaatcctg gcgaaatgcg gccttcggct tgccttctgc tcctggctgg actgcagctc    60
tctatcctgg tacccactga ggccaatgac ttttcgtcct tcctgagcgc caatgcatcg   120
ctggccgttg tggtggatca cgagtatatg acggttcatg gcgagaatat attggctcat   180
ttcgagaaaa tcctgagcga cgtaatacgg gagaatctaa ggaacggtgg cataaacgta   240
aaatatttta gctggaatgc agtgcgattg aagaaggatt ttttggctgc ataactgtt   300 acggattgcg agaatacatg gaacttttac aagaacactc aggaaacttc aattctactg   360
atcgccatta cggattccga ctgtcccagg ctgcccctaa atagagctct aatggtaccc   420
atcgttgaga cggcgatga attccccaa cttattctgg atgccaaggt ccagcagatt   480
ctaaattgga agaccgccgt tgtttttgtg atcaaacca tattgaggaa gaacgcactt   540
ctggtaaaat cgattgtgca cgaaagtata accaaccaca tcaccccaat ctccctgatc   600
ctttacgaga tcaacgactc cctgaggggc caacagaagc gagttgctct cgccaagct   660 ctgtctcaat tcgctcccaa aaagcacgag gagatgcgcc agcagttcct ggtcatatct   720
gcctttcacg aggacatcat cgaaatagcc gagaccctga acatgtttca cgtgggcaat   780
cagtggatga ttttcgtgct ggacatggtg gctcgggact tcgatgccgg cactgtgacc   840
ataaacctgg acggggagc caacatagcc ttcgccctca cgaaacggaa tcccaactgc   900
caggactcgc taaactgcac gatctcggaa attagtctcg ctctggtcaa cgctatttcc   960
aaaattaccg tcgaggagga gtccatatat ggtgagatct ccgatgagga atgggaggcc  1020
atccgcttta ccaagcagga aaagcaggcc gagattctgg agtacatgaa ggaattcctg  1080
aagaccaatg ccaagtgctc cagctgcgcg agatggcgcg tggagacggc cattacctgg  1140
ggcaaaagcc aggagaatcg caagtttcgc tcaactcccc aacgcgacgc taagaaccga  1200
aattttgagt tcatcaacat tggctattgg acaccgtgc tgggattcgt ctgccaggag  1260 ctcgccttc cgcacatcga gcaccacttc gcaacataa ccatggacat tctgaccgtg  1320
cacaatccac cctggcaaat ccttaccaag aacagcaatg gggtcatcgt ggagcacaag  1380
```

```
ggcattgtta tggagatcgt caaggagctg agtcgcgccc taaacttcag ctactacctt   1440
cacgaagcct ccgcatggaa ggaagaagat tcactcagca catcagcggg cggaaatgaa   1500
agcgacgagc tagttggttc catgacccttt cgtataccct atcgagtggt ggagatggtg   1560
cagggcaatc agttttcat cgctgccgtg cagccaccg ttgaggatcc cgaccaaaag    1620
cccttcaatt ataccagcc catcagtgtg cagaagtact ccttcatcac ccgcaagccg    1680
gatgaggtgt cccgcattta cttgttcacg gcacccttca ccgtggagac ttggttctgc   1740
ctaatgggca tcattctgct gactgctccc acgctgtacg ccattaatcg cctagctcct   1800
ctgaaggaga tgcgaatcgt gggcctgtcc acagttaaga gctgttttg gtatatattc    1860 ggggctttgt tacaacaggg aggcatgtac ttgcccacag cagacagtgg gcgcctagtg    1920
gtcggctttt ggtggatcgt ggttatcgtg ctggtgacca cctattgcgg caaccttgtg    1980
gccttcctca cgttccccaa atttcaaccg ggcgtggact atttgaatca actagaggac    2040
cacaaggaca ttgtacagta tggattgcga acggcacct tcttcgagcg gtacgttcag     2100
tcgacaacgc gggaggactt caaacactac ctggaacggg cgaaaatcta cggcagcgcc    2160
caagaggagg acatcgaggc ggtgaagcgt ggcgagcgca tcaacatcga ttggcggatc    2220
aatctgcagt tgattgttca gcggcacttc gagcgggaga aggagtgcca ctttgctttg    2280
ggcagggaga gcttcgtgga cgagcagatt gccatgattg tgccggccca gagtgcgtat    2340
ctgcacctgg taaaccgcca catcaagagc atgttccgga tgggcttcat cgagcgctgg    2400
caccagatga acttacccag cgcgggcaag tgcaacggga agagcgccca gcgccaggtt    2460
accaaccaca aggtgaacat ggacgacatg caagggtgct ttctggtcct gctcttgggc    2520
ttcacgttgg ctctttaat agtgtgcggc gagttctggt atcgtcgctt tcgggccagt    2580
cgaaaacggc gtcagttcac caactgacca ctggggaatc ctaagagctc ttgccatgga    2640
atagtgtaat gaatgagcag taactggcat gtacaacgct gatgaaaatc gtatatagat    2700
ataaacattt aaataagcta tcaaatataa atatatcaat tg                       2742
```

<210> SEQ ID NO 35
<211> LENGTH: 280
<212> TYPE: PRT
<213> ORGANISM: Drosophila melanogaster

<400> SEQUENCE: 35

```
Met Ala Cys Asn Glu Leu His Asn Gly Tyr Arg Ala Lys Phe Leu Thr
1               5                   10                  15

Ile Val Tyr Trp Ile Ala Ala Thr Tyr Val Leu Ala Asp Val Tyr Ser
            20                  25                  30

Ala Gln Leu Thr Ser Gln Phe Ala Arg Pro Ala Arg Glu Pro Pro Ile
        35                  40                  45

Asn Thr Leu Gln Arg Leu Gln Ala Ala Met Ile His Asp Gly Tyr Arg
    50                  55                  60

Leu Tyr Val Glu Lys Glu Ser Ser Leu Glu Met Leu Glu Asn Gly
65                  70                  75                  80

Thr Glu Leu Phe Arg Gln Leu Tyr Ala Leu Met Arg Gln Gln Val Ile
            85                  90                  95

Asn Asp Pro Gln Gly Phe Phe Ile Asp Ser Val Glu Ala Gly Ile Lys
            100                 105                 110

Leu Ile Ala Glu Gly Gly Glu Asp Lys Ala Val Leu Gly Gly Arg Glu
        115                 120                 125

Thr Leu Phe Phe Asn Val Gln Gln Tyr Gly Ser Asn Asn Phe Gln Leu
```

```
            130                 135                 140

Ser Gln Lys Leu Tyr Thr Arg Tyr Ser Ala Val Ala Val Gln Ile Gly
145                 150                 155                 160

Cys Pro Phe Leu Gly Ser Leu Asn Asn Val Leu Met Gln Leu Phe Glu
                165                 170                 175

Ser Gly Ile Leu Asp Lys Met Thr Ala Ala Glu Tyr Ala Lys Gln Tyr
                180                 185                 190

Gln Glu Val Glu Ala Thr Arg Ile Tyr Lys Gly Ser Val Gln Ala Lys
                195                 200                 205

Asn Ser Glu Ala Tyr Ser Arg Thr Glu Ser Tyr Asp Ser Thr Val Ile
            210                 215                 220

Ser Pro Leu Asn Leu Arg Met Leu Gln Gly Ala Phe Ile Ala Leu Gly
225                 230                 235                 240

Val Gly Ser Leu Ala Ala Gly Val Ile Leu Leu Glu Ile Val Phe
                245                 250                 255

Ile Lys Leu Asp Gln Ala Arg Leu Trp Met Leu Cys Ser Arg Leu Gln
                260                 265                 270

Trp Ile Arg Tyr Asp Arg Lys Val
                275                 280

<210> SEQ ID NO 36
<211> LENGTH: 732
<212> TYPE: PRT
<213> ORGANISM: Drosophila melanogaster

<400> SEQUENCE: 36

Met His Lys Phe Leu Ala Leu Gly Leu Leu Pro Tyr Leu Leu Gly Leu
1               5                   10                  15

Leu Asn Ser Thr Arg Leu Thr Phe Ile Gly Asn Asp Glu Ser Asp Thr
                20                  25                  30

Ala Ile Ala Leu Thr Gln Ile Val Arg Gly Leu Gln Gln Ser Ser Leu
            35                  40                  45

Ala Ile Leu Ala Leu Pro Ser Leu Ala Leu Ser Asp Gly Val Cys Gln
        50                  55                  60

Lys Glu Arg Asn Val Tyr Leu Asp Asp Phe Leu Gln Arg Leu His Arg
65                  70                  75                  80

Ser Asn Tyr Lys Ser Val Val Phe Ser Gln Thr Glu Leu Phe Phe Gln
                85                  90                  95

His Ile Glu Glu Asn Leu Gln Gly Ala Asn Glu Cys Ile Ser Leu Ile
                100                 105                 110

Leu Asp Glu Pro Asn Gln Leu Leu Asn Ser Leu His Asp Arg His Leu
            115                 120                 125

Gly His Arg Leu Ser Leu Phe Ile Phe Tyr Trp Gly Ala Arg Trp Pro
        130                 135                 140

Pro Ser Ser Arg Val Ile Arg Phe Arg Glu Pro Leu Arg Val Val
145                 150                 155                 160

Val Thr Arg Pro Arg Lys Lys Ala Phe Arg Ile Tyr Tyr Asn Gln Ala
                165                 170                 175

Arg Pro Cys Ser Asp Ser Gln Leu Gln Leu Val Asn Trp Tyr Asp Gly
                180                 185                 190

Asp Asn Leu Gly Leu Gln Arg Ile Pro Leu Leu Pro Thr Ala Leu Ser
            195                 200                 205

Val Tyr Ala Asn Phe Lys Gly Arg Thr Phe Arg Val Pro Val Phe His
        210                 215                 220
```

```
Ser Pro Pro Trp Phe Trp Val Thr Tyr Cys Asn Asn Ser Phe Glu Glu
225                 230                 235                 240

Asp Glu Glu Phe Asn Ser Leu Asp Ser Ile Glu Lys Arg Lys Val Arg
            245                 250                 255

Val Thr Gly Gly Arg Asp His Arg Leu Leu Met Leu Leu Ser Lys His
        260                 265                 270

Met Asn Phe Arg Phe Lys Tyr Ile Glu Ala Pro Gly Arg Thr Gln Gly
    275                 280                 285

Ser Met Arg Ser Glu Asp Gly Lys Asp Ser Asn Asp Ser Phe Thr Gly
        290                 295                 300

Gly Ile Gly Leu Leu Gln Ser Gly Gln Ala Asp Phe Phe Leu Gly Asp
305                 310                 315                 320

Val Gly Leu Ser Trp Glu Arg Arg Lys Ala Ile Glu Phe Ser Phe Phe
            325                 330                 335

Thr Leu Ala Asp Ser Gly Ala Phe Ala Thr His Ala Pro Arg Arg Leu
            340                 345                 350

Asn Glu Ala Leu Ala Ile Met Arg Pro Phe Lys Gln Asp Ile Trp Pro
        355                 360                 365

His Leu Ile Leu Thr Ile Ile Phe Ser Gly Pro Ile Phe Tyr Gly Ile
    370                 375                 380

Ile Ala Leu Pro Tyr Ile Trp Arg Arg Trp Ala Asn Ser Asp Val
385                 390                 395                 400

Glu His Leu Gly Glu Leu Tyr Ile His Met Thr Tyr Leu Lys Glu Ile
            405                 410                 415

Thr Pro Arg Leu Leu Lys Leu Lys Pro Arg Thr Val Leu Ser Ala His
        420                 425                 430

Gln Met Pro His Gln Leu Phe Gln Lys Cys Ile Trp Phe Thr Leu Arg
    435                 440                 445

Leu Phe Leu Lys Gln Ser Cys Asn Glu Leu His Asn Gly Tyr Arg Ala
450                 455                 460

Lys Phe Leu Thr Ile Val Tyr Trp Ile Ala Ala Thr Tyr Val Leu Ala
465                 470                 475                 480

Asp Val Tyr Ser Ala Gln Leu Thr Ser Gln Phe Ala Arg Pro Ala Arg
            485                 490                 495

Glu Pro Pro Ile Asn Thr Leu Gln Arg Leu Gln Ala Ala Met Ile His
        500                 505                 510

Asp Gly Tyr Arg Leu Tyr Val Glu Lys Glu Ser Ser Leu Glu Met
    515                 520                 525

Leu Glu Asn Gly Thr Glu Leu Phe Arg Gln Leu Tyr Ala Leu Met Arg
530                 535                 540

Gln Gln Val Ile Asn Asp Pro Gln Gly Phe Phe Ile Asp Ser Val Glu
545                 550                 555                 560

Ala Gly Ile Lys Leu Ile Ala Glu Gly Glu Asp Lys Ala Val Leu
            565                 570                 575

Gly Gly Arg Glu Thr Leu Phe Phe Asn Val Gln Tyr Gly Ser Asn
            580                 585                 590

Asn Phe Gln Leu Ser Gln Lys Leu Tyr Thr Arg Tyr Ser Ala Val Ala
        595                 600                 605

Val Gln Ile Gly Cys Pro Phe Leu Gly Ser Leu Asn Asn Val Leu Met
    610                 615                 620

Gln Leu Phe Glu Ser Gly Ile Leu Asp Lys Met Thr Ala Ala Glu Tyr
625                 630                 635                 640

Ala Lys Gln Tyr Gln Glu Val Glu Ala Thr Arg Ile Tyr Lys Gly Ser
```

```
                     645                 650                 655
Val Gln Ala Lys Asn Ser Glu Ala Tyr Ser Arg Thr Glu Ser Tyr Asp
            660                 665                 670

Ser Thr Val Ile Ser Pro Leu Asn Leu Arg Met Leu Gln Gly Ala Phe
            675                 680                 685

Ile Ala Leu Gly Val Gly Ser Leu Ala Ala Gly Val Ile Leu Leu
            690                 695                 700

Glu Ile Val Phe Ile Lys Leu Asp Gln Ala Arg Leu Trp Met Leu Cys
705                 710                 715                 720

Ser Arg Leu Gln Trp Ile Arg Tyr Asp Arg Lys Val
                725                 730

<210> SEQ ID NO 37
<211> LENGTH: 223
<212> TYPE: PRT
<213> ORGANISM: Drosophila melanogaster

<400> SEQUENCE: 37

Met Ile His Asp Gly Tyr Arg Leu Tyr Val Glu Lys Glu Ser Ser Ser
1               5                   10                  15

Leu Glu Met Leu Glu Asn Gly Thr Glu Leu Phe Arg Gln Leu Tyr Ala
            20                  25                  30

Leu Met Arg Gln Gln Val Ile Asn Asp Pro Gln Gly Phe Phe Ile Asp
        35                  40                  45

Ser Val Glu Ala Gly Ile Lys Leu Ile Ala Glu Gly Glu Asp Lys
    50                  55                  60

Ala Val Leu Gly Gly Arg Glu Thr Leu Phe Phe Asn Val Gln Gln Tyr
65                  70                  75                  80

Gly Ser Asn Asn Phe Gln Leu Ser Gln Lys Leu Tyr Thr Arg Tyr Ser
                85                  90                  95

Ala Val Ala Val Gln Ile Gly Cys Pro Phe Leu Gly Ser Leu Asn Asn
            100                 105                 110

Val Leu Met Gln Leu Phe Glu Ser Gly Ile Leu Asp Lys Met Thr Ala
        115                 120                 125

Ala Glu Tyr Ala Lys Gln Tyr Gln Glu Val Glu Ala Thr Arg Ile Tyr
    130                 135                 140

Lys Gly Ser Val Gln Ala Lys Asn Ser Glu Ala Tyr Ser Arg Thr Glu
145                 150                 155                 160

Ser Tyr Asp Ser Thr Val Ile Ser Pro Leu Asn Leu Arg Met Leu Gln
                165                 170                 175

Gly Ala Phe Ile Ala Leu Gly Val Gly Ser Leu Ala Ala Gly Val Ile
            180                 185                 190

Leu Leu Leu Glu Ile Val Phe Ile Lys Leu Asp Gln Ala Arg Leu Trp
        195                 200                 205

Met Leu Cys Ser Arg Leu Gln Trp Ile Arg Tyr Asp Arg Lys Val
    210                 215                 220

<210> SEQ ID NO 38
<211> LENGTH: 1229
<212> TYPE: DNA
<213> ORGANISM: Drosophila melanogaster

<400> SEQUENCE: 38
atttaacata cggcaagctt acaggtgtag cttaaatatt gggatttatt gttctaatct    60
taacattatt gttcttaact cttagccctc taatttaagt ttgttctcaa gcggtatcta   120
```

-continued

| | | | | |
|---|---|---|---|---|
| gatgcagaat atgttgttaa actgatgtag gttagcgccc cctgagcaaa aattttggat | | | | 180 |
| atgagatatt tggaaaacgg ttcgagcgag agctatggaa attttttttcc ctcaaaagtt | | | | 240 |
| gaacatctct ataaataaaa agtgtatata ggatgcagtt tgttgtctat agattttttat | | | | 300 |
| ttcaataaaa aagaaaaaca atcaataaat ggcatgcaat gaactacata acggataccg | | | | 360 |
| agccaagttt ttgaccatag tgtattggat agcagcgacc tatgttttgg ccgatgtata | | | | 420 |
| ttcagctcaa ctgaccagcc aatttgcacg tccagctcgc gagccaccaa tcaatactct | | | | 480 |
| tcagcgcctg caagcagcga tgattcatga cggttaccgg ctatatgtgg agaaggaaag | | | | 540 |
| cagttcattg gagatgttgg agaatgggac agaactgttt cgtcagcttt atgctctgat | | | | 600 |
| gaggcagcag gtgatcaatg accctcaagg atttttttatt gactctgtgg aagcgggaat | | | | 660 |
| taaactaatt gcagagggcg gcgaggacaa ggcagtactc ggagggcgtg aaacactgtt | | | | 720 |
| tttcaacgtt cagcaatacg gatcaaacaa ctttcagctc agtcaaaaac tttacactcg | | | | 780 |
| ttattcggct gtggctgttc aaatcggatg tcccttttcta ggtagcctca ataatgtctt | | | | 840 |
| gatgcagttg tttgagagcg gaatcctaga taagatgacc gctgccgaat acgcaaagca | | | | 900 |
| gtaccaggag gtagaagcca cgagaatata caagggcagc gtgcaggcga aaaacagtga | | | | 960 |
| ggcttacagt cgaaccgaaa gctatgacag cacggttatc agtccgctta atctacgaat | | | | 1020 |
| gctgcagggc gcttttatcg ctctcggagt tggttcattg gctgcaggtg taattttgct | | | | 1080 |
| gttagagata gtatttataa aactggatca agcgcgattg tggatgctgt gctcacggct | | | | 1140 |
| gcaatggatt agatatgaca ggaaagtgta agtcagtgta tttatttgc tgcagccgct | | | | 1200 |
| ttaaataata caataaacgt cagatcctt | | | | 1229 |

<210> SEQ ID NO 39
<211> LENGTH: 812
<212> TYPE: PRT
<213> ORGANISM: Aedes aegypti

<400> SEQUENCE: 39

```
Met Asn Lys Val Leu Ala Thr Pro Ala Ser Lys Ala Asp Lys Leu Glu
1               5                   10                  15

Ser Leu Ile Ser Ile Gly Leu Val Val Gln Asn Leu Cys Ser Gln Leu
            20                  25                  30

Gln Ser Met Arg Met Glu Ala His Leu Ser Asn Pro Ser Leu Leu Gln
        35                  40                  45

Glu Leu Val Asp Lys Leu Pro Ala Asn Ile Lys Leu His Trp Ala Leu
    50                  55                  60

His Gln Arg Gln Val Pro Val Val Asp Phe Arg Ala Phe Thr Tyr His
65                  70                  75                  80

Ala His Leu Ala Pro Leu Pro Asp Leu Ser Asn His Ser Gly Met Val
                85                  90                  95

Leu Gly Leu Ser Glu Met Ile Asn Leu Leu Ala Pro Lys Thr Leu Ala
            100                 105                 110

Ile Leu Val Leu Lys Glu Thr Lys Ile Asp Lys Ile Asp Arg Leu Thr
        115                 120                 125

Val Met Ile His His His Asn Ile Pro Thr Cys Ile Phe Asn Asn Gln
    130                 135                 140

Asp Glu Tyr Phe Gln Tyr Ile Gly Asn Asn Leu Lys Lys Ser Leu Glu
145                 150                 155                 160

Thr Thr Ser Leu Leu Phe Cys His Pro Glu Glu Met Leu Gly Glu Leu
                165                 170                 175
```

```
Ile Asp Arg Arg Leu Ala His Arg Leu Ser Leu Tyr Ile Phe Tyr Trp
        180                 185                 190

Gly Ala Arg Lys Ala Pro Thr Asn Leu Asp Arg Ser Leu Met Arg Glu
            195                 200                 205

Pro Leu Arg Val Ala Val Ile Thr Asn Pro Arg Lys Asn Ile Phe Arg
        210                 215                 220

Ile Phe Tyr Asn Gln Ala Lys Pro Asn Asn Arg Gly Glu Leu Leu Ser
225                 230                 235                 240

Ala Asn Trp Phe Asp Gly Asn Asp Met Thr Phe Gln Lys Val Pro Leu
                245                 250                 255

Leu Pro Thr Pro Thr Thr Val Tyr Lys Asn Phe Glu Gly Arg Val Phe
            260                 265                 270

Thr Ile Pro Val Ile His Lys Pro Pro Trp His Phe Val Thr Tyr Arg
        275                 280                 285

Lys Val Asn Glu Ser Ser Leu Asn Glu Thr Asp Val Asp Gln Leu Glu
        290                 295                 300

Leu Ser Ala Asn Gly Thr Asp Asn Glu Gln Leu Glu Val Phe Glu Val
305                 310                 315                 320

Thr Gly Gly Arg Asp His Asn Leu Ile Gln Leu Ile Ala His Arg Met
            325                 330                 335

Asn Phe Ser Phe Lys Tyr Val Asp Gln Glu Asp Arg Ile Gln Gly Thr
                340                 345                 350

Ala Val Gly Pro Pro Glu Asn Ala Ile Phe Thr Gly Ala Leu Gly Met
            355                 360                 365

Leu Gln Arg Arg Glu Val Asp Leu Phe Leu Gly Asp Val Ala Val Thr
370                 375                 380

Trp Glu Arg Met Gln Ala Val Glu Phe Ser Phe Thr Leu Ala Asp
385                 390                 395                 400

Ser Ala Ala Phe Val Thr His Ala Pro Arg Lys Leu Ser Glu Ala Leu
                405                 410                 415

Ala Leu Val Arg Pro Phe Gln Val Ala Val Trp Pro Leu Val Leu Leu
            420                 425                 430

Thr Ile Met Met Ser Gly Pro Ile Leu Tyr Met Ile Ile Ala Met Pro
        435                 440                 445

Tyr Arg Leu Glu Asp Trp Ala Arg Gly Thr Met Ala Arg Arg Arg Arg
450                 455                 460

Phe Lys Val Gln Arg Gly Ser Ala Phe Tyr His Met Gln Tyr Ile Gln
465                 470                 475                 480

Glu Met Asn Tyr Gly Thr Leu Pro Gly Gly Ala Glu Ile Ala Gly Thr
                485                 490                 495

Pro Arg His Pro Ser Leu Asp Arg Cys Ile Trp Tyr Thr Ile Asn Val
            500                 505                 510

Tyr Leu Arg Gln Ser Ala Thr Ile Pro Tyr Asn Gly His Val Ser Arg
        515                 520                 525

Phe Phe Ser Ile Leu Leu Trp Leu Cys Ala Thr Tyr Val Leu Gly Asp
        530                 535                 540

Val Tyr Ser Ala Gln Leu Thr Ser Gln Leu Ala Arg Pro Ala Arg Glu
545                 550                 555                 560

Gly Pro Ile Asp Thr Leu Gly Lys Leu Glu Val Phe Met Glu Arg Asp
                565                 570                 575

Gly Tyr Gln Leu Leu Val Glu Arg Gln Ser Ala Phe Gln Ala Ala Leu
            580                 585                 590

Val Asn Ser Thr Gly Ile Leu Gln Arg Leu Tyr Arg Ile Thr Gln Arg
```

```
                595                 600                 605
Gln Ser His Asn Glu Ser Tyr Leu Val Ser Val Glu Glu Gly Ile
610                 615                 620

Arg Ile Leu Val Asp Asn Ser Lys Arg Ala Val Phe Gly Gly Arg Glu
625                 630                 635                 640

Thr Leu Tyr Phe Asn Thr Lys Arg Tyr Gly Ala His Arg Phe Gln Leu
                645                 650                 655

Ser Glu Lys Leu Tyr Thr Arg Tyr Ser Ala Val Ala Val Gln Phe Gly
                660                 665                 670

Ser Pro Phe Leu Asp Ser Leu Asn Glu Val Ile Met Arg Leu Phe Glu
                675                 680                 685

Ala Gly Ile Ile Glu Lys Ile Thr Ile Ala Glu Tyr Glu Arg Met Phe
690                 695                 700

Gly Ser Gln Leu Gly Gln Phe Gly Asp Glu Ser Ala Lys Thr Thr Lys
705                 710                 715                 720

Pro Glu Ser Phe Glu Thr Glu Gly Gly Lys Ser Lys Ser Thr Glu
                725                 730                 735

Ser Asn Glu Lys Leu Gln Pro Met Asn Leu Arg Met Leu Gln Gly Ala
                740                 745                 750

Phe Leu Ala Leu Ala Cys Gly His Ser Leu Gly Val Leu Thr Leu Val
                755                 760                 765

Leu Glu Asn Lys Thr Lys Cys Ile Gln Ile Ser Phe Gly Trp Ile Lys
770                 775                 780

Ala Trp Leu His Arg Ile Gly Leu Ile Phe Cys Lys Leu Gly Lys Val
785                 790                 795                 800

Val Trp Arg Ser Trp Arg Arg Leu His Asn Asp Asp
                805                 810

<210> SEQ ID NO 40
<211> LENGTH: 779
<212> TYPE: PRT
<213> ORGANISM: Anopheles gambiae

<400> SEQUENCE: 40

Met Gly Val Gly Ser Asn Ser Lys Tyr Ile Leu Ala Leu Val Leu Leu
1               5                   10                  15

Arg Val Ala Leu Val Trp Gly Ala Phe Pro Thr Gln Arg Asn Leu Ile
                20                  25                  30

Ala Leu Tyr Glu Arg Ser Asn Gln Ser Gly Met Ile Arg Gly Ile Ser
                35                  40                  45

Glu Met Val Asn Leu Leu Ala Pro Lys Ser Leu Val Ile Leu Val Gln
                50                  55                  60

Asn Glu Thr Lys Ile Asp Arg Leu Asp Lys Leu Thr Val Met Ile His
65                  70                  75                  80

His His Asn Ile Pro Thr Cys Val Tyr Tyr Asp Leu Glu Ala Tyr Phe
                85                  90                  95

Ser Leu Ile Glu Glu Asn Leu Lys Lys Ser Leu Glu Ile Thr Ser Leu
                100                 105                 110

Ile Phe Cys His Pro Glu Asp Met Leu Gln Asp Ile Thr Asp Arg Arg
                115                 120                 125

Leu Ala His Arg Leu Ser Leu Phe Ile Phe Tyr Trp Gly Ala Ala Gln
                130                 135                 140

Leu Pro Pro Thr Leu Asn Pro Asn Leu Leu Met Glu Pro Phe Arg Val
145                 150                 155                 160
```

```
Ala Ile Ile Thr Asn Pro Arg Arg Asn Ile Phe Arg Ile Phe Tyr Asn
            165                 170                 175
Gln Ala Lys Pro Asn Asn Arg Gly Asp Met Leu Ser Val Asn Trp Phe
        180                 185                 190
Asp Gly Asn Asp Met Thr Phe Lys Arg Val Pro Leu Leu Pro Ser Pro
            195                 200                 205
Thr Glu Val Tyr Lys Asn Phe Glu Gly Arg Ile Phe Thr Ile Pro Val
        210                 215                 220
Ile His Lys Pro Pro Trp His Phe Ile Val Tyr Gly Asn Gly Ser Ala
225                 230                 235                 240
Ser Val Gly Asp Asn Gln Asn Ser Ser Ser Asp Ala Ala Gly Gly
            245                 250                 255
Phe Glu Leu Glu Leu Asp Glu Asn Val Thr Val Glu Ser Asp Asp Thr
            260                 265                 270
Tyr Phe Thr Val Lys Gly Gly Arg Asp His Asn Leu Met Gln Leu Ile
        275                 280                 285
Ala Glu Arg Met Asn Phe Thr Phe Gln Tyr Val Glu Pro Pro Glu Lys
        290                 295                 300
Ile Gln Gly Ile Ala Leu Gly Ser Glu Asp Asn Ala Ser Phe Ser Gly
305                 310                 315                 320
Ala Leu Gly Met Leu Gln Arg Arg Glu Val Glu Leu Tyr Leu Gly Asp
            325                 330                 335
Val Ala Val Thr Trp Glu Arg Met Lys Ala Val Glu Phe Ser Phe Phe
            340                 345                 350
Thr Leu Ala Asp Ser Ala Ala Phe Val Thr His Ala Pro Arg Lys Leu
        355                 360                 365
Asn Glu Ala Leu Ala Leu Val Arg Pro Phe Gln Ile Thr Val Trp Pro
        370                 375                 380
Pro Val Ile Ile Thr Ile Leu Ile Ser Gly Pro Ile Leu Tyr Ile Ile
385                 390                 395                 400
Ile Ser Thr Pro Tyr Arg Trp Arg Ser Ala Gln Thr Val His Ala Arg
            405                 410                 415
Asn Ala Arg Trp Arg Pro Thr Arg Ser Arg Leu Arg Lys Pro Ala Phe
            420                 425                 430
Tyr Asn Leu Arg Tyr Ile Glu Glu Met Ser Tyr Thr Arg Phe Arg Ala
        435                 440                 445
Glu Arg Thr Ser Leu Ile Asn Asn His His Ser Arg Gly Gln Asp
        450                 455                 460
Tyr Pro Ser Leu Asp Arg Cys Ile Trp Tyr Thr Ile Asn Val Tyr Leu
465                 470                 475                 480
Arg Gln Ser Ala Asn Ile Pro Phe Asp Gly His Leu Ala Arg Phe Phe
            485                 490                 495
Ser Ile Leu Leu Trp Leu Cys Ala Thr Tyr Val Leu Gly Asp Val Tyr
        500                 505                 510
Ser Ala Gln Leu Thr Ser Gln Leu Ala Arg Pro Ala Arg Glu Ser Pro
        515                 520                 525
Ile Asn Thr Leu Gly Arg Leu Glu Asn Arg Met Asn Arg Glu Gly Tyr
        530                 535                 540
Gln Leu Leu Val Glu Arg Gln Ser Ala Phe His Ala Ala Leu Val Asn
545                 550                 555                 560
Ser Thr Gly Val Leu Gln Arg Leu Tyr Arg Leu Thr Arg Gln Arg Ser
            565                 570                 575
Val Asn Asp Ser Phe Leu Val Lys Ser Val Glu Glu Gly Ile Arg Val
```

```
                    580                 585                 590
Leu Gln Ala Asp Pro Lys Tyr Ala Val Phe Gly Gly Arg Glu Thr Leu
            595                 600                 605

Tyr Phe Asn Thr Lys Arg Tyr Gly Ala Asn Arg Phe Gln Leu Ser Glu
        610                 615                 620

Lys Leu Tyr Thr Arg Tyr Ser Ala Val Ala Val Gln Ile Gly Cys Pro
625                 630                 635                 640

Phe Leu Asp Ser Leu Asn Glu Val Ile Met Arg Leu Phe Glu Ala Gly
                645                 650                 655

Ile Val Glu Lys Ile Thr Ile Ala Glu Tyr Glu Gln Met Phe Gly Arg
            660                 665                 670

Gln Lys Gly Gly Val Ser His Ala Glu Glu Thr Val Arg Thr Val Lys
        675                 680                 685

Ser Thr Asn Ser Glu Cys Asp Thr Asp Gly Thr Gly Ser Gly Lys Arg
    690                 695                 700

Lys Thr Asp Ser Asn Asp Lys Leu Gln Pro Met Asn Leu Arg Met Leu
705                 710                 715                 720

Gln Gly Ala Phe Leu Val Leu Ala Cys Gly His Leu Leu Gly Gly Ile
                725                 730                 735

Cys Leu Phe Ile Glu Arg His Met Gly Met Ile Asn Pro Cys Gly Asp
            740                 745                 750

Thr Leu Arg Gln Gly Trp Arg His Leu Asn Arg Val Val Arg Lys Leu
        755                 760                 765

Gly Arg Gly Gly Ser Phe Lys Thr Gln Ser Asn
    770                 775

<210> SEQ ID NO 41
<211> LENGTH: 740
<212> TYPE: PRT
<213> ORGANISM: Culex quinquefasciatus

<400> SEQUENCE: 41

Met Lys Val Gly Ile Val Trp Cys Leu Phe Val Leu Gly Arg Ser
1               5                   10                  15

Phe Val Gln Ala Tyr His Ser Gln Leu Val Pro Ile Ala Asp Pro Ser
            20                  25                  30

Asn His Ser Gly Met Val Thr Gly Leu Ser Glu Met Ile Asn Leu Leu
        35                  40                  45

Ser Pro Lys Thr Leu Val Leu Val Leu Asn Glu Thr Lys Ile His
    50                  55                  60

Lys Ile Asp Arg Leu Thr Val Ala Ile His Ser Tyr Asn Ile Pro Thr
65                  70                  75                  80

Cys Ile Phe Tyr Asp Leu Glu Gln Tyr Phe Glu Tyr Ile Ala Asn Asn
                85                  90                  95

Leu Lys Asn Ser Leu Asp Thr Thr Ser Leu Leu Leu Cys His Pro Ala
            100                 105                 110

Asp Met Leu Val Asp Leu Val Asp Arg Arg Leu Ala His Arg Leu Ser
        115                 120                 125

Leu Tyr Ile Phe Tyr Trp Gly Ala Arg Arg Leu Pro Ala Gly Phe Asp
    130                 135                 140

Arg Ala Leu Leu Arg Glu Pro Leu Arg Val Ala Val Ile Thr Asn Pro
145                 150                 155                 160

Lys Lys Lys Ile Phe Arg Ile Pro Tyr Asn Gln Ala Lys Pro Asn Asn
                165                 170                 175
```

```
Leu Gly Glu Leu Leu Ser Ala Asn Trp Phe Asp Gly Ser Asp Met Thr
            180                 185                 190

Phe Lys Arg Val Pro Leu Leu Pro Thr Pro Thr Glu Val Tyr Lys Asn
    195                 200                 205

Phe Glu Gly Arg Val Phe Thr Ile Pro Val Ile His Lys Pro Pro Trp
210                 215                 220

His Phe Leu Thr Tyr Thr Asn Leu Asn Glu Ser Cys Asn Asp Thr Asp
225                 230                 235                 240

Thr Glu Phe Asp Met Ala Asn Val Thr Ser Phe Gln Val Thr Gly Gly
                245                 250                 255

Arg Asp His Asn Leu Met Gln Leu Ile Ala Ala Arg Met Asn Phe Thr
            260                 265                 270

Phe Arg Tyr Ile Glu Pro Glu Lys Ile Gln Gly Thr Ala Met Gly
        275                 280                 285

Ser Gly Asp Asn Val Ser Ile Ser Gly Ala Leu Gly Met Leu Gln Arg
        290                 295                 300

Arg Glu Val Asp Leu Phe Leu Gly Asp Val Ala Val Thr Trp Glu Arg
305                 310                 315                 320

Met Gln Ala Val Glu Phe Ser Phe Phe Thr Leu Ala Asp Ser Ala Ala
                325                 330                 335

Phe Val Thr His Ala Pro Arg Lys Leu Ser Glu Ala Leu Ala Leu Val
            340                 345                 350

Arg Pro Phe Gln Val Thr Val Trp Pro Leu Val Ile Phe Thr Ile Ile
        355                 360                 365

Leu Ser Gly Pro Val Leu Tyr Leu Ile Ile Ala Met Pro Phe Arg Leu
370                 375                 380

Glu Asp Trp Met Lys Gly Thr Leu Asp Lys Ala Arg Arg Leu Gln Val
385                 390                 395                 400

Arg Arg Gly Pro Pro Phe Tyr Asp Met Gln Tyr Ile Arg Glu Met Gly
                405                 410                 415

Tyr Gly Leu Val Pro Arg Ala Asp Ile Ala Gly Thr Pro Gln His Pro
            420                 425                 430

Ser Leu Asn Arg Cys Val Trp Tyr Thr Ile Asn Val Tyr Leu Arg Gln
        435                 440                 445

Ser Ala Thr Ile Pro Tyr Asn Gly His Val Ala Arg Phe Phe Ser Ile
450                 455                 460

Leu Leu Trp Leu Cys Ala Thr Tyr Val Leu Gly Asp Val Tyr Ser Ala
465                 470                 475                 480

Gln Leu Thr Ser Gln Leu Ala Arg Pro Ala Arg Glu Gly Pro Ile Asn
                485                 490                 495

Thr Leu Gly Lys Leu Glu Glu Leu Met Glu Ser Pro Gly Gly Gly Tyr
            500                 505                 510

Gln Leu Leu Val Glu Arg Gln Ser Ala Phe Gln Val Ala Leu Ala Asn
        515                 520                 525

Ser Thr Gly Ile Leu Gln Arg Leu Tyr Arg Ile Thr Gln Arg His Pro
530                 535                 540

Asp Asn Glu Ser Tyr Leu Val Gly Ser Val Glu Glu Gly Ile Gln Ile
545                 550                 555                 560

Leu Leu Val Asn Ser Lys Arg Ala Val Phe Gly Arg Glu Thr Leu
                565                 570                 575

Tyr Phe Asn Thr Lys Arg Tyr Gly Ala His Arg Phe Gln Leu Ser Asp
            580                 585                 590

Asn Leu Tyr Thr Arg Tyr Ser Ala Val Ala Val Gln Phe Gly Ser Pro
```

```
                      595                 600                 605
Phe Leu Asp Ser Leu Asn Glu Val Ile Met Arg Leu Phe Glu Ala Gly
    610                 615                 620

Ile Ile Gly Lys Ile Thr Val Ala Glu Tyr Glu Arg Met Phe Gly Ser
625                 630                 635                 640

Lys Ser Gly Gly Gln Phe Ala Asp Glu Thr Val Glu Ser Thr Lys Ser
                    645                 650                 655

Asp Asp Gly Val Asp Ala Thr Gly Lys Ala Lys Lys Ser Ala Glu Ser
                660                 665                 670

Ser Glu Lys Leu Gln Pro Met Asn Leu Arg Met Leu Gln Gly Ala Phe
            675                 680                 685

Leu Ala Leu Gly Phe Gly His Ser Val Gly Ala Ile Ile Leu Leu Val
        690                 695                 700

Glu Asn Gln Leu Lys Gly Ile Lys Ser Val Tyr Gln Arg Val Leu Gly
705                 710                 715                 720

Val Leu Thr Arg Thr Gly Arg Val Val Arg Lys Ile Trp Thr Ala Ile
                    725                 730                 735

Arg Arg Ser Leu
            740

<210> SEQ ID NO 42
<211> LENGTH: 677
<212> TYPE: PRT
<213> ORGANISM: Bombyx mori

<400> SEQUENCE: 42

Met Thr Lys Leu Pro Lys Asp Phe Asn Val Ala Ile Lys Asp Ile Ala
1               5                  10                  15

Glu Ser Leu Pro Ser Lys Glu Met Thr Val Val Arg Gly Asn Ser Thr
            20                  25                  30

Asn Ile Arg Ser Gln Asp Val Phe Glu Leu Leu Arg Leu Leu Cys Gln
        35                  40                  45

His Asn Ile Gln Val Val Asn Leu Asp Ile Ala Ala Met Glu Asn Lys
    50                  55                  60

Glu Met Tyr Tyr Gly Tyr Leu Lys Lys Ala Leu Asp Val Ser Asp Glu
65                  70                  75                  80

Arg Thr Asn Leu Ile Leu Cys Glu Pro Tyr Glu Cys Glu Asn Leu Leu
                85                  90                  95

Leu Glu Leu Arg Glu Asn Asn Leu Ile His Arg Thr Ile Leu Tyr Ile
            100                 105                 110

Phe Phe Trp Pro Tyr Gly Ser Val Ser Asp Arg Phe Leu Asn Thr Met
        115                 120                 125

Val Glu Ala Met Arg Val Ala Val Ile Thr Asn Pro Arg Glu Ser Val
    130                 135                 140

Phe Arg Ile Tyr Tyr Asn Gln Ala Thr Pro Asn Arg Leu Asn His Leu
145                 150                 155                 160

Ser Leu Val Asn Trp Trp Ala Phe Arg Leu Tyr Lys Ser Pro Leu Leu
                165                 170                 175

Pro Ser Ala Asp Lys Val Tyr Lys Asn Phe Arg Gly Arg Val Phe Asp
            180                 185                 190

Val Pro Val Leu His Ala Pro Pro Trp His Phe Val Lys Tyr Asn Asn
        195                 200                 205

Asp Ser Ser Ile Asn Val Thr Gly Gly Arg Asp Asp Lys Leu Leu Lys
    210                 215                 220
```

```
Leu Ile Ala Asn Lys Leu Asn Phe Arg Tyr Arg Tyr Asp Pro Pro
225                 230                 235                 240

Asp Arg Ser Gln Gly Ser Gly Ile Ile Gly Asn Gly Thr Phe Lys Gly
                245                 250                 255

Thr Leu Gly Leu Ile Trp Lys Arg Gln Ala Asp Phe Phe Leu Gly Asp
            260                 265                 270

Val Thr Met Thr Trp Glu Arg Leu Gln Ala Val Glu Phe Ser Phe Leu
        275                 280                 285

Thr Leu Ala Asp Ser Gly Ala Phe Leu Thr His Ala Pro Ala Lys Leu
    290                 295                 300

Ser Glu Thr Leu Ala Ile Ile Arg Pro Phe Arg Trp Glu Val Trp Pro
305                 310                 315                 320

Leu Val Cys Ala Thr Leu Phe Ile Thr Gly Pro Ala Leu Trp Ile Val
                325                 330                 335

Ile Ala Ala Pro Ser Leu Trp Gln Arg Lys Lys Arg Asp Gln Met Gly
            340                 345                 350

Leu Leu Asn Asn Cys Cys Trp Phe Thr Val Thr Leu Phe Leu Arg Gln
        355                 360                 365

Ser Ser Thr Lys Glu Pro Ser Ser Thr His Lys Ala Arg Leu Val Thr
    370                 375                 380

Val Leu Ile Ser Leu Gly Ala Thr Tyr Val Ile Gly Asp Met Tyr Ser
385                 390                 395                 400

Ala Asn Leu Thr Ser Leu Leu Ala Arg Pro Ala Lys Glu Pro Pro Ile
                405                 410                 415

Gly Thr Leu Pro Ala Leu Glu Glu Ala Met Arg Glu His Gly Tyr Glu
            420                 425                 430

Leu Val Val Glu Ser His Ser Ser Leu Ser Ile Leu Glu Asn Gly
        435                 440                 445

Thr Gly Val Tyr Gly Arg Leu Ala Lys Leu Met Lys Arg Gln Arg Val
    450                 455                 460

Gln Arg Val His Asn Val Glu Ala Gly Val Arg Leu Val Leu Asn Arg
465                 470                 475                 480

Arg Arg Val Ala Val Leu Gly Gly Arg Glu Thr Leu Tyr Tyr Asp Thr
                485                 490                 495

Glu Arg Phe Gly Ser His Asn Phe His Leu Ser Glu Lys Leu Tyr Thr
            500                 505                 510

Arg Tyr Ser Ala Ile Ala Phe Gln Ile Gly Ser Pro Tyr Leu Glu Thr
        515                 520                 525

Ile Asn Asn Val Val Met Thr Leu Phe Glu Ala Gly Ile Leu Gly Lys
    530                 535                 540

Met Thr Thr Asp Glu Tyr Lys Asn Leu Pro Glu Gln Ser Arg Arg Ser
545                 550                 555                 560

Glu Pro Val Thr Glu Ser Glu Asn Leu Ser Thr Glu Lys Thr Gly Glu
                565                 570                 575

Thr Ala Ala Val Thr Gln Ile Gln Asn Glu Thr Ser Lys Gly Leu Glu
            580                 585                 590

Pro Val Ser Leu Thr Met Leu Arg Gly Ala Phe Cys Leu Leu Gly Ile
        595                 600                 605

Gly His Leu Leu Ala Gly Val Thr Leu Leu Ile Glu Ile Gln Leu Tyr
    610                 615                 620

Arg Arg Ala Arg Lys Arg Ala Leu Pro Pro Gln Thr Arg Asn Pro Thr
625                 630                 635                 640

Asn Thr Phe Lys Ala Lys Ala Lys Lys Cys Ile Leu Arg Gly Trp Arg
```

```
                          645                 650                 655
Arg Ile Lys Ala Ala Ala Ile Leu Ala Ile Asp Arg Ala Leu Ala Pro
                    660                 665                 670
Asp Arg Gly Ile Asp
            675

<210> SEQ ID NO 43
<211> LENGTH: 700
<212> TYPE: PRT
<213> ORGANISM: Danaus plexippus

<400> SEQUENCE: 43

Met Ile Leu Thr Tyr Ile Ile Leu Leu Cys Val Arg Asp Thr Gln Cys
1               5                   10                  15

Leu Phe Glu Val Arg Asp Ser Val Asp Val Asn Leu Lys Gln Leu Pro
            20                  25                  30

Lys Asp Phe Ser Lys Ala Val Val Asp Ile Ala Ile Gly Leu Pro Thr
        35                  40                  45

Asn Thr Ile Thr Val Val Arg Gly Asn Ser Thr Asp Val Arg Asp Ala
    50                  55                  60

Asp Ile Phe Glu Leu Phe Cys Ser Leu Gly Asp Asn Asn Ile Gln Val
65                  70                  75                  80

Thr Asn Leu Asp Leu Met Thr Pro Glu Ser Lys Asp Ile Tyr Tyr Lys
                85                  90                  95

Tyr Leu Lys Glu Gly Leu Asp Asn Ser Glu Glu Arg Thr Ser Leu Ile
            100                 105                 110

Leu Cys Lys Pro Lys Glu Cys Glu Asp Leu Leu Leu Glu Val Thr Ser
        115                 120                 125

Asn Asn Phe Ile His Arg Pro Ile Leu Tyr Ile Phe Phe Trp Ser Glu
    130                 135                 140

Asp Glu Val Pro Lys Asn Phe Thr Thr Cys Ile Lys Glu Ala Val Arg
145                 150                 155                 160

Val Ala Val Ile Thr Asn Pro Arg Lys Gly Val Phe Arg Leu Tyr Tyr
                165                 170                 175

Asn Gln Ala Asn Pro Asn Lys Pro Arg His Leu Lys Leu Val Asn Trp
            180                 185                 190

Trp Ala Gly Gln Leu Tyr Lys Ser Pro Ser Leu Pro Pro Ala Asn Lys
        195                 200                 205

Val Tyr Glu Asp Phe Gln Gly Arg Ile Leu Asn Val Pro Val Leu His
    210                 215                 220

Ala Pro Pro Trp His Phe Val Arg Tyr Met Asn Asp Ser Thr Val Asn
225                 230                 235                 240

Val Thr Gly Gly Arg Asp His Lys Leu Leu Ser Leu Leu Ala Lys Lys
                245                 250                 255

Leu Asn Phe Lys Tyr Lys Tyr Tyr Asp Pro Pro Glu Arg Ser Gln Gly
            260                 265                 270

Ser Arg Ile Ser Gly Asn Gly Thr Phe Lys Gly Thr Leu Gly Gln Ile
        275                 280                 285

Trp Gln Arg Lys Ala Asp Phe Phe Ile Gly Asp Val Thr Met Thr Trp
    290                 295                 300

Glu Arg Leu Gln Ala Val Glu Phe Ser Phe Leu Thr Leu Ala Asp Ser
305                 310                 315                 320

Gly Ala Phe Leu Thr His Ala Pro Asp Lys Leu Ser Glu Thr Leu Ala
                325                 330                 335
```

```
Ile Ile Arg Pro Phe Arg Trp Glu Val Trp Pro Leu Val Phe Ala Thr
            340                 345                 350

Ile Leu Val Thr Gly Pro Ala Leu Trp Val Ile Ala Thr Pro Tyr
            355                 360                 365

Ile Trp Gln Arg Arg Glu Arg Asp Gln Met Glu Leu Leu Asn Asn Cys
            370                 375                 380

Cys Trp Phe Thr Thr Ser Leu Phe Leu Arg Gln Thr Thr Arg Lys Glu
385                 390                 395                 400

Pro Ser Thr Ser Asn Lys Ala Arg Leu Val Ser Ile Leu Ile Ser Leu
                405                 410                 415

Gly Ala Thr Tyr Val Ile Gly Asp Met Tyr Ser Ala Asn Leu Thr Ser
            420                 425                 430

Leu Met Ala Arg Pro Ser Lys Glu Gln Ala Ile Gly Thr Leu Val Ala
            435                 440                 445

Leu Glu Glu Ala Met Arg Asn Asp Gly Tyr Glu Leu Val Val Glu Ser
            450                 455                 460

His Ser Ser Leu Ala Ile Leu Gln Asn Gly Thr Asp Ile Tyr Gly
465                 470                 475                 480

Arg Leu Ala Arg Leu Met Arg Arg Gln Arg Thr Gln Arg Val Lys Ser
            485                 490                 495

Val Glu Val Gly Val Asn Met Val Leu Ser Lys Arg Ile Ala Ile
            500                 505                 510

Leu Gly Gly Arg Glu Thr Leu Phe Tyr Asp Thr Glu Arg Phe Gly Ser
            515                 520                 525

His Asn Phe His Leu Ser Glu Lys Leu Tyr Thr Arg Tyr Ser Ala Ile
            530                 535                 540

Ala Leu Gln Ile Gly Cys Pro Tyr Leu Glu Thr Phe Asn Asn Val Leu
545                 550                 555                 560

Met Thr Leu Phe Glu Ala Gly Ile Leu Thr Lys Met Thr Ser Asp Glu
            565                 570                 575

Tyr Arg Asn Leu Pro Glu Gln Ser Arg Arg Ser Glu Lys Val Thr Glu
            580                 585                 590

Ser Glu Ser Lys Glu Asn Asn Asp Val Thr Glu Asn Ser Pro Thr Ala
            595                 600                 605

Gln Ile Gln Pro Glu Ser Thr Ile Gly Leu Glu Pro Val Ser Leu Thr
            610                 615                 620

Met Leu Arg Gly Ala Phe Cys Leu Leu Gly Ile Gly Tyr Phe Ile Ala
625                 630                 635                 640

Ala Val Val Leu Ala Thr Glu Ile Glu Ile Gln Arg Arg Lys Arg Ser
            645                 650                 655

Arg Ala Glu Arg Val Met Asp Thr Ser Leu Phe Pro Lys Ser Pro Arg
            660                 665                 670

Met Tyr Leu Arg His Tyr Leu Ile Arg Ile Phe Arg Thr Met Tyr Asn
            675                 680                 685

Ile Val Asp Gly Ala Leu Arg Pro Glu Met Lys Glu
            690                 695                 700

<210> SEQ ID NO 44
<211> LENGTH: 680
<212> TYPE: PRT
<213> ORGANISM: Tribolium castaneum

<400> SEQUENCE: 44

Met Arg Arg Asp His Gly Gly Asp Leu Val Ser Ala Ser Phe Asp Ile
1               5                   10                  15
```

```
Val Ala Gly Phe Leu Phe Glu Glu Ile Cys Ile Cys Phe Asp Lys Asn
             20                  25                  30

Thr Asn Ile Asn Phe Leu Gln His Leu Leu Val Arg Phe Val Ser Asn
         35                  40                  45

Asn Ile Ala Ile Lys Leu Phe Asn Ile Thr Thr Val Glu Val Gln Asp
50                  55                  60

Lys Tyr Phe Ala Phe Leu Asn Tyr Gln Val Thr Asn His Leu Gly Ala
65                  70                  75                  80

Asn Thr Ile Phe Phe Ser Ser His Lys Phe Tyr Glu His Val Leu Leu
                85                  90                  95

Glu Ile Asn Glu Arg Asp Phe Ile Arg Arg Asn Leu Ile Tyr Ile Phe
                100                 105                 110

Asn Trp Gly Arg Arg Pro Phe Ser Arg Tyr Phe Val Arg Asn Ile Ile
            115                 120                 125

Asn Val Met Lys Val Phe Val Ile Thr Asn Pro Arg Asn Asp Thr Phe
        130                 135                 140

Arg Ile Phe Tyr Asn Gln Ala Val Pro Tyr Lys Lys His His Leu Glu
145                 150                 155                 160

Met Val Asn Trp Trp Gln His Gly Val Gly Leu Phe Asn His Pro Thr
                165                 170                 175

Leu Pro Ala Lys Tyr Asn Asn Val Phe Lys Asp Phe Lys Glu Asn Val
            180                 185                 190

Phe Lys Ile Pro Val Ile His Lys Pro Pro Trp His Phe Val Gln Tyr
        195                 200                 205

Gly Asn Asp Ser Ile Lys Val Thr Gly Gly Arg Asp Asp Arg Ile Leu
    210                 215                 220

Ser Leu Leu Ser Lys Lys Leu Asn Phe Arg Tyr Asp Tyr Phe Asp Pro
225                 230                 235                 240

Pro Glu Arg Ile Gln Gly Ser Ser Ala Ser Glu Asn Gly Thr Phe Lys
                245                 250                 255

Gly Val Leu Gly Leu Ile Trp Lys Arg Gln Ala Glu Phe Phe Ile Gly
            260                 265                 270

Asp Val Ala Leu Ser His Glu Arg Ala Asn Tyr Val Glu Phe Ser Phe
        275                 280                 285

Ile Thr Leu Ala Asp Ser Gly Ala Phe Ile Thr His Ala Pro Ser Lys
    290                 295                 300

Leu Asn Glu Ala Leu Ala Leu Leu Arg Pro Phe Gln Trp Gln Val Trp
305                 310                 315                 320

Pro Ala Ile Gly Val Thr Phe Val Val Val Gly Pro Val Leu Tyr Ala
                325                 330                 335

Ile Ile Ala Leu Pro Asn Ala Trp Arg Pro Arg Phe Arg Val Arg Ser
            340                 345                 350

His Ala Arg Leu Phe Phe Asp Cys Thr Trp Phe Thr Thr Thr Val Leu
        355                 360                 365

Leu Lys Gln Thr Gly Lys Glu Pro Ser Ser Ser His Lys Ala Arg Phe
    370                 375                 380

Phe Ile Ile Ile Leu Ser Ile Ser Ser Thr Tyr Val Ile Asn Asp Met
385                 390                 395                 400

Tyr Ser Ala Asn Leu Thr Ser Leu Leu Ala Lys Pro Gly Arg Glu Lys
                405                 410                 415

Ala Ile Asn Asn Leu Asn Gln Leu Glu Lys Ala Met Ala Thr Arg Gly
            420                 425                 430
```

```
Tyr Asp Leu Tyr Val Glu Arg His Ser Ser Tyr Ser Leu Phe Glu
            435                 440                 445

Asn Gly Thr Gly Ile Tyr Ser Arg Leu Trp Gln Met Met Asn Arg Arg
        450                 455                 460

Gln Thr His Phe Leu Leu Glu Ser Val Glu Glu Gly Val Gln Leu Val
465                 470                 475                 480

Arg Asp Ser Thr Asn Lys Ala Val Ile Ala Gly Arg Glu Thr Leu Phe
                485                 490                 495

Phe Asp Ile Gln Arg Phe Gly Ala Ser Asn Phe His Leu Ser Glu Lys
            500                 505                 510

Leu Asn Thr Ala Tyr Ser Ala Ile Ala Leu Gln Leu Gly Cys Pro Tyr
        515                 520                 525

Ile Glu Glu Ile Asn Lys Ile Leu Met Ala Ile Phe Glu Ala Gly Ile
530                 535                 540

Ile Thr Lys Met Thr Glu Asn Glu Tyr Glu Gln Leu Gly Lys Lys Lys
545                 550                 555                 560

Gln Thr Thr Ser Glu Thr Glu Lys Glu Leu Ile Pro Gly Val Lys Lys
                565                 570                 575

Glu Asn Arg Arg Val Ala Lys Val Ser Glu Asp Asn Glu Lys Leu Gln
            580                 585                 590

Pro Ile Ser Ile Lys Met Leu Gln Gly Thr Phe Tyr Leu Leu Cys Ile
        595                 600                 605

Gly Asn Ile Phe Ser Gly Phe Ile Leu Leu Ala Glu Ile Leu Val Tyr
    610                 615                 620

Lys His Arg Lys Thr Tyr Lys His Lys Lys Arg Arg His Arg Phe Val
625                 630                 635                 640

Tyr Leu Arg Lys Ile Arg His Ser Val Ala Ser Lys Phe Gly Ala Val
                645                 650                 655

Val Asp Ala Val Arg Arg Val Tyr Arg Arg Ala Met His Asp Ala Phe
            660                 665                 670

Val Ala Thr Leu Glu Tyr Leu Glu
        675                 680

<210> SEQ ID NO 45
<211> LENGTH: 663
<212> TYPE: PRT
<213> ORGANISM: Apis mellifera
<220> FEATURE:
<221> NAME/KEY: misc_feature
<222> LOCATION: (42)..(42)
<223> OTHER INFORMATION: Xaa can be any naturally occurring amino acid

<400> SEQUENCE: 45

Ile Tyr Ile Phe Phe Leu Ile Arg Ser Thr Ile Tyr Tyr Val Ser Phe
1               5                   10                  15

Ser Gly Arg Asp Ile Phe Lys Asn Thr Val Ala Ser Ala Ile Cys Asn
            20                  25                  30

Glu Tyr Ser Ile Val Val Leu Thr Asn Xaa Asn Ala Asn Ile Ile Met
        35                  40                  45

Leu Ile Leu Ile Asn Ile Ile Phe Ile Ser Leu Tyr Leu Ser Ser Ser
50                  55                  60

Ile Ile Leu Ile Asp Tyr Asn Thr Tyr Leu Ile Gln Asn Leu Leu
65                  70                  75                  80

Val Asn Val Thr Ile Tyr Ile Asn Ile Tyr Arg Leu Leu Gly Leu His
            85                  90                  95

Arg Asp Gly Asp Phe Leu Phe Phe Thr Gln Ile Arg Arg Ser Asn Leu
```

```
                100                 105                 110
Met Ser Arg Asn Val Val Tyr Val Phe Leu Trp Leu Arg Ser Ser Val
            115                 120                 125

Ser Arg Thr Phe Lys Ala Asp Ile Leu Glu Ala Met Arg Val Cys Val
130                 135                 140

Ile Thr Ser Pro Arg Pro Gly Phe Tyr Gln Ile Tyr Tyr Ser Gln Ala
145                 150                 155                 160

Ser Ala Arg Pro Gly Tyr Gly Ser Ser Leu Lys Met Val Asn Trp Trp
                165                 170                 175

Ser Ala Met Asp Gly Leu Val Arg Phe Pro Leu Leu Pro Pro Pro Lys
            180                 185                 190

Gln Val Tyr Lys Asn Phe Glu Gly Arg Tyr Phe Asn Val Pro Val Leu
        195                 200                 205

His Lys Pro Pro Trp Thr Phe Val Glu Tyr Leu Asn Asp Ser Phe Arg
    210                 215                 220

Val Glu Gly Gly Arg Asp Asp Lys Leu Ile Asn Leu Leu Ala Asp Lys
225                 230                 235                 240

Leu His Phe Gln Phe Lys Tyr Ile Asp Pro Pro Asp Arg Thr Gln Gly
                245                 250                 255

Ser Gly Leu Asp Arg Gly Ser Ser Met Gln Gly Val Leu Gly Leu Ile
            260                 265                 270

Trp Gln Arg Glu Ala Asp Trp Phe Val Gly Asp Leu Ser Ile Thr Tyr
        275                 280                 285

Glu Arg Asn Leu Val Val Asp Phe Ser Phe Leu Thr Leu Val Asp Asn
    290                 295                 300

Glu Ala Phe Leu Thr His Ala Pro Gly Arg Leu Asn Glu Ala Phe Ser
305                 310                 315                 320

Leu Ile Arg Pro Phe His Trp Ser Val Trp Pro Leu Leu Leu Ile Thr
                325                 330                 335

Val Ile Phe Ala Gly Pro Ile Leu Tyr Ile Leu Val Asp Thr Thr Asp
            340                 345                 350

Gly His Pro Gln Gly Lys Ser Met Leu Tyr Trp Lys Cys Val Trp Trp
        355                 360                 365

Ser Val Thr Val Phe Leu Gln Gln Ala Ala Ile Ile Pro Ser Glu Asn
    370                 375                 380

Asn Lys Ile Arg Phe Val Ala Gly Leu Leu Met Leu Ser Val Thr Tyr
385                 390                 395                 400

Val Ile Gly Asp Met Tyr Ser Ala Ser Leu Thr Ser Ile Leu Ala Arg
                405                 410                 415

Pro Pro Lys Glu Pro Pro Ile Asn Thr Leu Lys Glu Leu Ser Glu Ala
            420                 425                 430

Met Arg Asp Ser Gly Leu Gln Leu Val Glu Val Gln Ser Ala Ser
        435                 440                 445

Gln Ala Met Leu Glu Asn Gly Thr Gly Val Tyr Glu Glu Leu Ser Gln
    450                 455                 460

Leu Val Thr Arg Gln Arg Glu Tyr Leu Ile Gly Ser Thr Glu Lys Gly
465                 470                 475                 480

Met Gln Leu Val Arg Asp Asn Lys Asn Tyr Ala Val Ile Gly Gly Arg
                485                 490                 495

Glu Thr Phe Tyr Tyr Asp Ile Lys Arg Phe Gly Ala Gln His Phe His
            500                 505                 510

Leu Ser Glu Lys Leu Asn Thr Arg Tyr Ser Ala Ile Ala Phe Gln Arg
        515                 520                 525
```

```
Ala Cys Pro Tyr Arg Asp Asn Phe Asp Asp Val Leu Met Arg Leu Phe
        530                 535                 540

Glu Gly Gly Ile Leu Ser Lys Ile Thr Glu Glu Tyr Gln Lys Leu
545                 550                 555                 560

Asn Asp Lys Leu Met Gly Ser Glu Glu Phe Asp Ser Thr Ser Val Val
            565                 570                 575

Ile Glu Pro Val Leu Glu Gly Ser Glu Pro Arg Gln Glu Asp Asp Asp
            580                 585                 590

Lys Gln Leu Thr Ile Ala Met Ser Met Lys Thr Leu Gln Gly Ala Phe
            595                 600                 605

Tyr Val Leu Ala Ile Gly Ser Ile Leu Ala Gly Leu Leu Leu Leu Ile
            610                 615                 620

Glu Met Arg Ser His Asp Lys Leu Glu Lys Asp Lys Val Ile Lys Leu
625                 630                 635                 640

Val Glu Ala Pro Phe Val Tyr Lys Arg Lys Val Pro Asn Lys Phe Gln
            645                 650                 655

Asn Arg Leu Tyr Asp Leu Lys
            660

<210> SEQ ID NO 46
<211> LENGTH: 704
<212> TYPE: PRT
<213> ORGANISM: Drosophila melanogaster

<400> SEQUENCE: 46

Met Arg Cys Leu Trp Ile Leu Ile Val Ala Phe Ile Ser Leu Ala Met
1               5                   10                  15

Ala Thr Ser Ile Pro Ile Pro Ile Ala Asn Pro Ala Pro Leu Ser Gly
            20                  25                  30

Tyr Glu Met Gln Leu Lys Ile Leu Leu Gln Lys Ile Leu Trp Val Ala
            35                  40                  45

Asn Val Lys Arg Cys Phe Ala Val Ile Thr Asp Leu His Tyr Pro
    50                  55                  60

Ile Tyr Asp Arg Ile Phe Phe Glu Ser Val Gly Arg Arg Val Ile Pro
65                  70                  75                  80

Phe Phe Val Met Arg Thr Asn Glu Ser Asp Asp Leu Gln Arg Pro Ser
                85                  90                  95

Arg Gln Val Glu Leu Phe Val Lys Ala Ile Lys Ser Ser Asp Cys Glu
            100                 105                 110

Leu Asn Val Ile Thr Ile Leu Asn Gly Trp Gln Val Gln Arg Phe Leu
            115                 120                 125

Gly Tyr Ile Tyr Asp Asn Arg Ser Leu Asn Met Gln Lys Lys Phe Val
130                 135                 140

Leu Leu His Asp Leu Arg Leu Phe Glu Ser Asp Met Ile His Leu Trp
145                 150                 155                 160

Ser Val Phe Ile Asp Ala Ile Phe Leu Lys Arg Gln Leu Asp Asn Lys
            165                 170                 175

Tyr Thr Ile Ser Thr Ile Ala Phe Pro Gly Ile Leu Ser Gly Val Leu
            180                 185                 190

Val Met Lys Asn Ile Ala Asn Trp Glu Leu Gly Lys Gly Leu Asn Gly
            195                 200                 205

Arg Ile Leu Phe Ala Asp Lys Thr Ser Asn Leu Phe Gly Thr Ser Leu
210                 215                 220

Pro Val Ala Ile Ser Glu His Val Pro Met Val Leu Trp Ala Asn Ala
```

```
            225                 230                 235                 240

Thr Lys Ser Phe Gln Gly Val Glu Val Glu Ile Met Asn Ala Leu Gly
                245                 250                 255

Lys Ala Leu Asn Phe Lys Pro Val Tyr Tyr Lys Pro Asn Gln Thr Glu
            260                 265                 270

Asn Met Asp Trp Thr Glu Leu Asp Gly Gly Ala Ser Val Ala Tyr Gly
        275                 280                 285

Ser Gly Asn Pro Asp Gly Tyr Ala Gln Asn Gly Thr His Ile Asp Ser
    290                 295                 300

Met Leu Val Asp Glu Val Ala Ala His Ser Ala Arg Phe Ala Ile Gly
305                 310                 315                 320

Asp Leu His Leu Phe Gln Val Tyr Leu Lys Leu Val Glu Leu Ser Ala
                325                 330                 335

Pro His Asn Phe Glu Cys Leu Thr Phe Leu Thr Pro Glu Ser Ser Thr
            340                 345                 350

Asp Asn Ser Trp Gln Thr Phe Ile Leu Pro Phe Ser Ala Gly Met Trp
        355                 360                 365

Val Gly Val Leu Leu Ser Leu Phe Val Val Gly Thr Val Phe Tyr Ala
    370                 375                 380

Ile Ser Phe Leu Asn Ala Ile Ile Asn Gly Asn Val Ser Ser Glu Phe
385                 390                 395                 400

Phe Arg Cys Leu Arg Pro Asn Arg Asn Val Pro Met Asp Pro Lys Ile
                405                 410                 415

Tyr Arg Arg Ile Ser Phe Arg Ile Ala Ile Ser Arg Tyr Arg Ser Ser
            420                 425                 430

Lys Gly Asp Arg Met Pro Arg Asp Leu Phe Asp Gly Tyr Thr Asn Cys
        435                 440                 445

Ile Leu Leu Thr Tyr Ser Met Leu Leu Tyr Val Ala Leu Pro Arg Met
    450                 455                 460

Pro Arg Asn Trp Pro Leu Arg Val Leu Thr Gly Trp Tyr Trp Ile Tyr
465                 470                 475                 480

Cys Ile Leu Leu Val Ala Thr Tyr Arg Ala Ser Phe Thr Ala Ile Leu
                485                 490                 495

Ala Asn Pro Ala Ala Arg Val Thr Ile Asp Thr Leu Glu Asp Leu Leu
            500                 505                 510

Arg Ser His Ile Pro Pro Ser Thr Gly Ala Thr Glu Asn Arg Gln Phe
        515                 520                 525

Phe Leu Glu Ala Asn Asp Glu Val Ala Arg Lys Val Gly Glu Lys Met
    530                 535                 540

Glu Val Phe Gly Tyr Ser Asp Asp Leu Thr Ser Arg Ile Ala Lys Gly
545                 550                 555                 560

Gln Cys Ala Tyr Tyr Asp Asn Glu Phe Tyr Leu Arg Tyr Leu Arg Val
                565                 570                 575

Ala Asp Glu Ser Gly Ser Ala Leu His Ile Met Lys Glu Cys Val Leu
            580                 585                 590

Tyr Met Pro Val Val Leu Ala Met Glu Lys Asn Ser Ala Leu Lys Pro
        595                 600                 605

Arg Val Asp Ala Ser Ile Gln His Leu Ala Glu Gly Gly Leu Ile Ala
    610                 615                 620

Lys Trp Leu Lys Asp Ala Ile Glu His Leu Pro Ala Glu Ala Leu Ala
625                 630                 635                 640

Gln Gln Glu Ala Leu Met Asn Ile Gln Lys Phe Trp Ser Ser Phe Val
                645                 650                 655
```

```
Ala Leu Leu Ile Gly Tyr Val Ile Ser Met Leu Thr Leu Leu Ala Glu
            660                 665                 670

Arg Trp His Phe Lys His Ile Val Met Lys His Pro Met Tyr Asp Val
        675                 680                 685

Tyr Asn Pro Ser Leu Tyr Tyr Asn Phe Lys Arg Ile Tyr Pro Gln His
    690                 695                 700

<210> SEQ ID NO 47
<211> LENGTH: 703
<212> TYPE: PRT
<213> ORGANISM: Drosophila melanogaster

<400> SEQUENCE: 47

Met Arg Cys Leu Trp Ile Leu Ile Val Ala Phe Ile Ser Leu Ala Met
1               5                   10                  15

Ala Thr Ser Ile Pro Ile Pro Ile Ala Asn Pro Ala Pro Leu Ser Gly
            20                  25                  30

Tyr Glu Met Gln Leu Lys Ile Leu Leu Gln Lys Ile Leu Trp Val Ala
        35                  40                  45

Asn Val Lys Arg Cys Phe Ala Val Ile Thr Asp Asp Leu His Tyr Pro
    50                  55                  60

Ile Tyr Asp Arg Ile Phe Phe Glu Ser Val Gly Arg Arg Val Ile Pro
65                  70                  75                  80

Phe Phe Val Met Arg Thr Asn Glu Ser Asp Asp Leu Gln Arg Pro Ser
                85                  90                  95

Arg Gln Val Glu Leu Phe Val Lys Ala Ile Lys Ser Ser Asp Cys Glu
            100                 105                 110

Leu Asn Val Ile Thr Ile Leu Asn Gly Trp Gln Val Gln Arg Phe Leu
        115                 120                 125

Gly Tyr Ile Tyr Asp Asn Arg Ser Leu Asn Met Gln Lys Lys Phe Val
    130                 135                 140

Leu Leu His Asp Leu Arg Leu Phe Glu Ser Asp Met Ile His Leu Trp
145                 150                 155                 160

Ser Val Phe Ile Asp Ala Ile Phe Leu Lys Arg Gln Leu Asp Asn Lys
                165                 170                 175

Tyr Thr Ile Ser Thr Ile Ala Phe Pro Gly Ile Leu Ser Gly Val Leu
            180                 185                 190

Val Met Lys Asn Ile Ala Asn Trp Glu Leu Gly Lys Gly Leu Asn Gly
        195                 200                 205

Arg Ile Leu Phe Ala Asp Lys Thr Ser Asn Leu Phe Gly Thr Ser Leu
    210                 215                 220

Pro Val Ala Ile Ser Glu His Val Pro Met Val Leu Trp Ala Asn Ala
225                 230                 235                 240

Thr Lys Ser Phe Gln Gly Val Glu Val Glu Ile Met Asn Ala Leu Gly
                245                 250                 255

Lys Ala Leu Asn Phe Lys Pro Val Tyr Tyr Lys Pro Asn Gln Thr Glu
            260                 265                 270

Asn Met Asp Trp Thr Glu Leu Asp Gly Gly Ala Ser Val Ala Tyr Gly
        275                 280                 285

Ser Gly Asn Pro Asp Gly Tyr Ala Gln Asn Gly Thr His Ile Asp Ser
    290                 295                 300

Met Leu Val Asp Glu Val Ala Ala His Ser Ala Arg Phe Ala Ile Gly
305                 310                 315                 320

Asp Leu His Leu Phe Gln Val Tyr Leu Lys Leu Val Glu Leu Ser Ala
```

```
                  325                 330                 335
Pro His Asn Phe Glu Cys Leu Thr Phe Leu Thr Pro Glu Ser Ser Thr
              340                 345                 350

Asp Asn Ser Trp Gln Thr Phe Ile Leu Pro Phe Ser Ala Gly Met Trp
              355                 360                 365

Val Gly Val Leu Leu Ser Leu Phe Val Val Gly Thr Val Phe Tyr Ala
              370                 375                 380

Ile Ser Phe Leu Asn Ala Ile Ile Asn Gly Asn Val Ser Ser Glu Phe
385                 390                 395                 400

Phe Arg Cys Leu Arg Pro Asn Arg Asn Val Pro Met Asp Pro Lys Ile
                  405                 410                 415

Tyr Arg Arg Ile Ser Phe Arg Ile Ala Ile Ser Arg Tyr Arg Ser Ser
                  420                 425                 430

Lys Gly Asp Arg Met Pro Arg Asp Leu Phe Asp Gly Tyr Thr Asn Cys
              435                 440                 445

Ile Leu Leu Thr Tyr Ser Met Leu Leu Tyr Val Ala Leu Pro Arg Met
450                 455                 460

Pro Arg Asn Trp Pro Leu Arg Val Leu Thr Gly Trp Tyr Trp Ile Tyr
465                 470                 475                 480

Cys Ile Leu Leu Val Ala Thr Tyr Arg Ala Ser Phe Thr Ala Ile Leu
                  485                 490                 495

Ala Asn Pro Ala Ala Arg Val Thr Ile Asp Thr Leu Glu Asp Leu Leu
              500                 505                 510

Arg Ser His Ile Pro Pro Ser Thr Gly Ala Thr Glu Asn Arg Gln Phe
          515                 520                 525

Phe Leu Glu Ala Asn Asp Glu Val Ala Arg Lys Val Gly Glu Lys Met
530                 535                 540

Glu Val Phe Gly Tyr Ser Asp Asp Leu Thr Ser Arg Ile Ala Lys Gly
545                 550                 555                 560

Gln Cys Ala Tyr Tyr Asp Asn Glu Phe Tyr Leu Arg Tyr Leu Arg Val
                  565                 570                 575

Ala Asp Glu Ser Gly Ser Ala Leu His Ile Met Lys Glu Cys Val Leu
              580                 585                 590

Tyr Met Pro Val Val Leu Ala Met Glu Lys Asn Ser Ala Leu Lys Pro
              595                 600                 605

Arg Val Asp Ala Ser Ile Gln His Leu Ala Glu Gly Leu Ile Ala Lys
610                 615                 620

Trp Leu Lys Asp Ala Ile Glu His Leu Pro Ala Glu Ala Leu Ala Gln
625                 630                 635                 640

Gln Glu Ala Leu Met Asn Ile Gln Lys Phe Trp Ser Ser Phe Val Ala
                  645                 650                 655

Leu Leu Ile Gly Tyr Val Ile Ser Met Leu Thr Leu Leu Ala Glu Arg
              660                 665                 670

Trp His Phe Lys His Ile Val Met Lys His Pro Met Tyr Asp Val Tyr
              675                 680                 685

Asn Pro Ser Leu Tyr Tyr Asn Phe Lys Arg Ile Tyr Pro Gln His
          690                 695                 700

<210> SEQ ID NO 48
<211> LENGTH: 522
<212> TYPE: PRT
<213> ORGANISM: Aedes aegypti

<400> SEQUENCE: 48
```

-continued

```
Phe Pro Phe Pro Leu Arg Gly Val Phe Ile Ser Arg Arg Leu Asp Phe
1               5                   10                  15

Trp Phe Asn Gly Lys Phe Arg Lys Gly Arg Lys Leu Phe Ser Asp Lys
            20                  25                  30

Thr Thr Asn Leu Asp Gly Gln Ser Met Lys Val Val Leu Glu His
            35                  40                  45

Thr Pro Ala Ile Phe Arg Thr Thr His Asn Glu Thr Asp Glu His Leu
        50              55                  60

Lys Tyr Tyr Gly Leu Glu Val Glu Leu Leu Lys Ala Ile Ser Glu Ala
65                  70                  75                  80

Met Lys Phe Glu Met Asp Phe Tyr Glu Ser Asp Asp Ala Ala Val Ala
                85                  90                  95

Met Trp Gly Thr Val Thr Asp Gly Glu Asn Ala Thr Gly Leu Leu Gly
                100                 105                 110

Glu Met Met Ser His Lys Phe Leu His Cys Phe Asn Tyr Val Phe Gln
            115                 120                 125

Asn Glu Gly His Ala Asp Phe Ala Leu Ala Asp Leu His His Thr Gln
            130                 135                 140

Tyr His Leu Glu Ile Met Asp Leu Ser Ile Pro Tyr Asn Thr Glu Cys
145                 150                 155                 160

Leu Thr Phe Leu Thr Pro Glu Ala Leu Thr Asp Asn Ser Trp Thr Thr
                165                 170                 175

Leu Ile Leu Pro Phe Thr Gly Met Trp Ala Gly Val Leu Ala Ser
                180                 185                 190

Leu Phe Ser Ile Gly Thr Val Phe Tyr Ala Leu Ser Arg Leu Leu Met
            195                 200                 205

Phe Val Arg His Glu Gln Ser Tyr Arg Ser Asp Leu Asp Met Ile Ala
            210                 215                 220

Lys Arg Ser Arg Lys Arg Asn Arg Lys Val His Phe Lys Ile Val Cys
225                 230                 235                 240

Gly Met Val Asn Ser Tyr Lys Arg Ala Leu Asp Pro Leu Pro Pro Arg
                245                 250                 255

Asp Ile Phe Asp Thr Phe Ser Gly Cys Ile Ile Tyr Thr Tyr Ser Met
                260                 265                 270

Leu Leu Leu Val Ser Leu Pro Arg Leu Pro Lys Gly Trp Pro Leu Arg
            275                 280                 285

Leu Leu Thr Gly Trp Tyr Trp Ile Tyr Cys Ile Leu Leu Val Val Ala
            290                 295                 300

Tyr Arg Ala Ser Leu Thr Ala Ile Leu Ala Asn Pro Val Ala Arg Val
305                 310                 315                 320

Thr Ile Asp Lys Leu Lys Asp Leu Ala Asp Ser Pro Ile Arg Cys Gly
                325                 330                 335

Ala Trp Gly Glu Gln Asn Lys Leu Phe Phe Gln Ser Ala Ser Asp Gln
                340                 345                 350

Val Ser Met Gln Ile Gly Gln Lys Leu Glu His Thr Pro Lys Ala Glu
            355                 360                 365

Ala Ala Val Glu Arg Val Val Glu Gly His Phe Ala Tyr Tyr Asp Asn
            370                 375                 380

Val Tyr Met Leu Lys His Leu Arg Ala Thr Arg Lys Ser Ala Lys Ala
385                 390                 395                 400

Arg Glu Thr Leu His Ile Met Glu Glu Cys Ala Val His Met Pro Ile
                405                 410                 415

Ser Ile Gly Leu Glu Lys Asn Ser Pro Leu Lys Pro Lys Val Asp Lys
```

|     |     |     | 420 |     |     |     | 425 |     |     |     | 430 |     |     |     |
| --- | --- | --- | --- | --- | --- | --- | --- | --- | --- | --- | --- | --- | --- | --- |

Tyr Val Arg Ala Leu Val Glu Ala Gly Leu Thr Lys Lys Trp Leu Ala
            435                      440                      445

Asp Ala Ile Glu Glu Phe Gln Ser Asn Val Glu Ile Pro Pro Gln Glu
450                      455                      460

Ala Thr Met Asp Leu Gln Lys Leu Thr Ala Ala Phe Ile Ala Leu Ala
465                      470                      475                      480

Ile Gly Tyr Gly Val Ser Leu Leu Ala Phe Ser Ala Glu Lys Leu Tyr
            485                      490                      495

Trp Arg Phe Val Val Glu Lys His Pro Ala Tyr Asp Lys Tyr Ile Val
            500                      505                      510

Gly Ser Tyr Arg Gly Lys Val Val Arg Phe
            515                      520

<210> SEQ ID NO 49
<211> LENGTH: 648
<212> TYPE: PRT
<213> ORGANISM: Anopheles gambiae

<400> SEQUENCE: 49

Met Cys Lys Thr Ser Arg Leu Val Trp Ile Leu Thr Ala Phe Val Leu
1                  5                      10                      15

Ile Leu Gly Val Lys His Cys Ala Asn Lys Gln Leu Asn Ser Ala Thr
            20                      25                      30

Lys Gly Asn Asp Arg Lys Ser Ser Gln Ser Ile His His Glu Glu Tyr
            35                      40                      45

Ser Thr Glu Leu His Leu Glu Met Leu Leu Leu Glu Leu Ala Ala Lys
50                      55                      60

Met Asp Tyr Gly His Cys Tyr Val Val Leu Phe Asp Glu Val Tyr Glu
65                  70                      75                      80

Ser Val Leu Asn Ala Ala Phe Phe Arg Gln Ile His Arg Ala Ala Arg
                  85                      90                      95

Tyr Ile Val Lys Ile Glu Gln Asp Glu Asp Thr Phe Asn Pro Arg Pro
            100                      105                      110

Ser Leu Lys Cys Ile Leu Glu Ser Thr Arg Lys Ala Gly Cys Gly Gly
            115                      120                      125

Tyr Ile Leu Leu Met Ala Asn Gly Ile Gln Met Ala Leu Tyr Glu Leu
            130                      135                      140

Ser Thr Ala Pro Phe Pro Met Gln Ile Lys Gly Val Phe Phe Ser Lys
145                      150                      155                      160

Ile Leu Asn Phe Trp Gln Gly Gly Lys Phe Arg Leu Ala Asn Ser Thr
                  165                      170                      175

Phe Phe Asp Asp Lys Thr Lys Asp Leu Arg Arg Gln Glu Met Arg Val
            180                      185                      190

Val Val Leu Glu His Thr Pro Ala Val Phe Lys Ser Ala Thr Thr Ser
            195                      200                      205

Asn Tyr Tyr Gly Leu Glu Ile Glu Leu Leu Lys Ala Ile Ser Lys Ala
210                      215                      220

Met His Phe Gln Met Val Phe Tyr Glu Thr Ser Asp Ala Asp Lys Glu
225                      230                      235                      240

Arg Trp Gly Arg Leu Gly Gly Asn Gly Thr Leu Thr Gly Ile Ile Lys
                  245                      250                      255

Glu Met Gln Glu Gly Lys Ala Asp Phe Ala Leu Ala Asp Leu His His
            260                      265                      270

-continued

```
Thr Glu Tyr Asn Leu Gly Phe Met Asp Leu Ser Val Pro Tyr Asn Thr
        275                 280                 285

Glu Cys Leu Thr Phe Leu Thr Pro Glu Ala Leu Ser Asp Asn Ser Trp
290                 295                 300

Lys Thr Leu Ile Leu Pro Phe Asn Gly Glu Met Trp Ala Gly Val Leu
305                 310                 315                 320

Leu Ser Leu Phe Ala Val Gly Phe Val Phe Tyr Ala Phe Ser Asn Thr
                325                 330                 335

Leu Met Leu Lys Trp Leu Arg His Lys Lys Pro Lys Thr Asn Met Ser
            340                 345                 350

Lys Ser Ser Ala Tyr Asp Arg Asn Lys Leu Lys Leu Arg Met Ile
        355                 360                 365

Pro Phe Lys Arg Gln Pro Glu Pro Trp His Asp Pro Leu Pro Ala Asn
    370                 375                 380

Asp Met Phe Asp Thr Phe Ser Asp Cys Ile Ile Tyr Thr Tyr Ser Met
385                 390                 395                 400

Leu Leu Leu Val Ser Leu Pro Arg Ile Pro Glu Lys Trp Pro Leu Arg
                405                 410                 415

Met Leu Thr Gly Trp Tyr Trp Val Tyr Cys Val Leu Val Val Ala
            420                 425                 430

Tyr Arg Ala Ser Phe Thr Ala Ile Leu Ala Asn Pro Ile Pro Arg Val
        435                 440                 445

Thr Ile Asp Thr Leu Gln Asp Leu Ala Glu Ser Ser Val Arg Cys Gly
    450                 455                 460

Ala Trp Gly Glu Gln Asn Arg Leu Phe Phe Gln Met Ala Gln Asp Gln
465                 470                 475                 480

Tyr Ser Gln Thr Ile Gly Ala Lys Leu Glu His Ala Pro Asn Gln Asn
                485                 490                 495

Glu Ala Val Glu Lys Val Ser Glu Gly Leu Tyr Ala Tyr Glu Asn
            500                 505                 510

Ile Tyr Ser Leu Arg Gln Leu Arg Ser Thr Arg Lys Ser Glu Lys Ala
        515                 520                 525

Arg Gln Thr Leu His Ile Met Gln Glu Cys Ala Val His Met Pro Ile
    530                 535                 540

Ser Ile Gly Leu Gly Lys Asn Ser Pro Leu Lys His Gln Val Asp Leu
545                 550                 555                 560

Tyr Val Arg Ala Leu Ile Glu Gly Gly Leu Thr Arg Lys Trp Leu Ser
                565                 570                 575

Asp Ala Ile Glu Gln Phe Gln Ser Asn Val Glu Ile Pro Pro Gln Glu
            580                 585                 590

Ala Ile Ile Asp Leu Lys Lys Met Tyr Ala Gly Ile Val Ala Leu Cys
        595                 600                 605

Phe Gly Tyr Val Ile Ala Leu Phe Ala Phe Val Val Glu Lys Ile Tyr
    610                 615                 620

Trp Arg Tyr Tyr Ile Glu Asn Asn Pro Ala Phe Asp Lys Tyr Leu His
625                 630                 635                 640

Gly Ile Val Phe Arg Gly Arg Gly
                645
```

<210> SEQ ID NO 50
<211> LENGTH: 747
<212> TYPE: PRT
<213> ORGANISM: Culex quinquefasciatus

<400> SEQUENCE: 50

```
Met Glu Val Val Lys Ile Cys Leu Val Phe Ala Leu Ala Ile Ala Ile
1               5                   10                  15

Ala Ser Ala Ala Leu Asn His Thr Leu Phe Glu Asp Glu Asn Asp Leu
            20                  25                  30

Val Asp Phe Gly Arg Leu Ile Val Asp Leu Val Gly Lys Thr Lys Pro
        35                  40                  45

Gly His Cys Tyr Ala Phe Val Thr Asp Pro Ile Tyr Arg Val Thr Leu
    50                  55                  60

Thr Asp Thr Leu Phe Lys Glu Ile Gly Gly His Pro Arg Phe Val Val
65                  70                  75                  80

Glu Ile Pro Glu Asp Glu Asp Thr Leu Arg Pro Gly Lys Gln Val Arg
                85                  90                  95

Cys Met Leu Glu Glu Ile Arg Lys Ile Gly Cys Gly Ala Tyr Val Val
            100                 105                 110

Leu Ile Ala Asn Gly Ile Gln Met Glu Arg Phe Leu Arg Tyr Gly Asp
        115                 120                 125

Lys Thr Arg Ile Leu Asp Thr Arg Ala Lys Phe Ile Ile Leu Tyr Asp
    130                 135                 140

Tyr Arg Leu Phe Val Pro Glu Leu His Tyr Leu Trp Lys Arg Ile Val
145                 150                 155                 160

Asn Val Val Phe Val Arg Thr Leu Thr Val Glu Asn Ser His Lys Arg
                165                 170                 175

Ser His Phe Glu Leu Ser Thr Val Pro Phe Pro Leu Pro Leu Lys Gly
            180                 185                 190

Val Phe Val Ser Lys Arg Leu Asp Phe Trp His Asn Gly Lys Phe Arg
        195                 200                 205

Tyr Gly Arg Lys Leu Phe Ser Asp Lys Thr Ala Ser Leu Asp Gly Gln
    210                 215                 220

Thr Met Arg Val Val Leu Glu His Thr Pro Ala Ile Phe Arg Thr
225                 230                 235                 240

Thr Leu Asn Glu Thr Ser Gly Glu Arg Arg Gln Arg Ile Lys Tyr Ser
            245                 250                 255

Gly Leu Glu Val Glu Leu Leu Lys Ala Val Ala Gln Ala Met Arg Phe
        260                 265                 270

Glu Met Ser Leu Tyr Glu Thr Glu Asp Ala Gly Thr Glu Lys Trp Gly
    275                 280                 285

Thr Ile Met Glu Asp Asp Asn Ser Thr Gly Leu Leu Gly Asp Met Asn
290                 295                 300

Glu Gly Arg Ala Asp Phe Ala Leu Ala Asp Leu His Tyr Thr Leu Tyr
305                 310                 315                 320

His Leu Gln Ile Met Asp Leu Ser Ile Pro Tyr Asn Thr Glu Cys Leu
            325                 330                 335

Thr Phe Leu Thr Pro Glu Ala Leu Thr Asp Asn Ser Trp Thr Thr Leu
        340                 345                 350

Ile Leu Pro Phe Thr Gly Gly Met Trp Ala Gly Val Leu Val Ser Leu
    355                 360                 365

Phe Ser Ile Gly Thr Val Phe Tyr Ala Leu Ser Arg Leu Met Met Tyr
370                 375                 380

Ile Arg His Glu Lys Ile Tyr Arg Arg Asp Leu Glu Leu Val Ala Lys
385                 390                 395                 400

Arg Lys Lys Val Lys Ser Ala Leu Arg Val Arg Phe Gly Asn Leu Lys
            405                 410                 415
```

```
Phe Leu Ala Val Lys Ile Met Ile Thr Asn Lys Met Lys Thr Ser Lys
                420                 425                 430

Ile Ser Lys Leu Arg Thr Arg Ile Asn His Val Ile Lys Arg Lys Pro
            435                 440                 445

Val Glu Lys Asp Thr Leu Asp Leu Ser Lys Leu Lys Met Leu Lys Met
    450                 455                 460

Val Pro Phe Lys Arg Gln Ala Leu Pro Trp Arg Asp Pro Leu Pro Pro
465                 470                 475                 480

Arg Asp Ile Phe Asp Thr Phe Ser Gly Cys Ile Ile Tyr Thr Tyr Ser
                485                 490                 495

Met Leu Leu Leu Val Ser Leu Pro Arg Leu Pro Lys Gly Trp Pro Leu
                500                 505                 510

Arg Leu Leu Thr Gly Trp Tyr Trp Ile Tyr Cys Ile Leu Leu Val Val
            515                 520                 525

Ala Tyr Arg Ala Ser Leu Thr Ala Ile Leu Ser Lys Pro Val Ala Arg
            530                 535                 540

Leu Thr Ile Asp Lys Leu Lys Asp Leu Ala Glu Ser Pro Ile Arg Cys
545                 550                 555                 560

Gly Ala Trp Gly Glu Gln Asn Arg Leu Phe Phe Gln Thr Ala Gln Asp
                565                 570                 575

Lys Pro Ser Met Ile Ile Gly Gly Lys Leu Glu His Thr Pro Asp Pro
                580                 585                 590

Asp Ala Ala Val Glu Arg Val Arg Gly Asn Phe Ala Tyr Tyr Asp
            595                 600                 605

Asn Val Tyr Ser Leu Lys His Leu Arg Ser Thr Arg Lys Ser Glu Lys
610                 615                 620

Ala Arg Gln Thr Leu His Ile Met Glu Glu Cys Ala Val His Met Pro
625                 630                 635                 640

Ile Ser Ile Gly Leu Glu Lys Asn Ser Pro Leu Lys Pro Lys Val Asp
                645                 650                 655

Lys Tyr Val Arg Ala Leu Val Glu Thr Gly Leu Thr Lys Lys Trp Leu
                660                 665                 670

Ala Asp Ala Ile Glu Ala Phe Gln Ser Asn Val Glu Leu Pro Pro Gln
                675                 680                 685

Glu Ala Thr Met Asp Leu Gln Lys Leu Thr Ala Ala Phe Ile Gly Leu
690                 695                 700

Ala Leu Gly Tyr Gly Ile Ser Leu Leu Ala Phe Gly Val Glu Lys Leu
705                 710                 715                 720

Tyr Trp Lys Cys Val Ile Glu Arg Asp Pro Ala Tyr Asp Lys Tyr Leu
                725                 730                 735

Thr Gly Thr Cys His Arg Arg Val Ile Arg Arg
                740                 745

<210> SEQ ID NO 51
<211> LENGTH: 690
<212> TYPE: PRT
<213> ORGANISM: Bombyx mori
<220> FEATURE:
<221> NAME/KEY: misc_feature
<222> LOCATION: (368)..(368)
<223> OTHER INFORMATION: Xaa can be any naturally occurring amino acid

<400> SEQUENCE: 51

Thr Ile Met Pro Leu Thr Leu Phe Ser Arg Ser Pro Arg Ser Gly Lys
1               5                   10                  15

Thr Arg Ala Val Ser Lys Ala Ser Pro Ile Leu Glu Asp Ile Tyr Glu
```

```
                    20                  25                  30
Gln Lys Asp Leu Glu Phe Val Leu Val Asp Leu Leu Asn His Ala Gly
                35                  40                  45

Arg Tyr His Asp Phe Thr Cys Val Ala Val Ile Cys Asp Ala Ile Tyr
             50                  55                  60

Tyr Asn Val Phe Asp Gly Ala Phe Phe Lys Arg Ile Asp Thr Val Pro
 65                  70                  75                  80

Phe Val Met Ile Val Val Glu Glu Tyr Asp Asp Leu Leu Ser Pro Asn
                 85                  90                  95

Phe Asp Ile Leu Glu Ala Leu Arg Glu Ala Arg Arg Asp Gly Cys Asn
                100                 105                 110

Met Tyr Ile Ile Leu Leu Ala Asn Gly Leu Gln Ala Ala Arg Leu Leu
                115                 120                 125

Lys Phe Gly Asp Arg His Arg Val Leu Asp Thr Arg Ala Lys Tyr Ile
            130                 135                 140

Ile Leu His Asp Tyr Arg Leu Phe His Ser Asp Leu His Tyr Leu Trp
145                 150                 155                 160

Lys Arg Ile Val Asn Val Ile Phe Leu Lys His His Arg Lys Ile Gly
                165                 170                 175

Ser Val Ala Lys Ser Gln Ala Trp Phe Asp Leu Ser Thr Val Pro Phe
                180                 185                 190

Pro Asn Pro Ile Lys Gly Val Phe Val Pro Arg Arg Val Asp Leu Trp
            195                 200                 205

Lys Ser Gly Lys Phe His Tyr Asn Thr Val Pro Phe Asp Asp Lys Thr
        210                 215                 220

Ser Asn Leu Asn Asp Glu Val Leu His Val Val Tyr Leu Asp His Val
225                 230                 235                 240

Pro Ser Val Val Val Asn Ser Asn Glu Thr Gly Gln Ile Gly Gly
                245                 250                 255

Val Glu Ile Glu Ile Ile Asn Thr Leu Ser Glu Lys Met Asn Phe Arg
            260                 265                 270

Pro Lys Leu Tyr Gln Pro Met Asn Val Glu Leu His Lys Trp Gly Gln
        275                 280                 285

Lys Gln Pro Asn Gly Ser Phe Ser Gly Leu Leu Gly Glu Met Val Asn
    290                 295                 300

Gly Arg Ala Asp Leu Ala Leu Gly Asn Leu Gln Tyr Thr Pro Tyr His
305                 310                 315                 320

Leu Glu Leu Ile Asp Leu Ser Ile Pro Tyr Thr Ser Gln Cys Trp Thr
                325                 330                 335

Phe Leu Thr Pro Glu Ala Leu Thr Asp Asn Ser Trp Lys Thr Leu Leu
            340                 345                 350

Leu Pro Phe Lys Leu Tyr Met Trp Ile Ala Val Leu Leu Val Leu Xaa
        355                 360                 365

Ile Thr Gly Thr Ile Phe Tyr Gly Leu Ala Arg Tyr Gln Thr Tyr Leu
    370                 375                 380

His Gly Leu Lys Arg Gln Glu Glu Met Lys Lys Pro Val Tyr Ser Lys
385                 390                 395                 400

Pro Val Gly Leu Tyr Leu Phe Gly Glu Ile Ile Asn Ser Ile Leu Tyr
                405                 410                 415

Thr Tyr Gly Met Leu Leu Val Val Ser Leu Pro Lys Leu Pro Thr Gly
            420                 425                 430

Trp Ser Ile Arg Phe Leu Thr Gly Trp Tyr Trp Leu Tyr Cys Ile Leu
        435                 440                 445
```

```
Leu Val Val Ser Tyr Arg Ala Ser Met Thr Ala Ile Leu Ala Asn Pro
        450                 455                 460

Ala Pro Arg Val Thr Ile Asp Thr Leu Val Glu Leu Ala Ala Ser Lys
465                 470                 475                 480

Leu Thr Cys Gly Gly Trp Gly Ile Glu Thr Lys Asn Phe Phe Gln Asp
                485                 490                 495

Ser Leu Asp Glu Ile Gly Gln Lys Ile Ser Asp Arg Phe Glu Ile Ser
                500                 505                 510

Asn Asp Pro Asn Ile Ala Ala Asp Lys Val Ala Gln Gly Thr Phe Ala
                515                 520                 525

Tyr Tyr Asp Asn Lys Asn Phe Leu Lys Tyr Ile Thr Val Arg Arg Gln
        530                 535                 540

Asn Gly Phe Ile Met Glu Thr Ile Asp Asn Thr Thr Asn Phe Thr Ser
545                 550                 555                 560

Ile Ser Thr Lys Ser Asn Asn Glu Arg Asn Leu His Ile Met Ser Asp
                565                 570                 575

Cys Val Val Asn Ile Pro Ile Ser Ile Gly Phe His Lys Asn Ser Pro
                580                 585                 590

Leu Lys Pro Leu Thr Asp Ile Tyr Ile Thr Arg Ile Val Glu Val Gly
        595                 600                 605

Leu Val Glu Lys Trp Leu Asn Asp Ala Met Tyr Thr Ile Lys Thr Leu
610                 615                 620

Glu Thr Asn Glu Glu Glu Ile Lys Ala Leu Met Asn Leu Lys Lys Leu
625                 630                 635                 640

Tyr Gly Ala Phe Ile Ala Leu Ala Ile Gly Tyr Phe Leu Ser Val Met
                645                 650                 655

Cys Leu Ile Gly Glu Leu Ala His Trp Asn Cys Val Lys Lys Asp
                660                 665                 670

Pro Asn Tyr Asp Lys Tyr Ala Leu His Lys Tyr Glu Lys Ile Asn
        675                 680                 685

Lys Lys
    690

<210> SEQ ID NO 52
<211> LENGTH: 694
<212> TYPE: PRT
<213> ORGANISM: Danaus plexippus

<400> SEQUENCE: 52

Ser Val Met Ser Tyr Pro Gly Ala Met Ser Arg Pro Arg Trp Trp Lys
1               5                   10                  15

Asp Val Val Phe Trp Glu Ser Tyr Val Gln Thr Arg Ala Asp Thr Ser
                20                  25                  30

Arg Ile Ile Lys Asn Ile Glu Ile Ser Lys Asp Leu Gln Asp Leu Val
        35                  40                  45

Ala Asp Leu Ile Asn Tyr Leu Val Arg Arg Asp Val Thr Cys Leu
    50                  55                  60

Thr Val Val Ser Asp Pro Val Tyr Leu Asn Val Phe Glu Gly Ala Leu
65                  70                  75                  80

Phe Lys Gly Ile Tyr Thr Val Pro Asn Ile Met Ile Val Val Glu Glu
                85                  90                  95

Arg Glu Asp Leu Leu Ser Pro Asn Phe Asn Thr Leu Glu Ser Leu Arg
                100                 105                 110

Gln Ala Arg Asn Asp Gly Cys Asn Val Tyr Leu Ile Ile Leu Ala Asn
```

```
                115                 120                 125
Gly Leu Gln Val Thr Arg Leu Leu Lys Phe Gly Tyr Lys His Arg Leu
130                 135                 140

Leu Asp Thr Arg Ala Lys Tyr Ile Met Leu His Asp Val Arg Leu Phe
145                 150                 155                 160

His Ser Ala Asn His Tyr Leu Trp Lys Ser Ile Val Asn Val Ile Phe
                165                 170                 175

Leu Lys Tyr His Ser Lys Val Ile Gly Asp Val Lys Ser Lys Ala Trp
                180                 185                 190

Phe Asp Leu Ser Thr Val Pro Phe Pro Asn Ile Ile Lys Glu Ile Phe
                195                 200                 205

Ile Pro Arg Arg Val Asp Ile Trp Arg Arg Asn Lys Phe His Tyr Gly
210                 215                 220

Arg Asp Leu Phe Ala Asp Lys Thr Gly Asn Leu Tyr Asp Glu Val Leu
225                 230                 235                 240

Asn Val Val Tyr Val Asp His Val Pro Ser Val Val Thr Lys Ser
                245                 250                 255

Asn Ala Thr Asn Lys Val Gly Val Glu Ile Glu Ile Leu Lys Thr
                260                 265                 270

Leu Ala Gln Lys Met His Phe Lys Pro Lys Leu Tyr Glu Pro Ile Asn
                275                 280                 285

Ala Glu Ser Gln Lys Trp Gly His Lys Gln Asp Asn Gly Ser Phe Ser
290                 295                 300

Gly Leu Leu Gly Glu Met Val Asn Ser Gly Ala Asp Val Ala Leu Gly
305                 310                 315                 320

Asn Leu Gln Tyr Thr Pro Ser His Leu Glu Met Thr Asp Leu Ser Ile
                325                 330                 335

Pro Tyr Thr Ser Gln Cys Trp Thr Phe Leu Thr Pro Glu Ala Leu Thr
                340                 345                 350

Asp Asn Ser Trp Lys Thr Leu Ile Leu Pro Phe Lys Leu Asn Met Trp
                355                 360                 365

Ile Ala Val Leu Leu Val Leu Leu Val Thr Gly Ser Ile Phe Tyr Gly
370                 375                 380

Leu Ala Ile Tyr Tyr Met Asn Leu Leu Asn Tyr Lys Gly Val Ser Glu
385                 390                 395                 400

Gly Phe Glu Ala Asn Asp Arg Lys Met Ser Tyr Thr Lys Pro Val Gly
                405                 410                 415

Leu Tyr Leu Phe Gly Glu Ile Ser Asn Ser Ile Leu Tyr Thr Tyr Gly
                420                 425                 430

Met Leu Val Val Ser Leu Pro Lys Leu Pro Thr Gly Trp Ser Ile
                435                 440                 445

Arg Leu Leu Thr Gly Trp Tyr Trp Leu Tyr Cys Ile Leu Leu Val Val
450                 455                 460

Ser Tyr Arg Ala Ser Met Thr Ala Ile Leu Ala Asn Pro Thr Pro Arg
465                 470                 475                 480

Val Thr Ile Asp Thr Leu Gln Glu Leu Val Asp Ser Lys Ile Ala Cys
                485                 490                 495

Gly Gly Trp Gly Ser Glu Thr Lys Asn Phe Phe Leu Gly Ser Leu Asp
                500                 505                 510

Glu Met Gly Gln Lys Ile Gly Glu Met Phe Glu Asn Val Asp Asp Pro
                515                 520                 525

Glu Gln Ala Thr Asn Lys Ile Ala Gln Gly Ile Phe Ala Tyr Tyr Asp
530                 535                 540
```

```
Ser Glu Asn Phe Leu Lys His Leu Thr Val Lys Arg Lys Asn Met Val
545                 550                 555                 560

Leu Met Thr Ser Pro Glu Asn Asn Thr Arg Asp Arg Asn Leu His Ile
                565                 570                 575

Met Lys Asp Cys Val Val Asn Ile Pro Ile Ser Ile Gly Phe His Lys
            580                 585                 590

Asn Ser Pro Leu Lys Pro Leu Ala Asp Val Tyr Leu Arg Arg Ile Val
        595                 600                 605

Glu Val Gly Leu Val Glu Lys Trp Leu Asn Asp Ala Met Tyr Lys Ile
    610                 615                 620

Arg Thr Arg Glu Lys Asn Glu Glu Val Lys Ala Leu Ile Asn Leu
625                 630                 635                 640

Lys Lys Leu Tyr Cys Ala Phe Val Ala Leu Ser Ile Gly Tyr Thr Leu
                645                 650                 655

Ser Ser Ile Cys Leu Phe Leu Glu Phe Met His Trp His Phe Val Val
            660                 665                 670

Lys Arg Asp Pro Gly Phe Asp Lys Tyr Ala Met Asn Glu Tyr Tyr Met
        675                 680                 685

His Lys Asn Lys Lys Lys
    690

<210> SEQ ID NO 53
<211> LENGTH: 690
<212> TYPE: PRT
<213> ORGANISM: Tribolium castaneum

<400> SEQUENCE: 53

Met Ile Lys Asn Leu Leu Pro Tyr Lys Cys Val Leu Ile Ser Asp
1               5                   10                  15

Asp Ile Tyr Gly Gly Thr Phe Thr Lys Ser Trp Tyr Arg Arg Phe Gly
                20                  25                  30

Pro Phe Ile Thr Phe Val Val Ile Arg Val Asp Glu Tyr Glu Asp Leu
                35                  40                  45

Leu Ser Pro Phe Glu Glu Thr Gln Ala Cys Leu Asp Thr Ala Lys Asn
50                  55                  60

Glu Gly Cys Gln Met Tyr Leu Ile Leu Ser Asn Ala Leu Gln Val
65                  70                  75                  80

Ser Arg Leu Leu Arg Phe Gly Asp Lys Tyr Arg Val Ile Asn Thr Arg
                85                  90                  95

Ala Lys Phe Val Leu Leu Tyr Asp Asn Arg Leu Phe Asp Lys Pro Leu
                100                 105                 110

Phe Tyr Leu Trp Lys Arg Ile Ile Asn Val Ile Phe Ile Arg Arg Tyr
            115                 120                 125

Ser Gly Gln Lys Ser Asp Thr Lys Lys Asn Met Pro Trp Tyr Glu Ile
130                 135                 140

Thr Thr Val Pro Phe Pro Thr Gln Ile Thr Ser Ile Leu Ile Pro Arg
145                 150                 155                 160

Arg Leu Asp Ile Trp Thr Lys Ser Lys Phe Arg Lys Gly Ile Asp Leu
                165                 170                 175

Phe Arg Asp Lys Thr Ser Asp Leu Arg Asn Gln Thr Leu Lys Val Ala
            180                 185                 190

Ala Phe Ser His Ile Pro Gly Thr Thr Lys Ser Leu Gln Glu Lys Thr
            195                 200                 205

Ala Arg Thr Val Ile Gly Asn Phe Ser Gly Thr Glu Val Glu Ile Leu
```

```
                210                 215                 220
Gln Thr Val Ser Ala Ala Met Asn Phe His Cys Glu Leu Tyr Glu Pro
225                 230                 235                 240

Val Asn Val Asp Val Asp Leu Trp Gly Gly Lys Gln Ser Ser Gly Lys
                245                 250                 255

Tyr Thr Gly Leu Val Gly Glu Met Val Ser Thr Asn Ala Asp Ile Ala
                260                 265                 270

Leu Gly Asp Leu Tyr Tyr Thr Pro Tyr Ile Leu Asp Leu Met Asp Leu
                275                 280                 285

Ser Ile Pro Tyr Asn Thr Glu Cys Leu Thr Phe Leu Thr Pro Glu Ser
290                 295                 300

Leu Thr Asp Asn Ser Trp Lys Thr Leu Ile Leu Pro Phe Lys Tyr Phe
305                 310                 315                 320

Arg Pro Ala Met Trp Ala Ala Val Leu Val Cys Leu Leu Ile Cys Gly
                325                 330                 335

Ala Val Phe His Ala Leu Ala Arg Phe His Glu Thr Ile Ser Gln Asn
                340                 345                 350

Lys Ser Gln Val Leu Glu Ile His Thr Lys Arg Lys Ile Ile Ile
                355                 360                 365

Leu Ser Ile Cys Pro Glu Ile Glu Lys Leu Asp Ser Asn Leu Lys Tyr
370                 375                 380

Thr Lys Met Arg Glu Gln Tyr Lys Pro Pro Arg Phe Glu Gly Gln Ser
385                 390                 395                 400

Ile Gly Leu Tyr Gln Phe Ser Glu Pro Phe Asn Ser Val Leu Tyr Thr
                405                 410                 415

Tyr Ser Met Leu Leu Leu Val Ser Leu Pro Lys Leu Pro Thr Gly Trp
                420                 425                 430

Ser Leu Arg Met Leu Thr Gly Trp Tyr Trp Leu Tyr Cys Leu Leu Leu
                435                 440                 445

Val Val Ala Tyr Arg Ala Ser Met Thr Ala Ile Leu Ala Arg Pro Thr
450                 455                 460

Pro Arg Val Thr Ile Asp Thr Leu Gln Glu Leu Val Asn Ser Arg Leu
465                 470                 475                 480

Lys Cys Gly Gly Trp Gly Glu Ile Asn Arg Gln Phe Phe Lys Ser Ser
                485                 490                 495

Leu Asp Pro Ile Thr Lys Leu Ile Gly Glu Asn Phe Glu Leu Val Asn
                500                 505                 510

Asp Ser Asn Glu Ala Val Asp Arg Val Ala Gln Gly Val Phe Ala Phe
                515                 520                 525

Tyr Glu Asn Ser Tyr Tyr Leu Lys Glu Ala Leu Val Lys Arg Gln Leu
                530                 535                 540

Arg Phe Gln Ile Ala Arg Thr Thr Gln Asn Gln Ser Glu Arg Glu Met
545                 550                 555                 560

Arg Asp Ile Ala Arg Glu Asp Arg Asn Leu His Ile Met Thr Asp Cys
                565                 570                 575

Val Ile Lys Met Pro Ile Ser Ile Gly Leu Gln Lys Asn Ser Pro Ile
                580                 585                 590

Lys Pro Arg Val Asp Lys Tyr Ile Arg Arg Val Leu Glu Ala Gly Leu
                595                 600                 605

Ile Lys Lys Trp Leu Gln Asp Val Met Ala Ser Ile Leu Asn Ala Glu
                610                 615                 620

Val Gln Ser Thr Gln Glu Glu Met Lys Ala Ile Met Asn Met Lys Lys
625                 630                 635                 640
```

```
Phe Phe Gly Ala Ile Val Ala Leu Phe Ile Gly Tyr Phe Ile Ser Val
                645                 650                 655

Val Val Leu Ile Val Glu Asn Val Tyr Phe His Phe Val Lys Arg
            660                 665                 670

Asn Pro His Tyr Asn Lys Tyr Thr Arg Ser Ile His Val Lys Lys
        675                 680                 685

Ala Glu
    690

<210> SEQ ID NO 54
<211> LENGTH: 699
<212> TYPE: PRT
<213> ORGANISM: Nasonia vitripennis

<400> SEQUENCE: 54

Met Tyr Phe Leu Ile Val Leu Ile Ile Cys Leu Gly Thr Ser Leu Ser
1               5                   10                  15

Val Thr Asp Asn Arg Arg Leu Ile Tyr Pro Ala Ser Asn Lys Gln Leu
            20                  25                  30

Gln Thr Leu Val Lys Leu Leu Ile Glu Glu Val Ala Glu Asn Ser Arg
        35                  40                  45

Cys Ile Val Ser Met Val Asp Thr Tyr Tyr Arg Arg Lys Val Asp Ile
    50                  55                  60

Ser Gln Ile Lys Ala Asn Lys Phe Leu Pro Thr Tyr Arg Val Leu Ile
65                  70                  75                  80

Arg Glu Asn Glu Glu Phe Ser Pro Pro Arg Arg Arg Leu Leu Arg Ile
                85                  90                  95

Leu Lys Glu Ser Lys His Leu Gly Cys Asp Val Tyr Leu Ile Met Met
            100                 105                 110

Ala Asn Gly Leu Gln Val Ala Ser Leu Leu Arg Tyr Ala Glu Glu Glu
        115                 120                 125

Arg Leu Met Asn Val Gln Gly Lys Phe Leu Phe Val Tyr Asp Phe Arg
    130                 135                 140

Ile Phe His Val Glu Met Leu Tyr Leu Trp Asn Arg Ile Ile Asn Val
145                 150                 155                 160

Ile Phe Ile Arg Arg Tyr Val Glu Phe Lys Arg Arg Ser Ser Asn Arg
                165                 170                 175

Gln Leu Gln Lys Tyr Glu Trp Tyr Asp Leu Asn Thr Ile Pro Phe Pro
            180                 185                 190

Ala Arg Lys Lys Gly Leu Ile Val Thr Arg Tyr Ile Asp Thr Trp Tyr
        195                 200                 205

Gln Asn Arg Phe Arg Tyr Gly Ile Asn His Phe Thr Ala Lys Thr Asp
    210                 215                 220

Asp Leu Arg Arg Gln Lys Leu Gln Val Ala Val Phe Glu His Val Pro
225                 230                 235                 240

Ala Val Thr Glu Asp Ala Gln Ala Tyr Tyr Lys Ser Gln Lys Asp Val
                245                 250                 255

Gly Ser Asn Ser Lys Pro Leu Gly Ile Glu Phe Glu Met Ile Leu Ile
            260                 265                 270

Ile Ala Asn Ala Leu Asn Phe Lys Pro Tyr Phe Tyr Gln Pro Asp Asn
        275                 280                 285

Ile Gln Thr Glu Arg Trp Gly Asp Ser Lys Asn Asp Thr Tyr Thr Gly
    290                 295                 300

Leu Phe Gly Glu Ala Lys Glu Gly Lys Ala Val Phe Tyr Leu Gly Asp
```

```
            305                 310                 315                 320
Leu His Tyr Thr Ser Arg His Ile Gln Ile Leu Asp Leu Ser Trp Pro
                325                 330                 335

Tyr Asn Thr Glu Cys Leu Thr Phe Leu Thr Leu Glu Ser Leu Thr Glu
                340                 345                 350

Asn Ser Trp Lys Leu Leu Ile Leu Pro Phe Arg Leu Asn Thr Trp Leu
                355                 360                 365

Ala Val Leu Phe Thr Leu Val Phe Ala Cys Ala Thr Ser Phe Val Phe
                370                 375                 380

Ser Arg Phe Tyr Met Arg His Val Asn Val Gly Glu Asn Asn Asp Ser
385                 390                 395                 400

Asp Ala Arg Lys Val Phe Ser Lys Ser Lys Thr Met Lys Val Leu Glu
                405                 410                 415

Lys Arg Pro Val Gln Ala Glu Glu Trp Lys Gly Leu Tyr Leu Phe Thr
                420                 425                 430

Asp Pro Gln Asn Ser Val Leu Tyr Thr Tyr Ser Met Leu Leu Gln Val
                435                 440                 445

Ser Leu Pro Ser Leu Pro Arg Ala Trp Ser Leu Arg Val Phe Ile Gly
                450                 455                 460

Trp Trp Trp Ile Phe Ser Ile Leu Ile Ala Val Thr Tyr Arg Ala Ser
465                 470                 475                 480

Met Thr Ala Thr Leu Ala Asn Ala Ile Asp Arg Val Thr Ile Asp Thr
                485                 490                 495

Ile Pro Glu Leu Gly Lys Ser Asn Val Ala Val Gly Ser Trp Asn Asp
                500                 505                 510

Glu Thr Arg Glu Phe Phe Ile Asn Ser Ser Asp Pro Tyr Leu Gln Lys
                515                 520                 525

Leu Ser Arg Arg Tyr Val Val Thr Lys Asp Glu Gln Ser Ala Leu Ala
                530                 535                 540

Ala Val Ala Asn Gly Thr Leu Cys Tyr Tyr Glu Asn Val Tyr Val Leu
545                 550                 555                 560

Gln Arg Glu Arg Val Lys Arg Gln Ile Leu Glu Asp Glu Leu Gln Lys
                565                 570                 575

Asn Gly Ser Gln Gly Lys His Lys Phe Gln Asp His Asn Leu His Ile
                580                 585                 590

Met Glu Glu Cys Val Val Asn Met Pro Ile Ser Leu Gly Met Asp Lys
                595                 600                 605

His Ser Pro Leu Lys His His Val Asp Lys Leu Val Lys Arg Ile Ile
610                 615                 620

Glu Ala Gly Phe Val Glu Lys Trp Leu Ser Asp Ile Thr Gln Gln Ser
625                 630                 635                 640

Lys Ile Leu Glu Leu Arg Gly Glu Gly Ile Ala Asp Lys Ala Leu Ile
                645                 650                 655

Asp Leu Asp Lys Leu Gln Gly Ala Val Val Ala Leu Gly Ile Gly Tyr
                660                 665                 670

Leu Phe Ser Leu Leu Ala Leu Ala Ala Glu Thr Trp His Trp Arg Tyr
                675                 680                 685

Ile Val Met Arg His Pro Asn Phe Asn Lys Tyr
                690                 695

<210> SEQ ID NO 55
<211> LENGTH: 658
<212> TYPE: PRT
<213> ORGANISM: Apis mellifera
```

-continued

<400> SEQUENCE: 55

```
Ser Tyr Lys Glu Ile Lys Trp Asn Ser Glu Phe Glu Asn Leu Ala Val
1               5                   10                  15

Asp Ile Thr Tyr Lys Trp Lys Asp Thr Ala Thr Cys Leu Asn Leu Ile
            20                  25                  30

Leu Asp Asn Phe His Asn Gly Ile Leu Asp Lys Ala Phe Tyr Arg Ala
        35                  40                  45

Val Ser Gly Ile Pro Leu Phe Lys Thr Leu Val Asp Glu Ser Glu Asp
    50                  55                  60

Leu Met Ser Pro Asn Phe Gln Thr Trp Gln Ile Leu Asn His Val Arg
65                  70                  75                  80

Lys Glu Gly Cys Asn Met Asn Ile Ile Phe Ile Leu Asn Ala Asp Gln
                85                  90                  95

Thr Met Arg Leu Leu Lys Phe Ser Asp Lys His Arg Met Leu Asp Ser
            100                 105                 110

Arg Thr Lys Phe Ile Leu Leu His Asp Arg Arg Leu Phe Thr Lys Gln
        115                 120                 125

His His Thr Ile Trp Thr Lys Ile Ile Asn Val Val Phe Ile Arg Lys
    130                 135                 140

Tyr Arg Leu Lys Asp Met Tyr Glu Leu Ser Thr Val Pro Tyr Pro Ala
145                 150                 155                 160

Pro Ile Lys Gly Ala Leu Val Thr Leu Arg Leu Asp Ile Trp Asn Lys
                165                 170                 175

Arg Asn Phe Gln Lys Lys Thr Asp Leu Tyr Thr Asp Lys Val Ser Asp
            180                 185                 190

Leu Gln Gly Asn Leu Leu Lys Val Val Thr Phe Asn Tyr Ile Pro Ser
        195                 200                 205

Ala Ile Lys Asn Ser Val Ile Asn Glu Asn Glu Asn Ser Gly Tyr
    210                 215                 220

Lys Lys Gly Leu Glu Ile Glu Val Leu Lys Ser Leu Gly Ser Ala Met
225                 230                 235                 240

Asn Phe Ile Pro Val Ile Tyr Glu Pro Ile Asn Trp Arg Thr Glu Gln
                245                 250                 255

Trp Gly Lys Lys Gln Ile Asn Gly Thr Ile Ser Gly Leu Leu Gly Glu
            260                 265                 270

Val Trp Ser Ala Arg Ala Asp Leu Ala Leu Gly Asn Leu His Tyr Thr
        275                 280                 285

Pro Tyr His Leu Asn Ile Leu Asp Leu Ser Ile Pro Tyr Asn Thr Glu
    290                 295                 300

Cys Leu Thr Phe Leu Thr Phe Glu Ser Lys Thr Asp Asn Ser Trp Lys
305                 310                 315                 320

Thr Leu Ile Leu Pro Phe Arg Leu Asn Met Trp Val Gly Val Leu Ile
                325                 330                 335

Thr Leu Leu Ile Gly Gly Phe Leu Phe Tyr Ala Leu Ala Thr Ala His
            340                 345                 350

Lys His Ile Glu Asp Ser Glu Asn Ser Ile Lys Met Ile Gln Cys Asp
        355                 360                 365

Thr Met Lys Thr Lys Ile Leu Glu Lys Lys Pro Glu Leu Leu Thr Lys
    370                 375                 380

Asn Lys Gly Ile Thr Lys Arg Asn Ser Ile Leu Tyr Thr Phe Gly Met
385                 390                 395                 400

Leu Val Ala Val Ser Leu Pro Lys Val Pro Ser Gly Trp Ala Ile Arg
```

```
            405                 410                 415
Ile Leu Thr Gly Trp Trp Trp Met Tyr Cys Leu Leu Val Val Val Ala
        420                 425                 430

Tyr Lys Ala Ser Met Thr Ala Ile Leu Ala Asn Pro Asp Thr Arg Val
        435                 440                 445

Thr Ile Asp Thr Leu Asp Ala Leu Ala Asp Ser Asn Ile Asn Cys Gly
        450                 455                 460

Gly Trp Gly Glu Gln Ser Lys Glu Phe Phe Met Thr Ser Leu Asp Lys
465                 470                 475                 480

Thr Gly Gln Arg Val Gly Gln Lys Phe Gln Glu Val Tyr Glu Val Asp
                485                 490                 495

Lys Ala Ile Asp Leu Val Ser Lys Gly Gln Phe Ala Tyr Tyr Asp Asn
                500                 505                 510

Ile His Phe Leu Arg Tyr Val Lys Val Met Gln Asn Thr Lys Thr Tyr
                515                 520                 525

Glu Lys Asn Ser Gln Phe Ile Asn Asp Phe Thr Leu His Ile Met Ser
        530                 535                 540

Lys Cys Ile Ile Asn Met Pro Ile Ser Leu Gly Leu Gln Lys Asn Ser
545                 550                 555                 560

Pro Leu Lys Pro Ala Val Asp Arg Phe Leu Arg Val Ile Glu Ala
                565                 570                 575

Gly Leu Val Lys Lys Trp Leu Asn Asp Val Met Leu Asp Thr Val Ile
                580                 585                 590

Leu Glu Glu Pro Gln Gln Ile Glu Glu Val Lys Ala Leu Met Asp Leu
        595                 600                 605

Lys Lys Leu Tyr Gly Ala Phe Val Leu Val Ala Gly Tyr Ile Leu
        610                 615                 620

Ser Ile Leu Val Leu Leu Ile Glu Ile Gly Tyr Trp Tyr Gly Val Val
625                 630                 635                 640

Lys Lys Asp Pro Leu Phe Asp Glu Tyr Ser Leu Asn Cys Tyr Ala
                645                 650                 655

Gln Gln

<210> SEQ ID NO 56
<211> LENGTH: 681
<212> TYPE: PRT
<213> ORGANISM: Zooternopsis nevadensis

<400> SEQUENCE: 56

Met Leu Ser Asp Leu Asn Cys Leu Val Ile Met Asn Asp Asn Ile Gln
1               5                   10                  15

Gln Asp Ile Phe Glu Gly His Phe Phe Lys Lys Leu Gly Ser Val Pro
            20                  25                  30

Tyr Tyr Lys Val Leu Val Lys Glu Lys Glu Asp Leu Gln Ser Pro Asn
        35                  40                  45

Tyr Lys Thr Leu Ser Val Ile Arg His Val Lys Arg Ala Gly Cys Gln
    50                  55                  60

Val Tyr Ile Leu Met Ile Ser Asn Gly Gly Lys Val Ser Arg Phe Leu
65              70                  75                  80

Lys Phe Gly Asp Arg His Arg Val Leu Asp Thr Arg Ala Lys Phe Ile
            85                  90                  95

Leu Leu His Asp His Arg Leu Phe His Ser Ser Leu Tyr Leu Trp
        100                 105                 110

Arg Lys Ile Val Asn Val Val Phe Leu His Gln Gln Gly Arg His His
```

```
            115                 120                 125
Gly Ser Val Ile Thr Arg Gln Lys Ile His Pro Trp Tyr Asp Ile Ser
130                 135                 140
Thr Val Pro Phe Pro Ser Pro Ile Asp Ser Thr Phe Val Pro Leu His
145                 150                 155                 160
Leu Asp Thr Trp His Gln Gly Lys Phe Arg Ser Gly Ala Asp Leu Phe
                    165                 170                 175
Arg Lys Lys Thr Ser Asp Leu Arg Gly Gln Gln Leu Arg Val Val Thr
                180                 185                 190
Phe Gln His Leu Pro Ala Ser Val Lys Met Ala Ser Pro Ser Leu Arg
            195                 200                 205
Ile Asp Ser Val Val Glu Gly Asn Gly Pro Val Gly Phe Gly Gly Leu
210                 215                 220
Glu Ile Glu Val Leu Arg Thr Leu Ala Thr Val Met Asn Phe His Pro
225                 230                 235                 240
Asp Val Tyr Glu Ala Glu Asn Ala Asp Val Glu Gln Trp Gly Arg Arg
                245                 250                 255
Gln Leu Asn Gly Ser Tyr Ser Gly Leu Leu Gly Glu Val Met Ser Gly
                260                 265                 270
Gln Ala Asp Ile Ala Leu Gly Asn Leu Tyr Tyr Thr Pro Tyr Tyr Leu
            275                 280                 285
Glu Leu Ile Asp Leu Thr Ile Pro Tyr Thr Thr Glu Cys Leu Thr Phe
290                 295                 300
Leu Thr Pro Glu Ser Leu Thr Asn Asn Ser Trp Met Thr Leu Ile Leu
305                 310                 315                 320
Pro Phe Arg Pro Leu Met Trp Ala Ala Val Phe Val Ala Leu Ile Leu
                325                 330                 335
Ala Gly Phe Val Phe Tyr Ala Leu Ala Asn Tyr His Ile His Ile Val
                340                 345                 350
Ser Thr Ala Met Asn Leu Gln Thr Asn Asn Ala Ile Met Val Gln Glu
            355                 360                 365
Arg Ser Lys Ile Asn Asp Ser Lys Val Ile His Ile Gln Glu Glu Arg
370                 375                 380
Asn Lys Thr Gly Asp Gly Leu Tyr Leu Phe Ser Lys Leu Glu Asn Gly
385                 390                 395                 400
Ile Leu Tyr Thr Tyr Gly Met Leu Leu Ile Ser Leu Pro Lys Phe
                405                 410                 415
Pro Ser Asp Trp Ser Leu Arg Val Leu Thr Gly Trp Trp Ile Tyr
                420                 425                 430
Cys Ile Leu Leu Val Val Ala Tyr Arg Ala Ser Met Thr Ala Ile Leu
            435                 440                 445
Ala Asn Pro Thr Pro Arg Val Thr Ile Asp Thr Met Glu Gln Leu Val
            450                 455                 460
Asp Asn His Ile Thr Cys Gly Gly Trp Gly Glu Glu Ile Lys Gln Phe
465                 470                 475                 480
Phe Leu Thr Ser Leu Asp Ile Ser Gly Gln Lys Ile Gly Leu Lys Phe
                485                 490                 495
Glu Val Ile Tyr Asp Thr Asp Leu Ala Val Lys Val Ala Lys Gly
                500                 505                 510
Glu Phe Ala Tyr Tyr Glu Asn Ile Tyr Phe Leu Gln Tyr Leu Arg Val
            515                 520                 525
Arg Arg Gln Leu Ile Val Lys Glu Val Gly Thr Lys Lys Asp Val Asn
530                 535                 540
```

```
Thr Asn Glu Glu Ser Gly Gly Asn Arg Asn Leu His Ile Met His Asp
545                 550                 555                 560

Cys Val Ile His Met Pro Val Ser Ile Gly Leu Gln Lys Asn Ser Pro
            565                 570                 575

Leu Lys Pro His Met Asp Arg Phe Leu Arg Arg Ile Val Glu Ala Gly
        580                 585                 590

Leu Ile Lys Lys Trp Leu Lys Asp Val Met Leu Ser Ile Val Ser Val
        595                 600                 605

Asp Asn Thr Asp Lys Glu Asp Gly Asn Lys Pro Leu Met Asn Leu Gln
        610                 615                 620

Lys Leu Tyr Gly Ala Phe Val Ala Leu Gly Val Gly Tyr Leu Ile Ser
625                 630                 635                 640

Ile Cys Ala Phe Ala Gly Glu Lys Ile His Trp Gln Cys Val Val Lys
            645                 650                 655

Lys Ser Pro Leu Phe Asp Lys Tyr Ala Ile Asn Ile Tyr Tyr Asp His
        660                 665                 670

Gln Lys Ser Ser Lys Ala Ile Lys Lys
        675                 680
```

<210> SEQ ID NO 57
<211> LENGTH: 2443
<212> TYPE: DNA
<213> ORGANISM: Drosophila melanogaster

<400> SEQUENCE: 57

```
cattatctgg ttaaacttat taacccctgg gccgcaaaac tttaattagt taaccctgtg      60
cccgctggaa actcggaatg cgagtaaatc aggttgatga gtgactgact gactggctgg    120
ctgactaacc gacagtccgt tggctaccgg ttcacggagt tcggacaact ttaattagat    180
ctgcatatgc aatgaggact cgagggttcg ttccggtaaa caggttaacg aactgccgga    240
acggacaagt ggccaacagt ttgcgtttgg cggcgaaagg atgcgctgtc tgtggattct    300
gattgtggct ttcatatccc tggcgatggc cacctcaatt cccattccca ttgccaaccc    360
agcaccactc agtggatatg agatgcaact gaaatattg ctacagaaaa tcctgtgggt      420
ggccaatgtg aagagatgct ttgccgtcat tacggatgat ctgcattatc ccatatacga    480
tcgaatattt ttcgaatcgg tgggtcgacg agtgataccc ttctttgtga tgcgaactaa    540
tgaaagtgat gatctacagc gaccttccag acaagttgaa ctctttgtta aggccatcaa    600
atccagtgat tgtgaactaa atgtgatcac catactgaat ggctggcagg tccaacgatt    660
tcttggctat atatacgata acagatcttt gaatatgcag aaaaagtttg tattattaca    720
tgatttgcga cttttttgaga gcgatatgat tcacctatgg agcgttttta tcgatgccat    780
tttcctcaaa aggcagctgg acaacaagta taccatttct accatagcct ttccgggcat    840
tttaagtggc gttttggtaa tgaaaaatat tgctaattgg gagttgggaa aaggtctgaa    900
tggaaggatt ctatttgcgg acaaaacaag caacttattc ggaacctctt tgccagttgc    960
catttccgag cacgtgccca tggttctatg ggcaaatgca accaagagct tccaaggagt   1020
cgaggttgag attatgaatg ccctgggcaa ggcacttaat ttcaagcccg tttactacaa   1080
gcccaatcaa acggagaata tggactggac ggagctggat ggtggtgcta tgttgcctta   1140
tggaagtggt aatccggatg gatatgcaca gaatgggaca cacattgact cgatgcttgt   1200
ggatgaggtg gctgcgcaca gtgcccgctt tgccattggg gatttgcatc tgttccaggt   1260
gtaccttaaa ttagtggagc taagtgcgcc gcataatttc gaatgcctga cctttctcac   1320
```

```
accggaatcg tcgacggata actcctggca gacctttatc ctgcccttca gcgctggaat   1380
gtgggtgggg gtgctgctct ccctttttcgt ggtgggcact gttttctatg ccatcagttt   1440
tttgaatgcc attatcaacg gcaatgtgtc ctctgagttt tttcgttgcc tacgaccaaa   1500
tcgcaacgtg cccatggatc caaagatcta tcgtcgcatt agttttcgca ttgccatcag   1560
tcggtatcgt tcatctaaag gagatcgaat gcctcgcgat cttttcgatg ctataccaa    1620 ctgcatcctg ctcacgtata gtatgctcct atatgtggcc ctaccccgaa tgcctcgaaa   1680
ttggcccctg agggtactca ctggttggta ctggatctac tgcatcctct tggtggccac   1740
atatagggcc agcttcactg ccattttggc caatccagct gccagggtca ctatagacac   1800
actggaggat ctgctgcgat ctcatatacc gccatccacc ggggcaactg agaatagaca   1860 gttttttcctg gaggccaatg atgaggttgc tcgaaaagtt ggcgaaaaga tggaggtgtt   1920
cggctacagc gatgatttga cctctcgcat agccaaggga cagtgcgcct actacgacaa   1980
cgagttctat ctgcgctact tacgagtggc agacgaatcc ggatcagctc tccacatcat   2040
gaaggaatgt gtcctctata tgcccgtagt gctggccatg gagaagaact cggctctgaa   2100
gccacgggta gatgcctcca ttcaacatct ggcggagggt ggtctgatag ccaagtggct   2160
caaggatgcc atagagcatc taccggcgga ggcacttgct caacaggagg ccctaatgaa   2220
tattcaaaaa ttctggagct cttttgtggc cttgctgatt ggttacgtaa tctcaatgct   2280
tacactgctc gctgaaagat ggcatttcaa gcacatagtt atgaaacatc ccatgtatga   2340
tgtgtacaac ccaagcttgt attataattt taagcgaata tatccgcagc attaatgtca   2400
aggtttctgc ctagaaatat atatattttt ttttgcacat cac                     2443
```

<210> SEQ ID NO 58
<211> LENGTH: 842
<212> TYPE: PRT
<213> ORGANISM: Drosophila melanogaster

<400> SEQUENCE: 58

```
Met Ser Tyr Tyr Trp Val Ala Leu Val Leu Phe Thr Ala Gln Ala Phe
1               5                   10                  15

Ser Ile Glu Gly Asp Arg Ser Ala Ser Tyr Gln Glu Lys Cys Ile Ser
            20                  25                  30

Arg Arg Leu Ile Asn His Tyr Gln Leu Asn Lys Glu Ile Phe Gly Val
        35                  40                  45

Gly Met Cys Asp Gly Asn Asn Glu Asn Glu Phe Arg Gln Lys Arg Arg
    50                  55                  60

Ile Val Pro Thr Phe Gln Gly Asn Pro Arg Pro Arg Gly Glu Leu Leu
65                  70                  75                  80

Ala Ser Lys Phe His Val Asn Ser Tyr Asn Phe Glu Gln Thr Asn Ser
                85                  90                  95

Leu Val Gly Leu Val Asn Lys Ile Ala Gln Glu Tyr Leu Asn Lys Cys
            100                 105                 110

Pro Pro Val Ile Tyr Tyr Asp Ser Phe Val Glu Lys Ser Asp Gly Leu
        115                 120                 125

Ile Leu Glu Asn Leu Phe Lys Thr Ile Pro Ile Thr Phe Tyr His Gly
    130                 135                 140

Glu Ile Asn Ala Asp Tyr Glu Ala Lys Asn Lys Arg Phe Thr Ser His
145                 150                 155                 160

Ile Asp Cys Asn Cys Lys Ser Tyr Ile Leu Phe Leu Ser Asp Pro Leu
                165                 170                 175
```

-continued

```
Met Thr Arg Lys Ile Leu Gly Pro Gln Thr Glu Ser Arg Val Val Leu
            180                 185                 190

Val Ser Arg Ser Thr Gln Trp Arg Leu Arg Asp Phe Leu Ser Ser Glu
        195                 200                 205

Leu Ser Ser Asn Ile Val Asn Leu Leu Val Ile Gly Glu Ser Leu Met
210                 215                 220

Ala Asp Pro Met Arg Glu Arg Pro Tyr Val Leu Tyr Thr His Lys Leu
225                 230                 235                 240

Tyr Ala Asp Gly Leu Gly Ser Asn Thr Pro Val Val Leu Thr Ser Trp
                245                 250                 255

Ile Lys Gly Ala Leu Ser Arg Pro His Ile Asn Leu Phe Pro Ser Lys
            260                 265                 270

Phe Gln Phe Gly Phe Ala Gly His Arg Phe Gln Ile Ser Ala Ala Asn
        275                 280                 285

Gln Pro Pro Phe Ile Phe Arg Ile Arg Thr Leu Asp Ser Ser Gly Met
    290                 295                 300

Gly Gln Leu Arg Trp Asp Gly Val Glu Phe Arg Leu Leu Thr Met Ile
305                 310                 315                 320

Ser Lys Arg Leu Asn Phe Ser Ile Asp Ile Thr Glu Thr Pro Thr Arg
                325                 330                 335

Ser Asn Thr Arg Gly Val Val Asp Thr Ile Gln Glu Gln Ile Ile Glu
            340                 345                 350

Arg Thr Val Asp Ile Gly Met Ser Gly Ile Tyr Ile Thr Gln Glu Arg
        355                 360                 365

Leu Met Asp Ser Ala Met Ser Val Gly His Ser Pro Asp Cys Ala Ala
    370                 375                 380

Phe Ile Thr Leu Ala Ser Lys Ala Leu Pro Lys Tyr Arg Ala Ile Met
385                 390                 395                 400

Gly Pro Phe Gln Trp Pro Val Trp Val Ala Leu Ile Cys Val Tyr Leu
                405                 410                 415

Gly Gly Ile Phe Pro Ile Val Phe Thr Asp Arg Leu Thr Leu Ser His
            420                 425                 430

Leu Met Gly Asn Trp Gly Glu Val Glu Asn Met Phe Trp Tyr Val Phe
        435                 440                 445

Gly Met Phe Thr Asn Ala Phe Ser Phe Thr Gly Lys Tyr Ser Trp Ser
    450                 455                 460

Asn Thr Arg Lys Asn Ser Thr Arg Leu Leu Ile Gly Ala Tyr Trp Leu
465                 470                 475                 480

Phe Thr Ile Ile Ile Thr Ser Cys Tyr Thr Gly Ser Ile Ile Ala Phe
                485                 490                 495

Val Thr Leu Pro Ala Phe Pro Asp Thr Val Asp Ser Val Leu Asp Leu
            500                 505                 510

Leu Gly Leu Phe Phe Arg Val Gly Thr Leu Asn Asn Gly Gly Trp Glu
        515                 520                 525

Thr Trp Phe Gln Asn Ser Thr His Ile Pro Thr Ser Arg Leu Tyr Lys
    530                 535                 540

Lys Met Glu Phe Val Gly Ser Val Asp Glu Gly Ile Gly Asn Val Thr
545                 550                 555                 560

Gln Ser Phe Phe Trp Asn Tyr Ala Phe Leu Gly Ser Lys Ala Gln Leu
                565                 570                 575

Glu Tyr Leu Val Gln Ser Asn Phe Ser Asp Glu Asn Ile Ser Arg Arg
            580                 585                 590
```

```
Ser Ala Leu His Leu Ser Glu Glu Cys Phe Ala Leu Phe Gln Ile Gly
            595                 600                 605
Phe Leu Phe Pro Arg Glu Ser Val Tyr Lys Ile Lys Ile Asp Ser Met
        610                 615                 620
Ile Leu Leu Ala Gln Gln Ser Gly Leu Ile Ala Lys Ile Asn Asn Glu
625                 630                 635                 640
Val Ser Trp Val Met Gln Arg Ser Ser Gly Arg Leu Leu Gln Ala
            645                 650                 655
Ser Ser Ser Asn Ser Leu Arg Glu Ile Gln Glu Glu Arg Gln Leu
            660                 665                 670
Thr Thr Ala Asp Thr Glu Gly Met Phe Leu Leu Met Ala Leu Gly Tyr
            675                 680                 685
Phe Leu Gly Ala Thr Ala Leu Val Ser Glu Ile Val Gly Gly Ile Thr
        690                 695                 700
Asn Lys Cys Arg Gln Ile Ile Lys Arg Ser Arg Lys Ser Ala Ala Ser
705                 710                 715                 720
Ser Trp Ser Ser Ala Ser Ser Gly Ser Met Leu Arg Thr Asn Ala Glu
            725                 730                 735
Gln Leu Ser His Asp Lys Arg Lys Ala Asn Arg Arg Glu Ala Ala Glu
            740                 745                 750
Val Ala Gln Lys Met Ser Phe Gly Met Arg Glu Leu Asn Leu Thr Arg
        755                 760                 765
Ala Thr Leu Arg Glu Ile Tyr Gly Ser Tyr Gly Ala Pro Glu Thr Asp
        770                 775                 780
His Gly Gln Leu Asp Ile Val His Thr Glu Phe Pro Asn Ser Ser Ala
785                 790                 795                 800
Lys Leu Asn Asn Ile Glu Asp Glu Glu Ser Arg Glu Ala Leu Glu Ser
            805                 810                 815
Leu Gln Arg Leu Asp Glu Phe Met Asp Gln Met Asp Asn Asp Gly Asn
            820                 825                 830
Pro Ser Ser His Thr Phe Arg Ile Asp Asn
            835                 840

<210> SEQ ID NO 59
<211> LENGTH: 2629
<212> TYPE: DNA
<213> ORGANISM: Drosophila melanogaster

<400> SEQUENCE: 59
cgatatgtca tattattggg tagctctggt cttatttacc gcgcaagcct tttcaattga      60
aggggataga tccgctagtt atcaagagaa gtgtattagc cgacggctta tcaaccatta    120
tcaattaaac aaagaaattt ttggtgtggg aatgtgcgat ggtaataatg aaaacgagtt    180
ccgtcaaaaa cgccgtattg tccctacatt tcaaggcaat ccaaggccac gaggtgaact    240
tttggccagt aagtttcacg taaattccta aacttcgag cagactaact cattggttgg    300
gttggttaac aaaattgccc aagagtacct caataaatgc ccaccggtca tatattatga    360
tagctttgtg gaaaatctg acggattaat tctagagaat ttgttcaaga ctattcctat    420
tactttctac cacggggaaa tcaatgcaga ctacgaagca aaaataaaac gttttacgag    480
ccatatagat tgcaattgca aaagctacat tcttttcctt tcggacccat taatgacgcg    540
aaagatttta ggcccgcaaa ctgaaagtcg tgtagttctt gtctcaaggt ccacccaatg    600
gagacttcgt gatttttgt cttcggagct atcctcaaac attgtaaatt tactagttat    660
tggggaatcg ctcatggctg acccgatgcg cgagcgccca tacgtactct acacccacaa    720
```

```
gctctatgca gatggacttg gctcaaacac tccggtagtg ctaaccagct ggataaaggg    780
agctttgtca cgtccacata taaatctttt cccatcgaag tttcaatttg ggtttgcggg    840
acacagattt caaatttcag ccgcaaatca gccgccgttt attttcgaa ttcgcacttt     900 agattcctca ggaatgggcc agttgcgttg ggacggagtt gaatttcgtc tgctgacaat    960
gatatctaag cggctaaact tttcgataga tatcactgag accccaacac ggtcgaatac   1020
gcgcggggta gtagacacca tccaggaaca gattatagaa agaacagtag acattggtat   1080
gtccggtata tatataacac aggaacggct gatggactca gccatgtcgg tggggcactc   1140
acccgattgt gcagctttca taacacttgc atcgaaggcg ctgccgaaat acagagccat   1200
aatgggaccg ttccaatggc cagtctgggt cgctctgatt tgcgtttacc tcggtggaat   1260
atttccgata gttttaccg accgtttgac acttagccat ttaatgggta attggggtga    1320
ggtagaaaac atgttctggt atgtatttgg catgttcaca aacgctttct ccttcaccgg   1380
aaaatactcg tggagcaaca cgcggaaaaa ttccacacgc cttctaattg gagcatattg   1440
gctctttaca attatcatta catcttgcta cacaggttcc atcatagcat tcgtaacgtt   1500
gccagctttt ccggacaccg ttgactctgt gttggatctg ctgggattgt tctttcgcgt   1560
tggaaccctg aacaatggtg gctgggagac ctggttccag aactcgaccc atataccgac   1620
gtctagattg tacaagaaaa tggagtttgt cgggtccgta gatgagggca ttggcaacgt   1680
tacccagagc ttcttttgga actatgcctt tcttggctca aaggctcagc tcgaatacct   1740
ggtgcagtca aatttttcag atgaaaatat ttcccgccga tcggcgcttc atttgagtga   1800
agagtgtttt gctcttttcc aaataggatt tctgtttccc cgagagtcag tgtataaaat   1860
caaaatcgac tcgatgatat tacttgccca gcaaagtggt cttattgcaa aaatcaataa   1920
cgaggtaagc tgggtcatgc agcgatcatc ttcaggacgc ctgctccagg caagttcttc   1980
gaattcctta cgcgaaataa ttcaggaaga gcgccaattg actacagcgg acacagaagg   2040
aatgttcctg ctcatggcac tgggctactt tctaggagcc acagccctgg tatccgagat   2100
cgtcggtggg attaccaaca agtgccgcca aataatcaag cgctcccgca agtcggccgc   2160
ctcctcttgg tcgtcggcgt caagtgggtc aatgcttcgc actaatgccg agcaacttc    2220 ccatgataag cgaaaggcca atagacgcga ggctgctgag gttgctcaaa aaatgagttt   2280
tggaatgcgc gagttaaatc ttacccgcgc aacgcttcgg gaaatatacg gaagctacgg   2340
ggcacctgaa acagatcatg gtcagctaga catcgtccac actgagtttc caaacagttc   2400
tgcaaaatta ataatattg aagacgaaga atctcgggaa gctcttgaat ctctgcagcg    2460
tttagacgaa tttatggacc agatggataa cgacggcaat ccttcctcac atacattccg   2520
tattgacaat taatcacaga aatttttaaa tgcaaataca aaataatcac tttagtgcac   2580
atgaaattat atgtattgaa ataaaaagtt tgatgcaaca acaaattttt              2629
```

<210> SEQ ID NO 60
<211> LENGTH: 16
<212> TYPE: DNA
<213> ORGANISM: Drosophila melanogaster

<400> SEQUENCE: 60

```
ccagctttct catgtg                                                     16
```

<210> SEQ ID NO 61
<211> LENGTH: 15
<212> TYPE: DNA

```
<213> ORGANISM: Drosophila melanogaster

<400> SEQUENCE: 61
ccagcttctc atgtg                                                    15

<210> SEQ ID NO 62
<211> LENGTH: 11
<212> TYPE: DNA
<213> ORGANISM: Drosophila melanogaster

<400> SEQUENCE: 62
ccagctatgt g                                                        11

<210> SEQ ID NO 63
<211> LENGTH: 39
<212> TYPE: DNA
<213> ORGANISM: Drosophila melanogaster

<400> SEQUENCE: 63
gagacttggt tctgcctaat gggcatcatt ctgctgact                          39

<210> SEQ ID NO 64
<211> LENGTH: 34
<212> TYPE: DNA
<213> ORGANISM: Drosophila melanogaster

<400> SEQUENCE: 64
gagacttggt tctgcctgca tcattctgct gact                               34

<210> SEQ ID NO 65
<211> LENGTH: 30
<212> TYPE: DNA
<213> ORGANISM: Drosophila melanogaster

<400> SEQUENCE: 65
gagacttggt tctgcctcat tctgctgact                                    30

<210> SEQ ID NO 66
<211> LENGTH: 26
<212> TYPE: DNA
<213> ORGANISM: Drosophila melanogaster

<400> SEQUENCE: 66
gagacttggg catcattctg ctgact                                        26

<210> SEQ ID NO 67
<211> LENGTH: 17
<212> TYPE: DNA
<213> ORGANISM: Drosophila melanogaster

<400> SEQUENCE: 67
gagacttggc tctgact                                                  17

<210> SEQ ID NO 68
<211> LENGTH: 17
<212> TYPE: DNA
<213> ORGANISM: Drosophila melanogaster

<400> SEQUENCE: 68
ttaagcaaga catctgg                                                  17

<210> SEQ ID NO 69
<211> LENGTH: 13
```

```
<212> TYPE: DNA
<213> ORGANISM: Drosophila melanogaster

<400> SEQUENCE: 69
ttaagcaatc tgg                                                       13

<210> SEQ ID NO 70
<211> LENGTH: 24
<212> TYPE: DNA
<213> ORGANISM: Drosophila melanogaster

<400> SEQUENCE: 70
cgaggacaag gcagtactcg gagg                                           24

<210> SEQ ID NO 71
<211> LENGTH: 14
<212> TYPE: DNA
<213> ORGANISM: Drosophila melanogaster

<400> SEQUENCE: 71
cgaggactcg gagg                                                      14

<210> SEQ ID NO 72
<211> LENGTH: 20
<212> TYPE: DNA
<213> ORGANISM: Drosophila melanogaster

<400> SEQUENCE: 72
gcccgtttaa gcaagacatc                                                20

<210> SEQ ID NO 73
<211> LENGTH: 20
<212> TYPE: DNA
<213> ORGANISM: Drosophila melanogaster

<400> SEQUENCE: 73
tcagcagaat gatgcccatt                                                20

<210> SEQ ID NO 74
<211> LENGTH: 20
<212> TYPE: PRT
<213> ORGANISM: Drosophila melanogaster

<400> SEQUENCE: 74

Cys Gly Glu Phe Trp Tyr Arg Arg Phe Arg Ala Ser Arg Lys Arg Arg
1               5                   10                  15

Gln Phe Thr Asn
            20

<210> SEQ ID NO 75
<211> LENGTH: 20
<212> TYPE: PRT
<213> ORGANISM: Drosophila melanogaster

<400> SEQUENCE: 75

Ser Lys Ala Ala Leu Arg Pro Arg Phe Asn Gln Tyr Pro Ala Thr Phe
1               5                   10                  15

Lys Pro Arg Phe
            20

<210> SEQ ID NO 76
<211> LENGTH: 20
<212> TYPE: DNA
```

<213> ORGANISM: Drosophila melanogaster

<400> SEQUENCE: 76
tagcagtcag cgggacaatg                                               20

<210> SEQ ID NO 77
<211> LENGTH: 20
<212> TYPE: DNA
<213> ORGANISM: Drosophila melanogaster

<400> SEQUENCE: 77
gagtggattg cgtgacgaga                                               20

<210> SEQ ID NO 78
<211> LENGTH: 18
<212> TYPE: DNA
<213> ORGANISM: Drosophila melanogaster

<400> SEQUENCE: 78
ggcgaggaca aggcagta                                                 18

<210> SEQ ID NO 79
<211> LENGTH: 20
<212> TYPE: DNA
<213> ORGANISM: Drosophila melanogaster

<400> SEQUENCE: 79
cggcagcggt catcttatct                                               20

<210> SEQ ID NO 80
<211> LENGTH: 20
<212> TYPE: DNA
<213> ORGANISM: Drosophila melanogaster

<400> SEQUENCE: 80
tgccaaggtc cagcagattc                                               20

<210> SEQ ID NO 81
<211> LENGTH: 20
<212> TYPE: DNA
<213> ORGANISM: Drosophila melanogaster

<400> SEQUENCE: 81
aacatgttca gggtctcggc                                               20

<210> SEQ ID NO 82
<211> LENGTH: 20
<212> TYPE: DNA
<213> ORGANISM: Drosophila melanogaster

<400> SEQUENCE: 82
gctaagctgt cgcacaaatg                                               20

<210> SEQ ID NO 83
<211> LENGTH: 21
<212> TYPE: DNA
<213> ORGANISM: Drosophila melanogaster

<400> SEQUENCE: 83
gttcgatccg taacccgatg t                                             21

<210> SEQ ID NO 84
<211> LENGTH: 27

```
<212> TYPE: DNA
<213> ORGANISM: Drosophila melanogaster

<400> SEQUENCE: 84
cggccgccac gtcgtcgtcc gcattac                                27

<210> SEQ ID NO 85
<211> LENGTH: 28
<212> TYPE: DNA
<213> ORGANISM: Drosophila melanogaster

<400> SEQUENCE: 85
gcggccgccc tttcgccgcc aaacgcaa                               28

<210> SEQ ID NO 86
<211> LENGTH: 40
<212> TYPE: DNA
<213> ORGANISM: Drosophila melanogaster

<400> SEQUENCE: 86
cgttacacgc atgccacgtc gtcgtccgca ttacaatatc                  40

<210> SEQ ID NO 87
<211> LENGTH: 40
<212> TYPE: DNA
<213> ORGANISM: Drosophila melanogaster

<400> SEQUENCE: 87
cgttacacgc atgccacgtc gtcgtccgca ttacaatatc                  40
```